(12) United States Patent
Long et al.

(10) Patent No.: US 10,654,808 B2
(45) Date of Patent: May 19, 2020

(54) TYROSINE KINASE INHIBITOR AND PHARMACEUTICAL COMPOSITION COMPRISING SAME

(71) Applicant: GUANGDONG RAYNOVENT BIOTECH CO., LTD., Guangdong (CN)

(72) Inventors: Chaofeng Long, Dongguan (CN); Zhengxia Chen, Dongguan (CN); Xiaoxin Chen, Dongguan (CN); Yang Zhang, Dongguan (CN); Zhuowei Liu, Dongguan (CN); Peng Li, Dongguan (CN); Shuhui Chen, Dongguan (CN); Guibai Liang, Dongguan (CN); Cheng Xie, Dongguan (CN); Zhengwei Li, Dongguan (CN); Zhifei Fu, Dongguan (CN); Guoping Hu, Dongguan (CN); Jian Li, Dongguan (CN)

(73) Assignee: GUANGDONG RAYNOVENT BIOTECH CO., LTD., Guangdong (CN)

(*) Notice: Subject to any disclaimer, the term of this patent is extended or adjusted under 35 U.S.C. 154(b) by 61 days.

(21) Appl. No.: 15/562,825

(22) PCT Filed: Apr. 7, 2016

(86) PCT No.: PCT/CN2016/078703
§ 371 (c)(1),
(2) Date: Jun. 5, 2018

(87) PCT Pub. No.: WO2016/161952
PCT Pub. Date: Oct. 13, 2016

(65) Prior Publication Data
US 2019/0119217 A1 Apr. 25, 2019

(30) Foreign Application Priority Data
Apr. 7, 2015 (CN) .................. 2015 1 0161674

(51) Int. Cl.
*C07D 215/48* (2006.01)
*C07D 405/14* (2006.01)
(Continued)

(52) U.S. Cl.
CPC ........ *C07D 215/48* (2013.01); *A61K 31/4709* (2013.01); *A61K 31/53* (2013.01); *A61P 35/00* (2018.01); *C07D 401/10* (2013.01); *C07D 401/12* (2013.01); *C07D 401/14* (2013.01); *C07D 405/12* (2013.01); *C07D 405/14* (2013.01); *C07D 417/10* (2013.01); *C07D 417/12* (2013.01); *C07D 471/04* (2013.01);
(Continued)

(58) Field of Classification Search
CPC .. C07D 215/48; C07D 401/10; C07D 401/12; C07D 401/14; C07D 405/12; C07D 405/14; C07D 417/10; C07D 417/12; C07D 471/04; C07D 487/04; C07D 491/056; C07D 498/04; A61K 31/4709; A61K 31/53
USPC .......................................... 544/183
See application file for complete search history.

(56) References Cited

U.S. PATENT DOCUMENTS 6,630,489 B1 * 10/2003 Crawley .............. C07D 215/48
  514/311
2004/0053908 A1 3/2004 Funahashi et al.
(Continued)

FOREIGN PATENT DOCUMENTS

CN 1478078 A 2/2004
CN 1890234 A 1/2007
(Continued)

OTHER PUBLICATIONS

Folkman, "Tumor Angiogenesis: Therapeutic Implications," Seminars in Medicine of the Beth Israel Hospital, Boston, *The New England Journal of Medicine*, Nov. 18, 1971 (pp. 1182-1971).
(Continued)

*Primary Examiner* — Kahsay Habte
(74) *Attorney, Agent, or Firm* — Lewis Roca Rothgerber Christie LLP

(57) ABSTRACT

The present invention relates to a tyrosine kinase inhibitor and a pharmaceutical composition comprising same. The tyrosine kinase inhibitor of the present invention has the structures as shown in the following formula (I) or (II):

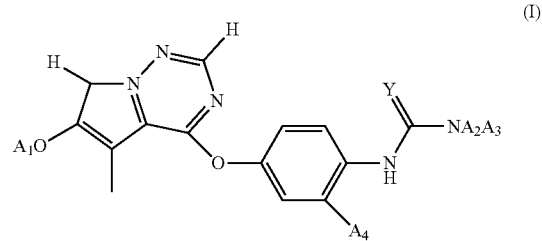

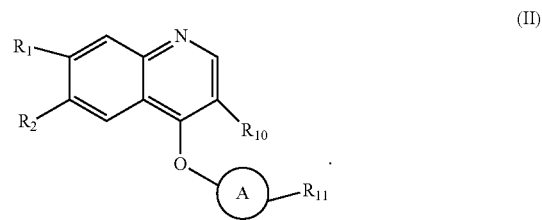

21 Claims, No Drawings

(51) Int. Cl.
*C07F 9/60* (2006.01)
*C07D 401/12* (2006.01)
*C07D 417/12* (2006.01)
*C07D 498/04* (2006.01)
*C07D 491/056* (2006.01)
*A61K 31/4709* (2006.01)
*A61K 31/53* (2006.01)
*A61P 35/00* (2006.01)
*C07D 401/10* (2006.01)
*C07D 401/14* (2006.01)
*C07D 405/12* (2006.01)
*C07D 417/10* (2006.01)
*C07D 471/04* (2006.01)
*C07D 487/04* (2006.01)

(52) U.S. Cl.
CPC ....... *C07D 487/04* (2013.01); *C07D 491/056* (2013.01); *C07D 498/04* (2013.01); *C07F 9/60* (2013.01)

(56) References Cited

U.S. PATENT DOCUMENTS

2005/0137395 A1 6/2005 Hong et al.
2006/0004006 A1 1/2006 Borzilleri et al.

FOREIGN PATENT DOCUMENTS

CN 101005843 A 7/2007
WO WO 2005/073224 A2 8/2005

OTHER PUBLICATIONS

International Search Report dated Jun. 30, 2016 for International Application No. PCT/CN2016/078703, with English Translation (10 pages).

* cited by examiner

TYROSINE KINASE INHIBITOR AND PHARMACEUTICAL COMPOSITION COMPRISING SAME

CROSS-REFERENCE TO RELATED APPLICATION

The present application is a National Phase Patent Application of International Patent Application Number PCT/CN2016/078703, filed on Apr. 7, 2016, which claims the benefit of and priority to Chinese Patent Application No. 2015101616744, filed Apr. 7, 2015, the entire contents of both of which are incorporated herein by reference.

FIELD OF THE INVENTION

The present invention pertains to the field of pharmaceutical technology, and in particular to a kind of tyrosine kinase inhibitors or pharmaceutically acceptable salts thereof, and pharmaceutical compositions comprising said tyrosine kinase inhibitors.

BACKGROUND

A protein tyrosine kinase is an enzyme which can transfer a phosphate group from ATP to a tyrosine residue located in protein substrates, the protein tyrosine kinase plays a role in normal cell growth. Many growth factor receptor proteins work via the protein tyrosine kinase and affect the signal via this process and then regulate cell growth, such as FGFR (fibroblast growth factor receptor), VEGFR (vascular endothelial growth factor receptor) and PDGFR (platelet-derived growth factor receptor). However, under certain conditions, these receptors mutate or overexpress and become abnormal, thereby causing uncontrolled cell proliferation, resulting in tumor growth, and eventually leading to a well-known disease, i.e., cancer. Growth factor receptor protein tyrosine kinase inhibitors play a role in the treatment of cancer and other diseases characterized by uncontrolled or abnormal cell growth by inhibiting the above phosphorylation process.

Uncontrolled angiogenesis is a sign of cancer. In 1971, Dr. Judah Folkman raised that tumor growth depends on angiogenesis (see Folkman, *New England Journal of Medicine*, 285: 1182-86 (1971)). According to Dr. Judah Folkman, the tumor can only grow to a certain size without additional blood vessels to nourish the tumor. In his simplest expression, it is pointed out that once a tumor has "survived", each increase in the population of tumor cells must be carried out by the increase in the number of new capillaries that converge on the tumor. According to the current understanding, the tumor's "survival" refers to the anterior phase of tumor growth, where the tumor cells which have a volume of several cubes of millimeters and no more than several million cells can survive on the existing host microvasculature.

It has been shown that the tumor can be treated by inhibiting angiogenesis rather than inhibiting the proliferation of tumor cells themselves. Angiogenesis has been associated with a large number of different types of cancer, which include solid tumors and blood-borne tumors. Solid tumors associated with angiogenesis include, but are not limited to rhabdomyosarcoma, retinoblastoma, ewing sarcoma, neuroblastoma and osteosarcoma. Angiogenesis is associated with breast cancer, prostate cancer, lung cancer, and colon cancer. Angiogenesis is also associated with blood-borne tumors, such as leukemia, lymphoma, multiple myeloma, and any one of various acute or chronic myeloid neoplasms, in which the presence of uncontrolled proliferation of white blood cells is usually accompanied by anemia, weakened blood clotting, and increased lymph nodes, liver and spleen, and it is believed that angiogenesis plays a role in bone marrow abnormalities, and the abnormalities cause leukemia, lymphoma and multiple myeloma.

Angiogenesis plays a major role in the metastasis of cancer, and if it is possible to inhibit or eliminate the activity of the blood vessel, it will not grow even if the tumor is present. In the disease state, the prevention of angiogenesis can reduce the damage caused by the invasion of the new microvascular system. Controlled therapy for a vasculogenic process may result in the removal or reduction of these diseases.

Wherein, the research that FGFR (fibroblast growth factor receptor), VEGFR (vascular endothelial growth factor receptor) and PDGFR (platelet-derived growth factor receptor) inhibitors inhibit angiogenesis is more and more mature.

SUMMARY OF THE INVENTION

The present invention provides tyrosine kinase inhibitors or pharmaceutically acceptable salts thereof, and pharmaceutical compositions comprising the tyrosine kinase inhibitors.

The technical solution of the present invention is as follows:

The present invention provides a compound or an enantiomer, a diastereomer, a geometric isomer, a solvate or a pharmaceutically acceptable salt thereof represented by formula (I) or formula (II);

wherein, the structural formula of formula (I) is as follows:

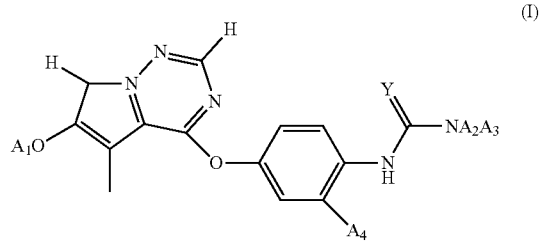

(I)

In the above-mentioned formula (I), Y is O or S, $A_1$ is hydroxy-$C_{1-6}$ alkyl, $A_2$ and $A_3$ are each independently H, $C_{1-6}$ alkyl (straight chain or branched chain $C_{1-6}$ alkyl), $C_{3-6}$ cycloalkyl, or $A_2$ and $A_3$ form a 3-6 membered saturated aliphatic ring, $A_4$ is halogen, $C_{1-6}$ alkyl or $C_{3-6}$ cycloalkyl.

Examples of the above-mentioned compounds of formula (I) are as follows:

Example 25

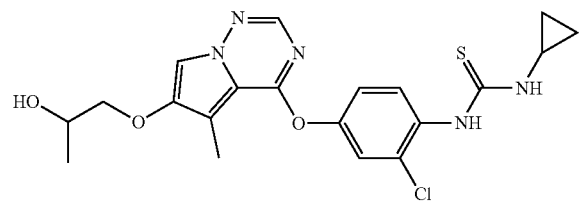 [SMILES: Cc1c(OCC(C)O)cn2ncnc(Oc3ccc(NC(=S)NC4CC4)c(Cl)c3)c12]

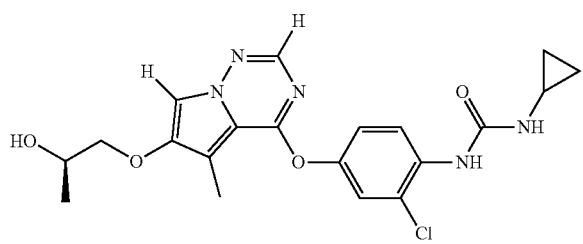 [SMILES: Cc1c(OC[C@@H](C)O)cn2ncnc(Oc3ccc(NC(=O)NC4CC4)c(Cl)c3)c12]

Example 126

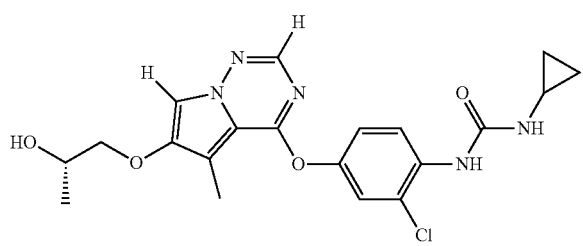 [SMILES: Cc1c(OC[C@H](C)O)cn2ncnc(Oc3ccc(NC(=O)NC4CC4)c(Cl)c3)c12]

Example 127

Wherein, the structural formula of formula (II) is as follows:

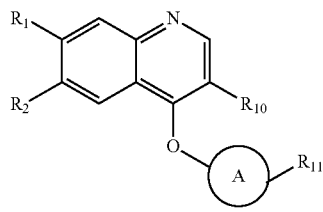

(II)

R₁ is selected from optionally substituted $C_{1-7}$ heteroalkyl and 5-6 membered heteroaryl;

preferably, R₁ is selected from optionally substituted $C_{1-6}$ alkoxy, $C_{1-6}$ heteroalkyl-O— and imidazolyl;

more preferably, R₁ is selected from the group consisting of $C_{1-6}$ alkoxy, $O(CH_2)_n R_{1d1}$ and

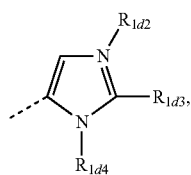

wherein n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl (including chain alkyl and cycloalkyl), $R_{1d2}$, $R_{1d3}$ and $R_{1d4}$ are each independently H, $C_{1-6}$ alkyl (including chain alkyl and cycloalkyl) or aryl (e.g. phenyl);

further preferably, R₁ is selected from $C_{1-3}$ alkoxy such as methoxy; $O(CH_2)$—$R_{1d1}$, wherein n is an integer of 1 to 3, $R_{1d1}$ is $C_{1-3}$ alkoxy or $NR_{1d5}R_{1d6}$, wherein $R_{1d5}$ and $R_{1d6}$ are each independently $C_{1-3}$ alkyl; and imidazolyl;

most preferably, R₁ is

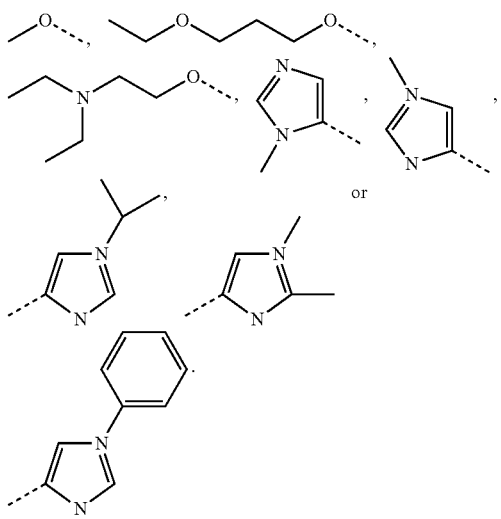

R₂ is selected from H, OH, NH₂, halogen, CN, —C(=O)N($R_{2d1}$)($R_{2d2}$), —N($R_{2d1}$)C(=O)$R_{2d2}$, —C(=O)O$R_{2d3}$ and optionally substituted $C_{1-7}$ alkyl (including chain alkyl and cycloalkyl);

preferably, R₂ is selected from H, CN, halo $C_{1-3}$ alkyl, hydroxy $C_{1-3}$ hydroxy, —C(=O)N($R_{2d1}$)($R_{2d2}$), —N($R_{2d1}$)C(=O)$R_{2d2}$ and —C(=O)O$R_{2d3}$;

more preferably, R₂ is selected from H, CN, CF₃,

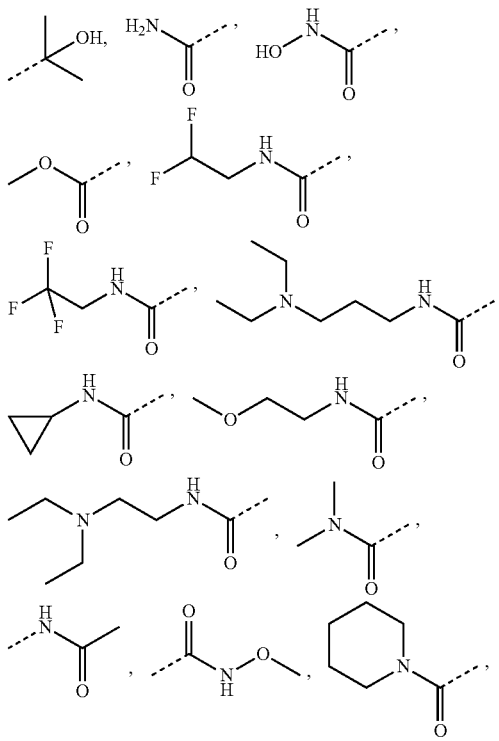

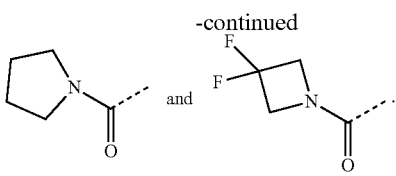 and 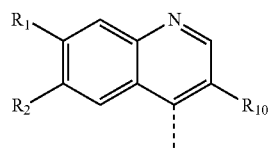

Wherein, $R_{2d1}$, $R_{2d2}$ and $R_{2d3}$ are each independently selected from H, OH, $NH_2$, CN and optionally substituted $C_{1-7}$ alkyl, $C_{1-7}$ heteroalkyl, 3-6 membered cycloalkyl and 3-6 membered heterocycloalkyl, or $R_{2d1}$ and $R_{2d2}$ together form a 4-7 membered ring;

preferably, $R_{2d1}$ and $R_{2d2}$ are each independently selected from H, OH, halogen and optionally substituted $C_{1-7}$ alkyl, $C_{1-7}$ heteroalkyl and $C_{3-5}$ cycloalkyl; or $R_{2d1}$ and $R_{2d2}$ together form a 4-7 membered ring;

preferably, $R_{2d1}$ and $R_{2d2}$ are each independently selected from H, OH, haloalkyl, $C_{1-6}$ alkyl, $C_{3-6}$ cycloalkyl, $C_{1-6}$ alkoxy, N,N-di($C_{1-6}$ alkyl)-$C_{1-6}$ alkyl, $R_{2d3}$ is $C_{1-6}$ alkyl; or $R_{2d1}$ and $R_{2d2}$ together form a 4-7 membered ring;

more preferably, $R_{2d1}$ and $R_{2d2}$ are each independently selected from H, OH, haloalkyl, $C_{1-3}$ alkyl, $C_{3-6}$ cycloalkyl, $C_{1-3}$ alkoxy, N,N-di($C_{1-3}$ alkyl)-$C_{1-3}$ alkyl, $R_{2d3}$ is $C_{1-3}$ alkyl; or $R_{2d1}$ and $R_{2d2}$ together form a 4-6 membered ring;

further preferably, $R_{2d1}$, $R_{2d2}$ and $R_{2d3}$ are each independently selected from H, OH, methyl,

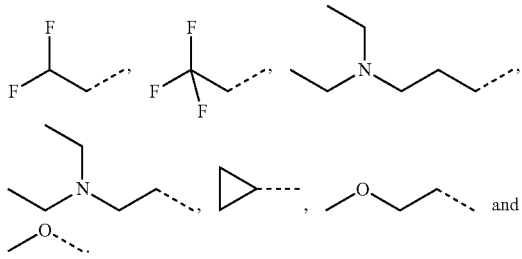

In some embodiments of the present invention, the structural unit —N($R_{2d1}R_{2d2}$) is selected from the group consisting of optionally substituted

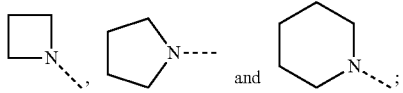

more specifically, the structural unit —N($R_{2d1}R_{2d2}$) is selected from the group consisting of

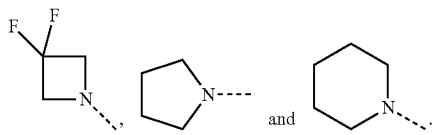

Alternatively, in the above-mentioned formula (II), $R_1$ and $R_2$ together with two carbon atoms on the benzene ring form a 4-7 membered ring; preferably, $R_1$ and $R_2$ together with two carbon atoms on the benzene ring form an optionally substituted 5 to 6 membered ring.

In some embodiments of the present invention, the above-mentioned structural unit

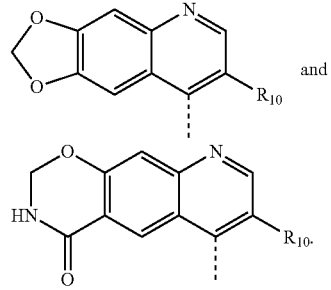

is selected from optionally substituted

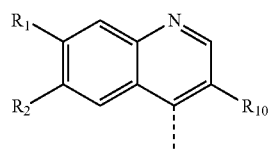

In some embodiments of the present invention, the above-mentioned structural unit

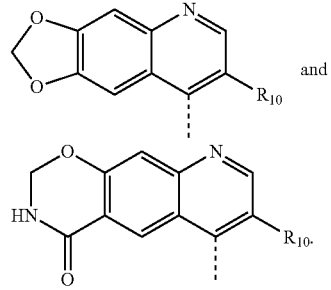

is selected from

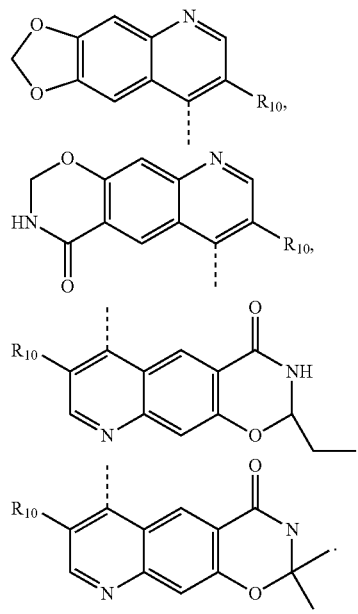

$R_{10}$ is selected from H, OH, $NH_2$, CN and halogen; preferably H or halogen.

A is a monocyclic or polycyclic ring selected from optionally substituted 3-6 membered cycloalkyl, 3-6 membered cycloalkyl-$C_{1-3}$ alkyl, 6-10 membered aromatic ring and 6-10 membered heteroaromatic ring;

preferably, A is a monocyclic or bicyclic ring selected from optionally substituted phenyl, benzofuranyl, benzopyrazolyl, indolyl, benzothiazolyl, cyclobutyl, -cyclobutyl-methylene- and

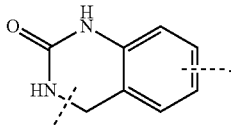

more preferably, A is a monocyclic or bicyclic ring selected from optionally substituted

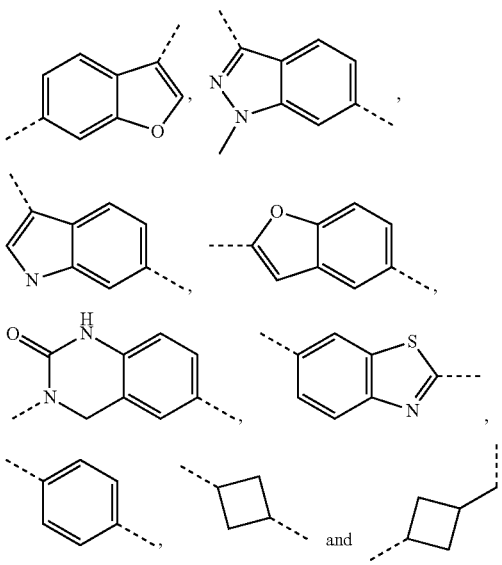

further preferably, A is selected from

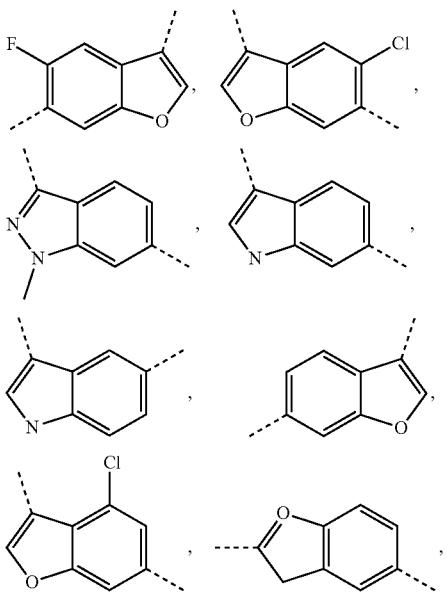

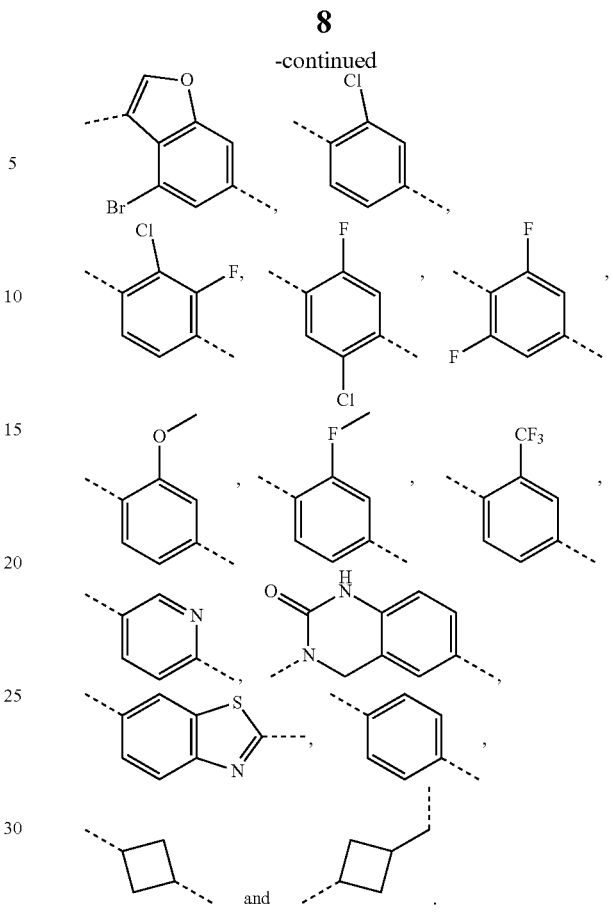

$R_{11}$ is selected from H, OH, $NH_2$, CN, halogen and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl and

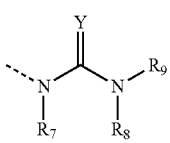

(wherein, Y is O or S, $R_7$, $R_8$ and $R_9$ are each independently selected from H, and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

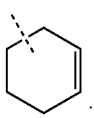

Preferably, the above-mentioned $R_7$, $R_8$ and $R_9$ are each independently selected from H and optionally substituted $C_{1-5}$ alkyl, $C_{1-5}$ heteroalkyl, 3-6 membered cycloalkyl, 4-6 membered heterocycloalkyl, 6 membered aryl, 5-6 membered heteroaryl, 3-6 membered cycloalkyl-$C_{1-2}$ alkyl-, 3-6 membered heterocycloalkyl-$C_{1-2}$ alkyl-, 6 membered aryl-$C_{1-2}$ alkyl-, 5-6 membered heteroaryl-$C_{1-2}$ alkyl-, $C_{3-6}$ alkynyl and

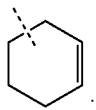

More preferably, the above-mentioned $R_7$, $R_8$ and $R_9$ are each independently selected from H and optionally substituted $C_{1-4}$ alkyl, $C_{1-2}$ alkyl-S—$C_{1-3}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

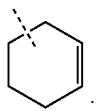

Further preferably, the above-mentioned $R_7$, $R_8$ and $R_9$ are each independently selected from H or optionally substituted groups consisting of Me,

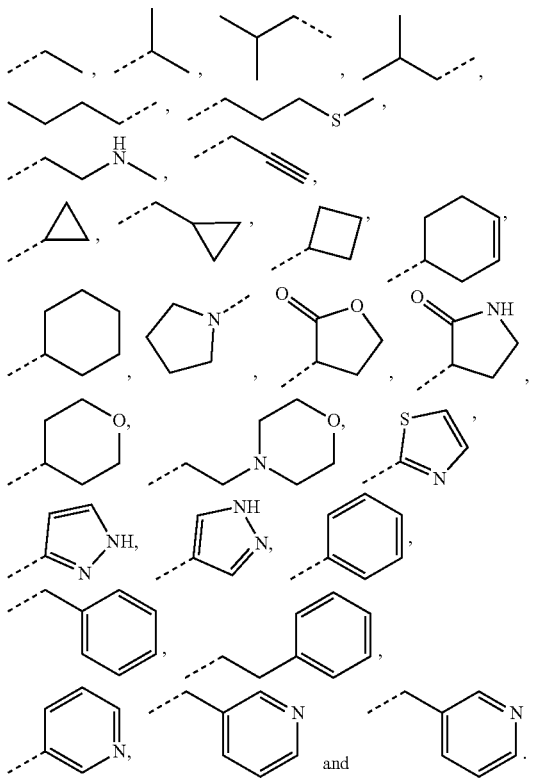

and

Most preferably, the above-mentioned $R_7$, $R_8$ and $R_9$ are each independently selected from H, Me,

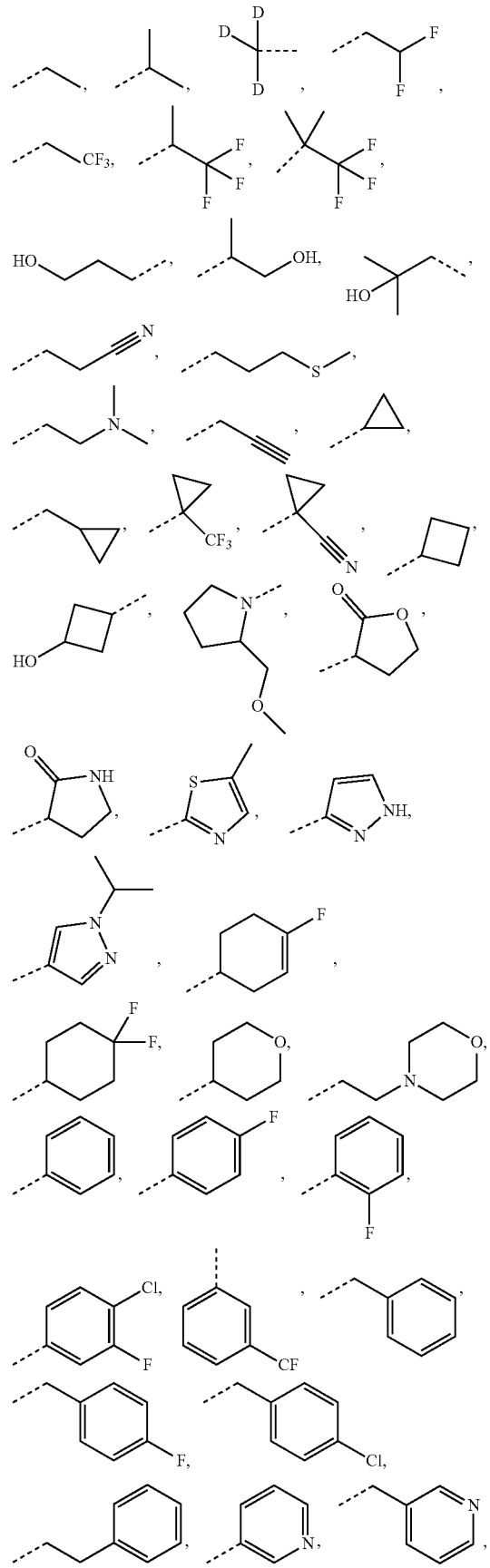

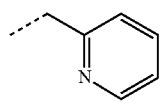 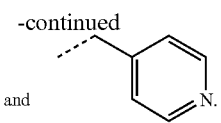 and

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

is selected from optionally substituted

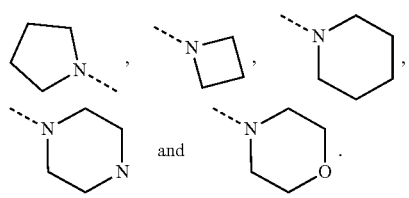

In some embodiments of the present invention, the above-mentioned structural unit

is selected from

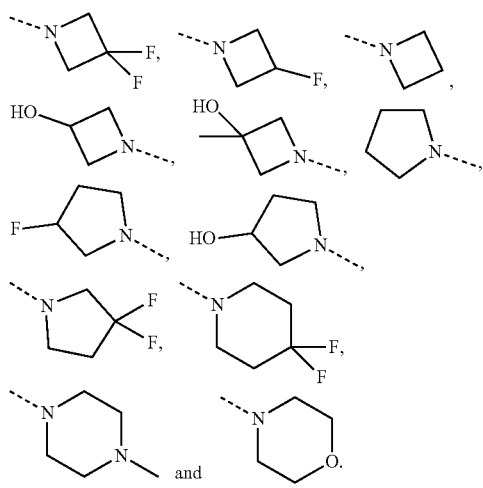

Preferably, the above-mentioned $R_7$ and $R_8$ together form an optionally substituted 4-7 membered ring, and preferably the above-mentioned $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

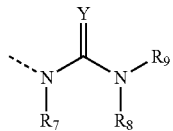

is selected from optionally substituted

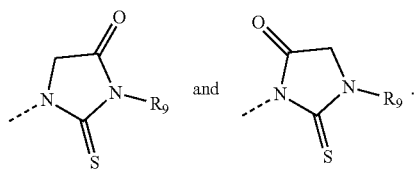

In some embodiments of the present invention, the above-mentioned structural unit

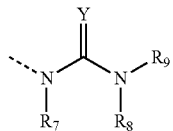

is selected from

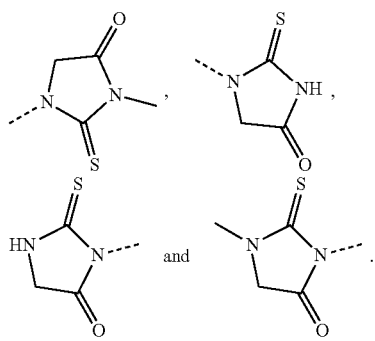

Alternatively, $R_8$ may form a 4-7 membered ring with two adjacent carbon atoms on ring A), —C(=O)N($R_{11d1}$)($R_{11d2}$), —$C_{1-3}$ alkyl-C(=O)N($R_{11d1}$)($R_{11d2}$), —NH—C(=O)N($R_{11d1}$)($R_{11d2}$), —$C_{1-3}$ alkyl-NH—C(=O)N($R_{11d1}$)($R_{11d2}$), $C_{1-7}$ alkyl-N($R_{11d1}$)—S(=O)—N($R_{11d2}$)—, 3-6 membered alkyl-N($R_{11d1}$)—P(=O)(O$R_{11d2}$)—$C_{1-3}$ alkyl- (wherein, $R_{11d1}$ and $R_{11d2}$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 5-6 membered aryl-$C_{1-3}$ alkyl-; or optionally, $R_{11d1}$ and $R_{11d2}$ together form a 4-7 membered ring;

preferably, the above-mentioned $R_{11d1}$ and $R_{11d2}$ are each independently selected from H, OH, NH$_2$, CN, halogen, optionally substituted C$_{1-3}$ alkyl, C$_{1-3}$ heteroalkyl and C$_{3-5}$ cycloalkyl.

Preferably, the above-mentioned $R_{11d1}$ and $R_{11d2}$ are each independently selected from H, Me,

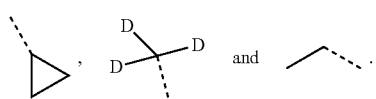

Preferably, the above-mentioned $R_{11d1}$ and $R_{11d2}$ together form an optionally substituted 4-5 membered ring.

In some embodiments of the present invention, the above-mentioned structural unit —N($R_{11d1}$)($R_{11d2}$) is selected from optionally substituted

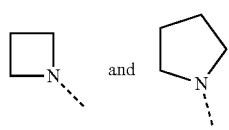

In some embodiments of the present invention, the above-mentioned structural unit —N($R_{11d1}$)($R_{11d2}$) is selected from

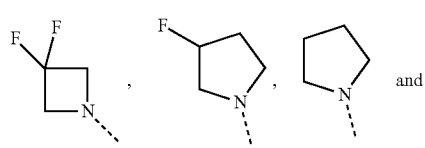

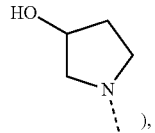

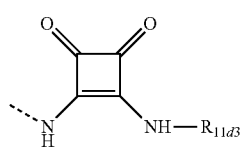

(wherein, $R_{11d3}$ is selected from optionally substituted H, C$_{1-7}$ alkyl, C$_{1-7}$ heteroalkyl, 3-6 membered cycloalkyl, 3-6 membered heterocycloalkyl, 5-6 membered aryl, 5-6 membered heteroaryl, 5-6 membered heterocycloalkyl-C$_{1-3}$ alkyl-, 5-6 membered aryl-C$_{1-3}$ alkyl- and 5-6 membered heteroaryl-C$_{1-3}$ alkyl-), 3-6 membered heterocycloalkylamino-, 5-6 membered arylamino-, 5-6 membered aryl-C$_{1-3}$ alkylamino-;

preferably, the above-mentioned $R_{11}$ is selected from H, CN and optionally substituted

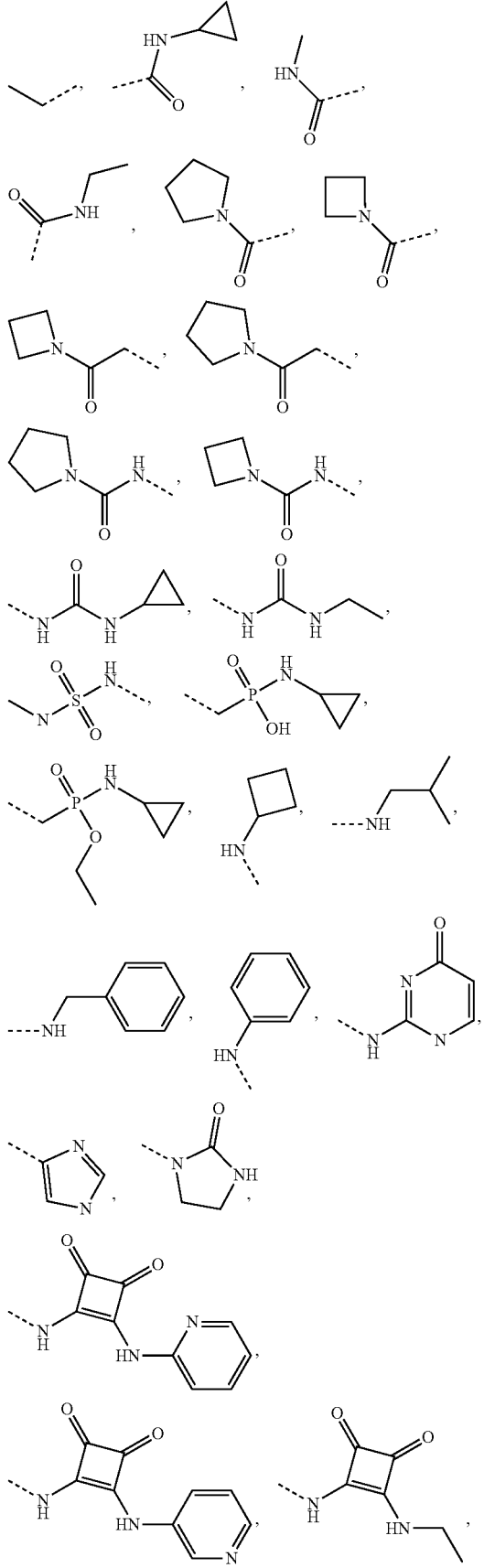

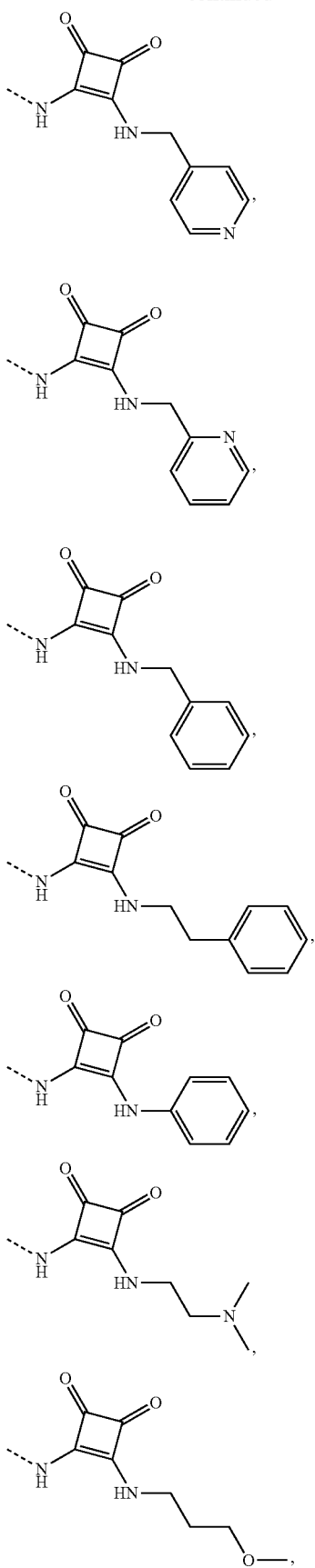
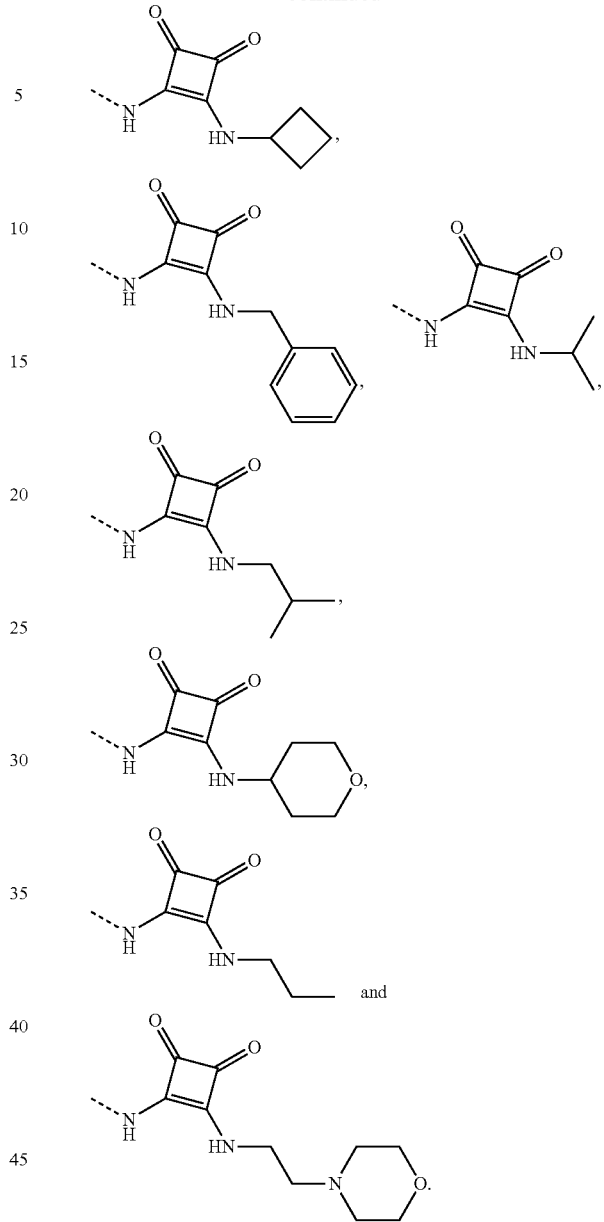
More preferably, the above-mentioned $R_{11}$ is selected from H, CN,
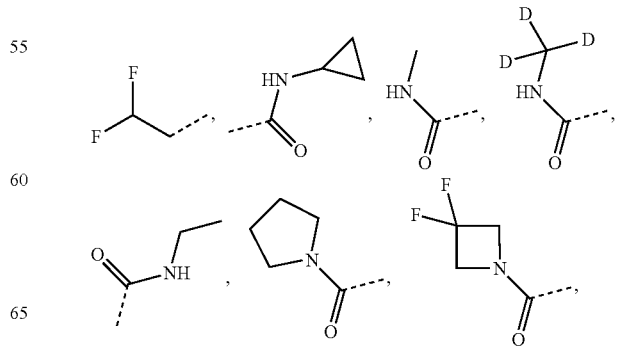

-continued
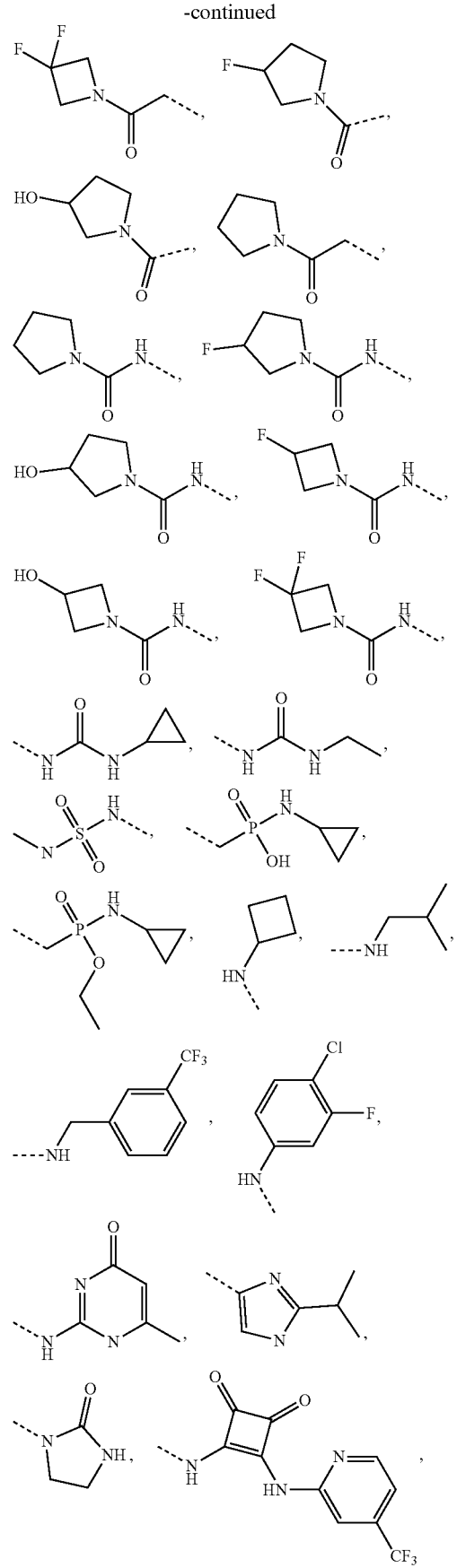
-continued
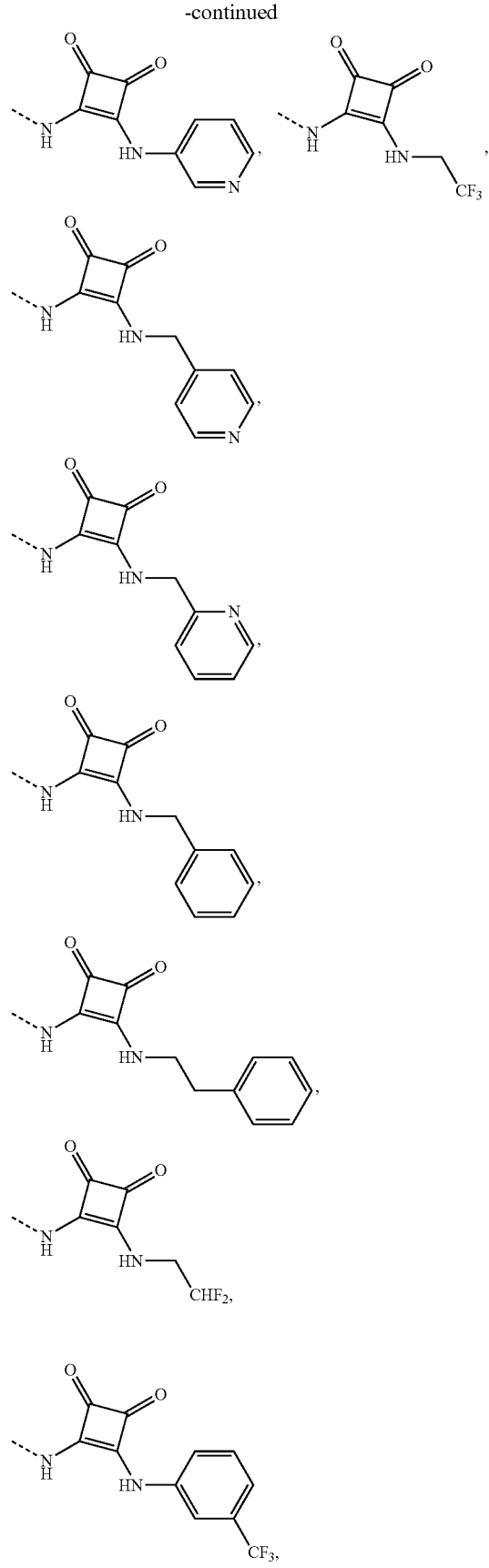

-continued

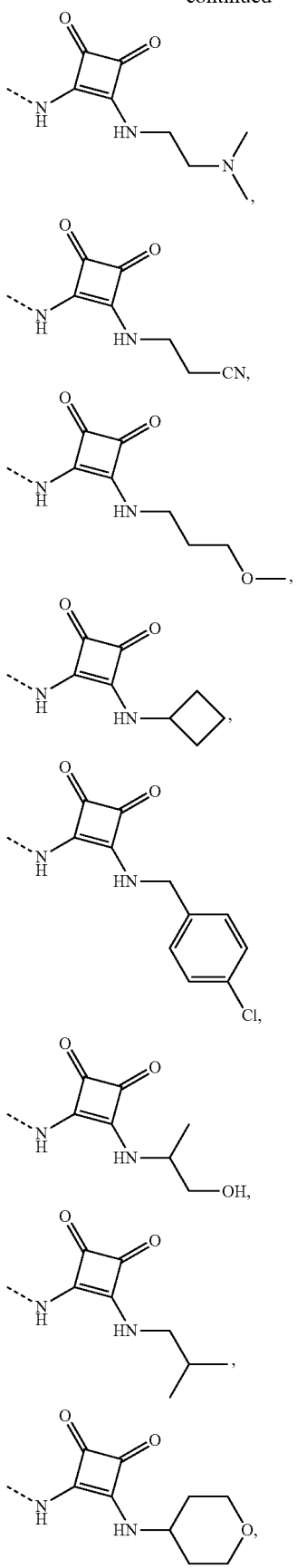

-continued

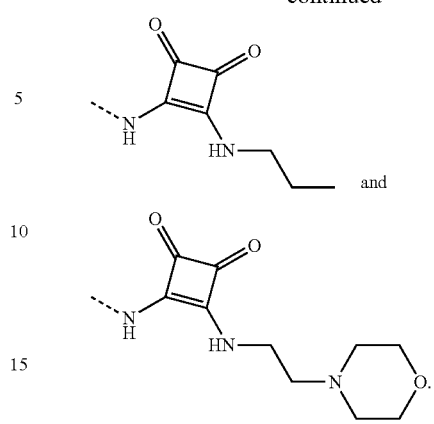

and

Preferably, the formula (II) is represented by formula (III):

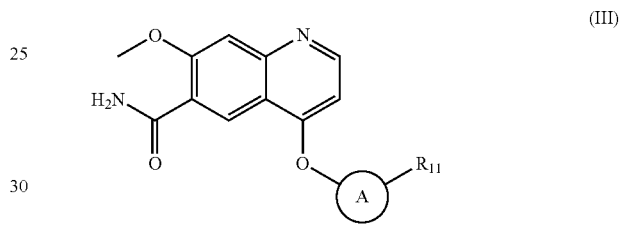

wherein, in the formula (III), A is a monocyclic or polycyclic ring selected from optionally substituted 3-6 membered cycloalkyl, 3-6 membered cycloalkyl-$C_{1-3}$ alkyl, 6-10 membered aromatic ring and 6-10 membered heteroaromatic ring;

preferably, A is a monocyclic or bicyclic ring selected from optionally substituted phenyl, benzofuranyl, benzopyrazolyl, indolyl, benzothiazolyl, cyclobutyl, -cyclobutylmethylene- and

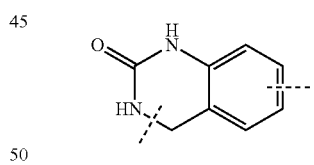

More preferably, A is a monocyclic or bicyclic ring selected from optionally substituted

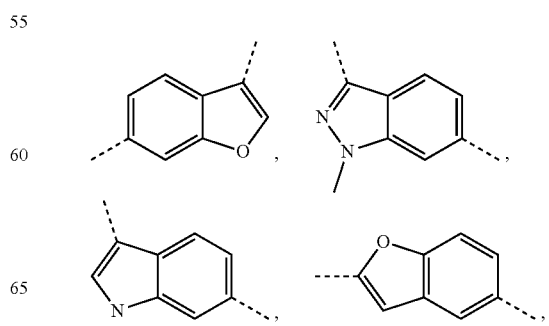

-continued

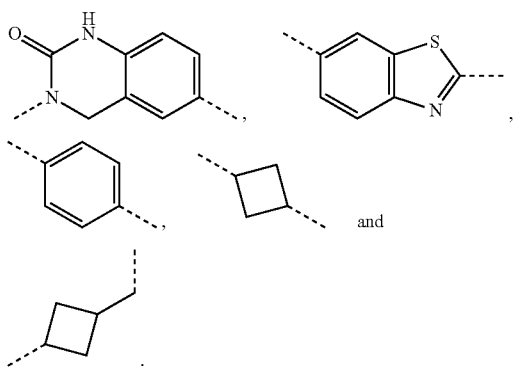

further preferably, A is selected from

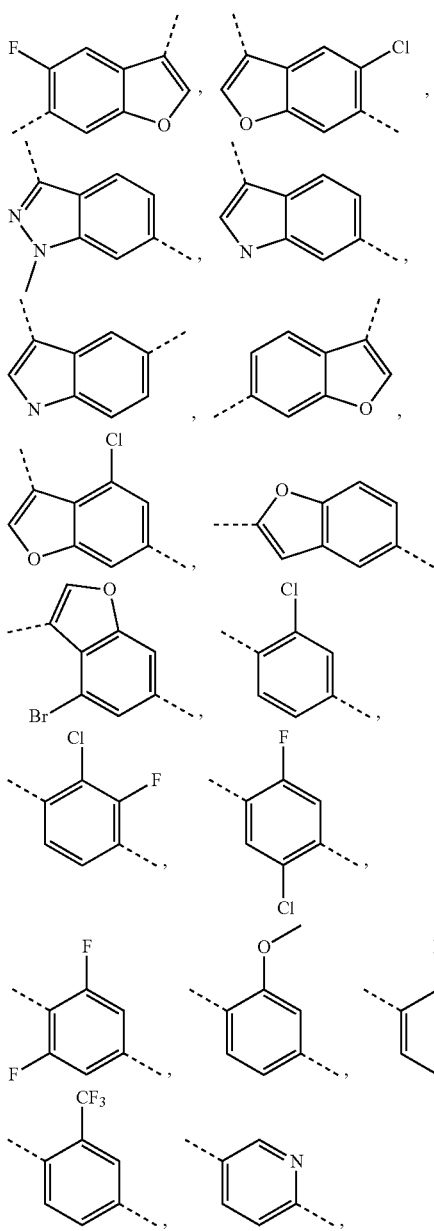

-continued

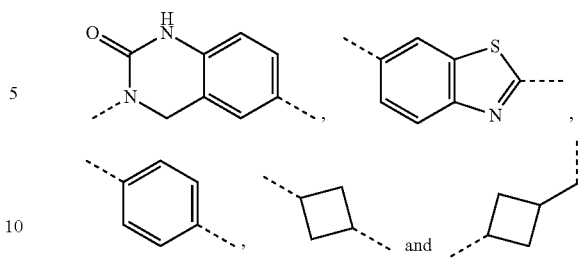

R₁₁ is selected from H, OH, NH$_2$, CN, halogen and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl,

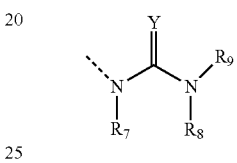

(wherein, Y is O or S, $R_7$, $R_8$ and $R_9$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$, alkyl-, 5-6 membered aryl-$C_{1-3}$ alkyl-, $C_{2-7}$ alkynyl and

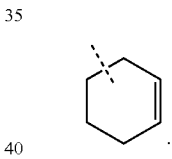

preferably, the above-mentioned $R_7$, $R_8$ and $R_9$ are each independently selected from H and optionally substituted $C_{1-5}$ alkyl, $C_{1-5}$ heteroalkyl, 3-6 membered cycloalkyl, 4-6 membered heterocycloalkyl, 6 membered aryl, 5-6 membered heteroaryl, 3-6 membered cycloalkyl-$C_{1-2}$ alkyl-, 3-6 membered heterocycloalkyl-$C_{1-2}$ alkyl-, 6 membered aryl-$C_{1-2}$ alkyl-, 5-6 membered heteroaryl-$C_{1-2}$ alkyl-, $C_{3-6}$ alkynyl and

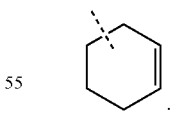

More preferably, the above-mentioned $R_7$, $R_8$ and $R_9$ are each independently selected from H and optionally substituted $C_{1-4}$ alkyl, $C_{1-2}$ alkyl-S—$C_{1-3}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

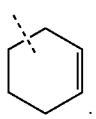

Further preferably, the above-mentioned $R_7$, $R_8$ and $R_9$ are each independently selected from H and optionally substituted Me,

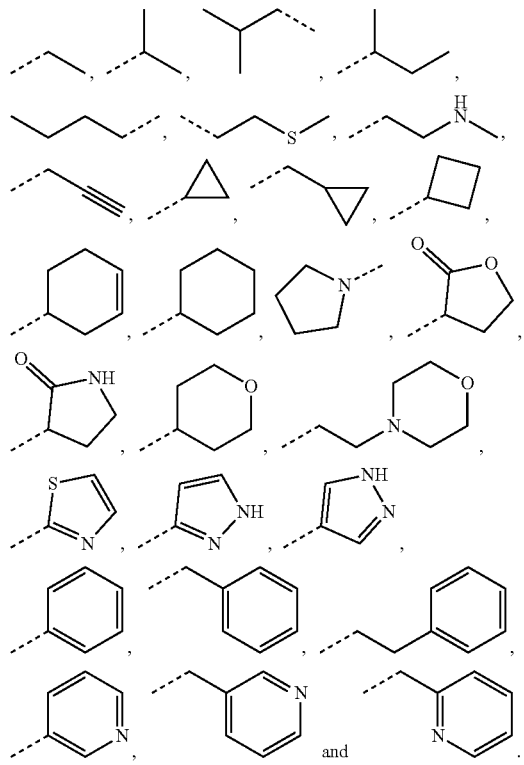

Most preferably, the above-mentioned $R_7$, $R_8$ and $R_9$ are each independently selected from H, Me,

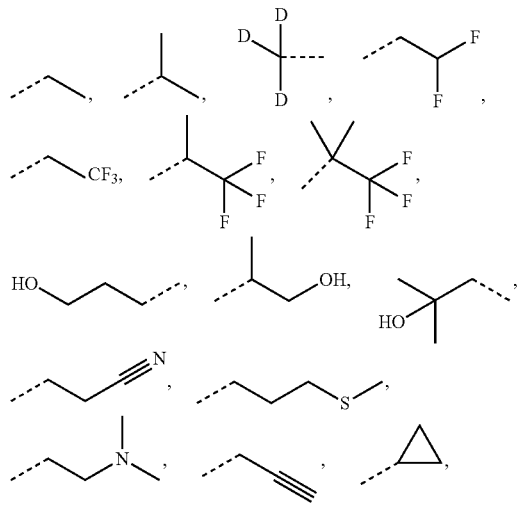

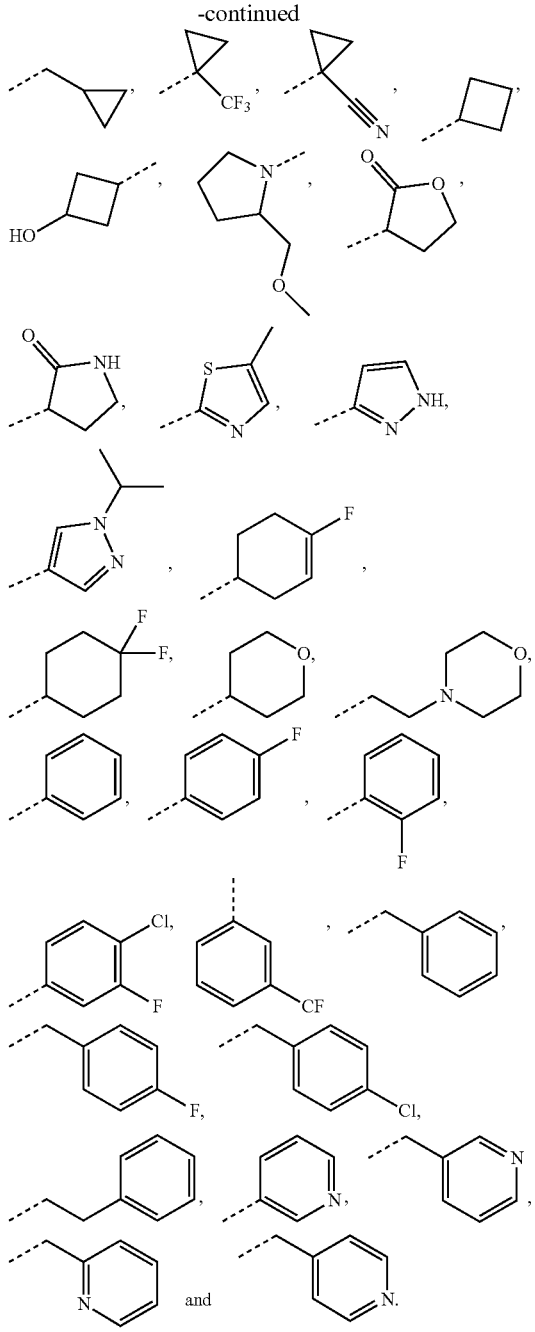

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

is selected from optionally substituted

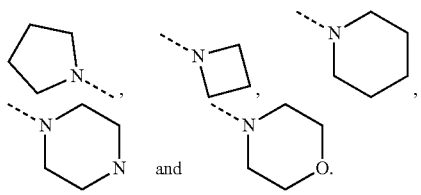

In some embodiments of the present invention, the above-mentioned structural unit

is selected from

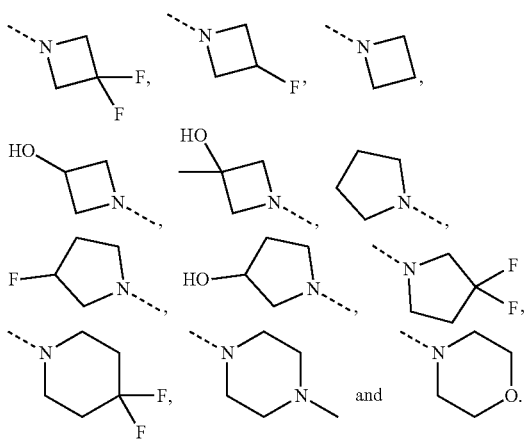

Preferably, the above-mentioned $R_7$ and $R_8$ together form an optionally substituted 4-7 membered ring, and preferably the above-mentioned $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

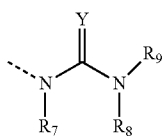

is selected from optionally substituted

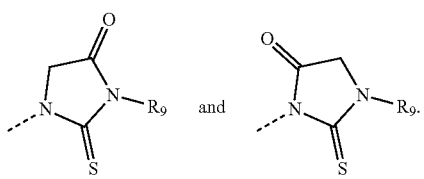

In some embodiments of the present invention, the above-mentioned structural unit

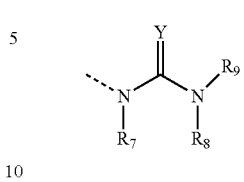

is selected from

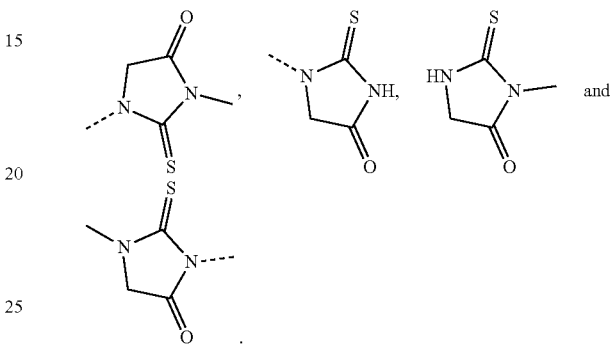

Alternatively, $R_8$ may form a 4-7 membered ring with two adjacent carbon atoms on ring A),
—C(=O)N($R_{11d1}$)($R_{11d2}$), —$C_{1-3}$ alkyl-C(=O)N($R_{11d1}$)($R_{11d2}$), —NH—C(=O)N($R_{11d1}$)($R_{11d2}$), —$C_{1-3}$ alkyl-NH—C(=O)N($R_{11d1}$)($R_{11d2}$), $C_{1-7}$ alkyl N($R_{11d1}$)—S(=O)—N($R_{11d2}$)—, 3-6 membered cycloalkyl-N($R_{11d1}$)—P(=O)(O$R_{11d2}$)—$C_{1-3}$ alkyl-, (wherein, $R_{11d1}$ and $R_{11d2}$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 5-6 membered aryl-$C_{1-3}$ alkyl-; or optionally, $R_{11d1}$ and $R_{11d2}$ together form a 4-7 membered ring;

preferably, the above-mentioned $R_{11d1}$ and $R_{11d2}$ are each independently selected from H, OH, NH2, CN, halogen and optionally substituted $C_{1-3}$ alkyl, $C_{1-3}$ heteroalkyl and $C_{3-5}$ cycloalkyl.

Preferably, the above-mentioned $R_{11d1}$ and $R_{11d2}$ are each independently selected from H, Me,

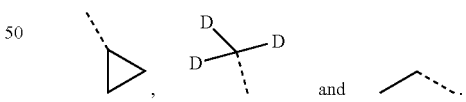

Preferably, the above-mentioned $R_{11d1}$ and $R_{11d2}$ together form an optionally substituted 4-5 membered ring.

In some embodiments of the present invention, the above-mentioned structural unit —N($R_{11d1}$)($R_{11d2}$) is selected from optionally substituted

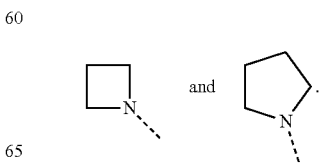

In some embodiments of the present invention, the above-mentioned structural unit —N(R$_{11d1}$)(R$_{11d2}$) is selected from

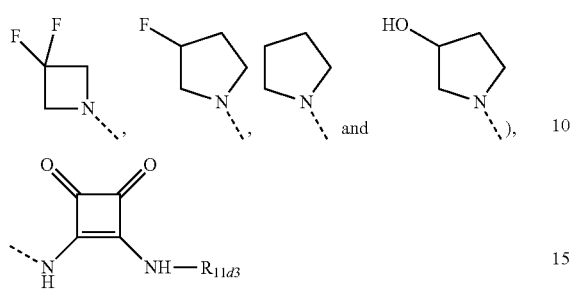

(wherein, R$_{11d3}$ is selected from optionally substituted H, C$_{1-7}$ alkyl, C$_{1-7}$ heteroalkyl, 3-6 membered cycloalkyl, 3-6 membered heterocycloalkyl, 5-6 membered aryl, 5-6 membered heteroaryl, 5-6 membered heterocycloalkyl-C$_{1-3}$ alkyl-, 5-6 membered aryl-C$_{1-3}$ alkyl-, 5-6 membered heteroaryl-C$_{1-3}$ alkyl-), 3-6 membered heterocycloalkylamino-, 5-6 membered arylamino-, 5-6 membered aryl-C$_{1-3}$ alkylamino-;

preferably, the above-mentioned R$_{11}$ is selected from H, CN and optionally substituted

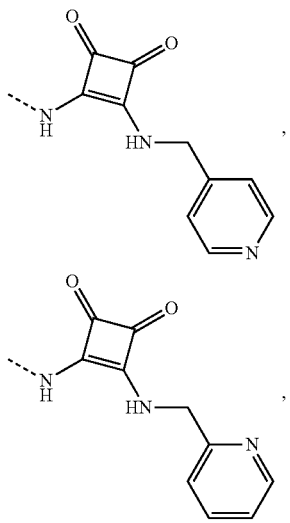

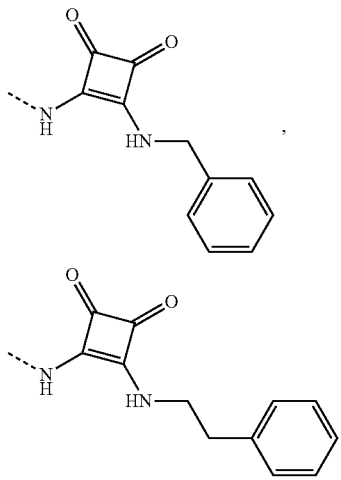

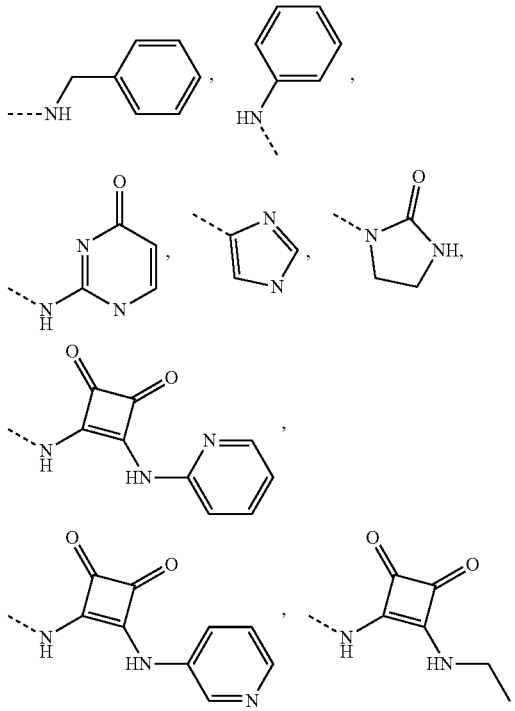

-continued

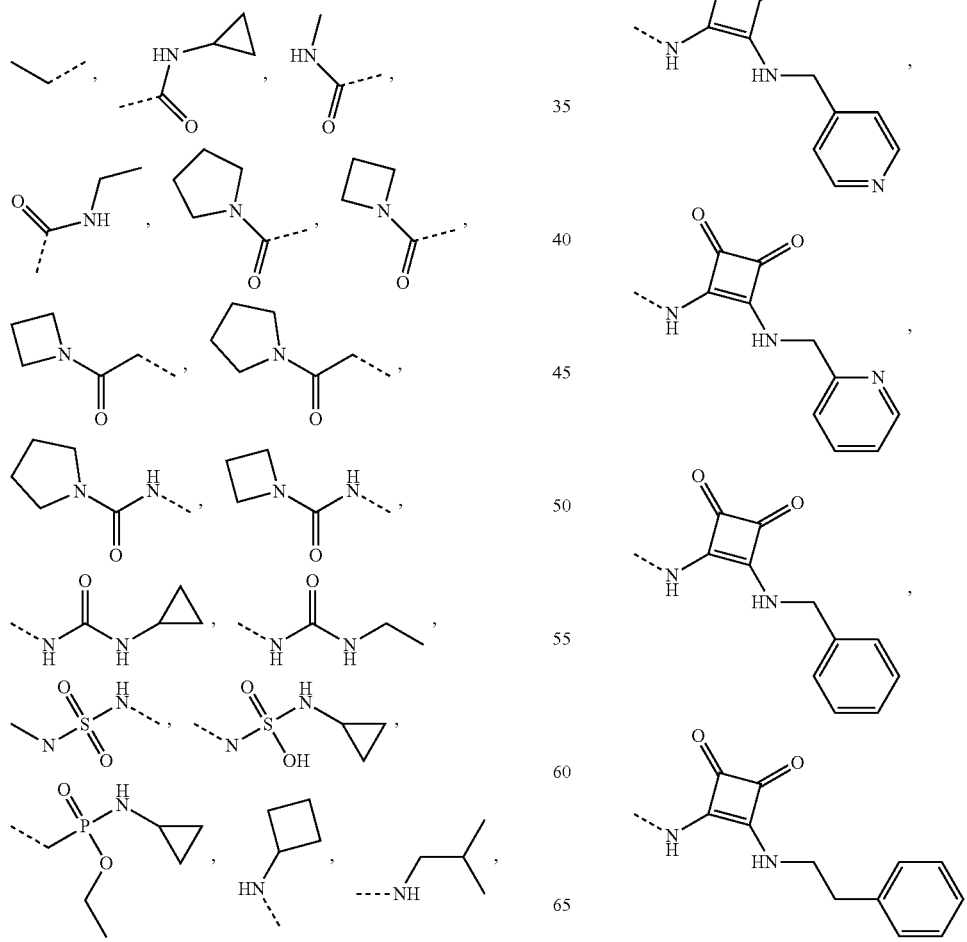

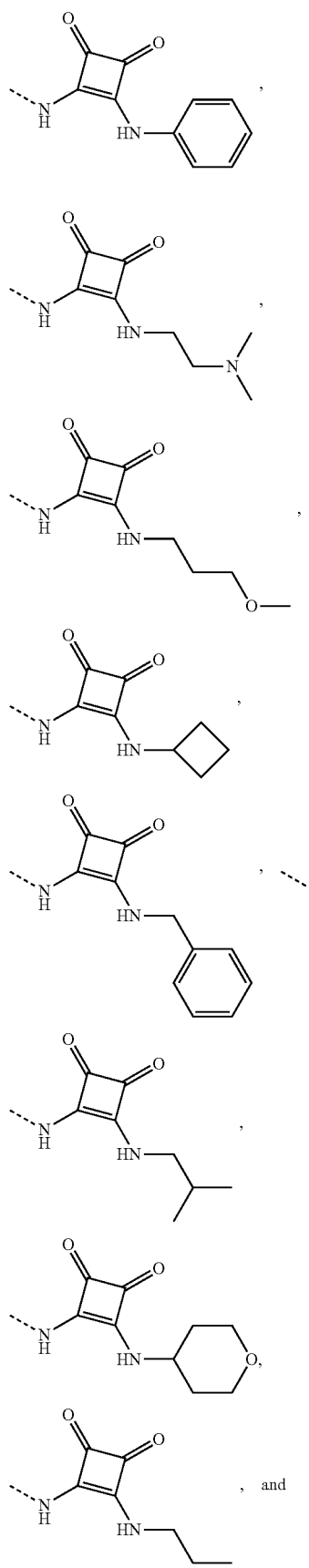
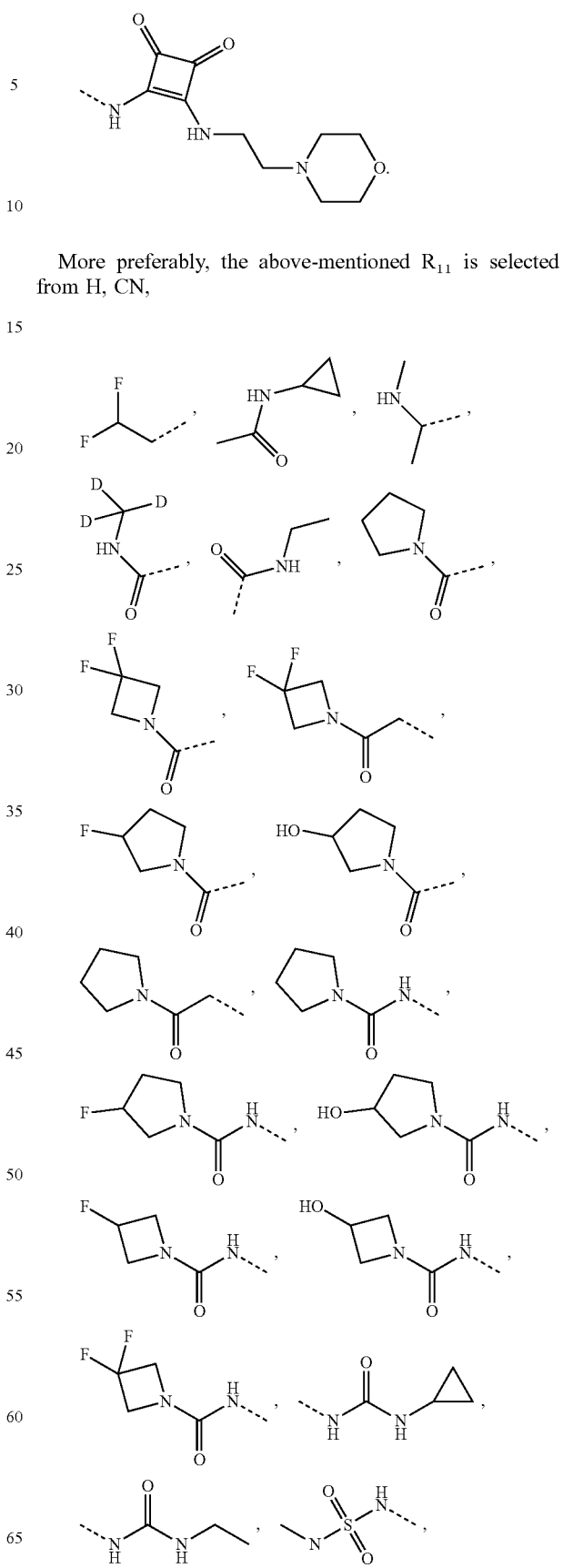
More preferably, the above-mentioned $R_{11}$ is selected from H, CN, -continued
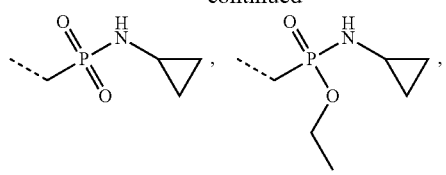
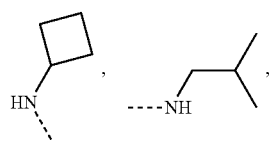
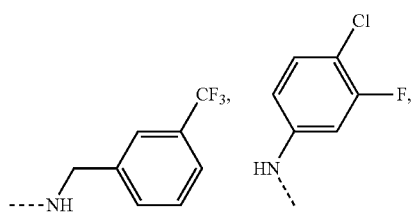
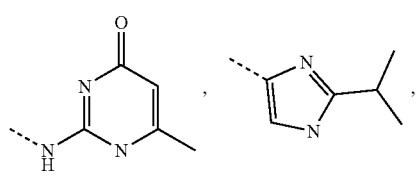
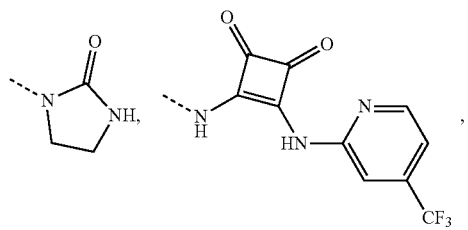
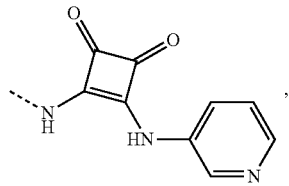
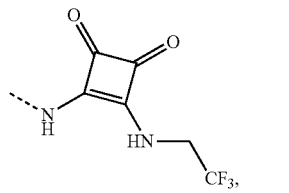
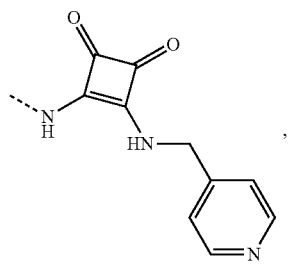
-continued
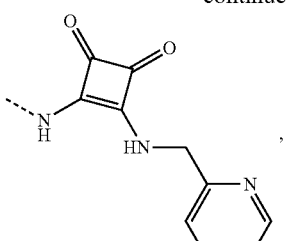
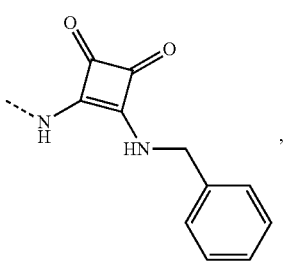
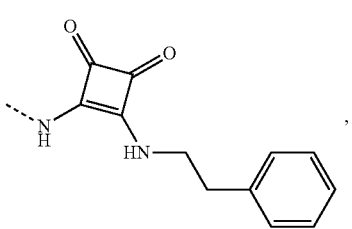
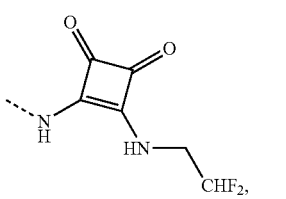
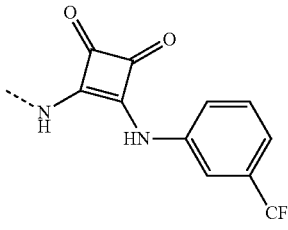
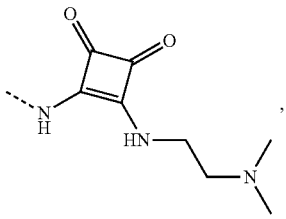
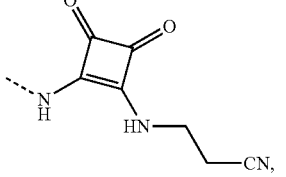

-continued

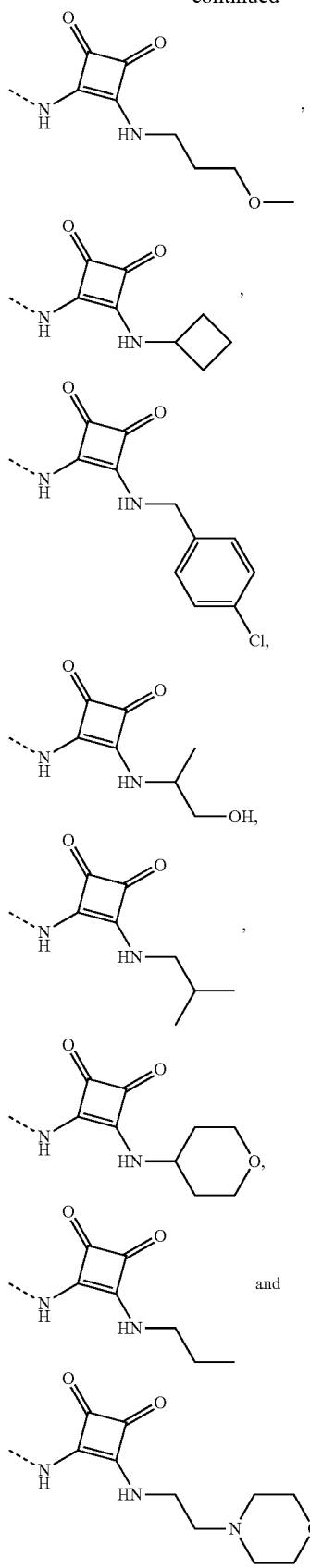

Preferably formula (II) is represented by formula (IV):

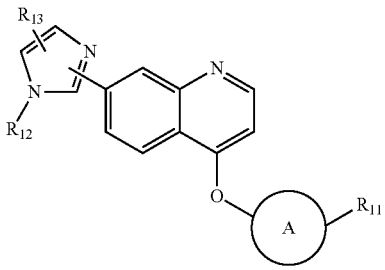

(IV)

wherein, in the formula (IV), A is a monocyclic or polycyclic ring selected from optionally substituted 3-6 membered cycloalkyl, 3-6 membered cycloalkyl-$C_{1-3}$ alkyl, 6-10 membered aromatic ring or 6-10 membered heteroaromatic ring;

preferably, A is a monocyclic or bicyclic ring selected from optionally substituted phenyl, benzofuranyl, benzopyrazolyl, indolyl, benzothiazolyl, cyclobutyl, -cyclobutyl-methylene- and

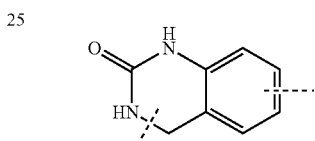

More preferably, A is a monocyclic or bicyclic ring selected from optionally substituted

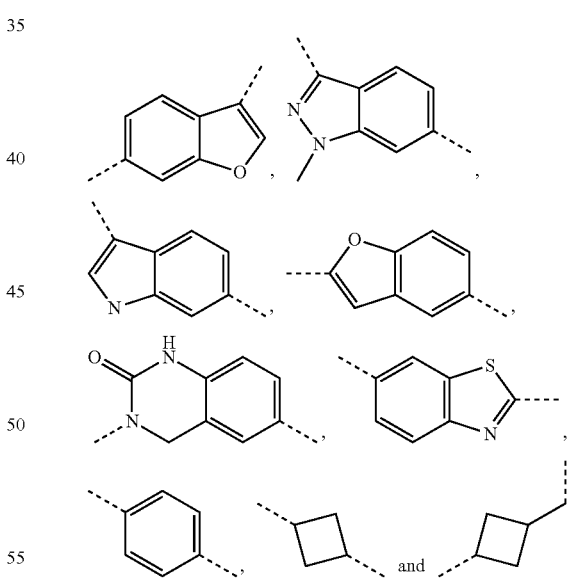

Further preferably, A is selected from

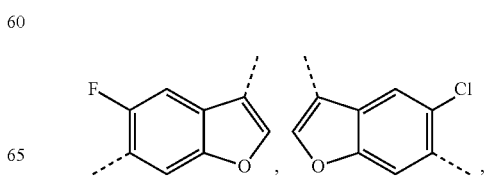

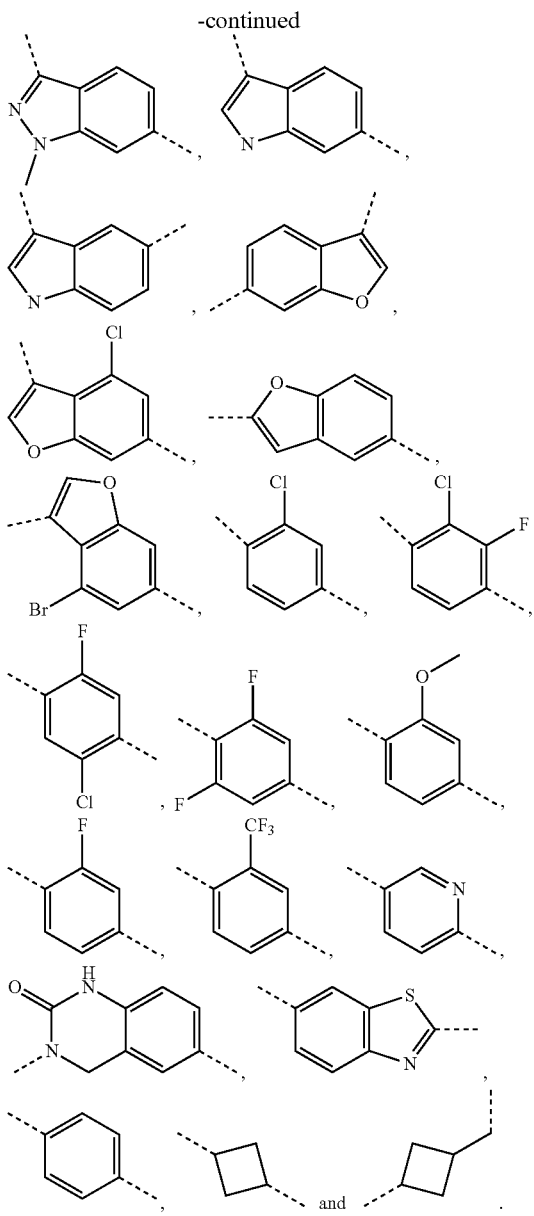

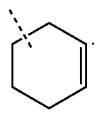

Preferably, the above-mentioned $R_7$, $R_8$ and $R_9$ are each independently selected from H and optionally substituted $C_{1-5}$ alkyl, $C_{1-5}$ heteroalkyl, 3-6 membered cycloalkyl, 4-6 membered heterocycloalkyl, 6 membered aryl, 5-6 membered heteroaryl, 3-6 membered cycloalkyl-$C_{1-2}$ alkyl-, 3-6 membered heterocycloalkyl-$C_{1-2}$ alkyl-, 6 membered aryl-$C_{1-2}$ alkyl-, 5-6 membered heteroaryl-$C_{1-2}$ alkyl-, $C_{3-6}$ alkynyl and

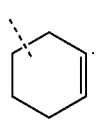

More preferably, the above-mentioned $R_7$, $R_8$ and $R_9$ are each independently selected from H and optionally substituted $C_{1-4}$ alkyl, $C_{1-2}$ alkyl-S—$C_{1-3}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

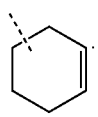

Further preferably, the above-mentioned $R_7$, $R_8$ and $R_9$ are each independently selected from H and optionally substituted Me,

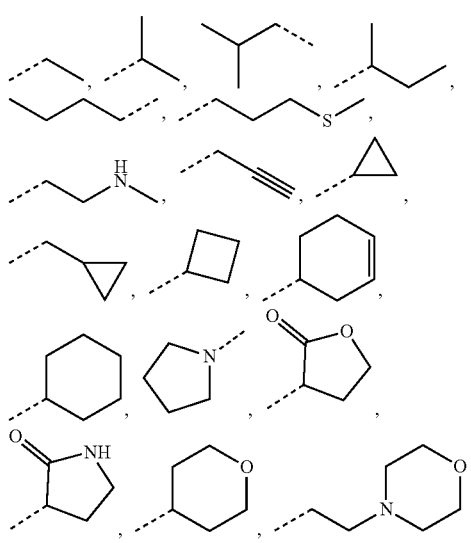

$R_{11}$ is selected from H, OH, $NH_2$, CN, halogen and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl and

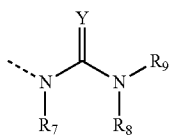

wherein, Y is O or S, $R_7$, $R_8$ and $R_9$ are each independently selected from H, and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

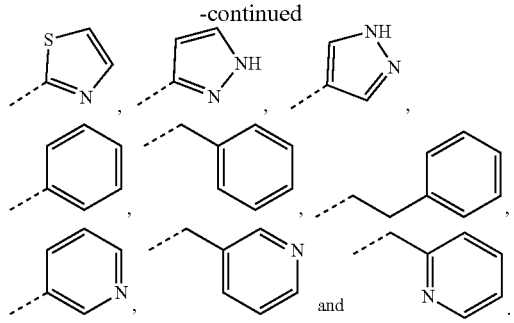

Most preferably, the above-mentioned $R_7$, $R_8$ and $R_9$ are each independently selected from H, Me,

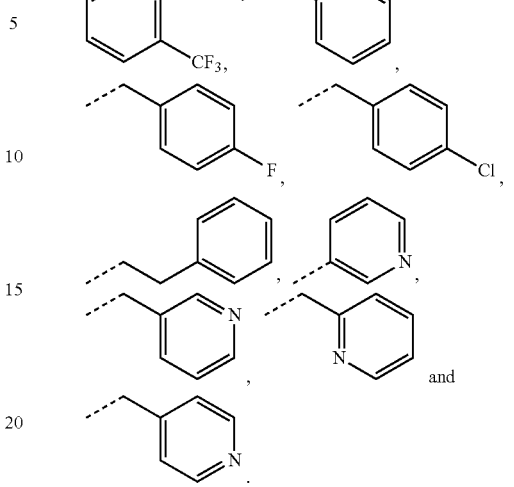

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

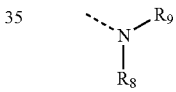

is selected from optionally substituted

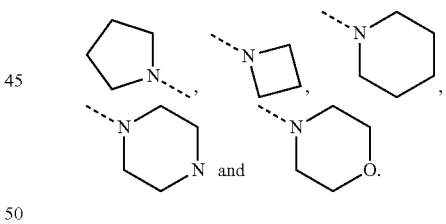

In some embodiments of the present invention, the above-mentioned structural unit

is selected from

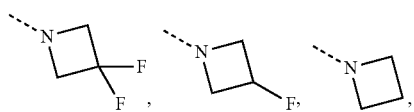

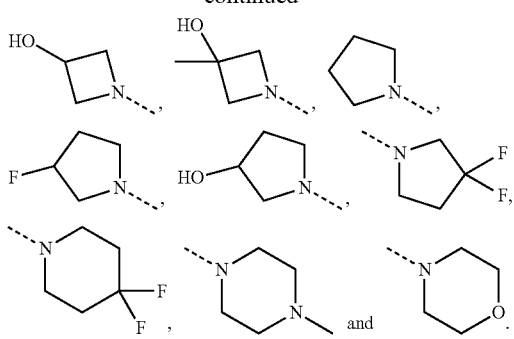

Preferably, the above-mentioned $R_7$ and $R_8$ together form an optionally substituted 4-7 membered ring, and preferably $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

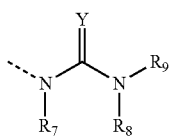

is selected from optionally substituted

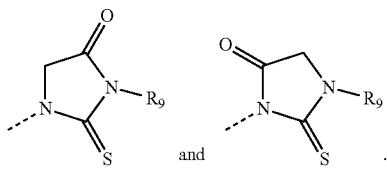

In some embodiments of the present invention, the above-mentioned structural unit

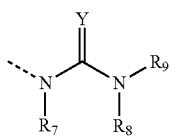

is selected from

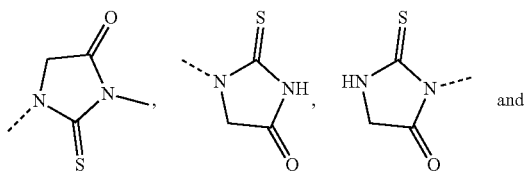

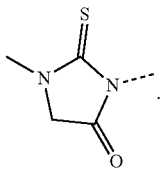

Alternatively, $R_8$ may form a 4-7 membered ring with two adjacent carbon atoms on ring A), —C(=O)N($R_{11d1}$)($R_{11d2}$), —$C_{1-3}$ alkyl-C(=O)N($R_{11d1}$)($R_{11d2}$), —NH—C(=O)N($R_{11d1}$)($R_{11d2}$), —$C_{1-3}$ alkyl-NH—C(=O)N($R_{11d1}$)($R_{11d2}$), $C_{1-7}$ alkyl-N($R_{11d1}$)—S(=O)—N($R_{11d2}$)—, 3-6 membered cycloalkyl-N($R_{11d1}$)—P(=O)(O$R_{11d2}$)—$C_{1-3}$ alkyl- (wherein, $R_{11d1}$ and $R_{11d2}$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 5-6 membered aryl-$C_{1-3}$ alkyl-; or optionally, $R_{11d1}$ and $R_{11d2}$ together form a 4-7 membered ring;

Preferably, the above-mentioned $R_{11d1}$ and $R_{11d2}$ are each independently selected from H, OH, $NH_2$, CN, halogen and optionally substituted $C_{1-3}$ alkyl, $C_{1-3}$ heteroalkyl and $C_{3-5}$ cycloalkyl.

Preferably, the above-mentioned $R_{11d1}$ and $R_{11d2}$ are each independently selected from H, Me,

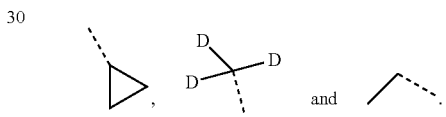

Preferably, the above-mentioned $R_{11d1}$ and $R_{11d2}$ together form an optionally substituted 4-5 membered ring.

In some embodiments of the present invention, the above-mentioned structural unit —N($R_{11d1}$)($R_{11d2}$) is selected from optionally substituted

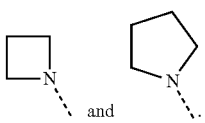

In some embodiments of the present invention, the above-mentioned structural unit —N($R_{11d1}$)($R_{11d2}$) is selected from

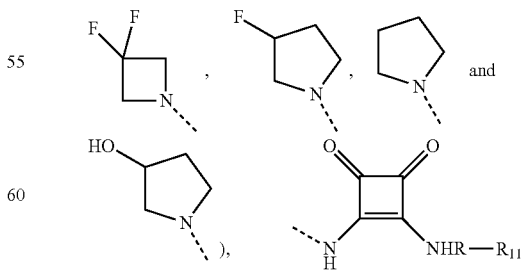

(wherein, $R_{11d3}$ is selected from optionally substituted H, $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 5-6 membered heterocycloalkyl-C$_{1-3}$ alkyl-, 5-6 membered aryl-C$_{1-3}$ alkyl- and 5-6 membered heteroaryl-C$_{1-3}$ alkyl-),
3-6 membered heterocycloalkylamino-, 5-6 membered arylamino-, 5-6 membered aryl-C$_{1-3}$ alkylamino-;
preferably, the above-mentioned R$_{11}$ is selected from H, CN and optionally substituted
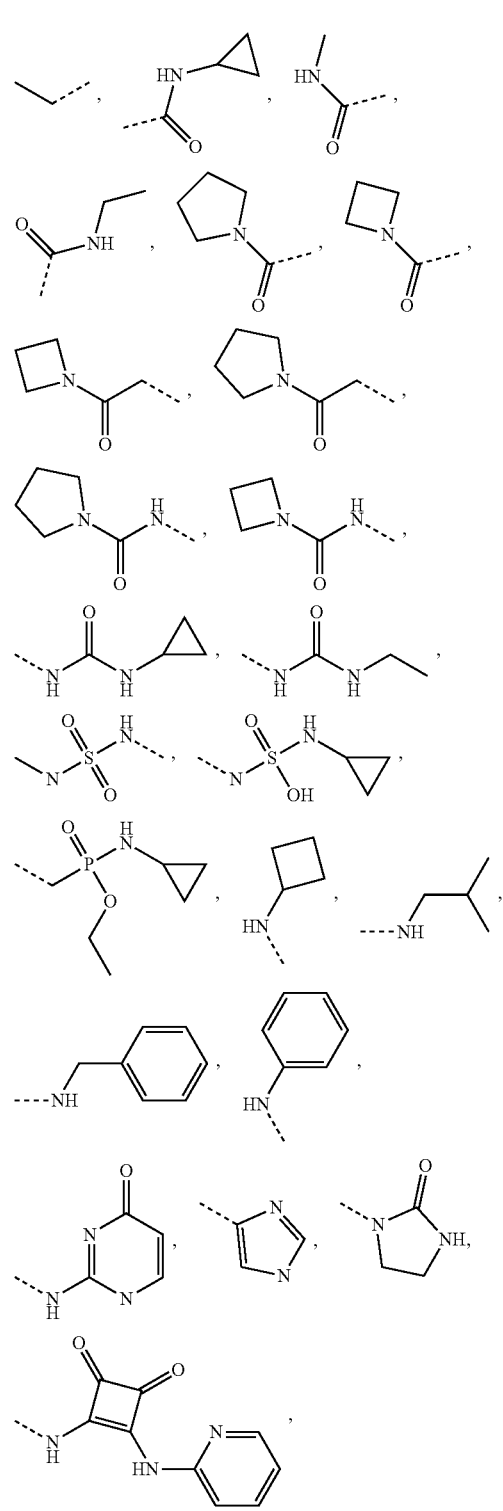
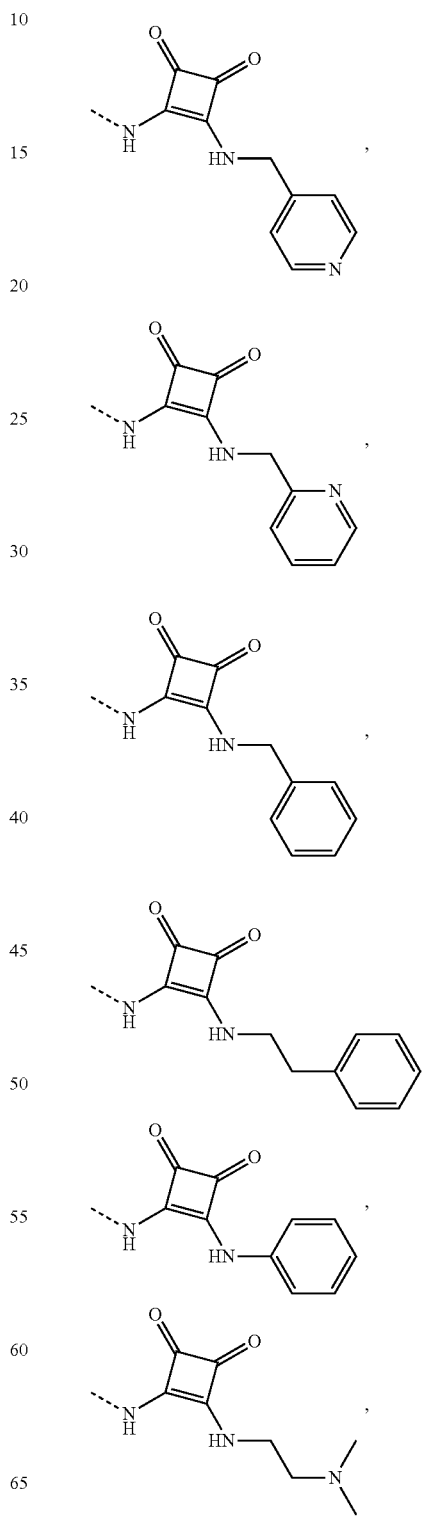

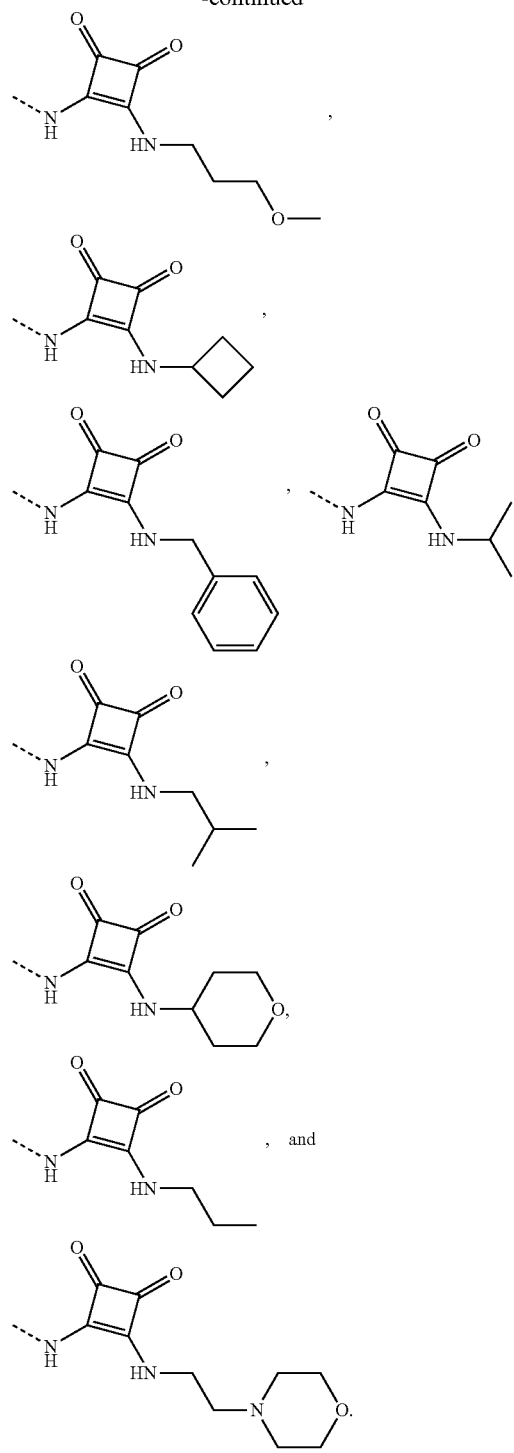
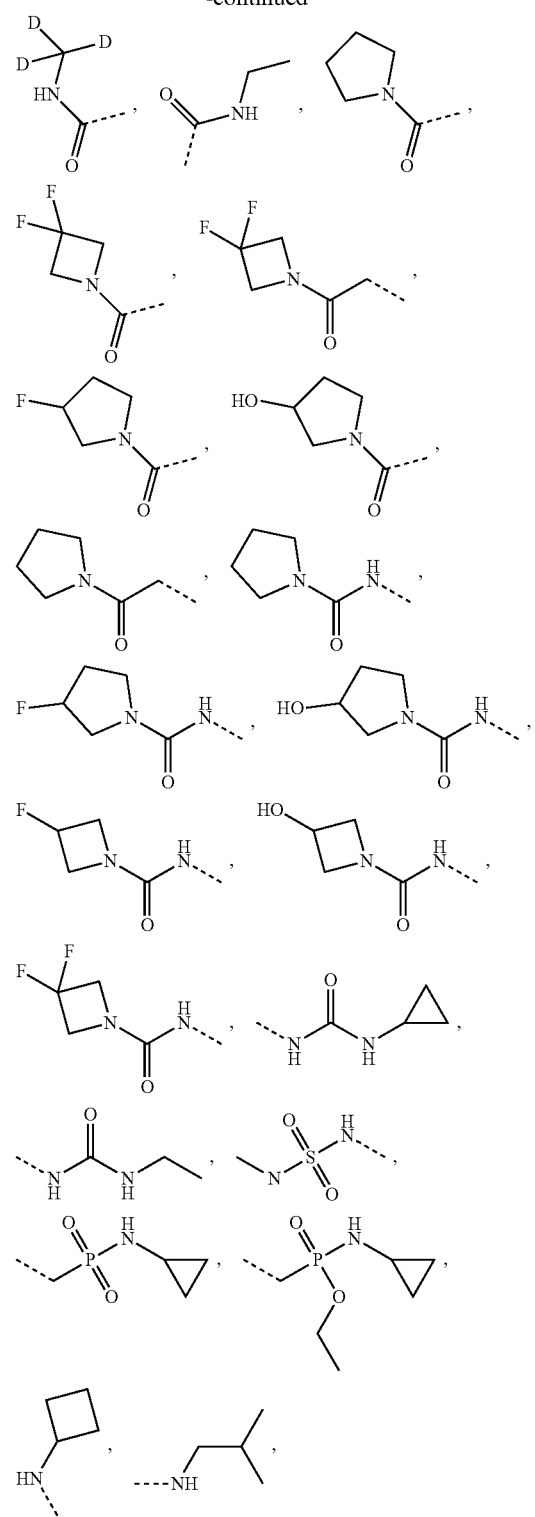
More preferably, the above-mentioned $R_{11}$ is selected from H, CN,
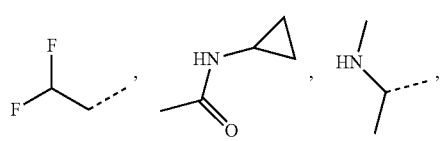
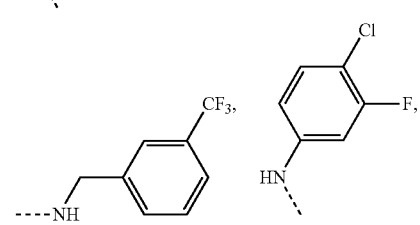

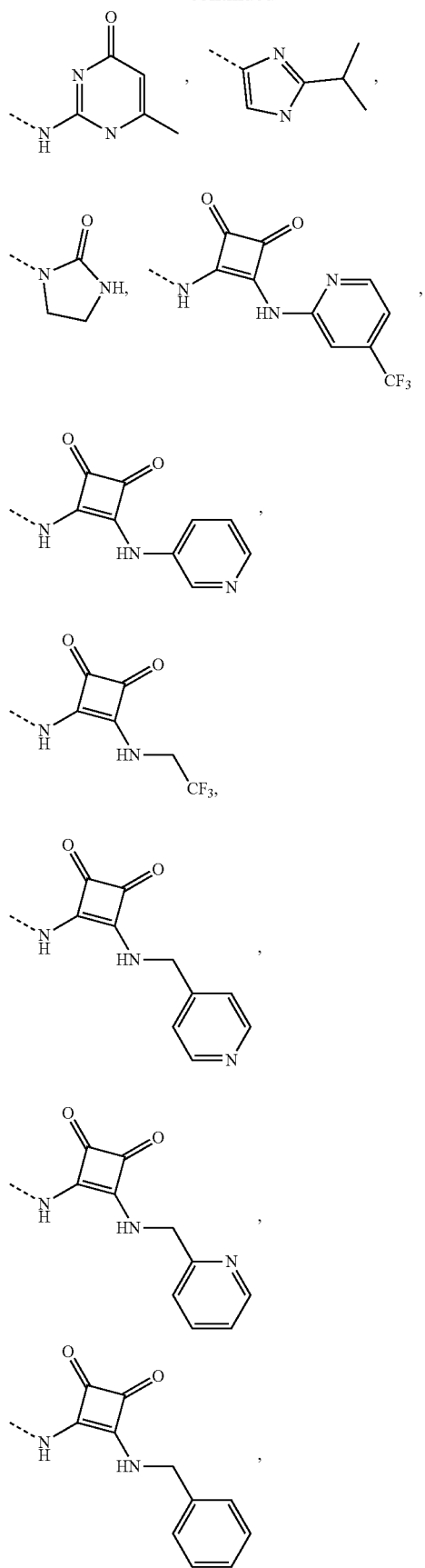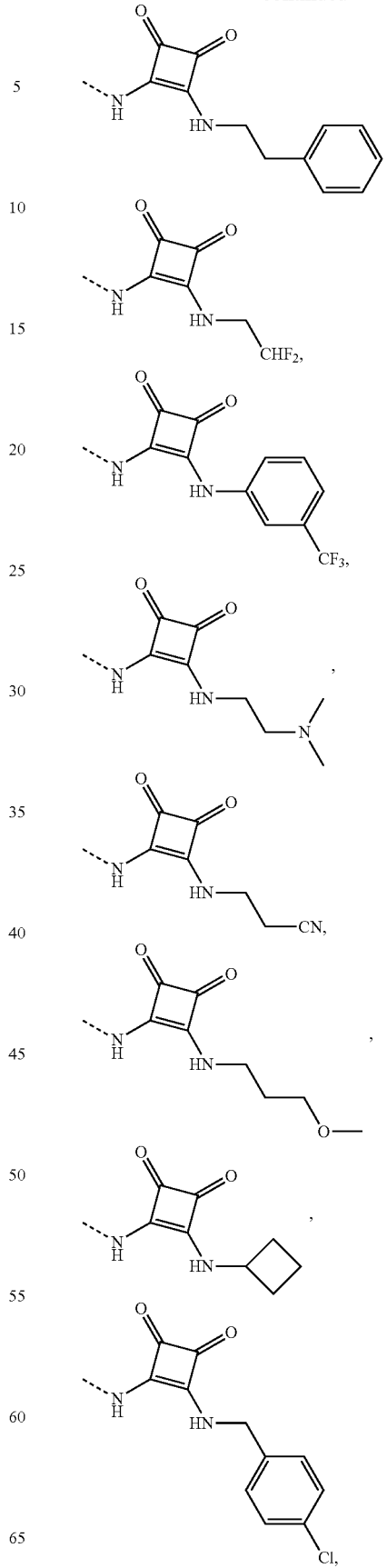

-continued

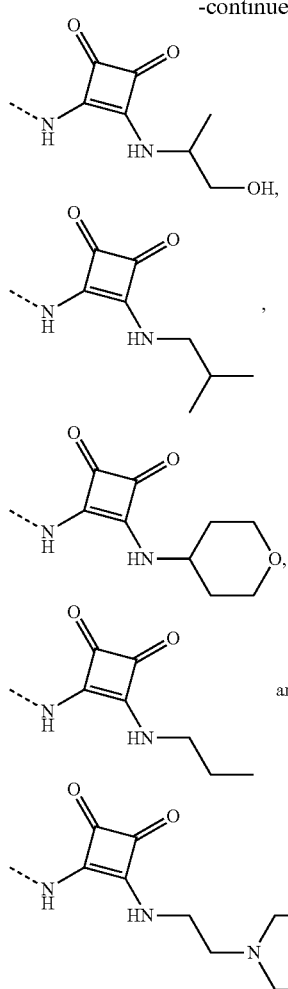

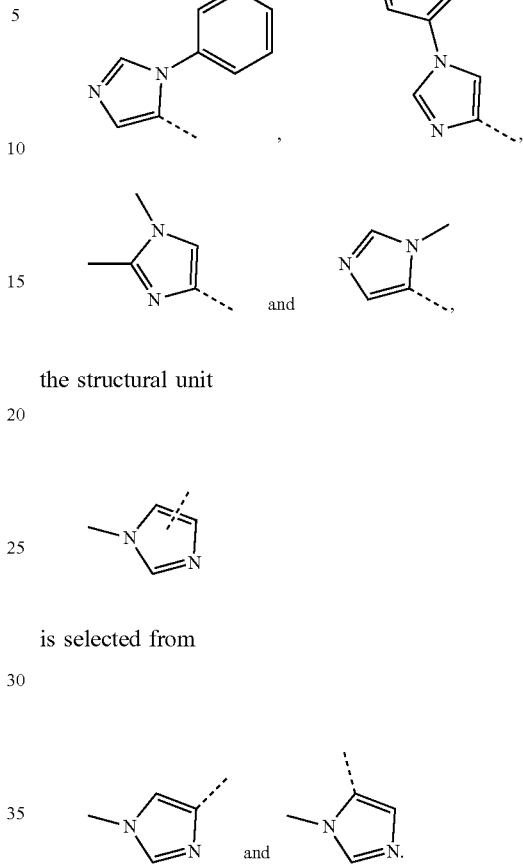

the structural unit is selected from $R_{12}$ and $R_{13}$ are each independently selected from H, OH, NH$_2$, CN and optionally substituted $C_{1-7}$ alkyl, $C_{1-7}$ heteroalkyl, 3-6 membered cycloalkyl, 3-6 membered heterocycloalkyl, 5-6 membered aryl and 5-6 membered heteroaryl;

preferably, the above-mentioned $R_{12}$ and $R_{13}$ are each independently selected from H, methyl, isopropyl and phenyl.

In some embodiments of the present invention, the above-mentioned

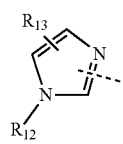

is selected from

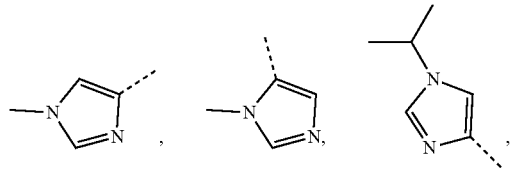

The above-mentioned formula (II) may be a compound represented by the following general formula:

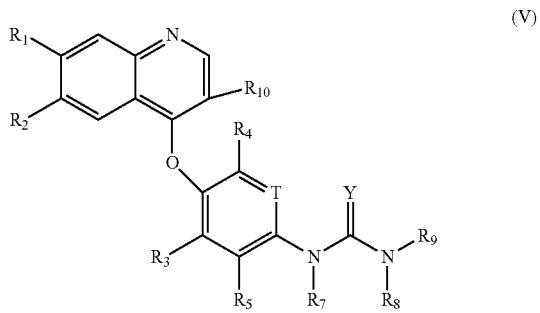

(V)

wherein, in the formula (V), Y is O or S;

T is selected from N and C(R$_6$);

R$_1$ is selected from optionally substituted $C_{1-7}$ heteroalkyl and 5-6 membered heteroaryl;

preferably, R$_1$ is selected from optionally substituted $C_{1-6}$ alkoxy, $C_{1-6}$ heteroalkyl-O— and imidazolyl;

more preferably, R$_1$ is selected from $C_{1-6}$ alkoxy, O(CH$_2$)$_n$R$_{1d1}$ and

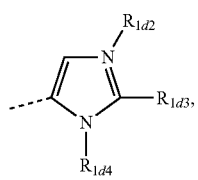

wherein n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl (including chain alkyl and cycloalkyl), $R_{1d2}$, $R_{1d3}$ and $R_{1d4}$ are each independently H, $C_{1-6}$ alkyl (including chain alkyl and cycloalkyl) or aryl (e.g. phenyl);

further preferably, $R_1$ is selected from $C_{1-3}$ alkoxy such as methoxy; $O(CH_2)_nR_{1d1}$, where n is an integer of 1 to 3, $R_{1d1}$ is $C_{1-3}$ alkoxy or $NR_{1d5}R_{1d6}$, wherein $R_{1d5}$ and $R_{1d6}$ are independently $C_{1-3}$ alkyl; and imidazolyl;

most preferably, $R_1$ is

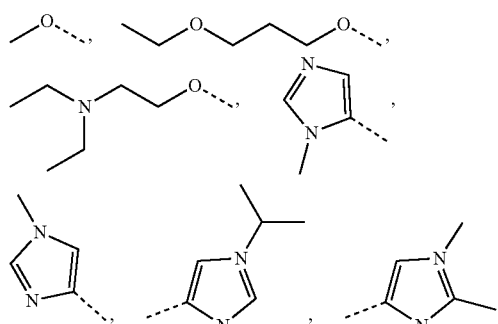

and

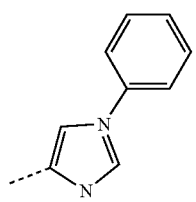

$R_2$ is selected from H, OH, $NH_2$, halogen, CN, —C(=O)N($R_{2d1}$)($R_{2d2}$), —N($R_{2d1}$)C(=O)$R_{2d2}$, —C(=O)O$R_{2d3}$ and optionally substituted $C_{1-7}$ alkyl (including chain alkyl and cycloalkyl);

preferably, $R_2$ is selected from H, CN, halo $C_{1-3}$ alkyl, hydroxy $C_{1-3}$ hydroxy, —C(=O)N($R_{2d1}$)($R_{2d2}$), —N($R_{2d1}$)C(=O)$R_{2d2}$ and —C(=O)O$R_{2d3}$;

more preferably, $R_2$ is selected from H, CN, $CF_3$,

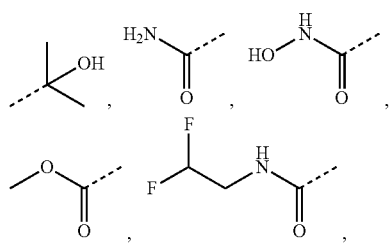

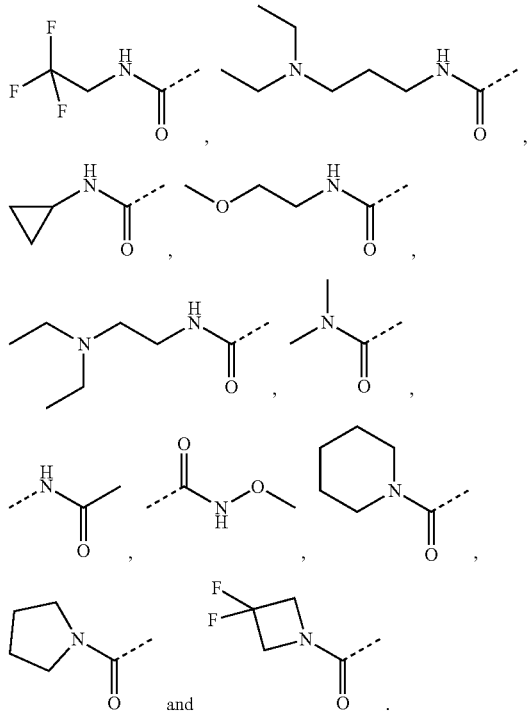

wherein, $R_{2d1}$, $R_{2d2}$ and $R_{2d3}$ are each independently selected from H, OH, $NH_2$, CN and optionally substituted $C_{1-7}$ chain alkyl, $C_{1-7}$ heteroalkyl, 3-6 membered cycloalkyl, 3-6 membered heterocycloalkyl, or $R_{2d1}$ and $R_{2d2}$ together form a 4-7 membered ring;

preferably, $R_{2d1}$ and $R_{2d2}$ are each independently selected from H, OH, halogen and optionally substituted $C_{1-7}$ alkyl, $C_{1-7}$ heteroalkyl and $C_{3-5}$ cycloalkyl; or, $R_{2d1}$ and $R_{2d2}$ together form a 4-7 membered ring; preferably, $R_{2d1}$ and $R_{2d2}$ are each independently selected from H, OH, haloalkyl, $C_{1-6}$ alkyl, $C_{3-6}$ cycloalkyl, $C_{1-6}$ alkoxy and N,N-di($C_{1-6}$ alkyl)-$C_{1-6}$ alkyl, $R_{2d3}$ is $C_{1-6}$ alkyl; or, $R_{2d1}$ and $R_{2d2}$ together form a 4-7 membered ring;

more preferably, $R_{2d1}$ and $R_{2d2}$ are each independently selected from H, OH, haloalkyl, $C_{1-3}$ alkyl, $C_{3-6}$ cycloalkyl, $C_{1-3}$ alkoxy and N,N-di($C_{1-3}$ alkyl)-$C_{1-3}$ alkyl, $R_{2d3}$ is $C_{1-3}$ alkyl; or, $R_{2d1}$ and $R_{2d2}$ together form a 4-6 membered ring;

further preferably, $R_{2d1}$, $R_{2d2}$, $R_{2d3}$ are each independently selected from H, OH, methyl,

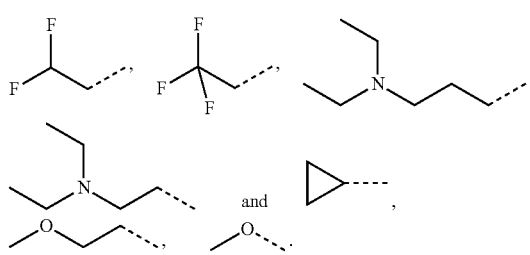

In some embodiments of the present invention, the structural unit —N($R_{2d1}R_{2d2}$) is selected from optionally substituted

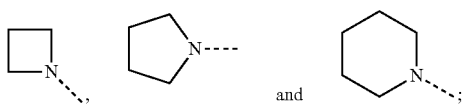 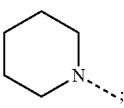 and ;

more specifically, the structural unit —N($R_{2d1}R_{2d2}$) is selected from

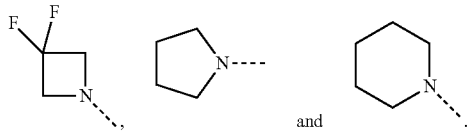 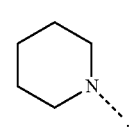 and .

Alternatively, in the above-mentioned formula (II), $R_1$ and $R_2$ together with two carbon atoms on the benzene ring form a 4-7 membered ring;

preferably, $R_1$ and $R_2$ together with two carbon atoms on the benzene ring form an optionally substituted 5 to 6 membered ring.

In some embodiments of the present invention, the above-mentioned structural unit

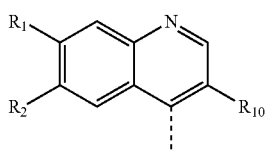

is selected from optionally substituted

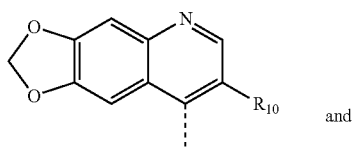 and

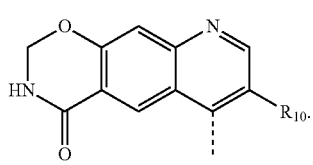.

In some embodiments of the present invention, the above-mentioned structural unit

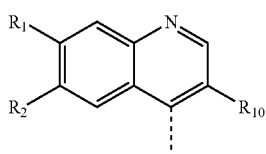

is selected from

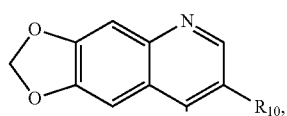

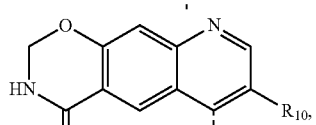

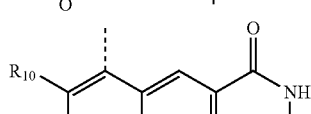 and

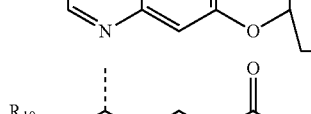.

$R_3$, $R_4$, $R_5$, $R_6$ are each independently selected from H, OH, $NH_2$, CN, halogen and optionally substituted $C_{1-7}$ alkyl and $C_{1-7}$ heteroalkyl;

preferably, the above-mentioned $R_3$, $R_4$, $R_5$, $R_6$ are each independently selected from H, OH, CN, $NH_2$, halogen and optionally substituted $C_{1-3}$ alkyl and $C_{1-3}$ alkoxy;

more preferably, the above-mentioned $R_3$, $R_4$, $R_5$, $R_6$ are each independently selected from H, F, Cl, Br, I, OH, CN, $NH_2$,

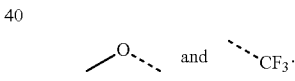

$R_7$, $R_8$, $R_9$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

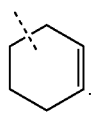.

Preferably, the above-mentioned $R_7$, $R_8$ and $R_9$ are each independently selected from H and optionally substituted $C_{1-5}$ alkyl, $C_{1-5}$ heteroalkyl, 3-6 membered cycloalkyl, 4-6 membered heterocycloalkyl, 6 membered aryl, 5-6 membered heteroaryl, 3-6 membered cycloalkyl-$C_{1-2}$ alkyl-, 3-6 membered heterocycloalkyl-$C_{1-2}$ alkyl-, 6 membered aryl-$C_1$ alkyl-, 5-6 membered heteroaryl-$C_{1-2}$ alkyl-, $C_{3-6}$ alkynyl and

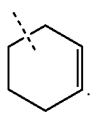

More preferably, the above-mentioned $R_7$, $R_8$ and $R_9$ are each independently selected from H and optionally substituted $C_{1-4}$ alkyl, $C_{1-2}$ alkyl-S—$C_{1-3}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

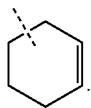

Further preferably, the above-mentioned $R_7$, $R_8$ and $R_9$ are each independently selected from H and optionally substituted Me,

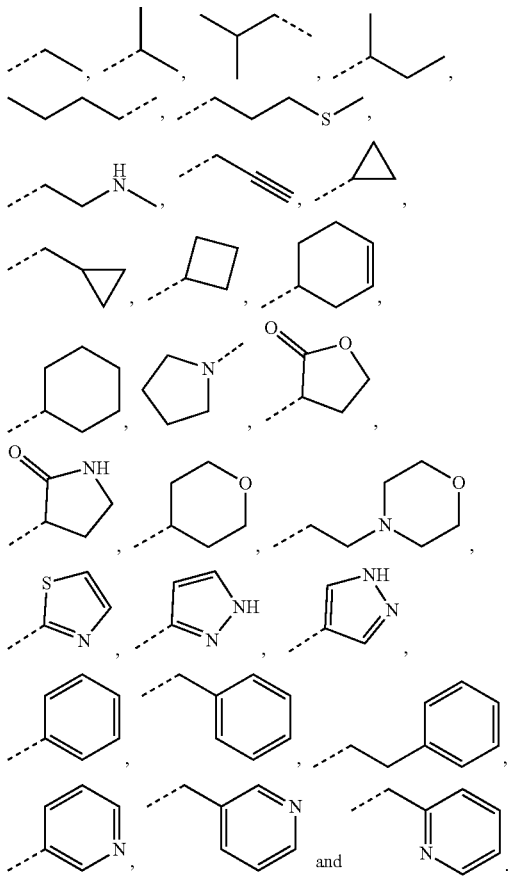

Most preferably, the above-mentioned $R_7$, $R_8$ and $R_9$ are each independently selected from H, Me,

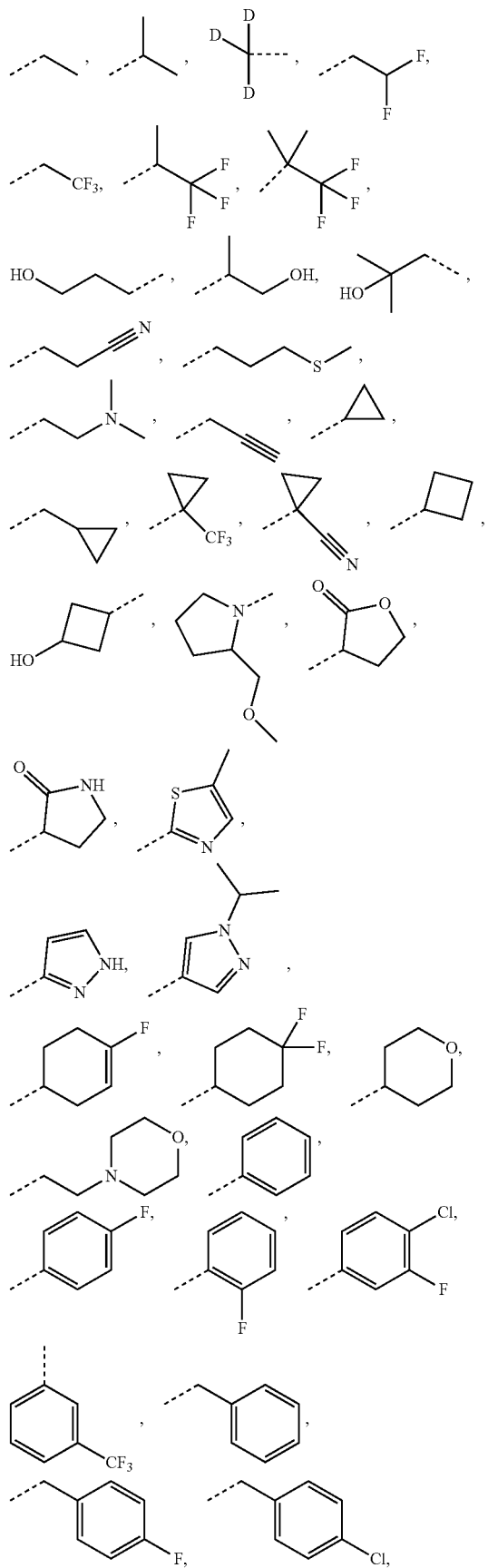

-continued

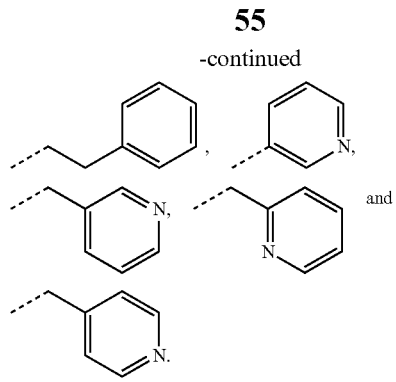

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

is selected from optionally substituted

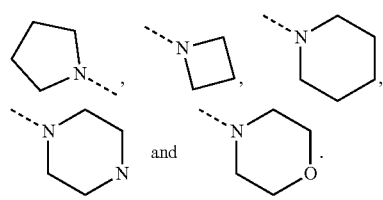

In some embodiments of the present invention, the above-mentioned structural unit

is selected from

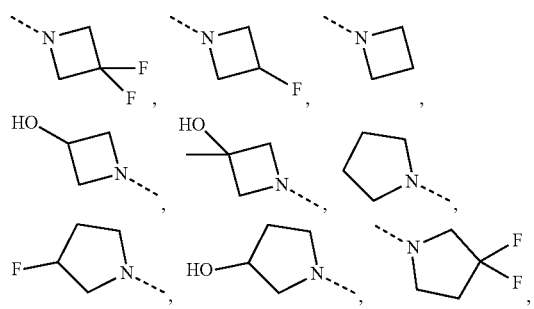

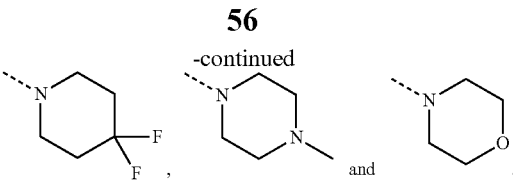

Preferably, the above-mentioned $R_7$ and $R_8$ together form an optionally substituted 4-7 membered ring, and preferably $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

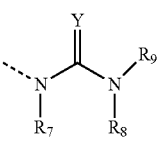

is selected from the optionally substituted

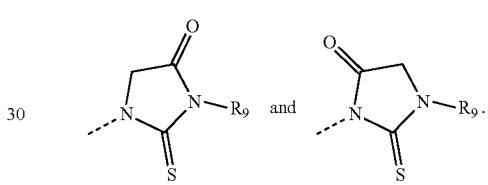

In some embodiments of the present invention, the above-mentioned structural unit

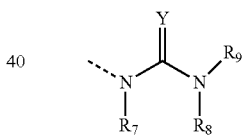

is selected from

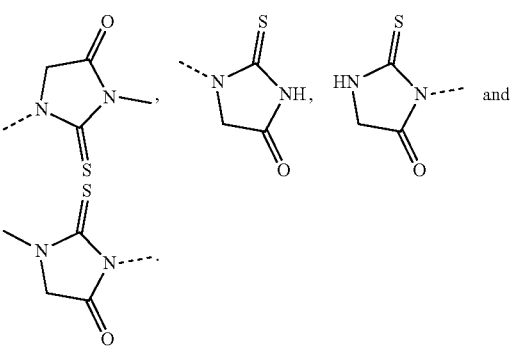

and

Alternatively, $R_5$ and $R_7$ together form a 4-7 membered ring; preferably, $R_5$ and $R_7$ together form an optionally substituted 5-6 membered ring.

In some embodiments of the present invention, the above-mentioned structural unit

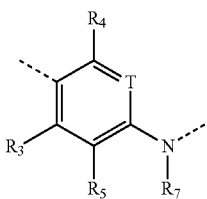

is selected from

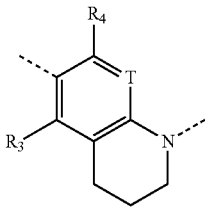 and 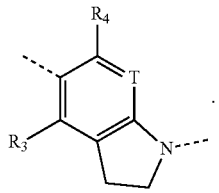

In some embodiments of the present invention, the above-mentioned structural unit

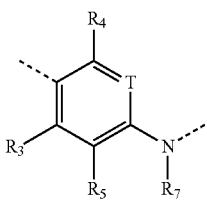

is selected from

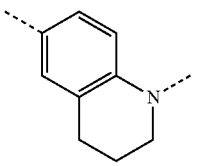 and 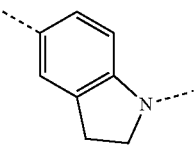

$R_{10}$ is selected from H, OH, $NH_2$, CN and halogen; preferably H or halogen.

Preferably, formula (II) has a general structure represented by the following formula (VI):

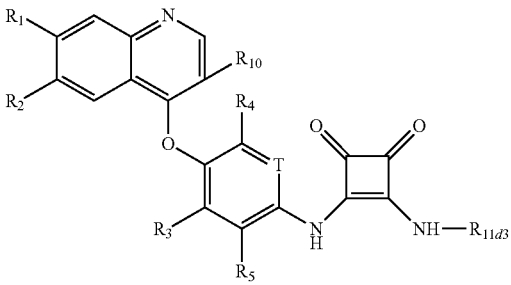

(VI)

wherein, the above-mentioned formula (VI), T is selected from N and $C(R_6)$;

$R_1$ is selected from optionally substituted $C_{1-7}$ heteroalkyl and 5-6 membered heteroaryl;

preferably, $R_1$ is selected from optionally substituted $C_{1-6}$ alkoxy, $C_{1-6}$ heteroalkyl-O— and imidazolyl;

more preferably, $R_1$ is selected from $C_{1-6}$ alkoxy, $O(CH_2)_n R_{1d1}$ and

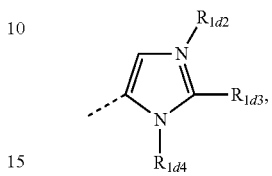

wherein, n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl (including chain alkyl and cycloalkyl), $R_{1d2}$, $R_{1d3}$ and $R_{1d4}$ are each independently H, $C_{1-6}$ alkyl (including chain alkyl and cycloalkyl) or aryl (e.g. phenyl);

further preferably, $R_1$ is selected from $C_{1-3}$ alkoxy such as methoxy; $O(CH_2)_n R_{1d1}$, where n is an integer of 1 to 3, $R_{1d1}$ is $C_{1-3}$ alkoxy or $NR_{1d5}R_{1d6}$, wherein $R_{1d5}$ and $R_{1d6}$ are independently $C_{1-3}$ alkyl; and imidazolyl;

most preferably, $R_1$ is

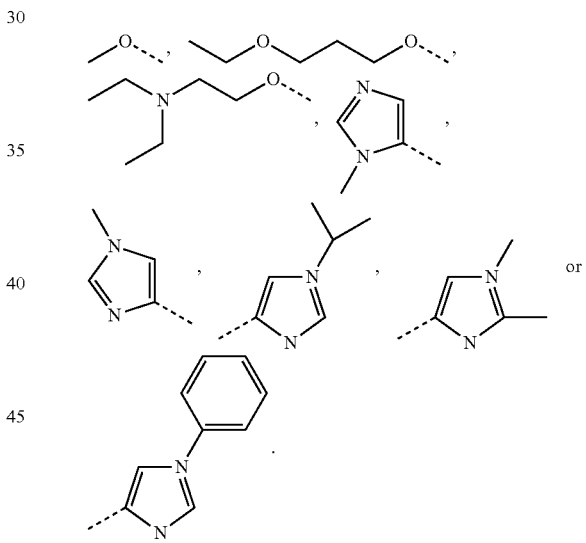

$R_2$ is selected from H, OH, $NH_2$, halogen, CN, —C(=O)N($R_{2d1}$)($R_{2d2}$), —N($R_{2d1}$)C(=O)$R_{2d2}$, —C(=O)O$R_{2d3}$ and optionally substituted $C_{1-7}$ alkyl (including chain alkyl and cycloalkyl);

preferably, $R_2$ is selected from H, CN, halo $C_{1-3}$ alkyl, hydroxy $C_{1-3}$ hydroxy, —C(=O)N($R_{2d1}$)($R_{2d2}$), —N($R_{2d1}$)C(=O)$R_{2d2}$ and —C(=O)O$R_{2d3}$;

more preferably, $R_2$ is selected from H, CN, $CF_3$,

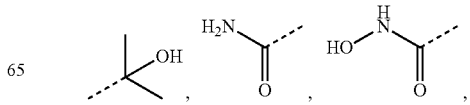

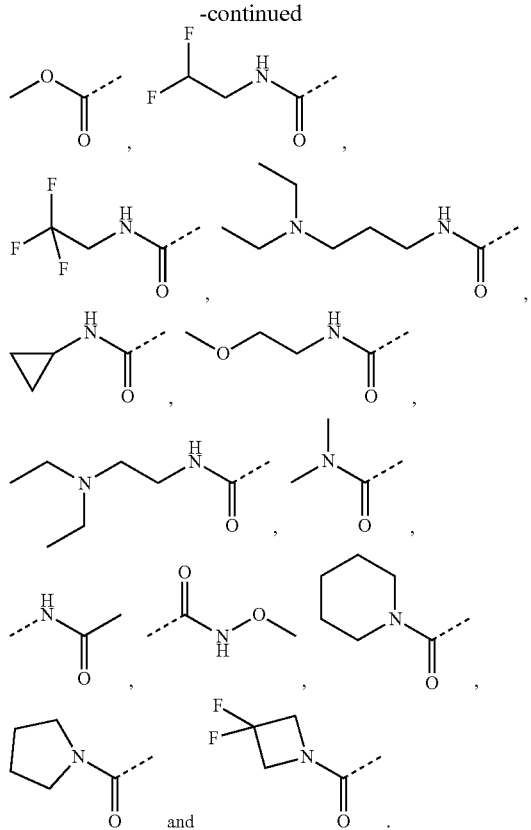

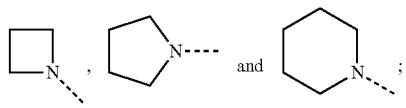

more specifically, the structural unit —N($R_{2d1}R_{2d2}$) is selected from

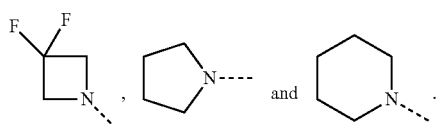

Alternatively, in the above-mentioned formula (II), $R_1$ and $R_2$ together with two carbon atoms on the benzene ring form a 4-7 membered ring; preferably, $R_1$ and $R_2$ together with two carbon atoms on the benzene ring form an optionally substituted 5 to 6 membered ring.

In some embodiments of the present invention, the above-mentioned structural unit

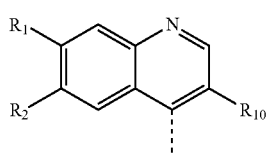

is selected from optionally substituted

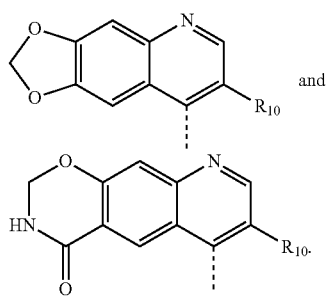

In some embodiments of the present invention, the above-mentioned structural unit

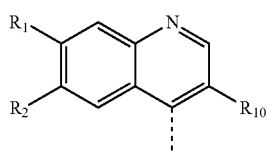

is selected from

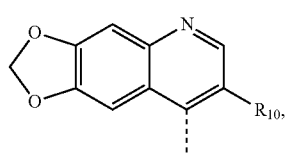

wherein, $R_{2d1}$, $R_{2d2}$ and $R_{2d3}$ are each independently selected from H, OH, $NH_2$, CN and optionally substituted $C_{1-7}$ chain alkyl, $C_{1-7}$ heteroalkyl, 3-6 membered cycloalkyl, 3-6 membered heterocycloalkyl, or $R_{2d1}$ and $R_{2d2}$ together form a 4-7 membered ring;

preferably, $R_{2d1}$ and $R_{2d2}$ are each independently selected from H, OH, halogen and optionally substituted $C_{1-7}$ alkyl, $C_{1-7}$ heteroalkyl and $C_{3-5}$ cycloalkyl; or, $R_{2d1}$ and $R_{2d2}$ together form a 4-7 membered ring;

preferably, $R_{2d1}$ and $R_{2d2}$ are each independently selected from H, OH, haloalkyl, $C_{1-6}$ alkyl, $C_{3-6}$ cycloalkyl, $C_{1-6}$ alkoxy and N,N-di($C_{1-6}$ alkyl)-$C_{1-6}$ alkyl, $R_{2d3}$ is $C_{1-6}$ alkyl; or, $R_{2d1}$ and $R_{2d2}$ together form a 4-7 membered ring;

more preferably, $R_{2d1}$ and $R_{2d2}$ are each independently selected from H, OH, haloalkyl, $C_{1-3}$ alkyl, $C_{3-6}$ cycloalkyl, $C_{1-3}$ alkoxy and N,N-di($C_{1-3}$ alkyl)-$C_{1-3}$ alkyl, $R_{2d3}$ is $C_{1-3}$ alkyl; or, $R_{2d1}$ and $R_{2d2}$ together form a 4-6 membered ring;

further preferably, $R_{2d1}$, $R_{2d2}$, $R_{2d3}$ are each independently selected from H, OH, methyl,

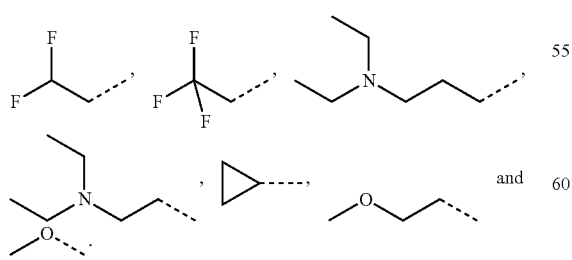

In some embodiments of the present invention, the structural unit —N($R_{2d1}R_{2d2}$) is selected from optionally substituted

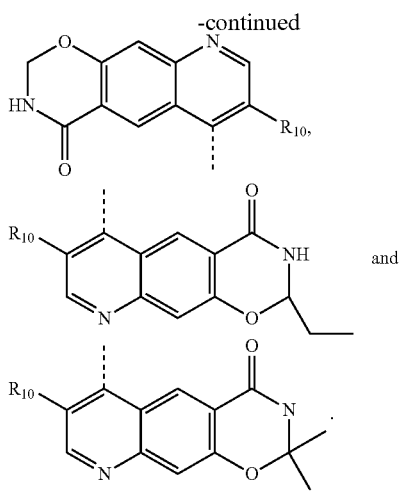

$R_3$, $R_4$, $R_5$, $R_6$ are each independently selected from H, OH, $NH_2$, CN, halogen and optionally substituted $C_{1-7}$ alkyl and $C_{1-7}$ heteroalkyl;

preferably, the above-mentioned $R_3$, $R_4$, $R_5$, $R_6$ are each independently selected from H, OH, CN, $NH_2$, halogen and optionally substituted $C_{1-3}$ alkyl and $C_{1-3}$ alkoxy;

more preferably, the above-mentioned $R_3$, $R_4$, $R_5$, $R_6$ are each independently selected from H, F, Cl, Br, I, OH, CN, $NH_2$,

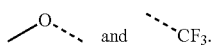

$R_{10}$ is selected from H, OH, $NH_2$, CN and halogen; preferably H or halogen.

$R_{11d3}$ is selected from optionally substituted H, $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 5-6 membered heterocycloalkyl-$C_{1-3}$ alkyl-, 5-6 membered aryl-$C_{1-3}$ alkyl- and 5-6 membered heteroaryl-$C_{1-3}$ alkyl-.

Preferably, the above-mentioned formula (II) has the general formula represented by formula (VII):

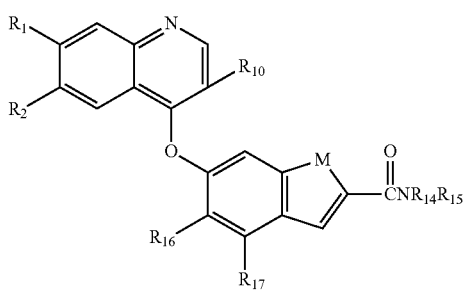

(VII)

wherein, the above-mentioned formula (VII), M is O or N, $R_1$ is selected from optionally substituted $C_{1-7}$ heteroalkyl and 5-6 membered heteroaryl;

preferably, $R_1$ is selected from optionally substituted $C_{1-6}$ alkoxy, $C_{1-6}$ heteroalkyl-O— and imidazolyl;

more preferably, $R_1$ is selected from $C_{1-6}$ alkoxy, $O(CH_2)_n R_{1d1}$ and

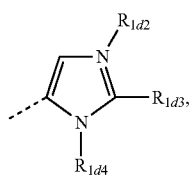

wherein, n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl (including chain alkyl and cycloalkyl), $R_{1d2}$, $R_{1d3}$ and $R_{1d4}$ are each independently H, $C_{1-6}$ alkyl (including chain alkyl and cycloalkyl) or aryl (e.g. phenyl);

further preferably, $R_1$ is selected from $C_{1-3}$ alkoxy such as methoxy; $O(CH_2)_n R_{1d1}$, where n is an integer of 1 to 3, $R_{1d1}$ is $C_{1-3}$ alkoxy or $NR_{1d5}R_{1d6}$, wherein $R_{1d5}$ and $R_{1d6}$ are independently $C_{1-3}$ alkyl; and imidazolyl;

most preferably, $R_1$ is

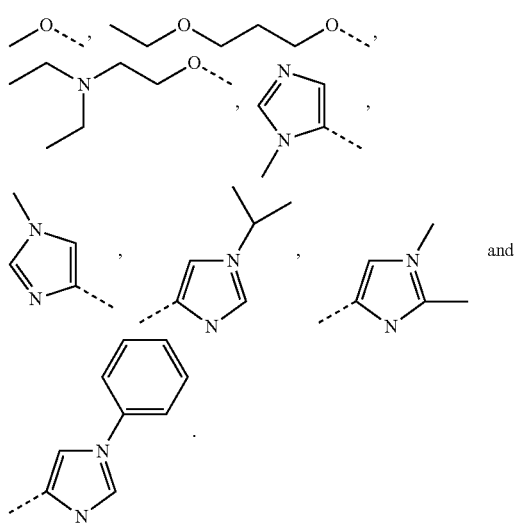

$R_2$ is selected from H, OH, $NH_2$, halogen, CN, —C(=O)N($R_{2d1}$)($R_{2d2}$), —N($R_{2d1}$)C(=O)$R_{2d2}$, —C(=O)O$R_{2d3}$, optionally substituted $C_{1-7}$ alkyl (including chain alkyl and cycloalkyl);

preferably, $R_2$ is selected from H, CN, halo $C_{1-3}$ alkyl, hydroxy $C_{1-3}$ hydroxy, —C(=O)N($R_{2d1}$)($R_{2d2}$), —N($R_{2d1}$)C(=O)$R_{2d2}$ and —C(=O)O$R_{2d3}$;

more preferably, $R_2$ is selected from H, CN, $CF_3$,

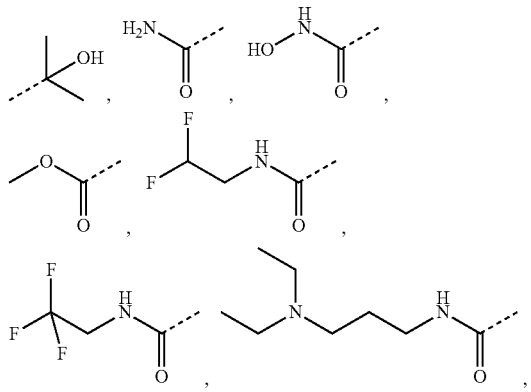

-continued

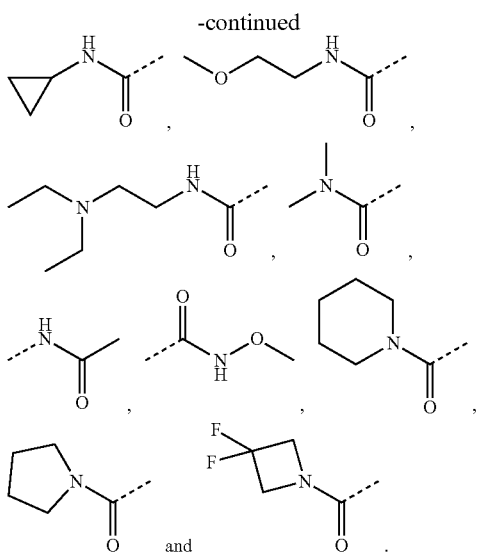

wherein, $R_{2d1}$, $R_{2d2}$ and $R_{2d3}$ are each independently selected from H, OH, $NH_2$, CN and optionally substituted $C_{1-7}$ chain alkyl, $C_{1-7}$ heteroalkyl, 3-6 membered cycloalkyl, 3-6 membered heterocycloalkyl, or $R_{2d1}$ and $R_{2d2}$ together form a 4-7 membered ring;

preferably, $R_{2d1}$ and $R_{2d2}$ are each independently selected from H, OH, halogen and optionally substituted $C_{1-7}$ alkyl, $C_{1-7}$ heteroalkyl and $C_{3-5}$ cycloalkyl; or, $R_{2d1}$ and $R_{2d2}$ together form a 4-7 membered ring;

preferably, $R_{2d1}$ and $R_{2d2}$ are each independently selected from H, OH, haloalkyl, $C_{1-6}$ alkyl, $C_{3-6}$ cycloalkyl, $C_{1-6}$ alkoxy and N,N-di($C_{1-6}$ alkyl)-$C_{1-6}$ alkyl, $R_{2d3}$ is $C_{1-6}$ alkyl; or, $R_{2d1}$ and $R_{2d2}$ together form a 4-7 membered ring;

more preferably, $R_{2d1}$ and $R_{2d2}$ are each independently selected from H, OH, haloalkyl, $C_{1-3}$ alkyl, $C_{3-6}$ cycloalkyl, $C_{1-3}$ alkoxy and N,N-di($C_{1-3}$ alkyl)-$C_{1-3}$ alkyl, $R_{2d3}$ is $C_{1-3}$ alkyl; or, $R_{2d1}$ and $R_{2d2}$ together form a 4-6 membered ring;

further preferably, $R_{2d1}$, $R_{2d2}$, $R_{2d3}$ are each independently selected from H, OH, methyl,

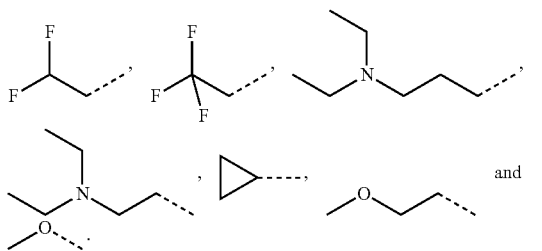

In some embodiments of the present invention, the structural unit —$N(R_{2d1}R_{2d2})$ is selected from optionally substituted

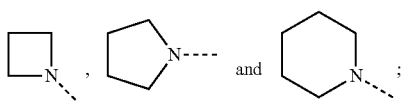

more specifically, the structural unit —$N(R_{2d1}R_{2d2})$ is selected from

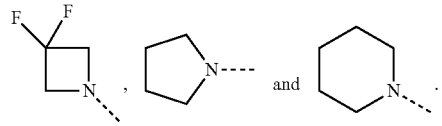

Alternatively, in the above-mentioned formula (II), $R_1$ and $R_2$ together with two carbon atoms on the benzene ring form a 4-7 membered ring; preferably, $R_1$ and $R_2$ together with two carbon atoms on the benzene ring form an optionally substituted 5 to 6 membered ring.

In some embodiments of the present invention, the above-mentioned structural unit

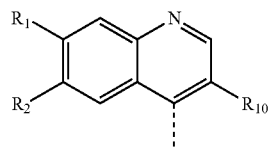

is selected from optionally substituted

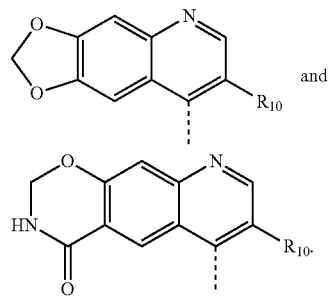

In some embodiments of the present invention, the above-mentioned structural unit

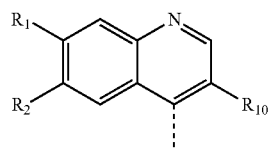

is selected from

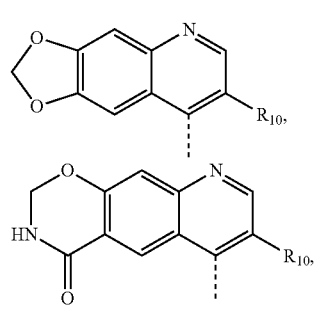

-continued

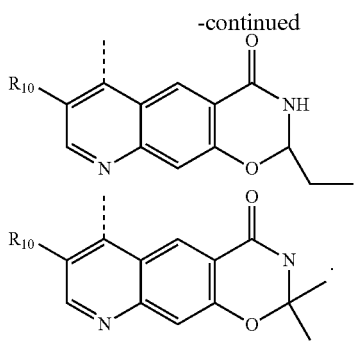
and $R_{10}$ is selected from H, OH, $NH_2$, CN and halogen; preferably H or halogen.

$R_{14}$ and $R_{15}$ are each independently H, $C_{1-6}$ alkyl, $C_{3-6}$ cycloalkyl or haloalkyl, or $R_{14}$ and $R_{15}$ may form a 4-7 membered ring, preferably a 3-6 membered ring, the ring may be replaced by a group such as halogen;

$R_{16}$ and $R_{17}$ are each independently H, $C_{1-6}$ alkyl, halogen.

preferably, the above-mentioned formula (II) has the general formula represented by formula (VIII):

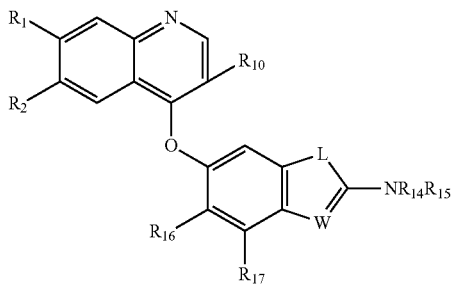

(VIII)

wherein, in the above-mentioned formula (VIII), L and W are each independently S or N, $R_1$ is selected from optionally substituted $C_{1-7}$ heteroalkyl and 5-6 membered heteroaryl;

preferably, $R_1$ is selected from optionally substituted $C_{1-6}$ alkoxy, $C_{1-6}$ heteroalkyl-O— and imidazolyl;

more preferably, $R_1$ is selected from $C_{1-6}$ alkoxy, $O(CH2)nR_{1d1}$ and

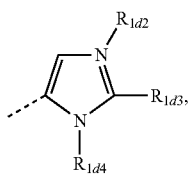

wherein, n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl (including chain alkyl and cycloalkyl), $R_{1d2}$, $R_{1d3}$ and $R_{1d4}$ are each independently H, $C_{1-6}$ alkyl (including chain alkyl and cycloalkyl) or aryl (e.g. phenyl);

further preferably, $R_1$ is selected from $C_{1-3}$ alkoxy such as methoxy; $O(CH_2)_nR_{1d1}$, where n is an integer of 1 to 3, $R_{1d1}$ is $C_{1-3}$ alkoxy or $NR_{1d5}R_{1d6}$, wherein $R_{1d5}$ and $R_{1d6}$ are independently $C_{1-3}$ alkyl; and imidazolyl;

most preferably, $R_1$ is

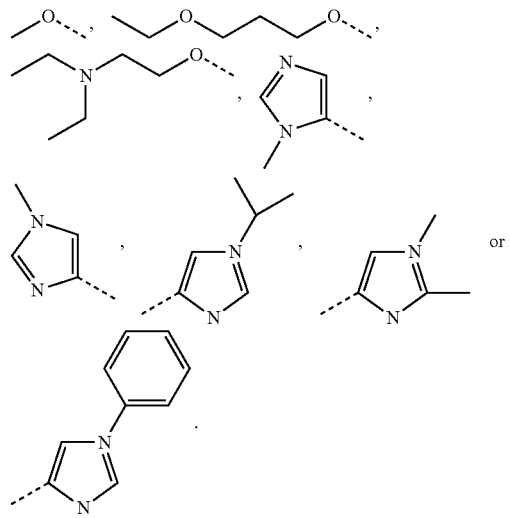

$R_2$ is selected from H, OH, $NH_2$, halogen, CN, —C(=O)N($R_{2d1}$)($R_{2d2}$), —N($R_{2d1}$)C(=O)$R_{2d2}$, —C(=O)O$R_{2d3}$, optionally substituted $C_{1-7}$ alkyl (including chain alkyl and cycloalkyl);

preferably, $R_2$ is selected from H, CN, halo $C_{1-3}$ alkyl, hydroxy $C_{1-3}$ hydroxy, —C(=O)N($R_{2d1}$)($R_{2d2}$), —N($R_{2d1}$)C(=O)$R_{2d2}$ and —C(=O)O$R_{2d3}$;

more preferably, $R_2$ is selected from H, CN, $CF_3$,

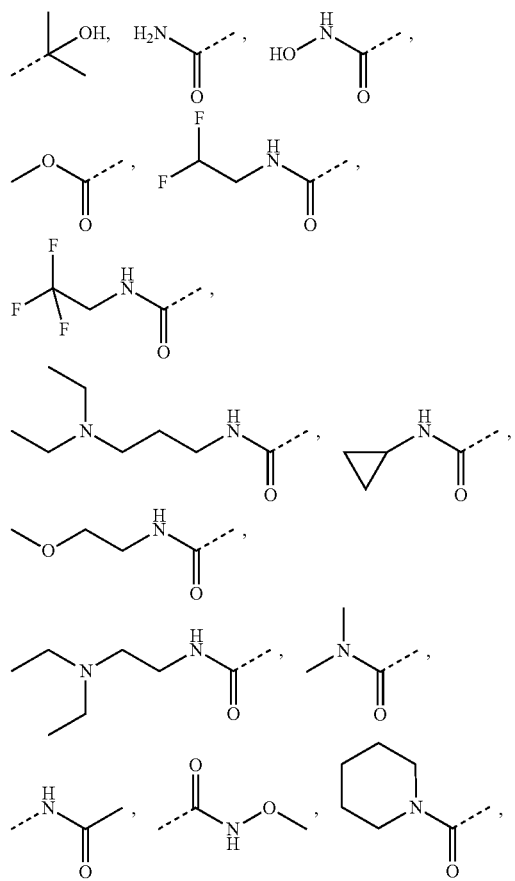

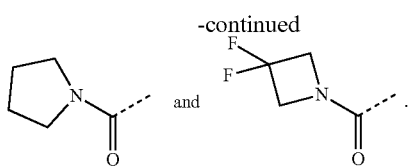 and 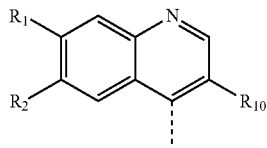

wherein, $R_{2d1}$, $R_{2d2}$ and $R_{2d3}$ are each independently selected from H, OH, $NH_2$, CN and optionally substituted $C_{1-7}$ chain alkyl, $C_{1-7}$ heteroalkyl, 3-6 membered cycloalkyl, 3-6 membered heterocycloalkyl, or $R_{2d1}$ and $R_{2d2}$ together form a 4-7 membered ring;

preferably, $R_{2d1}$ and $R_{2d2}$ are each independently selected from H, OH, halogen, optionally substituted $C_{1-7}$ alkyl, $C_{1-7}$ heteroalkyl and $C_{3-5}$ cycloalkyl; or, $R_{2d1}$ and $R_{2d2}$ together form a 4-7 membered ring;

preferably, $R_{2d1}$ and $R_{2d2}$ are each independently selected from H, OH, haloalkyl, $C_{1-6}$ alkyl, $C_{3-6}$ cycloalkyl, $C_{1-6}$ alkoxy and N,N-di($C_{1-6}$ alkyl)-$C_{1-6}$ alkyl, $R_{2d3}$ is $C_{1-6}$ alkyl; or, $R_{2d1}$ and $R_{2d2}$ together form a 4-7 membered ring;

more preferably, $R_{2d1}$ and $R_{2d2}$ are each independently selected from H, OH, haloalkyl, $C_{1-3}$ alkyl, $C_{3-6}$ cycloalkyl, $C_{1-3}$ alkoxy and N,N-di($C_{1-3}$ alkyl)-$C_{1-3}$ alkyl, $R_{2d3}$ is $C_{1-3}$ alkyl; or, $R_{2d1}$ and $R_{2d2}$ together form a 4-6 membered ring;

further preferably, $R_{2d1}$, $R_{2d2}$, $R_{2d3}$ are each independently selected from H, OH, methyl,

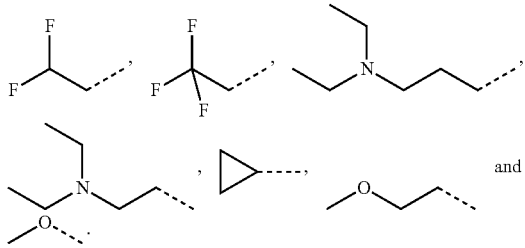

In some embodiments of the present invention, the structural unit —$N(R_{2d1}R_{2d2})$ is selected from optionally substituted

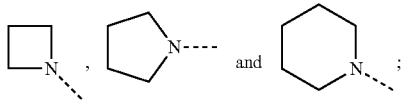

more specifically, the structural unit —$N(R_{2d1}R_{2d2})$ is selected from

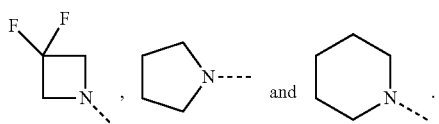

Alternatively, in the above-mentioned formula (II), $R_1$ and $R_2$ together with two carbon atoms on the benzene ring form a 4-7 membered ring; preferably, $R_1$ and $R_2$ together with two carbon atoms on the benzene ring form an optionally substituted 5 to 6 membered ring.

In some embodiments of the present invention, the above-mentioned structural unit

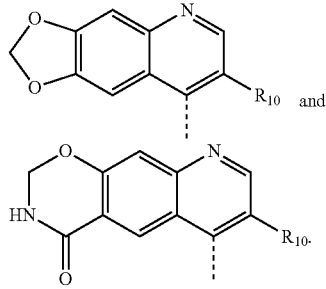

is selected from optionally substituted

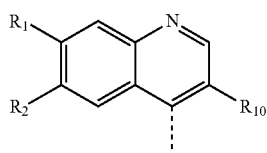 and

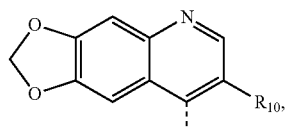

In some embodiments of the present invention, the above-mentioned structural unit

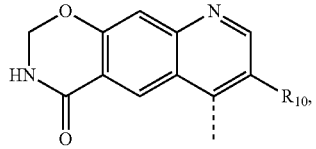

is selected from

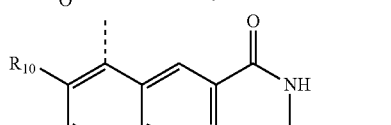

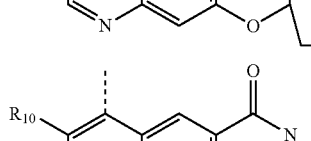

$R_{10}$ is selected from H, OH, $NH_2$, CN and halogen; preferably H or halogen;

$R_{14}$ and $R_{15}$ are each independently H, $C_{1-6}$ alkyl, $C_{3-6}$ cycloalkyl, haloalkyl, or $R_{14}$ and $R_{15}$ may form a 4-7 membered ring, preferably a 3-6 membered ring, the ring may be replaced by a group such as halogen;

$R_{16}$ and $R_{17}$ are each independently H, $C_{1-6}$ alkyl or halogen.

The above-mentioned formula (II) may be a compound represented by the following general formula:

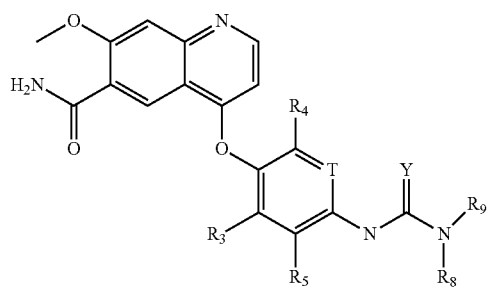
(IX)

wherein, in the above-mentioned formula (IX), Y is O or S;

T is selected from N and C($R_6$);

$R_3$, $R_4$, $R_5$, $R_6$ are each independently selected from H, OH, $NH_2$, CN, halogen and optionally substituted $C_{1-7}$ alkyl and $C_{1-7}$ heteroalkyl;

preferably, the above-mentioned $R_3$, $R_4$, $R_5$, $R_6$ are each independently selected from H, OH, CN, $NH_2$, halogen and optionally substituted $C_{1-3}$ alkyl and $C_{1-3}$ alkoxy;

more preferably, the above-mentioned $R_3$, $R_4$, $R_5$, $R_6$ are each independently selected from H, F, Cl, Br, I, OH, CN, $NH_2$,

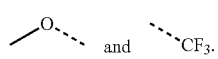

$R_7$, $R_8$, $R_9$ are each independently selected from H and optionally substituted $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

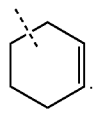

preferably, the above-mentioned $R_7$, $R_8$ and $R_9$ are each independently selected from H and optionally substituted $C_{1-5}$ alkyl, $C_{1-5}$ heteroalkyl, 3-6 membered cycloalkyl, 4-6 membered heterocycloalkyl, 6 membered aryl, 5-6 membered heteroaryl, 3-6 membered cycloalkyl-$C_{1-2}$ alkyl-, 3-6 membered heterocycloalkyl-$C_{1-2}$ alkyl-, 6 membered aryl-$C_{1-2}$ alkyl-, 5-6 membered heteroaryl-$C_{1-2}$ alkyl-, $C_{3-6}$ alkynyl and

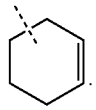

more preferably, the above-mentioned $R_7$, $R_8$ and $R_9$ are each independently selected from H and optionally substituted $C_{1-4}$ alkyl, $C_{1-2}$ alkyl-S—$C_{1-3}$ alkyl-, $C_{1-2}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

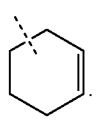

Further preferably, the above-mentioned $R_7$, $R_8$ and $R_9$ are each independently selected from H and optionally substituted Me,

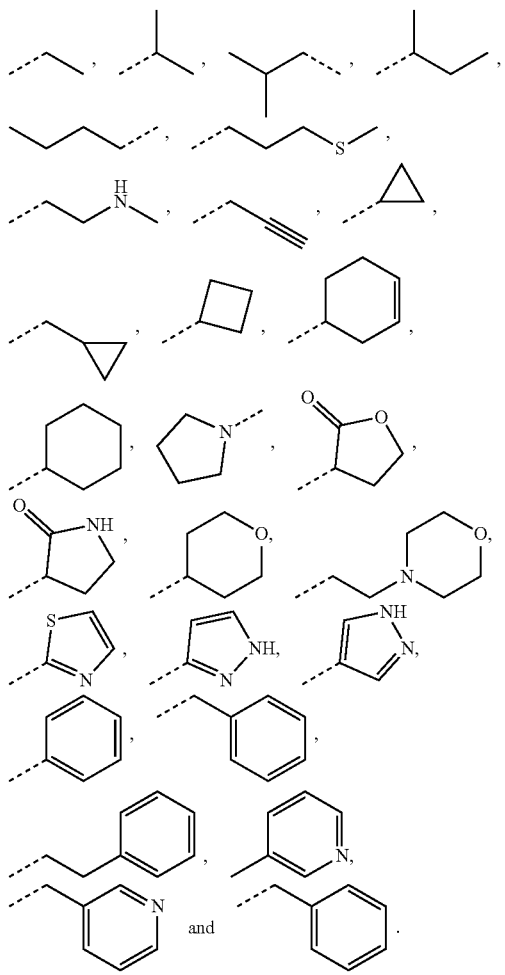

Most preferably, the above-mentioned $R_7$, $R_8$ and $R_9$ are each independently selected from H, Me,

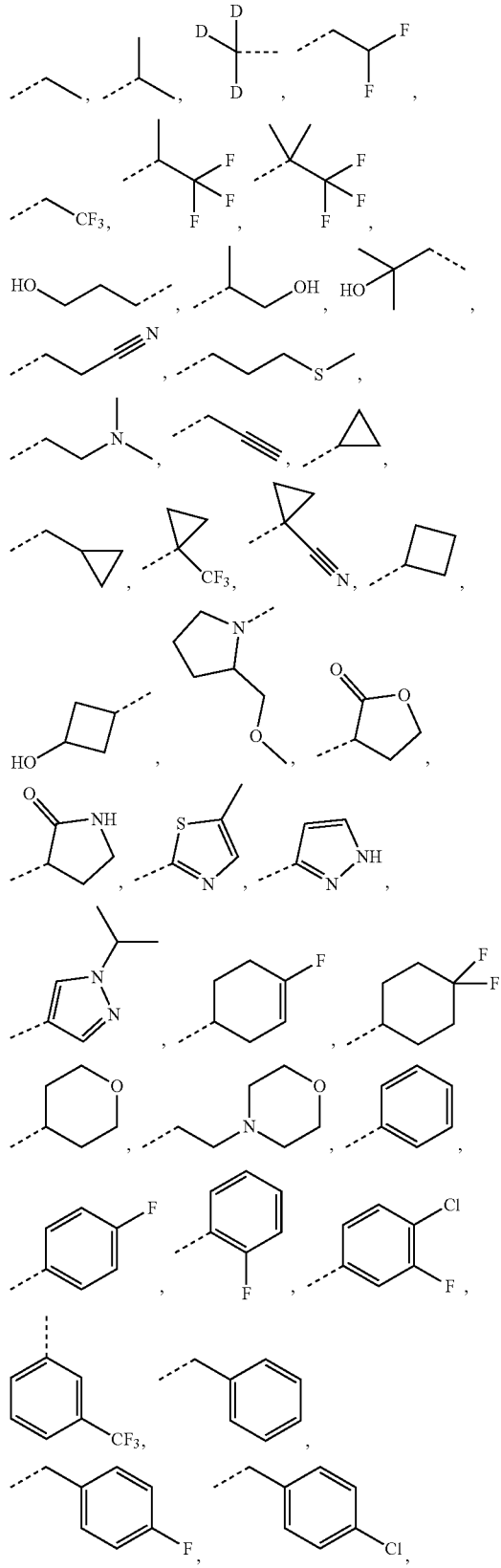

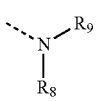

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

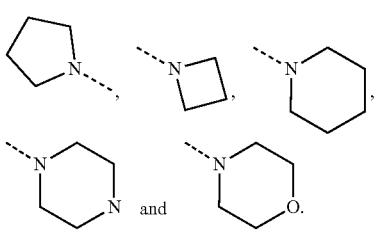

is selected from optionally substituted

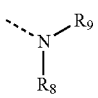

In some embodiments of the present invention, the above-mentioned structural unit is selected from

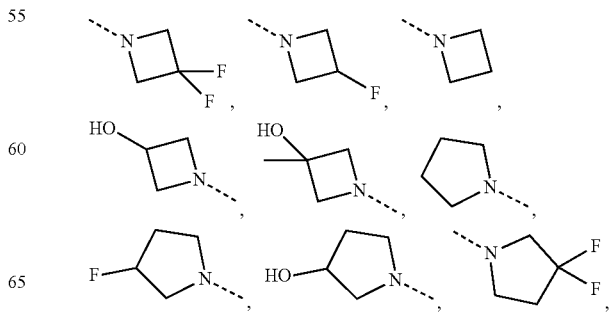

-continued

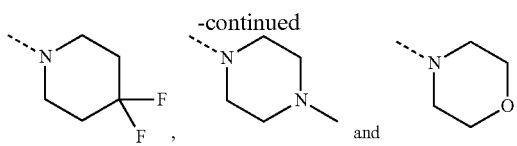

Preferably, the above-mentioned $R_7$ and $R_8$ together form an optionally substituted 4-7 membered ring, and preferably $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

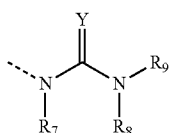

is selected from optionally substituted

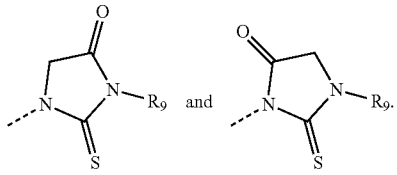

In some embodiments of the present invention, the above-mentioned structural unit

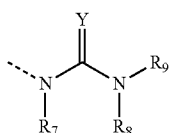

is selected from

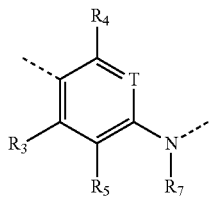

is selected from

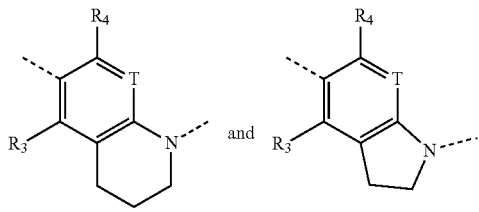

In some embodiments of the present invention, the above-mentioned structural unit

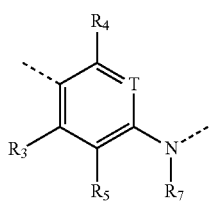

is selected from

Alternatively, $R_5$ and $R_7$ together form a 4-7 membered ring; preferably, $R_5$ and $R_7$ together form an optionally substituted 5-6 membered ring.

In some embodiments of the present invention, the above-mentioned structural unit The above-mentioned formula (II) may be a compound represented by the following general formula:

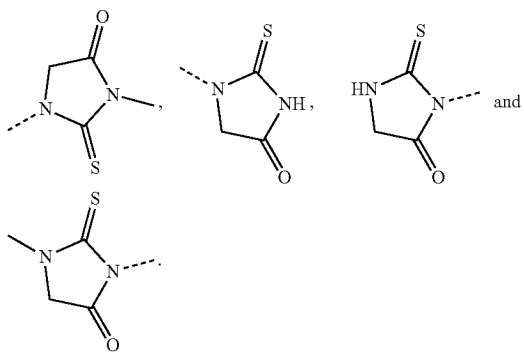

(X)

wherein, in the above-mentioned formula (X), Y is O or S;

T is selected from N and C(R$_6$);

R$_3$, R$_4$, R$_5$, R$_6$ are each independently selected from H, OH, NH2, CN, halogen and optionally substituted C$_{1-7}$ alkyl and C$_{1-7}$ heteroalkyl;

preferably, the above-mentioned R$_3$, R$_4$, R$_5$, R$_6$ are each independently selected from H, OH, CN, NH2, halogen and optionally substituted C$_{1-3}$ alkyl and C$_{1-3}$ alkoxy;

more preferably, the above-mentioned R$_3$, R$_4$, R$_5$, R$_6$ are each independently selected from H, F, Cl, Br, I, OH, CN, NH$_2$,

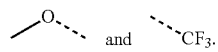

R$_7$, R$_8$, R$_9$ are each independently selected from H and optionally substituted C$_{1-7}$ alkyl, C$_{1-7}$ heteroalkyl, 3-6 membered cycloalkyl, 3-6 membered heterocycloalkyl, 5-6 membered aryl, 5-6 membered heteroaryl, 3-6 membered cycloalkyl-C$_{1-3}$ alkyl-, 3-6 membered heterocycloalkyl-C$_{1-3}$ alkyl-, 3-6 membered heterocycloalkyl-C$_{1-3}$ alkyl-, 5-6 membered aryl-C$_{1-3}$ alkyl-, C$_{2-7}$ alkynyl and

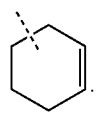

preferably, the above-mentioned R$_7$, R$_8$ and R$_9$ are each independently selected from H and optionally substituted C$_{1-5}$ alkyl, C$_{1-5}$ heteroalkyl, 3-6 membered cycloalkyl, 4-6 membered heterocycloalkane, 6 membered aryl, 5-6 membered heteroaryl, 3-6 membered cycloalkyl-C$_{1-2}$ alkyl-, 3-6 membered heterocycloalkyl-C$_{1-2}$ alkyl-, 6 membered aryl-C$_{1-2}$ alkyl-, 5-6 membered heteroaryl-C$_{1-2}$ alkyl-, C$_{3-6}$ alkynyl and

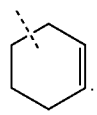

More preferably, the above-mentioned R$_7$, R$_8$ and R$_9$ are each independently selected from H and optionally substituted C$_{1-4}$ alkyl, C$_{1-2}$ alkyl-S—C$_{1-3}$ alkyl-, C$_{1-2}$ alkyl-N—C$_{1-3}$ alkyl-, C$_{1-2}$ alkyl-O—C$_{1-3}$ alkyl-, 3-6 membered cycloalkyl, 3-6 membered cycloalkyl-C$_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-C$_{1-2}$ alkyl-, phenyl-C$_{1-2}$ alkyl-, pyridyl-C$_{1-2}$ alkyl-, C$_{0-2}$ alkyl-alkynyl-C$_{1-2}$ alkyl- and

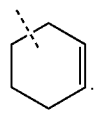

Further preferably, the above-mentioned R$_7$, R$_8$ and R$_9$ are each independently selected from H and optionally substituted Me,

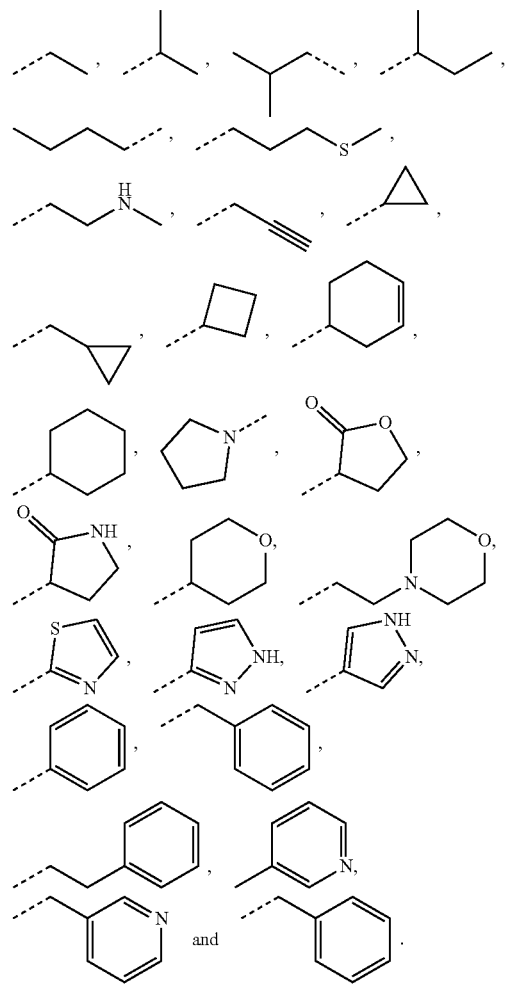

Most preferably, the above-mentioned R$_7$, R$_8$ and R$_9$ are each independently selected from H, Me,

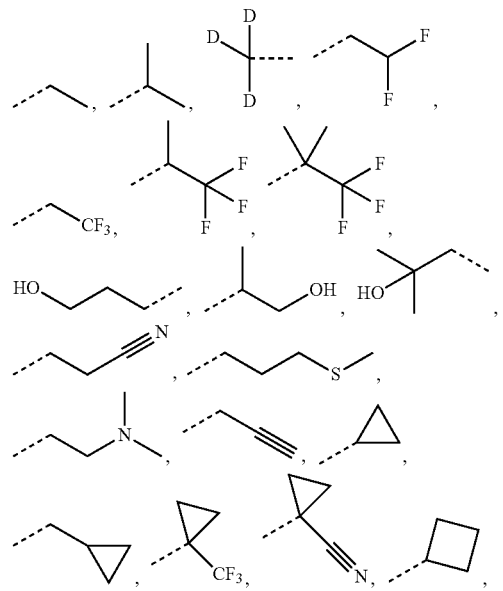

is selected from optionally substituted

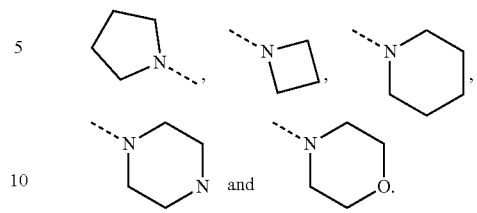

In some embodiments of the present invention, the above-mentioned structural unit

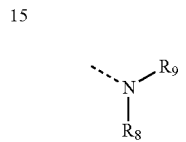

is selected from

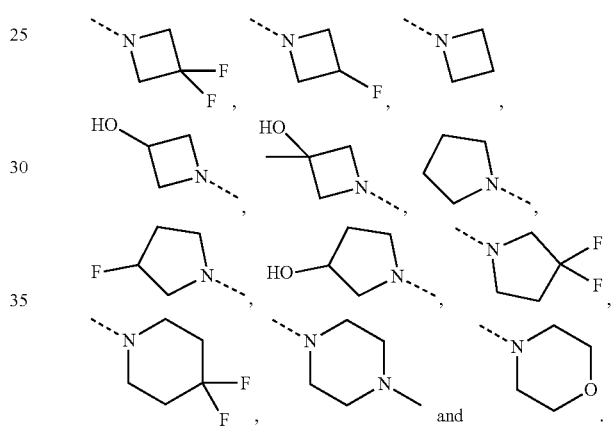

Preferably, the above-mentioned $R_7$ and $R_8$ together form an optionally substituted 4-7 membered ring, and preferably $R_7$ and $R_8$ together form an optionally substituted 4-6 membered ring, and in some embodiments of the present invention, the above-mentioned $R_7$ and $R_8$ together form an optionally substituted 5 membered ring.

In some embodiments of the present invention, the above-mentioned structural unit

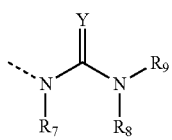

is selected from optionally substituted

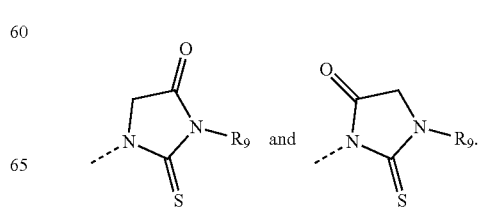

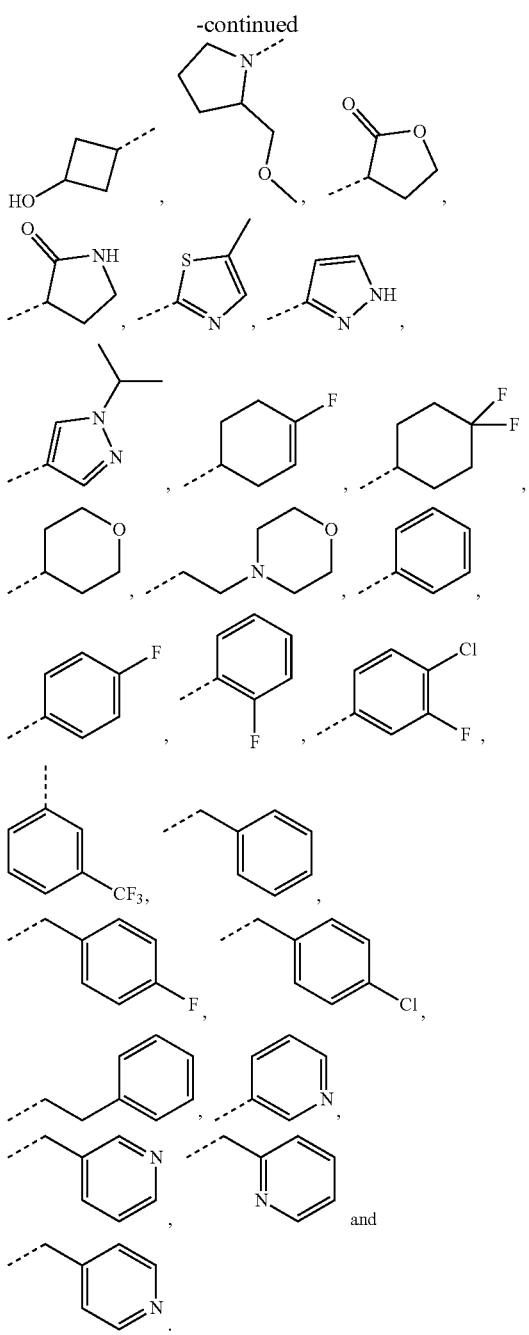

Preferably, the above-mentioned $R_8$ and $R_9$ together form an optionally substituted 4-7 membered ring, preferably, the above-mentioned $R_8$ and $R_9$ together form an optionally substituted 4-6 membered ring, and in some embodiments of the present invention, the above-mentioned $R_8$ and $R_9$ together form an optionally substituted 5 membered ring.

In some embodiments of the present invention, the above-mentioned structural unit

In some embodiments of the present invention, the above-mentioned structural unit

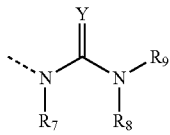

is selected from

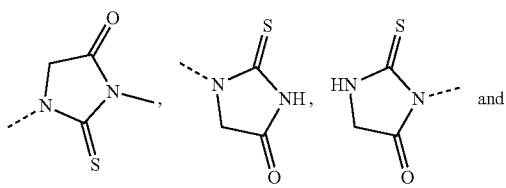

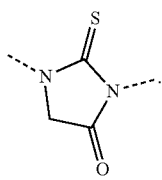

Alternatively, $R_5$ and $R_7$ together form a 4-7 membered ring; preferably, $R_5$ and $R_7$ together form an optionally substituted 5-6 membered ring.

In some embodiments of the present invention, the above-mentioned structural unit

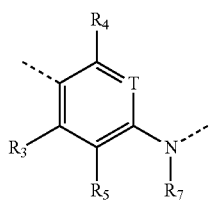

is selected from

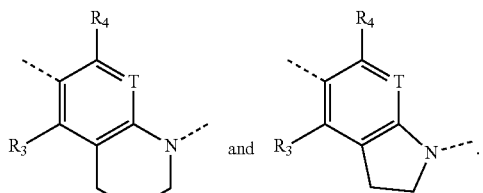

In some embodiments of the present invention, the above-mentioned structural unit

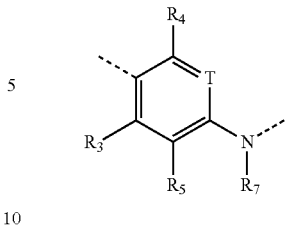

is selected from

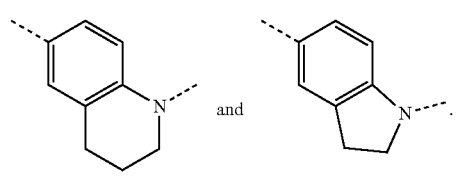

$R_{12}$ and $R_{13}$ are each independently selected from H, OH, NH2, CN and optionally substituted $C_{1-7}$ alkyl, $C_{1-7}$ heteroalkyl, 3-6 membered cycloalkyl, 3-6 membered heterocycloalkyl, 5-6 membered aryl and 5-6 membered heteroaryl;

preferably, the above-mentioned $R_{12}$, $R_{13}$ are each independently selected from H, methyl, isopropyl and phenyl.

In some embodiments of the present invention, the above-mentioned

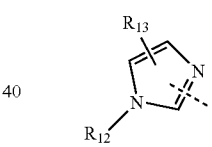

is selected from

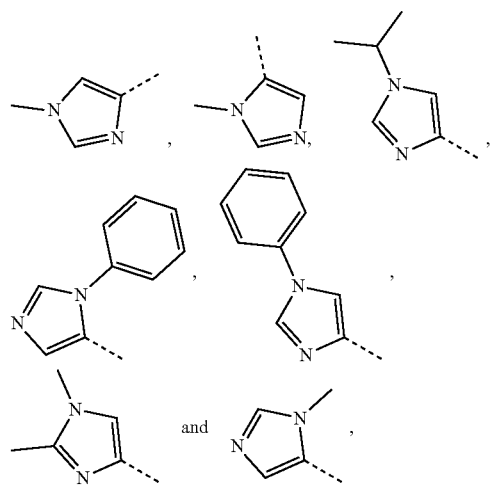

the structural unit

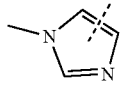

is selected from

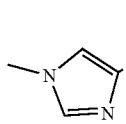 and 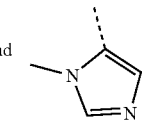.

The "hetero" used in the present invention refers to a heteroatom or heteroatom group, which is selected from —O—, —N—, —S—, =O, =S, —C(=O)—, —C(=O)O—, —S(=O)— and —S(=O)$_2$—;

The number of the heteroatom or heteroatom group is each independently 1, 2, 3 or 4.

In some embodiments of the present invention, the substituents of the above-mentioned $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 5-6 membered aryl-$C_{1-3}$ alkyl-, 5-6 membered heteroaryl-$C_{1-3}$ alkyl-, 6-10 membered aryl, 6-10 membered heteroaryl, —C(=O)N($R_{2d1}$)($R_{2d2}$), —N($R_{2d1}$)C(=O)$R_{2d2}$, —C(=O)O$R_{2d3}$, —C(=O)N($R_{11d1}$)($R_{11d2}$), —$C_{1-3}$ alkyl-C(=O)N($R_{11d1}$)($R_{11d2}$), —NH—C(=O)N($R_{11d1}$)($R_{11d2}$), —$C_{1-3}$ alkyl-NH—C(=O)N($R_{11d1}$)($R_{11d2}$), $C_{1-7}$ alkyl-N($R_{11d1}$)—S(=O)—N($R_{11d2}$)—, 3-6 membered cycloalkyl-N($R_{11d1}$)—P(=O)(O$R_{11d2}$)—$C_{1-3}$ alkyl-,

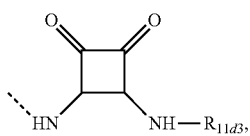

5-6 membered heterocycloalkylamino-, 5-6 membered arylamino-, 5-6 membered aryl-$C_{1-3}$ alkylamino-,

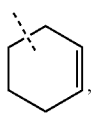, $C_{2-7}$ alkynyl and imidazolyl are independently selected from OH, CN, NH$_2$ and halogen, or selected from optionally halo-substituted, hydroxyl-substituted or ammonia-substituted $C_{1-6}$ alkyl, $C_{1-6}$ heteroalkyl, 3-7 membered cycloalkyl, 3-7 membered heterocycloalkyl, 5-7 membered aryl and 5-7 membered heteroaryl;

the number of the substituents is 0, 1, 2, 3, or 4.

In some embodiments of the present invention, the substituents is selected from F, Cl, Br, I, CN, OH, NH2, $C_{1-5}$ alkyl, $C_{1-5}$ haloalkyl, $C_{1-5}$ alkoxy and $C_{1-2}$ alkyl-O—$C_{1-2}$ alkyl- In some embodiments of the present invention, the above-mentioned substituents are selected from F, Cl, Br, I, CN, OH, NH$_2$, Me, —CF$_3$,

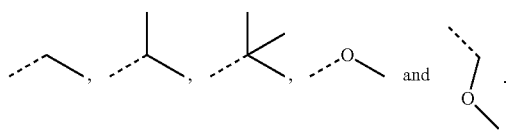

Specifically, the compounds of the present invention are selected from:

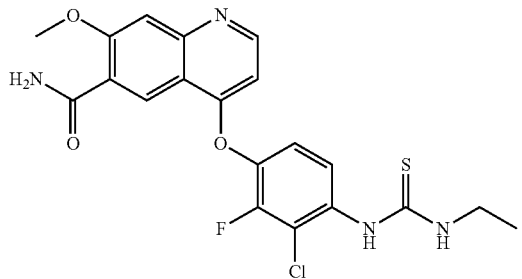

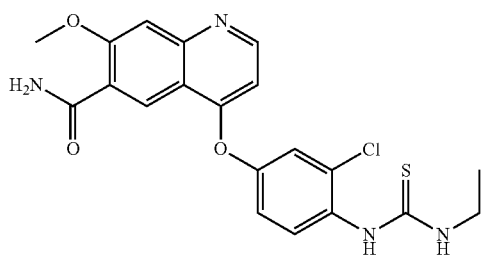

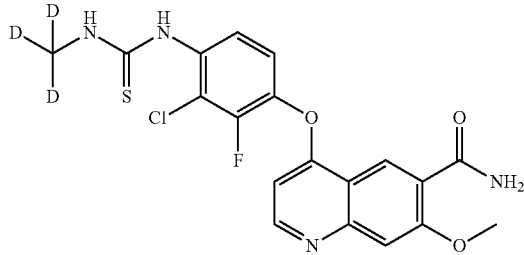

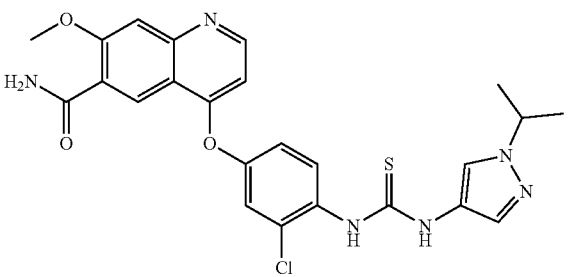

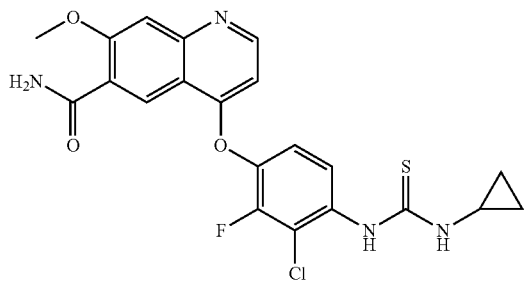

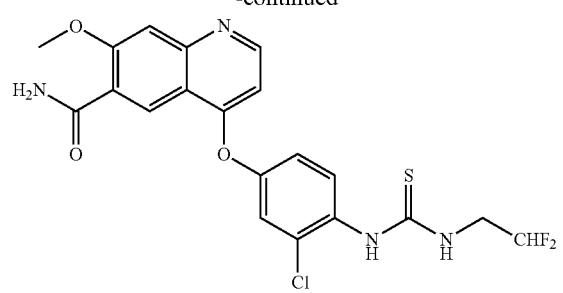
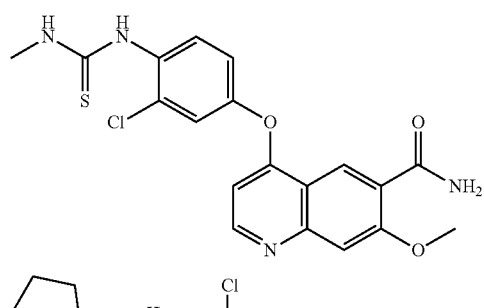
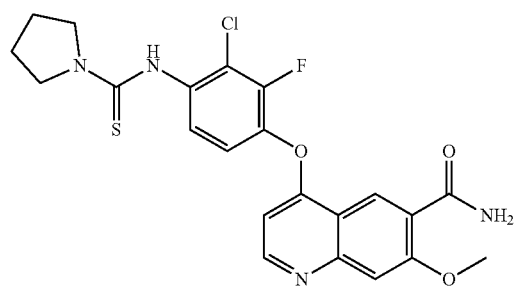
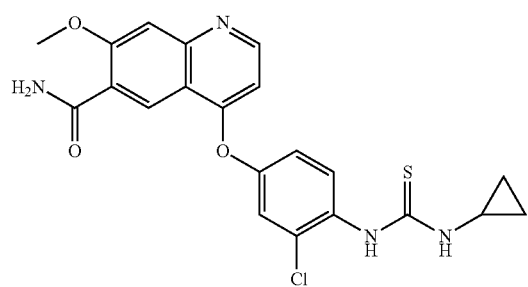
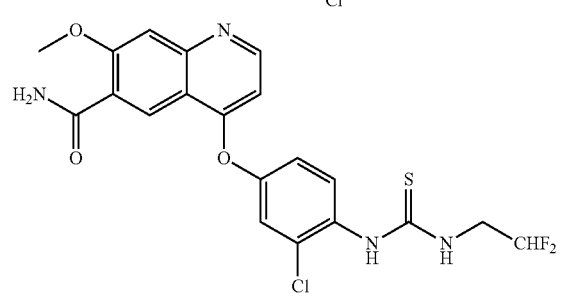
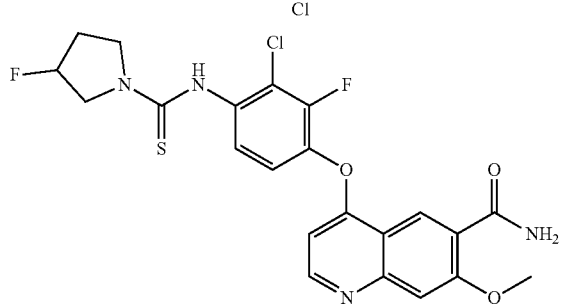
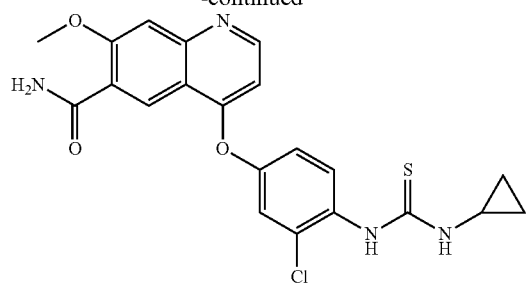
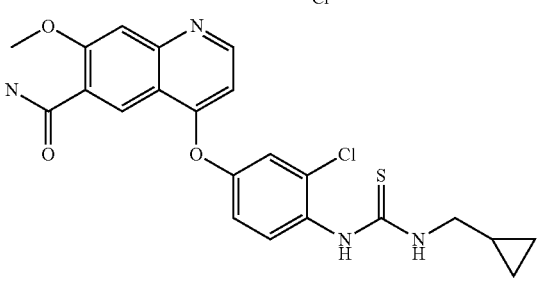
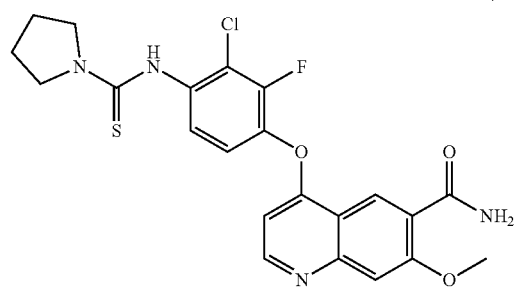
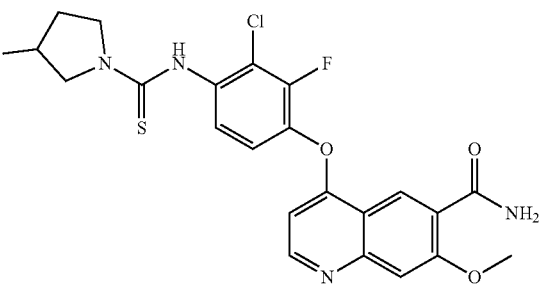
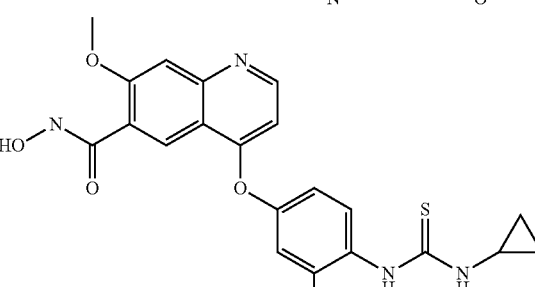
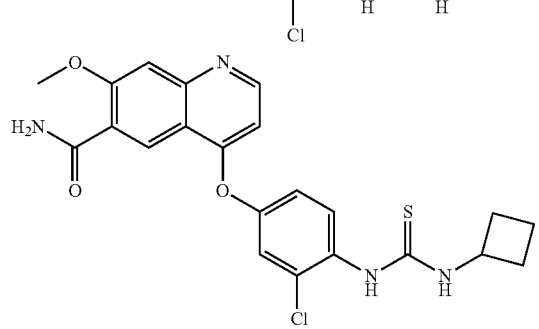

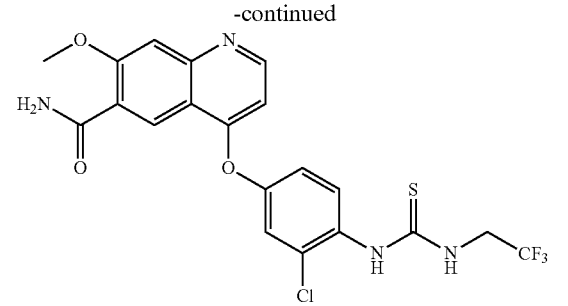
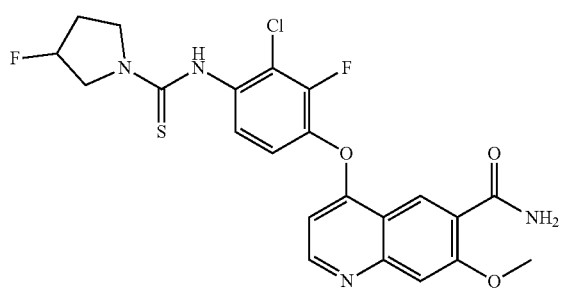
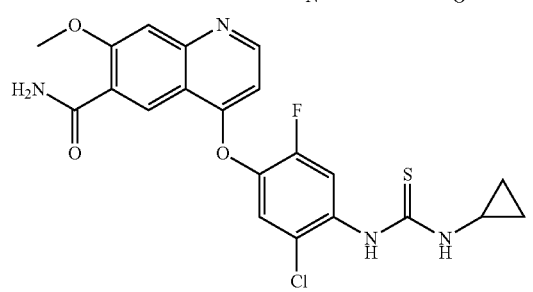
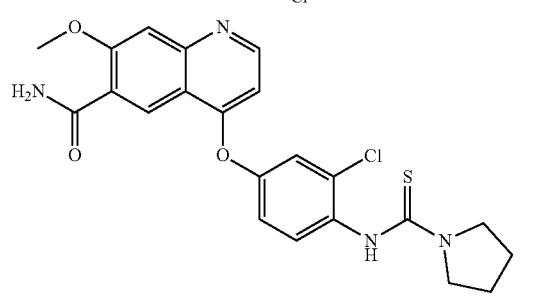
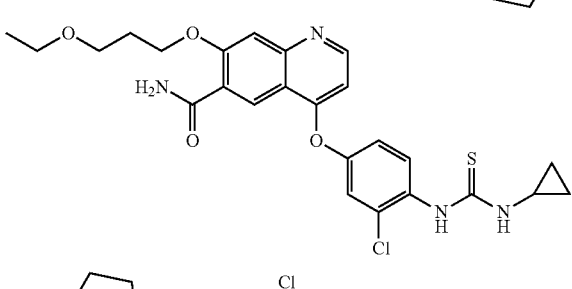
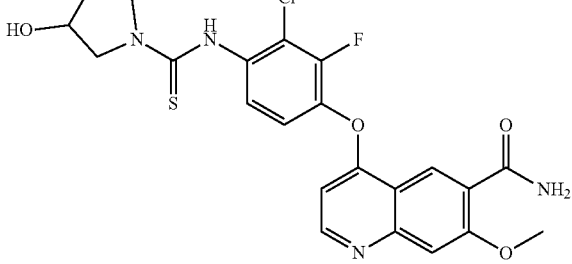
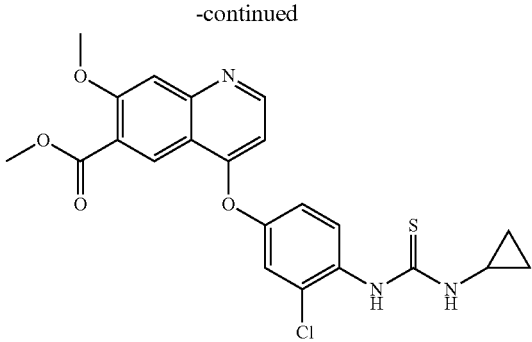
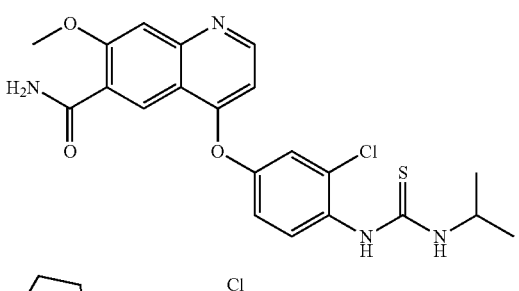
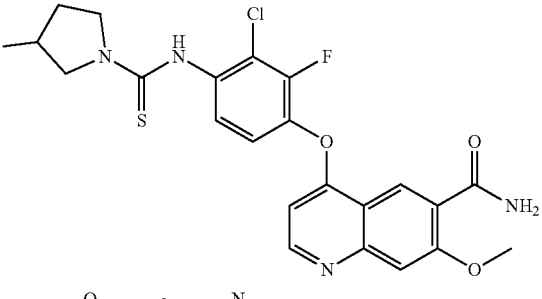
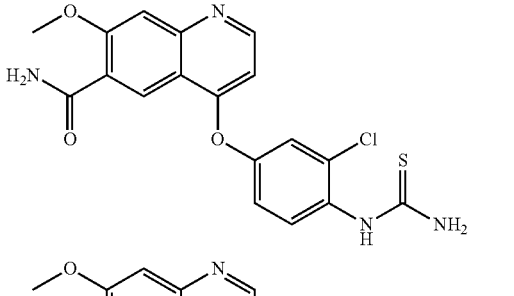
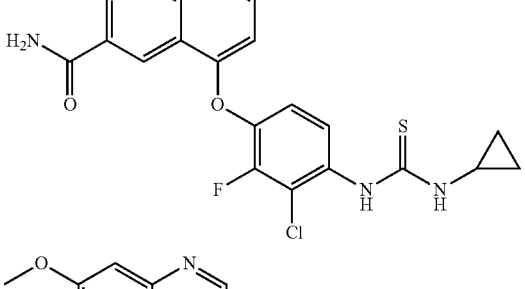
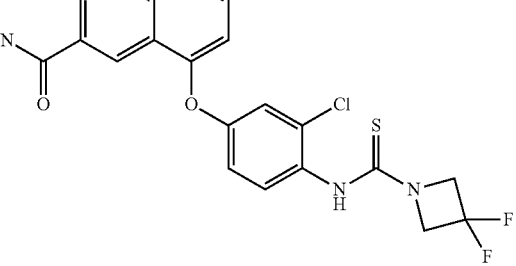

87
-continued
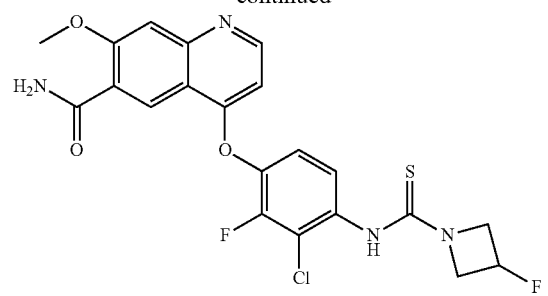
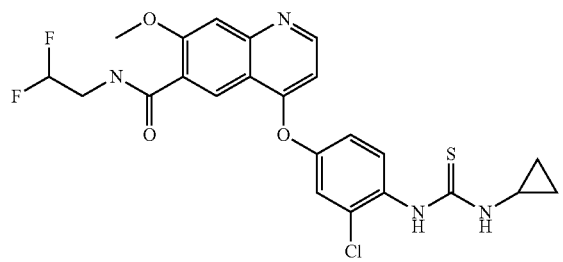
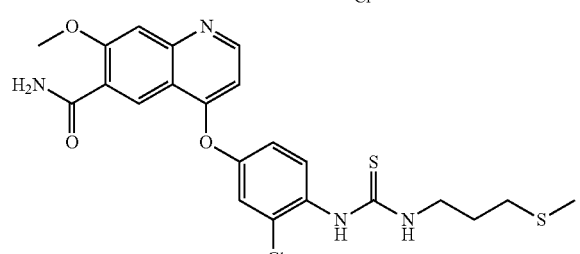
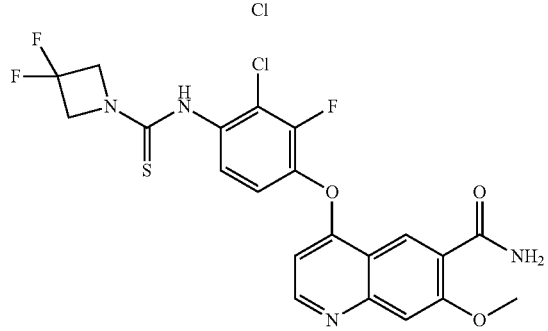
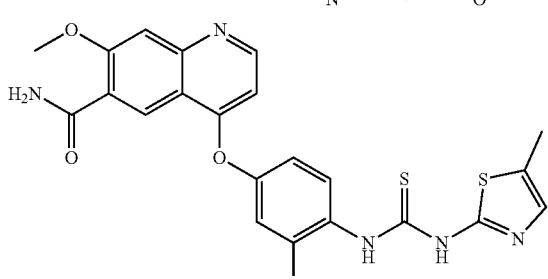
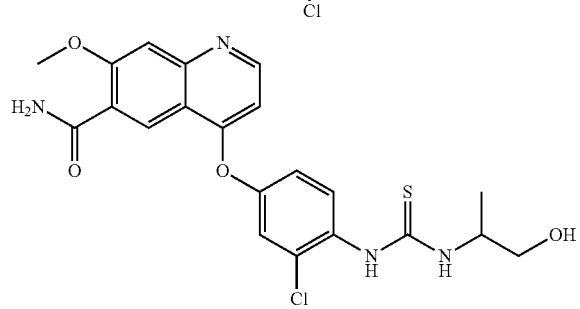
88
-continued
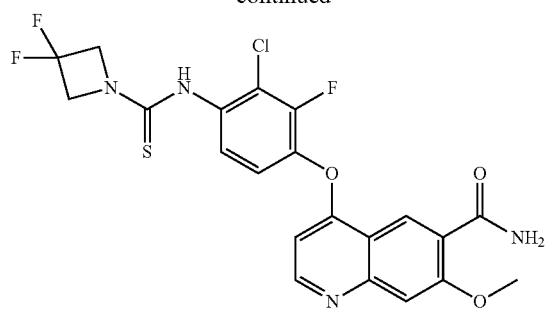
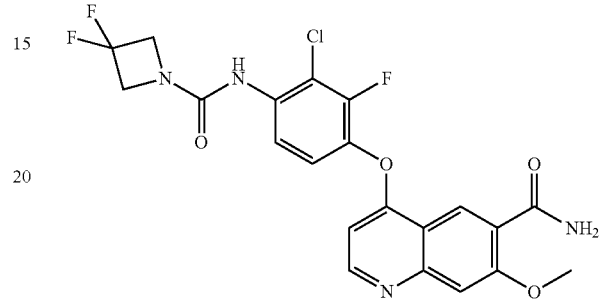
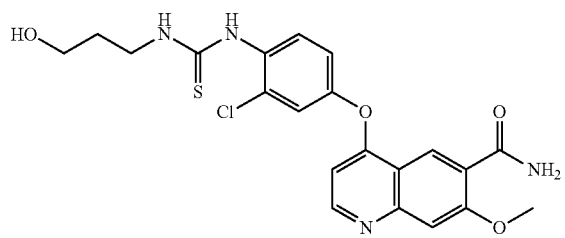
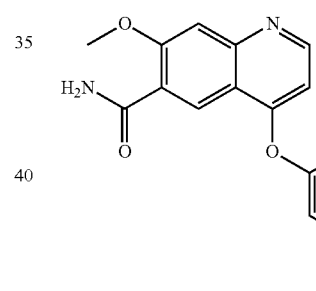
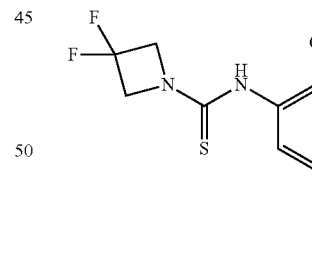
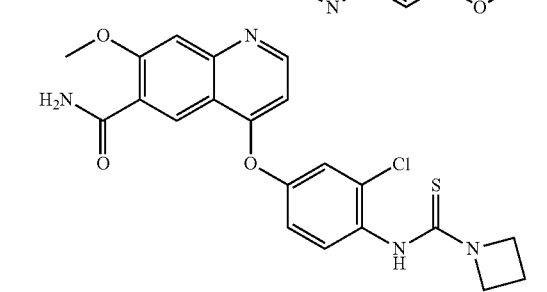

89
-continued
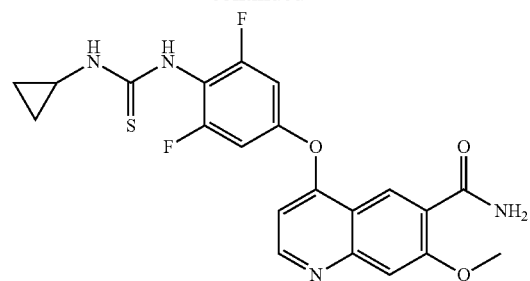
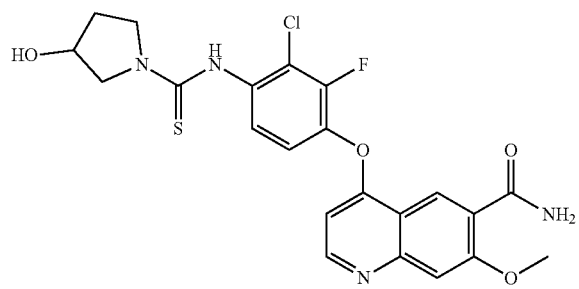
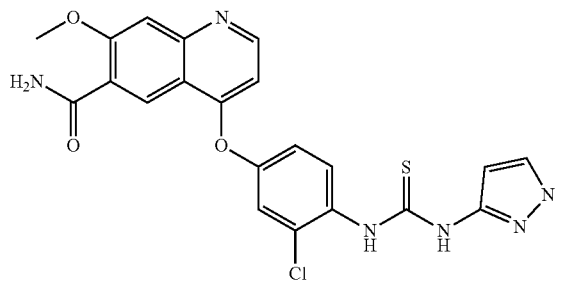
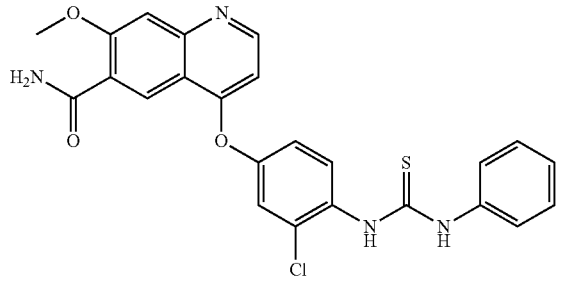
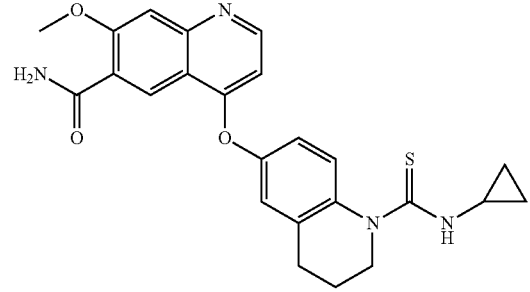
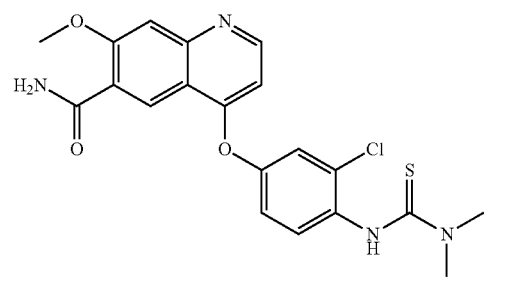
90
-continued
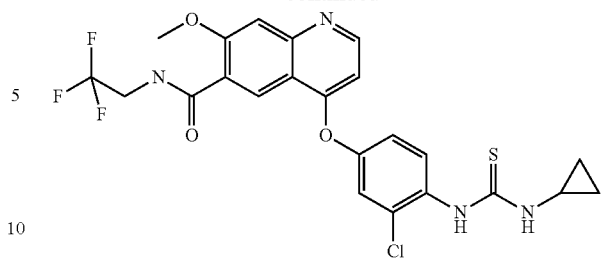
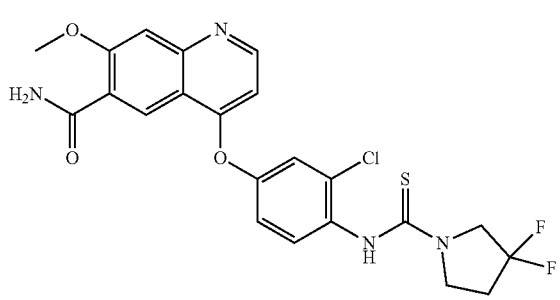
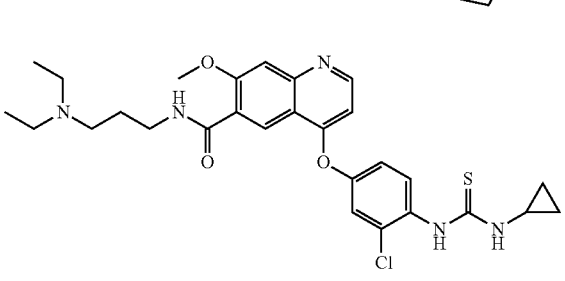
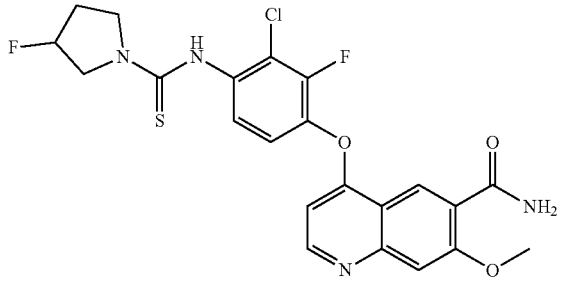
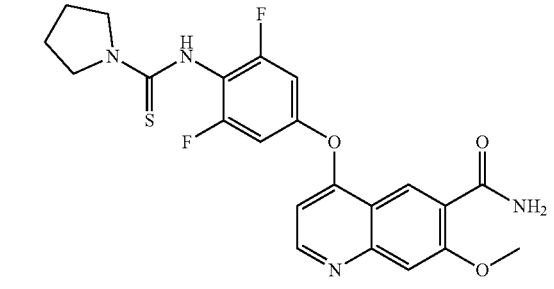
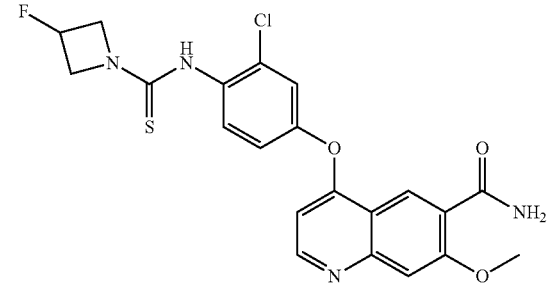

91
-continued
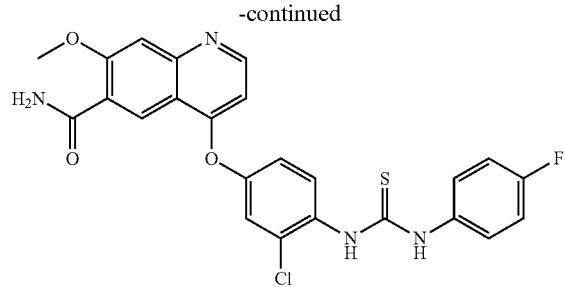
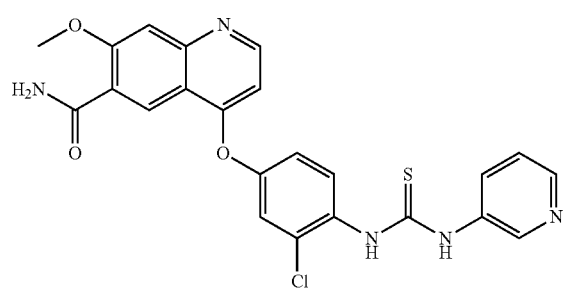
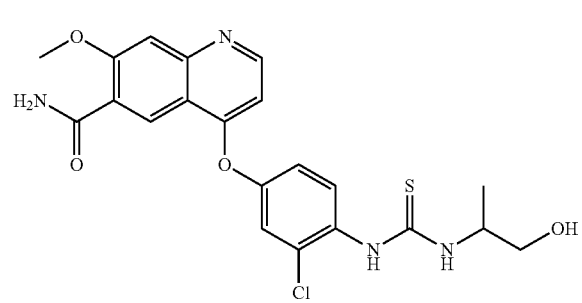
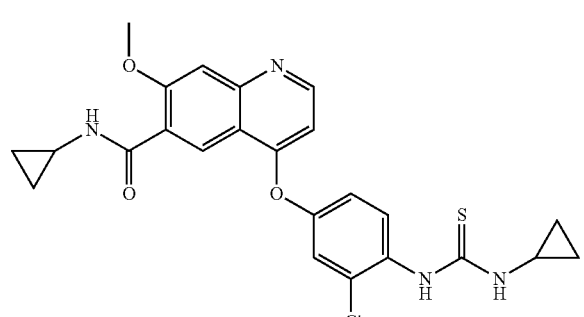
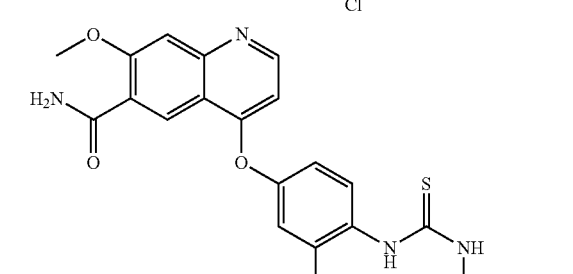
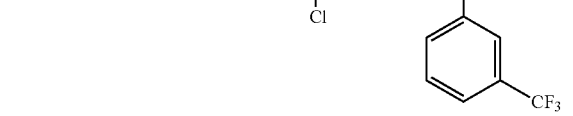
92
-continued
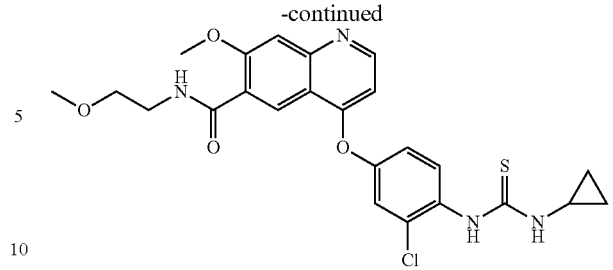
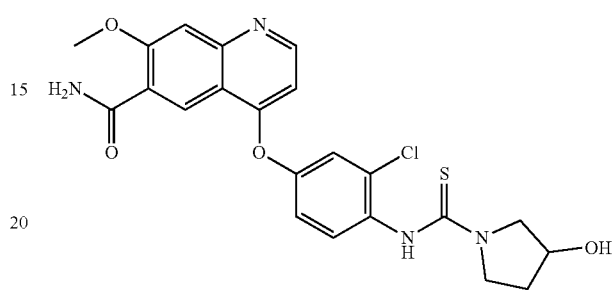
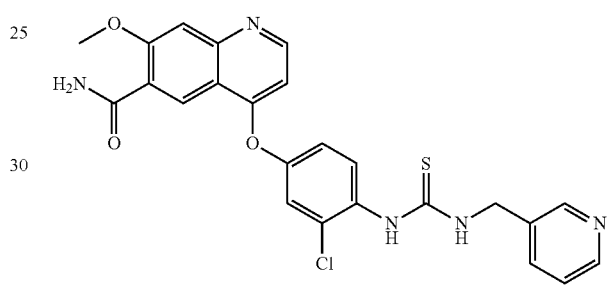
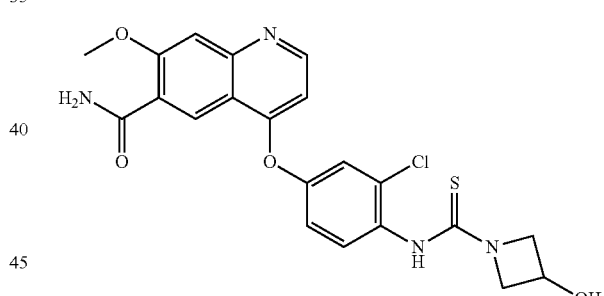
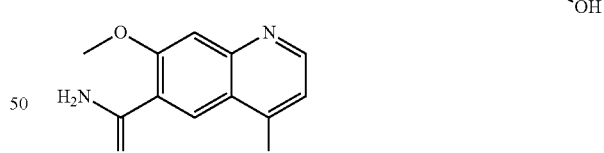
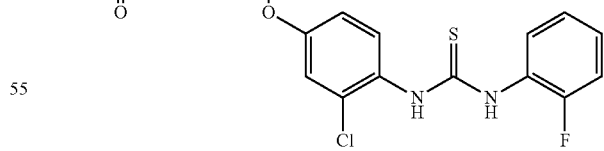
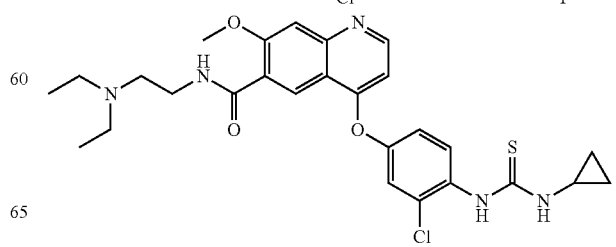

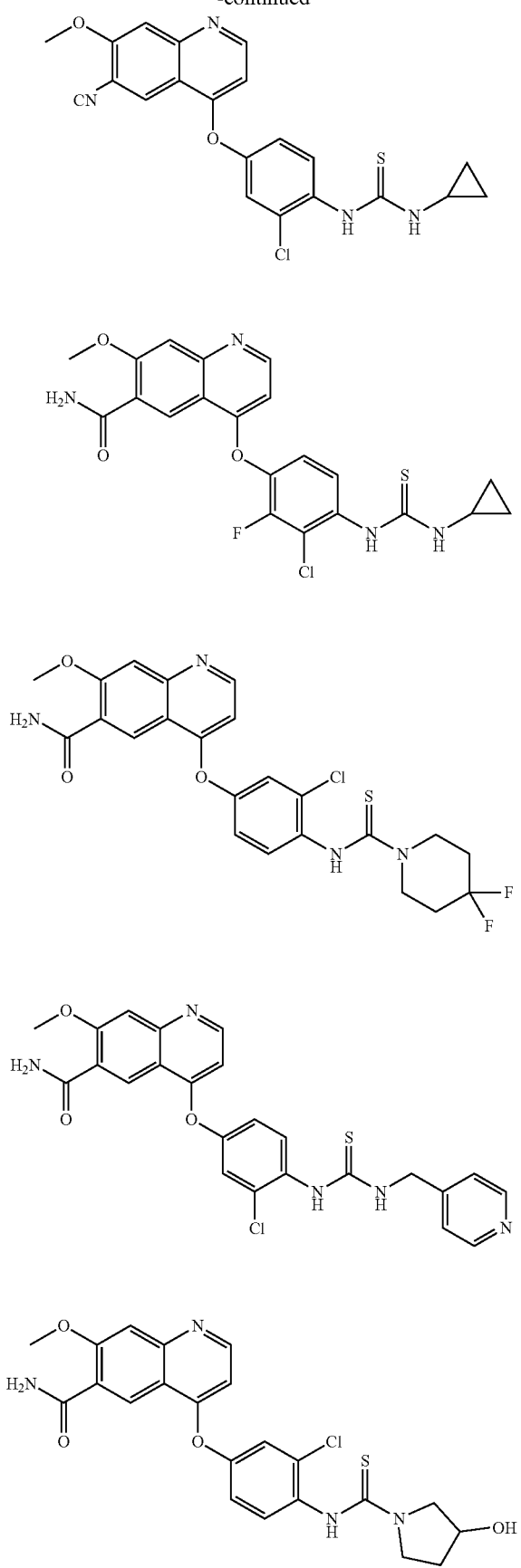
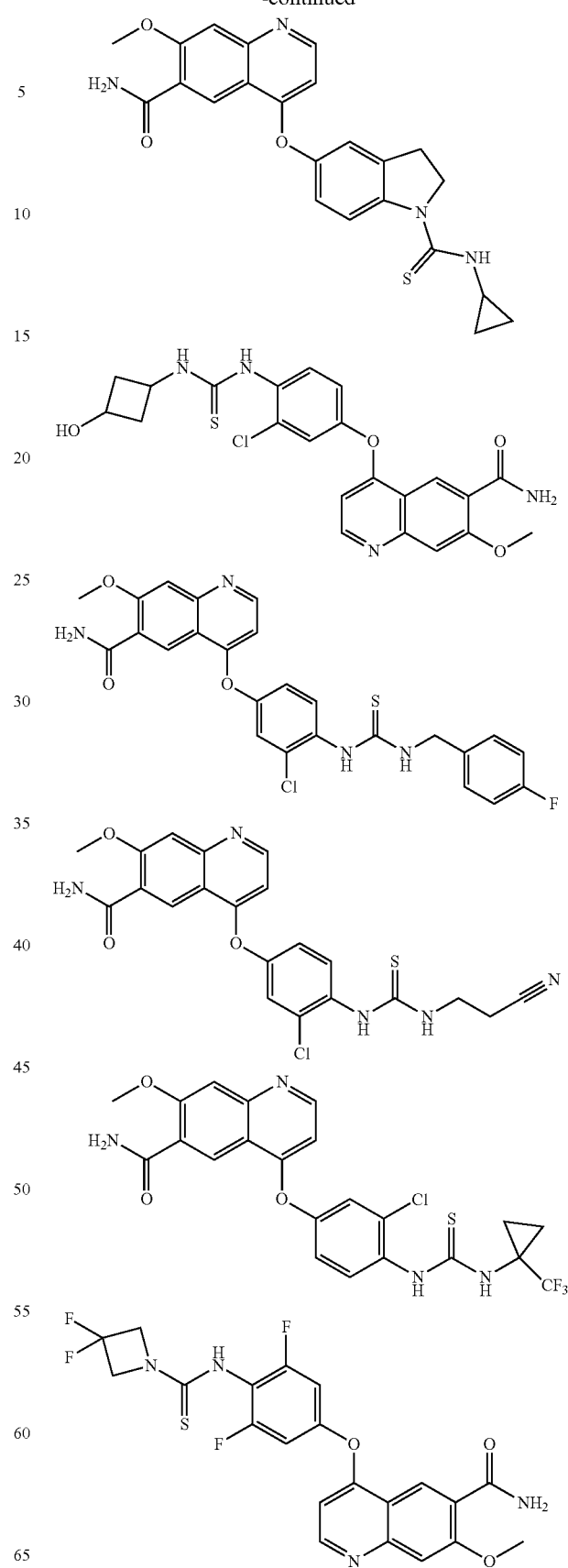

95
-continued
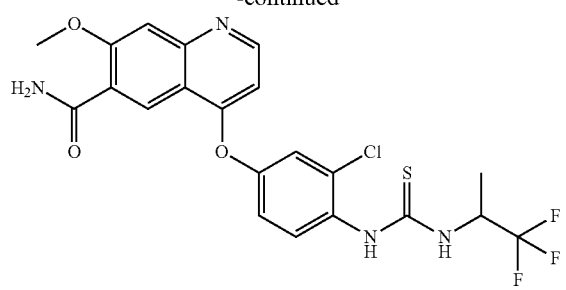
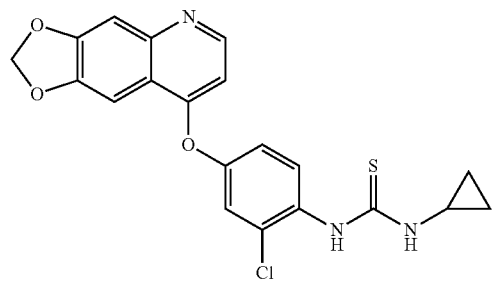
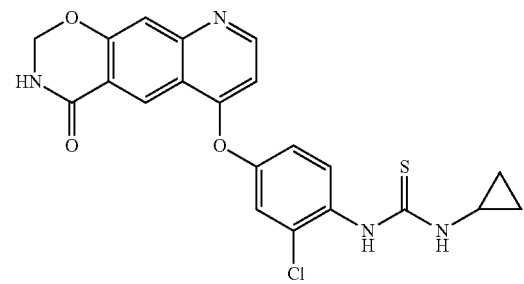
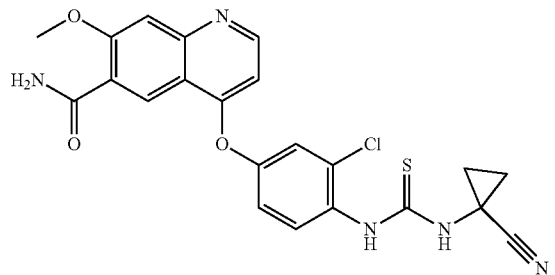
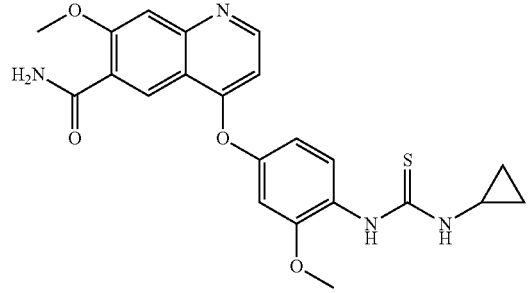
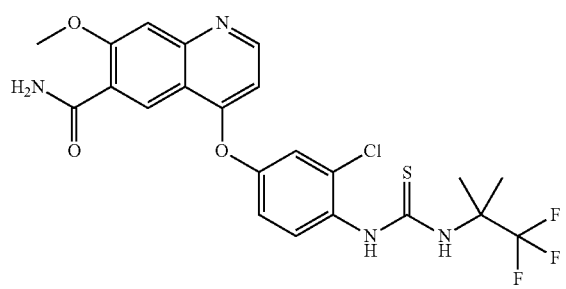
96
-continued
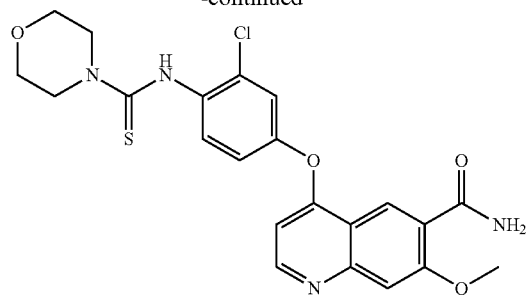
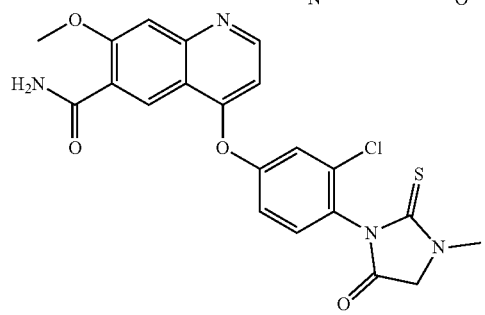
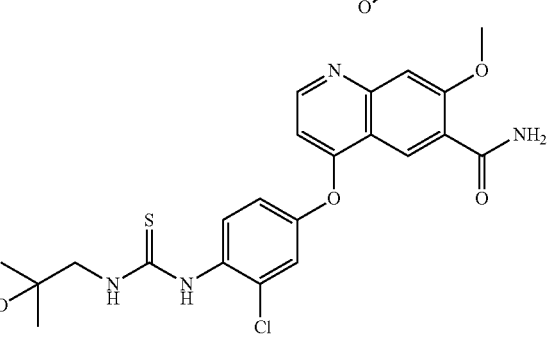
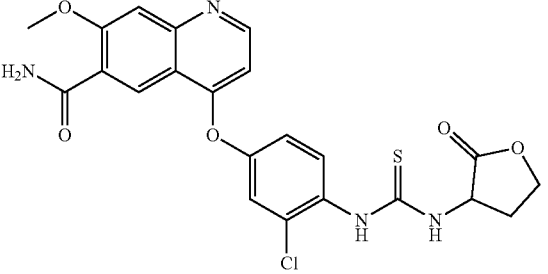
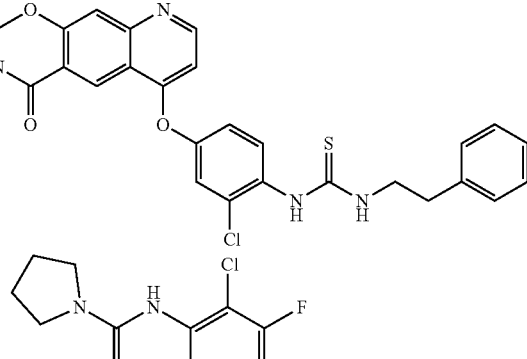
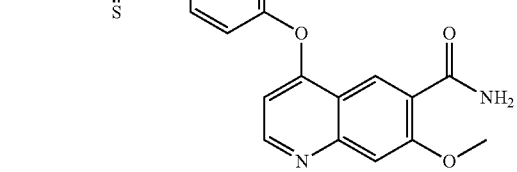

97
-continued
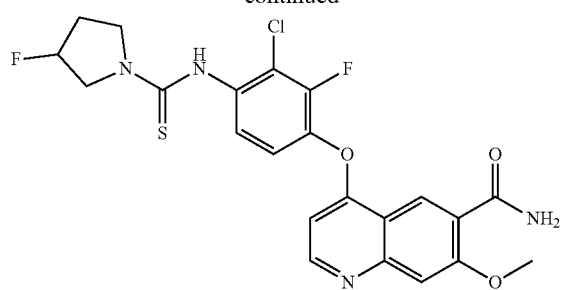
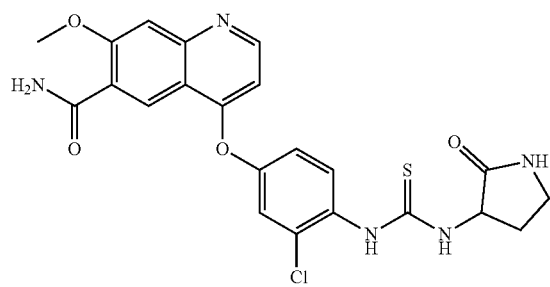
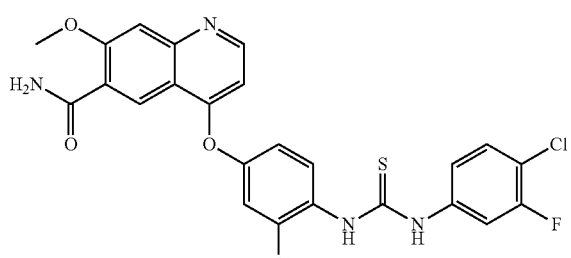
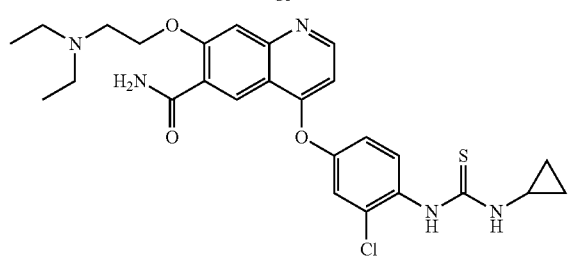
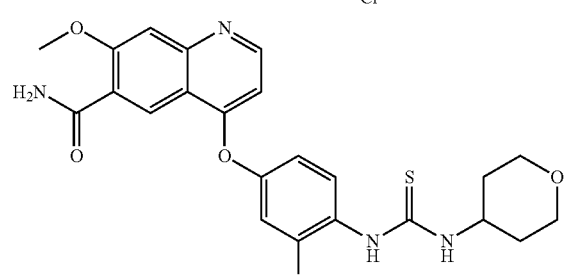
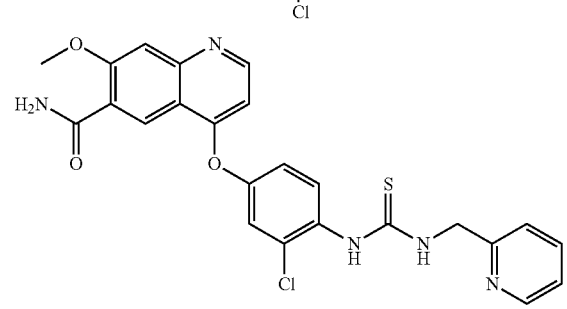
98
-continued
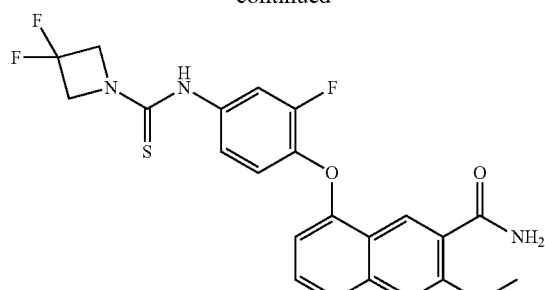
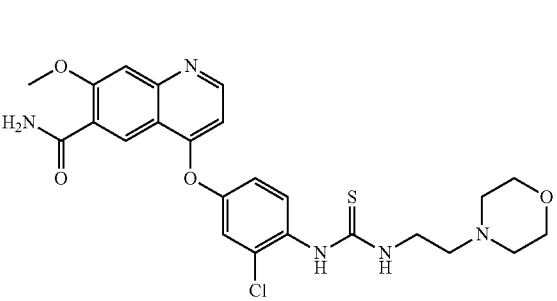
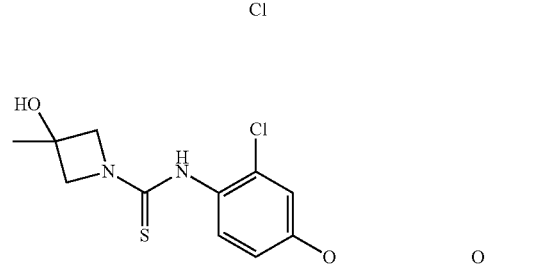
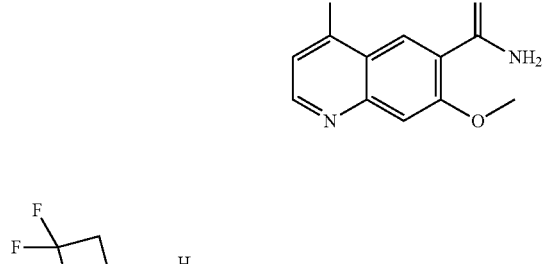
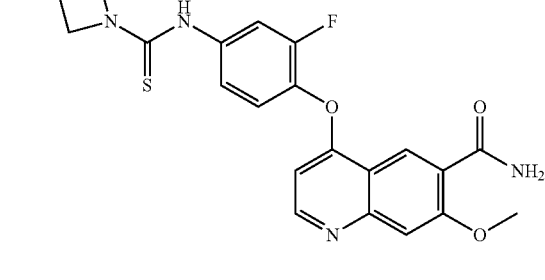
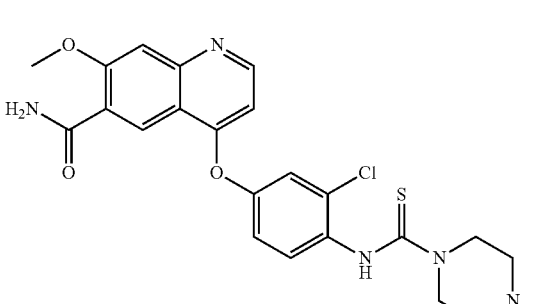

99
-continued
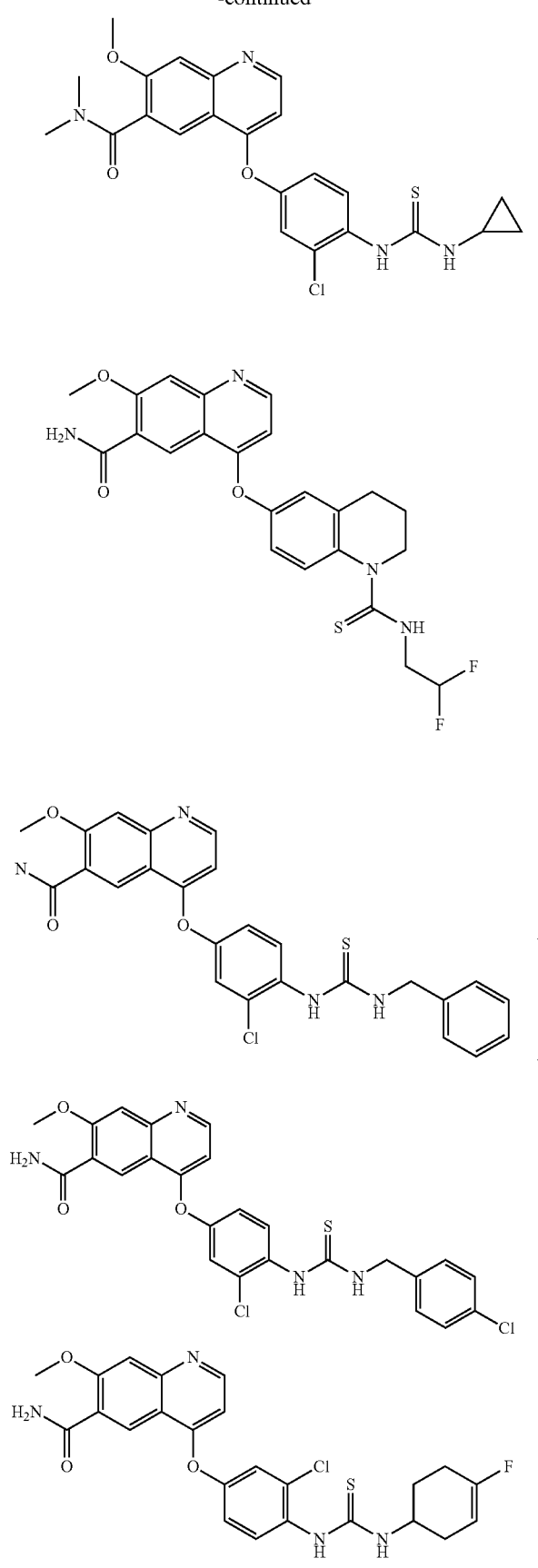
100
-continued
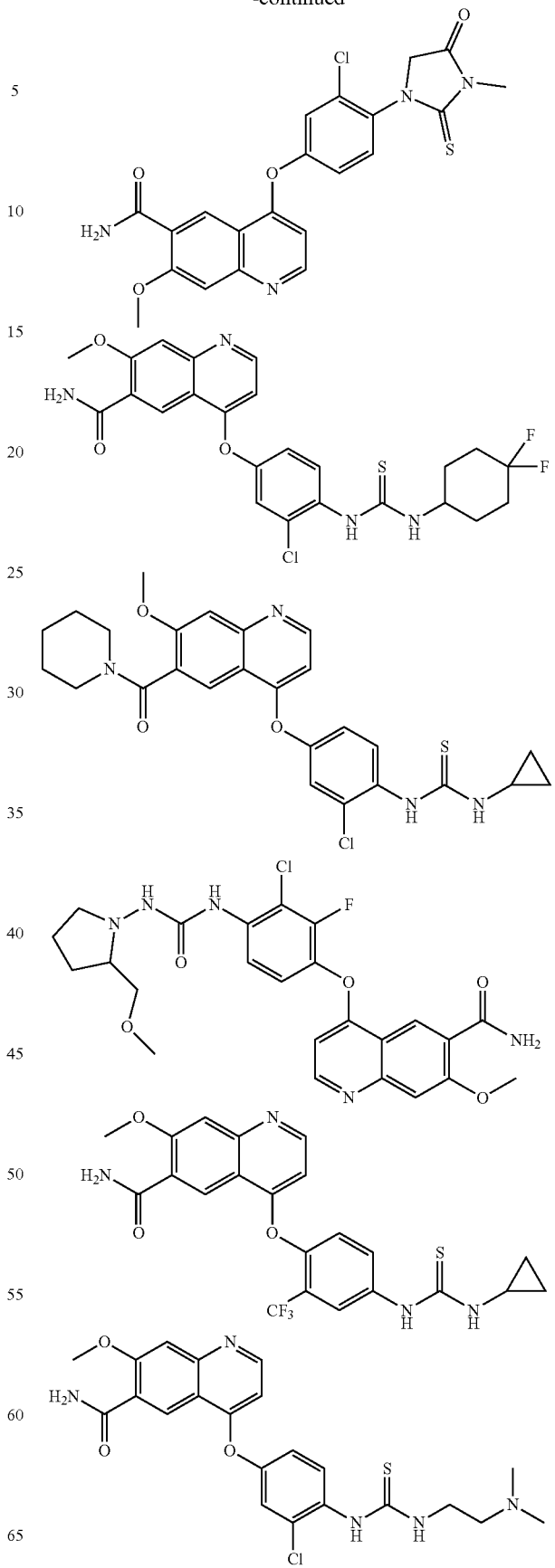

101
-continued
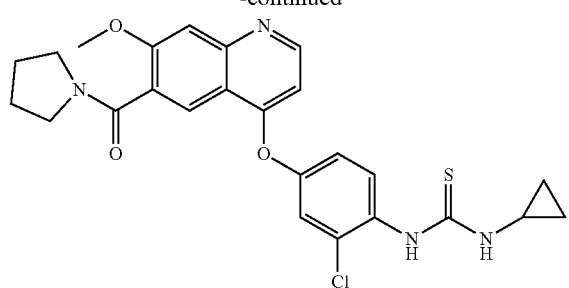
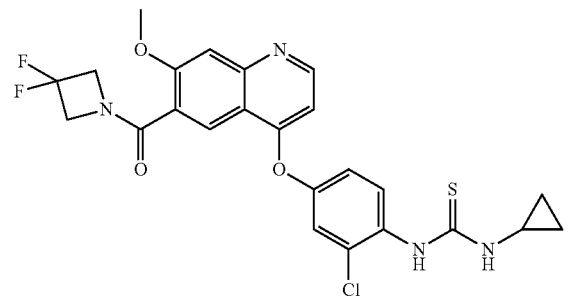
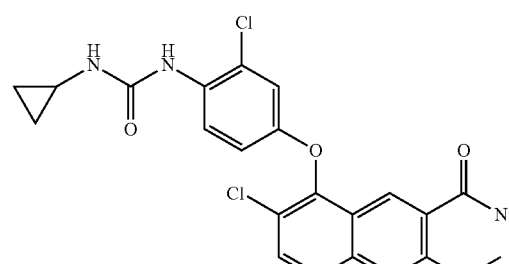
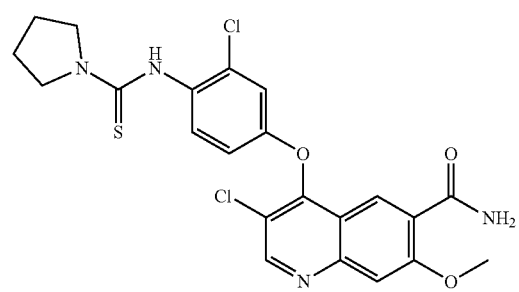
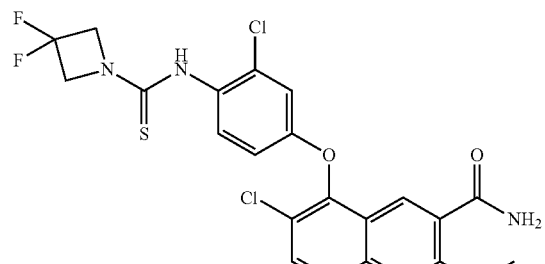
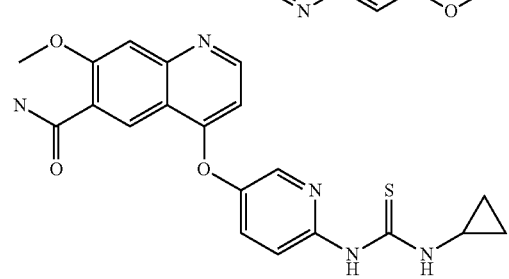
102
-continued
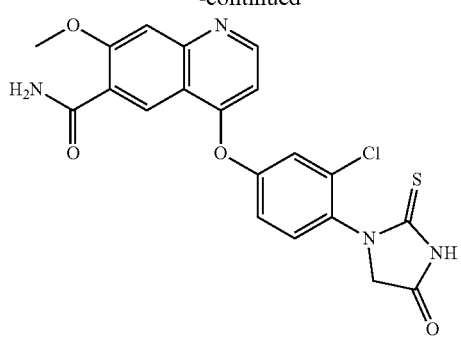
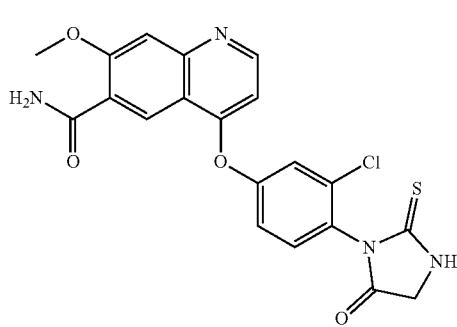
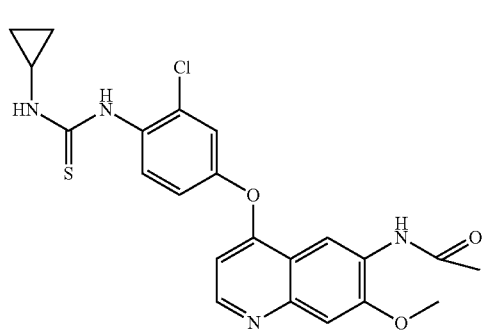
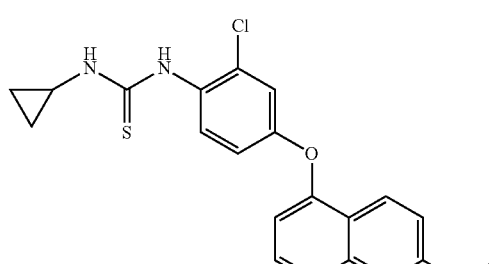
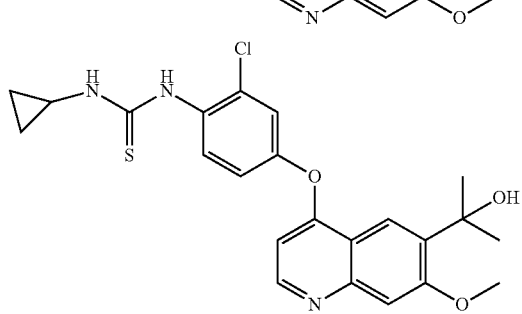

103
-continued
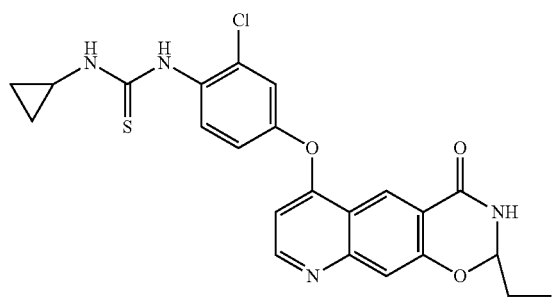
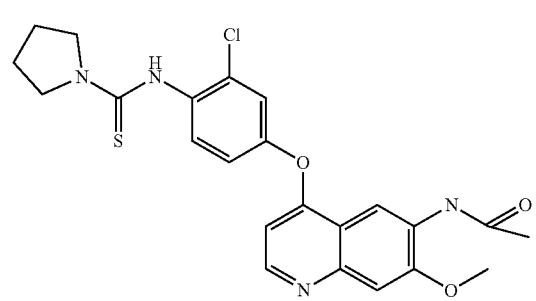
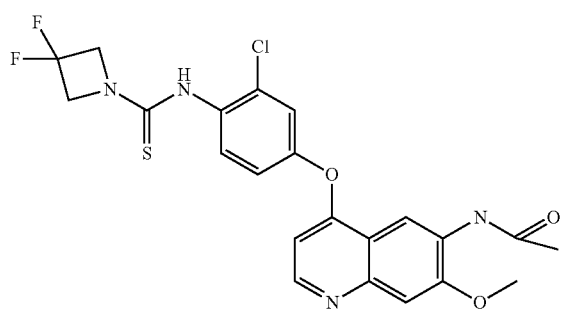
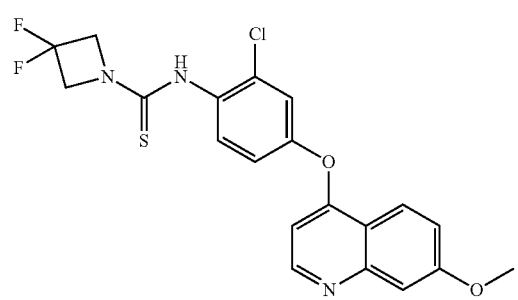
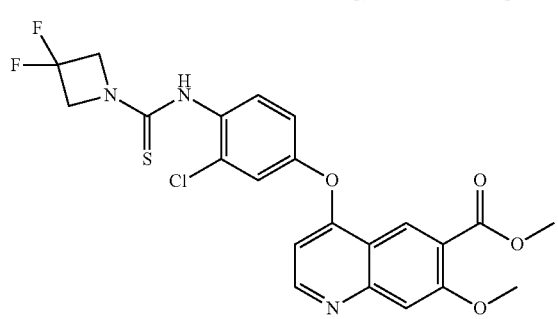
104
-continued
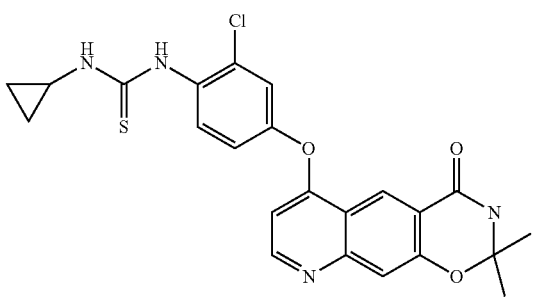
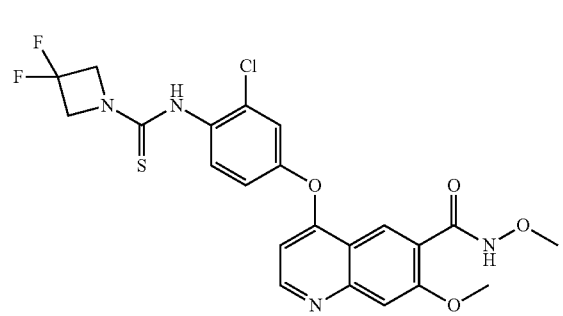
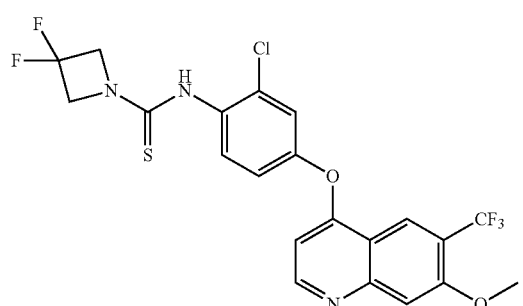
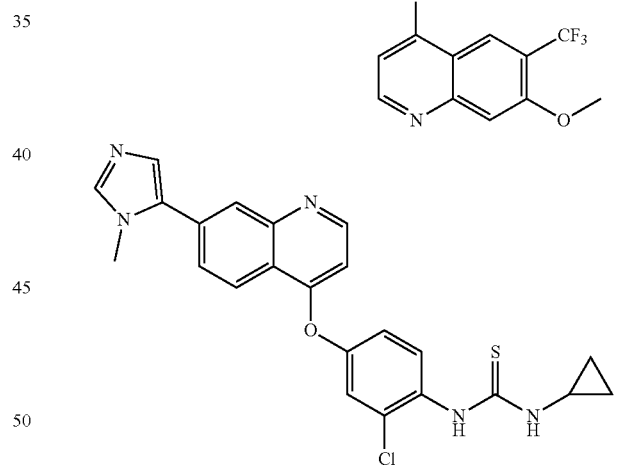
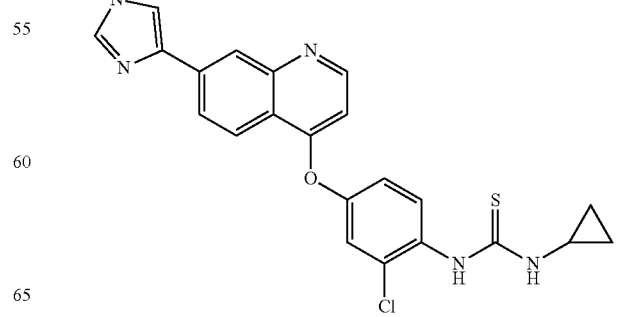

105
-continued
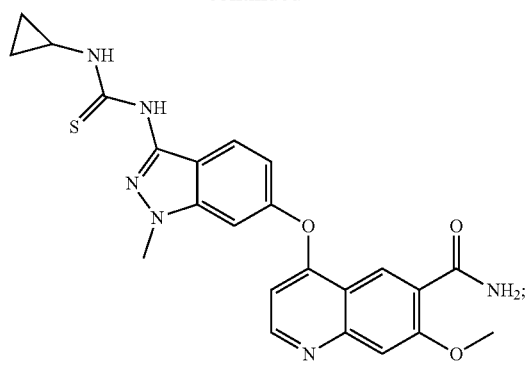
106
-continued
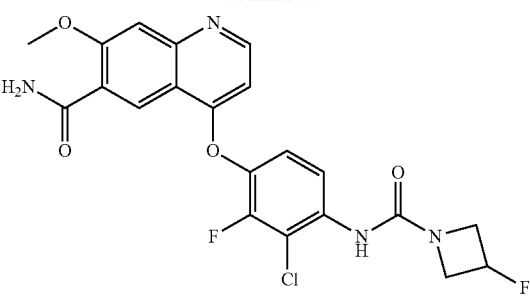
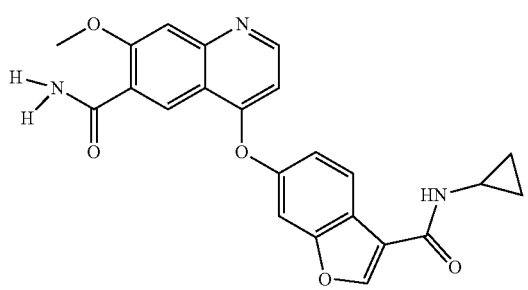
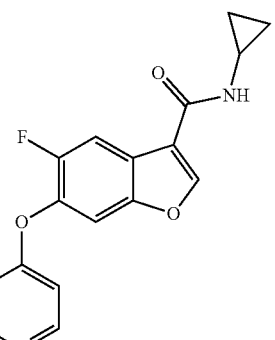
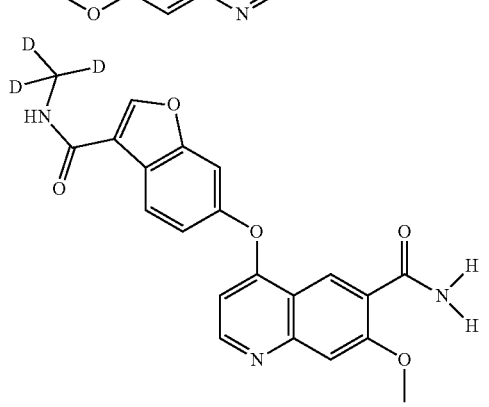
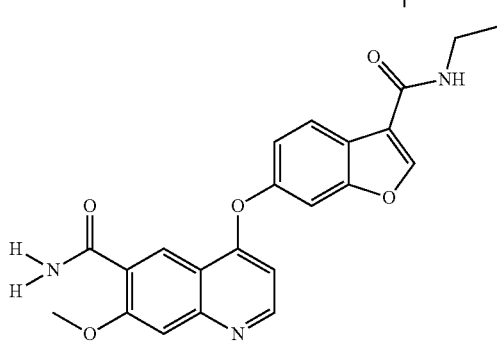

107
-continued
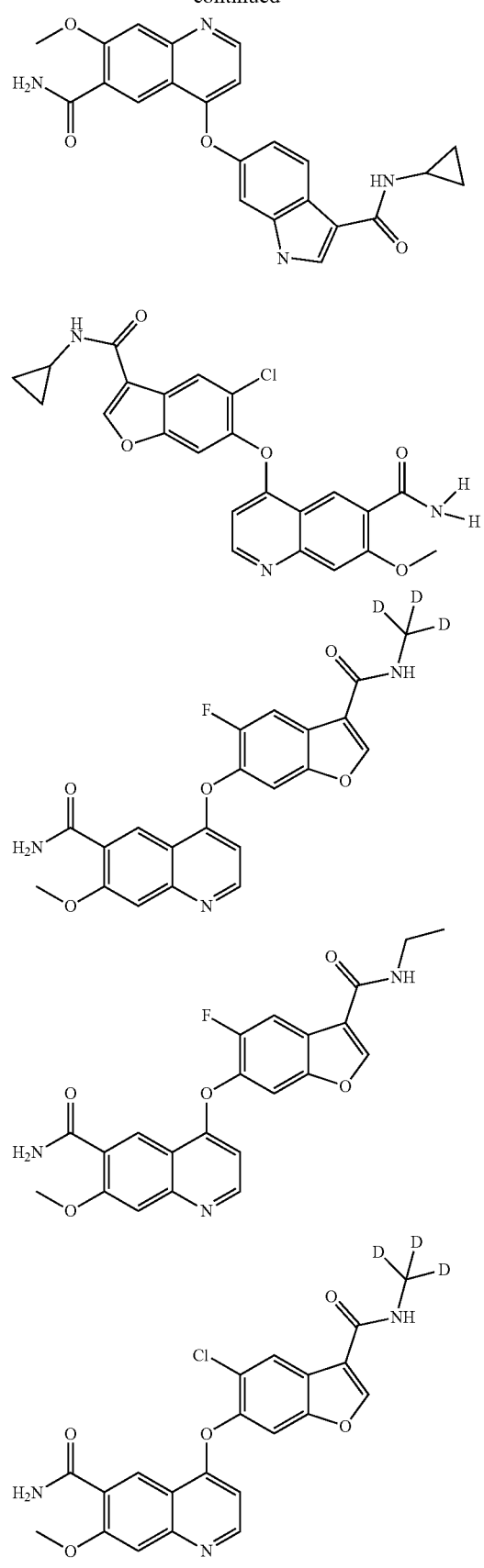
108
-continued
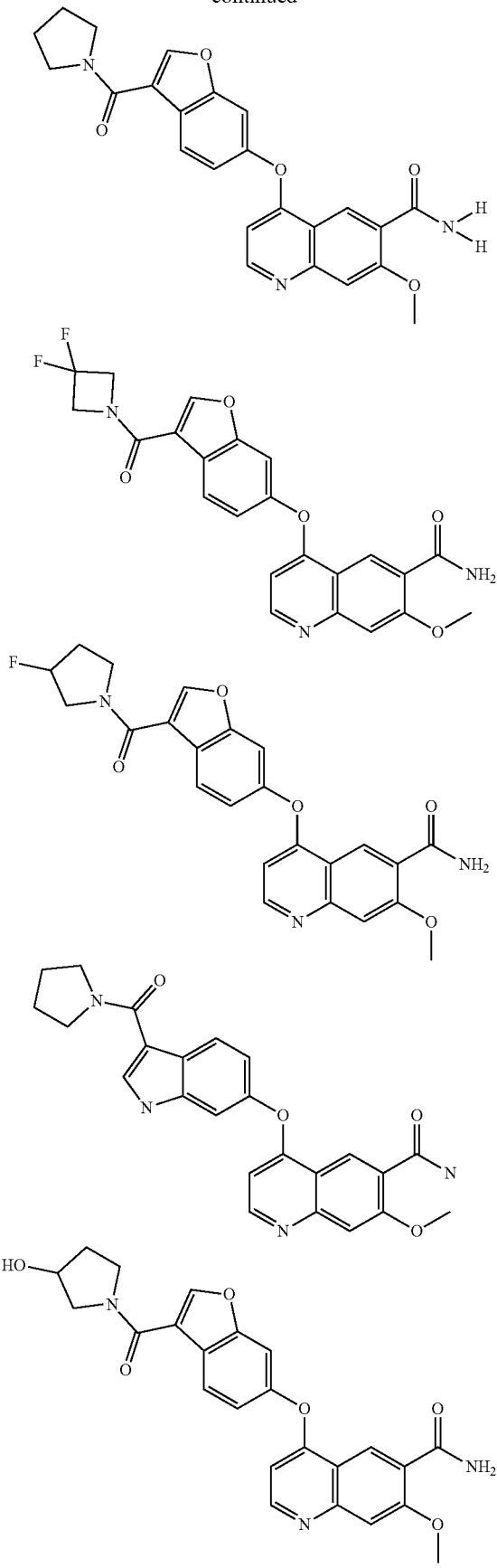

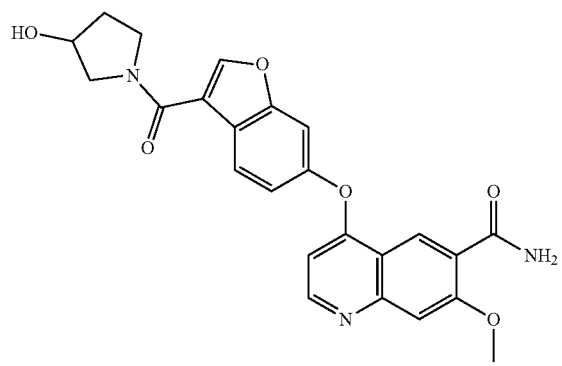
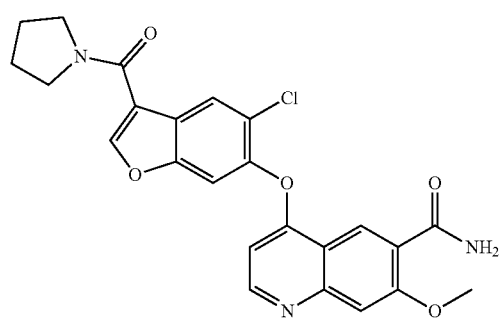
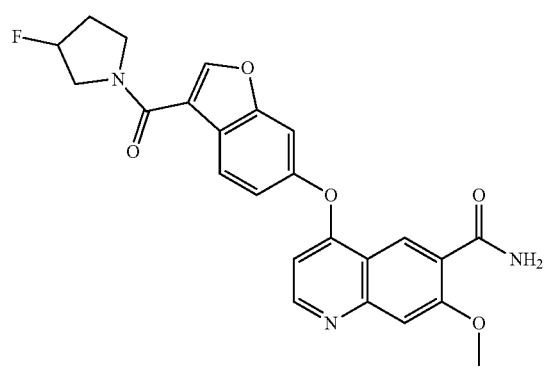
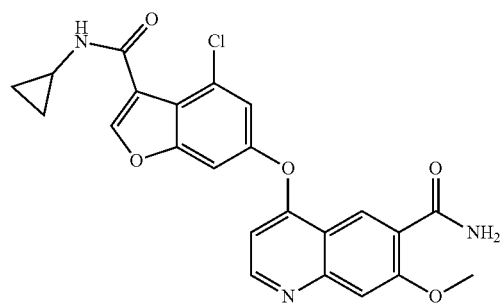
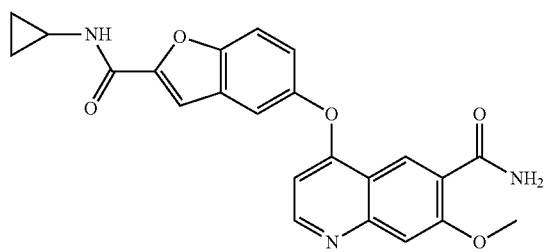
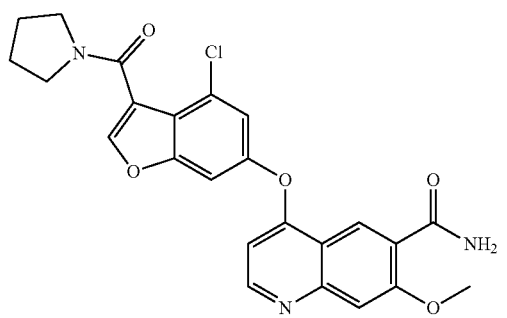
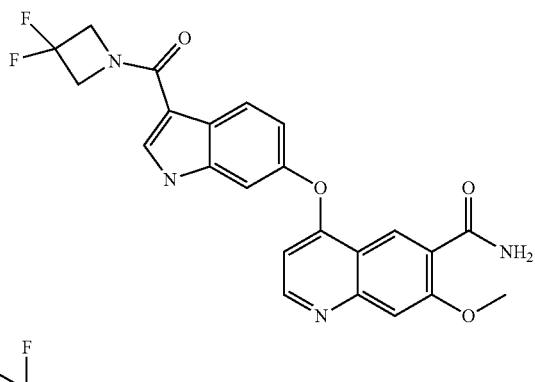
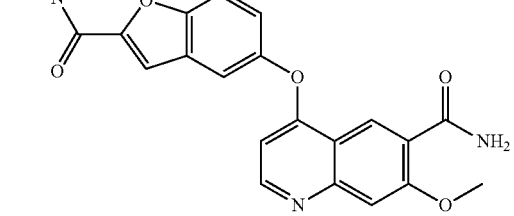
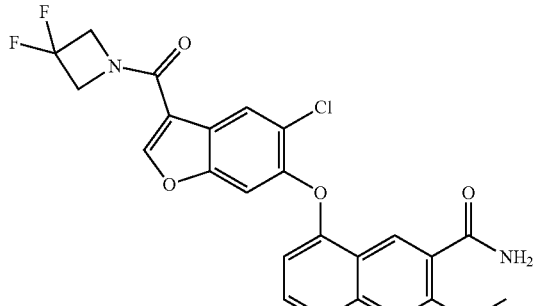
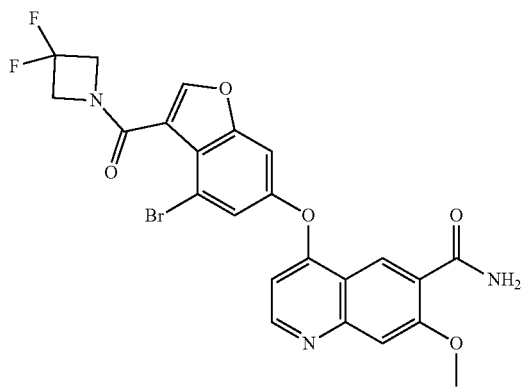

111
-continued
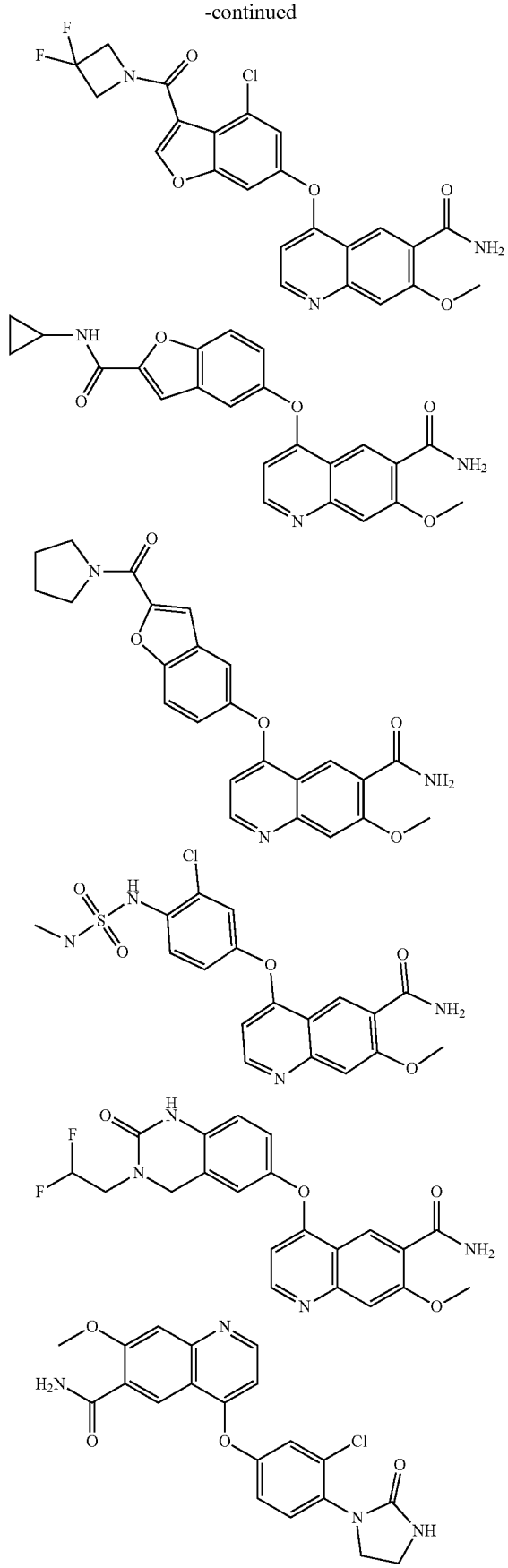
112
-continued
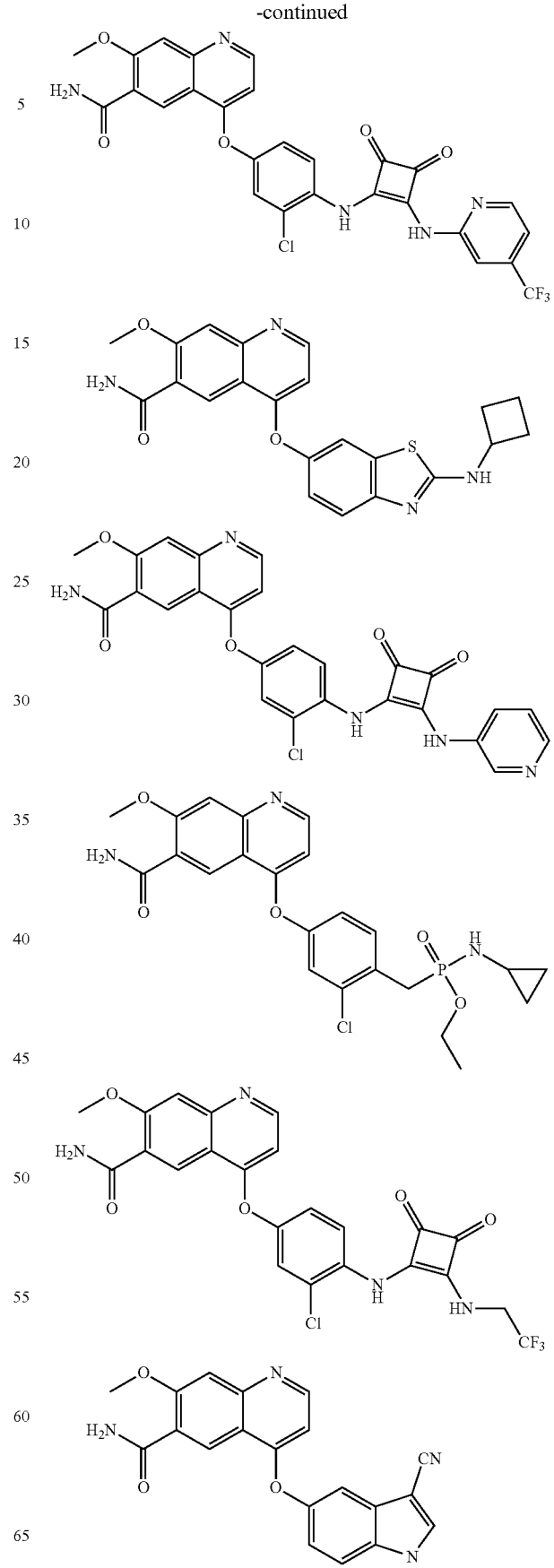

113
-continued
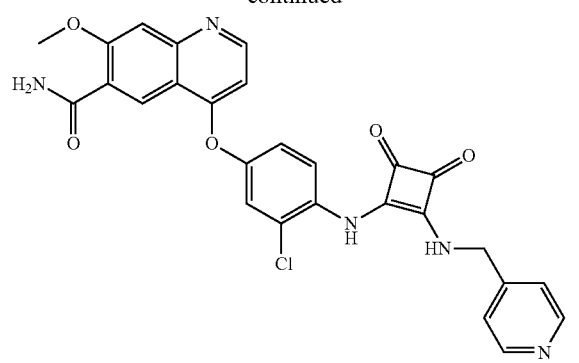
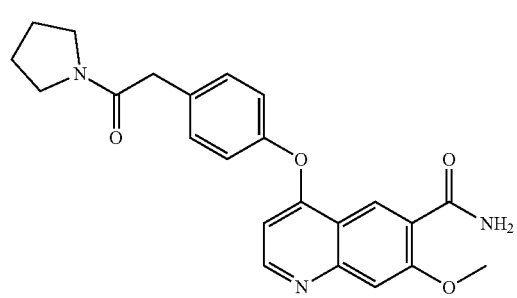
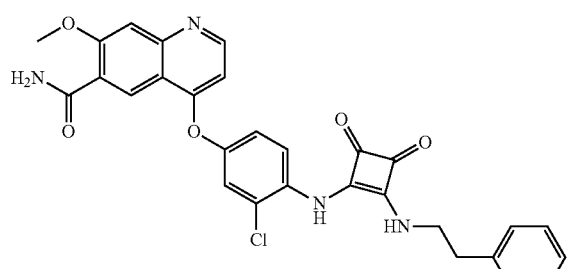
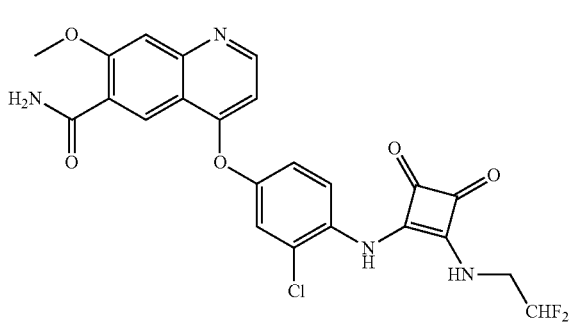
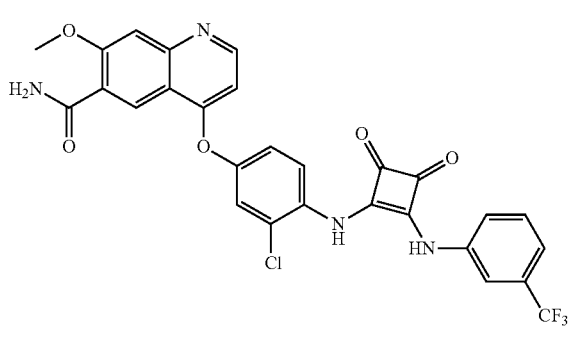
114
-continued
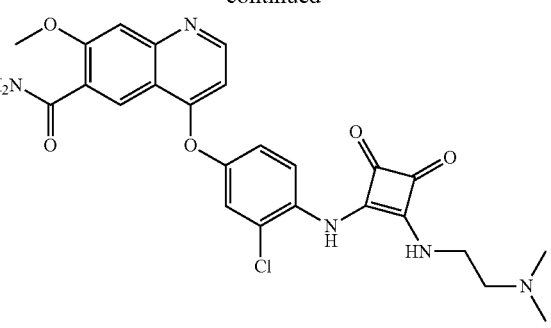
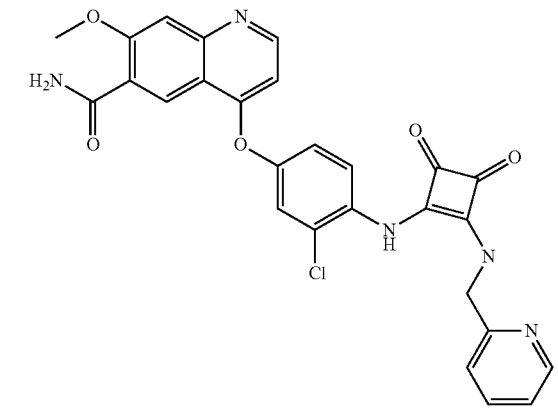
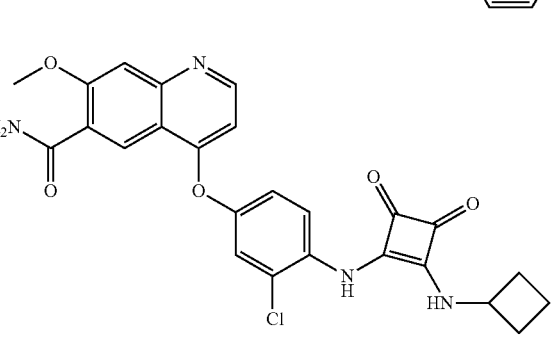
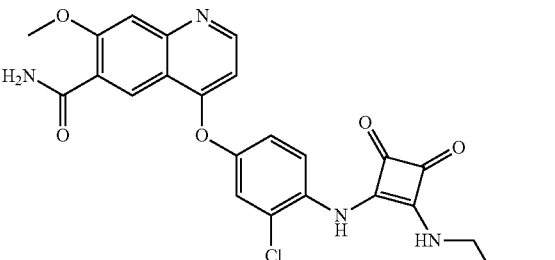
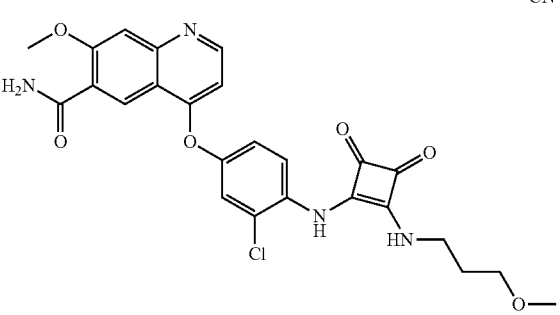

115
-continued
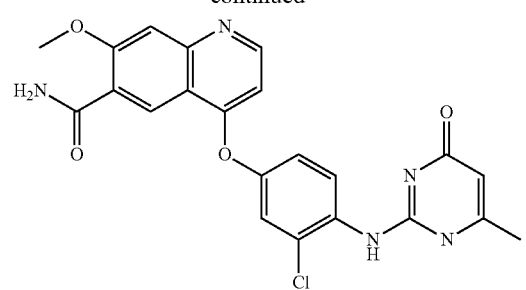
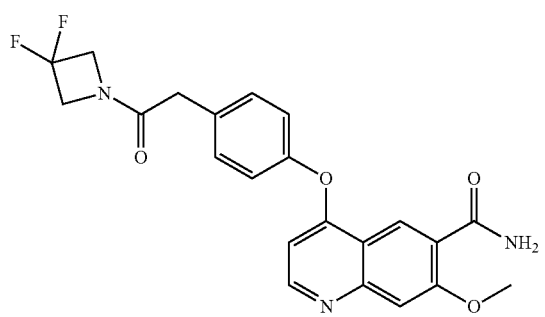
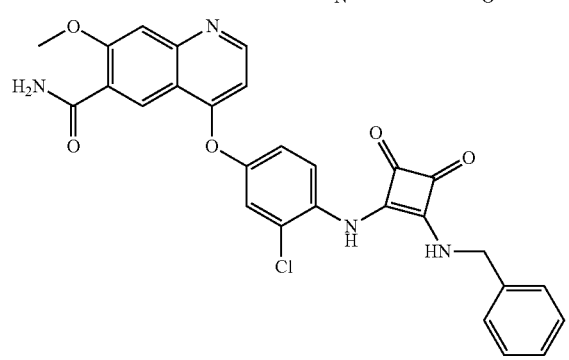
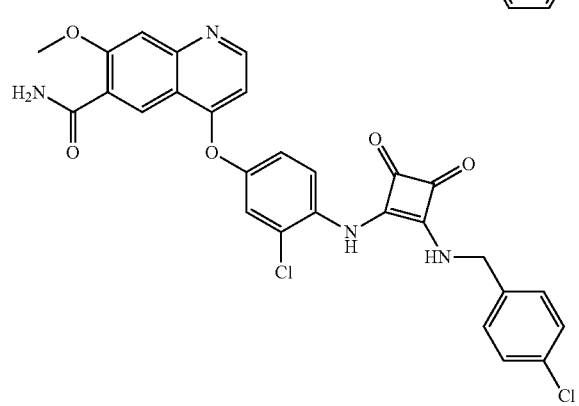
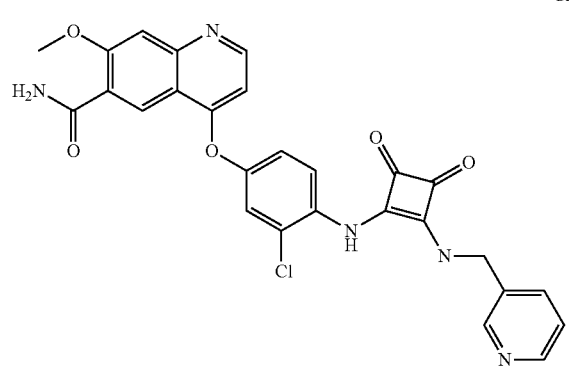
116
-continued
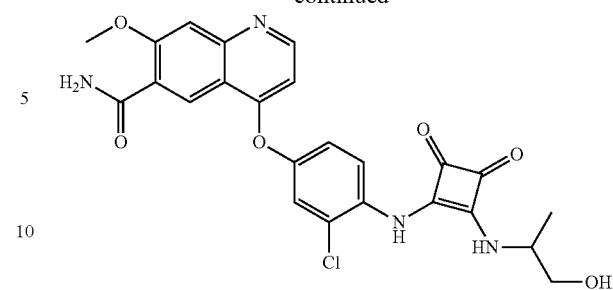
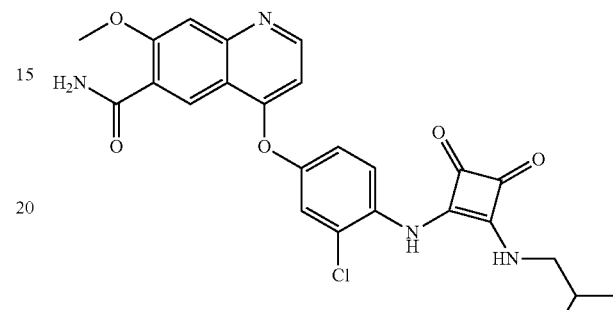
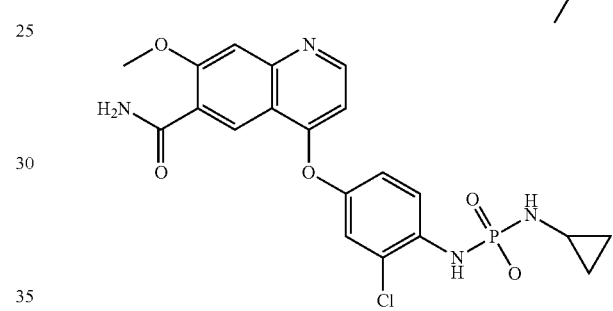
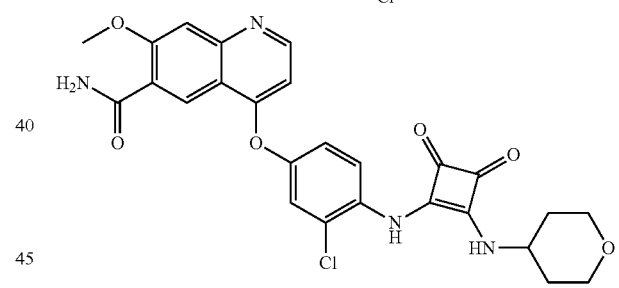
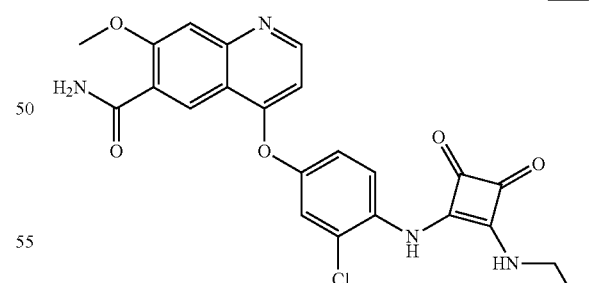
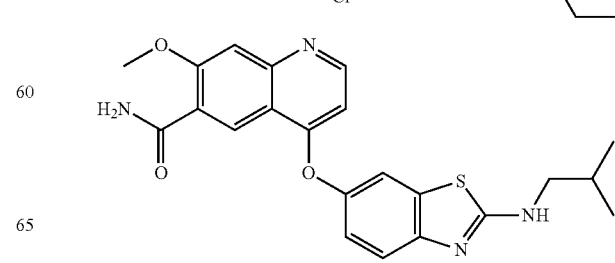

117
-continued
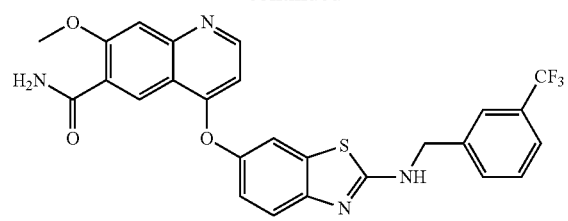
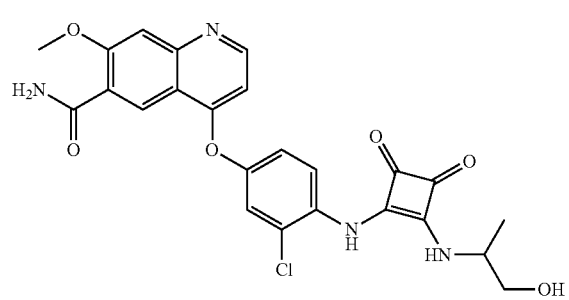
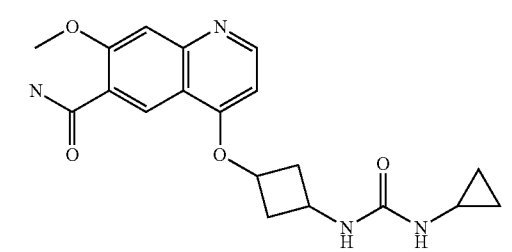
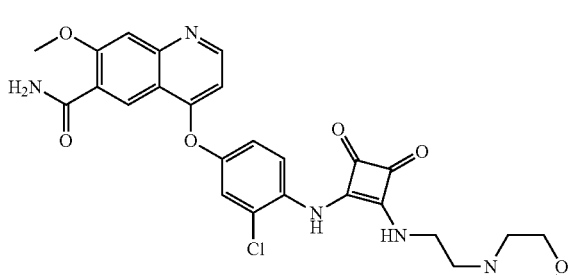
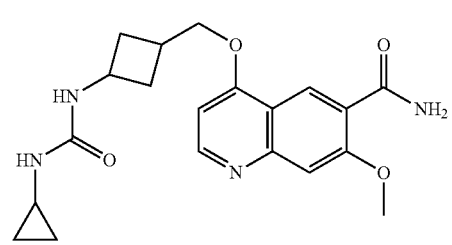
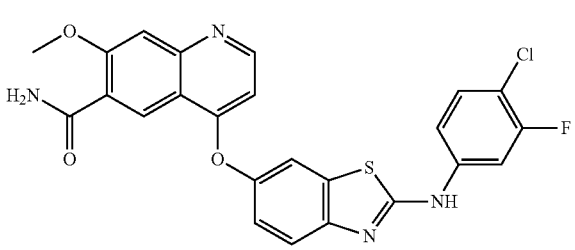
118
-continued
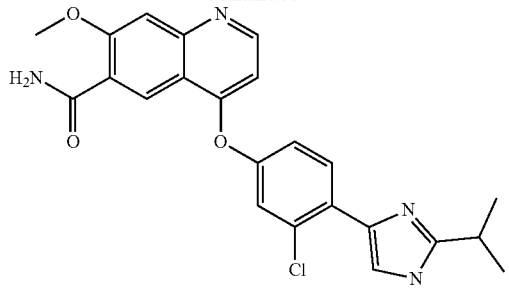
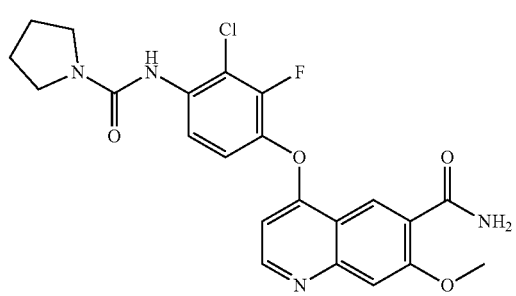
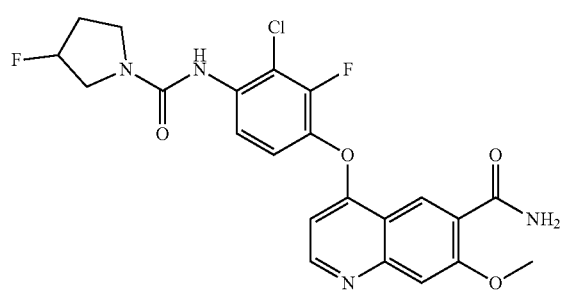
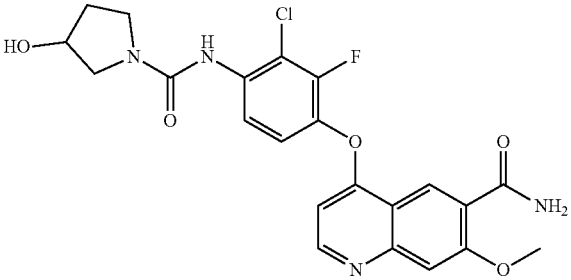
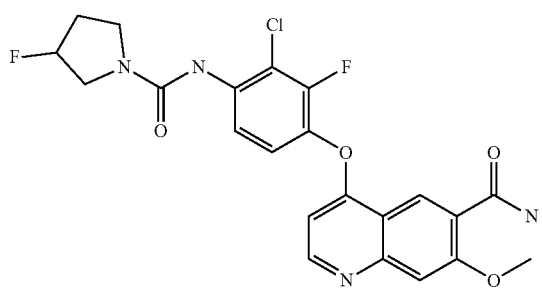

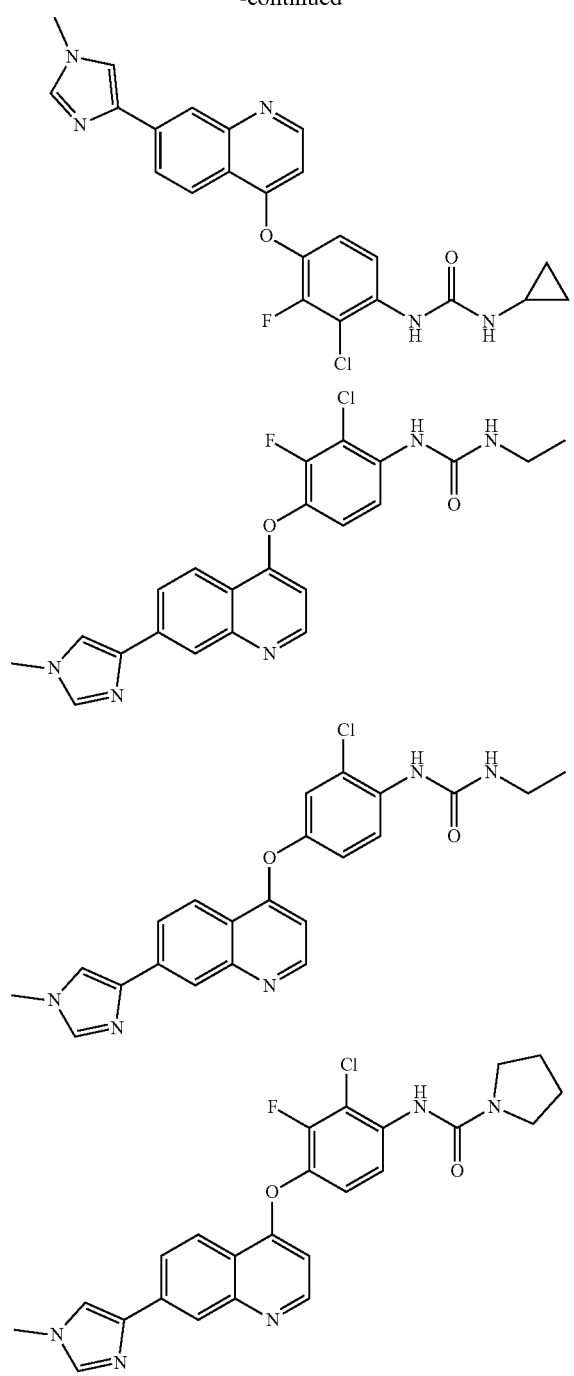
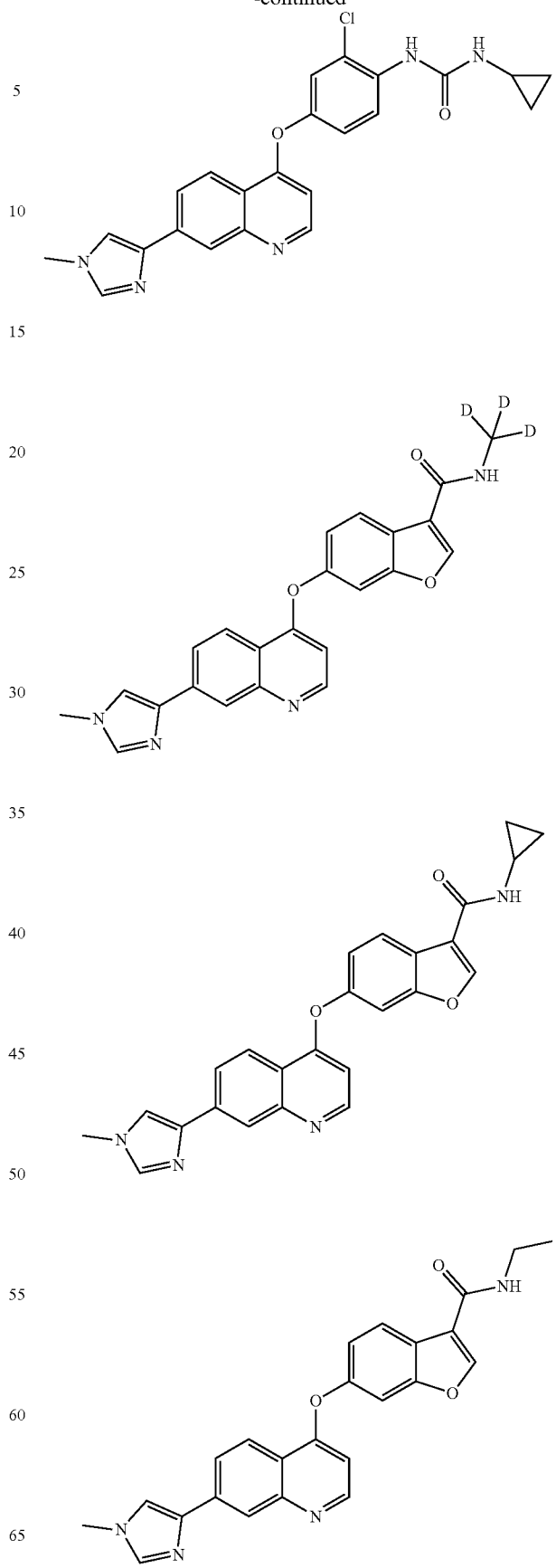

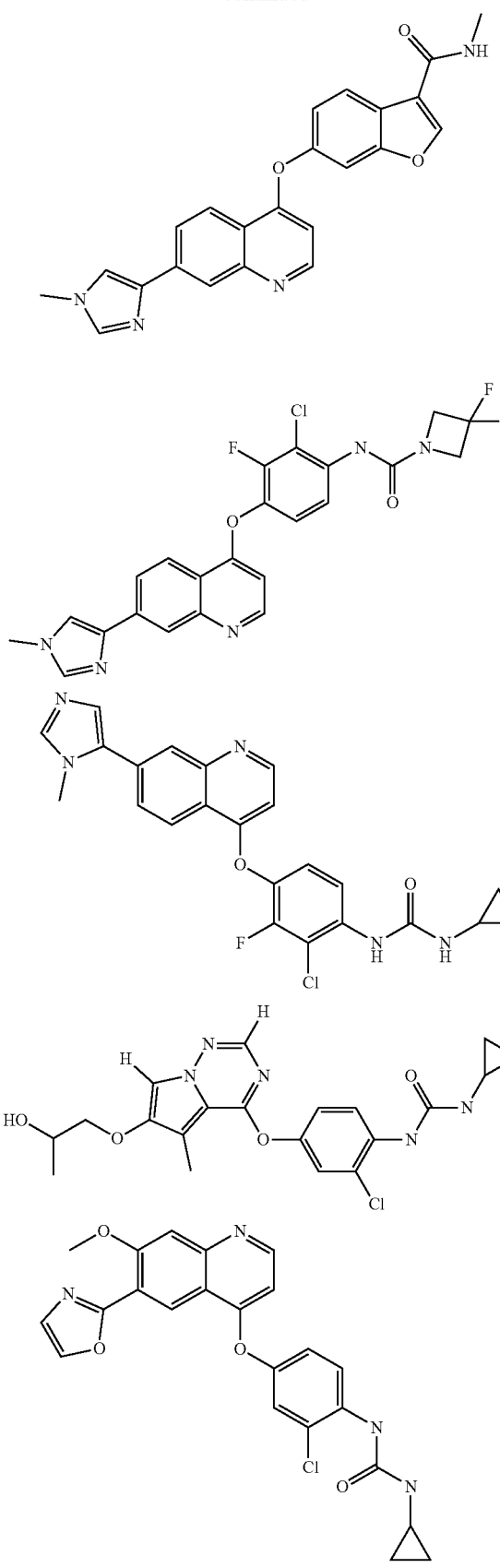
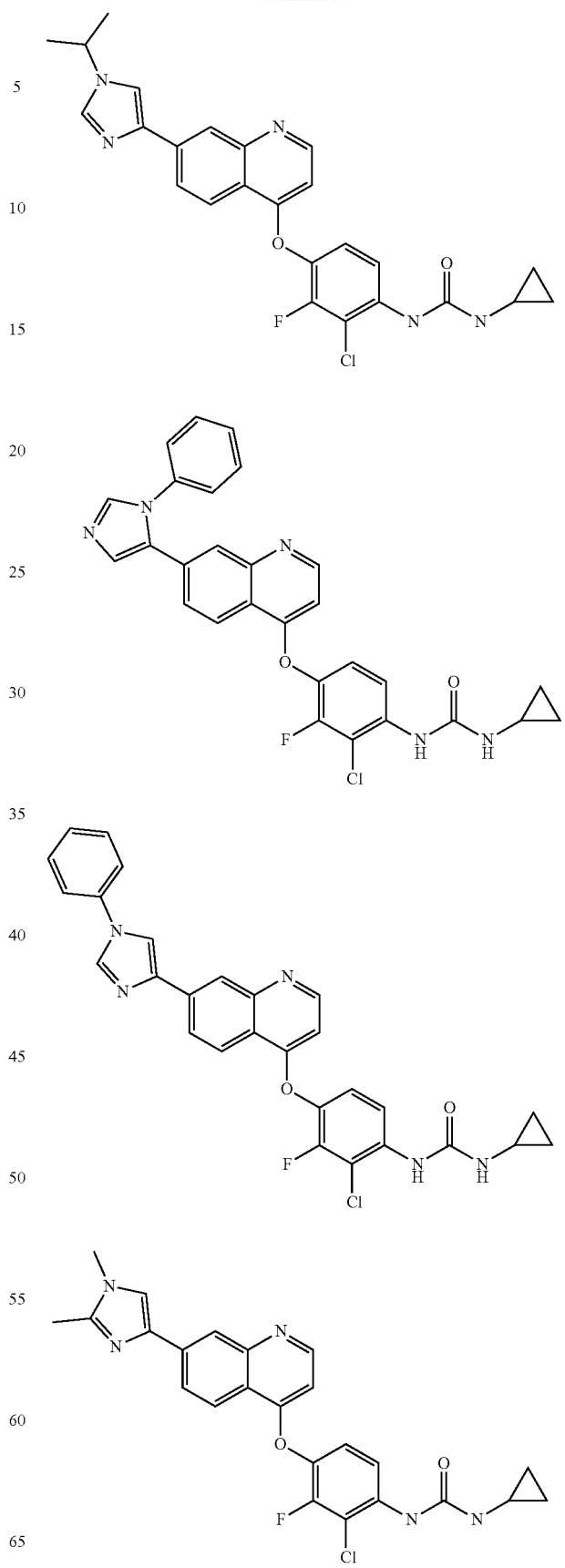

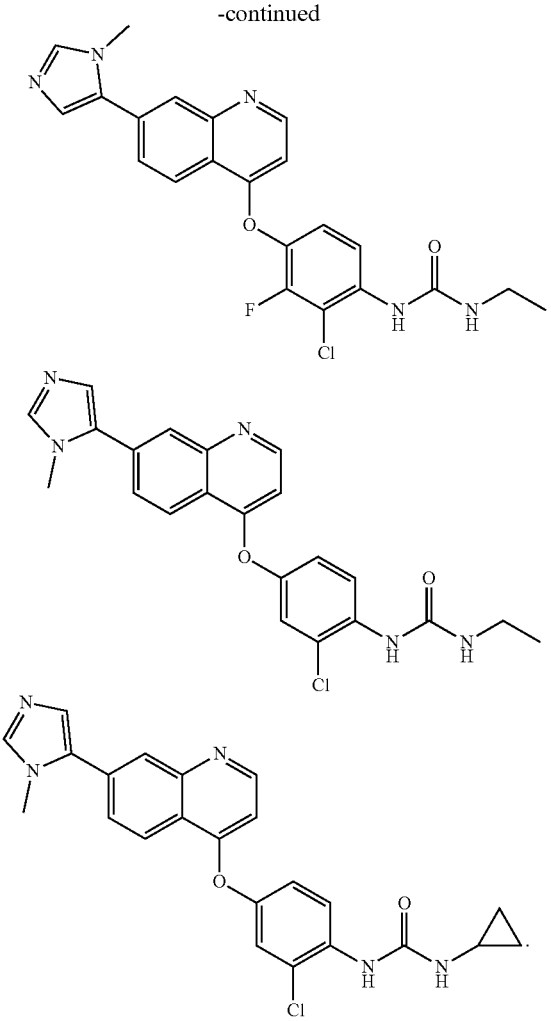

DEFINITION AND DESCRIPTION

Unless otherwise indicated, the following terms and phrases as used herein are intended to have the following meanings. A particular term or phrase should not be considered as undefined or unclear without specific definition, but should be understood in their ordinary sense. When a trade name appears in the present invention, it is intended to refer to its corresponding product or its active ingredient.

$C_{1-7}$ is selected from $C_1$, $C_2$, $C_3$, $C_4$, $C_5$, $C_6$ and $C_7$; 3-6 membered is selected from 3, 4, 5 and 6 membered.

As used herein, the term "therapeutically acceptable" refers to those compounds, materials, compositions and/or dosage forms which are suitable for use in contact with the tissue or organ of humans and animals without excessive toxicity, irritation, allergic response, or other problems or complications within a range of reliable medical judgment, commensurate with a reasonable benefit/risk ratio.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable acid addition salts include inorganic acid salts including for example, hydrochloric acid, hydrobromic acid, nitric acid, carbonic acid, bicarbonate, phosphoric acid, hydrogen phosphate, dihydrogen phosphate, sulfuric acid, bisulfate, hydroiodic acid, phosphorous acid and the like; organic acid salts including such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid; salts of amino acids (such as arginine); and salts of organic acids such as glucuronic acid (see Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

As used herein, "pharmaceutically acceptable salts" belong to derivatives of the compounds of the present invention, wherein, the parent compound is modified by forming an acid addition salt with an acid or forming a base addition salt with a base. Examples of pharmaceutically acceptable salts include, but are not limited to inorganic or organic acid salts of bases such as amines, alkali or organic salts of acids such as carboxylic acids, and the like.

Pharmaceutically acceptable salts include conventional non-toxic salts or quaternary ammonium salts of parent compounds, such as salts formed by non-toxic inorganic or organic acids. Conventional non-toxic salts include, but are not limited to salts derived from inorganic acids and organic acids, which are selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethane disulfonic acid, ethanesulfonic acid, fumaric acid, glucoheptose, gluconic acid, glutamic acid, glycolic acid, hydrobromic acid, hydrochloric acid, hydroiodide, hydroxyl, naphthalenol, isethionic acid, lactic acid, lactose, dodecyl sulfonate, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, calcium folinate, succinic acid, sulfamic acid, p-aminobenzenesulfonic acid, sulfuric acid, tannin, tartaric acid and p-toluenesulfonic acid.

The pharmaceutically acceptable salts of the present invention can be synthesized from the parent compounds containing acids or bases by conventional chemical methods. In general, such salts are prepared by reacting these compounds in the form of free acids or bases with a stoichiometric amount of a suitable base or acid in water or an organic solvent or a mixture of the two. In general, nonaqueous media such as ether, ethyl acetate, ethanol, isopropanol or acetonitrile are preferred.

In addition to the form of the salt, the compounds provided by the present invention also may be in the form of prodrugs. The prodrugs of the compounds described herein readily undergo chemical changes under physiological conditions to provide the compounds of the present invention.

In addition, prodrugs can be converted to the compounds of the invention by chemical or biochemical methods in an in vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention.

The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and D and L isomers can be prepared using chiral synthons, or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the present invention may contain non-natural proportions of atomic isotopes at one or more atoms constituting the compound. For example, the compounds can be labeled with radioisotopes, such as tritium ($^3$H), iodine-125 ($^{125}$I) or C-14 ($^{14}$C). All isotopic compositions of the compounds of the present invention, whether radioactive or not, are included within the scope of the present invention.

The term "pharmaceutically acceptable carrier" refers to any formulation or carrier medium that can deliver an effective amount of the active substance of the present invention without interfering with the biological activity of the active substance and that is non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of topical pharmaceuticals. Additional information concerning carriers can be found in Remington: The Science and Practice of Pharmacy, 21st Ed., Lippincott, Williams & Wilkins (2005) which is incorporated herein by reference.

The term "excipient" generally refers to carriers, diluents and/or vehicles used in formulating drug compositions effective for the desired use.

For drugs or pharmacologically active agents, the term "effective amount" or "therapeutically effective amount" refers to the amount of the drugs or agents, which is non-toxic but can achieve the desired effect. For oral dosage forms of the present invention, the "effective amount" of the active substance in the composition refers to the amount required to achieve the desired effect when used in combination with another active substance in the composition. The amount of the effective amount varies from person to person, depending on the age and general condition of the receptor and on the specific active substance. A suitable effective amount in the case may be determined by a person skilled in the art in accordance with routine testing.

The term "active ingredient" "therapeutic agent" "active substance" or "active agent" refers to a chemical entity which is effective in treating target disorder, disease or symptoms.

The term "substituted" refers to that any one or more of the hydrogen atoms on a particular atom is substituted with a substituent, including a variant of heavy hydrogen and hydrogen, as long as the valence of the particular atom is normal and the substituted compound is stable. When the substituent is a ketone group (i.e., =O), it means that two hydrogen atoms are substituted. Ketone substitutions do not occur on aromatic groups. The term "optionally substituted" refers to that it may be substituted or may not be substituted, unless otherwise specified, the kind and number of substituents may be arbitrarily when they are chemically achievable.

When any variable (e.g., R) occurs more than once in the composition or structure of the compound, its definition in each case is independent. Thus, for example, if a group is substituted with 0-2 R, the group may optionally be substituted up to at least two R, and in each case R has a separate option. In addition, combinations of substituents and/or variants thereof are permissible only if such combination produces a stable compound.

When one of the variables is selected from a single bond, it indicates that the two groups to which they are attached are directly connected, for example, when L represents a single bond in A-L-Z, the structure is actually A-Z.

When a bond of a substituent may be cross-linked to two atoms on a ring, the substituent may be bonded to any atom on the ring. When the listed substituents do not be specified which atom to pass through to the compounds included in the general formula but not specifically mentioned, such substituents may be bonded through any of their atoms. The combination of substituents and/or variants thereof is permissible only if such combination produces a stable compound.

For example, the structural unit

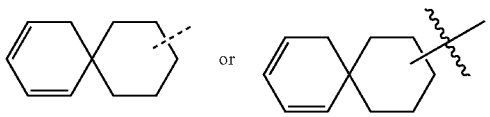

indicates that it may be substituted at any position on a cyclohexyl group or a cyclic diene.

Substituents of alkyl and heteroalkyl atoms group are generally referred to as "alkyl substituents" and they may be selected from, but not limited to, one or more of the following groups: —R', —OR', =O, =NR', =N—OR', —NR'R", —SR', halogen, —SiR'R"R''', OC(O)R', —C(O)R', —CO$_2$R', —CONR'R", —OC(O)NR'R", —NR"C(O)R', NR' C(O)NR"R''', —NR"C(O)$_2$R', —NR''''-C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro (C$_1$-C$_4$) alkyl, the number of substituents is 0-(2m'+1), where m' is the total number of carbon atoms in such groups. R', R", R''', R'''' and R''''' are each independently preferably hydrogen, substituted or unsubstituted heteroalkyl, substituted or unsubstituted aryl (e.g., aryl substituted with 1 to 3 halogens), substituted or unsubstituted groups such as alkyl, alkoxy group, thioalkoxy group or aralkyl group. When the compound of the present invention comprises more than one R group, for example, each R group is independently selected as each of these groups when more than one R', R", R''', R'''' and R''''' groups are present. When R' and R" are attached to the same nitrogen atom, they may bind to the nitrogen atom to form a 5-, 6- or 7-membered ring. For example, —NR'R" is intended to include but is not limited to 1-pyrrolidinyl and 4-morpholinyl. According to the above discussion of substituents, it will be understood by those skilled in the art that the term "alkyl" is intended to include groups in which carbon atoms are bonded to non-hydrogen groups such as haloalkyl (e.g., —CF$_3$, —CH$_2$CF$_3$) and acyl groups (e.g., —C(O)CH$_3$, —C(O)CF$_3$, —C(O)CH$_2$OCH$_3$, etc.).

Similar with the substituents of the alkyl, the aryl and heteroaryl substituents are collectively referred to as "aryl substituents", they are selected from, for example, —R', —OR', —NR'R", —SR', -halogen, —SiR'R"R''', OC(O)R', —C(O)R', —CO$_2$R', —CONR'R", —OC(O)NR'R", —NR"C(O)R', NR' C(O)NR"R''', —NR"C(O)$_2$R', —NR''''—C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro (C$_1$-C$_4$) alkoxy and fluoro (C$_1$-C$_4$) alkyl, etc, the number of substituents is between 0 and the total number of open valences on the aromatic ring; wherein R', R", R''', R'''' and R''''' are each independently preferably selected from hydrogen, substituted or unsubstituted alkyl, substituted or unsubstituted heteroalkyl, substituted or unsubstituted aryl and substituted or unsubstituted heteroaryl. When the compounds of the present invention include more than one R group, for example each R group is independently selected, as each of these groups when more than one R', R", R''', R'''' and R''''' groups are present.

The two substituents on adjacent atoms of aryl or heteroaryl ring may be optionally substituted with the substituents represented by the general formula -TC(O)—(CRR')qU-, where T and U are independently selected from —NR—, —O—, CRR'— and a single bond, and q is an integer of 0 to 3. Alternatively, the two substituents on adjacent atoms of an aryl or heteroaryl ring may be optionally substituted with the substituent represented by the general formula -A(CH$_2$)rB-, where A and B are independent selected from —CRR'—, —O—, —NR—, —S—, —S(O)—, S(O)$_2$—, —S(O)$_2$NR'— and a single bond, and r is an integer of 1 to 4. Optionally, a single bond on the resulting new ring may be replaced by a double bond. Alternatively, the two substituents on the adjacent atom of the aryl or heteroaryl ring may be optionally substituted by -A(CH$_2$)rB-, wherein s and d are each independently selected from an integer of 0 to 3, X is —O—, —NR', —S—, —S(O)—, —S(O)$_2$— and —S(O)$_2$NR'—. The substituents R, R', R" and R''' are each independently preferably selected from hydrogen and substituted or unsubstituted (C$_1$-C$_6$) alkyl.

The term "halo" or "halogen" itself or as a part of another substituent represent fluorine, chlorine, bromine or iodine atom, unless otherwise specified. In addition, the term "haloalkyl" is intended to include monohaloalkyl and polyhaloalkyl. For example, the term "halo (C$_1$-C$_4$) alkyl" is intended to include but is not limited to trifluoromethyl, 2,2,2-trifluoroethyl 4-chlorobutyl and 3-bromopropyl, etc.

Examples of haloalkyl include, but are not limited to trifluoromethyl, trichloromethyl, pentafluoroethyl, and pentachloroethyl. The "alkoxy" represents the above-mentioned alkyl having a specific number of carbon atoms attached through an oxygen bridge. C$_{1-6}$ alkoxy include C$_1$, C$_2$, C$_3$, C$_4$, C$_5$ and C$_6$ alkoxy. Examples of alkoxy include, but are not limited to methoxy, ethoxy, n-propoxy, isopropoxy, n-butoxy, sec-butoxy, t-butoxy, n-pentyloxy and S-pentyloxy. The "cycloalkyl" includes saturated cyclic groups such as cyclopropyl, cyclobutyl or cyclopentyl. 3-7 cycloalkyl includes C$_3$, C$_4$, C$_5$, C$_6$ and C$_7$ cycloalkyl. The "alkenyl" includes straight or branched configuration of chain hydrocarbon, wherein one or more carbon-carbon double bonds, such as vinyl and propenyl, are present at any stable site on the chain.

The term "halogen" or "halogen" refers to fluorine, chlorine, bromine and iodine.

Unless otherwise specified, the term "hetero" represents heteroatom or heteroatom group (i.e. atoms group containing heteroatoms), which includes atoms other than carbon (C) and hydrogen (H) and atoms group containing such heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)2-, and optionally substituted groups including —C(=O)N(H)—, —N(H)—, —C(=NH)—, —S(=O)$_2$ N(H)— or —S(=O) N(H)—.

Unless otherwise specified, the term "ring" represents substituted or unsubstituted cycloalkyl, heterocycloalkyl, cycloalkenyl, heterocycloalkenyl, cycloalkynyl, heterocycloalkynyl, aryl or heteroaryl. The so-called ring includes single ring, combined ring, spirocyclic, fused ring or bridged ring. The number of atoms on the ring is usually defined as the number of rings, for example "5-7 membered ring" means that 5 to 7 atoms are arranged around the ring. Unless otherwise specified, the ring optionally contains 1 to 3 heteroatoms. Thus, the term "5-7 membered ring" includes for example phenyl, pyridinyl and piperidinyl; and on the other hand, the term "5-7 membered heterocycloalkyl ring" includes pyridyl and piperidinyl, but does not include phenyl. The term "ring" also includes the ring system containing at least one ring, in which each "ring" independently meets the above definition.

Unless otherwise specified, the term "heterocycle" or "heterocyclyl" refers to stable monocyclic bicyclic or tricyclic ring containing heteroatoms or heteroatoms group, which may be saturated, partially unsaturated or unsaturated (aromatic) and contain carbon atoms and 1, 2, 3 or 4 heteroatoms independently selected from N, O and S, wherein any of the above heterocycles may be fused to a benzene ring to form a bicyclic. The nitrogen and sulfur heteroatoms may optionally be oxidized (i.e. NO and S(O)$_p$). The nitrogen atom may be a substituted or unsubstituted (i.e. N or NR, wherein R is H or other substituents already defined herein). The heterocyclic ring may be attached to the side groups of any heteroatom or carbon atom to form a stable structure. If the resulting compound is stable, the heterocyclic ring described herein may be substituted at the carbon or nitrogen position. The nitrogen atom in the heterocycle is optionally quaternized. In a preferred embodiment, when the total number of S and O atoms in the heterocycle exceeds one, these heteroatoms are not adjacent to each other. Another preferred embodiment is that the total number of S and O atoms in the heterocycle does not exceed one. As used herein, the term "aromatic heterocyclic" or "heteroaryl" refers to stable aromatic ring of 5, 6, 7 membered monocyclic or bicyclic or 7, 8, 9 or 10 membered bicyclic heterocyclyl, which contains carbon atoms and 1, 2, 3 or 4 heteroatoms independently selected from N, O and S. The nitrogen atom may be substituted or unsubstituted (i.e. N or NR, wherein R is H or other substituents already defined herein). The nitrogen and sulfur heteroatoms may optionally be oxidized (i.e. NO and S(O)$_p$). It is worth noting that the total number of S and O atoms on the aromatic heterocycle does not exceed one. The bridge ring is also included in the definition of the heterocycle. A bridge ring is formed when one or more atoms (i.e. C, O, N or S) are attached to two non-adjacent carbon atoms or nitrogen atoms. Preferred bridge rings include but are not limited to one carbon atom, two carbon atoms, one nitrogen atom, two nitrogen atoms and one carbon-nitrogen. It is noteworthy that a bridge always converts a monocyclic ring into a tricyclic ring. In the bridge ring, the substituents on the ring can also appear on the bridge.

Examples of heterocyclic compounds include, but are not limited to acridinyl, azocinyl, benzimidazolyl, benzofuranyl, benzsulfanylfuryl, benzsulfanylphenyl, benzoxazolyl, benzoxazolinyl, benzothiazolyl, benzotriazolyl, benzotetrazoyl, benzisoxazolyl, benzisothiazolyl, benzimidazolyl, tetrazolyl, 4aH-tetrazolyl, carbolinyl, chromanyl, chromene, cinnolinyl, decahydroquinolyl, 2H, 6H-1, 5,2-dithiazinyl, dihydrofuro[2,3-b] tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridyl, phenanthroline, phenazine, phenothiazinyl, benzoxanthin, phenoxazinyl, phthalazinyl, piperazinyl, piperidinyl, piperidone, 4-piperidone, piperonyl, pteridinyl, purine, pyran, pyrazinyl, pyrazolidinyl, pyrazolinyl, pyrazolyl, pyridazinyl, pyridoxazoles, pyridoimidazole, pyridothiazole, pyridyl, pyrimidinyl, pyrrolidinyl, pyrrolinyl, 2H-pyrryl, pyrryl, pyrazolyl, quinazolinyl, quinolyl, 4H-quinoline, quinoxalinyl, quinuclidinyl, tetrahydrofuranyl, tetrahydroisoquinolyl, tetrahydroquinolinyl, tetrazolyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolyl, thienyl, isothienyl, thieno-oxazolyl, thienothi- azolyl, thienoimidazolyl, thienyl, triazinyl, 1,2,3-triazolyl, 1,2,4-triazolyl, 1,2,5-triazolyl, 1,3,4-triazolyl and xanthene, and also include fused ring and spiro compounds.

Unless otherwise specified, the term "hydrocarbyl" or its subordinate concept (e.g., alkyl, alkenyl, alkynyl, phenyl, etc.) itself or as part of another substituent represents straight, branched or cyclic hydrocarbon atoms group or combinations thereof, which may be fully saturated, mono or polyunsaturated, and may be mono-, di- or poly-substituted, and may be monovalent (e.g., methyl), divalent (e.g., methylene) or polyvalent (e.g., methenyl), and may include divalent or polyvalent radical having a specified number of carbon atoms (e.g., $C_1$-$C_{10}$ represent 1 to 10 carbons). "Hydrocarbyl" includes but is not limited to aliphatic and aromatic groups, the aliphatic groups include chain and cyclic, and specifically include but not limited to alkyl, alkenyl, alkynyl, the aromatic groups include but not limited to 6-12 membered aromatic groups such as benzene, naphthalene, etc. In some Examples, the term "hydrocarbyl" refers to straight or branched atoms group or combinations thereof, which may be fully saturated, mono or polyunsaturated, and may include divalent and polyvalent radicals. Examples of saturated hydrocarbon atoms group include, but are not limited to methyl, ethyl, n-propyl, isopropyl, n-butyl, t-butyl, isobutyl, sec-butyl, isobutyl, cyclohexyl, (cyclohexyl) methyl, cyclopropylmethyl, and n-pentyl, n-hexyl, n-heptyl, n-octyl and other homolog or isomer of radicals. The unsaturated alkyl group has one or more double bonds or triple bond, examples of which include, but are not limited to vinyl, 2-propenyl, butenyl, butenyl, crotonyl, 2-isopentenyl, 2-(butadienyl), 2,4-pentadienyl, 3-(1,4-pentadienyl), ethynyl, 1- and 3-propynyl, 3-butynyl, and higher homologues and isomers.

Unless otherwise specified, the term "heterohydrocarbyl" or its subordinate concept (such as heteroalkyl, heteroalkenyl, heteroalkynyl, heteroaryl, etc.) itself or in conjunction with another term represents stable, straight, branched hydrocarbon radicals or combinations thereof, which consists of a certain number of carbon atoms and at least one heteroatom. In some examples, the term "heteroalkyl" itself or in combination with another term represents stable, straight, branched hydrocarbon atoms group or composition thereof, which consists of a certain number of carbon atoms and at least one heteroatom. In a typical example, the heteroatoms are selected from B, O, N and S, where the nitrogen and sulfur atoms are optionally oxidized and the nitrogen heteroatoms are optionally quaternized. The heteroatom or heteroatom group may be located at any internal position of the heterohydrocarbon (including the position of the remainder of the molecule where the hydrocarbon moiety attached to). Examples include but are not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. At most two heteroatoms may be continuous, such as —CH$_2$—NH—OCH$_3$.

The terms 'alkoxy" "alkylamino" and "alkylthio" (or thioalkoxy) are conventional expressions and refer to those alkyl that are attached to the remainder of the molecule through one oxygen atom, amino or sulfur atom, respectively.

Unless otherwise specified, the term "cycloalkyl" "heterocycloalkyl" or its subordinate concept (such as aryl, heteroaryl, cycloalkyl, heterocycloalkyl, cycloalkenyl, heterocycloalkenyl, cycloalkynyl, heterocycloalkynyl, etc.) themselves or in conjunction with other terms represents a cyclized "hydrocarbyl" "heterohydrocarbyl" respectively. In addition, the heteroatom may occupy the position of the remainder of the molecule where the heterocycle is attached to for a heterohydrocarbyl or heterocycloalkyl (such as heteroalkyl, heterocycloalkyl). Examples of cycloalkyl include, but are not limited to cyclopentyl, cyclohexyl, 1-cyclohexenyl, 3-cyclohexenyl, cycloheptyl, etc. Nonlimiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl and 2-piperazinyl.

Unless otherwise specified, the term "aryl" refers to polyunsaturated aromatic hydrocarbon substituent, which may be mono-substituted, di-substituted or poly-substituted, and may be monovalent, divalent or polyvalent, and may be monocyclic or polycyclic (e.g., 1 to 3 rings; wherein at least one ring is aromatic), which are fused together or covalently linked. The term "heteroaryl" refers to aryl (or ring) containing one to four heteroatoms. In one exemplary embodiment, the heteroatom is selected from B, N, O and S, where the nitrogen and sulfur atoms are optionally oxidized and the nitrogen atom is optionally quaternized, the heteroaryl may be attached to the remainder of the molecule by heteroatom. Non-limiting examples of the aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolyl, 5-isoquinolinyl 2-quinoxalinyl, 5-quinoxalinyl, 3-quinolinyl and 6-quinolinyl. The substituents of any one of the aryl and heteroaryl ring systems are selected from the substituents described below.

For convenience, the aryl, when used in conjunction with other terms (e.g., aryloxy, arylthio, aralkyl), include aryl and heteroaryl rings as defined above. Thus, the term "aralkyl" is intended to include those atoms group (e.g., benzyl, phenethyl, pyridylmethyl, etc.) in which aryl is attached to alkyl, including those alkyl in which carbon atom (such as methylene) has been replaced by, for example, oxygen atom, such as phenoxymethyl, 2-pyridyloxymethyl, 3-(1-naphthyloxy) propyl, etc.

The term "leaving group" refers to a functional group or atom that may be substituted by another functional group or atom by a substitution reaction (e.g., an affinity substitution reaction). For example, representative leaving groups include trifluoromethanesulfonate; chlorine, bromine, iodine; sulfonate groups such as methanesulfonate, tosylate, p-bromobenzenesulfonate, p-toluenesulfonate, etc.; acyloxy such as acetoxy, trifluoroacetoxy, etc.

The term "protecting group" includes but is not limited to "amino protecting group" "hydroxy protecting group" or "mercapto protecting group". The term "amino protecting group" refers to a chemical group that prevents an otherwise reactive amino group from participating in undesirable chemical reactions and which may be subsequently removed easily during the process steps when protection of the reactive amino group is no longer required. Representative amino protecting groups include but are not limited to formyl; acyl groups such as alkanoyl (such as acetyl, trichloroacetyl or trifluoroacetyl); alkoxycarbonyl such as t-butoxycarbonyl (Boc); aryl methoxycarbonyl such as benzyloxycarbonyl (Cbz) and 9-fluorenylmethyloxycarbonyl (Fmoc); aryl methyl such as benzyl (Bn), trityl (Tr), 1,1-bis-(4'-methoxy phenyl) methyl; silyl such as trimethylsilyl (TMS) and t-butyldimethylsilyl (TBS), etc. The term "hydroxy protecting group" refers to a substituent of an hydroxy group that is commonly employed to block or protect the hydroxy functionality while reactions are carried out on other functional groups on the compound. Representative hydroxy protecting groups include but are not limited to alkyl such as methyl, ethyl and t-butyl; acyl such as alkanoyl (e.g., acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and t-butyl Dimethylsilyl (TBS), etc.

The compounds of the present invention may be prepared by a variety of synthetic methods well known to those skilled in the art, including the specific embodiments listed below, the embodiments formed by combining the specific embodiments listed below with other chemical synthesis methods, and the equivalent replacement methods well known to those skilled in the art, the preferred embodiments include but are not limited to the examples of the present invention.

The solvents used in the present invention are commercially available. The present invention uses the following abbreviations: aq represents water; HATU represents O-(7-azabenzotriazole-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxy benzene acid; eq represents equivalent, equal quantity; CDI represents carbonyl diimidazole; DCM represents methylene chloride; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; r.t. represents room temperature; 0/N represents overnight; THF represents tetrahydrofuran; Boc$_2$O represents di-t-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl) benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide.

The compounds are named by hand or ChemDraw® software, and the commercially available compounds use the names in catalog provided by the suppliers.

DETAILED DESCRIPTION

The present invention will now be described in further detail with reference to specific embodiments which are given by way of illustration only and are not intended to limit the scope of the invention Process A

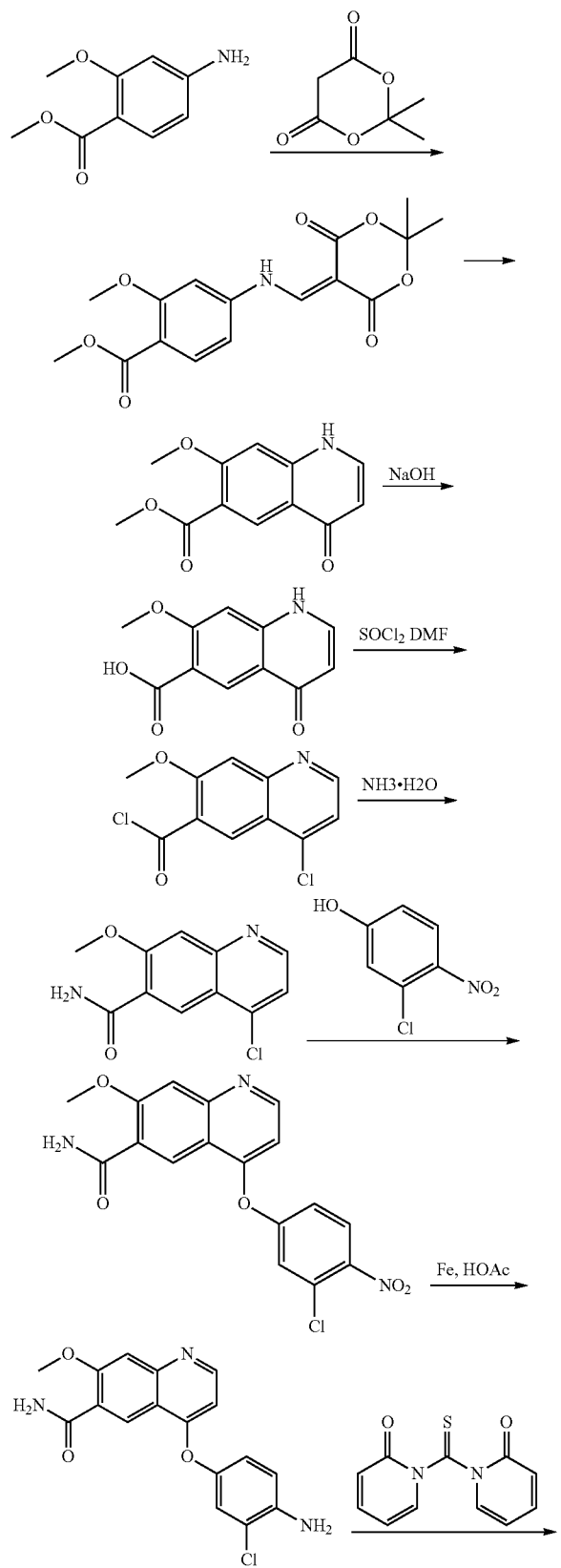

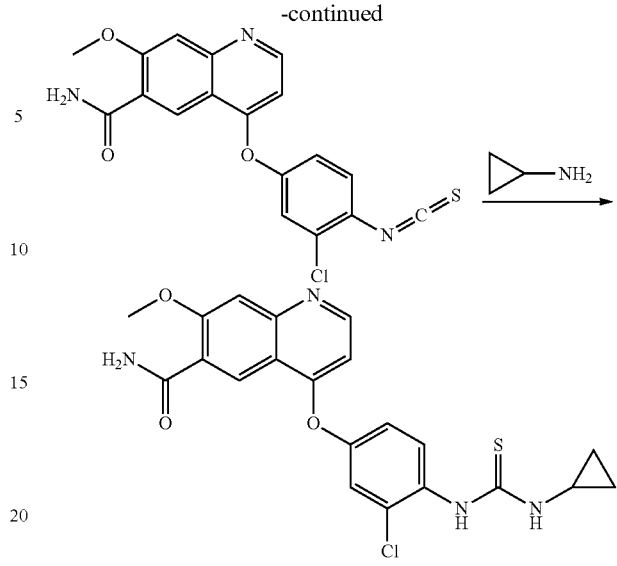

Compound 1A

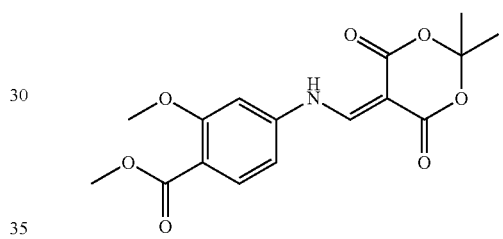

Methyl 2-methoxy-4-amino-benzoate (500.00 g, 2.76 mol), 2,2-dimethyl-1,3-dioxane-4,6-dione (397.73 g, 2.76 mol) and trimethyl orthoformate (292.84 g, 2.76 mol) were added to isopropanol (5.00 L). The reaction solution was heated up to an outer temperature of 90° C. and kept refluxing for 1 hour. The completion of the reaction was detected by TLC. The reaction solution was cooled to an outer temperature of 20° C. in an ice bath and then filtered. The solid was washed with MTBE (300 ml*2) and then concentrated to dryness in a water bath. Compound 1A (873.00 g, 2.47 mol, the yield was 89.62% and the purity was 95%) was obtained as a light red powder. NMR (DMSO) demonstrated that the product was correct.

$^1$H NMR (400 MHz, DMSO-$d_6$) ppm 1.67 (s, 6H) 3.76 (s, 3H) 3.86 (s, 3H) 7.19 (dd, J=8.41, 1.63 Hz, 1H) 7.43 (d, J=1.25 Hz, 1H) 7.71 (d, J=8.28 Hz, 1H) 8.69 (d, J=10.04 Hz, 1H) 11.25 (d, J=9.03 Hz, 1H)

Compound 1B

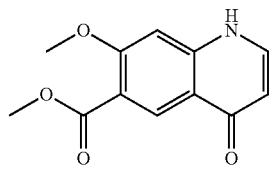

Compound 1A (270.00 g, 805.23 mmol) was added to diphenyl ether (2.70 L). The system was heated up to an outer temperature of 220° C. and kept refluxing for half an hour. The completion of the reaction was detected by TLC. The reaction solution was spontaneously cooled to 140° C. and then methyl tert-butyl ether (1 L) was slowly added dropwise. The reaction solution was allowed to stand for 12 hours and then cooled to 30° C. The reaction solution was filtered and the solid was washed with methyl tert-butyl ether (300 ml*3) and then dried by an oil pump. Compound 1B (160.00 g, 583.14 mmol, the yield was 72.42% and the purity was 85%) was obtained as a gray solid. NMR (DMSO) demonstrated that the product was correct.

$^1$H NMR (400 MHz, DMSO-$d_6$) ppm 3.81 (s, 3H) 3.90 (s, 3H) 5.99 (d, J=7.28 Hz, 1H) 7.02 (s, 1H) 7.84-7.92 (m, 1H) 8.43 (s, 1H) 11.72 (d, J=3.76 Hz, 1H)

Compound 1C

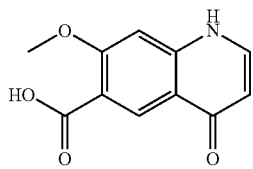

Sodium hydroxide (233.60 g, 5.84 mol) was dissolved in tap water (1.50 L) and added to a methanol (1.50 L) solution of compound 1B (680.00 g, 2.92 mol). The reaction solution was stirred at an outer temperature of 30° C. for two hours. The completion of the reaction was detected by TLC. The reaction solution was dried by a water pump. The residue was added with water (1 L) and hydrochloric acid (3 equiv., 1.5 L) till the pH value was 3. The solution was filtered and the obtained solid was washed with water (300 ml*2) and methyl tert-butyl ether (300 ml*2). The solid was then dried with toluene (300 ml*3). Compound 1C (650.00 g, crude) was obtained as a yellow solid. NMR (DMSO) demonstrated that the product was correct.

$^1$H NMR (400 MHz, DMSO-$d_6$) ppm 3.89 (s, 3H) 6.22 (d, J=7.28 Hz, 1H) 7.14 (s, 1H) 8.04 (d, J=7.28 Hz, 1H) 8.42 (s, 1H)

Compound 1D

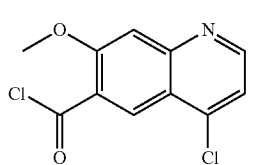

Compound 1C (140.00 g, 638.72 mmol) and N,N-dimethylformamide (9.34 g, 127.74 mmol) were added to 1,2-dichloroethane (500.00 mL), and then thionyl chloride (379.94 g, 3.19 mol) was added to the above reaction system. The reaction solution was protected by nitrogen and then heated up to an outer temperature of 110° C. and kept refluxing for two hours. The system was gradually changed from a gray turbidity system to a black uniform system. The completion of the reaction was detected by TLC. The reaction solution was dried by a water pump and then directly used in the next step. Compound 1D (140.00 g, crude) was obtained as a gray solid.

LCMS (ESI) m/z: 252 (M+1)$^+$

Compound 1E

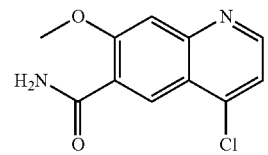

Compound 1D (300.00 g, 1.17 mol) was dissolved in dichloromethane (750.00 ml) and added to aqueous ammonia (1.03 kg, 5.85 mol), and the ice bath was controlled at 0-5° C. The reaction solution was stirred at 25° C. for half an hour. The completion of the reaction was detected by TLC. The turbid liquid was then filtered. The solid was washed with water (50 ml) and then dried. The filtrate was extracted with a mixture of dichloromethane and isopropanol (3:1, 100 ml*3) and dried. The organic phase was washed with a NaCl solution (50 ml), dried over sodium sulfate and then was dried by a water pump. The residue was beaten with a mixture of methylene chloride and ethyl acetate (1:1, 20 ml) for 15 hours and then filtered and spin-dried. Compound 1E (176.00 g, 669.34 mmol, the yield was 57.21%, and the purity was 90%) was obtained as a gray solid.

$^1$H NMR (400 MHz, DMSO-$d_6$) ppm 4.02 (s, 3H) 7.58 (s, 1H) 7.64 (d, J=4.77 Hz, 1H) 7.77-7.93 (m, 2H) 8.48 (s, 1H) 8.81 (d, J=5.02 Hz, 1H)

Compound 1F

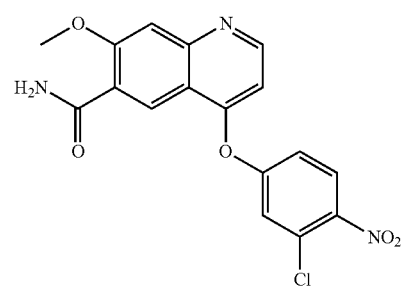

3-chloro-4-nitro-phenol (4.5 g, 0.026 mol) was added to a toluene (100 ml) solution of 4-chloro-6-amide-7-methoxy-quinoline (5 g, 0.021 mol), after stirring at 140° C. for 12 hours, the detection was performed by a thin layer preparation chromatography, the results showed that 4-chloro-6-amide-7-methoxy-quinoline had reacted completely. The reaction solution was cooled to 22° C. and concentrated under reduced pressure to give a residue, the residue was purified by column chromatography (with ethyl acetate firstly, and then with dichloromethane/methanol=20:1) to give compound 1F (pale yellow solid, 5 g, the yield was 70%).

1H NMR (400 MHz, METHANOL-d4) 9.02-9.11 (m, 1H), 8.89-8.98 (m, 1H), 7.64-7.78 (m, 2H), 7.54-7.61 (m, 1H), 7.45 (dd, J=2.64, 8.66 Hz, 1H), 7.10 (d, J=6.78 Hz, 1H), 4.23 (s, 3H)

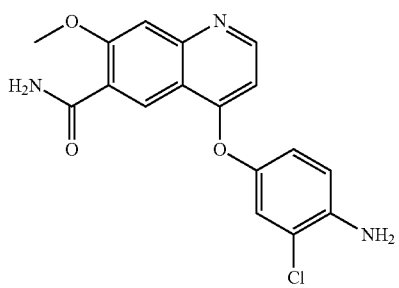

Compound 1G

Iron powder (3.8 g, 66.9 mmol) and acetic acid (10 mL) were added to an ethanol (50 ml) solution of compound 1F (5 g, 13.4 mmol), after stirring at 80° C. for 16 hours, the detection was performed by a thin layer preparation chromatography, the results showed that the reaction was complete. The reaction solution was cooled to 22° C. and concentrated under reduced pressure to give a residue, the residue was purified by column chromatography (dichloromethane/methanol=40-20:1) to give compound 1G (yellow solid, 2.1 g, the yield was 46%).

1H NMR (400 MHz, METHANOL-d4) 8.97 (s, 1H), 8.62 (d, J=5.27 Hz, 1H), 7.51 (s, 1H), 7.20 (d, J=2.01 Hz, 1H), 6.94-7.03 (m, 2H), 6.56 (d, J=5.52 Hz, 1H), 4.14 (s, 3H)

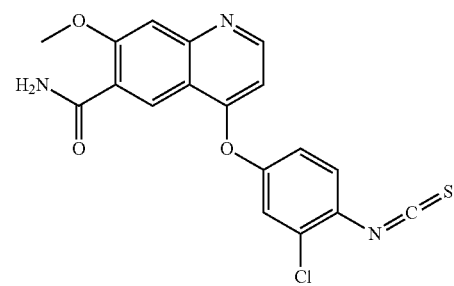

Compound 1H 1,1'-thiocarbonyldi-2(1H)-pyridone (760 mg, 3.3 mmol) was added to a 1,4-dioxane (2.5 ml) solution of compound 1G (1.03 g, 3 mmol). The reaction was stirred at 15° C. for 1 hour and then heated to react under refluxing for 12 hours. The solvent was distilled off under reduced pressure and the residue was isolated by column chromatography (ethyl acetate, Rf=0.24) to give compound 1H (pale yellow solid, 810 mg, the yield was 70%). LCMS (ESI) m/z: 385.9 $(M+1)^+$ $^1$H NMR (400 MHz, CHLOROFORM-d) 9.22 (s, 1H), 8.74 (d, J=5.02 Hz, 1H), 7.83 (br. s., 1H), 7.58 (s, 1H), 7.28 (s, 1H), 7.11 (dd, J=2.51, 8.78 Hz, 1H), 6.55 (d, J=5.02 Hz, 1H), 4.16 (s, 3H)

Example 1

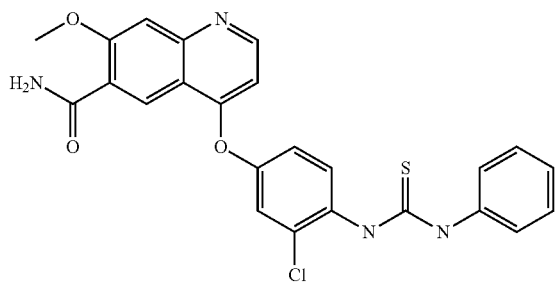 [SMILES: COc1cc2nccc(Oc3ccc(NC(=S)Nc4ccccc4)c(Cl)c3)c2cc1C(N)=O]

Cyclic propylamine (222.65 mg, 3.9 mmol) was added in one portion to 20 ml of tetrahydrofuran solution of compound 1H (500 mg, 1.3 mmol) at room temperature under the protection of nitrogen, and then stirred at room temperature for 16 hours. The solvent was distilled off at 35° C. under reduced pressure. The residue was purified by preparative HPLC to give a compound of Example 1 (yellow solid, 90 mg, the yield was 15.63%). LCMS (ESI) m/z: 443.0 $(M+1)^+$ $^1$H NMR (400 MHz, METHANOL-$d_4$) 9.03 (s, 1H), 8.93 (d, J=6.78 Hz, 1H), 7.91 (br. s., 1H), 7.57-7.68 (m, 2H), 7.39 (d, J=8.78 Hz, 1H), 7.21 (br. s., 1H), 4.22 (s, 3H), 2.73 (br. s., 1H), 0.53-1.09 (m, 4H)

The following compounds were also prepared by using the similar methods as described in Example 1 mentioned above.

| Examples | Structures | NMR | LCMS (ESI) m/z: $(M + 1)^+$ |
|---|---|---|---|
| Example 2 | 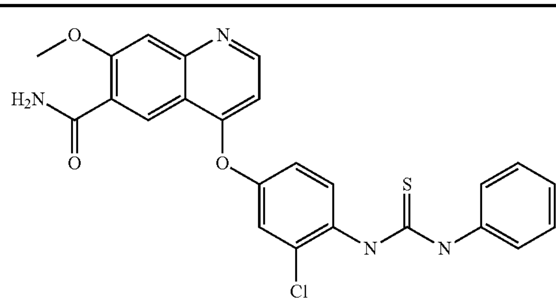 | $^1$H NMR (400 MHz, METHANOL-$d_4$) ppm 4.16-4.33 (m, 3 H) 7.20 (d, J = 7.03 Hz, 1 H) 7.25-7.34 (m, 1 H) 7.36-7.49 (m, 3 H) 7.50-7.55 (m, 2 H) 7.61 (s, 1 H) 7.65 (d, J = 2.51 Hz, 1 H) 7.93 (d, J = 8.53 Hz, 1 H) 8.95 (d, J = 7.03 Hz, 1 H) 9.05 (s, 1 H) | 479.1 |

-continued

| Examples | Structures | NMR | LCMS (ESI) m/z: (M + 1)+. |
|---|---|---|---|
| Example 3 | 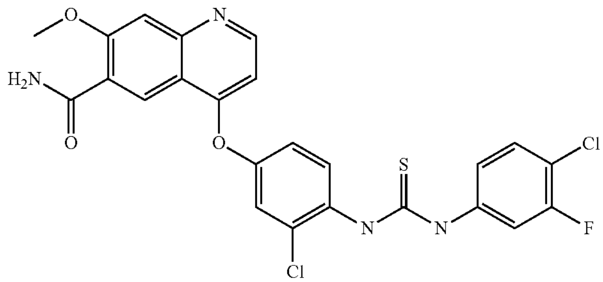 [SMILES: COc1cc2nccc(Oc3ccc(NC(=S)Nc4ccc(Cl)c(F)c4)c(Cl)c3)c2cc1C(N)=O] | ¹H NMR (400 MHz, METHANOL-d₄) ppm 4.23 (s, 3 H) 7.18 (d, J = 7.03 Hz, 1 H) 7.26-7.33 (m, 1 H) 7.38-7.48 (m, 2 H) 7.60 (s, 1 H) 7.67 (d, J = 2.51 Hz, 1 H) 7.76 (dd, J = 6.53, 2.51 Hz, 1 H) 7.92 (d, J = 9.03 Hz, 1 H) 8.94 (d, J = 7.03 Hz, 1 H) 9.06 (s, 1 H) | 531.0 |
| Example 4 | 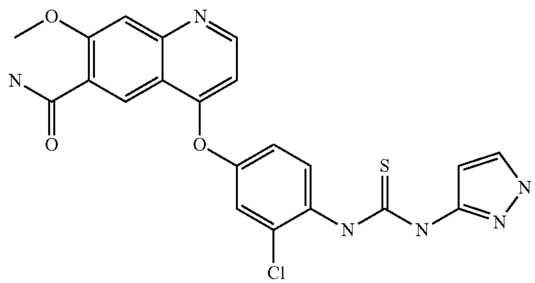 [SMILES: COc1cc2nccc(Oc3ccc(NC(=S)Nc4cc[nH]n4)c(Cl)c3)c2cc1C(N)=O] | ¹H NMR (400 MHz, METHANOL-d4) 9.07 (s, 1H), 8.95 (d, J = 6.78 Hz, 1H), 8.35 (d, J = 8.78 Hz, 1H), 7.68 (d, J = 2.26 Hz, 2H), 7.62 (s, 1H), 7.42 (dd, J = 2.51, 8.78 Hz, 1H), 7.21 (d, J = 6.78 Hz, 1H), 6.09 (d, J = 2.26 Hz, 1H), 4.24 (s, 3H) | 469.1 |
| Example 5 | 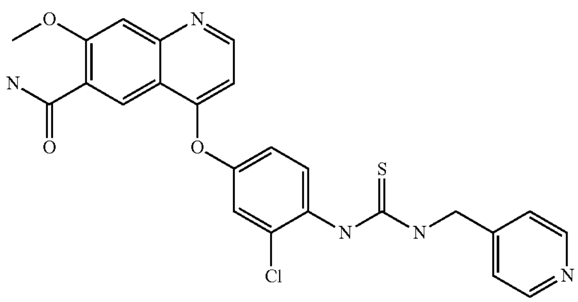 [SMILES: COc1cc2nccc(Oc3ccc(NC(=S)NCc4ccncc4)c(Cl)c3)c2cc1C(N)=O] | ¹H NMR (400 MHz, METHANOL-d4) 9.06 (s, 1H), 8.96 (d, J = 6.78 Hz, 1H), 8.82 (d, J = 6.53 Hz, 2H), 8.09 (d, J = 6.02 Hz, 2H), 7.92 (d, J = 8.78 Hz, 1H), 7.71 (d, J = 2.26 Hz, 1H), 7.64 (s, 1H), 7.45 (dd, J = 2.51, 8.78 Hz, 1H), 7.21 (d, J = 6.78 Hz, 1H), 5.18 (s, 2H), 4.24 (s, 3H) | 494.0 |
| Example 6 | 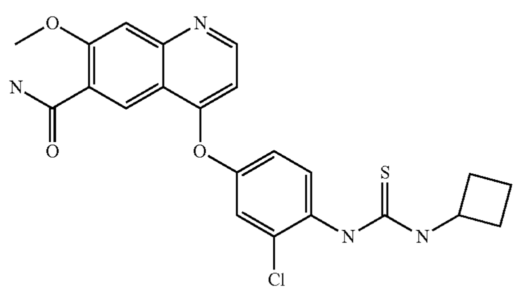 [SMILES: COc1cc2nccc(Oc3ccc(NC(=S)NC4CCC4)c(Cl)c3)c2cc1C(N)=O] | ¹H NMR (400 MHz, METHANOL-d4) 8.97 (s, 1H), 8.69 (d, J = 5.27 Hz, 1H), 7.87 (br. s., 1H), 7.55 (s, 1H), 7.47 (d, J = 2.51 Hz, 1H), 7.26 (dd, J = 2.51, 8.78 Hz, 1H), 6.76 (d, J = 5.27 Hz, 1H), 4.15 (s, 3H), 3.16 (s, 1H), 2.43 (br. s., 2H), 2.31 (s, 1H), 1.78 | 457.0 |
| Example 7 | 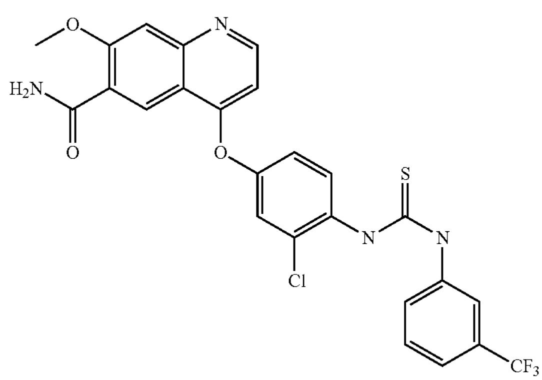 [SMILES: COc1cc2nccc(Oc3ccc(NC(=S)Nc4cccc(C(F)(F)F)c4)c(Cl)c3)c2cc1C(N)=O] | ¹H NMR (400 MHz, METHANOL-d₄) ppm 4.23 (s, 3 H) 7.15 (d, J = 6.53 Hz, 1 H) 7.41 (dd, J = 8.53, 2.51 Hz, 1 H) 7.50-7.55 (m, 1 H) 7.57-7.63 (m, 2 H) 7.67 (d, J = 2.51 Hz, 1 H) 7.79 (d, J = 8.03 Hz, 1 H) 7.94 (d, J = 8.53 Hz, 1 H) 8.00 (s, 1 H) 8.93 (d, J = 6.53 Hz, 1 H) 9.05 (s, 1 H) | 547.1 |

-continued

| Examples | Structures | NMR | LCMS (ESI) m/z: (M + 1)+. |
|---|---|---|---|
| Example 8 | 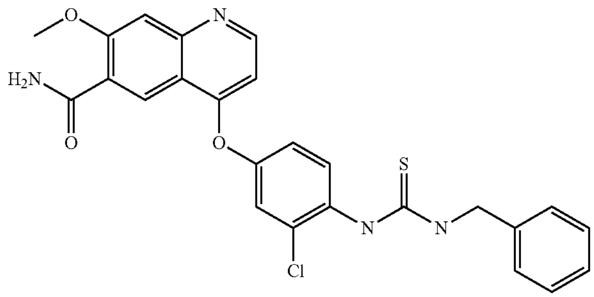 [SMILES: COc1cc2nccc(Oc3ccc(NC(=S)NCc4ccccc4)c(Cl)c3)c2cc1C(N)=O] | $^1$H NMR (400 MHz, METHANOL-d$_4$) ppm 4.17-4.21 (m, 1 H) 4.23 (s, 4 H) 4.17-4.23 (m, 3 H) 7.19 (d, J = 6.53 Hz, 1 H) 7.31 (d, J = 7.03 Hz, 1 H) 7.35-7.45 (m, 5 H) 7.60 (s, 1 H) 7.64 (d, J = 2.51 Hz, 1 H) 7.97-8.04 (m, 1 H) 8.94 (d, J = 7.03 Hz, 1 H) 9.06 (s, 1 H) | 593.1 |
| Example 9 | 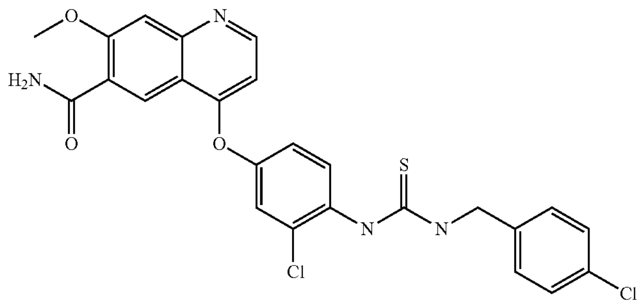 [SMILES: COc1cc2nccc(Oc3ccc(NC(=S)NCc4ccc(Cl)cc4)c(Cl)c3)c2cc1C(N)=O] | $^1$H NMR (400 MHz, METHANOL-d$_4$) ppm 4.23 (s, 3 H) 7.17 (d, J = 7.03 Hz, 1 H) 7.34-7.44 (m, 5 H) 7.60 (s, 1 H) 7.64 (d, J = 3.01 Hz, 1 H) 7.96 (br. s., 1 H) 8.93 (d, J = 6.53 Hz, 1 H) 9.05 (s, 1 H) | 527.1 |
| Example 10 | 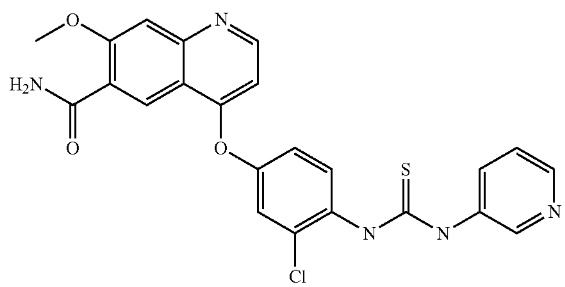 [SMILES: COc1cc2nccc(Oc3ccc(NC(=S)Nc4cccnc4)c(Cl)c3)c2cc1C(N)=O] | $^1$H NMR (400 MHz, METHANOL-d$_4$) ppm 4.24 (s, 3 H) 7.19 (d, J = 6.78 Hz, 1 H) 7.48 (dd, J = 8.78, 2.51 Hz, 1 H) 7.66 (s, 1 H) 7.73 (d, J = 2.51 Hz, 1 H) 7.95 (d, J = 8.78 Hz, 1 H) 8.09 (dd, J = 8.41, 5.90 Hz, 1 H) 8.62 (d, J = 5.52 Hz, 1 H) 8.76 (d, J = 8.78 Hz, 1 H) 8.97 (d, J = 6.78 Hz, 1 H) 9.06 (s, 1 H) 9.62 (s, 1 H). | 480.0 |
| Example 11 | 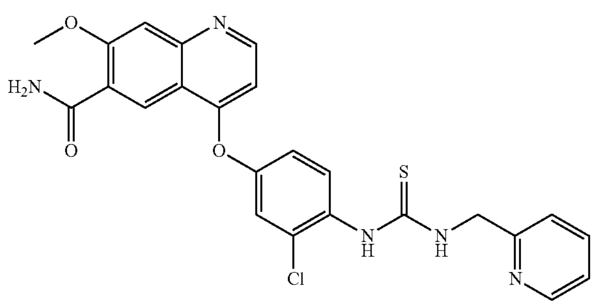 [SMILES: COc1cc2nccc(Oc3ccc(NC(=S)NCc4ccccn4)c(Cl)c3)c2cc1C(N)=O] | $^1$H NMR (400 MHz, METHANOL-d$_4$) ppm 4.24 (s, 3 H) 5.09 (s, 2 H) 7.24 (d, J = 6.78 Hz, 1 H) 7.44 (dd, J = 8.66, 2.64 Hz, 1 H) 7.65 (s, 1 H) 7.70 (d, J = 2.51 Hz, 1 H) 7.87 (d, J = 8.78 Hz, 1 H) 8.12 (dd, J = 7.78, 6.02 Hz, 1 H) 8.72 (d, J = 8.28 Hz, 1 H) 8.80 (d, J = 5.77 Hz, 1 H) 8.93 (s, 1 H) 8.96 (d, J = 6.78 Hz, 1 H) 9.05 (s, 1 H) | 494.1 |
| Example 12 | 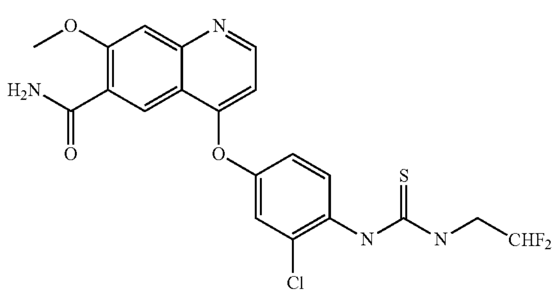 [SMILES: COc1cc2nccc(Oc3ccc(NC(=S)NCC(F)F)c(Cl)c3)c2cc1C(N)=O] | $^1$H NMR (400 MHz, METHANOL-d$_4$) ppm 4.05 (td, J = 14.56, 4.02 Hz, 8 H) 4.23 (s, 13 H) 6.01 (t, J = 4.14 Hz, 1 H) 6.15 (t, J = 4.02 Hz, 2 H) 6.29 (t, J = 4.14 Hz, 1 H) 7.18 (d, J = 6.78 Hz, 1 H) 7.41 (dd, J = 8.78, 2.76 Hz, 1 H) 7.62 (s, 1 H) 7.66 (d, J = 2.51 Hz, 1 H) 7.97 (d, J = 8.78 Hz, 1 H) 8.95 (d, J = 6.78 Hz, 1 H) 9.06 (s, 1 H). | 467.2 |

| Examples | Structures | NMR | LCMS (ESI) m/z: (M + 1)+. |
|---|---|---|---|
| Example 14 | 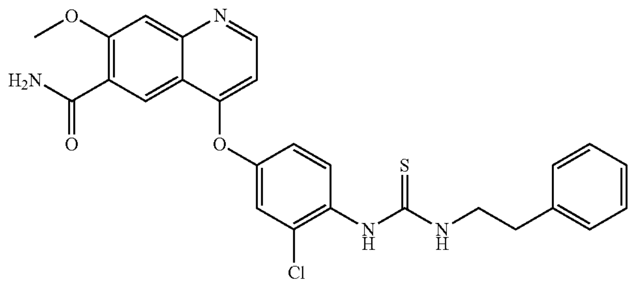 [SMILES: COc1cc2nccc(Oc3ccc(NC(=S)NCCc4ccccc4)c(Cl)c3)c2cc1C(N)=O] | ¹H NMR (400 MHz, METHANOL-d₄) ppm 3.00 (t, J = 7.28 Hz, 2 H) 3.87 (br. s., 2 H) 4.22 (s, 3 H) 7.13 (d, J = 6.27 Hz, 1 H) 7.17-7.26 (m, 1 H) 7.27-7.38 (m, 5 H) 7.61 (s, 2 H) 7.87 (d, J = 8.03 Hz, 1 H) 8.92 (d, J = 6.78 Hz, 1 H) 9.04 (s, 1 H) | 507.0 |
| Example 15 | 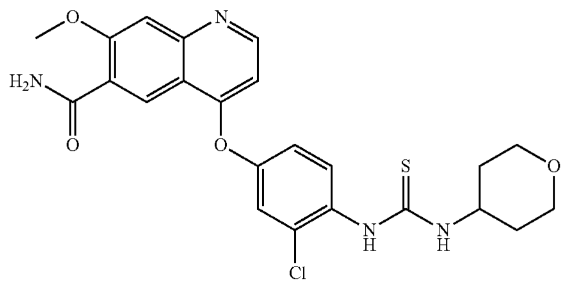 [SMILES: COc1cc2nccc(Oc3ccc(NC(=S)NC4CCOCC4)c(Cl)c3)c2cc1C(N)=O] | ¹H NMR (400 MHz, METHANOL-d₄) ppm 1.63 (d, J = 9.79 Hz, 1 H) 2.08 (d, J = 11.80 Hz, 2 H) 3.56 (t, J = 11.29 Hz, 2 H) 4.00 (d, J = 11.29 Hz, 2 H) 4.23 (s, 3 H) 7.19 (d, J = 6.02 Hz, 1 H) 7.38 (d, J = 7.78 Hz, 1 H) 7.63 (br. s., 2 H) 8.03 (br. s., 1 H) 8.94 (d, J = 6.53 Hz, 1 H) 9.05 (s, 1 H) | 487.0 |
| Example 16 | 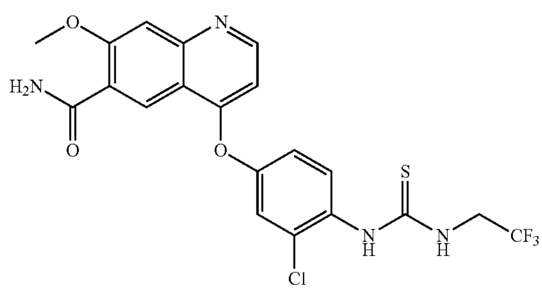 | ¹H NMR (400 MHz, METHANOL-d₄) ppm 4.14-4.32 (m, 3 H) 4.52 (q, J = 9.29 Hz, 2 H) 7.09-7.24 (m, 1 H) 7.33-7.44 (m, 1 H) 7.58-7.70 (m, 2 H) 7.98 (d, J = 8.78 Hz, 1 H) 8.86-8.98 (m, 1 H) 9.05 (s, 1 H) | 485.0 |
| Example 17 | 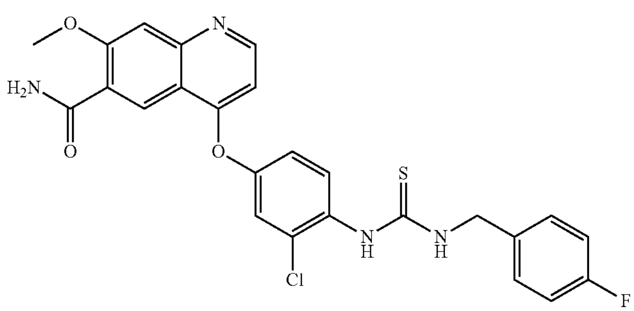 [SMILES: COc1cc2nccc(Oc3ccc(NC(=S)NCc4ccc(F)cc4)c(Cl)c3)c2cc1C(N)=O] | ¹H NMR (400 MHz, METHANOL-d₄) ppm 4.23 (s, 3 H) 4.86 (br. s., 2 H) 7.10 (t, J = 8.78 Hz, 2 H) 7.15 (d, J = 6.53 Hz, 1 H) 7.38 (dd, J = 8.78, 2.51 Hz, 1 H) 7.44 (dd, J = 8.16, 5.65 Hz, 2 H) 7.61 (s, 1 H) 7.63 (d, J = 2.51 Hz, 1 H) 7.96 (br. s., 1 H) 8.92 (d, J = 6.78 Hz, 1 H) 9.05 (s, 1 H) | 511.0 |
| Example 18 | 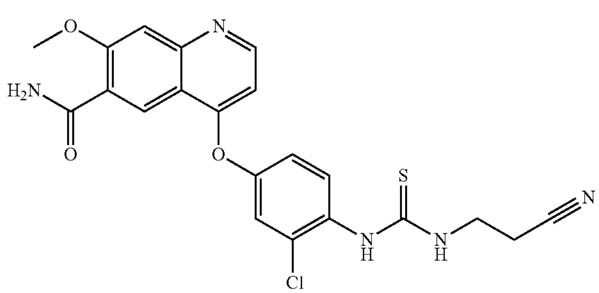 [SMILES: COc1cc2nccc(Oc3ccc(NC(=S)NCCC#N)c(Cl)c3)c2cc1C(N)=O] | ¹H NMR (400 MHz, METHANOL-d₄) ppm 2.63 (t, J = 6.53 Hz, 1 H) 2.93 (t, J = 6.53 Hz, 1 H) 3.90 (t, J = 6.53 Hz, 2 H) 4.23 (s, 3 H) 7.16-7.23 (m, 1 H) 7.36-7.43 (m, 1 H) 7.61 (s, 1 H) 7.66 (dd, J = 8.03, 2.51 Hz, 1 H) 7.94 (d, J = 8.53 Hz, 1 H) 8.95 (d, J = 7.03 Hz, 1 H) 9.06 (s, 1 H) | 455.9 |

-continued

| Examples | Structures | NMR | LCMS (ESI) m/z: (M + 1)+. |
|---|---|---|---|
| Example 19 | 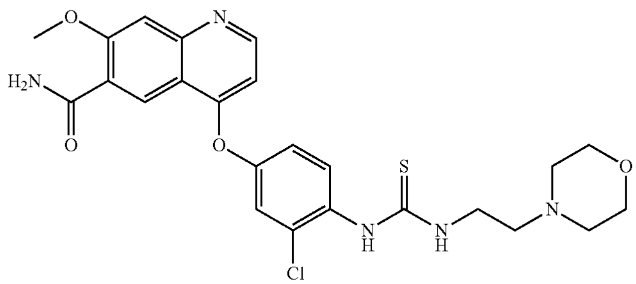 [SMILES: COc1cc2nccc(Oc3ccc(NC(=S)NCCN4CCOCC4)c(Cl)c3)c2cc1C(N)=O] | 1H NMR (400 MHz, METHANOL-d4) ppm 3.22-3.30 (m, 2 H) 3.51 (t, J = 6.02 Hz, 2 H) 3.70 (d, J = 12.05 Hz, 2 H) 3.87 (t, J = 12.30 Hz, 2 H) 4.05-4.17 (m, 4 H) 4.24 (s, 3 H) 7.29 (d, J = 6.53 Hz, 1 H) 7.44 (dd, J = 8.78, 2.26 Hz, 1 H) 7.64 (s, 1 H) 7.69 (d, J = 2.51 Hz, 1 H) 7.87 (d, J = 8.53 Hz, 1 H) 8.97 (d, J = 6.53 Hz, 1 H) 9.06 (s, 1 H) | 516.1 |
| Example 20 | 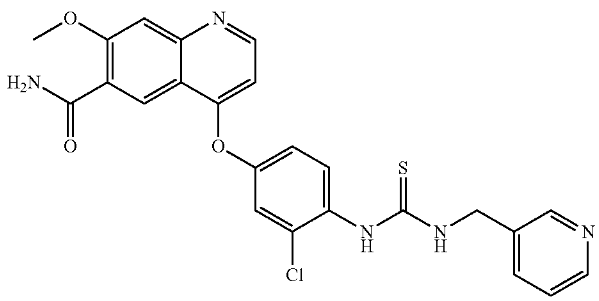 [SMILES: COc1cc2nccc(Oc3ccc(NC(=S)NCc4cccnc4)c(Cl)c3)c2cc1C(N)=O] | 1H NMR (400 MHz, METHANOL-d4) ppm 4.24 (s, 3 H) 5.09 (s, 2 H) 7.24 (d, J = 6.78 Hz, 1 H) 7.44 (dd, J = 8.66, 2.64 Hz, 1 H) 7.65 (s, 1 H) 7.70 (d, J = 2.51 Hz, 1 H) 7.87 (d, J = 8.78 Hz, 1 H) 8.12 (dd, J = 7.78, 6.02 Hz, 1 H) 8.72 (d, J = 8.28 Hz, 1 H) 8.80 (d, J = 5.77 Hz, 1 H) 8.93 (s, 1 H) 8.96 (d, J = 6.78 Hz, 1 H) 9.05 (s, 1 H) | 494.1 |
| Example 21 | 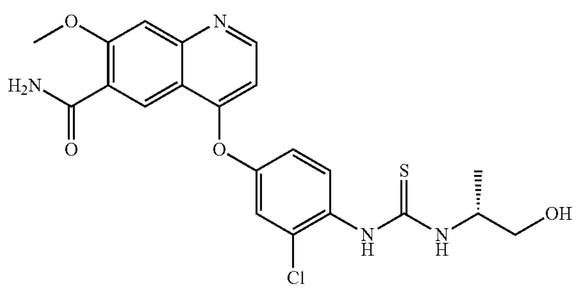 [SMILES: COc1cc2nccc(Oc3ccc(NC(=S)N[C@H](C)CO)c(Cl)c3)c2cc1C(N)=O] | 1H NMR (400 MHz, METHANOL-d4) ppm 1.30 (d, J = 6.78 Hz, 3 H) 3.67 (d, J = 4.77 Hz, 2 H) 4.19-4.27 (m, 4 H) 7.19 (d, J = 6.78 Hz, 1 H) 7.37 (dd, J = 8.78, 2.51 Hz, 1 H) 7.60-7.66 (m, 3 H) 8.04 (br. s., 1 H) 8.95 (d, J = 6.78 Hz, 1 H) 9.05 (s, 1 H) | 483.1 (M + 23) |
| Example 22 | 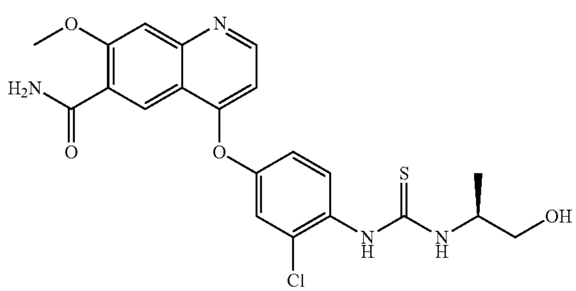 [SMILES: COc1cc2nccc(Oc3ccc(NC(=S)N[C@@H](C)CO)c(Cl)c3)c2cc1C(N)=O] | 1H NMR (400 MHz, METHANOL-d4) ppm 1.30 (d, J = 6.78 Hz, 3 H) 3.67 (d, J = 4.77 Hz, 2 H) 4.19-4.28 (m, 4 H) 7.20 (d, J = 6.78 Hz, 1 H) 7.37 (dd, J = 8.91, 2.64 Hz, 1 H) 7.60-7.65 (m, 2 H) 8.04 (br. s., 1 H) 8.94 (d, J = 6.78 Hz, 1 H) 9.03-9.08 (m, 1 H) | 461.1 |
| Example 23 | 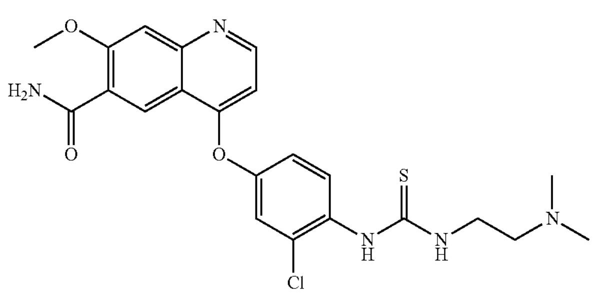 | 1H NMR (400 MHz, METHANOL-d4) ppm 2.99-3.05 (m, 6 H) 3.49 (t, J = 6.15 Hz, 2 H) 4.09 (t, J = 6.15 Hz, 2 H) 4.24 (s, 3 H) 7.26 (d, J = 6.78 Hz, 1 H) 7.43 (dd, J = 8.66, 2.64 Hz, 1 H) 7.64 (s, 1 H) 7.69 (d, J = 2.51 Hz, 1 H) 7.89 (d, J = 8.78 Hz, 1 H) 8.96 (d, J = 6.78 Hz, 1 H) 9.06 (s, 1 H) | 474.1 |

-continued

| Examples | Structures | NMR | LCMS (ESI) m/z: (M + 1)+. |
|---|---|---|---|
| Example 27 | 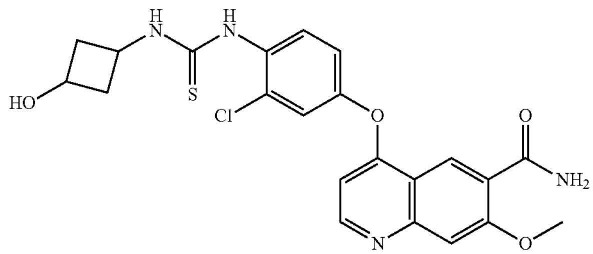 [SMILES: COc1cc2nccc(Oc3ccc(NC(=S)NC4CC(O)C4)c(Cl)c3)c2cc1C(N)=O] | N/A | 473.0 |
| Example 28 | 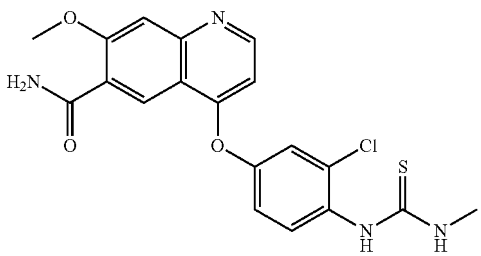 | $^1$H NMR (400 MHz, DMSO-d6) ppm 2.95 (s, 3 H) 4.09 (s, 3 H) 6.98 (s, 1 H) 7.42 (d, J = 8.02 Hz, 1 H) 7.74 (d, J = 16.00, Hz, 2 H) 7.83 (d, J = 8.03 Hz, 1 H) 7.93 (s, 1 H) 8.00 (s, 1 H) 8.11 (s, 1 H) 8.75 (s, 1 H) 8.95 (d, J = 6.03 Hz, 1 H) 9.50 (s, 1 H) | 417.0 |
| Example 29 | 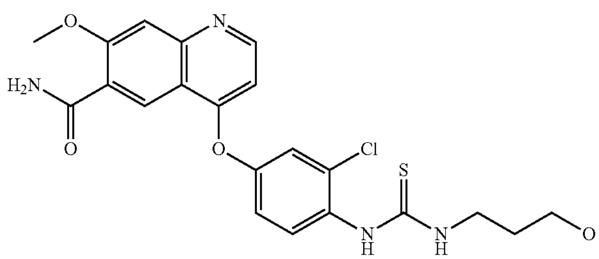 [SMILES: COc1cc2nccc(Oc3ccc(NC(=S)NCCCO)c(Cl)c3)c2cc1C(N)=O] | $^1$H NMR (400 MHz, DMSO-d$_6$) = 9.49 (s, 1H), 9.01-9.02 (d, J = 6.4 Hz, 1H), 8.71-8.72 (d, J = 4.0 Hz, 1H), 8.32-8.33 (m, 1H), 8.00 (s, 1H), 7.89-7.93 (m, 2H), 7.79 (s, 1H), 7.72 (d, J = 2.4 Hz, 1H), 7.40-7.43 (dd, J$_1$ = 2.4 Hz, J$_2$ = 8.8 Hz, 1H), 6.98-7.00 (d, J = 6.0 Hz, 1H), 4.08 (s, 3H), 3.48 (s, 4H), 2.8$_{0-2}$.85 (m, 1H), 1.67-1.72 (m, 2H) | 461.1 |
| Example 30 | 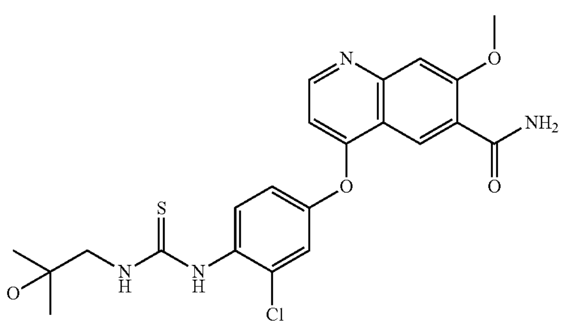 [SMILES: COc1cc2nccc(Oc3ccc(NC(=S)NCC(C)(C)O)c(Cl)c3)c2cc1C(N)=O] | $^1$H NMR (400 MHz, DMSO-d$_6$) = 9.64 (s, 1H), 9.00-9.02 (d, J = 6.8 Hz, 1H), 8.73 (s, 1H), 8.32-8.33 (m, 1H), 8.01-8.05 (m, 2H), 7.94 (s, 1H), 7.79 (s, 1H), 7.71$_{-7}$.72 (d, J = 2.4 Hz, 1H), 7.40-7.43 (dd, J$_1$ = 2.8 Hz, J$_2$ = 8.8 Hz, 1H), 6.96-6.97 (d, J = 6.8 Hz, 1H), 4.08 (s, 3H), 3.50 (s, 2H), 1.16-1.19 (d, J = 12.4 Hz, 6H) | 475.1 |
| Example 32 | 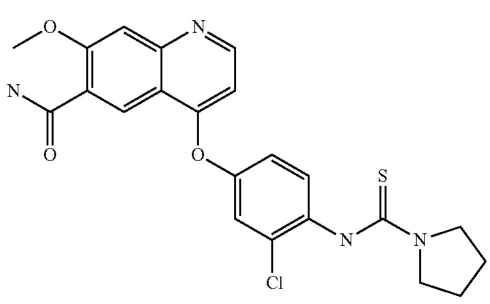 [SMILES: COc1cc2nccc(Oc3ccc(NC(=S)N4CCCC4)c(Cl)c3)c2cc1C(N)=O] | $^1$H NMR (400 MHz, DMSO-d$_6$) 9.01 (d, J = 6.2 Hz, 1H), 8.95 (s, 1H), 8.73 (s, 1H), 7.98 (br. s., 1H), 7.91 (br. s., 1H), 7.66-7.73 (m, 2H), 7.59 (d, J = 8.8 Hz, 1H), 7.42 (dd, J = 2.6, 8.6 Hz, 1H), 6.82 (d, J = 6.2 Hz, 1H), 4.09 (s, 3H), 3.65-3.75 (m, 3H), 1.77-2.14 (m, 5H). | 456.9 |

-continued

| Examples | Structures | NMR | LCMS (ESI) m/z: (M + 1)+. |
|---|---|---|---|
| Example 33 | 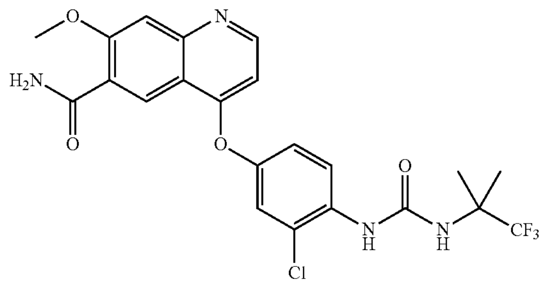 [SMILES: COc1cc2nccc(Oc3ccc(NC(=O)NC(C)(C)C(F)(F)F)c(Cl)c3)c2cc1C(N)=O] | ¹H NMR (400 MHz, DMSO-d₆): 9.33-9.40 (m, 1H), 8.71-8.77 (m, 1H), 8.62-8.66 (m, 1H), 8.30-8.36 (m, 1H), 7.86-7.93 (m, 1H), 7.73-7.82 (m, 2H), 7.51-7.60 (m, 2H), 7.24-7.31 (m, 1H), 6.58-6.65 (m, 1H), 4.03-4.08 (m, 3H), 1.76-1.86 (m, 6H). | 497.2 |
| Example 35 | 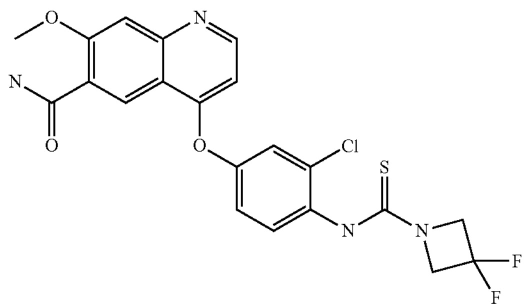 [SMILES: COc1cc2nccc(Oc3ccc(NC(=S)N4CC(F)(F)C4)c(Cl)c3)c2cc1C(N)=O] | ¹H NMR (400 MHz, METHANOL-d₄) = 9.43 (s, 1H), 8.82-8.72 (m, 1H), 7.74 (d, J = 8.5 Hz, 1H), 7.66-7.61 (m, 1H), 7.56 (s, 1H), 7.39 (dd, J = 2.4, 8.7 Hz, 1H), 7.15 (d, J = 6.8 Hz, 1H), 4.62 (t, J = 11.9 Hz, 4H), 4.23 (s, 3H), | 479.0 |
| Example 36 | 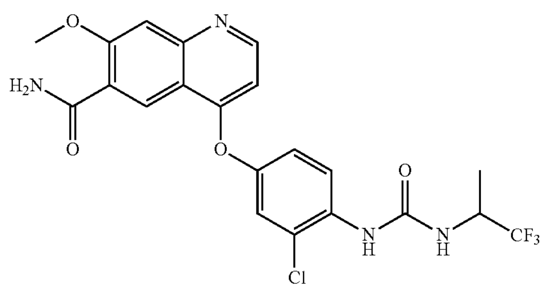 [SMILES: COc1cc2nccc(Oc3ccc(NC(=O)NC(C)C(F)(F)F)c(Cl)c3)c2cc1C(N)=O] | ¹H NMR (400 MHz, DMSO-d₆) □ 9.70 (br. s., 1H), 8.99 (d, J = 6.2 Hz, 1H), 8.84-8.94 (m, 1H), 8.72 (s, 1H), 7.99 (br. s., 1H), 7.84-7.95 (m, 2H), 7.66-7.78 (m, 2H), 7.43 (dd, J = 2.5, 8.8 Hz, 1H), 6.93 (d, J = 6.3 Hz, 1H), 5.28-5.46 (m, 1H), 4.08 (s, 3H), 2.07 (s, 1H), 1.35 (d, J = 6.8 Hz, 3H). | 483.1 |
| Example 41 | 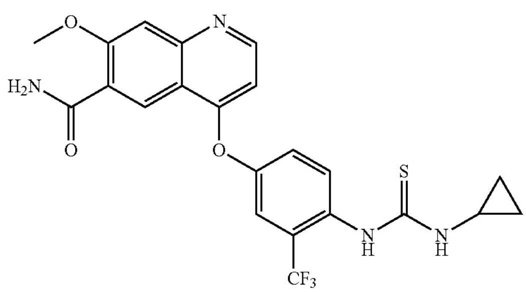 [SMILES: COc1cc2nccc(Oc3ccc(NC(=S)NC4CC4)c(C(F)(F)F)c3)c2cc1C(N)=O] | ¹H NMR (400 MHz, METHANOL-d₄) 9.08 (br. s., 1H), 8.96 (d, J = 6.02 Hz, 1H), 7.88 (d, J = 16.56 Hz, 2H), 7.57-7.76 (m, 2H), 7.24 (br. s., 1H), 4.24 (br. s., 3H), 2.74 (br. s., 1H), 2.57-3.05 (m, 1H), 0.94 (br. s., 2H), 0.86-1.10 (m, 1H), 0.76 (br. s., 2H) | 477.9 |
| Example 42 | 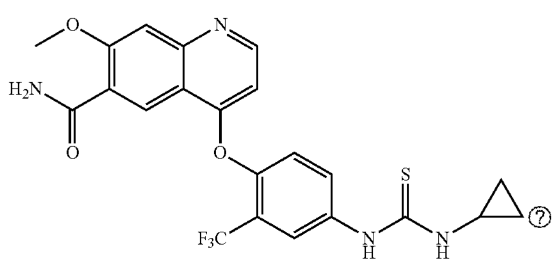 [SMILES: COc1cc2nccc(Oc3ccc(NC(=S)NC4CC4)cc3C(F)(F)F)c2cc1C(N)=O] | ¹H NMR (400 MHz, METHANOL-d₄) 8.93-9.07 (m, 2H), 8.18 (br. s., 1H), 8.01 (d, J = 8.03 Hz, 1H), 7.52-7.69 (m, 2H), 7.17 (d, J = 6.53 Hz, 1H), 4.24 (s, 3H), 2.86 (br. s., 1H), 0.93 (d, J = 5.02 Hz, 2H), 0.74 (br. s., 2H) | 477.3 |

-continued

| Examples | Structures | NMR | LCMS (ESI) m/z: (M + 1)+. |
|---|---|---|---|
| Example 43 | | ¹H NMR (400 MHz, METHANOL-d₄) = 9.05 (s, 1H), 8.87 (d, J = 6.5 Hz, 1H), 8.34 (d, J = 2.8 Hz, 1H), 7.83 (dd, J = 2.8, 9.0 Hz, 1H), 7.61 (s, 1H), 7.24 (d, J = 9.3 Hz, 1H), 6.97 (d, J = 6.3 Hz, 1H), 4.21 (s, 3H), 3.23-3.15 (m, 1H), 0.95-0.90 (m, 2H), 0.77-0.67 (m, 2H). | 410.0 |
| Example 43 | | ¹H NMR (400 MHz, METHANOL-d₄) = 9.05 (s, 1H), 8.87 (d, J = 6.5 Hz, 1H), 8.34 (d, J = 2.8 Hz, 1H), 7.83 (dd, J = 2.8, 9.0 Hz, 1H), 7.61 (s, 1H), 7.24 (d, J = 9.3 Hz, 1H), 6.97 (d, J = 6.3 Hz, 1H), 4.21 (s, 3H), 3.23-3.15 (m, 1H), 0.95-0.90 (m, 2H), 0.77-0.67 (m, 2H). | 410.0 |
| Example 51 | 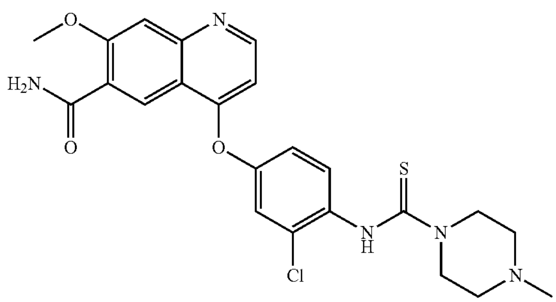 | ¹H NMR (400 MHz, DMSO-d₆): 10.93-11.09 (m, 1H), 9.82 (s, 1H), 8.96-9.04 (m, 1H), 8.73 (s, 1H), 7.96-8.03 (m, 1H), 7.87-7.93 (m, 1H), 7.72 (s, 2H), 7.48-7.56 (m, 1H), 7.40-7.47 (m, 1H), 6.77-6.88 (m, 1H), 4.82-4.98 (m, 2H), 4.08 (s, 3H), 3.60-3.63 (m, 2H), 3.02-3.15 (m, 4H), 2.83 (br. s., 3H). | 486.1 |
| Example 52 | 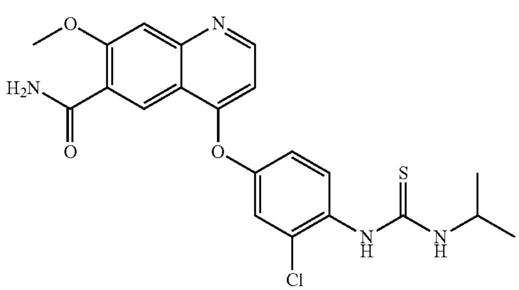 [SMILES: COc1cc2nccc(Oc3ccc(NC(=S)NC(C)C)c(Cl)c3)c2cc1C(N)=O] | ¹H NMR (400 MHz, DMSO-d₆): 9.25 (br. s., 1H), 8.99 (d, J = 6.5 Hz, 1H), 8.72 (s, 1H), 8.19-8.32 (m, 1H), 7.99 (br. s., 2H), 7.91 (br. s., 1H), 7.73 (s, 1H), 7.69 (d, J = 2.5 Hz, 1H), 7.40 (dd, J = 2.6, 8.9 Hz, 1H), 6.93 (d, J = 6.0 Hz, 1H), 4.33-4.44 (m, 1H), 4.09 (s, 3H), 1.20 (d, J = 6.2 Hz, 6H). | 445.1 |
| Example 55 | 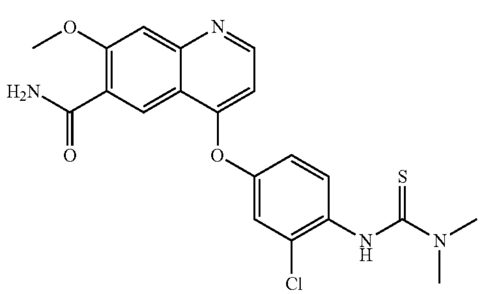 | ¹H NMR (400 MHz, DMSO-d₆) □ 9.10 (s, 1H), 9.03 (d, J = 6.3 Hz, 1H), 8.74 (s, 1H), 7.99 (br. s., 1H), 7.92 (br. s., 1H), 7.75 (s, 1H), 7.71 (d, J = 2.5 Hz, 1H), 7.53 (d, J = 8.5 Hz, 1H), 7.43 (dd, J = 2.5, 8.5 Hz, 1H), 6.83 (d, J = 6.2 Hz, 1H), 4.09 (s, 3H), 3.32 (s, 6H). | 431.1 |

-continued

| Examples | Structures | NMR | LCMS (ESI) m/z: (M + 1)+. |
|---|---|---|---|
| Example 56 | 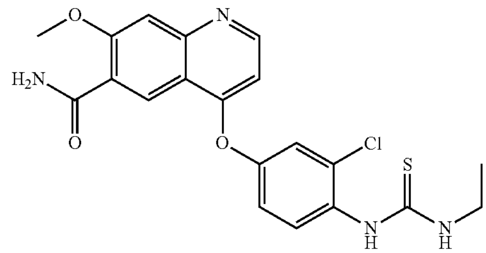 [SMILES: CCNC(=S)Nc1ccc(Oc2ccnc3cc(OC)c(C(N)=O)cc23)cc1Cl] | 1H NMR (400 MHz, METHANOL-d4) ppm 1.25 (t, J = 6.8 Hz, 1 H) 3.64 (m, 2 H) 4.15 (s, 3 H) 7.16-7.23 (m, 1 H) 7.36-7.43 (m, 1 H) 7.61 (s, 1 H) 7.66 (dd, J = 8.03, 2.51 Hz, 1 H) 7.94 (d, J = 8.53 Hz, 1 H) 8.95 (d, J = 7.03 Hz, 1 H) 9.00 (s, 1 H) | 431.9 |
| Example 57 | 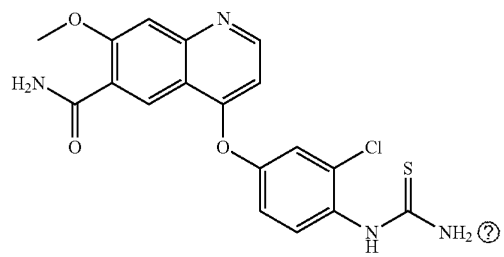 [SMILES: COc1cc2nccc(Oc3ccc(NC(N)=S)c(Cl)c3)c2cc1C(N)=O] | 1H NMR (400 MHz, DMSO-d6) □ 9.55-9.64 (m, 1H), 9.02 (d, J = 6.5 Hz, 1H), 8.73 (s, 1H), 7.87-8.08 (m, 3H), 7.76-7.86 (m, 2H), 7.72 (d, J = 2.2 Hz, 1H), 7.42 (dd, J = 2.2, 8.8 Hz, 1H), 7.02 (d, J = 6.5 Hz, 1H), 4.08 (s, 3H). | 402.9 |
| Example 59 | 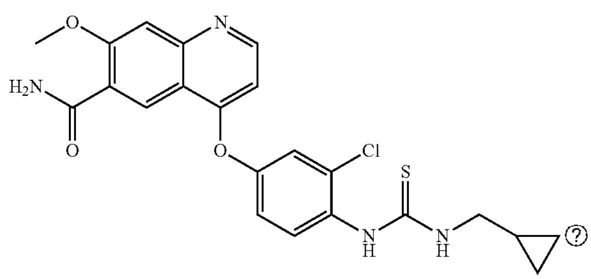 [SMILES: COc1cc2nccc(Oc3ccc(NC(=S)NCC4CC4)c(Cl)c3)c2cc1C(N)=O] | 1H NMR (400 MHz, DMSO-d6) □ 9.35 (br. s., 1H), 8.96 (d, J = 6.0 Hz, 1H), 8.72 (s, 1H), 8.32 (br. s., 1H), 7.97 (br. s., 2H), 7.89 (br. s., 1H), 7.64-7.74 (m, 2H), 7.40 (s, 1H), 6.84-6.98 (m, 1H), 4.08 (s, 3H), 2.52-2.54 (m, 2H), 1.04-1.14 (m, 1H), 0.48 (d, J = 6.8 Hz, 1H), 0.26 (d, J = 4.5 Hz, 2H). | 457.0 |
| Example 60 | 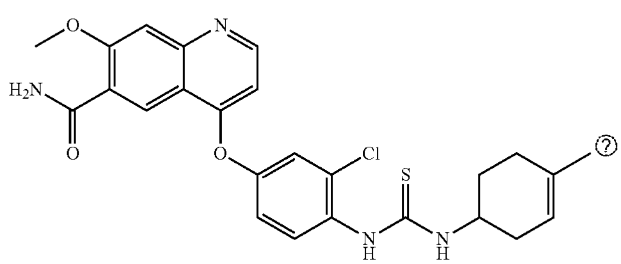 | 1H NMR (400 MHz, DMSO-d6) 9.21-9.42 (m, 1H), 8.69-8.76 (m, 1H), 8.61-8.67 (m, 1H), 8.27-8.39 (m, 1H), 7.80-7.92 (m, 2H), 7.71-7.77 (m, 1H), 7.50-7.57 (m, 2H), 7.24-7.30 (m, 1H), 6.58-6.64 (m, 1H), 5.17-5.28 (m, 1H), 4.32-4.50 (m, 1H), 4.01-4.09 (m, 3H), 2.22-2.40 (m, 3H), 1.94-2.08 (m, 2H), 1.76-1.87 (m, 1H) | 501.1 |
| Example 61 | 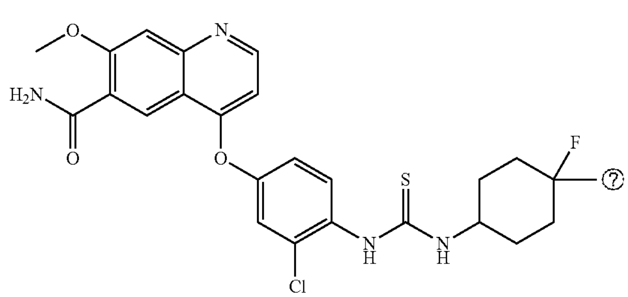 | 1H NMR (DMSO-d6, 400 MHz): = 9.17-9.26 (m, 1H), 8.71-8.78 (m, 1H), 8.61-8.67 (m, 1H), 8.13-8.23 (m, 1H), 7.70-7.91 (m, 3H), 7.52-7.59 (m, 2H), 7.25-7.32 (m, 1H), 6.59-6.67 (m, 1H), 4.19-4.37 (m, 1H), 4.03-4.06 (m, 3H), 1.91-2.10 (m, 6H), 1.52-1.66 ppm (m, 2H) | 521.0 |

-continued

| Examples | Structures | NMR | LCMS (ESI) m/z: (M + 1)+ |
|---|---|---|---|
| Example 63 | 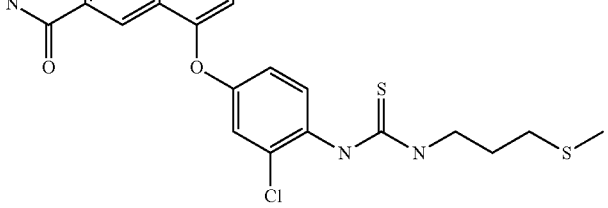 | $^{1}$H NMR (400 MHz, METHANOL-d$_4$) 9.06 (s, 1H), 8.95 (d, J = 7.03 Hz, 1H), 7.95 (br. s., 1H), 7.59-7.68 (m, 2H), 7.39 (dd, J = 2.76, 8.78 Hz, 1H), 7.20 (d, J = 6.53 Hz, 1H), 4.24 (s, 3H), 3.74 (br. s., 2H), 2.61 (t, J = 7.03 Hz, 2H), 2.14 (s, 3H), 1.98 (quin, J = 6.90 Hz, 2H) | 490.9 |
| Example 64 | 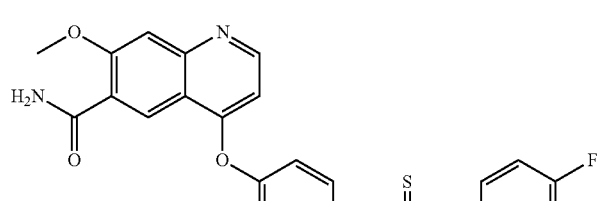 | 9.05 (br. s., 1H), 8.94 (br. s., 1H), 7.89 (br. s., 1H), 7.64 (d, J = 15.56 Hz, 2H), 7.51 (br. s., 2H), 7.42 (br. s., 1H), 7.18 (d, J = 6.53 Hz, 3H), 4.23 (br. s., 3H) | 498.2 |
| Example 65 | 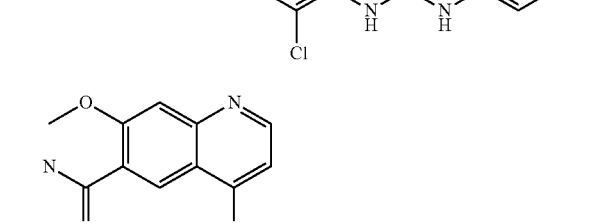 | $^{1}$H NMR (400 MHz, METHANOL-d$_4$) 9.06 (s, 1H), 8.95 (d, J = 6.53 Hz, 1H), 7.95 (d, J = 8.53 Hz, 1H), 7.74 (t, J = 7.28 Hz, 1H), 7.65 (d, J = 12.05 Hz, 2H), 7.42 (d, J = 7.03 Hz, 1H), 7.34 (br. s., 1H), 7.16-7.29 (m, 3H), 4.24 (s, 3H) | 519.1 |
| Example 66 | 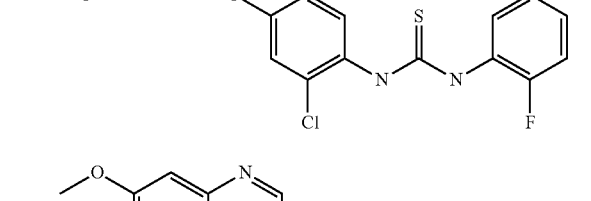 | $^{1}$H NMR (400 MHz, DMSO-d$_6$) 9.33 (s, 1H), 8.95-9.05 (m, 1H), 8.73 (s, 1H), 7.94-8.02 (m, 1H), 7.83-7.93 (m, 1H), 7.65-7.77 (m, 2H), 7.56 (s, 1H), 7.38-7.48 (m, 1H), 6.77-6.87 (m, 1H), 4.06-4.15 (m, 5H), 3.88 (s, 2H), 2.56-2.66 (m, 2H). | 493.0 |
| Example 67 | 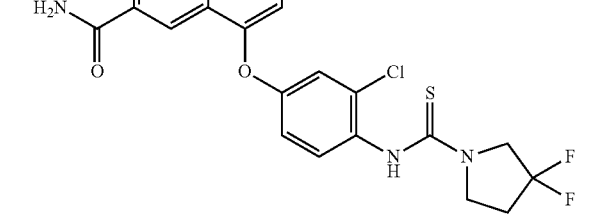 | $^{1}$H NMR (400 MHz, DMSO-d$_6$) 9.62 (s, 1H), 8.98 (d, J = 6.2 Hz, 1H), 8.73 (s, 1H), 7.97 (br. s., 1H), 7.89 (br. s., 1H), 7.63-7.72 (m, 2H), 7.53 (d, J = 8.8 Hz, 1H), 7.42 (dd, J = 2.6, 8.6 Hz, 1H), 6.81 (d, J = 6.0 Hz, 1H), 4.09 (s, 7H), 2.04-2.17 (m, 4H). | 529.1 (MS + 23) |

-continued

| Examples | Structures | NMR | LCMS (ESI) m/z: (M + 1)+. |
|---|---|---|---|
| Example 68 | 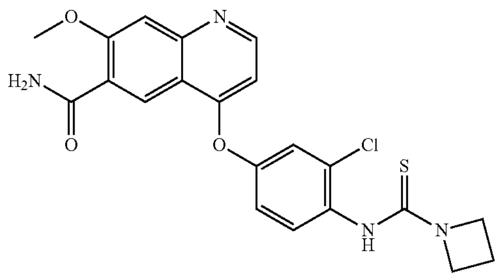 [SMILES: COc1cc2nccc(Oc3ccc(NC(=S)N4CCC4)c(Cl)c3)c2cc1C(N)=O] | ¹H NMR (400 MHz, DMSO-d₆) 9.16 (s, 1H), 8.98 (d, J = 6.2 Hz, 1H), 8.71 (s, 1H), 7.96-8.01 (m, 1H), 7.87-7.91 (m, 1H), 7.68-7.73 (m, 2H), 7.61 (d, J = 8.8 Hz, 1H), 7.38-7.44 (m, 1H), 6.82 (d, J = 6.2 Hz, 1H), 4.06-4.13 (m, 7H), 2.17-2.25 (m, 2H). | 443.0 |
| Example 69 | 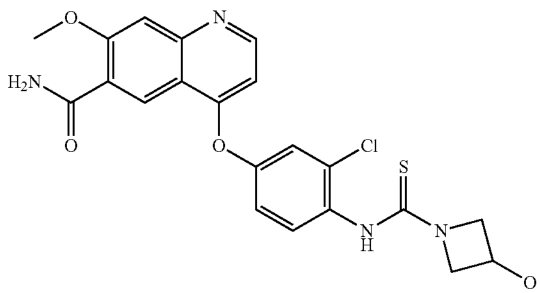 [SMILES: COc1cc2nccc(Oc3ccc(NC(=S)N4CC(O)C4)c(Cl)c3)c2cc1C(N)=O] | ¹H NMR (400 MHz, DMSO-d₆) □ 9.25 (s, 1H), 9.01 (d, J = 6.5 Hz, 1H), 8.73 (s, 1H), 7.96-8.01 (m, 1H), 7.89-7.94 (m, 1H), 7.70-7.76 (m, 2H), 7.62 (d, J = 8.8 Hz, 1H), 7.39-7.46 (m, 1H), 6.85 (d, J = 6.2 Hz, 1H), 4.47-4.51 (m, 1H), 4.27-4.35 (m, 2H), 4.08 (s, 3H), 3.86 (d, J = 7.5 Hz, 2H). | 459.1 |
| Example 70 | 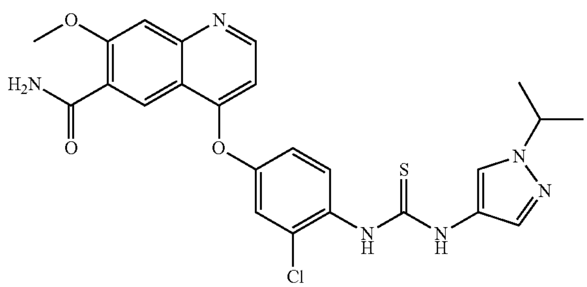 [SMILES: COc1cc2nccc(Oc3ccc(NC(=S)Nc4cnn(C(C)C)c4)c(Cl)c3)c2cc1C(N)=O] | ¹H NMR (400 MHz, METHANOL-d₄) 9.06 (s, 1H), 8.95 (d, J = 6.53 Hz, 1H), 8.12 (br. s., 1H), 7.98 (d, J = 8.53 Hz, 1H), 7.59-7.79 (m, 3H), 7.41 (d, J = 8.53 Hz, 1H), 7.21 (d, J = 6.53 Hz, 1H), 4.5₁-4.65 (m, 1H), 4.24 (s, 3H), 1.54 (d, J = 6.78 Hz, 6H) | 511.2 |
| Example 71 | 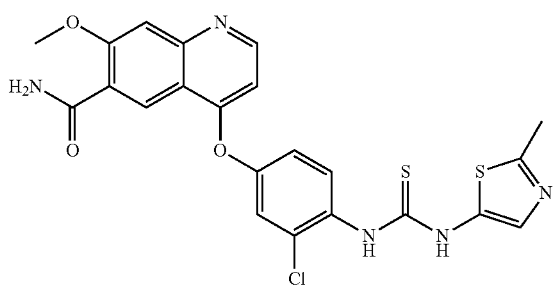 [SMILES: COc1cc2nccc(Oc3ccc(NC(=S)Nc4cnc(C)s4)c(Cl)c3)c2cc1C(N)=O] | ¹H NMR (400 MHz, METHANOL-d₄) d 9.06 (s, 1H), 8.95 (d, J = 6.53 Hz, 1H), 8.28 (d, J = 8.53 Hz, 1H), 7.69 (d, J = 2.51 Hz, 1H), 7.63 (s, 1H), 7.44 (dd, J = 2.76, 8.78 Hz, 1H), 7.23 (s, 1H), 7.17 (d, J = 6.53 Hz, 1H), 4.24 (s, 3H), 2.42 (s, 3H) | 500.1 |
| Example 73 | 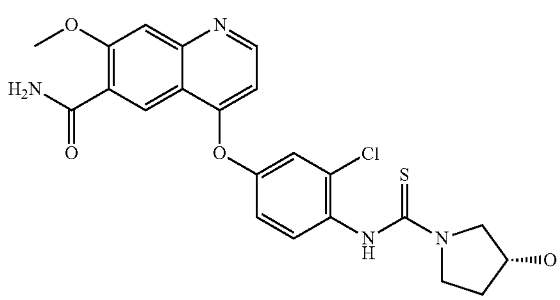 [SMILES: COc1cc2nccc(Oc3ccc(NC(=S)N4CC[C@@H](O)C4)c(Cl)c3)c2cc1C(N)=O] | ¹H NMR (400 MHz, DMSO-d₆) 9.04 (d, J = 6.5 Hz, 1H), 8.90-9.01 (m, 1H), 8.73 (s, 1H), 7.99 (br. s., 1H), 7.92 (br. s., 1H), 7.76 (s, 1H), 7.72 (d, J = 2.5 Hz, 1H), 7.58 (s, 1H), 7.39-7.49 (m, 1H), 6.84 (d, J = 6.5 Hz, 1H), 4.39-4.51 (m, 1H), 4.25-4.34 (m, 1H), 4.08 (s, 4H), 3.68-3.70 (m, 2H), 1.8₁-₂.14 (m, 2H). | 472.9 |

| Examples | Structures | NMR | LCMS (ESI) m/z: (M + 1)+. |
|---|---|---|---|
| Example 74 | 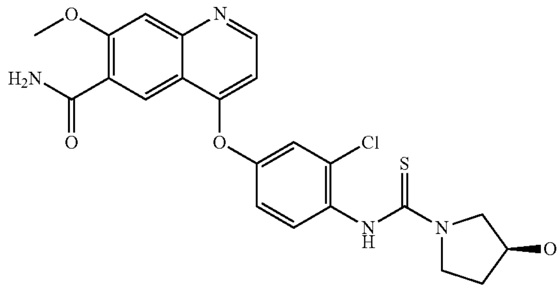 [SMILES: COc1cc2nccc(Oc3ccc(NC(=S)N4CC[C@H](O)C4)c(Cl)c3)c2cc1C(N)=O] | $^1$H NMR (400 MHz, DMSO-d$_6$) 9.04 (d, J = 6.2 Hz, 1H), 8.92-9.01 (m, 1H), 8.72 (s, 1H), 7.99 (br. s., 1H), 7.91 (br. s., 1H), 7.79 (s, 1H), 7.72 (s, 1H), 7.58 (d, J = 8.5 Hz, 1H), 7.43 (d, J = 8.2 Hz, 1H), 6.84 (d, J = 6.2 Hz, 1H), 4.42-4.55 (m, 1H), 4.28-4.38 (m, 1H), 4.05-4.15 (m, 4H), 3.80-3.84 (m, 2H), 1.8$_{1-2}$.19 (m, 2H). | 472.9 |
| Example 75 | 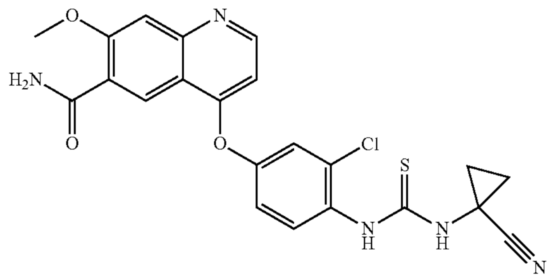 | $^1$H NMR (400 MHz, DMSO-d$_6$) 11.07 (s, 1H), 8.99-9.00 (d, J = 6.4 Hz, 1H), 8.71 (s., 1H), 7.8$_{1-7}$.99 (m, 3H), 7.77-7.75 (m, 1H) 7.6$_{1-7}$.60 (m, 1H), 7.46-7.17 (m, 1H), 6.94-6.93 (m, 1H), 4.07 (s, 3H), 1.64-1.55 (m, 4H) | 490.8 (MS + 23) |
| Example 85 | 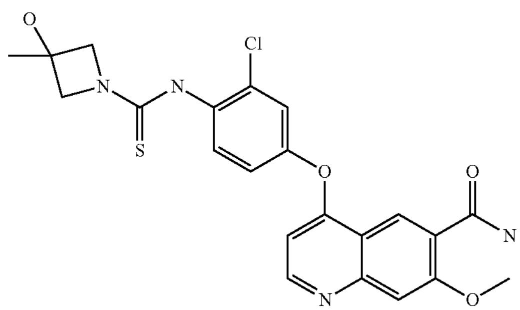 [SMILES: COc1cc2nccc(Oc3ccc(NC(=S)N4CC(C)(O)C4)c(Cl)c3)c2cc1C(N)=O] | $^1$H NMR (400 MHz, METHANOL-d$_4$) = 9.06 (s, 1H), 8.97 (d, J = 6.5 Hz, 1H), 7.82-7.76 (m, 1H), 7.73-7.62 (m, 2H), 7.55 (dt, J = 2.5, 8.3 Hz, 1H), 7.21-7.15 (m, 1H), 4.66-4.57 (m, 1H), 4.23 (s, 3H), 4.089-4.154 (m, 4H), 1.553 (s, 3H). | 473.1 |
| Example 86 | 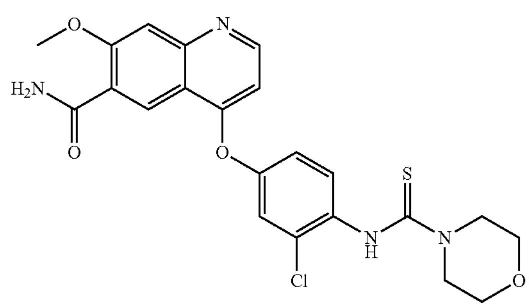 [SMILES: COc1cc2nccc(Oc3ccc(NC(=S)N4CCOCC4)c(Cl)c3)c2cc1C(N)=O] | $^1$H NMR (400 MHz, METHANOL-d$_4$) = 9.06 (s, 1H), 8.97 (d, J = 6.5 Hz, 1H), 7.82-7.76 (m, 1H), 7.73-7.62 (m, 2H), 7.55 (dt, J = 2.5, 8.3 Hz, 1H), 7.21-7.15 (m, 1H), 4.66-4.57 (m, 1H), 4.237 (s, 3H), 4.12-4.01 (m, 4H), 3.82-3.725 (m, 4H) | 495.0 |
| Example 87 | 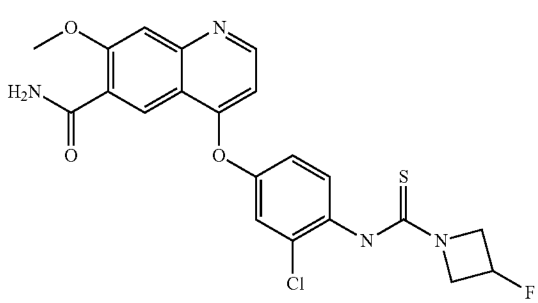 [SMILES: COc1cc2nccc(Oc3ccc(NC(=S)N4CC(F)C4)c(Cl)c3)c2cc1C(N)=O] | $^1$H NMR (400 MHz, METHANOL-d$_4$) ppm 4.21 (s, 3 H) 4.22-4.28 (m, 2 H) 4.49-4.51 (m, 2 H) 5.25-5.56 (m, 1H) 7.16-7.23 (m, 1 H) 7.36-7.43 (m, 1 H) 7.61 (s, 1 H) 7.66 (dd, J = 8.03, 2.51 Hz, 1 H) 7.94 (d, J = 8.53 Hz, 1 H) 8.95 (d, J = 7.03 Hz, 1 H) 9.00 (s, 1 H) | 425.1 |

-continued
| Examples | Structures | NMR | LCMS (ESI) m/z: (M + 1)+. |
|---|---|---|---|
| Example 92 | 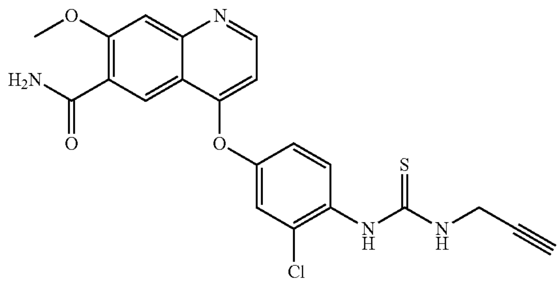 [SMILES: C#CCNC(=S)Nc1ccc(Oc2ccnc3cc(OC)c(C(N)=O)cc23)cc1Cl] | ¹H NMR (400 MHz, METHANOL-d₄) = 9.06-9.03 (m, 1H), 8.95 (d, J = 6.8 Hz, 1H), 7.83-7.77 (m, 1H), 7.68-7.62 (m, 1H), 7.55 (dd, J = 2.8, 8.8 Hz, 1H), 7.14 (d, J = 6.5 Hz, 1H), 5.64-5.61 (m, 1H), 5.54 (d, J = 2.5 Hz, 1H), 4.23 (s, 3H), 2.40 (d, J = 1.3 Hz, 1H) | 441.0 |
| Example 93 | 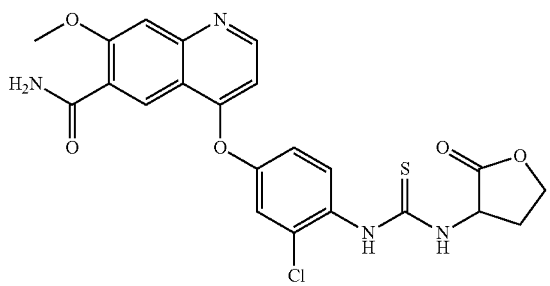 [SMILES: COc1cc2nccc(Oc3ccc(NC(=S)NC4CCOC4=O)c(Cl)c3)c2cc1C(N)=O] | ¹H NMR (400 MHz, METHANOL-d₄) = 9.06 (s, 1H), 8.97 (d, J = 6.5 Hz, 1H), 7.82-7.76 (m, 1H), 7.73-7.62 (m, 2H), 7.55 (dt, J = 2.5, 8.3 Hz, 1H), 7.21-7.15 (m, 1H), 4.66-4.57 (m, 1H), 4.23 (s, 3H), 3.93-3.77 (m, 2H), 2.31-1.97 (m, 2H) | 487.1 |
| Example 94 | 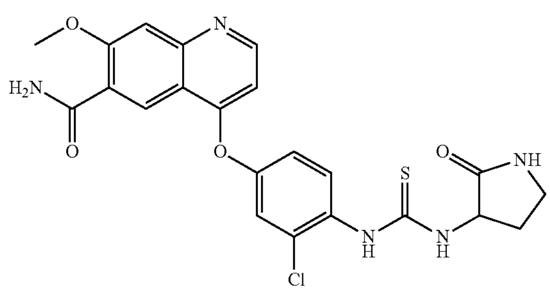 [SMILES: COc1cc2nccc(Oc3ccc(NC(=S)NC4CCNC4=O)c(Cl)c3)c2cc1C(N)=O] | ¹H NMR (400 MHz, METHANOL-d₄) = 8.97 (s, 1H), 8.69 (d, J = 5.5 Hz, 1H), 7.89 (d, J = 8.8 Hz, 1H), 7.56 (s, 1H), 7.48 (d, J = 2.5 Hz, 1H), 7.27 (dd, J = 2.8, 9.0 Hz, 1H), 6.76 (d, J = 5.5 Hz, 1H), 4.64-4.64 (m, 1H), 4.15 (s, 3H), 3.41 (dd, J = 4.0, 9.5 Hz, 2H), 2.79 (d, J = 3.8 Hz, 1H), 2.05-1.94 (m, 1H | 486.0 |
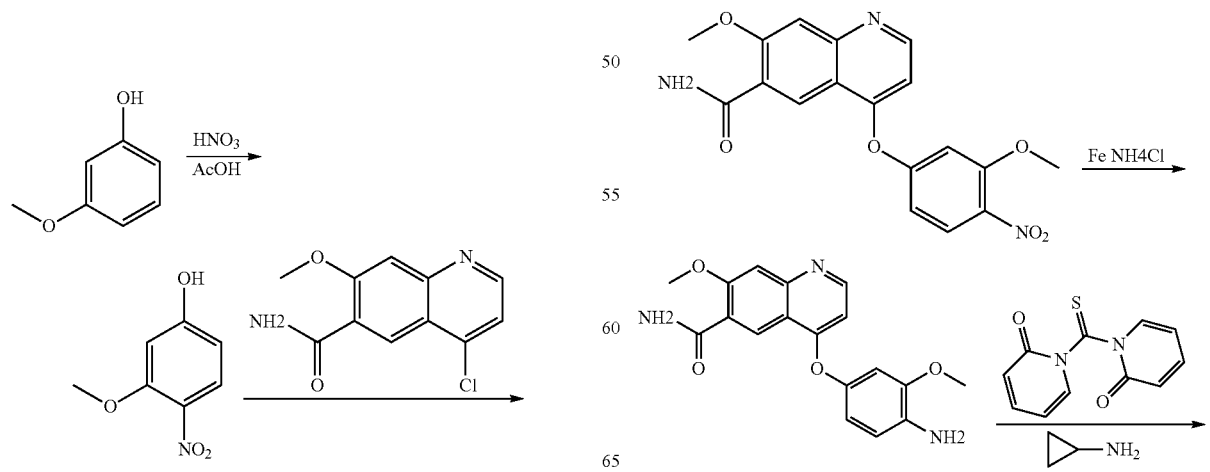
Process B

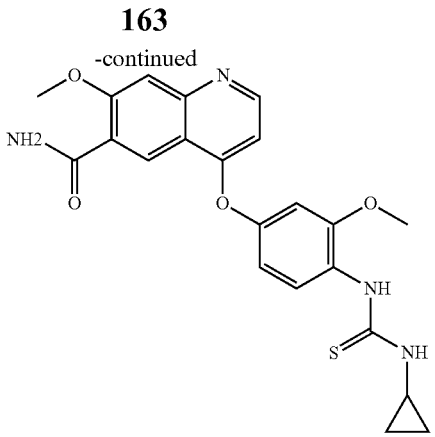

Compound 72A

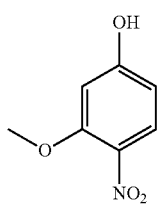

Concentrated nitric acid (55.83 mg, 886.09 μmol) was added to a solution of trimethoxyphenol (100 mg, 805.54 μmop in acetic acid (2 mL) and stirred at 0° C. for 3 hours. The aqueous phase was extracted with ethyl acetate (20 mL*2). The combined organic layers were washed with NaCl solution (20 mL*2), and then dried over sodium sulfate, filtered and evaporated, and the residue was purified by column chromatography to give compound 72A (48 mg, 35.23%).

¹H NMR (400 MHz, METHANOL-d₄)=10.914 (s, 1H), 7.901-7.887 (d, 1H), 6.614-6.609 (d, 1H), 6.50-6.48 (m, 1H), 3.875 (s, 3H)

Compound 72B

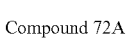

Compound 1E (600 mg, 2.54 mmol) was added to a solution of compound 72A (428.81 mg, 2.54 mmol) in chlorobenzene (10 mL) and stirred at 130° C. for 16 hours. After rotary drying under vacuum, the residue was washed with ethyl acetate ester (30 ml) to give compound 72B (820 mg). LCMS (ESI) m/z: 370 (M+1).

Compound 72C

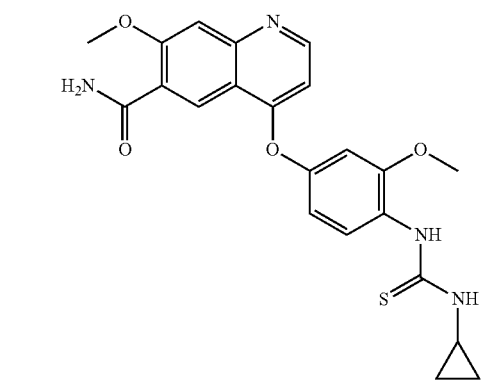 [SMILES: COc1cc(Oc2ccnc3cc(OC)c(C(N)=O)cc23)ccc1NC(=S)NC1CC1]

Reduced iron powder (1.36 g, 24.40 mmol) and ammonium chloride (1.30 g, 24.37 mmol) were added to a solution of compound 72C (900 mg, 2.44 mmol) in ethanol/water (8.5:1.5, 20 mL) and reacted at 100° C. for 1 hour, water (20 mL) was added and extracted with a solution of ethanol/dichloromethane (3:1) (50 mL*3). The combined organic layers were dried over sodium sulfate, filtered and evaporated to give compound 72C (700 mg) which can be used directly in the next step without further purification.

LCMS (ESI) m/z: 340 (M+1)

Example 72

1,1'-thiocarbonyldi-2(1H)-pyridone (116.85 mg, 503.09 μmol) was added to a solution of compound 72C (450 mg, 1.33 mmol) in dioxane (10 ml), and reacted at 120° C. under the protection of nitrogen for 2 hours, after cooling to 28° C., cyclopropylamine (1.14 g, 19.95 mmol) was added and stirred at 28° C. for 2 hours, the solution was removed under vacuum and the residue was purified by preparative HPLC to give a compound of Example 72 (120 mg, the yield was 20.58%). LCMS (ESI) m/z: 439 (M+1)

¹H NMR (400 MHz, METHANOL-d₄)=9.43 (s, 1H), 8.88-8.70 (m, 1H), 7.91 (br. s., 1H), 7.68-7.50 (m, 2H), 7.38 (d, J=6.5 Hz, 1H), 7.24-7.06 (m, 1H), 4.31-4.15 (m, 3H), 3.95-3.75 (s, 3H), 1.02-0.62 (m, 4H)

Process C

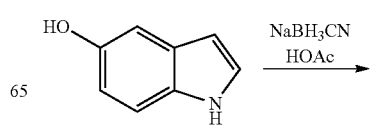

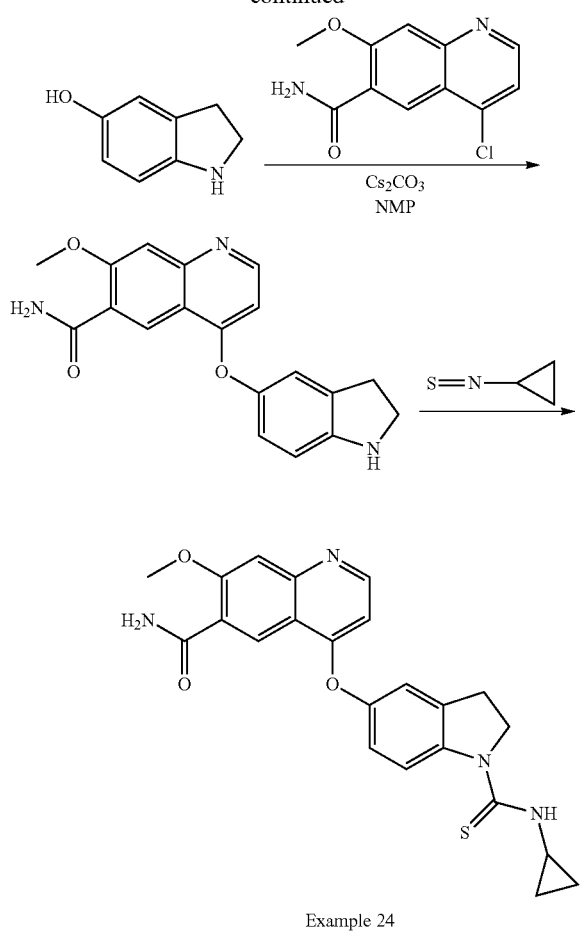

Example 24

Compound 24A

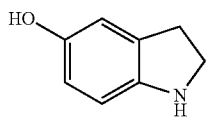

Sodium cyanoborohydride (4.72 g, 75.1 mmol) was added portionwise to a solution of 5-hydroxy-1H-indole (4 g, 30 mmol) in acetic acid (120 ml). The reaction solution was stirred at 25° C. for 12 hours, and then rotary evaporated to remove the solvent, the residue was dissolved in ethyl acetate (200 ml), and washed with saturated sodium bicarbonate. The aqueous layer was extracted with ethyl acetate (3×150 ml). The organic layers were combined and washed with saturated NaCl solution, dried over anhydrous sodium sulfate, filtered and evaporated to dryness. The residue was purified by column chromatography (petroleum ether/ethyl acetate=3:1, Rf=0.3) to give compound 24A (creamy white solid, 1.3 g, 32%).

$^1$H NMR (400 MHz, CHLOROFORM-d)=6.69 (s, 1H), 6.59-6.49 (m, 2H), 3.55 (t, J=8.3 Hz, 2H), 3.01 (t, J=8.3 Hz, 2H), 2.20 (s, 1H)

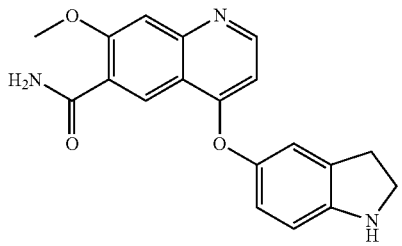

Compound 24B

Compound 1E (100 mg, 423 μmol), compound 24A (63 mg, 465 μmol) and cesium carbonate (303 mg, 930 μmol) were added to NMP (1 mL). The reaction solution was heated to 120° C. and stirred for 2 hours, and then the reaction was quenched with water, and extracted with ethyl acetate (3×10 ml). The organic layer was washed with saturated NaCl solution, dried over anhydrous sodium sulfate, filtered and evaporated to dryness. The residue was chromatographed on a silica gel plate (dichloromethane/methanol=10:1, Rf=0.2) and purified to give compound 24B (yellow solid, 80 mg, 57%).

LCMS (ESI) m/z: 336.1 (M+1)$^+$

Example 24

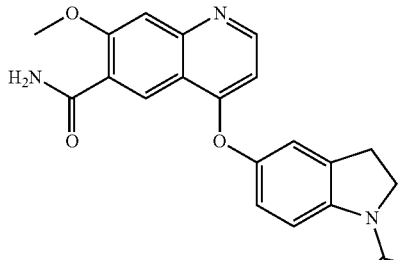

Compound 24B (25 mg, 75 μmol) and cyclopropyl isothiocyanate (15 mg, 150 μmol) were added to tetrahydrofuran (2 ml). The reaction solution was stirred at 25° C. for 15 hours. The solvent was removed by rotary distillation under reduced pressure and the residue was isolated by preparative HPLC to give a compound of Example 24 (yellow solid, 18 mg, 49%). LCMS (ESI) m/z: 435.1 (M+1)$^+$ $^1$H NMR (400 MHz, METHANOL-d$_4$) 9.06 (s, 1H), 8.88 (d, J=7.0 Hz, 1H), 8.75 (d, J=8.5 Hz, 1H), 7.59 (s, 1H), 7.27 (s, 1H), 7.16 (dd, J=2.5, 9.0 Hz, 1H), 7.01 (d, J=7.0 Hz, 1H), 4.27-4.21 (m, 5H), 3.21 (t, J=8.3 Hz, 2H), 3.08 (br. s., 1H), 0.88 (d, J=5.5 Hz, 2H), 0.76-0.70 (m, 2H)

Process D

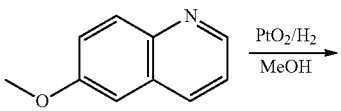

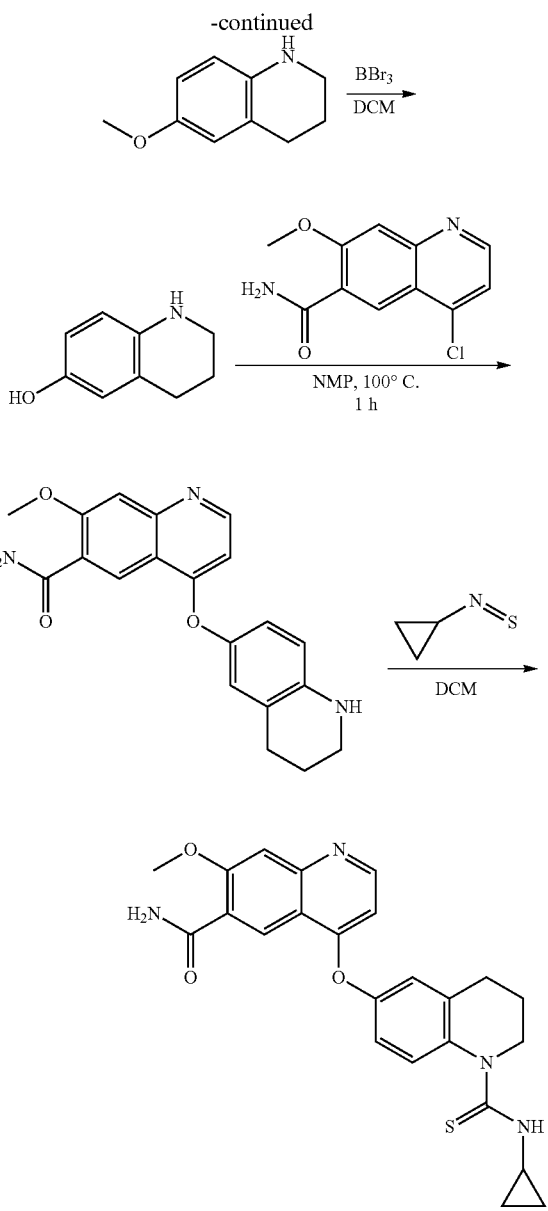

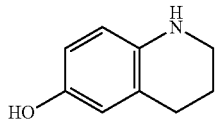

Compound 26B

Compound 26A (3.00 g, 18.38 mmol) was dissolved in 50 ml of dichloromethane, BBr$_3$ (13.81 g, 55.14 mmol) was added at 0° C., and then stirred at 15° C. for 2 hours. The reaction solution was concentrated and the reaction was quenched by 5 ml of methanol. Saturated sodium bicarbonate solution (20 ml) was added and stirred for 30 min, then extracted with 20 ml of ethyl acetate three times. The organic phases were combined and dried over anhydrous sodium sulfate and concentrated to give a crude product. The crude product was purified by silica gel column chromatography (petroleum ether/ethyl acetate was from 3:1 to 1:1) to give compound 26B (1.95 g, the yield was 71.11%).

$^1$H NMR (400 MHz, DMSO-d$_6$) 8.24 (s, 1H), 6.22-6.35 (m, 3H), 4.93 (br. s., 1H), 3.02-3.10 (m, 2H), 2.57 (t, J=6.4 Hz, 2H), 1.67-1.80 (m, 2H).

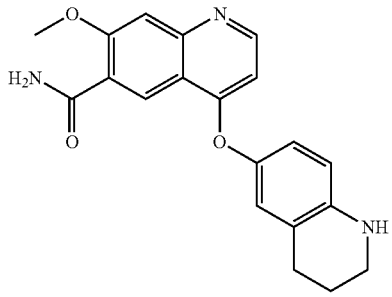

Compound 26C

Compound 26C was prepared in a similar manner as that described in compound 24B, excepting that the starting material used for the synthesis of the compound was prepared by 5-hydroxy tetrahydroquinoline.

Example 26

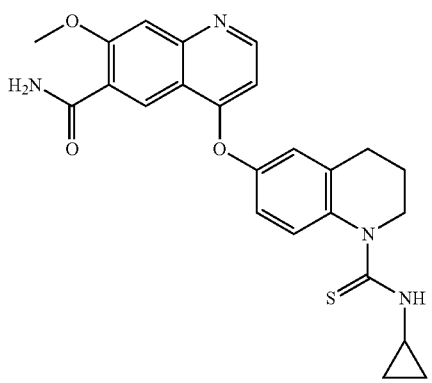 [SMILES: COc1cc2nccc(Oc3ccc4c(c3)CCCN4C(=S)NC3CC3)c2cc1C(N)=O]

Compound 26A

6-Methoxyquinoline (3.0 g, 18.85 mmol) and PtO$_2$ (0.2 g 0.8 mmol) were dissolved in methanol (20 mL) and heated to 45° C. and stirred for 24 hours. The reaction was detected by TLC. After the reaction was cooled to room temperature, the residue was isolated by silica gel column chromatography (petroleum ether/ethyl acetate=10:1) to obtain a compound 26A (pale yellow oil, 1.2 g, the yield was 39%) after spin-drying the solvent.

$^1$H NMR (400 MHz, CHLOROFORM-d) δ 6.5$_{1-6}$.66 (m, 2H), 6.45 (d, J=8.5 Hz, 1H), 3.73 (s, 3H), 3.20-3.30 (m, 2H), 2.76 (t, J=6.5 Hz, 2H), 1.86-1.98 (m, 2H).

Compound 26C (90 mg, 257.6 μmol) was dissolved in tetrahydrofuran (5 ml) and cyclopropylthiocyanate (51.1 mg, 515.2 μmol) was added at room temperature and stirred at room temperature for 12 hours under the protection of nitrogen. The reaction solution was spin-dried under vacuum and then separated by HPLC (hydrochloric acid) and lyophilized to give a compound of Example 26 (yellow solid, 65 mg, the yield was 56.2%).

$^1$H NMR (400 MHz, DMSO-d$_6$) δ 9.05 (d, J=6.5 Hz, 1H), 8.72 (s, 1H), 8.29 (br. s., 1H), 8.01 (br. s., 1H), 7.93 (br. s., 1H), 7.81 (s, 1H), 7.37 (d, J=8.8 Hz, 1H), 7.28 (d, J=2.5 Hz, 1H), 7.18 (dd, J=2.5, 8.8 Hz, 1H), 7.00 (d, J=6.5 Hz, 1H), 4.09 (s, 3H), 3.98-3.98 (m, 1H), 4.01 (t, J=6.2 Hz, 2H), 3.06 (br. s., 1H), 2.76 (t, J=6.6 Hz, 2H), 1.91 (quin, J=6.4 Hz, 2H), 0.66-0.77 (m, 2H), 0.56-0.66 (m, 2H).

Example 34

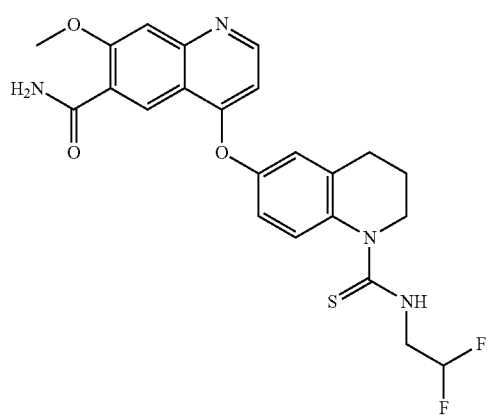 [SMILES: COc1cc2nccc(Oc3ccc4c(c3)CCCN4C(=S)NCC(F)F)c2cc1C(N)=O]

The compound of this Example was prepared by using a similar method as described in Example 26.

$^1$H NMR (400 MHz, DMSO-d$_6$) δ 8.89 (d, J=5.8 Hz, 1H), 8.70 (s, 1H), 8.33 (s, 1H), 7.93 (br. s., 1H), 7.84 (br. s., 1H), 7.58 (s, 1H), 7.44 (d, J=8.8 Hz, 1H), 7.28 (d, J=2.3 Hz, 1H), 7.20 (dd, J=2.5, 8.8 Hz, 1H), 6.83 (d, J=6.0 Hz, 1H), 6.37-6.42 (m, 1H), 6.26 (s, 1H), 6.10-6.14 (m, 1H), 4.05-4.13 (m, 5H), 3.93-4.01 (m, 2H), 2.76 (t, J=6.6 Hz, 2H), 1.93 (t, J=6.6 Hz, 2H).

Process E

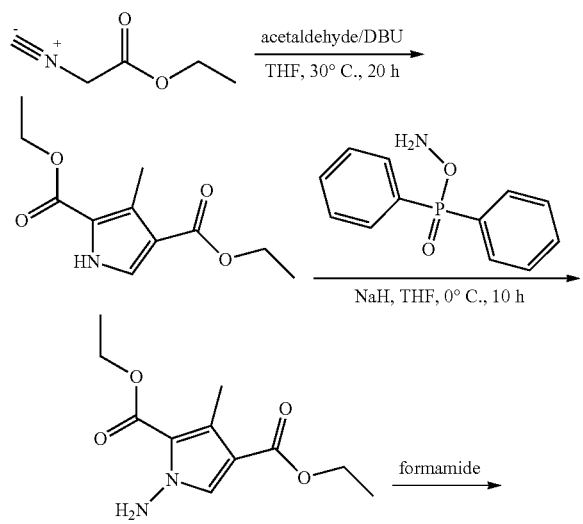

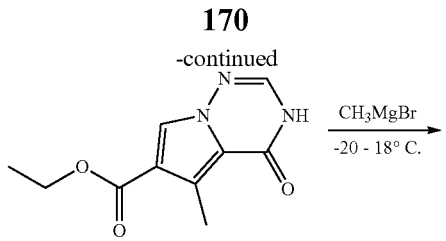

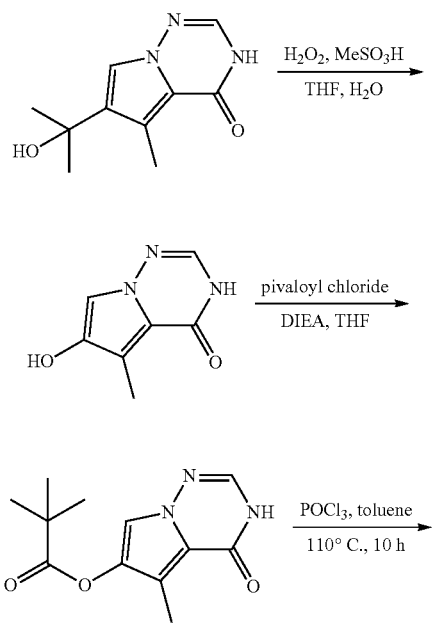

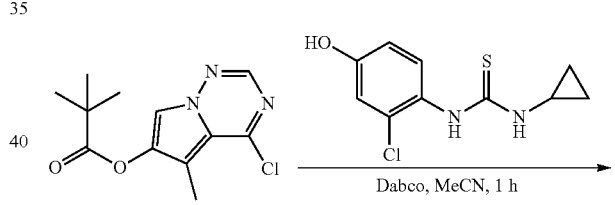

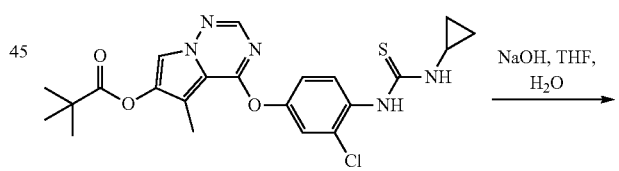

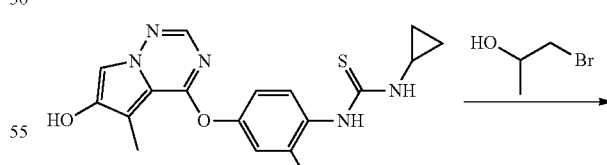

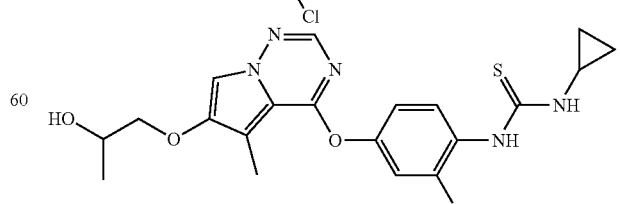

Example 25

Compound 25A

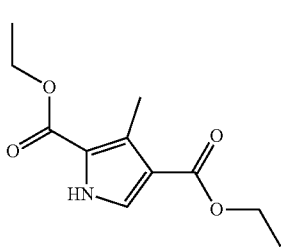

A solution of ethyl isocyanoacetate (9.06 g, 80.13 mmol) and DBU (12.20 g, 80.13 mmol) in 120 ml of tetrahydrofuran was heated to 50° C. and then a solution of acetaldehyde in 40 ml of tetrahydrofuran was added dropwise to the solution over 30 minutes. The resulting mixed solution was stirred for one hour at 50° C., cooled to room temperature, neutralized with acetic acid and then rotary evaporated to dryness. The resulting residue was dissolved in 300 ml of ethyl acetate and then washed successively with 1 mol of hydrochloric acid, saturated sodium bicarbonate solution and saturated NaCl solution. The organic layer was dried over anhydrous sodium sulfate, filtered and rotary evaporated to dryness. The residue was purified by column chromatography to give compound 25A as a pale yellow solid (3.7 g, the yield was 20.5%).

$^1$H NMR (400 MHz, CHLOROFORM-d)=9.38 (br. s., 1H), 7.50 (d, J=3.3 Hz, 1H), 4.36 (q, J=7.0 Hz, 2H), 4.30 (q, J=7.3 Hz, 2H), 2.62 (s, 3H), 1.40 (t, J=6.3 Hz, 3H), 1.38-1.32 (m, 3H)

Compound 25B

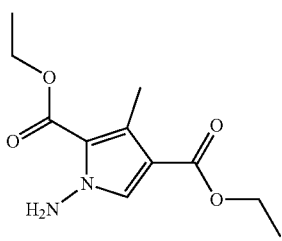

60% sodium hydride (550 mg, 13.75 mmol) was suspended in 150 ml of dry tetrahydrofuran and cooled to 0° C. The compound 25A (2.2 g, 9.77 mmol) and O-(diphenyl phosphine) hydroxylamine (3.3 g, 14.15 mmol) was added to the suspension. The mixture was then stirred at 0° C. for 2 hours. The mixture was poured into 200 ml of saturated aqueous ammonium chloride and extracted with 100 ml of ethyl acetate. The organic layer was washed with 100 ml saturated NaCl solution, then dried over anhydrous sodium sulfate, filtered and rotary evaporated to give compound 25B (yellow, 3.38 g, crude) which was used directly in the next step.

$^1$H NMR (400 MHz, CHLOROFORM-d)=7.50 (s, 1H), 5.65 (br. s., 2H), 4.37 (q, J=7.2 Hz, 2H), 4.28 (q, J=7.0 Hz, 2H), 2.59 (s, 3H), 1.41 (t, J=7.2 Hz, 3H), 1.35 (t, J=7.2 Hz, 3H)

Compound 25C

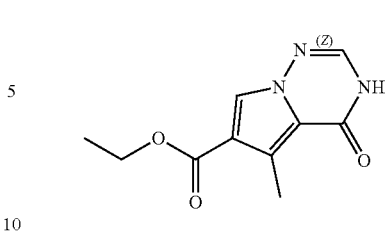

Compound 25B (1.55 g, 6.45 mmol) was dissolved in formamide (16.98 g, 377 mmol) and placed in a microwave tube, and then reacted in a microwave reactor at 180° C. for 30 minutes. After cooling to 80° C., the mixture was poured into 100 ml of water, filtered and the filter cake was washed with 200 ml of water, and then dried to give a gray compound 25C (solid, 1.38 g, the yield was 96.72%).

$^1$H NMR (400 MHz, DMSO-$d_6$)=11.63 (br. s., 1H), 7.91 (s, 1H), 7.83 (s, 1H), 4.22 (q, J=7.0 Hz, 2H), 2.60 (s, 3H), 1.27 (t, J=7.0 Hz, 3H).

Compound 25D

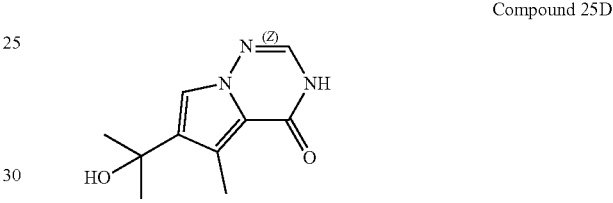

27 ml of 3 M methylmagnesium bromide was added dropwise to 50 ml of solution of compound 25C (3.5 g, 15.82 mmol) in tetrahydrofuran over 10 minutes in a dry ice bath under the protection of nitrogen, and the mixture was then heated to 18 to 20° C. and then stirred at this temperature for six hours. The reaction was slowly quenched with saturated ammonium chloride solution and then extracted with ethyl acetate (50 ml*3). The combined extracts were washed with saturated NaCl solution (20 ml*2), dried over anhydrous sodium sulfate, filtered and rotary evaporated to give a yellow compound 25D (solid, crude, 3.2 g) which was used directly in the next step.

$^1$H NMR (400 MHz, DMSO-$d_6$)=11.28 (br. s., 1H), 7.71-7.57 (m, 1H), 7.28 (s, 1H), 4.85 (s, 1H), 2.53 (s, 3H), 1.45 (s, 6H)

Compound 25E

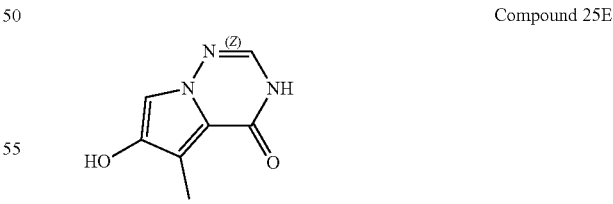

Compound 25D (7.2 g, 34.74 mmol) was dissolved in 50 ml of tetrahydrofuran and cooled to minus 15° C., and then 30% hydrogen peroxide solution (39.38 g, 347.4 mmol) was added to the mixture. The ice-cold methanesulfonic acid (33.39 g, 347.4 mmol) was diluted with 10 ml of water, and added dropwise to the previous solution between minus 20 and 15° C. The mixture was then stirred at minus 15 to 10° C. for 4 hours. The reaction was then quenched by the addition of cold saturated sodium sulphite at 0° C. and then basified with 28% ammonia. The mixture was extracted with ethyl acetate (100 mL*3). The combined organic layers were washed with saturated NaCl solution, dried over anhydrous sodium sulfate, filtered and rotary evaporated to give 800 mg of compound 25E (crude, yellow, semi-liquid and semi-solid) which was used directly in the next step.

LCMS (ESI) m/z: 165.8 (M+1)

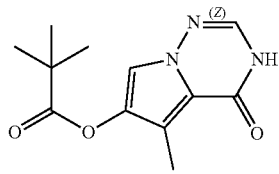

Compound 25F

The compound 25E (2.5 g, 15.15 mmol) and 4-dimethylaminopyridine (55.49 mg, 0.454 mmol) were suspended in 50 ml of tetrahydrofuran and then cooled to 0° C., followed by addition of pivaloyl chloride over about 3 minutes. The mixture was stirred at 18° C. for 18 hours. 100 ml of saturated sodium bicarbonate solution was added and then extracted with ethyl acetate (100 ml*3). The combined organic layers were washed with saturated NaCl solution, dried over anhydrous sodium sulfate, filtered and rotary evaporated to give yellow compound 25F (solid, crude, 3.2 g) which was used directly in the next step.

$^1$H NMR (400 MHz, CHLOROFORM-d)=10.59 (br. s., 1H), 7.52 (s, 2H), 2.41 (s, 3H), 1.39 (s, 9H)

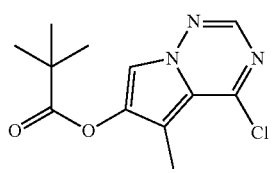

Compound 25G

Compound 25F (3.5 g, 14.04 mmol) was suspended in 80 ml of toluene and then phosphorus oxychloride (17 g, 110.87 mmol) and diisopropylethylamine (2.18 g, 16.85 mmol) were added. The mixture was heated to 110° C. and stirred for 17 hours and then cooled to 19° C., and rotary evaporated. The residue was washed with a solution of sodium hydrogen phosphate and then extracted with ethyl acetate (50 ml*3). The organic layers were combined washed with saturated NaCl solution, dried over sodium sulfate, filtered and rotary evaporated. The residue was purified by column chromatography to give yellow compound 25G (solid, 3.1 g, the yield was 82.48%).

LCMS (ESI) m/z: 267.9 [M+1]$^+$

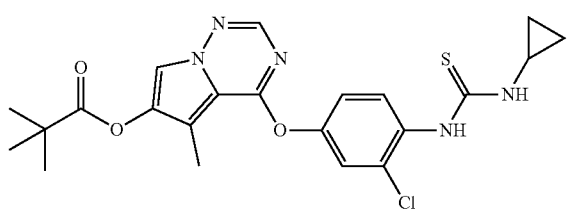

Compound 25H

The compound 25G (118 mg, 0.44 mmol), 2-chloro-4-hydroxyphenol cyclopropylthiourea (117 mg, 0.729 mmol) and triethylene diamine (140 mg, 1.25 mmol) were dissolved in 8 ml of acetonitrile, and then stirred at 18° C. for 1 hour under the protection of nitrogen. The mixture was dispersed in 10 ml of water and 30 ml of ethyl acetate and separated to give an organic layer which was washed with saturated NaCl solution, dried over anhydrous sodium sulfate, filtered and rotary evaporated. The residue was purified by thin layer chromatography to give compound 25H (pale yellow oil, 160 mg, the yield was 76.58%).

$^1$H NMR (400 MHz, CHLOROFORM-d)=8.54 (br. s., 1H), 8.30 (br. s., 1H), 7.93 (s, 1H), 7.88 (s, 1H), 7.42 (d, J=2.5 Hz, 1H), 7.28 (s, 1H), 7.25 (dd, J=2.5, 9.0 Hz, 1H), 2.76 (br. s., 1H), 2.49-2.40 (m, 3H), 1.49-1.37 (m, 9H), 1.01 (d, J=5.5 Hz, 2H), 0.89 (br. s., 2H)

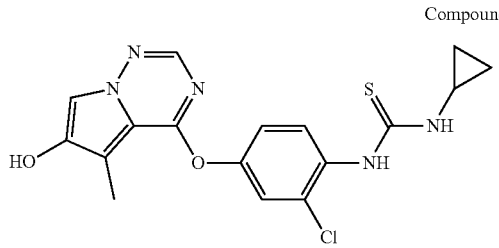

Compound 25I

The compound 25H (160 mg, 0.337 mmol) was dissolved in 2 ml of methanol and 2 ml of tetrahydrofuran and then 0.17 ml of 4 M sodium hydroxide solution was added at 17° C., and then continued to stir for 1.5 hours. The reaction solution was treated with 1 M hydrochloric acid till the pH value was 3, and then extracted with ethyl acetate (10 ml*3). The combined organic layers were washed with saturated NaCl solution, dried over anhydrous sodium sulfate, filtered and rotary evaporated to give compound 25I (yellow solid, crude, 150 mg) which was used directly in the next step.

LCMS (ESI) m/z: 389.9 [M+1]$^+$

Example 25

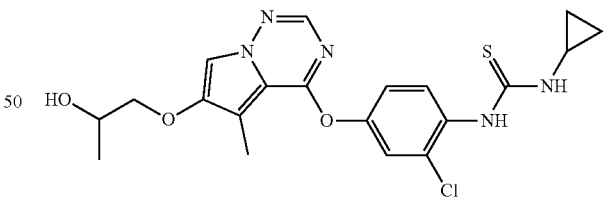

Compound of Example 25I (80 mg, 0.205 mmol), 1-bromoisopropanol (324 mg, 2.33 mmol) and cesium carbonate (200 mg, 0.613 mmol) were dissolved in 5 ml of ethanol and then heated to 50° C. and stirred for 2 hours, and then 1-bromoisopropanol (324 mg, 2.33 mmol) and cesium carbonate (200 mg, 0.613 mmol) were added and stirred overnight at room temperature, then 1-bromoisopropanol (324 mg, 2.33 mmol) and cesium carbonate (200 mg, 0.613 mmol) were added again, and then the mixture was heated to 50° C. and stirred for 2 hours. 50 ml of methylene chloride and 10 ml of water were added to the mixture and the resulting organic layer was separated and rotary evaporated.

The residue was purified by preparative HPLC to give a compound of Example 25 (20.8 mg, the yield was 26.16%).

LCMS (ESI) m/z: 448.1 [M+1]+

$^1$H NMR (400 MHz, METHANOL-$d_4$)=7.86-7.78 (m, 1H), 7.71-7.64 (m, 2H), 7.60-7.41 (m, 2H), 4.36-4.08 (m, 1H), 3.64-3.43 (m, 1H), 3.31-3.15 (m, 1H), 2.90 (dd, J=3.5, 7.0 Hz, 1H), 2.45 (s, 3H), 1.43-1.24 (m, 3H) 1.08-0.83 (m, 4H)

The following compounds were also prepared by using the similar methods as described in Example 25 mentioned above.

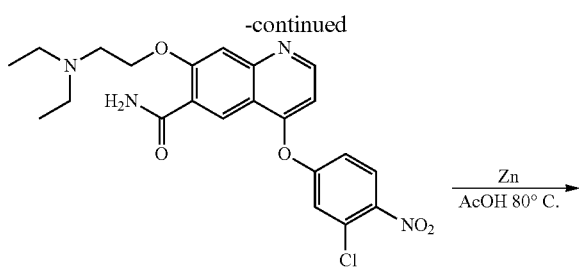

| Examples | Structures | NMR | LCMS (ESI) m/z: (M + 1)+ |
|---|---|---|---|
| Example 126 | 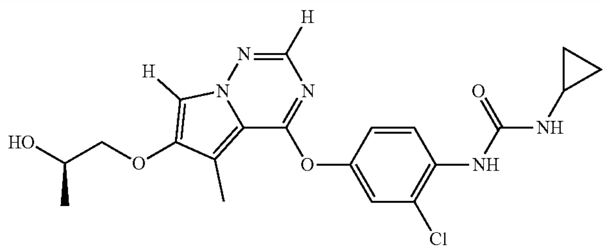 [SMILES: Cc1c(OC[C@@H](C)O)cn2ncnc(Oc3ccc(NC(=O)NC4CC4)c(Cl)c3)c12] | $^1$H NMR (Methanol-$d_4$, Bruker Avance 400 MHz): δ 8.15 (d, J = 8.0 Hz, 1 H), 7.81 (s, 1 H), 7.65 (s, 1 H), 7.40 (d, J = 2.0 Hz, 1 H), 7.20 (dd, J = 8.0, 2.0 Hz, 1 H), 4.22-4.12 (m, 1 H), 3.98-3.90 (m, 2 H), 2.70-2.60 (m, 1 H), 2.47 (s, 3 H), 1.31 (d, J = 4.0 Hz, 3 H), 0.84-0.74 (m, 2 H), 0.64-0.52 (m, 2 H). | 432.1 |
| Example 127 | 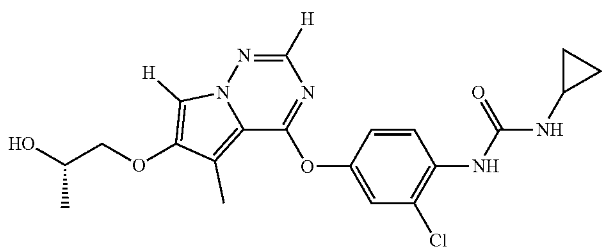 [SMILES: Cc1c(OC[C@H](C)O)cn2ncnc(Oc3ccc(NC(=O)NC4CC4)c(Cl)c3)c12] | $^1$H NMR (Methanol-$d_4$, Bruker Avance 400 MHz): δ 8.15 (d, J = 8.0 Hz, 1 H), 7.81 (s, 1 H), 7.65 (s, 1 H), 7.40 (d, J = 2.0 Hz, 1 H), 7.20 (dd, J = 8.0, 2.0 Hz, 1 H), 4.22-4.12 (m, 1 H), 3.98-3.90 (m, 2 H), 2.70-2.60 (m, 1 H), 2.47 (s, 3 H), 1.31 (d, J = 4.0 Hz, 3 H), 0.84-0.74 (m, 2 H), 0.64-0.52 (m, 2 H). | 432.1 |

Process F

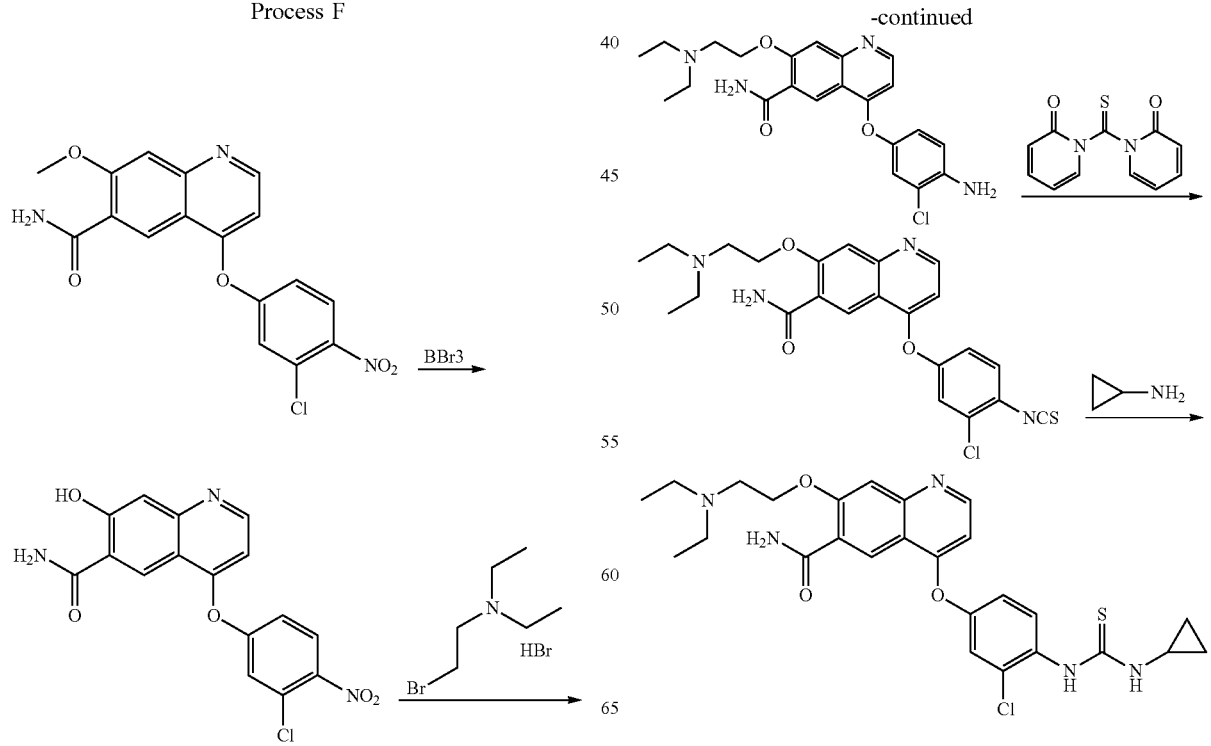

Compound 31A

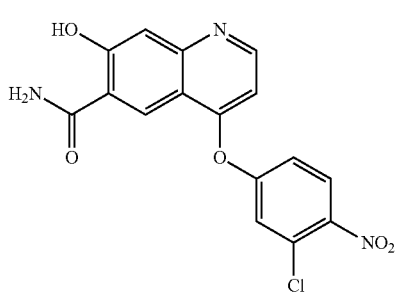

Boron tribromide (15.6 g, 62.27 mmol) was added dropwise to 20 ml of Example 1F (2 g, 5.35 mmol) solution over 10 minutes at minus 65° C., The reaction solution was heated to 20° C. over 30 minutes, and then stirred at this temperature for 16 hours. The reaction was quenched with 20 ml of methanol and 100 ml of saturated sodium bicarbonate was added and the mixture was extracted with dichloromethane/methanol (5:1). The organic layers were combined and washed with saturated NaCl solution, dried over anhydrous sodium sulfate, filtered and concentrated to give compound 31A (yellow solid, crude, 1.69 g) which was used directly in the next step.

$^1$H NMR (400 MHz, DMSO-$d_6$)=13.02 (br. s., 1H), 8.91 (s, 1H), 8.77 (d, J=5.0 Hz, 2H), 8.27 (d, J=9.0 Hz, 1H), 8.18 (br. s., 1H), 7.86 (d, J=2.5 Hz, 1H), 7.52 (dd, J=2.5, 9.0 Hz, 1H), 7.45-7.39 (m, 1H), 6.86 (d, J=5.5 Hz, 1H)

Compound 31B

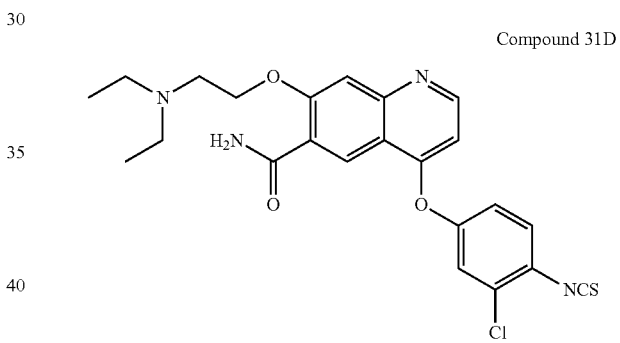

Potassium carbonate (115.26 mg, 0.834 mmol) was added to a solution of compound 31A (100 mg, 0.278 mmol) and 2-bromo-N,N-diethylethanamine hydrobromide (87.07 mg, 0.333 mmol) in 4 ml of DMF. Under the protection of nitrogen, the reaction solution was heated to 80° C. and stirred for 16 hours and poured into 40 ml of water and stirred for 20 minutes. The aqueous layer was extracted with a mixed solvent of dichloromethane/methanol (10:1) (30 ml*3). The organic layers were combined, washed with saturated NaCl solution, dried over anhydrous sodium sulfate, filtered and concentrated to give 127.57 mg of crude compound 31B as an oil which was used directly in the next step.

LCMS (ESI) m/z: 459.0 [M+1]$^+$

Compound 31C

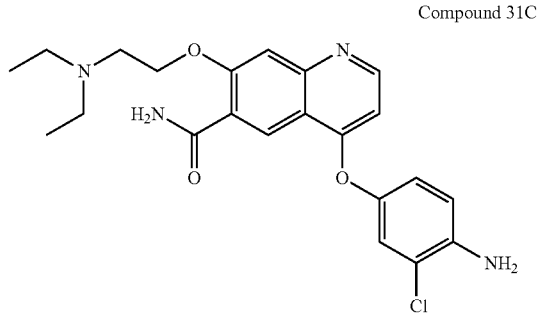 [SMILES: CCN(CC)CCOc1cc2nccc(Oc3ccc(N)c(Cl)c3)c2cc1C(N)=O]

Zinc power (181.78 mg, 2.78 mmol) was added to 5 mL of ethanol solution of compound 31B (127.57 mg, 0.278 mmol) and acetic acid (166.94 mg, 2.78 mmol) and then the reaction solution is heated to 80° C. under nitrogen and stirred for 16 hours. After cooling the mixture was basified with 10 ml of saturated sodium bicarbonate and diluted with 20 ml of ethanol, filtered, and the filtrate was concentrated. The residue was purified by preparative HPLC to give the compound 31C (yellow solid, 33.3 mg, the yield was 28%).

$^1$H NMR (400 MHz, CHLOROFORM-d)=9.29-9.21 (m, 1H), 8.82 (br. s., 1H), 8.65 (d, J=5.3 Hz, 1H), 7.50 (s, 1H), 7.14 (d, J=2.5 Hz, 1H), 6.95-6.83 (m, 2H), 6.46 (d, J=5.3 Hz, 1H), 5.89-5.76 (m, 1H), 4.41-4.30 (m, 2H), 3.01-2.91 (m, 2H), 2.71-2.57 (m, 4H), 1.13-1.00 (m, 6H)

Compound 31D

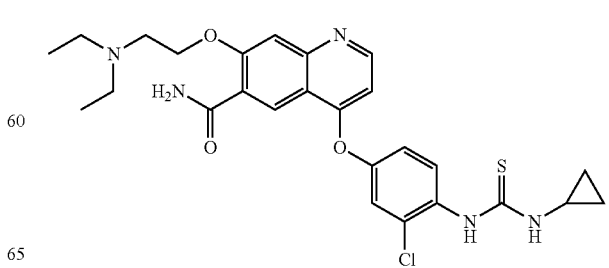

1,1'-thiocarbonyl di-2 (1H) pyridone (29.53 mg, 0.128 mmol) was added 1.5 ml dioxane solution of compound 31C (50 mg, 0.1166 mmol). The mixture was heated to 80 to 100° C. and stirred for 16 hours. The residue obtained by rotary evaporation was purified by preparative thin layer chromatography to give the compound 31D (yellow oil, 40 mg, the yield was 72.86%).

LCMS (ESI) m/z: 471.0 [M+1]$^+$

Example 31

Cyclopropylamine (164 mg, 2.87 mmol) was added to 2 ml of tetrahydrofuran solution of compound 31D (40 mg, 0.08493 mmol) and then stirred at 20° C. for 16 hours. The final mixture was purified by preparative HPLC to give a compound of Example 31 (white oil, 15 mg, the yield was 29.39%). LCMS (ESI) m/z: 528.0 [M+1]$^+$ $^1$H NMR (400 MHz, METHANOL-d$_4$)=8.99 (d, J=6.8 Hz, 1H), 8.79 (s, 1H), 7.94 (br. s., 1H), 7.77 (s, 1H), 7.65 (br. s., 1H), 7.41 (d, J=7.0 Hz, 1H), 7.27 (d, J=6.0 Hz, 1H), 4.86-4.75 (m, 2H), 3.83 (br. s., 2H), 3.49-3.39 (m, 4H), 2.14-2.03 (m, 1H), 1.45 (t, J=7.3 Hz, 6H), 0.94 (br. s., 2H), 0.78 (br. s., 2H)

The following compounds were also prepared by using the similar methods as described in Example 31 mentioned above.

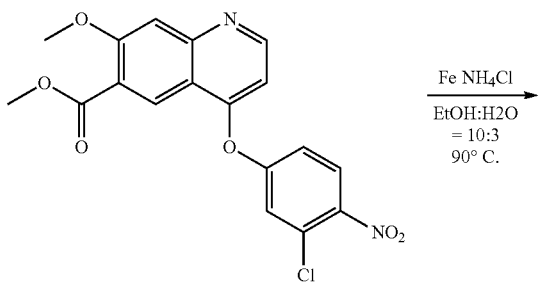

| Examples | Structures | NMR | LCMS (ESI) m/z: (M + 1) $^+$. |
|---|---|---|---|
| Example 58 | 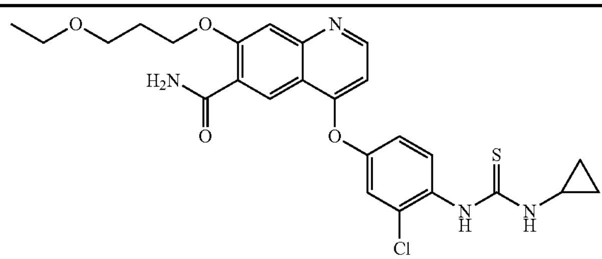 | $^1$H NMR (400 MHz, DMSO-d$_6$) = 9.30 (br. s., 1H), 9.00 (d, J = 6.5 Hz, 1H), 8.74 (s, 1H), 8.45-8.67 (m, 1H), 7.94 (d, J = 7.8 Hz, 2H), 7.76 (s, 1H), 7.70 (br. s., 1H), 7.41 (d, J = 8.0 Hz, 1H), 6.89 (br. s., 1H), 4.34 (t, J = 5.8 Hz, 2H), 3.58-3.61 (m, 2H), 3.42-3.44 (m, 2H), 2.99 (br. s., 1H), 2.12 (quin, J = 5.8 Hz, 2H), 1.11 (t, J = 6.9 Hz, 3H), 0.77 (br. s., 2H), 0.60 (br. s., 2H). | 515.1 |
| Example 174 | 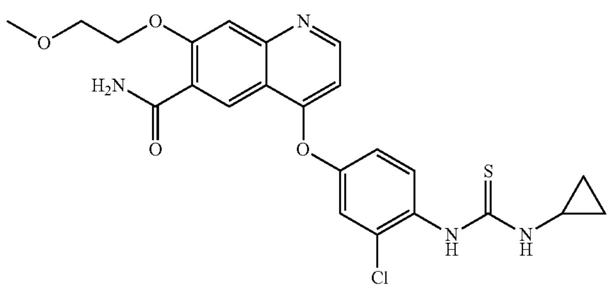 [SMILES: COCCOc1cc2nccc(Oc3ccc(NC(=S)NC4CC4)c(Cl)c3)c2cc1C(N)=O] | $^1$H NMR (400 MHz, METHANOL-d$_4$) = 9.12 (s, 1H), 8.94 (d, J = 6.8 Hz, 1H), 7.93 (br. s., 1H), 7.65 (s, 2H), 7.40 (d, J = 6.5 Hz, 1H), 7.21 (d, J = 5.3 Hz, 1H), 4.63-4.50 (m, 2H), 4.00-3.88 (m, 2H), 3.51 (s, 3H), 2.94-2.63 (m, 1H), 1.04-0.58 (m, 4H) | 487.2 |

Process G

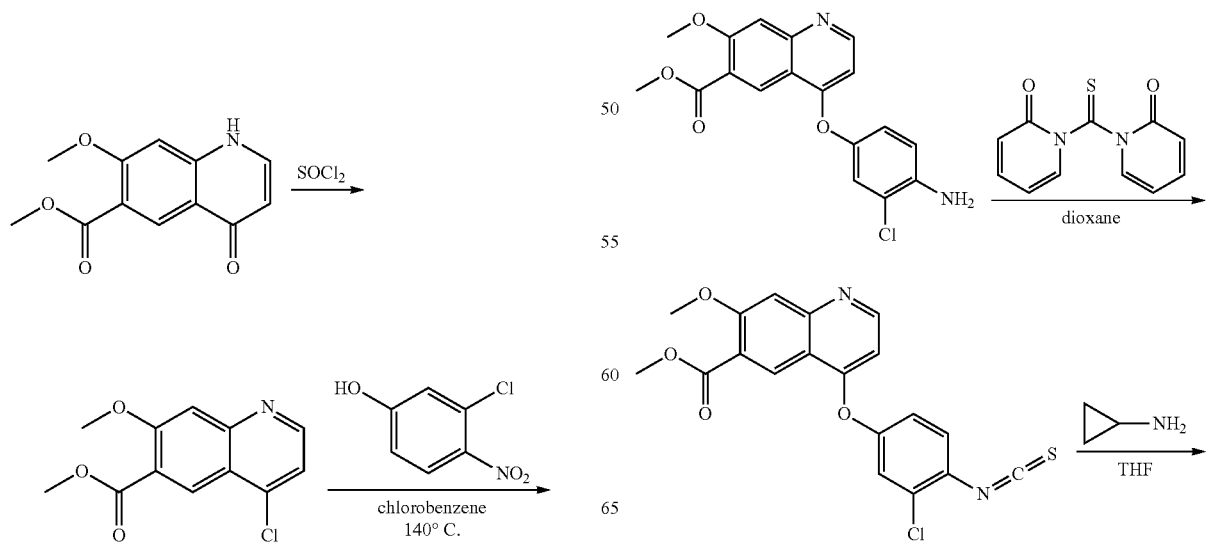

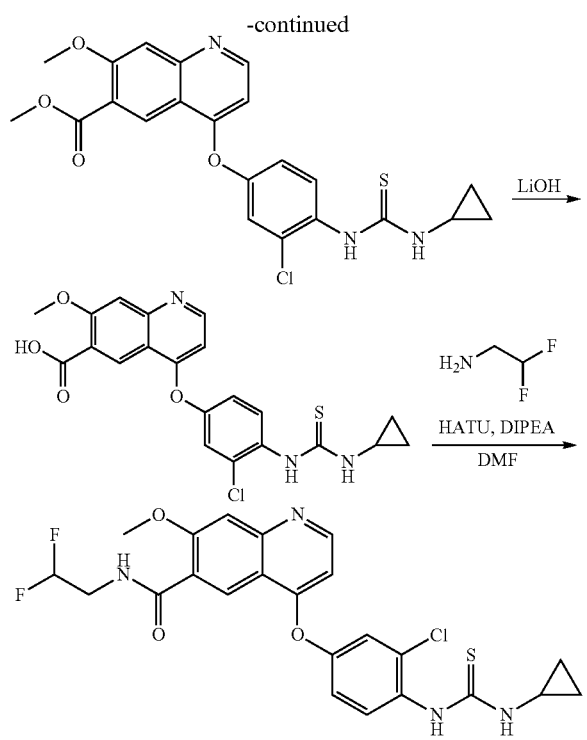

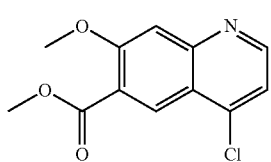

Compound 1B (3.00 g, 12.86 mmol) was added to thionyl chloride (30.00 mL). N,N-Dimethylformamide (93.99 mg, 1.29 mmol) was then added to the reaction system. The reaction solution was protected by nitrogen and then heated up to an outer temperature of 90° C. and reacted under refluxing for 1 hour. The completion of the reaction was detected by TLC. The aqueous phase was combined and concentrated to dryness. The residue was dissolved in ice water (50 ml) and extracted with ethyl acetate (20 ml*2). The aqueous phase was extracted with dichloromethane (30 ml*5). The dichloromethane phase was washed with NaCl solution (20 ml*2) and dried over sodium sulfate, and then pump-dried by a water pump to give compound 37A (2.60 g, 9.81 mmol, the yield was 76.32%, and the purity was 95%) as a gray solid.

$^1$H NMR (400 MHz, DMSO-$d_6$) ppm 3.87 (s, 3H) 3.98 (s, 3H) 7.60 (s, 1H) 7.66 (d, J=4.77 Hz, 1H) 8.41 (s, 1H) 8.83 (d, J=4.77 Hz, 1H)

Compound 37B

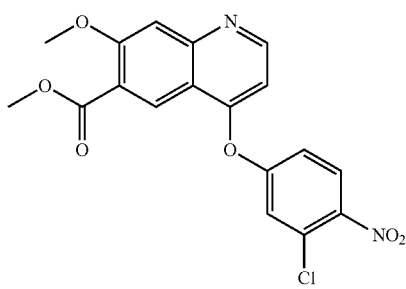

Compound 37A (5.00 g, 19.87 mmol) and 3-chloro-4-nitro-phenol (3.45 g, 19.87 mmol) were added to chlorobenzene (50 mL). The reaction solution was heated up to an outer temperature of 140° C. and reacted under refluxing for 15 hours under the protection of nitrogen. The completion of the reaction was detected by TLC. The reaction solution was spin-dried with an oil pump under vacuum and the residue was purified by silica gel column chromatography (the mobile phase was ethyl acetate:methanol=10:1) to give compound 37B (4.90 g, the yield was 63.43%).

Compound 37C

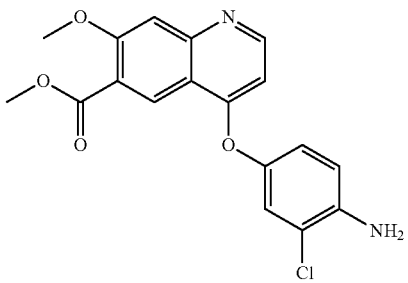

The compound 37B (1.60 g, 4.12 mmol), iron powder (230.08 mg, 4.12 mmol) and ammonium chloride (220.38 mg, 4.12 mmol) were added to a mixed solution of ethanol (20 mL) and water (6 mL). The reaction solution was heated up to an outer temperature of 90° C. and reacted under refluxing for 2 hours. The completion of the reaction was detected by TLC. The reaction solution was filtered through celite and the filtrate was directly spin-dried. The residue was purified by flash chromatography on a silica gel column (the mobile phase was ethyl acetate:methanol=10:1) to give compound 37C (1.20 g, 3.34 mmol, the yield was 81.18%).

$^1$H NMR (400 MHz, METHANOL-$d_4$) 8.75 (s, 1H), 8.63 (d, J=5.52 Hz, 1H), 7.47 (s, 1H), 7.21 (d, J=2.26 Hz, 1H), 6.94-7.03 (m, 2H), 6.55 (d, J=5.52 Hz, 1H), 4.05 (s, 3H), 3.96 (s, 3H)

Compound 37D

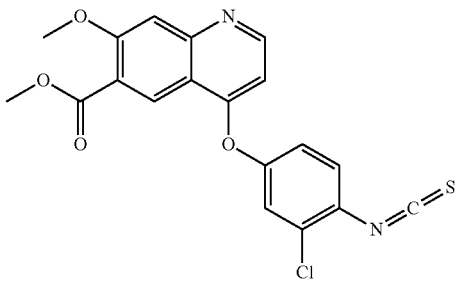

The compound 37C (1.20 g, 3.34 mmol) and 1,1'-thiocarbonyldi-2(1H)-pyridone (1.16 g, 5.01 mmol) were added to dioxane (15 ml). The reaction solution stirred at 25° C. for half an hour and refluxed for 12 hours at 120° C. under the protection of nitrogen. The completion of the reaction was detected by TLC. The reaction solution was spin-dried with a water pump under vacuum. The residue was purified by silica gel column chromatography (the mobile phase was ethyl acetate:methanol=10:1) to give compound 37D (610.00 mg, 1.52 mmol, the yield was 45.56%).

$^1$H NMR (400 MHz, METHANOL-$d_4$) 7.13-7.20 (m, 2H), 5.95-6.05 (m, 3H), 5.77 (dd, J=2.51, 8.53 Hz, 1H), 5.15 (d, J=5.02 Hz, 1H), 5.03 (d, J=9.03 Hz, 1H), 4.89 (t, J=6.78 Hz, 1H), 2.52 (s, 3H), 2.42 (s, 3H)

Compound 37E

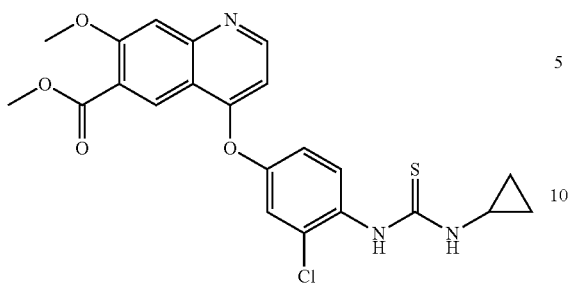

Compound 37D (280.00 mg, 698.53 μmop and cyclopropylamine (39.88 mg, 698.53 μmop were added to tetrahydrofuran (5 mL) and stirred for 2 hours at an outer temperature of 25° C. The completion of the reaction was detected by TLC. The reaction solution was spin-dried under vacuum. The residue was purified by HPLC to give compound 37E (230.00 mg, 502.26 μmol, the yield was 71.90%).

$^1$H NMR (400 MHz, METHANOL-d$_4$) 8.76 (s, 1H), 8.69 (d, J=5.52 Hz, 1H), 7.83 (d, J=8.78 Hz, 1H), 7.46-7.54 (m, 2H), 7.28 (dd, J=2.38, 8.66 Hz, 1H), 6.77 (d, J=5.27 Hz, 1H), 4.06 (s, 3H), 3.97 (s, 3H), 2.79 (br. s., 1H), 0.92 (br. s., 3H), 0.77 (br. s., 3H)

Compound 37F

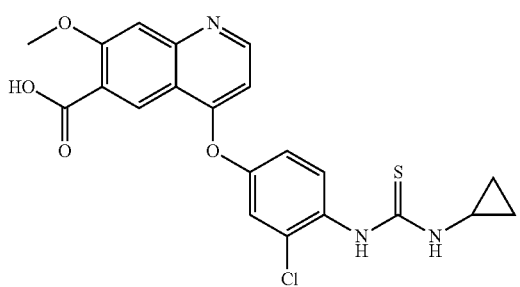

Compound 37E (230.00 mg, 502.26 μmop and lithium hydroxide (120.29 mg, 5.02 mmol) were added to a mixture of tetrahydrofuran (3 ml), methanol (2 ml) and water (1 ml). The reaction solution was stirred at 25° C. for 2 hours. The completion of the reaction was detected by TLC. The reaction solution was adjusted till the pH value was 5 with saturated citric acid (5 ml) and extracted with a mixture of dichloromethane and isopropanol (16 ml, the ratio was 3:1). The organic phase was spin-dried to give compound 37F (195.00 mg, 439.29 μmol, the yield was 87.46%).

$^1$H NMR (400 MHz, METHANOL-d$_4$) 9.04 (s, 1H), 8.98 (d, J=6.53 Hz, 1H), 8.18 (br. s., 1H), 8.01 (d, J=8.03 Hz, 1H), 7.64 (s, 1H), 7.58 (d, J=9.03 Hz, 1H), 7.17 (d, J=6.53 Hz, 1H), 4.24 (s, 3H), 2.86 (br. s., 1H), 0.93 (d, J=5.02 Hz, 2H), 0.74 (br. s., 2H)

Example 37

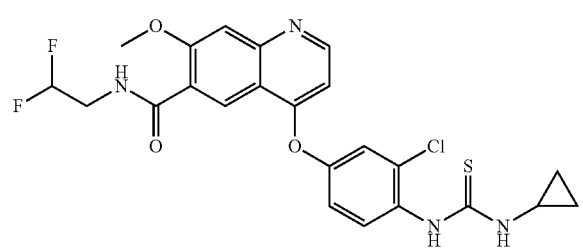 [SMILES: COc1cc2nccc(Oc3ccc(NC(=S)NC4CC4)c(Cl)c3)c2cc1C(=O)NCC(F)F]

Compound 37F (20.00 mg, 45.06 μmol), 2,2-difluoroethylamine (6.00 mg, 74.02 μmol), tetramethyluronium hexafluorophosphate (17.13 mg, 45.06 μmop and diisopropylethylamine (5.82 mg, 45.06 μmop were added to N,N-dimethylformamide (1 ml) in a small tube. The reaction solution was stirred at 25° C. for 15 hours. The completion of the reaction was detected by LCMS. The reaction solution was added to water (4 ml) and extracted with dichloromethane (10 ml). The organic phase was spin-dried and the residue was dissolved in N,N-dimethylformamide (3 ml) and then sent to HPLC (hydrochloric acid system) to give a compound of Example 37 (4.80 mg, 9.47 μmol, the yield was 21.01%).

$^1$H NMR (400 MHz, METHANOL-d$_4$) 7.34-7.45 (m, 2H), 6.37 (br. s., 1H), 6.02-6.13 (m, 2H), 5.84 (d, J=9.03 Hz, 1H), 5.66 (br. s., 1H), 4.69 (t, J=3.76 Hz, 1H), 4.55 (t, J=4.02 Hz, 1H), 4.41 (t, J=3.76 Hz, 1H), 2.67 (s, 3H), 2.32 (dt, J=3.51, 15.06 Hz, 2H), 1.17 (br. s., 1H), −0.61 (br. s., 2H), −0.76 (br. s., 2H).

The following compounds were also prepared by using the similar methods as described in Example 37 mentioned above.

| Examples | Structures | NMR | LCMS (ESI) m/z: [M + 1]$^+$ |
|---|---|---|---|
| Example 38 | 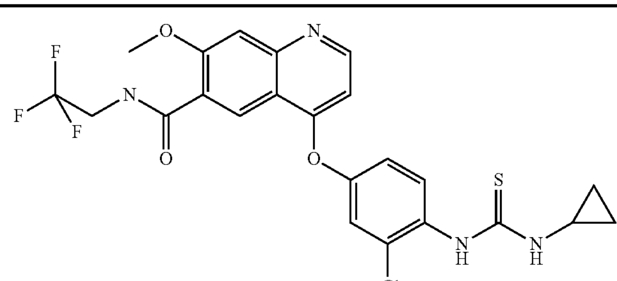 | $^1$H NMR (400 MHz, METHANOL-d$_4$) 8.88-9.02 (m, 2H), 7.93 (br. s., 1H), 7.65 (s, 2H), 7.40 (d, J = 6.78 Hz, 1H), 7.23 (d, J = 5.77 Hz, 1H), 4.14-4.30 (m, 5H), 2.77 (br. s., 1H), 0.94 (br. s., 2H), 0.78 (br. s., 2H) | 525.0 |

-continued

| Examples | Structures | NMR | LCMS (ESI) m/z: [M + 1]+ |
|---|---|---|---|
| Example 39 | 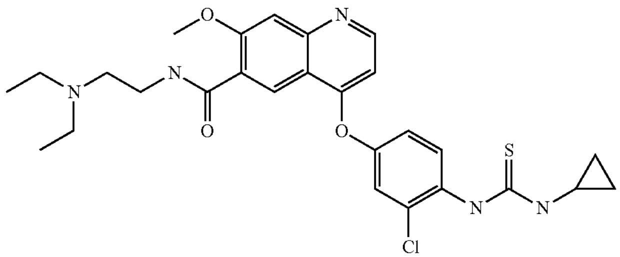 [SMILES: CCN(CC)CCNC(=O)c1cc2c(Oc3ccc(NC(=S)NC4CC4)c(Cl)c3)ccnc2cc1OC] | $^1$H NMR (400 MHz, METHANOL-d$_4$) 9.10 (s, 1H), 8.97 (d, J = 6.53 Hz, 1H), 7.93 (br. s., 1H), 7.59-7.73 (m, 2H), 7.41 (d, J = 7.53 Hz, 1H), 7.22 (d, J = 5.02 Hz, 1H), 4.26 (s, 3H), 3.90 (t, J = 6.02 Hz, 2H), 3.49 (t, J = 6.27 Hz, 2H), 3.39 (dd, J = 3.51, 7.03 Hz, 4H), 2.74 (d, J = 12.55 Hz, 1H), 1.42 (t, J = 7.28 Hz, 6H), 0.94 (br. s., 2H), 0.79 (br. s., 2H) | 542.1 |
| Example 40 | 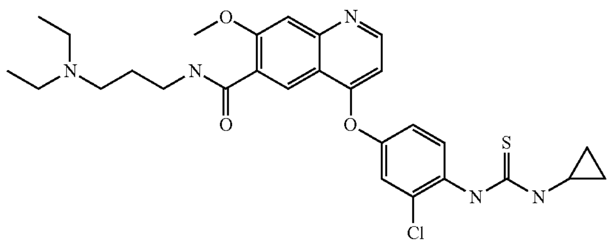 [SMILES: CCN(CC)CCCNC(=O)c1cc2c(Oc3ccc(NC(=S)NC4CC4)c(Cl)c3)ccnc2cc1OC] | $^1$H NMR (400 MHz, METHANOL-d$_4$) 8.88-9.01 (m, 2H), 7.94 (br. s., 1H), 7.58-7.74 (m, 2H), 7.41 (d, J = 7.78 Hz, 1H), 7.15-7.28 (m, 1H), 4.17-4.32 (m, 3H), 3.61 (t, J = 6.40 Hz, 2H), 3.25-3.32 (m, 6H), 2.62-2.92 (m, 1H), 2.06-2.22 (m, 2H), 1.29-1.47 (m, 6H), 0.94 (br. s., 2H), 0.78 (br. s., 2H) | 556.2 |
| Example 47 | 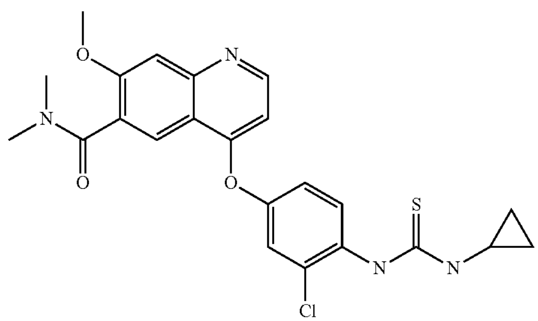 [SMILES: COc1cc2nccc(Oc3ccc(NC(=S)NC4CC4)c(Cl)c3)c2cc1C(=O)N(C)C] | $^1$H NMR (400 MHz, METHANOL-d$_4$) 8.94 (d, J = 6.78 Hz, 1H), 8.53 (s, 1H), 7.92 (br. s., 1H), 7.57-7.68 (m, 2H), 7.39 (d, J = 6.78 Hz, 1H), 7.23 (d, J = 6.02 Hz, 1H), 4.1$_{1-4}$.26 (m, 3H), 3.13-3.26 (m, 3H), 2.90-3.02 (m, 3H), 2.62-2.88 (m, 1H), 0.94 (br. s., 2H), 0.78 (br. s., 2H) | 471.3 |
| Example 48 | 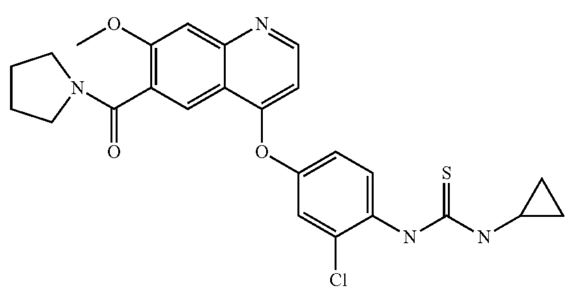 [SMILES: COc1cc2nccc(Oc3ccc(NC(=S)NC4CC4)c(Cl)c3)c2cc1C(=O)N1CCCC1] | $^1$H NMR (400 MHz, METHANOL-d$_4$) 8.94 (d, J = 6.78 Hz, 1H), 8.57 (s, 1H), 7.92 (br. s., 1H), 7.64 (s, 2H), 7.40 (d, J = 7.03 Hz, 1H), 7.23 (d, J = 6.27 Hz, 1H), 4.1$_{1-4}$.23 (m, 3H), 3.68 (t, J = 6.78 Hz, 2H), 3.35 (br. s., 2H), 2.76 (br. s., 1H), 2.88 (s, 1H), 1.9$_{0-2}$.13 (m, 4H), 0.94 (br. s., 2H), 0.78 (br. s., 2H) | 497.2 |
| Example 49 | 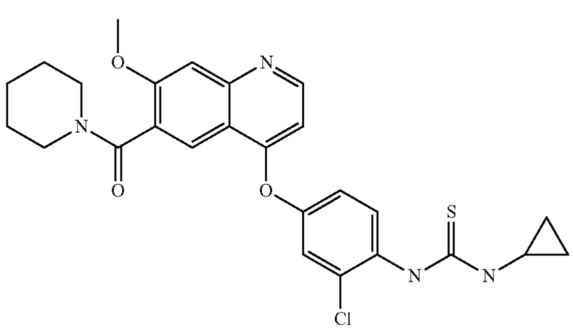 [SMILES: COc1cc2nccc(Oc3ccc(NC(=S)NC4CC4)c(Cl)c3)c2cc1C(=O)N1CCCCC1] | $^1$H NMR (400 MHz, METHANOL-d$_4$) 8.93 (d, J = 6.78 Hz, 1H), 8.50 (s, 1H), 7.92 (br. s., 1H), 7.63 (d, J = 11.04 Hz, 2H), 7.40 (d, J = 7.03 Hz, 1H), 7.23 (d, J = 5.77 Hz, 1H), 4.12-4.22 (m, 3H), 3.70-3.90 (m, 2H), 3.23-3.32 (m, 2H), 2.76 (br. s., 1H), 1.74 (br. s., 4H), 1.60 (br. s., 2H), 0.94 (br. s., 2H), 0.78 (br. s., 2H) | 533.2 |

-continued

| Examples | Structures | NMR | LCMS (ESI) m/z: [M + 1]⁺ |
|---|---|---|---|
| Example 50 | 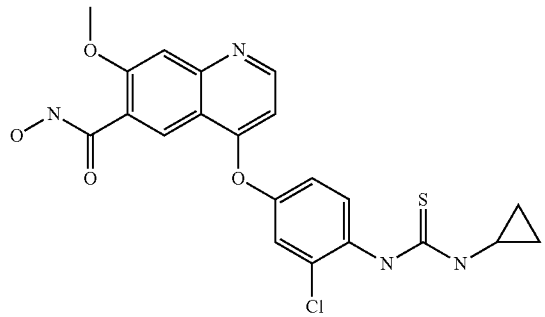 [SMILES: COc1cc2nccc(Oc3ccc(NC(=S)NC4CC4)c(Cl)c3)c2cc1C(=O)NO] | ¹H NMR (400 MHz, METHANOL-d₄) 8.87-8.99 (m, 1H), 7.93 (br. s., 1H), 7.54-7.69 (m, 2H), 7.40 (d, J = 7.28 Hz, 1H), 7.23 (br. s., 1H), 4.09-4.28 (m, 3H), 2.76 (br. s., 1H), 0.94 (br. s., 2H), 0.78 (br. s., 2H) | 459.2 |
| Example 53 | 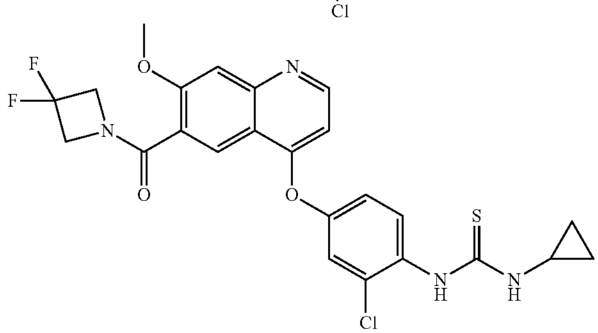 | ¹H NMR (400 MHz, METHANOL-d4) 8.95 (d, J = 6.53 Hz, 1H), 8.71 (s, 1H), 7.93 (br. s., 1H), 7.58-7.68 (m, 2H), 7.40 (d, J = 8.03 Hz, 1H), 7.24 (d, J = 5.52 Hz, 1H), 4.61 (t, J = 12.05 Hz, 2H), 4.49 (t, J = 11.80 Hz, 2H), 4.20 (s, 3H), 2.62-2.86 (m, 1H), 0.94 (br. s., 2H), 0.78 (br. s., 2H) | 519.1 |
| Example 54 | 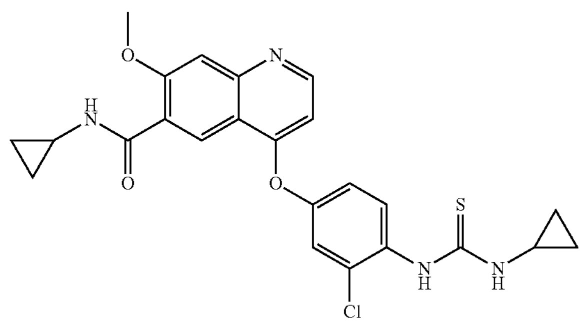 [SMILES: COc1cc2nccc(Oc3ccc(NC(=S)NC4CC4)c(Cl)c3)c2cc1C(=O)NC1CC1] | ¹H NMR (400 MHz, METHANOL-d₄) 8.94 (d, J = 6.78 Hz, 1H), 8.84 (s, 1H), 7.95 (br. s., 1H), 7.64 (d, J = 2.01 Hz, 1H), 7.57 (s, 1H), 7.35-7.43 (m, 1H), 7.24 (d, J = 5.02 Hz, 1H), 4.14-4.24 (m, 3H), 2.96 (tt, J = 3.76, 7.28 Hz, 1H), 2.77 (br. s., 1H), 0.85-1.01 (m, 4H), 0.65-0.83 (m, 4H) | 483.1 |
| Example 62 | 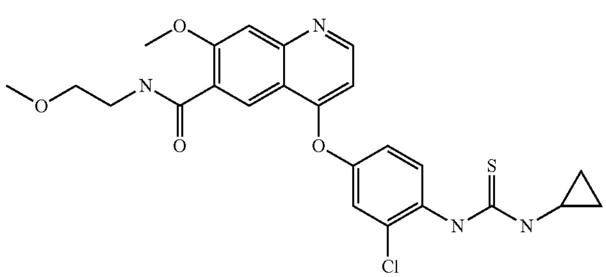 [SMILES: COCCNC(=O)c1cc2c(Oc3ccc(NC(=S)NC4CC4)c(Cl)c3)ccnc2cc1OC] | ¹H NMR (400 MHz, METHANOL-d₄) ppm 0.61-1.10 (m, 4 H) 3.44 (s, 3H) 4.15 (m, 3 H) 3.04 (s, 3 H) 7.16-7.23 (m, 1 H) 7.36-7.43 (m, 1 H) 7.61 (s, 1 H) 7.66 (dd, J = 8.03, 2.51 Hz, 1 H) 7.94 (d, J = 8.53 Hz, 1 H) 8.95 (d, J = 7.03 Hz, 1 H) 9.00 (s, 1 H) | 501.1 |
| Example 183 | 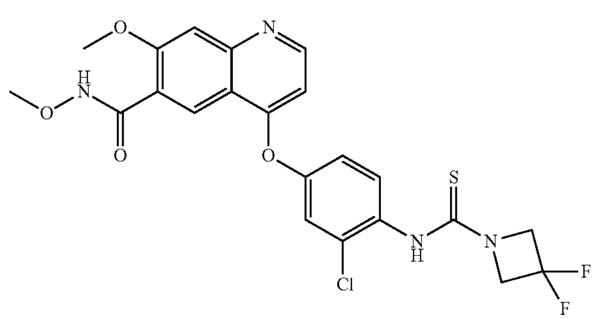 [SMILES: CONC(=O)c1cc2c(Oc3ccc(NC(=S)N4CC(F)(F)C4)c(Cl)c3)ccnc2cc1OC] | ¹H NMR (400 MHz, METHANOL-d₄) = 8.99-8.81 (m, 2H), 7.74 (d, J = 8.5 Hz, 1H), 7.68-7.63 (m, 1H), 7.62-7.57 (m, 1H), 7.45-7.38 (m, 1H), 7.21-7.15 (m, 1H), 4.61 (t, J = 11.9 Hz, 4H), 4.22-4.16 (m, 3H), 3.89 (s, 2H) | 546.2 |

Process H

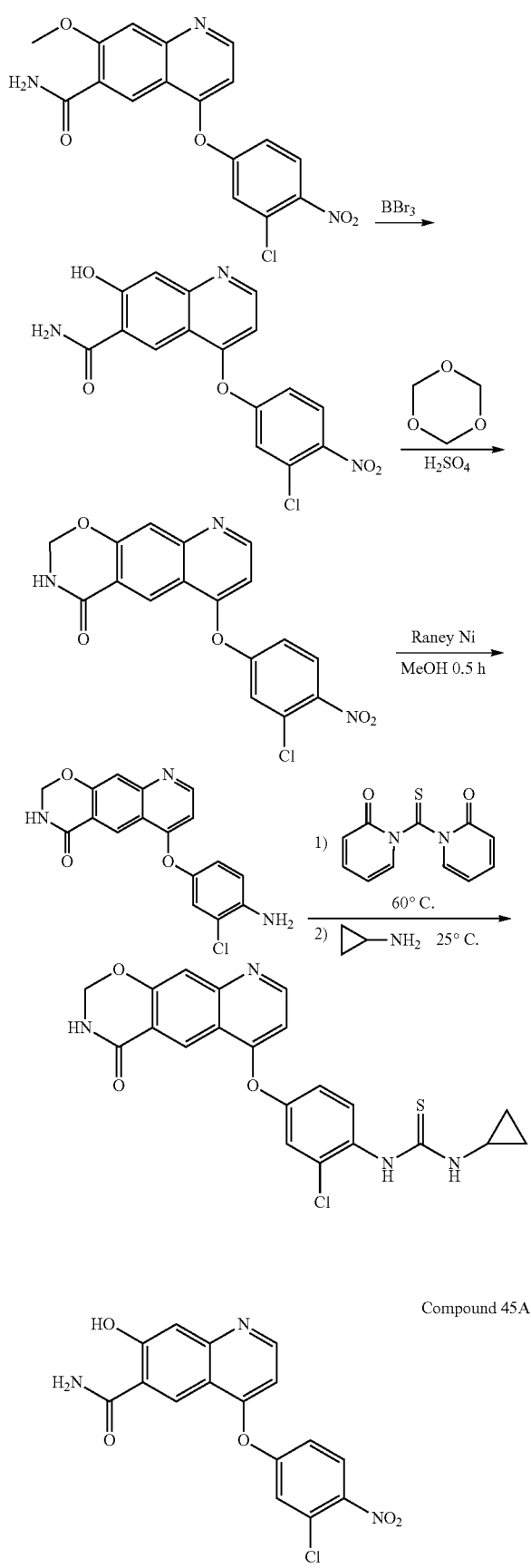

Compound 45A

Boron tribromide (15.6 g, 62.27 mmol) was added dropwise to 20 ml solution of the compound 1F (2 g, 5.35 mmol) at minus 65° C. over 10 minutes, and heated to 20° C. over 30 minutes, and then stirred at this temperature for 16 hours. The reaction was quenched with 20 ml of methanol and then 100 ml of saturated sodium bicarbonate was added. The mixture was extracted with dichloromethane/methanol (5:1). The organic layers were combined and washed with saturated NaCl solution, dried over anhydrous sodium sulfate, filtered and concentrated to give compound 45A (yellow solid, crude, 1.69 g) which was used directly in the next step.

$^1$H NMR (400 MHz, DMSO-$d_6$)=13.02 (br. s., 1H), 8.91 (s, 1H), 8.77 (d, J=5.0 Hz, 2H), 8.27 (d, J=9.0 Hz, 1H), 8.18 (br. s., 1H), 7.86 (d, J=2.5 Hz, 1H), 7.52 (dd, J=2.5, 9.0 Hz, 1H), 7.45-7.39 (m, 1H), 6.86 (d, J=5.5 Hz, 1H)

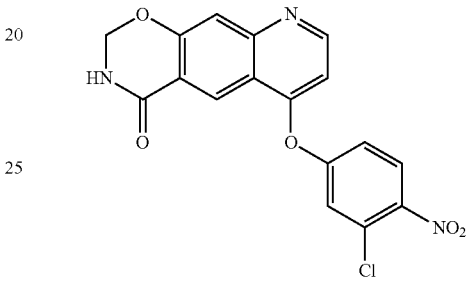

Compound 45B 20 drops of concentrated sulfuric acid was added dropwise to 100 ml of chloroform solution of compound 45A (500 mg, 1.39 mmol) and trioxymethylene (313.03 mg, 3.47 mmol) and heated to 65-70° C., and then stirred at this temperature for 2.5 hours. The reaction solution was cooled to 25° C. and basified with 50 ml of saturated sodium bicarbonate, and then added 25 ml of ethanol and the solution was separated to give the organic layer which was then concentrated. The residue was purified by preparative HPLC to give compound 45B (yellow solid, 120 mg, the yield was 23.22%).

$^1$H NMR (400 MHz, METHANOL-$d_4$)=8.94 (s, 1H), 8.80 (d, J=5.0 Hz, 1H), 8.18 (d, J=9.0 Hz, 1H), 7.70 (d, J=2.5 Hz, 1H), 7.61 (s, 1H), 7.46 (dd, J=2.5, 9.0 Hz, 1H), 6.88 (d, J=5.5 Hz, 1H), 5.36 (s, 2H)

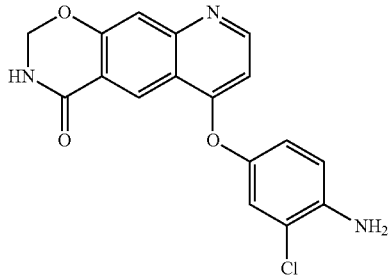

Compound 45C

Raney nickel (5 mg) was added to 20 ml of a methanol solution of compound 45B (35 mg 0.094 mmol) and then stirred at 25-28° C. for half an hour at 15 psi hydrogen. The reaction solution was filtered and concentrated to give compound 45C (yellow oil, crude, 30 mg) which was used directly in the next step.

LCMS (ESI) m/z: 341.9 [M+1]$^+$

Example 45

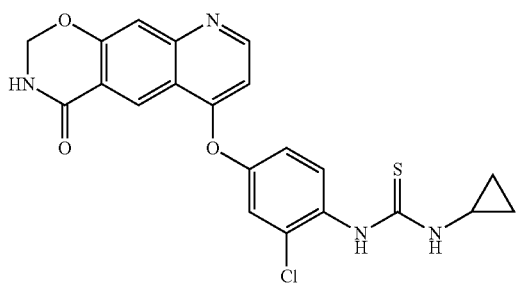 [SMILES: O=C1NCOc2cc3nccc(Oc4ccc(NC(=S)NC5CC5)c(Cl)c4)c3cc21]

1,1'-thiocarbonyldi-2(1H) pyridone (30 mg, 129.04 μmop was added to 3 ml dioxane solution of compound 45C (30 mg, 0.8779 mmol) and heated to 60-70° C., and then stirred for 1 hour at this temperature then cooled to 25° C. Cyclopropylamine (82 mg, 1.44 mmol) was added to the mixture and stirred at 25-28° C. for 1 hour. The reaction solution was concentrated and the residue was purified by preparative HPLC to give the compound of Example 45 (yellow solid, 12 mg, the yield was 26.83%). LCMS (ESI) m/z: 440.9 [M+1]$^+$ $^1$H NMR (400 MHz, METHANOL-d$_4$)=9.21 (s, 1H), 9.04-8.95 (m, 1H), 7.96 (br. s., 1H), 7.68 (s, 2H), 7.42 (d, J=8.8 Hz, 1H), 7.27 (br. s., 1H), 5.49 (s, 2H), 2.75 (br. s., 1H), 0.94 (br. s., 2H), 0.79 (br. s., 2H)

Example 46

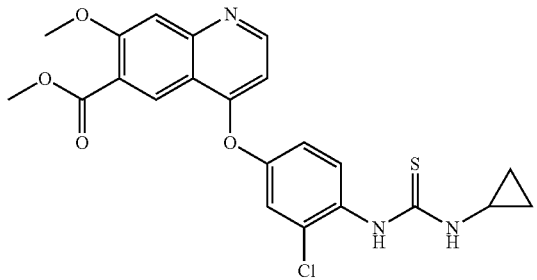 [SMILES: COC(=O)c1cc2c(Oc3ccc(NC(=S)NC4CC4)c(Cl)c3)ccnc2cc1OC]

This example has the same structure as Compound 37E.

Example 178

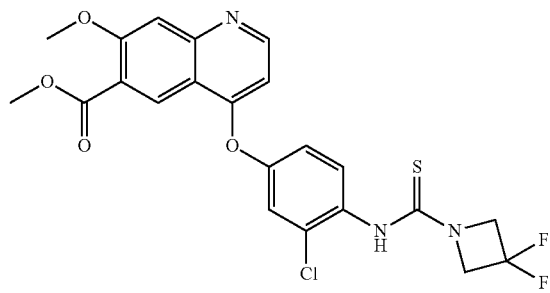 [SMILES: COC(=O)c1cc2c(Oc3ccc(NC(=S)N4CC(F)(F)C4)c(Cl)c3)ccnc2cc1OC]

This Example is prepared by the method as described in compound 37E.

$^1$H NMR (400 MHz, METHANOL-d$_4$) 8.88-8.98 (m, 1H), 7.75 (d, J=8.53 Hz, 1H), 7.66 (br. s., 1H), 7.59 (s, 1H), 7.41 (d, J=7.03 Hz, 1H), 7.17 (d, J=7.03 Hz, 1H), 4.62 (t, J=11.80 Hz, 4H), 4.16 (s, 3H), 4.00 (s, 3H)

Process I

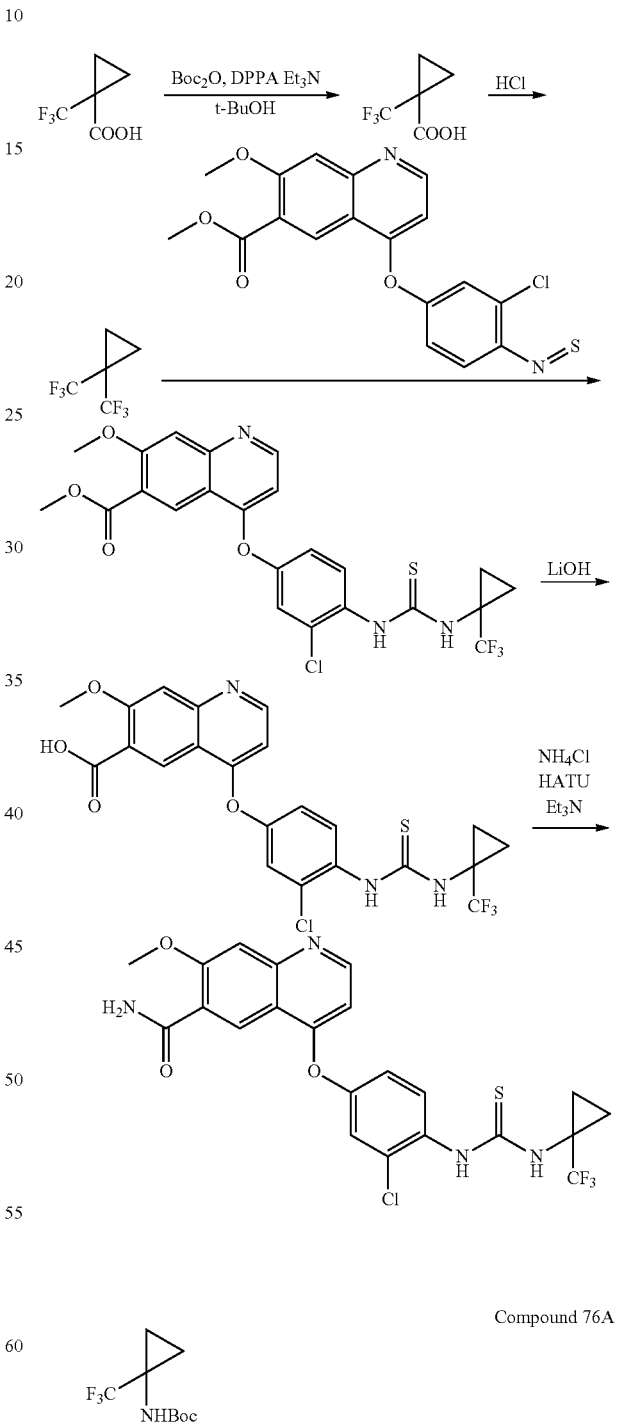

Compound 76A 1-(trifluoromethyl) cyclopropylcarboxylic acid (300.00 mg, 1.95 mmol), triethylamine (197.32 mg, 1.95 mmol) and di-tert-butyl dicarbonate tert-butyl carbonate (851.18 mg, 3.90 mmol) were added to tert-butanol (5 ml) at 25° C. [Azide (phenoxy) phosphoryl] oxybenzene (590.30 mg, 2.15 mmol) was slowly added to the reaction system. The reaction solution was refluxed at 100° C. for 18 hours under the protection of nitrogen. The completion of the reaction was detected by TLC. The reaction solution was spin-dried and the residue was dissolved in methyl tert-butyl ether (8 ml) and washed with water (3 ml). The aqueous phase was extracted with ethyl acetate (5 ml*3). The organic phases were combined and washed successively with citric acid (1 N, 3 mL), saturated sodium carbonate (3 mL) and saturated sodium chloride (3 mL), and then spin-dried to give the compound 76A (350.00 mg, 1.55 mmol, the yield was 79.70%) as a white solid.

$^1$H NMR (400 MHz, CHLOROFORM-d) 1.45 (br. s., 9H), 1.27 (br. s., 2H), 1.12 (br. s., 2H)

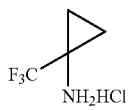

Compound 76B

Compound 76A (100.00 mg, 444.03 μmol) and hydrochloric acid (5.10 g, 139.88 mmol) were added to water (5 mL) and protected with nitrogen. The reaction solution was refluxed at 120° C. for 2 hours and then stirred at 25° C. for 12 hours. The completion of the reaction was detected by TLC. The reaction solution was spin-dried. After adding acetone (2 ml*2), the residue was spin-dried to give compound 76B (50.00 mg, crude) as a white solid.

$^1$H NMR (400 MHz, METHANOL-d$_4$) 2.17 (br. s., 2H), 2.14 (br. s., 2H), 1.95-2.01 (m, 1H), 1.83 (br. s., 1H)

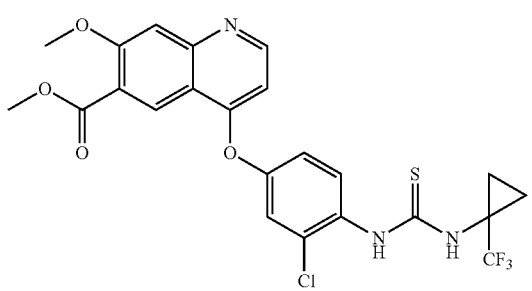

Compound 76C

Compound of Example 37D (100.00 mg, 249.48 μmop, 1-(trifluoromethyl) cyclopropylamine (50 mg, crude) and triethylamine (75.73 mg, 748.44 μmol) were added to a sealed tube of tetrahydrofuran (2 ml) and stirred at 25° C. for 2 hours. The reaction was detected by LCMS but not impure. The reaction solution was concentrated to dryness and the residue was dissolved in N,N-dimethylformamide (0.2 ml) and acetonitrile (3 ml) and purified by preparative HLPC (TFA) to give compound 76C (70.00 mg, crude) as a white solid.

LCMS (ESI) m/z: 526.2 [M+1]$^+$.

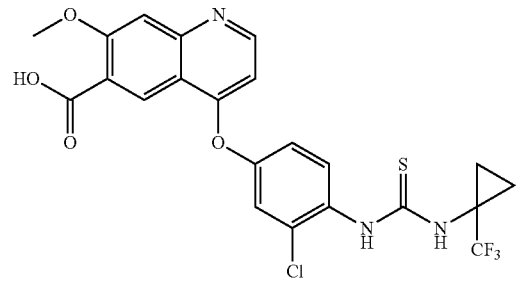

Compound 76D

Compound 76C (52.60 mg, 100.01 μmol) was added to a mixture of tetrahydrofuran (1.5 ml), methanol (1 mL) and water (0.5 mL). Lithium hydroxide (23.95 mg, 1.00 mmol) was added to the reaction system at 25° C. and stirred at this temperature for 2 hours. The completion of the reaction was detected by LCMS. The reaction solution was acidified with citric acid (1 N, 5 mL) and extracted with a mixture of dichloromethane and isopropanol (with a ratio of 3:1, 10 ml*5). The combined organic phase was washed with saturated NaCl solution (5 mL), dried over sodium sulfate, filtered and spin-dried. The residue was washed with a mixture of petroleum ether and ethyl acetate (5:1, 5 ml) to give compound 76D (100.00 mg, crude) as a yellow solid.

LCMS (ESI) m/z: 511.9 [M+1]$^+$.

Example 76

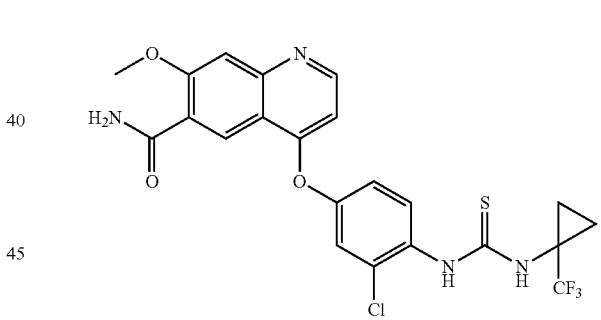

Compound 76D (50.00 mg, 97.68 μmop, triethylamine (29.65 mg, 293.04 μmop and HATU (44.57 mg, 117.22 μmop were added to a sealed tube of dichloromethane (3 mL). Ammonium chloride (7.84 mg, 146.52 μmop was then added to the reaction system. The reaction solution was stirred at 25° C. for 12 hours. The reaction was detected by LCMS but not complete. The reaction solution was spin-dried. The residue was dissolved in N,N-dimethylformamide (0.2 ml) and acetonitrile (3 ml) and purified by HPLC (hydrochloric acid) to give a compound of Example 76 (5.90 mg, the yield was 11.82%) as a white solid.

$^1$H NMR (400 MHz, METHANOL-d$_4$) 9.06 (s, 1H), 8.95 (d, J=7.03 Hz, 1H), 7.81 (br. s., 1H), 7.66 (d, J=2.51 Hz, 1H), 7.61 (s, 1H), 7.41 (dd, J=2.26, 8.78 Hz, 1H), 7.23 (d, J=6.53 Hz, 1H), 4.23 (s, 3H), 1.53 (br. s., 2H), 1.44 (br. s., 2H)

Process J

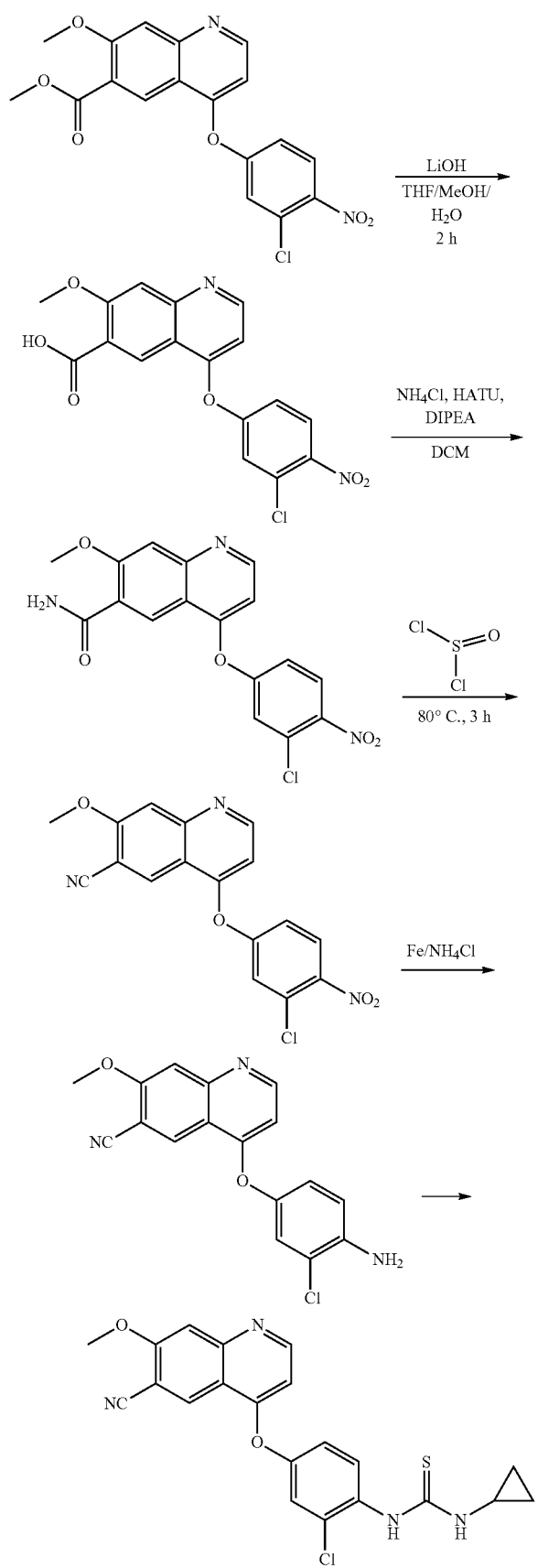

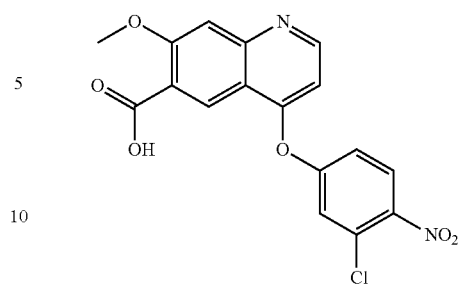

Compound 80A

LA Compound 37B (500.00 mg, 1.29 mmol) was dissolved in a solution of tetrahydrofuran (6 ml) and lithium hydroxide (308.96 mg 12.90 mmol) was added thereto, the reaction solution was stirred at 20° C. for 4 hours and became a yellow clear solution. The reaction was complete detected by LCMS. The reaction solution was added with citric acid (1 mol/L) to adjust till the pH value was 5-6 and then extracted with a mixture of dichloromethane and isopropanol (3:1, 25 ml). The organic phase was washed with saturated NaCl solution (10 mL*1), dried over anhydrous sodium sulfate, filtered and concentrated under reduced pressure to give compound 80A (pale yellow solid, 390 mg, crude). LCMS (ESI) m/z: 375.0 [M+1]$^+$.

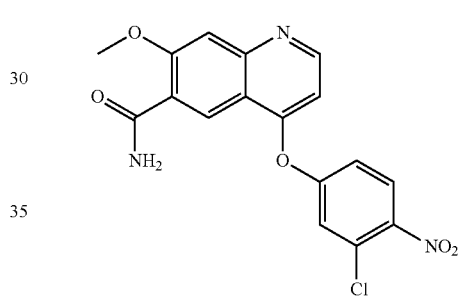

Compound 80B

Compound 80A (350 mg, 934.01 μmol) was dissolved in dichloromethane (6 mL), and DIEA (21.84 mg, 168.96 μmol), HATU (426.16 mg, 1.12 mmol) and ammonium chloride (74.94 mg, 1.40 mmol) were added thereto. The reaction was stirred at 20° C. for 12 hours. The reaction was substantially complete detected by LCMS. The reaction was quenched with water (5 mL) and the reaction solution was extracted with ethyl acetate (15 ml*3). The organic phase was washed with saturated NaCl solution (10 mL*2), dried over anhydrous sodium sulfate and concentrated under reduced pressure to get a residue which was then purified by preparative HPLC (containing 0.1% HCl) to give compound 80B (yellow solid, 12 mg, the yield was 42.53%).
LCMS (ESI) m/z: 374.0 [M+1]$^+$

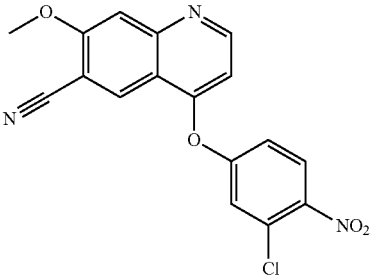

Compound 80C

Compound 80B (100.00 mg, 267.56 μmol) was dissolved in a solution of thionyl chloride (2 ml), the reaction solution was stirred at 25° C. for 10 minutes and then heated to 80° C. and stirred for 3 hours. The reaction was complete detected by LCMS. The reaction solution was concentrated under reduced pressure to get a residue which was then purified by thin layer chromatography to give compound 80C (yellow solid, 85 mg, the yield was 71.44%).

LCMS (ESI) m/z: 355.9 [M+1]$^+$

Compound 80D

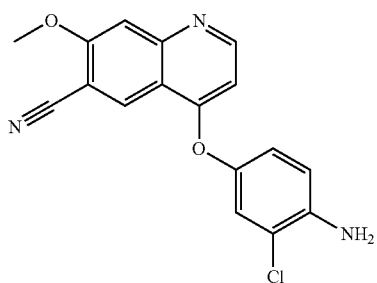

Compound 80C (100 mg, 281.11 μmol) was dissolved in a mixed solution of ethanol and water (6 ml), and iron powder (36.11 mg, 646.55 μmop and ammonium chloride (85.71 mg, 1.60 mmol) were added thereto. The reaction solution was stirred at 90° C. for 2 hours. The reaction was substantially complete detected by LCMS. The reaction was filtered through celite and the filtrate was concentrated under reduced pressure to give compound 80D (yellow solid, 72.00 mg, crude).

LCMS (ESI) m/z: 325.9 [M+1]$^+$

Compound 80E

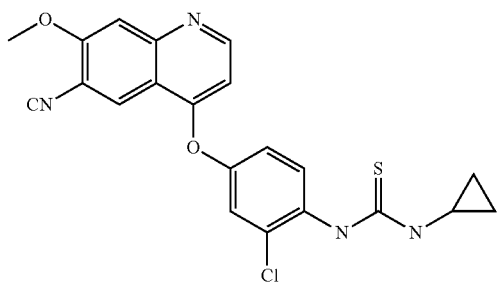

Compound 80D (72.00 mg, 221.03 μmop was dissolved in the solution of dioxane (3 ml), and 1,1'-thiocarbonyldi-2 (1H) pyridone (102.67 mg, 442.06 mmol) was added thereto. The reaction solution was stirred at 10° C. for 10 minutes. The reaction solution was then heated to 110° C. and stirred at 110° C. for 2 hours. The reaction was complete detected by LCMS. The reaction was quenched with water (10 ml) and then extracted with ethyl acetate (30 ml*3). The organic phase was washed with saturated NaCl solution (10 mL*2) and dried over anhydrous sodium sulfate, and concentrated under reduced pressure to give the compound 80E (pale yellow solid, 72 mg, crude).

LCMS (ESI) m/z: 367.8 [M+1]$^+$

Example 80

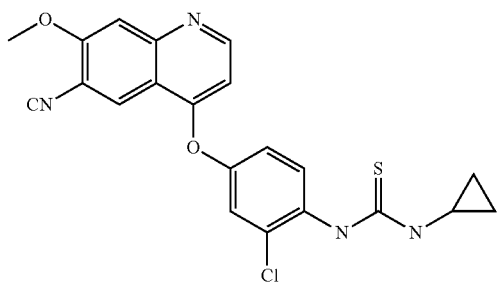

Compound 80E (50.00 mg, 135.94 μmop was dissolved in the solution of dioxane (3 ml) and cyclopropylamine (15.52 mg 271.88 μmop was added thereto. The reaction solution was stirred at 20° C. for 2 hours. The reaction was complete detected by LCMS. The reaction solution was concentrated under reduced pressure to get a residue which was then purified by preparative HPLC (containing 0.5% HCl, v/v) to give compound of Example 80 (yellow solid, 8 mg, the yield was 13.85%).

LCMS (ESI) m/z: 425.1 [M+1]$^+$ $^1$H NMR (400 MHz, METHANOL-d$_4$) ppm 0.61-1.10 (m, 3H) 4.25 (s, 3H) 7.16-7.23 (m, 1H) 7.28-7.35 (m, 1H) 7.40 (dd, J=8.03, 2.51 Hz, 1H) 7.61 (s, 1H) 7.66 (m, 1H) 9.00 (d, J=7.03 Hz, 1H) 9.01 (s, 1H) LCMS (ESI) m/z: 431.9 (M+1).

Example 81

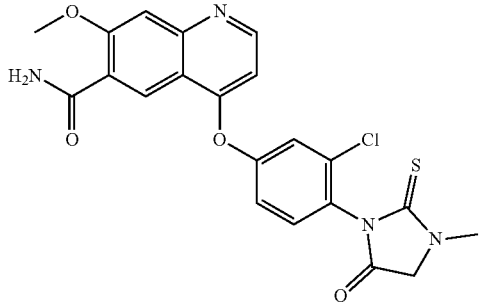

Compound 1H (60 mg, 155 μmop was added to 1,2-dichloroethane (2 ml) and then 2-methylaminoacetic acid (27.71 mg, 311.02 μmop and triethylamine (47 mg, 466 mmol) were added thereto. The reaction solution was reacted at 120° C. in the microwave for 20 minutes and concentrated to give the solid crude which was then purified by preparative HPLC (containing 0.5% HCl, v/v) to give the compound of Example 81 (15 mg, the yield was 19.16%) as a yellow powder.

LCMS (ESI) m/z: 457.1 [M+1]$^+$ $^1$H NMR (400 MHz, DMSO-d$_6$) 8.98 (d, J=6.2 Hz, 1H), 8.72 (s, 1H), 7.94-8.03 (m, 1H), 7.87 (d, J=2.5 Hz, 2H), 7.6$_{2-7}$.73 (m, 2H), 7.54-7.61 (m, 1H), 6.91 (d, J=6.2 Hz, 1H), 4.48-4.67 (m, 2H), 4.08 (s, 3H), 3.32 (s, 3H).

Example 82

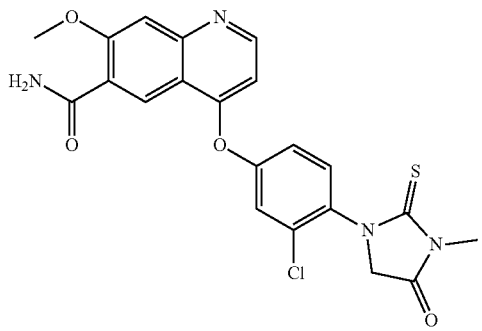

Compound 1H (100 mg, 249 µmol), ethylene glycol (5 ml), potassium carbonate (86 mg, 624 µmop and chloroacetyl chloride (112.71 mg, 997.95 µmop were stirred at 80° C. for 1 hour. the reaction solution was filtrated and concentrated to give the crude product which was then purified by preparative HPLC (containing 0.5% HCl, v/v) to give the compound of Example 82 (12.00 mg, the yield was 9.75%) as a yellow powder.

LCMS (ESI) m/z: 478.9 [M+1]+

$^1$H NMR (400 MHz, DMSO-$d_6$) 8.90-8.98 (m, 1H), 8.72 (s, 1H), 7.92-8.03 (m, 1H), 7.83-7.92 (m, 1H), 7.71 (s, 1H), 7.65 (s, 1H), 7.37-7.46 (m, 1H), 7.26 (s, 1H), 6.85-6.93 (m, 1H), 4.13 (s, 2H), 4.08 (s, 3H), 3.22 (s, 3H).

Process K

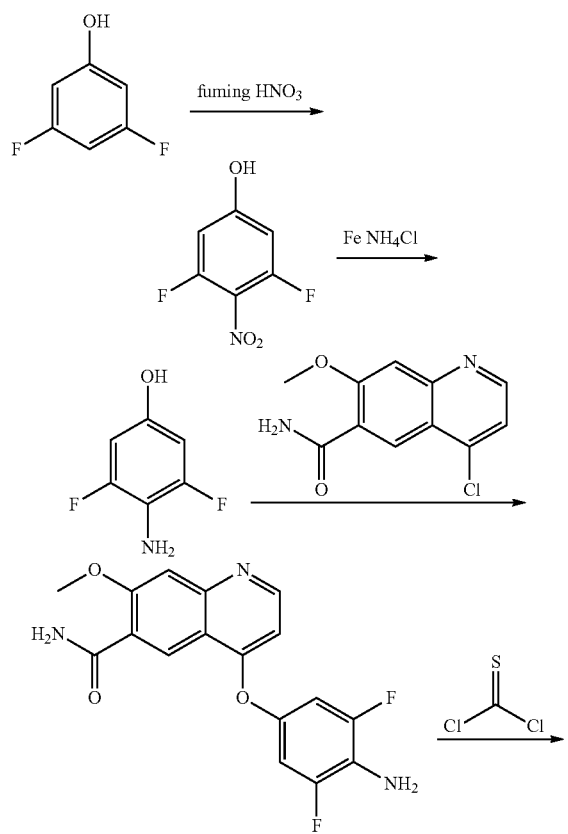

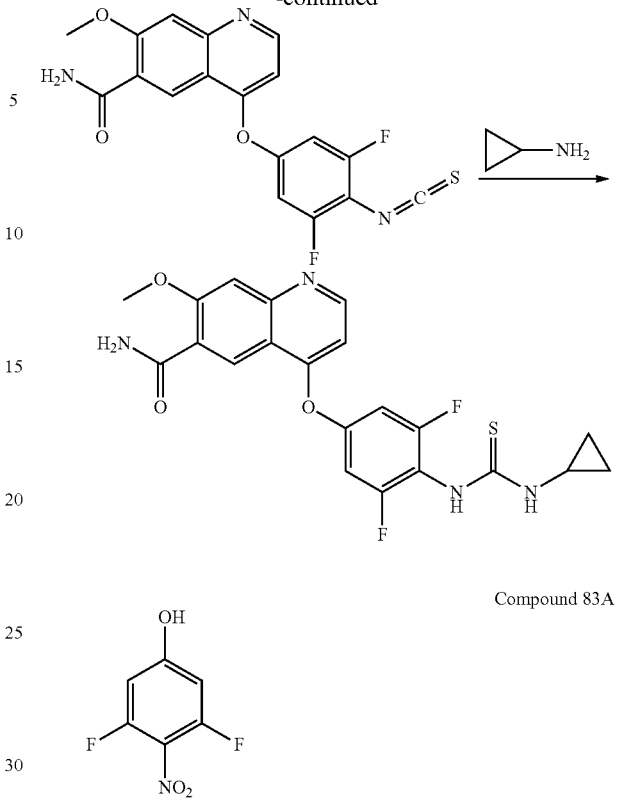

Compound 83A

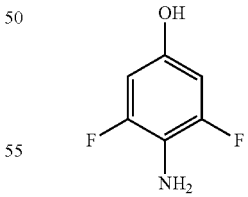

3,5-difluoro p-nitrophenol (1.00 g, 7.69 mmol) was dissolved in dichloromethane (10 mL). The reaction solution was protected by nitrogen and then stirred at 0° C. for 10 minutes. Concentrated nitric acid (538.39 mg, 7.69 mmol) was added slowly to the reaction system and then stirred at 0° C. for 2 hours. The reaction was complete detected by TLC. The reaction was added with ice water (10 ml) and then extracted with dichloromethane (5 ml*5). The organic phases were combined and washed with saturated NaCl solution (5 mL), dried over sodium sulfate, filtered and then spin-dried. The residue was purified by flash chromatography on a silica gel column (the mobile phase was petroleum ether:ethyl acetate=10:1) to give compound 83A (580.00 mg, 3.31 mmol, the yield was 43.08%) as a red oily matter.

$^1$H NMR (400 MHz, METHANOL-$d_4$) 6.61 (s, 1H), 6.58 (s, 1H)

Compound 83B

Compound 83A (580.00 mg, 3.31 mmol) was dissolved in a mixed solution of ethanol (5 ml) and water (1.5 ml). Iron powder (425.19 mg, 7.61 mmol) and ammonium chloride (1.01 g, 18.87 mmol) were added to the reaction system at 25° C. The reaction solution was heated to 90° C. and refluxed for 2 hours. The reaction was complete detected by TLC. The reaction solution was filtered through celite and the filtrate was spin-dried. The residue was purified by flash chromatography on a silica gel column (the mobile phase was petroleum ether:ethyl acetate=5:1) to give compound 83B (413.00 mg, 2.70 mmol, the yield was 81.69%, and the purity was 95%) as a gray solid.

$^1$H NMR (400 MHz, DMSO-d$_6$) 9.22 (s, 1H), 6.28-6.39 (m, 2H), 4.37 (s, 2H)

Compound 83C

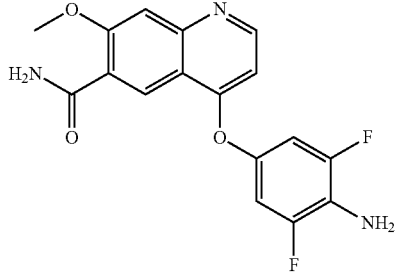

Compound 83B (534.00 mg, 3.68 mmol) and the compound of Example 1E (1.05 g, 4.42 mmol) were added to a sealed tube of N-methylpyrrolidone (3 ml). The reaction solution was stirred for 5 minutes and added with cesium carbonate (2.40 g, 7.36 mmol). The reaction solution was heated to 140° C. and reacted in the microwave for 2 hours. LCMS detected that the reaction was complete. The reaction was added with water (15 ml) and then extracted with a mixed solution of dichloromethane and isopropanol (with a ratio of 3:1, 10 ml*3). The system was difficult to stratify. The reaction solution was completely separated after filtrating through celite. The organic phase was washed with saturated NaCl solution (5 ml), dried over sodium sulfate, filtered and the spin-dried to give a compound 83C as a grey oil which was used directly in the next step.

LCMS (ESI) m/z: 345.9 [M+1]$^+$

Compound 83D

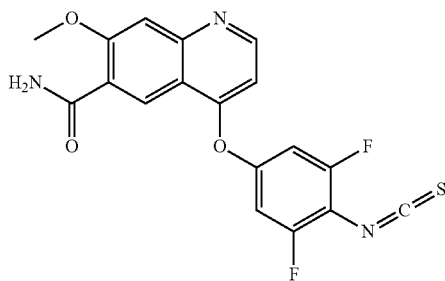

Compound 83C (150.00 mg, 434.40 μmop and sodium carbonate (101.29 mg, 955.68 μmop were added to tetrahydrofuran (3 ml) and stirred at 0° C. for 10 minutes. Thiophosgene (54.94 mg, 477.84 μmop was added to the reaction system at 0° C. The reaction solution was then stirred at 25° C. for 2 hours. LCMS detected that the reaction was complete. Water was added to the reaction system and the reaction solution was then extracted with ethyl acetate (5 ml*3). The organic phase was washed with saturated NaCl solution (3 ml), dried over sodium sulfate, filtered and spin-dried to give a compound 83D (150.00 mg, crude) as a black oily matter. LCMS demonstrated that the product was correct.

LCMS (ESI) m/z: 388.1 [M+1]$^+$

Example 83

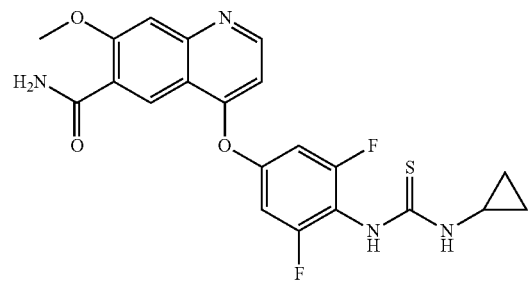 [SMILES: COc1cc2nccc(Oc3cc(F)c(NC(=S)NC4CC4)c(F)c3)c2cc1C(N)=O]

Example 83D (150.00 mg, 387.24 μmop was added to tetrahydrofuran (3 ml). Cyclopropylamine (66.32 mg, 1.16 mmol) was then added to the reaction system. The reaction solution was protected by nitrogen and then stirred at 20° C. for 1 hour. LCMS detected that the reaction was complete. The reaction solution was added with water (10 ml) and then extracted with ethyl acetate (8 ml*3). The organic phase was combined and washed with saturated NaCl solution, dried over sodium sulfate, filtered and spin-dried. The residue was dissolved in N,N-dimethylformamide (0.2 ml) and acetonitrile (3 ml), and then sent to HPLC (hydrochloric acid) to purify to give a compound of Example 83 (19.50 mg, 43.64 μmol, the yield was 11.27%, the purity was 99.472%) as a gray solid.

$^1$H NMR (400 MHz, METHANOL-d$_4$) 8.95-9.10 (m, 2H), 7.67 (br. s., 1H), 7.29 (d, J=7.03 Hz, 3H), 4.24 (br. s., 3H), 2.73 (br. s., 1H), 0.94 (br. s., 2H), 0.76 (br. s., 2H)

The following compounds were also prepared by using the similar methods as described in Example 83 mentioned above.

| Examples | Structures | NMR | LCMS (ESI) m/z: (M + 1)$^+$ |
|---|---|---|---|
| Example 90 | 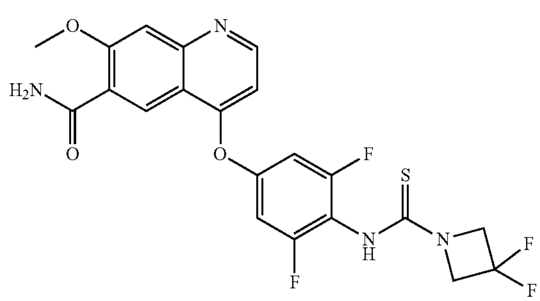 [SMILES: COc1cc2nccc(Oc3cc(F)c(NC(=S)N4CC(F)(F)C4)c(F)c3)c2cc1C(N)=O] | $^1$H NMR (400 MHz, METHANOL-d$_4$) 9.01 (s, 1H), 8.94 (d, J = 6.53 Hz, 1H), 7.62 (s, 1H), 7.27 (d, J = 7.53 Hz, 2H), 7.18 (d, J = 6.53 Hz, 1H), 4.62 (t, J = 11.80 Hz, 4H), 4.22 (s, 3H) | 481.1 |

| Examples | Structures | NMR | LCMS (ESI) m/z: (M + 1)+. |
|---|---|---|---|
| Example 91 | 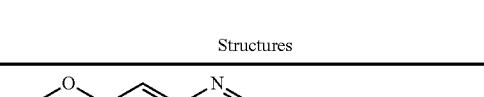 | ¹H NMR (400 MHz, METHANOL-d₄) 7.51 (s, 1H), 7.46 (d, J = 7.03 Hz, 1H), 6.13 (s, 1H), 5.79 (d, J = 6.53 Hz, 1H), 5.74 (d, J = 7.03 Hz, 2H), 2.63-2.77 (m, 3H), 2.26-2.44 (m, 2H), 2.08-2.25 (m, 2H), 0.66 (br. s., 2H), 0.43-0.58 (m, 2H) | 459.2 |

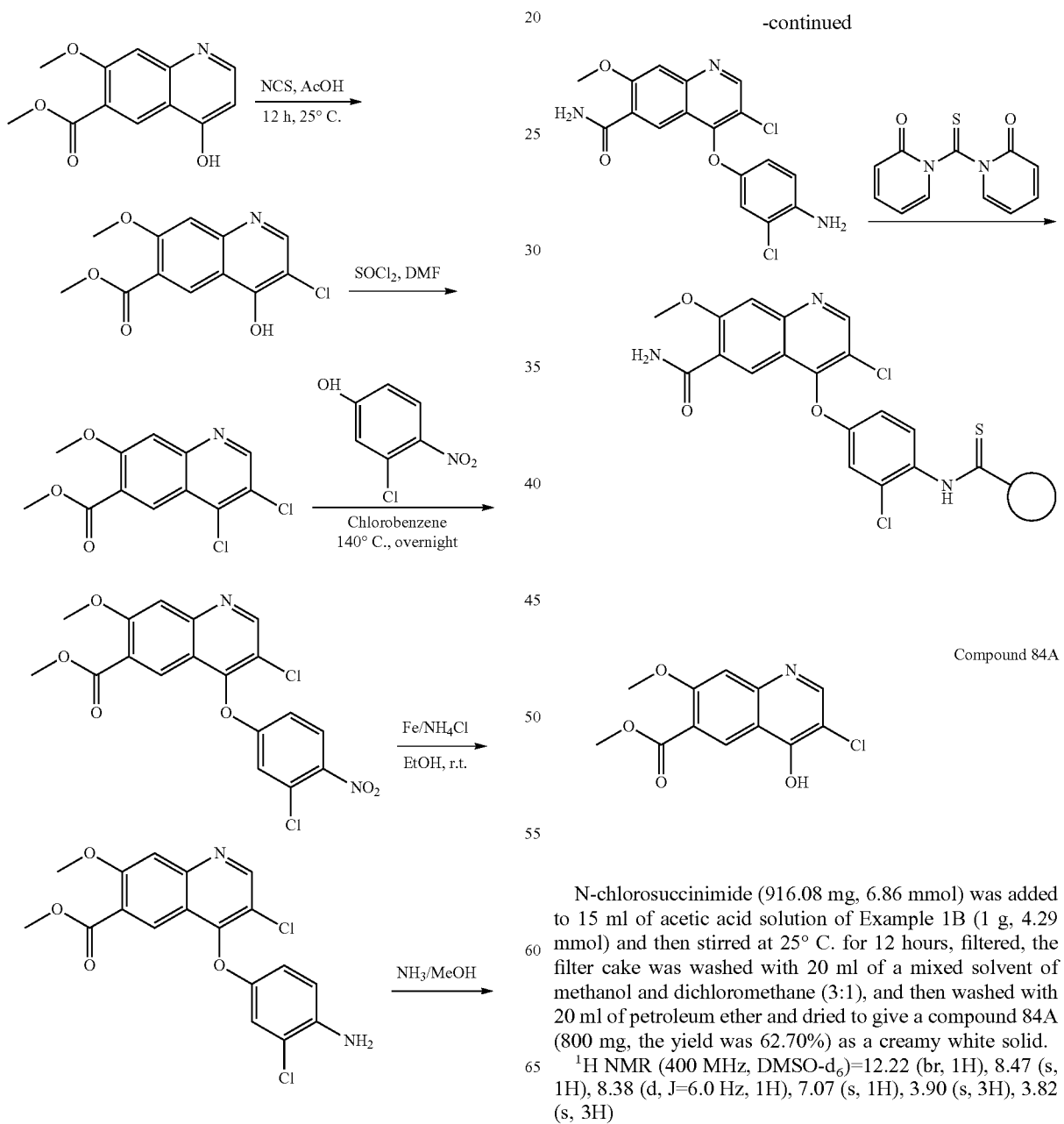

Compound 84A

N-chlorosuccinimide (916.08 mg, 6.86 mmol) was added to 15 ml of acetic acid solution of Example 1B (1 g, 4.29 mmol) and then stirred at 25° C. for 12 hours, filtered, the filter cake was washed with 20 ml of a mixed solvent of methanol and dichloromethane (3:1), and then washed with 20 ml of petroleum ether and dried to give a compound 84A (800 mg, the yield was 62.70%) as a creamy white solid.

¹H NMR (400 MHz, DMSO-d₆)=12.22 (br, 1H), 8.47 (s, 1H), 8.38 (d, J=6.0 Hz, 1H), 7.07 (s, 1H), 3.90 (s, 3H), 3.82 (s, 3H)

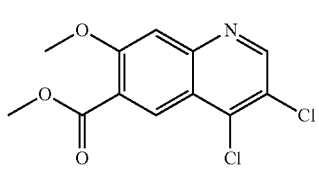

Compound 84B

Compound 84A (800 mg, 2.99 mmol) was dissolved in 10 ml of thionyl chloride, and then DMF (65.56 mg, 897.00 μmol) was added thereto. The reaction solution was heated to 120° C. for 2.5 hours, and then concentrated and purified by column chromatography to give a compound 84B (500 mg, the yield was 58.45%) as an orange solid.
$^1$H NMR (400 MHz, DMSO-$d_6$)=9.02 (s, 1H), 8.42 (s, 1H), 7.64 (s, 1H), 4.01 (s, 3H), 3.90 (s, 3H)

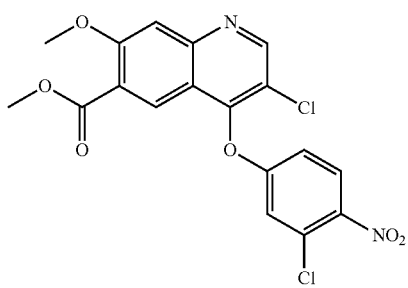

Compound 84C 3-chloro-4-nitrophenol (273.34 mg, 1.58 mmol) was added to 20 ml of chlorobenzene solution of compound 84B (300.42 mg, 1.05 mmol). The mixture was then heated to 130-140° C. and stirred for 96 hours and spin-dried. The residue was then purified by preparative HPLC to give a yellow compound 84C as a solid (200 mg, the yield was 45.01%).
$^1$H NMR (400 MHz, DMSO-$d_6$)=9.09 (s, 1H), 8.19 (s, 1H), 8.13 (d, J=9.0 Hz, 1H), 7.71 (s, 1H), 7.59 (d, J=2.5 Hz, 1H), 7.15 (dd, J=2.8, 9.3 Hz, 1H), 4.01 (s, 3H), 3.83 (s, 3H)

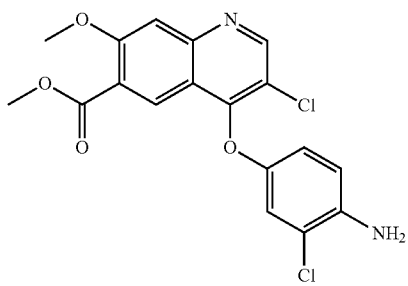

Compound 84D

Ammonium chloride (252.79 mg, 4.73 mmol) and iron powder (395.91 mg, 7.09 mmol) were added to 40 ml of ethanol solution of compound 84C (200 mg, 0.472 mmol), the mixture was protected by nitrogen and then heated to 70° C. and stirred for 16 hours, filtered, and the filtrate was rotary evaporated to give 400 mg compound 84D (crude, gray solid) which was used directly in the next step. LCMS (ESI) m/z: 393.1 [M+1]$^+$

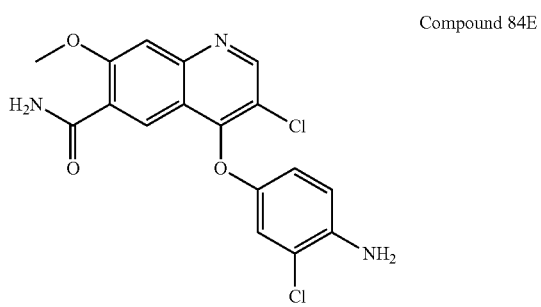 [SMILES: COc1cc2ncc(Cl)c(Oc3ccc(N)c(Cl)c3)c2cc1C(N)=O]

Compound 84E

Compound 84D (360 mg, 457.76 mmol) was added in one portion to 7.86% ammonia methanol solution (94.22 g, 434.87 mmol), and then stirred at 20 to 29° C. for 16 hours and rotary evaporated. Then 15 ml of a mixed solution of methylene chloride and methanol (5:1) was added to the residue which was then washed with 4 ml of water, dried over anhydrous sodium sulfate and concentrated by filtration to give an off-white compound 84E as a solid (100 mg, the yield was 57.76%) which was used directly in the next step.
LCMS (ESI) m/z: 377.9 [M+1]$^+$ Example 84

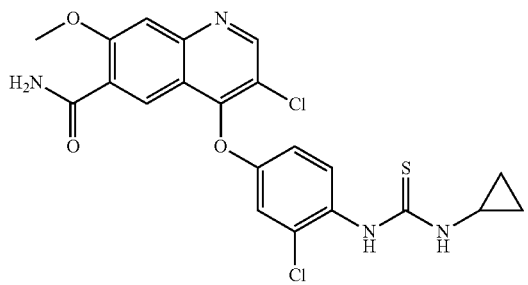 [SMILES: COc1cc2ncc(Cl)c(Oc3ccc(NC(=S)NC4CC4)c(Cl)c3)c2cc1C(N)=O]

1,1'-thiocarbonyldi-2(1H) pyridone (70.01 mg 0.301 mmol) was added to a solution of compound 84E (38 mg, 0.1 mmol) in 3.8 ml of dioxane, and then heated to 60-70° C. and stirred for 2 hours. After cooling to 20° C., cyclopropylamine (41 mg, 0.718 mmol) was added and then stirred at 25-28° C. for 16 hours. The mixture was cooled by rotary evaporation and the residue was purified by preparative HPLC to give a yellow compound of Example 84 as a solid (20 mg, the yield was 35.95%). LCMS (ESI) m/z: 477.0 [M+1]$^+$ $^1$H NMR (400 MHz, METHANOL-$d_4$)=9.24-9.08 (m, 1H), 8.87-8.57 (m, 1H), 7.70-7.49 (m, 2H), 7.33-7.14 (m, 1H), 6.98-6.86 (m, 1H), 4.22-4.06 (m, 3H), 2.89-2.66 (m, 1H), 0.98-0.59 (m, 4H)

The following compounds were also prepared by using the similar methods as described in Example 84 mentioned above.

| Examples | Structures | NMR | LCMS (ESI) m/z: (M + 1)+. |
|---|---|---|---|
| Example 88 | 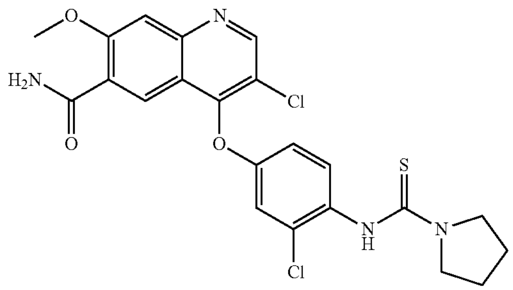 [SMILES: COc1cc2ncc(Cl)c(Oc3ccc(NC(=S)N4CCCC4)c(Cl)c3)c2cc1C(N)=O] | ¹H NMR (400 MHz, METHANOL-d₄) = 9.18-9.03 (m, 1H), 8.91-8.56 (m, 1H), 7.72-7.61 (m, 1H), 7.53-7.39 (m, 1H), 7.19-7.08 (m, 1H), 6.95-6.68 (m, 2H), 4.28-4.03 (m, 3H), 3.77 (br. s., 4H), 2.26-1.87 (m, 4H) | 491.1 |
| Example 89 | 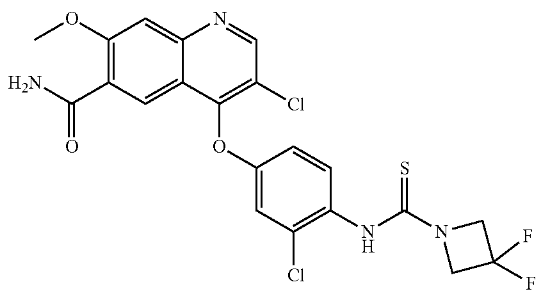 [SMILES: COc1cc2ncc(Cl)c(Oc3ccc(NC(=S)N4CC(F)(F)C4)c(Cl)c3)c2cc1C(N)=O] | ¹H NMR (400 MHz, METHANOL-d₄) = 9.11 (s, 1H), 8.64-8.53 (m, 1H), 7.66 (s, 1H), 7.47 (d, J = 9.0 Hz, 1H), 7.17 (d, J = 2.8 Hz, 1H), 6.96 (dd, J = 2.8, 8.8 Hz, 1H), 4.53 (t, J = 11.9 Hz, 4H), 4.16 (s, 3H) | 535.1 [M + 23]+ |
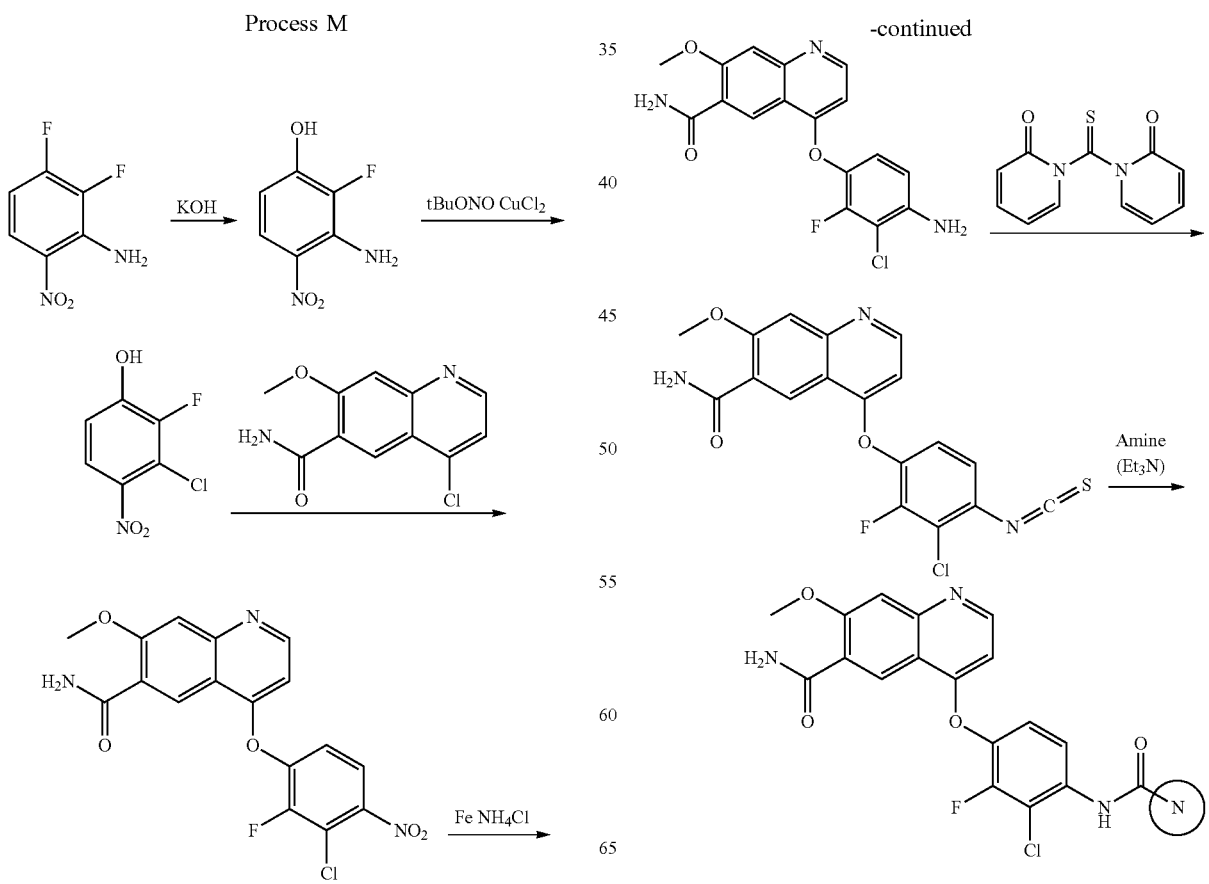
Process M

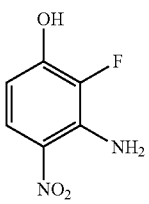

Compound 95A 2,3-difluoro-6-nitro-phenylamine (4.80 g, 27.57 mmol) was added to dioxane (75.00 mL). Potassium hydroxide (6.19 g, 110.28 mmol) was dissolved in water (20.00 ml) and added to the reaction system. The reaction solution was heated to 100° C. for 15 hours. The reaction was complete detected by TLC. The reaction solution was added with water (20 ml) and extracted with ethyl acetate (20 ml*3). The organic phase was washed with water (10 ml) and NaCl solution (10 ml), dried over sodium sulfate, filtered and then spin-dried. The residue was recrystallized with a mixture of ethyl acetate and petroleum ether (with a ratio of 5:1, 20 ml) to give a compound 95A (3.50 g, 20.34 mmol, the yield was 73.76%) as a yellow solid.

$^1$H NMR (400 MHz, CHLOROFORM-d) 7.94 (dd, J=1.88, 9.66 Hz, 1H), 6.34-6.47 (m, 1H), 6.16 (br. s., 3H)

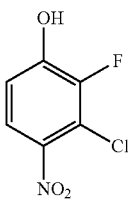

Compound 95B

Compound 95A (1.00 g, 5.81 mmol) was added to acetonitrile (6.00 mL). Copper chloride (898.69 mg, 8.71 mmol) was then added to the reaction system. The system was protected by nitrogen and then reduced to 0° C. in ice bath. Tert-butyl ester (898.69 mg, 8.71 mmol) was slowly added to the reaction system at 0-10° C. The reaction solution was stirred at 0° C. for 1 hour and then stirred at 25° C. for 5 hours. The reaction was basically complete detected by TLC. The reaction solution was added with water (5 mL) and then extracted with ethyl acetate (10 ml*3). The organic phase was combined and washed with water (5 mL), dried over sodium sulfate, filtered and then spin-dried. The residue was purified by flash chromatography on a silica gel column (the mobile phase was petroleum ether:ethyl acetate=10:1) to give compound 95B (390.00 mg, 1.73 mmol, the yield was 29.79%, and the purity was 85%) as a yellow solid.

$^1$H NMR (400 MHz, METHANOL-d$_4$) 7.86 (dd, J=1.51, 9.03 Hz, 1H), 7.01 (t, J=8.78 Hz, 1H)

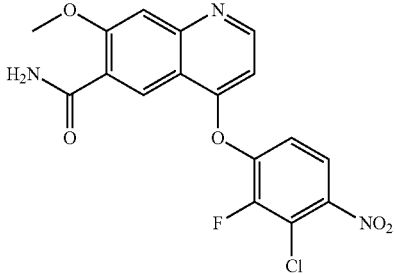

Compound 95C

Compound 95B (350.00 mg, 1.83 mmol) and 4-chloro-7-methoxy-quinoline-6-carboxamide (476.38 mg, 2.01 mmol) were added to chlorobenzene (5.00 mL). The reaction solution was protected by nitrogen and then allowed to react at 140° C. for 15 hours. The reaction was detected by LCMS but not complete. The reaction solution was directly spin-dried and the residue was purified by flash chromatography on a silica gel column (the mobile phase was dichloromethane:methanol=5:1) to give compound 95C (200.00 mg, 362.49 μmol, the yield was 19.81%, the purity was 71%) as a yellow solid.

$^1$H NMR (400 MHz, METHANOL-d$_4$) 8.95 (s, 1H), 8.75-8.80 (m, 1H), 8.07 (d, J=8.28 Hz, 1H), 7.56-7.66 (m, 2H), 6.85 (d, J=5.02 Hz, 1H), 4.15-4.21 (m, 3H)

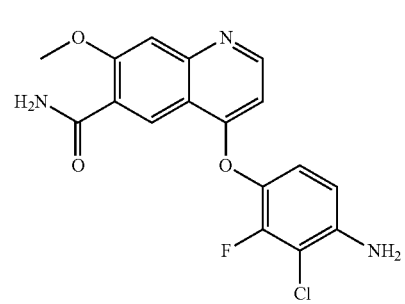

Compound 95D

Compound 95C (350.00 mg, 893.45 μmop, iron powder (114.77 mg, 2.05 mmol) and ammonium chloride (272.41 mg, 5.09 mmol) were added to a mixture of ethanol (5.00 ml) and water (1.50 ml) at 30° C. The reaction solution was heated to 90° C. and refluxed for 5 hours. The reaction was complete detected by LCMS. The reaction was filtered through celite and the filtrate was directly spin-dried. The residue was purified by flash chromatography on a silica gel column (the mobile phase was ethyl acetate:petroleum ether=1:1) to give compound 95D (199.00 mg, 390.57 μmol, the yield was 43.72%, the purity was 71%) as a brown solid.

$^1$H NMR (400 MHz, METHANOL-d$_4$) 8.99 (s, 1H), 8.65 (d, J=5.27 Hz, 1H), 7.54 (s, 1H), 7.11 (t, J=8.66 Hz, 1H), 6.76 (d, J=9.03 Hz, 1H), 6.56 (d, J=5.27 Hz, 1H), 4.15 (s, 3H)

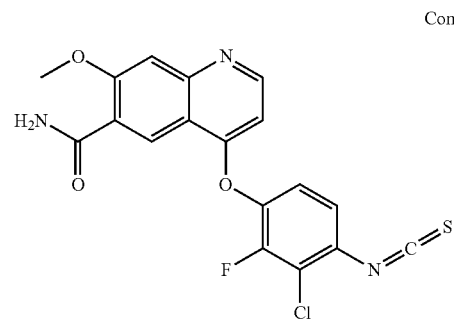

Compound 95E

Compound 95D (200.00 mg, 552.87 μmop and 1,1'-thiocarbonyldi-2(1H)-pyridone (154.09 mg, 663.44 μmop were added to dioxane (3.00 ml). The reaction solution was stirred at 28° C. for half an hour and stirred at 100° C. for 1 hour. The reaction was detected by LCMS but not complete. 1,1'-thiocarbonyldi-2(1H)-pyridone (154.09 mg, 663.44 μmop was added and stirred for half an hour and only a small amount of material was left detected by LCMS. 1,1'-thiocarbonyldi-2(1H)-pyridone (154.09 mg, 663.44 μmop was added and reacted for half an hour. The reaction was basically complete detected by LCMS. The reaction solution was spin-dried to give compound 95E, and the residue was used directly in the next reaction. LCMS (ESI) m/z: 403.8 [M+1]+

Example 95

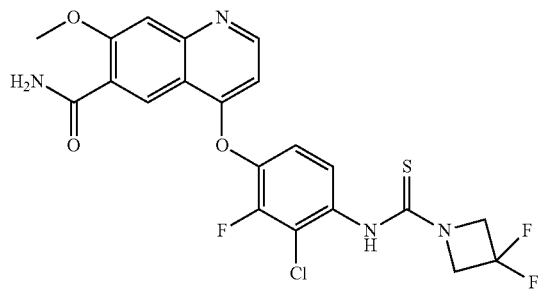 [SMILES: COc1cc2nccc(Oc3ccc(NC(=S)N4CC(F)(F)C4)c(Cl)c3F)c2cc1C(N)=O]

Compound 95E (100.00 mg, 247.64 μmop, 3,3-difluoro-cyclobutane hydrochloride (64.16 mg, 495.28 μmop and triethylamine (50.12 mg, 495.28 μmop were added to tetrahydrofuran (2.00 mL). The reaction solution was stirred at 28° C. for 1 hour. The reaction was complete detected by LCMS. The reaction was spin-dried and the residue was dissolved in N,N-dimethylformamide (0.5 ml) and acetonitrile (3 ml), and then sent to HPLC (hydrochloric acid) for purification to give a compound of Example 95 (14.00 mg, 28.18 μmol, the yield was 11.38%, the purity was 100%) as a white solid.

$^1$H NMR (400 MHz, METHANOL-$d_4$) 9.05 (s, 1H), 8.95 (d, J=6.53 Hz, 1H), 7.63 (s, 1H), 7.5$_{1-7}$.60 (m, 2H), 7.19 (d, J=6.53 Hz, 1H), 4.63 (t, J=11.80 Hz, 4H), 4.23 (s, 3H)

The following compounds were also prepared by using the similar methods as described in Example 95 mentioned above.

| Examples | Structures | NMR | LCMS (ESI) m/z: 448.1 [M + 1]+ |
|---|---|---|---|
| Example 98 | 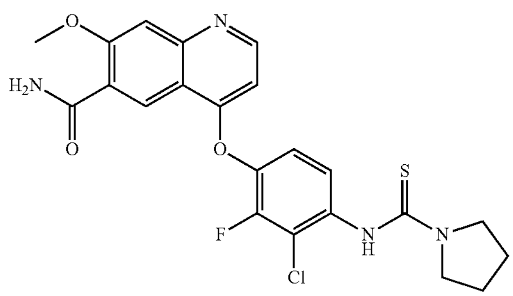 [SMILES: COc1cc2nccc(Oc3ccc(NC(=S)N4CCCC4)c(Cl)c3F)c2cc1C(N)=O] | $^1$H NMR (400 MHz, METHANOL-$d_4$) 8.84-9.19 (m, 1H), 7.64 (br. s., 1H), 7.52 (br. s., 2H), 7.32 (br. s., 1H), 4.23 (br. s., 3H), 3.59-3.99 (m, 4H), 1.9$_{0-2}$.31 (m, 4H) | 475.1 |
| Example 78 | 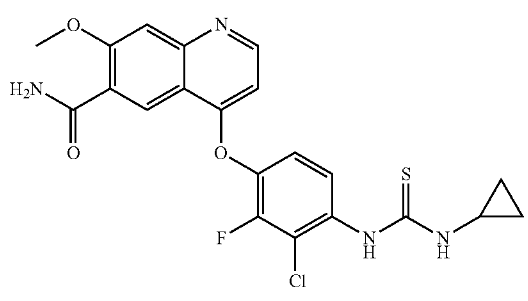 [SMILES: COc1cc2nccc(Oc3ccc(NC(=S)NC4CC4)c(Cl)c3F)c2cc1C(N)=O] | $^1$H NMR (400 MHz, CD$_3$OD) 9.05 (s, 1H), 8.95 (d, J = 6.4 Hz, 1H), 7.86-7.72 (m, 1H), 7.66 (s, 1H), 7.55-7.51 (m, 1H), 7.22 (m, 2H), 4.22 (s, 3H), 2.76 (m, 1H), 0.94 (m, 2H), 0.79 (m, 2H). | 461.0 |
| Example 103 | 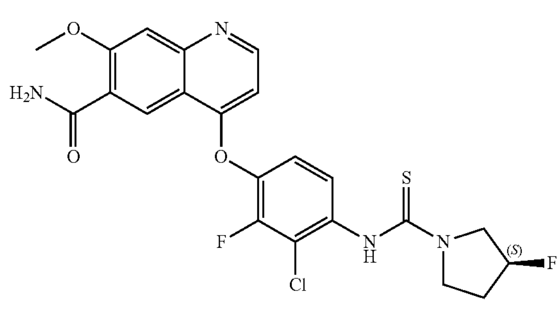 | $^1$H NMR (400 MHz, METHANOL-$d_4$) 9.06 (s, 1H), 9.02 (d, J = 6.53 Hz, 1H), 7.67 (s, 1H), 7.49-7.59 (m, 2H), 7.34 (d, J = 6.78 Hz, 1H), 5.26-5.53 (m, 1H), 4.10-4.37 (m, 4H), 3.76-4.04 (m, 3H), 2.43 (br. s., 2H) | 493.1 |

-continued

| Examples | Structures | NMR | LCMS (ESI) m/z: 448.1 [M + 1]⁺ |
|---|---|---|---|
| Example 105 | Chiral | 1H NMR (400 MHz, METHANOL-d4) 9.07 (s, 1H), 9.00 (d, J = 6.78 Hz, 1H), 8.31 (d, J = 8.78 Hz, 1H), 7.64 (s, 1H), 7.55 (t, J = 8.78 Hz, 1H), 7.27 (d, J = 6.78 Hz, 1H), 4.24 (s, 3H), 3.51 (d, J = 4.52 Hz, 2H), 3.35 (br. s., 4H), 3.14 (br. s., 1H), 2.84-2.93 (m, 1H), 2.02-2.12 (m, 1H), 1.87-1.97 (m, 2H), 1.76-1.84 (m, 1H) | 534.2 |
| Example 106 | Chiral | ¹H NMR (400 MHz, METHANOL-d₄) 9.06 (s, 1H), 9.02 (d, J = 6.78 Hz, 1H), 7.68 (s, 1H), 7.48-7.58 (m, 2H), 7.36 (d, J = 6.78 Hz, 1H), 4.46-4.69 (m, 1H), 4.19-4.29 (m, 2H), 3.64-4.05 (m, 3H), 1.99-2.35 (m, 2H) | 491.1 |
| Example 108 | 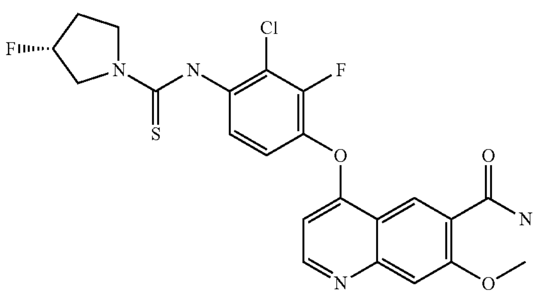 [SMILES: COc1cc2nccc(Oc3ccc(NC(=S)N4CC[C@@H](F)C4)c(Cl)c3F)c2cc1C(N)=O] | ¹H NMR (400 MHz, METHANOL-d₄) = 8.97 (s, 1H), 8.68 (d, J = 4.8 Hz, 1H), 7.52 (br. s., 1H), 7.46-7.33 (m, 2H), 6.75 (d, J = 4.5 Hz, 1H), 5.58-5.25 (m, 1H), 4.14 (br. s., 3H), 3.97 (d, J = 12.0 Hz, 1H), 3.90-3.73 (m, 2H), 2.41 (br. s., 2H) | 493.0 |
| Example 111 | 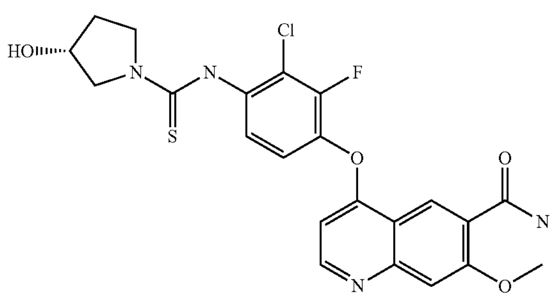 | ¹H NMR (400 MHz, METHANOL-d₄) = 8.99 (s, 1H), 8.73-8.66 (m, 1H), 7.56 (s, 1H), 7.48-7.37 (m, 2H), 6.78 (d, J = 5.3 Hz, 1H), 4.73-4.40 (m, 2H), 4.15 (s, 3H), 3.84 (br. s., 2H), 3.73-3.59 (m, 1H), 2.39-2.06 (m, 2H) | 491.2 |
| Example 112 | 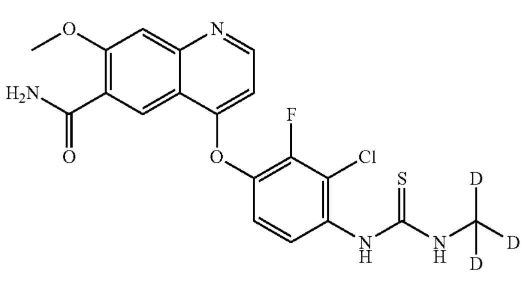 [SMILES: [2H]C([2H])([2H])NC(=S)Nc1ccc(Oc2ccnc3cc(OC)c(C(N)=O)cc23)c(F)c1Cl] | ¹H-NMR (CD₃OD 400 MHz) δ ppm 8.98 (s, 1H), 8.68 (d, J = 5.2 Hz, 1H), 7.59-7.54 (m, 2H), 7.43-7.38 (m, 1H), 6.73 (d, J = 4.8 Hz, 1H), 4.15 (s, 3H). | 438.0 |

| Examples | Structures | NMR | LCMS (ESI) m/z: 448.1 [M + 1]⁺ |
|---|---|---|---|
| Example 123 | 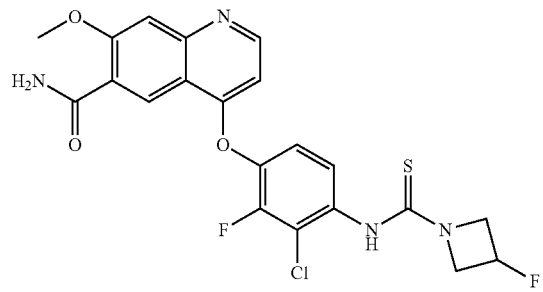 | ¹H NMR (400 MHz, METHANOL-d₄) ppm 4.15 (s, 3 H) 4.23-4.37 (m, 2 H) 4.49-4.66 (m, 2 H) 5.32-5.56 (m, 1 H) 6.74 (d, J = 5.27 Hz, 1 H) 7.39-7.51 (m, 2 H) 7.54-7.60 (m, 1 H) 8.67-8.73 (m, 1 H) 8.99 (s, 1 H) | 479.1 |
| Example 124 | 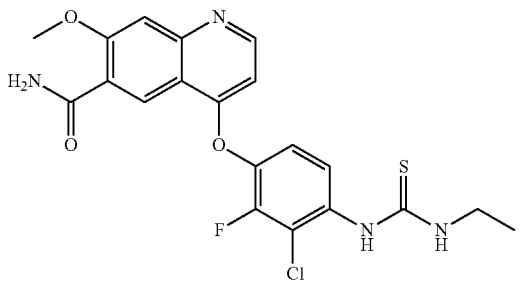 [SMILES: CCNC(=S)Nc1ccc(Oc2ccnc3cc(OC)c(C(N)=O)cc23)c(F)c1Cl] | ¹H NMR (400 MHz, METHANOL-d₄) ppm 1.26 (br. s., 3 H) 3.66 (br. s., 2 H) 4.15 (s, 3 H) 6.74 (d, J = 4.02 Hz, 1 H) 7.41 (t, J = 8.41 Hz, 1 H) 7.51-7.70 (m, 2 H) 8.69 (d, J = 5.27 Hz, 1 H) 8.99 (s, 1 H) | 449.3 |
| Example 77 | 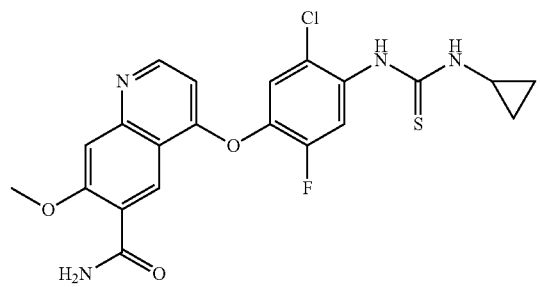 [SMILES: COc1cc2nccc(Oc3cc(Cl)c(NC(=S)NC4CC4)cc3F)c2cc1C(N)=O] | ¹H NMR (400 MHz, CD₃OD) δ 9.03 (s, 1H), 8.93 (d, J = 6.4 Hz, 1H), 8.22-8.04 (m, 1H), 7.84-7.76 (m, 1H), 7.65 (s, 1H), 7.17 (m, 1H), 4.21 (s, 3H), 2.74 (m, 1H), 0.95 (m, 2H), 0.80 (m, 2H). | 460.9 |
| Example 101 | 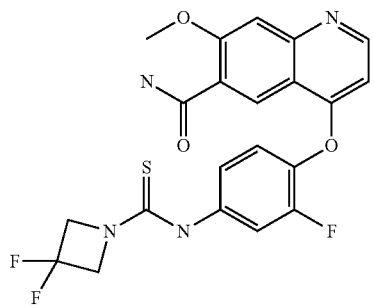 [SMILES: COc1cc2nccc(Oc3ccc(NC(=S)N4CC(F)(F)C4)cc3F)c2cc1C(N)=O] | 1H NMR (400 MHz, METHANOL-d4) d = 9.06 (s, 1H), 8.90 (d, J = 6.5 Hz, 1H), 7.91-7.84 (m, 1H), 7.60 (s, 1H), 7.55-7.42 (m, 2H), 7.04 (d, J = 6.3 Hz, 1H), 4.67-4.53 (m, 4H), 4.22 (s, 3H) LCMS (ESI) m/z: 463 (M + 1) | 463.1 |

Process N

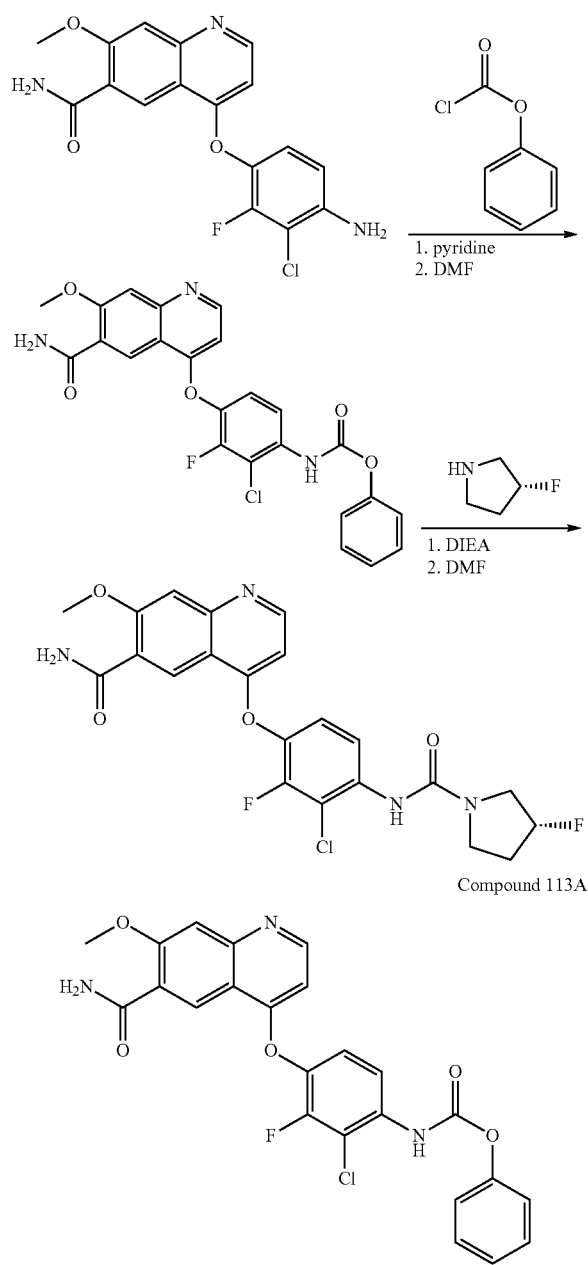

Compound 113A

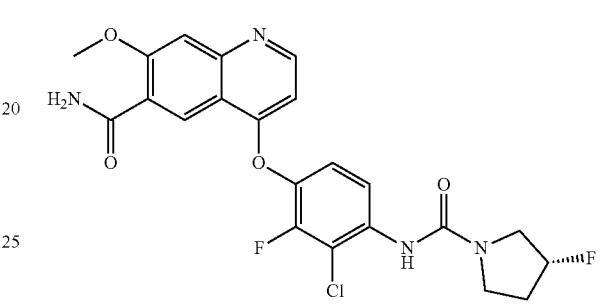

Compound 95D (600 mg, 1.66 mmol) and pyridine (131.20 mg, 1.66 mmol) were added to N,N-dimethylformamide (2 ml) under the protection of nitrogen at 28° C., and then phenyl chloroformate (389.53 mg, 2.49 mmol) was added thereto and stirred at 28° C. for 2 hours under the protection of nitrogen. Compound 113A (799 mg) was obtained by evaporation and used directly in the next step without further purification.

LCMS (ESI) m/z: 482.1 [M+1]$^+$

Example 113

N,N-diisopropylethylamine (100 mg, 276.43 μmop and (3R)-3-fluoropyrrole hydrochloride (21.87 mg, 276.44 μmop were added to N,N-dimethylformamide (0.3 ml), and then compound 113A (95.44 mg, 552.86 μmop was added to the mixture containing N,N-dimethylformamide (2 ml) and stirred at 28° C. for 1 hour under the protection of nitrogen. The reaction solution was filtered and purified by liquid chromatography to give a compound of Example 113 (yellow solid, 30 mg, the yield was 22.53%). LCMS (ESI) m/z: 477.2 [M+1]$^+$ $^1$H NMR (400 MHz, METHANOL-d$_4$)=9.00 (s, 1H), 8.68 (d, J=5.3 Hz, 1H), 7.66 (dd, J=1.8, 9.0 Hz, 1H), 7.56 (s, 1H), 7.40 (t, J=8.7 Hz, 1H), 6.65 (d, J=5.3 Hz, 1H), 5.46-5.29 (m, 1H), 4.15 (s, 3H), 3.89-3.58 (m, 4H), 2.43-2.14 (m, 2H), 1.31 (s, 5H), 0.91 (d, J=9.5 Hz, 3H)

The following compounds were also prepared by using the similar methods as described in Example 113 mentioned above.

| Examples | Structures | NMR | LCMS (ESI) m/z: [M + 1] |
|---|---|---|---|
| Example 107 | 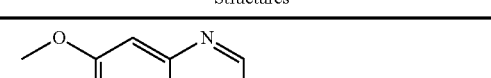 | $^1$H NMR (400 MHz, METHANOL-d$_4$) = 9.11 (s, 1H), 9.01 (d, J = 6.8 Hz, 1H), 8.21 (d, J = 9.0 Hz, 1H), 7.63 (s, 1H), 7.47 (t, J = 8.9 Hz, 1H), 7.16 (d, J = 6.5 Hz, 1H), 4.25 (s, 3H), 2.67 (tt, J = 3.7, 7.0 Hz, 1H), 0.81 (d, J = 5.5 Hz, 2H), 0.58 (br. s., 2H) | 448.1 |

| Examples | Structures | NMR | LCMS (ESI) m/z: [M + 1] |
|---|---|---|---|
| Example 115 | 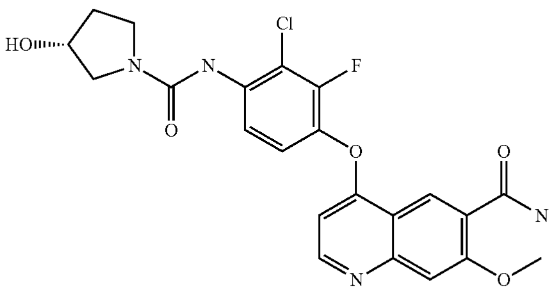 [SMILES: COc1cc2nccc(Oc3ccc(NC(=O)N4CC[C@@H](O)C4)c(Cl)c3F)c2cc1C(N)=O] | ¹H NMR (400 MHz, METHANOL-d₄) = 8.99 (s, 1H), 8.68 (d, J = 5.3 Hz, 1H), 7.68 (dd, J = 1.8, 9.0 Hz, 1H), 7.56 (s, 1H), 7.38 (t, J = 8.7 Hz, 1H), 6.64 (d, J = 5.5 Hz, 1H), 4.64-4.49 (m, 2H), 4.15 (s, 3H), 3.72-3.61 (m, 3H), 3.53 (d, J = 11.0 Hz, 1H), 2.22-2.05 (m, 2H) | 475.2 |
| Example 117 | 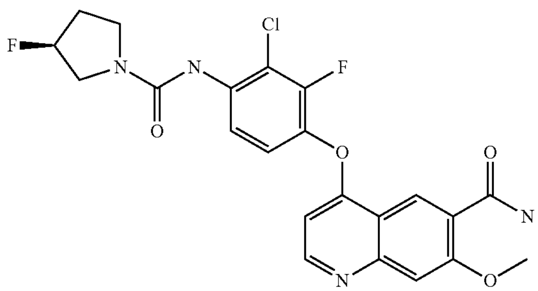 [SMILES: COc1cc2nccc(Oc3ccc(NC(=O)N4CC[C@H](F)C4)c(Cl)c3F)c2cc1C(N)=O] | ¹H NMR (400 MHz, METHANOL-d₄) = 8.97 (s, 1H), 8.67 (d, J = 5.5 Hz, 1H), 7.65 (dd, J = 1.8, 9.0 Hz, 1H), 7.53 (s, 1H), 7.38 (t, J = 8.7 Hz, 1H), 6.63 (d, J = 5.0 Hz, 1H), 5.47-5.27 (m, 1H), 4.19-4.11 (m, 3H), 3.91-3.72 (m, 2H), 3.71-3.57 (m, 1H), 2.42-2.14 (m, 2H) | 477.1 |
| Example 118 | 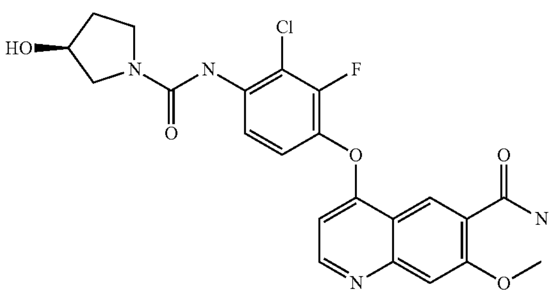 [SMILES: COc1cc2nccc(Oc3ccc(NC(=O)N4CC[C@H](O)C4)c(Cl)c3F)c2cc1C(N)=O] | ¹H NMR (400 MHz, METHANOL-d₄) = 8.99 (s, 1H), 8.67 (d, J = 5.5 Hz, 1H), 7.73-7.65 (m, 1H), 7.55 (s, 1H), 7.38 (t, J = 8.8 Hz, 1H), 6.64 (d, J = 5.3 Hz, 1H), 4.65-4.49 (m, 2H), 4.15 (s, 3H), 3.73-3.61 (m, 3H), 3.53 (d, J = 11.0 Hz, 1H), 2.21-2.05 (m, 2H) | 475.3 |
| Example 119 | 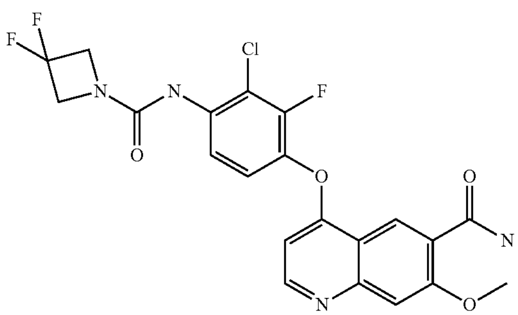 [SMILES: COc1cc2nccc(Oc3ccc(NC(=O)N4CC(F)(F)C4)c(Cl)c3F)c2cc1C(N)=O] | ¹H NMR (400 MHz, METHANOL-d₄) = 8.98 (br. s., 1H), 8.68 (d, J = 5.3 Hz, 1H), 7.71-7.51 (m, 2H), 7.41 (d, J = 8.5 Hz, 1H), 6.63 (d, J = 3.8 Hz, 1H), 4.50 (t, J = 12.2 Hz, 4H), 4.15 (br. s., 3H) | 481.0 |
| Example 120 | 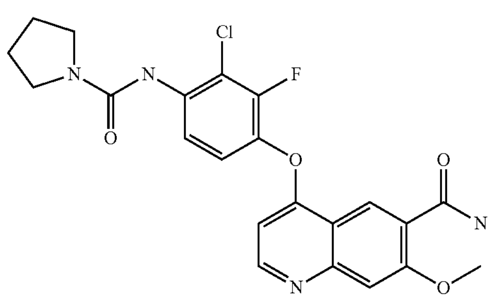 [SMILES: COc1cc2nccc(Oc3ccc(NC(=O)N4CCCC4)c(Cl)c3F)c2cc1C(N)=O] | ¹H NMR (400 MHz, METHANOL-d₄) = 8.99 (s, 1H), 8.68 (d, J = 5.3 Hz, 1H), 7.70 (d, J = 9.3 Hz, 1H), 7.56 (s, 1H), 7.38 (t, J = 8.7 Hz, 1H), 6.64 (d, J = 5.3 Hz, 1H), 4.19-4.11 (m, 3H), 3.55 (br. s., 4H), 2.04 (br. s., 4H) | 459.1 |

-continued
| Examples | Structures | NMR | LCMS (ESI) m/z: [M + 1] |
|---|---|---|---|
| Example 121 | 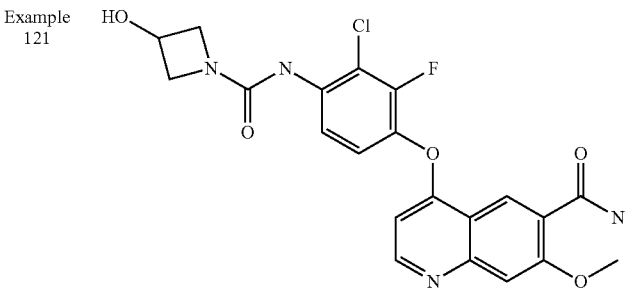 | ¹H NMR (400 MHz, METHANOL-d₄) = 8.99 (s, 1H), 8.68 (d, J = 5.3 Hz, 1H), 7.65 (d, J = 9.3 Hz, 1H), 7.57 (s, 1H), 7.39 (t, J = 8.5 Hz, 1H), 6.64 (d, J = 5.3 Hz, 1H), 4.96 (s, 1H), 4.39-4.33 (m, 2H), 4.18-4.13 (m, 3H), 3.95 (dd, J = 4.4, 8.9 Hz, 2H) | 461 |
| Example 122 | 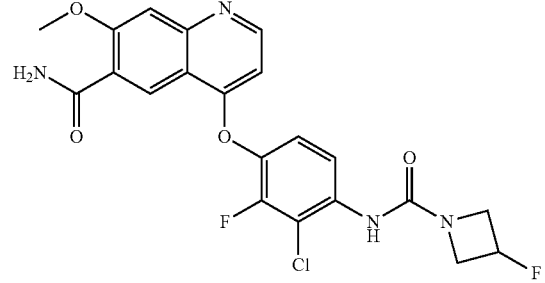 | ¹H NMR (400 MHz, METHANOL-d₄) ppm 4.15-4.32 (m, 5 H) 4.37-4.54 (m, 2 H) 5.30-5.56 (m, 1 H) 6.64 (br. s., 1 H) 7.40 (d, J = 7.78 Hz, 1 H) 7.51-7.69 (m, 2 H) 8.68 (br. s., 1 H) 8.99 (br. s., 1 H) | 463.1 |
| Example 125 | 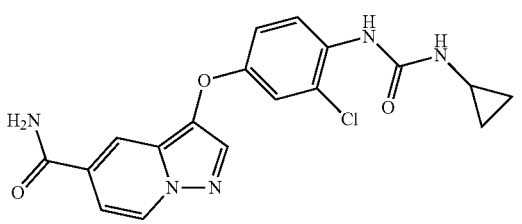 [SMILES: NC(=O)c1ccn2ncc(Oc3ccc(NC(=O)NC4CC4)c(Cl)c3)c2c1] | ¹H NMR (DMSO-d₆, 400 MHz): δ 8.70 (d, J = 7.2 Hz, 1 H), 8.20 (s, 1 H), 8.14 (s, 1 H), 8.06 (s, 1 H), 8.00 (d, J = 7.2 Hz, 1 H), 7.83 (d, J = 7.2 Hz, 1 H), 7.57 (s, 1 H), 7.31 (d, J = 7.2 Hz, 1 H), 7.08-7.12 (m, 2H), 6.98 (dd, J = 7.2, 1.6 Hz, 1 H), 2.53-2.55 (m, 1 H), 0.64 (d, J = 8.0 Hz, 2 H), 0.41 (brs, 2 H). | 386.0 |
| Example 128 | 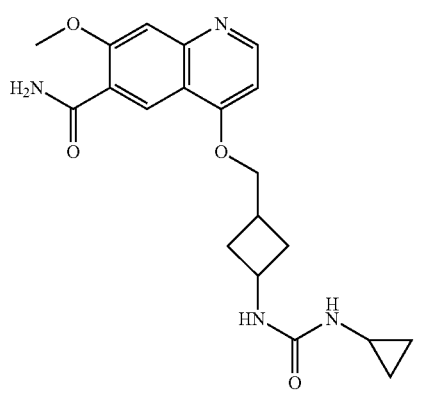 [SMILES: COc1cc2nccc(OCC3CC(NC(=O)NC4CC4)C3)c2cc1C(N)=O] | H NMR (DMSO-d₆): 8.92 (s, 1 H), 8.71 (d, J = 5.8 Hz, 1 H), 7.47 (s, 1 H), 6.97 (d, J = 5.5 Hz, 1 H), 4.29 (d, J = 4.8 Hz, 2 H), 4.13 (s, 3 H), 2.47-2.68 (m, 4 H), 1.97-2.10 (m, 2 H), 0.68-0.77 (m, 2 H), 0.42-0.54 (m, 2 H). | 385.2 |

| Examples | Structures | NMR | LCMS (ESI) m/z: [M + 1] |
|---|---|---|---|
| Example 129 | 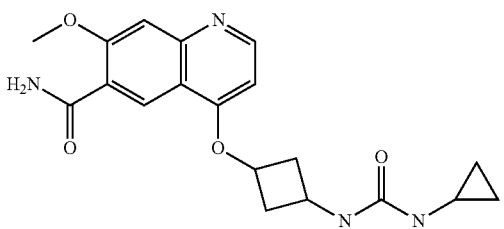 | H NMR (MeOD-d$_4$): 8.86-9.01 (m, 2 H), 7.59 (brs., 1 H), 7.22-7.37 (m, 1 H), 5.47 (brs., 0.7 H), 5.11 (brs., 0.3 H), 4.57 (brs., 0.7 H), 4.07-4.27 (m, 3.3 H), 3.19 (brs., 0.7 H), 2.74-2.91 (m, 3.3 H), 2.56 (brs., 2 H), 0.77-0.85 (m, 2 H), 0.52-0.63 (m, 2 H) | 371.3 |

Process O

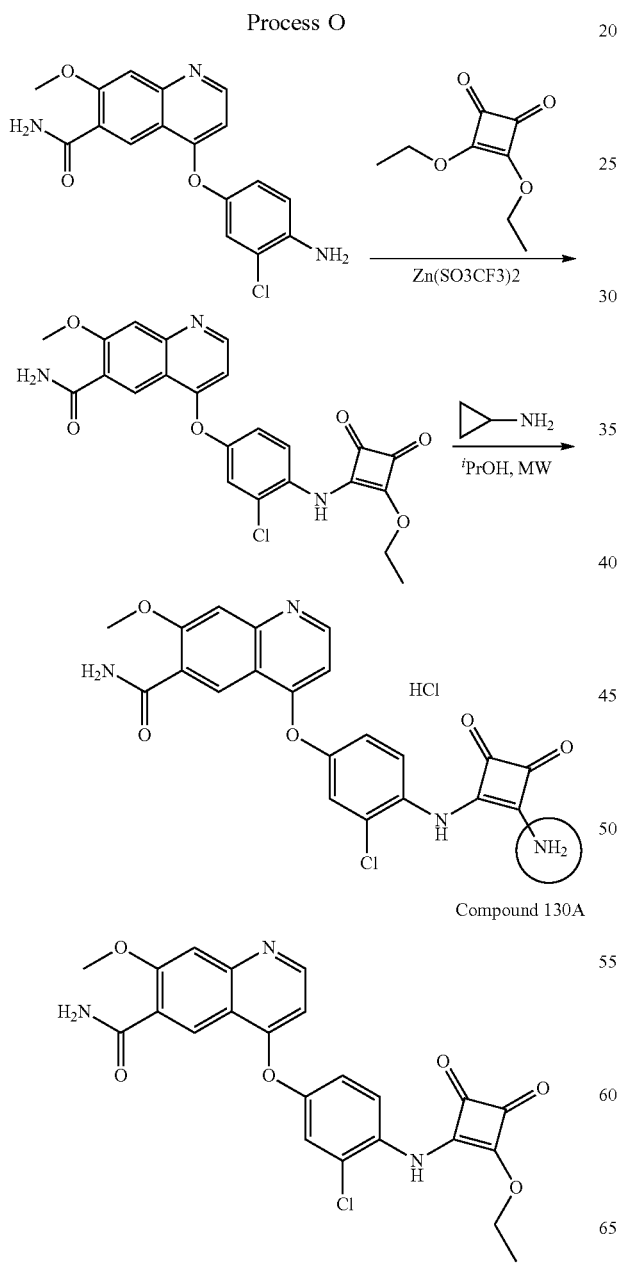

Compound 130A

Zinc trifluoromethanesulfonate (1.59 g, 4.36 mmol) was added to a solution of compound 1G (1.5 g, 4.36 mmol) and 3,4-diethoxycyclobutan-3-ene-1,2-dione (2.3 g, 13.06 mmol) in ethanol (20 mL). The mixture was stirred at 23° C. for 3 days and then a yellow solid was precipitated, then filtered and the filter cake was washed with ethanol (20 ml) to give compound 130A (yellow solid, 1.02 g, the yield was 50%).

$^1$H NMR (400 MHz, METHANOL-d$_4$) ppm 1.20 (t, J=7.15 Hz, 3H) 1.51 (t, J=7.03 Hz, 2H) 3.63 (q, J=7.03 Hz, 2H) 4.18-4.28 (m, 3H) 7.10 (d, J=6.78 Hz, 1H) 7.45 (dd, J=8.66, 2.64 Hz, 1H) 7.57-7.61 (m, 1H) 7.66-7.73 (m, 2H) 8.92-8.97 (m, 1H) 9.06 (s, 1H)

Example 130

Cyclopropylamine (5 mg, 0.085 mmol) was added to a solution of compound 130A (40 mg, 0.085 mmol) in isopropanol (5 ml) at 21° C., and then the reaction solution was irradiated in the microwave at 130° C. for 4 minutes and purified by preparative HPLC (0.5% HCl) to give a compound of Example 130 (yellow solid, 5.6 mg, the yield was 8%). LCMS (ESI) m/z: 479.0 (M+1)$^+$ $^1$H NMR (Methanol-d$_4$, Bruker Avance 400 MHz): δ 9.05 (s, 1H), 8.93 (d, J=6.8 Hz, 1H), 8.07-8.01 (m, 1H), 7.67-7.59 (m, 2H), 7.42 (dd, J=8.9, 2.6 Hz, 1H), 7.12 (d, J=6.8 Hz, 1H), 4.23 (s, 3H), 3.27-3.19 (m, 1H), 0.99-0.91 (m, 2H), 0.86-0.73 (m, 2H).

The following compounds were also prepared by using the similar methods as described in Example 130 mentioned above.

| Nos. | Structures | NMR | LCMS (ESI) m/z: [M + 1] |
|---|---|---|---|
| Example 136 | 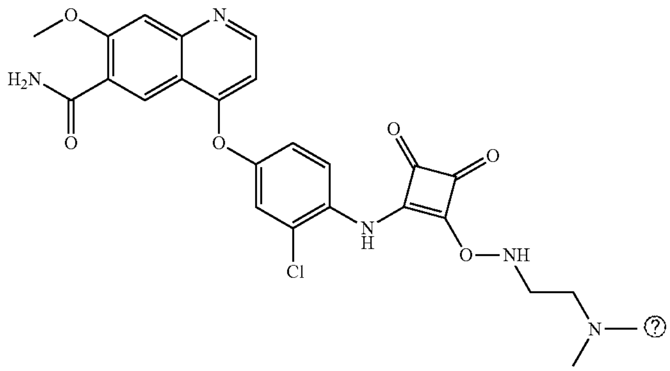 | $^1$H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.23 (s, 3H), 4.18 (d, J = 10.29 Hz, 2H), 3.53 (br. s., 2H), 3.00-3.08 (m, 6H) | 510.1 |
| Example 137 | 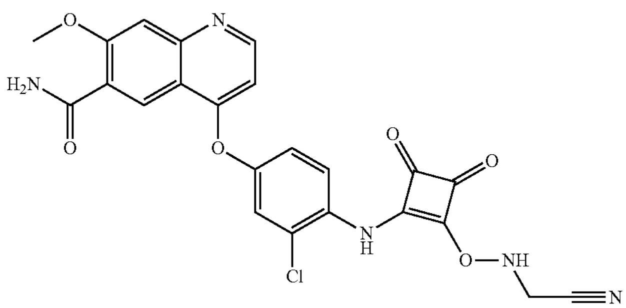 [SMILES: COc1cc2nccc(Oc3ccc(Nc4c(ONCC#N)c(=O)c4=O)c(Cl)c3)c2cc1C(N)=O] | $^1$H NMR (400 MHz, METHANOL-d4) 9.06 (s, 1H), 8.93 (d, J = 6.78 Hz, 1H), 7.99 (d, J = 8.78 Hz, 1H), 7.65 (d, J = 2.51 Hz, 1H), 7.60 (s, 1H), 7.43 (dd, J = 2.64, 8.91 Hz, 1H), 7.13 (d, J = 6.78 Hz, 1H), 4.23 (s, 3H), 4.04 (s, 2H), 3.99-4.02 (m, 1H), 2.91 (t, J = 6.27 Hz, 2H) | 492.1 |
| Example 138 | 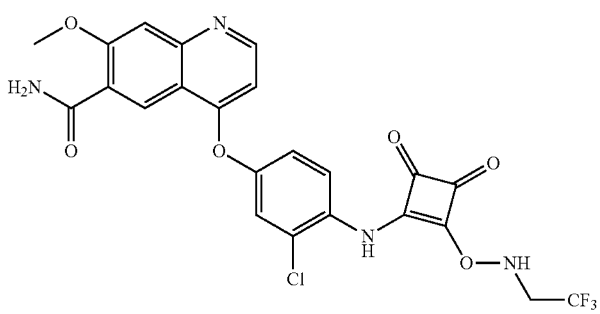 [SMILES: COc1cc2nccc(Oc3ccc(Nc4c(ONCC(F)(F)F)c(=O)c4=O)c(Cl)c3)c2cc1C(N)=O] | $^1$H NMR (400 MHz, METHANOL-d4) 9.06 (s, 1H), 8.94 (d, J = 6.78 Hz, 1H), 8.01 (d, J = 8.78 Hz, 1H), 7.66 (d, J = 2.76 Hz, 1H), 7.61 (s, 1H), 7.43 (dd, J = 2.64, 8.91 Hz, 1H), 7.13 (d, J = 6.78 Hz, 1H), 4.49 (q, J = 9.03 Hz, 2H), 4.23 (s, 3H) | 521.0 |
| Example 139 | 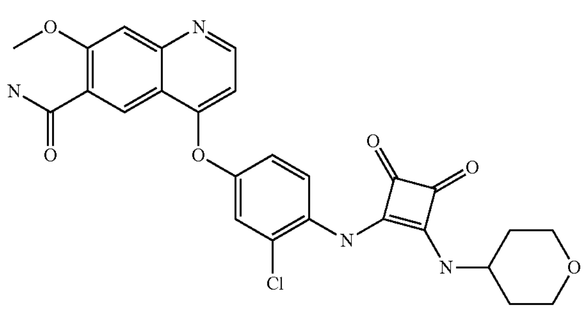 [SMILES: COc1cc2nccc(Oc3ccc(Nc4c(NC5CCOCC5)c(=O)c4=O)c(Cl)c3)c2cc1C(N)=O] | $^1$H NMR (400 MHz, METHANOL-d4) 9.05 (s, 1H), 8.92 (d, J = 6.78 Hz, 1H), 8.05 (d, J = 9.03 Hz, 1H), 7.64 (d, J = 2.51 Hz, 1H), 7.60 (s, 1H), 7.41 (dd, J = 2.64, 8.91 Hz, 1H), 7.10 (d, J = 6.53 Hz, 1H), 4.26-4.34 (m, 1H), 4.23 (s, 3H), 4.03 (d, J = 12.05 Hz, 2H), 3.58 (t, J = 10.79 Hz, 2H), 2.08 (d, J = 12.30 Hz, 2H), 1.70 (dd, J = 3.14, 11.67 Hz, 2H) | 523.0 |

-continued

| Nos. | Structures | NMR | LCMS (ESI) m/z: [M + 1] |
|---|---|---|---|
| Example 140 | 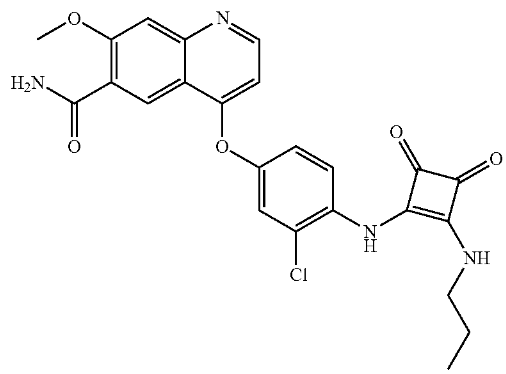 [SMILES: CCCNc1c(Nc2ccc(Oc3ccnc4cc(OC)c(C(N)=O)cc34)cc2Cl)c(=O)c1=O] | ¹H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.23 (s, 3H), 3.74(t, J = 6.8 Hz, 2H), 1.74 (m, 2H), 1.06 (t, J = 7.2 Hz, 3H) | 481.1 |
| Example 141 | 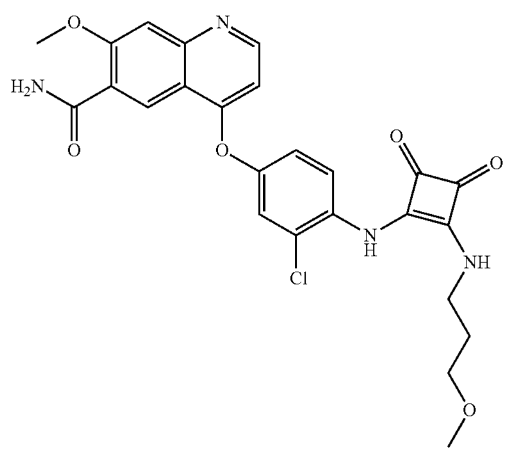 [SMILES: COCCCNc1c(Nc2ccc(Oc3ccnc4cc(OC)c(C(N)=O)cc34)cc2Cl)c(=O)c1=O] | ¹H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.23 (s, 3H), 3.87(t, J = 6.4 Hz, 2H), 3.56 (m, 2H), 3.38 (s, 3H), 1.96 (m, 2H) | 511.2 |
| Example 142 | 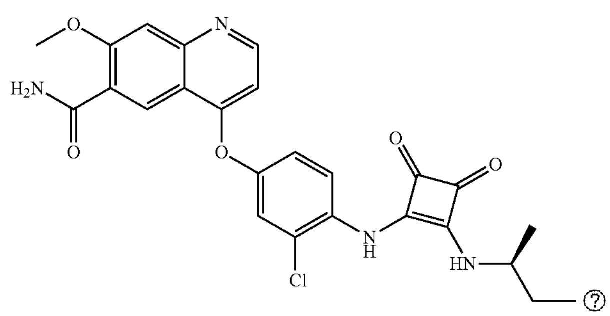 [SMILES: CC[C@H](C)Nc1c(Nc2ccc(Oc3ccnc4cc(OC)c(C(N)=O)cc34)cc2Cl)c(=O)c1=O] | ¹H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.36 (m, 1H), 4.22 (s, 3H), 3.75(m, 1H), 3.53 (m, 1H), 1.35 (d, J = 6.4 Hz, 3H) | 497.1 |
| Example 143 | 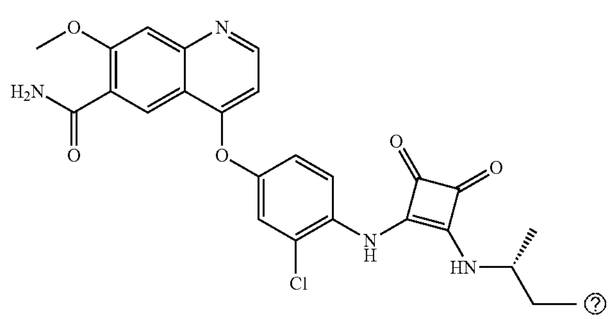 [SMILES: CC[C@@H](C)Nc1c(Nc2ccc(Oc3ccnc4cc(OC)c(C(N)=O)cc34)cc2Cl)c(=O)c1=O] | ¹H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.36 (m, 1H), 4.22 (s, 3H), 3.75(m, 1H), 3.53 (m, 1H), 1.35 (d, J = 6.4 Hz, 3H) | 497.1 |

-continued

| Nos. | Structures | NMR | LCMS (ESI) m/z: [M + 1] |
|---|---|---|---|
| Example 144 | 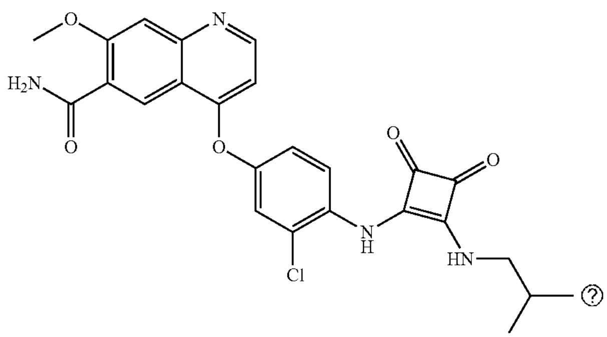 [SMILES: COc1cc2nccc(Oc3ccc(Nc4c(NCC(C)C)c(=O)c4=O)c(Cl)c3)c2cc1C(N)=O] | $^1$H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.23 (s, 3H), 3.62(d, J = 6.4 Hz, 2H), 1.94 (m, 1H), 1.05 (d, J = 6.8 Hz, 6H) | 495.0 |
| Example 145 | 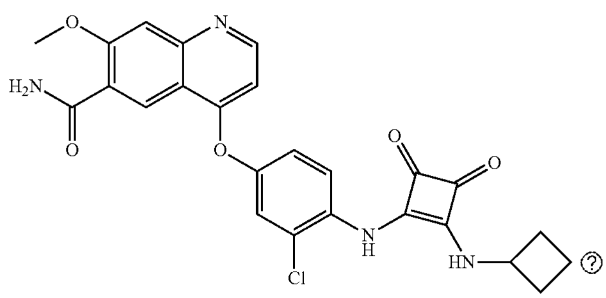 [SMILES: COc1cc2nccc(Oc3ccc(Nc4c(NC5CCC5)c(=O)c4=O)c(Cl)c3)c2cc1C(N)=O] | $^1$H NMR (400 MHz. METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 4.72 (m, 1H), 4.23 (s, 3H), 2.47(m, 2H), 2.12 (m, 2H), 1.73 (m, 2H) | 493.1 |
| Example 146 | 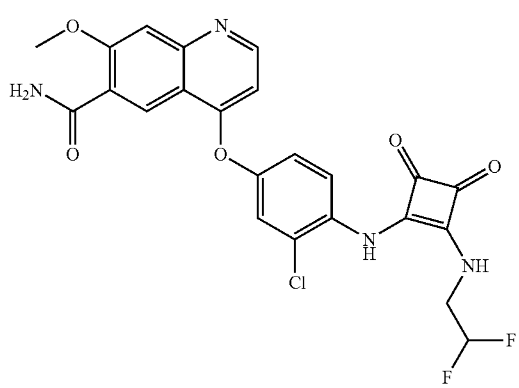 [SMILES: COc1cc2nccc(Oc3ccc(Nc4c(NCC(F)F)c(=O)c4=O)c(Cl)c3)c2cc1C(N)=O] | $^1$H NMR (400 MHz, METHANOL-d4) 9.05 (s, 1H), 8.94 (d, J = 6.53 Hz, 1H), 7.93 (d, J = 8.53 Hz, 1H), 7.64 (d, J = 11.04 Hz, 2H), 7.43 (d, J = 7.53 Hz, 1H), 7.16 (d, J = 6.53 Hz, 1H), 6.12 (m, 1H), 4.23 (s, 3H), 4.16(m, 2H) | 510.1 |
| Example 147 | 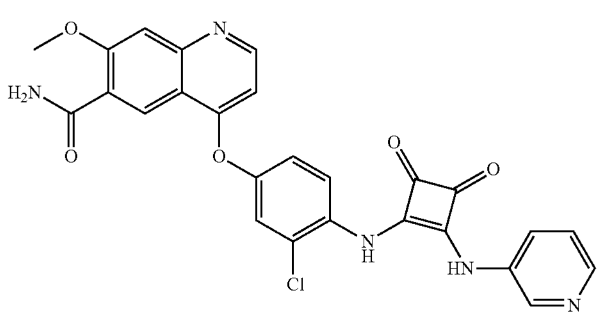 [SMILES: COc1cc2nccc(Oc3ccc(Nc4c(Nc5cccnc5)c(=O)c4=O)c(Cl)c3)c2cc1C(N)=O] | $^1$H NMR (Methanol-d$_4$, Bruker Avance 400 MHz): 9.29 (d, J = 2.51 Hz, 1H), 9.05 (s, 1H), 8.94 (d, J = 6.78 Hz, 1H), 8.59 (dd, J = 2.13, 8.16 Hz, 1H), 8.54 (d, J = 5.52 Hz, 1H), 8.05 (dd, J = 5.77, 8.78 Hz, 1H), 7.97 (d, J = 9.03 Hz, 1H), 7.70 (d, J = 2.76 Hz, 1H), 7.61 (s, 1H), 7.46 (dd, J = 2.76, 9.03 Hz, 1H), 7.12 (d, J = 6.78 Hz, 1H), 4.22 (s, 3H) | 516.7 |

-continued

| Nos. | Structures | NMR | LCMS (ESI) m/z: [M + 1] |
|---|---|---|---|
| Example 148 | 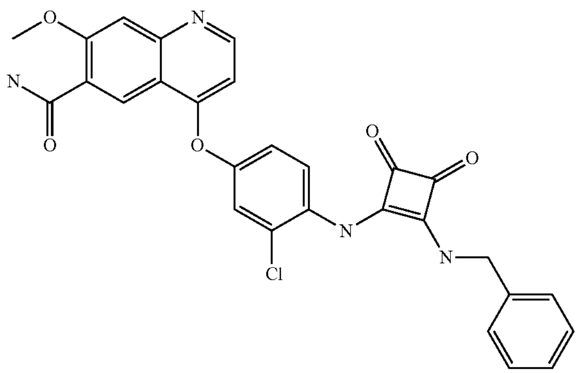 [SMILES: COc1cc2nccc(Oc3ccc(Nc4c(NCc5ccccc5)c(=O)c4=O)c(Cl)c3)c2cc1C(N)=O] | $^1$H NMR (400 MHz, METHANOL-d$_4$) 9.02 (s, 1H), 8.91 (d, J = 6.78 Hz, 1H), 8.00 (d, J = 9.03 Hz, 1H), 7.36-7.63 (m, 2H), 7.35-7.47 (m, 6H), 7.09 (d, J = 6.78 Hz, 1H), 4.93 (br. s., 2H), 4.21 (s, 3H) | 528.9 |
| Example 149 | 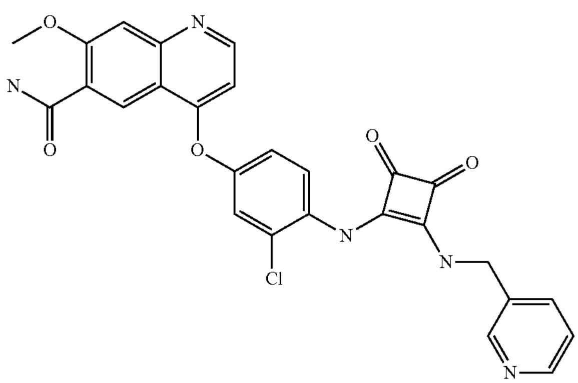 [SMILES: COc1cc2nccc(Oc3ccc(Nc4c(NCc5cccnc5)c(=O)c4=O)c(Cl)c3)c2cc1C(N)=O] | $^1$H NMR (400 MHz, METHANOL-d$_4$) 9.03 (s, 1H), 9.00 (s, 1H), 8.92 (d, J = 7.03 Hz, 1H), 8.85 (d, J = 5.77 Hz, 1H), 8.75 (d, J = 8.28 Hz, 1H), 8.15 (dd, J = 6.02, 8.03 Hz, 1H), 7.93 (d, J = 8.78 Hz, 1H), 7.58-7.66 (m, 2H), 7.38-7.46 (m, 1H), 7.12 (d, J = 7.03 Hz, 1H), 5.17 (s, 2H), 5.07 (s, 1H), 4.22 (s, 3H) | 529.9 |
| Example 150 | 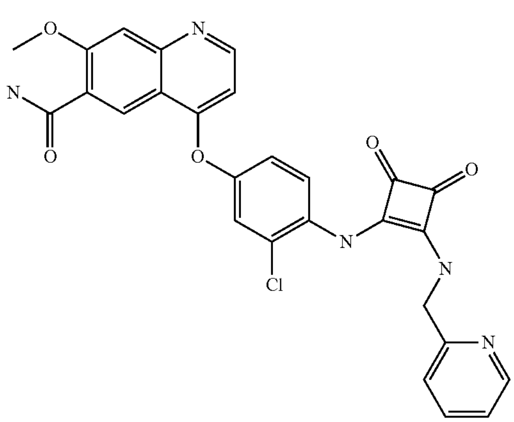 [SMILES: COc1cc2nccc(Oc3ccc(Nc4c(NCc5ccccn5)c(=O)c4=O)c(Cl)c3)c2cc1C(N)=O] | $^1$H NMR (400 MHz, METHANOL-d$_4$) 9.03 (s, 1H), 8.93 (d, J = 6.78 Hz, 1H), 8.85 (d, J = 5.27 Hz, 1H), 8.62 (t, J = 7.78 Hz, 1H), 8.17 (d, J = 8.03 Hz, 1H), 8.01 (t, J = 6.65 Hz, 1H), 7.93 (d, J = 8.78 Hz, 1H), 7.65 (d, J = 2.51 Hz, 1H), 7.61 (s, 1H), 7.43 (dd, J = 2.76, 9.03 Hz, 1H), 7.13 (d, J = 6.78 Hz, 1H), 5.32 (s, 2H), 4.22 (s, 3H) | 529.9 |

| Nos. | Structures | NMR | LCMS (ESI) m/z: [M + 1] |
|---|---|---|---|
| Example 151 | 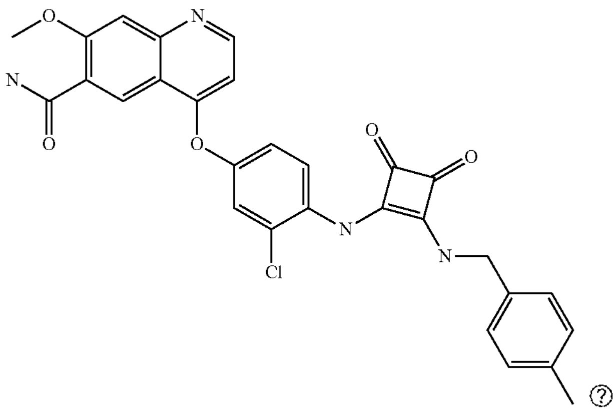 | ¹H NMR (400 MHz, METHANOL-d₄) 9.03 (s, 1H), 8.91 (d, J = 6.78 Hz, 1H), 8.00 (d, J = 8.78 Hz, 1H), 7.36-7.64 (m, 2H), 7.36-7.44 (m, 3H), 7.24-7.34 (m, 1H), 7.10 (d, J = 6.78 Hz, 1H), 4.92 (br. s., 2H), 4.21 (s, 3H) | 563.4 |
| Example 152 | 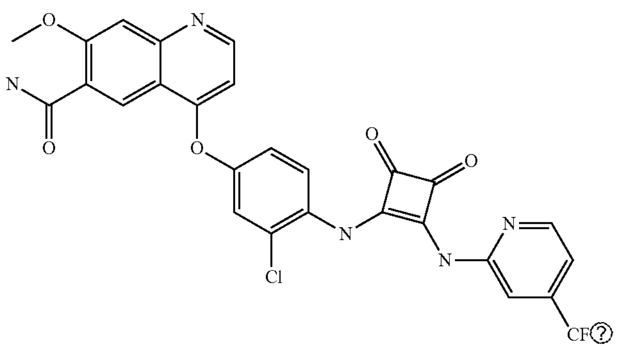 | — | 583.1 |
| Example 153 | 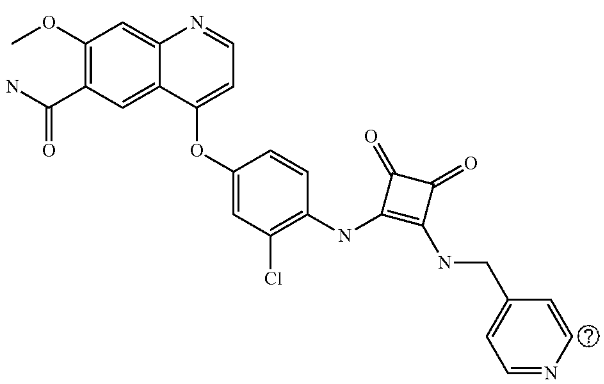 [SMILES: COc1cc2nccc(Oc3ccc(Nc4c(NCc5ccncc5)c(=O)c4=O)c(Cl)c3)c2cc1C(N)=O] | ¹H NMR (400 MHz, METHANOL-d₄) 9.04 (s, 1H), 8.93 (d, J = 6.53 Hz, 1H), 8.88 (d, J = 6.53 Hz, 2H), 8.18 (d, J = 6.27 Hz, 2H), 7.96 (d, J = 9.03 Hz, 1H), 7.66 (d, J = 2.51 Hz, 1H), 7.61 (s, 1H), 7.43 (dd, J = 2.64, 8.91 Hz, 1H), 7.13 (d, J = 6.78 Hz, 1H), 5.27 (s, 2H), 4.22 (s, 3H) | 529.9 |
| Example 154 | 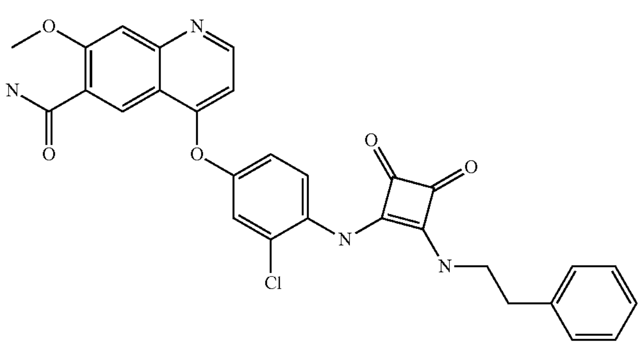 [SMILES: COc1cc2nccc(Oc3ccc(Nc4c(NCCc5ccccc5)c(=O)c4=O)c(Cl)c3)c2cc1C(N)=O] | ¹H NMR (400 MHz, METHANOL-d₄) 9.03 (s, 1H), 8.91 (d, J = 6.78 Hz, 1H), 7.91 (d, J = 8.78 Hz, 1H), 7.55-7.63 (m, 2H), 7.37 (dd, J = 2.76, 9.03 Hz, 1H), 7.26-7.34 (m, 4H), 7.23 (t, J = 6.27 Hz, 1H), 7.10 (d, J = 6.78 Hz, 1H), 4.21 (s, 3H), 4.02 (t, J = 6.65 Hz, 2H), 3.00 (t, J = 6.90 Hz, 2H) | 542.9 |

| Nos. | Structures | NMR | LCMS (ESI) m/z: [M + 1] |
|---|---|---|---|
| Example 155 | 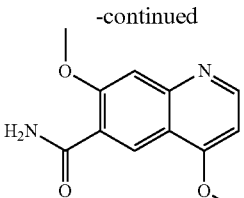 | $^1$H NMR (400 MHz, METHANOL-d$_4$) 9.00-9.05 (m, 1H), 8.90 (d, J = 6.78 Hz, 1H), 7.93-8.01 (m, 2H), 7.76 (d, J = 8.28 Hz, 1H), 7.64 (d, J = 2.51 Hz, 1H), 7.53-7.61 (m, 2H), 7.37-7.47 (m, 2H), 7.05 (d, J = 6.53 Hz, 1H), 4.20 (s, 3H) | 582.9 |
| Example 160 | 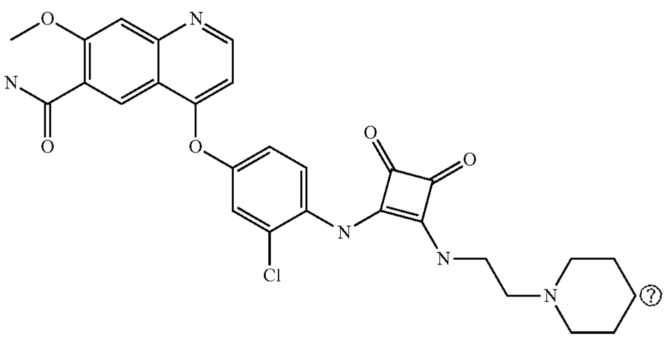 [SMILES: COc1cc2nccc(Oc3ccc(Nc4c(NCCN5CCCCC5)c(=O)c4=O)c(Cl)c3)c2cc1C(N)=O] | $^1$H NMR (400 MHz, METHANOL-d$_4$) 9.03 (s, 1H), 8.93 (d, J = 6.53 Hz, 1H), 7.90 (d, J = 8.53 Hz, 1H), 7.62 (d, J = 8.78 Hz, 2H), 7.41 (d, J = 8.78 Hz, 1H), 7.15 (d, J = 6.78 Hz, 1H), 4.14-4.25 (m, 5H), 4.09 (d, J = 11.29 Hz, 2H), 3.89 (t, J = 12.05 Hz, 2H), 3.66 (d, J = 12.30 Hz, 2H), 3.54 (br. s., 2H) | 551.2 |

Process P

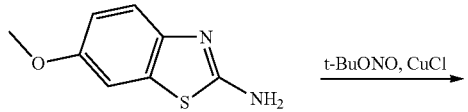

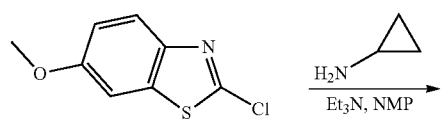

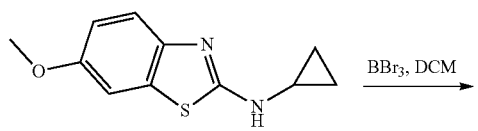

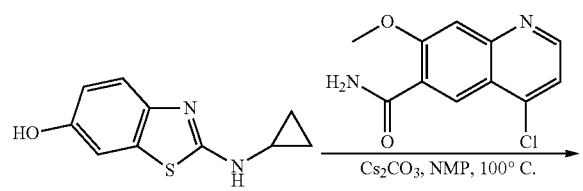

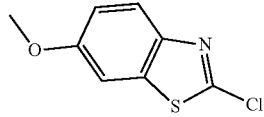

Compound 131A 6-methoxybenzothiazol-2-amine (30 g, 0.17 mol) was slowly added in portions to a mixed solution of t-butyl nitrite (27.8 g, 0.27 mol) and cuprous chloride (19.8 g 0.20 mol) in acetonitrile (300 mL). After completion of the dropwise addition, the reaction solution was continued stirring for 2 hours at 25° C. The reaction solution was poured into hydrochloric acid (6 mol/L, 600 ml) and stirred for 10 minutes, filtered. The filtrate was extracted with ethyl acetate (50 ml×3). The organic phases were combined, washed with saturated NaCl solution, dried over anhydrous sodium sulfate and filtered, and the filtrate was concentrated to give a crude product which was then purified by column chromatography (petroleum ether/ethyl acetate=40:1-10:1) to give a yellow solid compound 131A (13.8 g, the yield was 41.4%).

$^1$H NMR (CDCl$_3$, 400 MHz) 7.82 (d, J=9.00 Hz, 1H), 7.23 (d, J=2.35 Hz, 1H), 7.07 (dd, J=2.35, 9.00 Hz, 1H), 3.87 (s, 4H)

Compound 131B

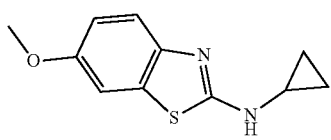

The compound 131A (13.8 g, 0.069 mol), cyclopropylamine (7.9 g, 0.138 mol) and triethylamine (28.8 mL, 0.21 mol) were added to NMP (160 ml). Under the protection of nitrogen, the mixture was heated to 100° C. and stirred for 18 hours. When reaction was complete, the reaction system was cooled to room temperature and added with water (100 ml), the reaction solution was then extracted with ethyl acetate (120 ml×3). The organic phases were combined, washed with saturated NaCl solution, dried over anhydrous sodium sulfate and filtered, and the filtrate was concentrated to give a crude product which was then purified by column chromatography (petroleum ether/ethyl acetate=20:1-2:1) to give a yellow solid compound 131B (10.8 g, the yield was 71%).

$^1$H NMR (CDCl$_3$, 400 MHz) 7.43 (d, J=8.61 Hz, 1H), 7.17 (d, J=2.35 Hz, 1H), 6.83-7.01 (m, 2H), 3.82 (s, 4H), 2.70 (tt, J=3.42, 6.55 Hz, 1H), 0.81-0.89 (m, 2H), 0.68-0.77 (m, 2H)

Compound 131C

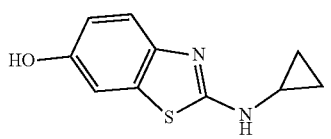

Compound 131B (9 g, 41 mmol) was dissolved in anhydrous dichloromethane (100 ml) and boron tribromide (14 mL, 82 mmol) was added dropwise at 0° C. After completion of the dropwise addition, the reaction solution was stirred at 10-15° C. overnight. After completion of the reaction, the reaction solution was quenched with ice water, adjusted till the pH value was neutral with 15% sodium hydroxide solution, and extracted with ethyl acetate (100 ml×4). The organic phase was combined, washed with saturated NaCl solution, dried over anhydrous sodium sulfate and filtered, and the filtrate was concentrated to give a yellow solid compound 131C (5.3 g, 63%).

$^1$H NMR (DMSO-d$_6$, Bruker Avance 400 MHz): δ 9.13 (s, 1H), 7.98 (s, 1H), 7.21 (d, J=8.5 Hz, 1H), 7.08 (d, J=2.5 Hz, 1H), 6.68 (dd, J=2.5, 8.5 Hz, 1H), 2.68-2.58 (m, 1H), 0.76-0.68 (m, 2H), 0.56-0.49 (m, 2H)

Example 131

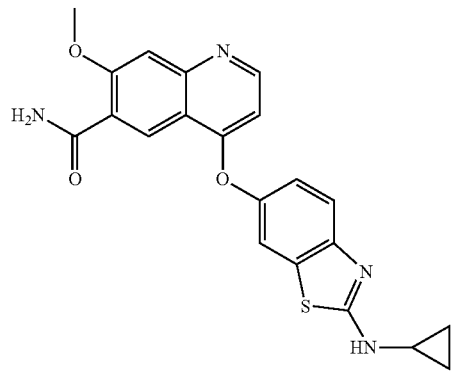 [SMILES: COc1cc2nccc(Oc3ccc4nc(NC5CC5)sc4c3)c2cc1C(N)=O]

Compounds 131C (1.5 g, 7.28 mmol), the compound of Example 1E (2.1 g, 8.74 mmol) and cesium carbonate (4.7 g, 14.56 mmol) were added to 25 ml of NMP. The mixture was heated to 100° C. under the protection of nitrogen and stirred overnight. The reaction system was added with water (15 ml) and extracted with ethyl acetate (30 ml×3). The organic phase was combined, washed with saturated NaCl solution, dried over anhydrous sodium sulfate and filtered, and the filtrate was concentrated to give a crude product which was isolated by column chromatography to give a compound of Example 131 as a white solid (340 mg, 11.5%).

Process Q

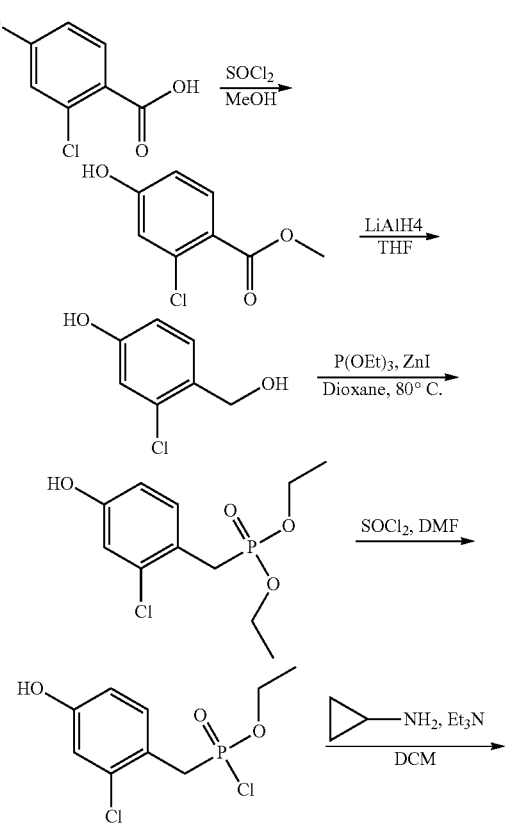

-continued

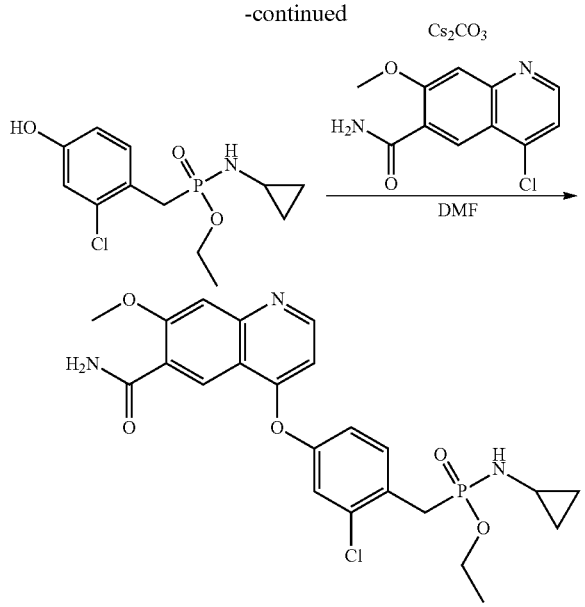

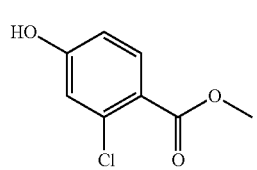

Compound 132A

SOCl$_2$ (1.5 ml) was added to 2-chloro-4-hydroxy-benzoic acid (5 g, 0.03 mmol) in methanol (10 ml). The mixture was slowly warmed from room temperature to reflux temperature and the reaction solution was refluxed for 12 hours and concentrated under reduced pressure to give compound 132A (red solid, 5.4 g, the yield was 100%).

1H NMR (400 MHz, DMSO-d6) δ: 10.71 (s, 1H), 7.84-7.71 (m, 1H), 6.91 (d, J=2.4 Hz, 1H), 6.82 (dd, J=2.4, 8.7 Hz, 1H), 3.79 (s, 3H).

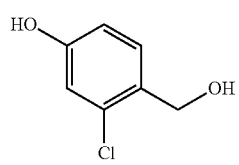

Compound 132B

Compound 132A (500 mg, 2.68 mmol) was slowly added to lithium aluminum tetrahydrate (255 mg, 6.70 mmol) in 10 ml of tetrahydrofuran at 0° C. The reaction solution was stirred at room temperature overnight, quenched by the addition of water (0.26 ml) and 10% sodium hydroxide (0.26 mL), and then added with water (0.78 ml) again. The mixed solution was stirred at room temperature for 30 minutes and filtered, and the filtrate was concentrated under reduced pressure to give compound 132B (400 mg, the yield was 94%).

1H NMR (400 MHz, DMSO-d6) δ: 9.93-9.55 (m, 1H), 7.30 (d, J=8.3 Hz, 1H), 6.85-6.65 (m, 2H), 5.14 (t, J=5.6 Hz, 1H), 4.44 (d, J=5.4 Hz, 2H).

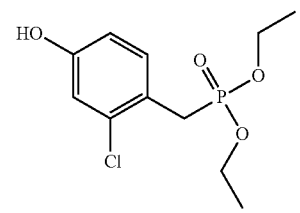

Compound 132C

Compound 132B (100 mg, 0.63 mmol), triethoxyphosphine (300 mg, 1.9 mmol) and zinc iodide (302 mg, 0.95 mmol) were dissolved in dioxane (10 mL). The mixture was stirred at 80° C. for 14 hours and diluted by addition of water and ethyl acetate. The organic phase was washed with saturated NaCl solution, dried over anhydrous sodium sulfate and concentrated under reduced pressure. The residue was purified by preparative thin layer chromatography to give compound 132C (110 mg, 72%).

$^1$H NMR (400 MHz, DMSO-d6) δ: 9.82 (s, 1H), 7.21 (dd, J=2.6, 8.5 Hz, 1H), 6.88-6.78 (m, 1H), 6.72 (dd, J=2.3, 8.3 Hz, 1H), 4.05 (m, 2H), 3.94 (m, 4H), 1.17 (t, J=7.1 Hz, 6H).

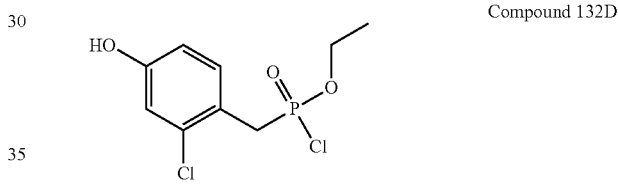

Compound 132D 1 drop of DMF was added dropwise to a solution of compound 132C (100 mg, 0.36 mmol) in thionyl chloride (3 ml). The reaction solution was heated and refluxed for 12 hours, and then concentrated under reduced pressure to give a crude of compound 132D.

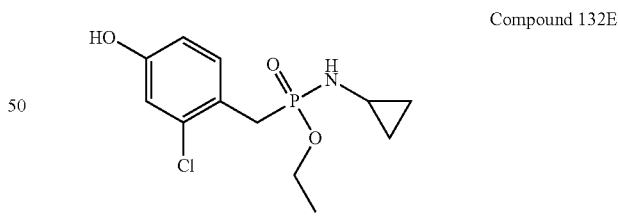

Compound 132E

Compound 132D (100 mg, crude), triethylamine (202 mg, 2 mmol) and cyclopropylamine (100 mg, 1.8 mmol) were dissolved in dichloromethane (3 ml). The mixture was stirred at room temperature for 2 hours and diluted by addition of water and methylene chloride. The organic phase was washed with saturated NaCl solution, dried over anhydrous sodium sulfate, filtered and concentrated under reduced pressure to give a residue. The residue was purified by preparative thin layer chromatography to give compound 132E (50 mg, the yield was 49%). LCMS (ESI) m/z: 290 [M+1]$^+$

Example 132

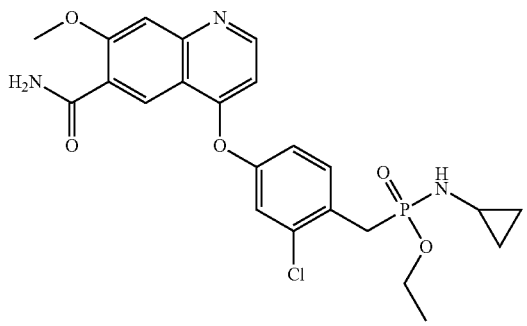 [SMILES: CCOP(=O)(Cc1ccc(Oc2ccnc3cc(OC)c(C(N)=O)cc23)cc1Cl)NC1CC1]

Compound 132E (100 mg, 0.34 mmol), the compound of Example 1E (81 mg, 0.34 mmol) and cesium carbonate (318 mg, 0.98 mmol) were dissolved in DMF (4 mL). The mixture was stirred at 80° C. for 12 hours, dissolved in methanol and purified by preparative HPLC to give a compound of Example 132 (20 mg, the yield was 12%). LCMS (ESI) m/z: 490 [M+1]$^+$ $^1$H NMR (400 MHz, DMSO-d6) δ: 8.71 (d, J=5.3 Hz, 1H), 8.65 (s, 1H), 7.87 (s, 1H), 7.76 (s, 1H), 7.62 (dd, J=2.4, 8.6 Hz, 1H), 7.54 (s, 1H), 7.51 (d, J=2.0 Hz, 1H), 7.30 (dd, J=2.4, 8.5 Hz, 1H), 6.55 (d, J=5.3 Hz, 1H), 5.18 (d, J=11.5 Hz, 1H), 4.04 (s, 3H), 3.95-3.81 (m, 2H), 3.32 (s, 2H), 2.27 (s, 1H), 1.27-1.14 (m, 3H), 0.57-0.45 (m, 2H), 0.43-0.31 (m, 2H).

Example 133

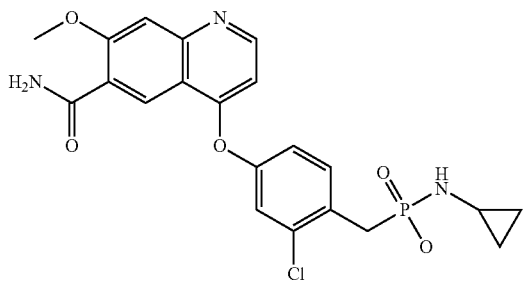 [SMILES: COc1cc2nccc(Oc3ccc(CP(=O)(O)NC4CC4)c(Cl)c3)c2cc1C(N)=O]

Lithium hydroxide (100 mg, 2.38 mmol) was added to a mixed solution of compound of Example 132 (150 mg, 0.31 mmol) in a mixture solution of tetrahydrofuran (5 mL) and water (1 mL) and heated to 50° C. for 12 hours. After completion of the reaction, the reaction solution was diluted with water and ethyl acetate, and isolated by preparative HPLC to give a compound of Example 133 (30 mg, the yield was 21%) after stratification.

LCMS (ESI) m/z: 462 [M+1]$^+$ $^1$H NMR (400 MHz, METHANOL-d4) δ: 9.06-8.89 (m, 1H), 8.65 (d, J=5.4 Hz, 1H), 7.76 (dd, J=2.3, 8.5 Hz, 1H), 7.53 (s, 1H), 7.33 (d, J=2.0 Hz, 1H), 7.15 (dd, J=2.3, 8.5 Hz, 1H), 6.67 (d, J=5.5 Hz, 1H), 4.14 (s, 3H), 3.28 (d, J=19.4 Hz, 2H), 2.45-2.33 (m, 1H), 0.50-0.38 (m, 4H).

Process R

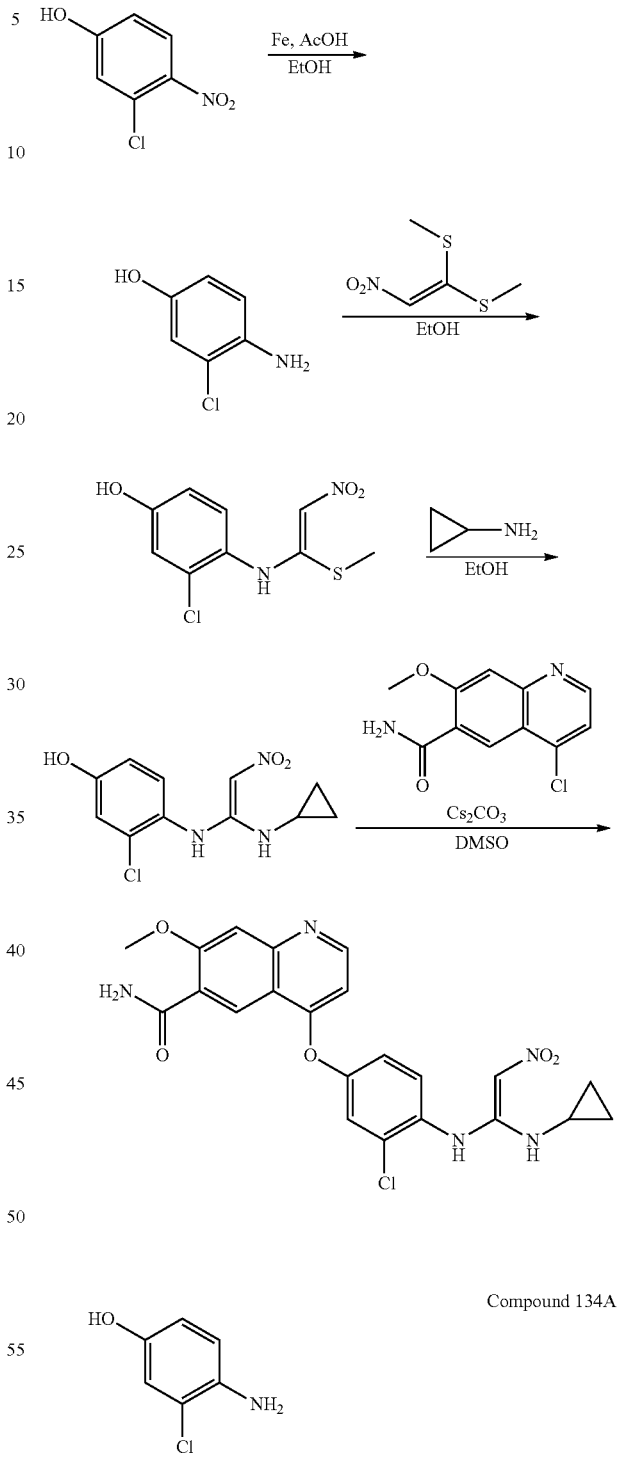

3-chloro-4-nitrophenol (5.0 g, 28.8 mmol) was added to ethanol (50 ml) at 26° C. and then iron powder (9.6 g, 172.9 mmol) and acetic acid (10 mL) were added thereto. The solution was stirred at 80° C. for 16 hours and then cooled to 15° C. The solution was concentrated and purified by column chromatography to give compound 134A (pale red solid, 3.6 g, the yield was 88%).

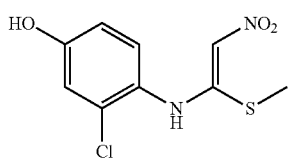

Compound 134B

Compound 134A (15 g, 10.4 mmol) was added to a solution of ethanol (15 mL) at 15° C., and then (2-nitro-1,1)-trans-methylthio (3.4 g, 20.8 mmol) was added thereto, stirred at 80° C. for 16 hours and then cooled to 12° C. The solution was concentrated and purified by column chromatography to give compound 134B (yellow solid, 1.1 mg, the yield was 41%).

$^1$H NMR (DMSO-d$_6$, Bruker Avance 400 MHz): δ 11.25 (s, 1H), 10.26 (s, 1H), 7.28 (d, J=8.5 Hz, 1H), 6.96 (d, J=2.3 Hz, 1H), 6.80 (dd, J=8.7, 2.4 Hz, 1H), 6.74 (s, 1H), 2.43 (s, 3H).

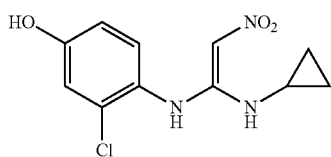

Compound 134C

Compound 134B (1.1 g, 4.22 mmol) was added to a solution of ethanol (15 mL) at 12° C. and then cyclopropylamine (481 mg, 8.44 mmol) was added thereto and stirred at 80° C. for 16 hours, and then cooled to 15° C. The solution was concentrated and purified by column chromatography to give compound 134C (pale yellow solid, 845 mg, the yield was 74%).

$^1$H NMR (DMSO-d$_6$, Bruker Avance 400 MHz): δ 10.57-9.68 (m, 2H), 7.25 (d, J=8.8 Hz, 1H), 6.98 (d, J=2.3 Hz, 1H), 6.82 (dd, J=8.5, 2.3 Hz, 1H), 2.74-2.55 (m, 1H), 1.00-0.61 (m, 4H).

Compound 134

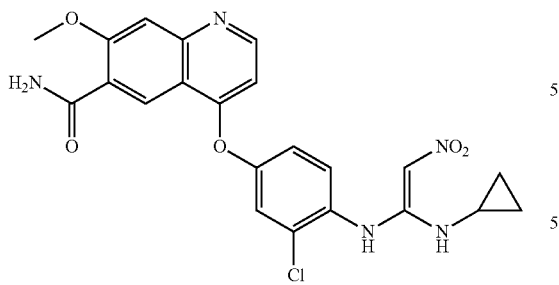

Compound 134C (845 mg, 3.13 mmol) was added to a solution of dimethylsulfoxide (5 ml) at 15° C. and then the compound of Example 1E (247 mg, 1.04 mmol) and cesium carbonate (678 mg, 2.08 mmol) were added thereto, and stirred under the protection of nitrogen for 16 hours at 80° C. The solution was purified by HPLC to give compound 134 (yellow solid, 112 mg, the yield was 21%). LCMS (ESI) m/z: 470 (M+1).

$^1$H NMR (Methanol-d$_4$, Bruker Avance 400 MHz): δ 9.12 (d, J=6.3 Hz, 1H), 8.74 (s, 1H), 8.05-7.87 (m, 4H), 7.74-7.53 (m, 2H), 7.22-7.06 (m, 1H), 2.82-2.60 (m, 1H), 1.07-0.67 (m, 4H).

Process S

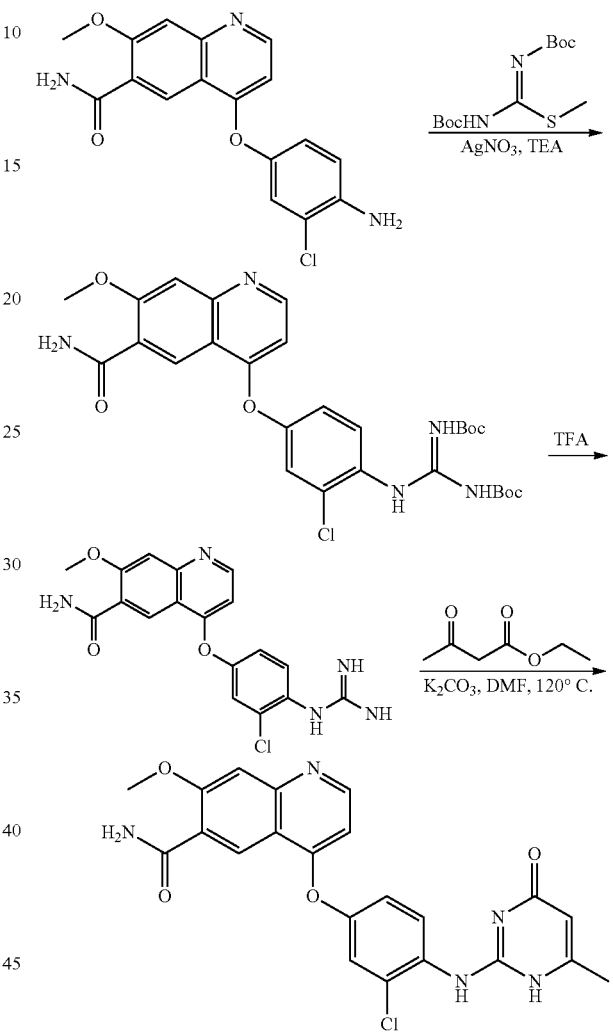

Compound 135A

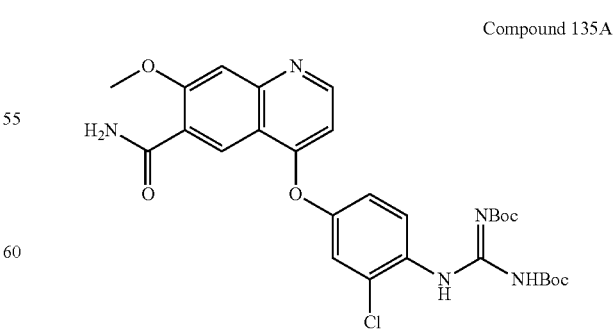

13-di-tert-butoxycarbonyl-2-methylisoleucluth sulfate (580 mg, 2.0 mmol) and silver nitrate (850 mg, 5.0 mmol) were added to a solution of compound of Example 1G (343 mg, 1.00 mmol) and triethylamine (500 mg 5.0 mmol) in N N-dimethylformamide/dichloromethane (10 ml/10 mL), and the mixture was stirred at 12° C. for 12 hours. After filtration, the filtrate was added with acetic acid (50 ml) and water (50 ml), extracted and separated, and the organic layer was washed with water (30 ml×3), dried over sodium sulfate, filtered and evaporated. The residue was purified by column chromatography (dichloromethane/methanol=500:1-20:1) to give compound 135A (white solid, 300 mg, the yield was 51%).

H NMR (DMSO-$d_6$): (s, 1H), (s, 1H), (d, J=5.2 Hz, 1H), (s, 1H), (d, J=9.2 Hz, 1H), (s, 1H), (s, 1H), (s, 1H), (s, 1H), (m, 1H), (d, J=5.2 Hz, 3H), (s, 3H), (s, 9H), (s, 9H).

Compound 135B

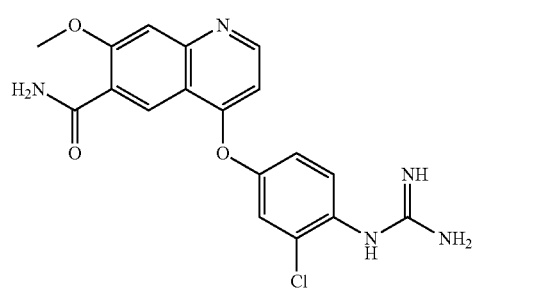

Triethylamine (2 ml) was added to compound 135A (300 mg, 0.5 mmol) in dichloromethane (2 ml) at 0° C., and the mixture was allowed to react at 14° C. for 2 hours. The solvent was evaporated under reduced pressure to give compound 135B (320 mg, black oily matter) which was used directly in the next step without further purification. LCMS (ESI) m/z: 386.10 (M+1)

Example 135

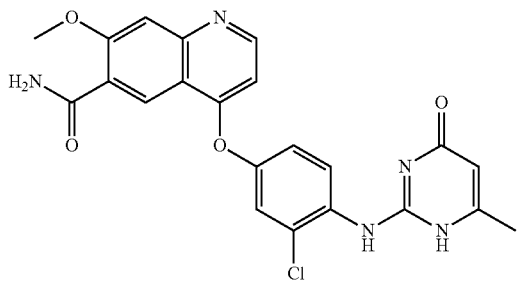

Compound 5 (130 mg, 1 mmol) was added to a mixture of compound 135B (200 mg) and potassium carbonate (280 mg, 2 mmol) in DMF (5 mL). The mixture was stirred at 140° C. for 2 hours, filtered, and the filtrate was added with ethyl acetate (20 ml) and water (20 ml), extracted and separated. The organic layer was washed with water (20 ml×3), dried over sodium sulfate, filtered and evaporated. The residue was purified by preparative HPLC (5% c HCl as additive) to give a compound of Example 135 (white solid, 1.2 mg). LCMS (ESI) m/z: 452.0 (M+1)

LCMS (ESI) m/z: 452.0 (M+1)

H NMR (DMSO-$d_6$): (s, 1H), (d, J=6.8 Hz, 1H), (d, J=8.8 Hz, 1H), (s, 1H), (s, 1H), (m, 1H), (d, J=6.8 Hz, 1H), (s, 1H), (s, 3H), (s, 3H).

Process T

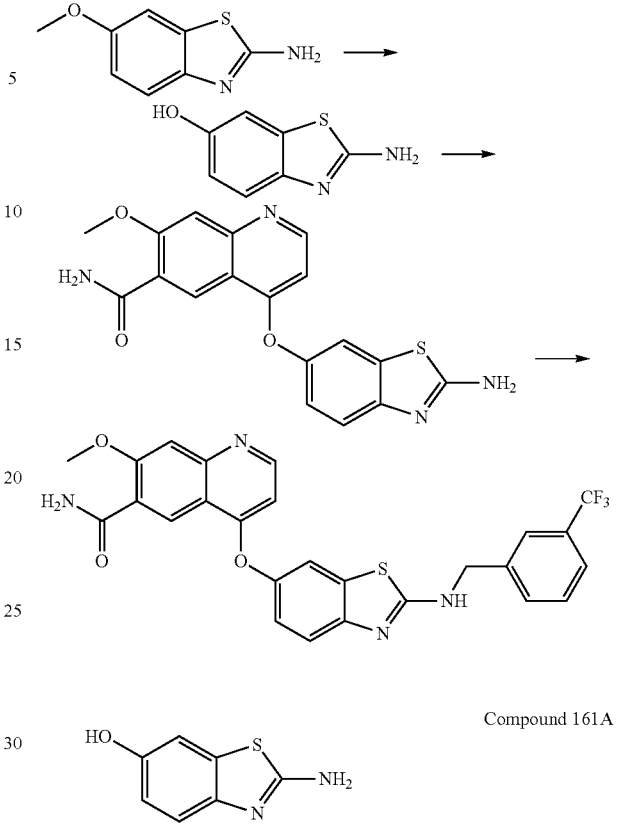

Compound 161A

Hydrobromic acid (208.60 g, 1.3 mol) was added to a 250 ml round bottom flask equipped with a mechanical stirrer over 15 minutes, and then 2-amino-5-methoxybenzothiazole (17 g, 94.32 mmol) was added thereto. The mixture was heated and refluxed for 4 hours, then cooled to 0-5° C. until a solid precipitated, then stirred for half an hour at 0-5° C. and then the suction filtration under reduced pressure was performed. The solid was transferred to a 1 L round bottom flask and slowly added with saturated sodium carbonate solution under mechanical stirring to adjust till the pH was 6.5 to 7, and then stirred at room temperature for 0.5 hour, filtered and the filter cake was washed with 300 ml of water, and then dried under vacuum at 50° C. to give a gray compound 161A as solid (11.7 g, the yield was 74.64%).

$^1$H NMR (400 MHz, DMSO-$d_6$)=9.11 (s, 1H), 7.15 (s, 1H), 7.12 (s, 2H), 7.03 (d, J=2.3 Hz, 1H), 6.65 (dd, J=2.3, 8.5 Hz, 1H)

Compound 161B

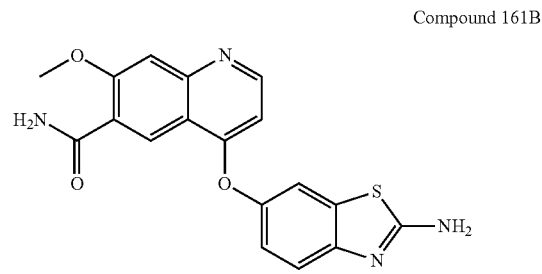 [SMILES: COc1cc2nccc(Oc3ccc4nc(N)sc4c3)c2cc1C(N)=O]

Compound 161A (105.34 mg, 0.634 mmol), the compound of Example 1E (100 mg, 0.422 mmol), cesium carbonate (275.36 mg, 0.845 mmol) and 2.5 ml of DMF were mixed and then placed in a microwave reactor at 100° C. for 30 minutes, cooled to room temperature, 20 ml of water was poured thereinto, and filtered. The filter cake and then washed with water and finally dried to give a yellow solid crude of compound 161B (70 mg) which was used directly in the next step.

$^1$H NMR (400 MHz, DMSO-$d_6$)=8.92 (d, J=6.3 Hz, 1H), 8.78-8.72 (m, 1H), 8.50-8.13 (m, 2H), 7.98 (br. s., 1H), 7.96 (s, 1H), 7.91 (br. s., 1H), 7.82 (d, J=2.3 Hz, 1H), 7.65 (s, 1H), 7.52 (d, J=8.5 Hz, 1H), 7.27 (dd, J=2.1, 8.7 Hz, 1H), 6.84 (d, J=6.3 Hz, 1H), 4.09 (s, 3H)

Example 161

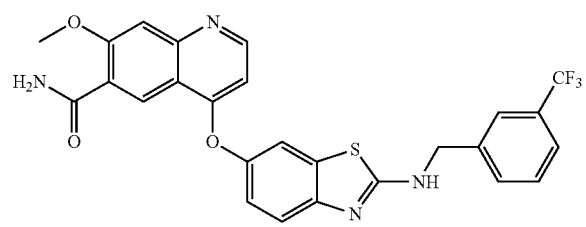 [SMILES: COc1cc2nccc(Oc3ccc4nc(NCc5cccc(C(F)(F)F)c5)sc4c3)c2cc1C(N)=O]

Compound 161B (35 mg, 0.0955 mmol) was dissolved in 2 ml of dry DMF and m-trifluoromethylbenzaldehyde (24.95 mg, 143.29 μmol) was added thereto. The mixture was stirred at room temperature for 10 minutes, sodium triacetylborohydride (60.74 mg, 286.59 μmol) was added thereto and then stirred overnight at room temperature, and then heated to 100-110° C. for three hours. The mixture was added with m-trifluoromethylbenzaldehyde (24.95 mg, 143.29 μmol) and triacetylborohydride (60.74 mg, 286.59 μmol) and then heated to 90-110° C. and stirred overnight. The mixture was finally purified by preparative HPLC to give a yellow compound of Example 161 as a solid (5 mg, the yield was 8.2%).

$^1$H NMR (400 MHz, METHANOL-$d_4$)=9.08 (s, 1H), 8.84 (d, J=6.8 Hz, 1H), 7.78-7.68 (m, 3H), 7.65-7.55 (m, 4H), 7.29 (d, J=8.8 Hz, 1H), 6.97 (d, J=6.8 Hz, 1H), 4.79 (s, 2H), 4.22 (s, 3H). LCMS: 525 [M+1]

The compounds of the following examples are prepared according to the method described in Example 161:

| Examples | Structures | NMR | LCMS (ESI) m/z: (M + 1) |
|---|---|---|---|
| Example 156 | 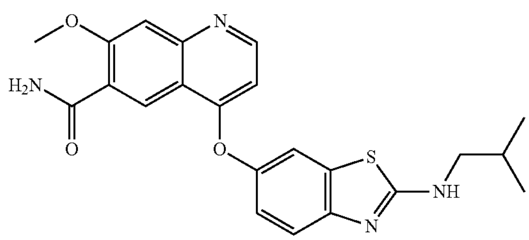 [SMILES: COc1cc2nccc(Oc3ccc4nc(NCC(C)C)sc4c3)c2cc1C(N)=O] | $^1$H NMR (400 MHz, DMSO-$d_6$): 9.26-9.50 (m, 1H), 8.99 (d, J = 6.8 Hz, 1H), 8.76 (s, 1H), 8.02 (br. s., 1H), 7.93 (d, J = 16.0 Hz, 2H), 7.81 (s, 1H), 7.65 (d, J = 8.8 Hz, 1H), 7.37 (d, J = 8.5 Hz, 1H), 6.92 (d, J = 6.5 Hz, 1H), 4.10 (s, 3H), 3.29-3.35 (m, 2H), 1.9$_{0-2}$.05 (m, 1H), 0.98 (d, J = 6.5 Hz, 6H). | 423.1 |
| Example 157 | 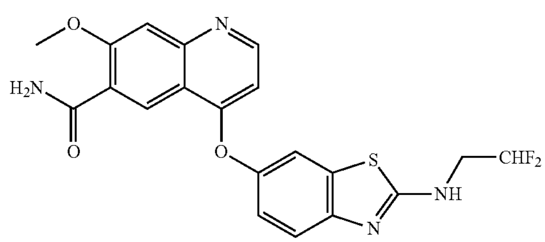 [SMILES: COc1cc2nccc(Oc3ccc4nc(NCC(F)F)sc4c3)c2cc1C(N)=O] | $^1$H NMR (400 MHz, DMSO-$d_6$) □ 11.01-11.14 (m, 1H), 8.92-9.00 (m, 1H), 8.77 (s, 1H), 8.16-8.22 (m, 1H), 7.99-8.04 (m, 1H), 7.98 (d, J = 2.5 Hz, 1H), 7.89-7.96 (m, 1H), 7.82 (d, J = 8.8 Hz, 1H), 7.74 (s, 1H), 7.63-7.71 (m, 1H), 7.44 (s, 1H), 7.35-7.41 (m, 1H), 6.91 (s, 1H), 4.08 (s, 3H). | 430.9 |
| Example 158 | 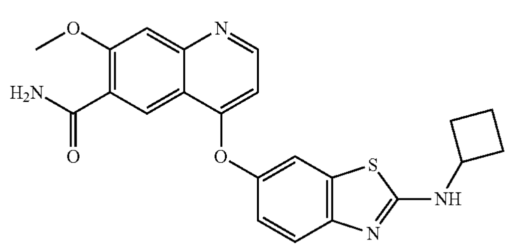 [SMILES: COc1cc2nccc(Oc3ccc4nc(NC5CCC5)sc4c3)c2cc1C(N)=O] | $^1$H NMR (400 MHz, DMSO-$d_6$) □ 9.18-9.52 (m, 1H), 8.98 (d, J = 6.5 Hz, 1H), 8.76 (s, 1H), 8.02 (br. s., 1H), 7.95 (br. s., 1H), 7.89 (s, 1H), 7.81 (s, 1H), 7.63 (d, J = 8.5 Hz, 1H), 7.34 (d, J = 8.8 Hz, 1H), 6.90 (d, J = 6.5 Hz, 1H), 4.45-4.45 (m, 1H), 4.37 (br. s., 1H), 4.09 (s, 3H), 2.39 (d, J = 8.0 Hz, 2H), 2.04 (quin, J = 9.2 Hz, 2H), 1.64-1.82 (m, 2H). | 421.1 |

| Examples | Structures | NMR | LCMS (ESI) m/z: (M + 1) |
|---|---|---|---|
| Example 159 | 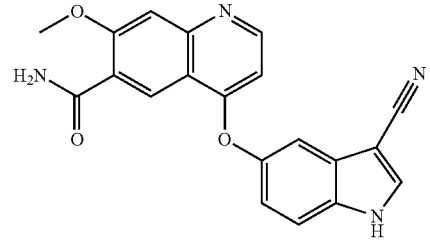 [SMILES: COc1cc2nccc(Oc3ccc4[nH]cc(C#N)c4c3)c2cc1C(N)=O] | $^1$H NMR (400 MHz, DMSO-d$_6$) □ 11.01-11.14 (m, 1H), 8.92-9.00 (m, 1H), 8.77 (s, 1H), 8.16-8.22 (m, 1H), 7.99-8.04 (m, 1H), 7.98 (d, J = 2.5 Hz, 1H), 7.89-7.96 (m, 1H), 7.82 (d, J = 8.8 Hz, 1H), 7.74 (s, 1H), 7.63-7.71 (m, 1H), 7.44 (s, 1H), 7.35-7.41 (m, 1H), 6.91 (s, 1H), 4.08 (s, 3H). | 495.1 |

Process U

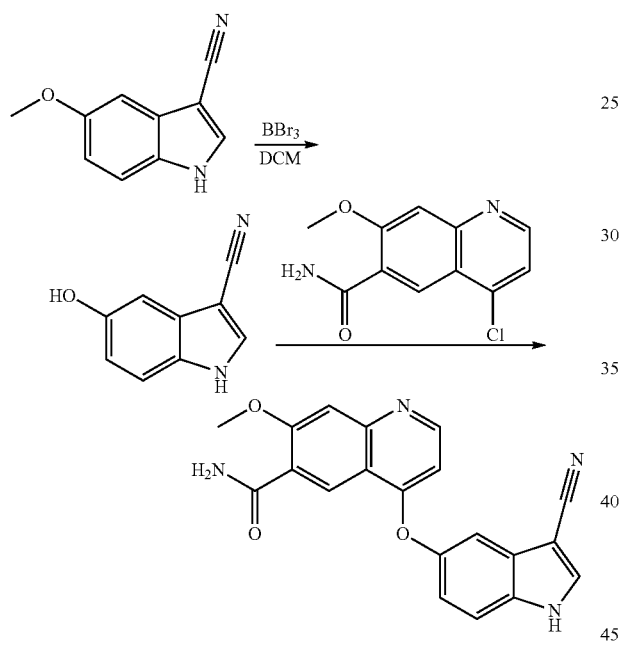

Compound 162A

A solution of boron tribromide in dichloromethane (2 mol/L, 1.92 ml) was added dropwise to a solution of 5-methyl-3-nitrile-1H-indole (220 mg, 1.28 mmol) in dichloromethane (3 ml). The reaction solution was stirred at 0° C. for 2 hours and then quenched by the addition of methanol. The solution was extracted with methyl t-butyl ether (3×30 ml), the organic layer was washed with saturated NaCl solution, then dried over anhydrous sodium sulfate, and spin-dried to remove the solvent after filtration. The residue was separated by column chromatography (petroleum ether/ethyl acetate=3:1, Rf=0.3) to give compound 162A (gray solid, 544 mg, 43%).

$^1$H NMR (400 MHz, METHANOL-d4) 7.84 (s, 1H), 7.34 (d, J=8.78 Hz, 1H), 7.00 (d, J=2.26 Hz, 1H), 6.84 (dd, J=2.26, 8.78 Hz, 1H)

Example 162

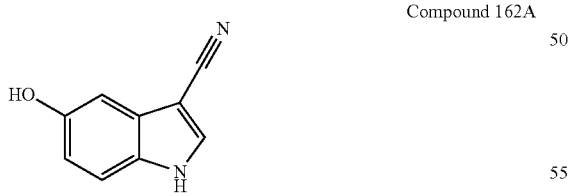

Compound 16A (62 mg, 392 mmol), compound 1E (111 mg, 470 µmol) and cesium carbonate (383 mg, 1.81 mmol) were added to NMP (2 mL). The reaction solution was heated to 110° C. in microwave for 30 minutes, filtered, and then isolated by preparative HPLC to give a compound of Example 162 (yellow solid, 18 mg, 13%).

LCMS (ESI) m/z: 359.0 (M+1)

$^1$H NMR (400 MHz, METHANOL-d4) 9.12 (s, 1H), 8.84 (d, J=6.53 Hz, 1H), 8.18 (s, 1H), 7.78 (d, J=8.78 Hz, 1H), 7.73 (d, J=2.01 Hz, 1H), 7.59 (s, 1H), 7.33 (dd, J=2.26, 8.78 Hz, 1H), 6.93 (d, J=6.78 Hz, 1H), 4.23 (s, 3H)

Example 163

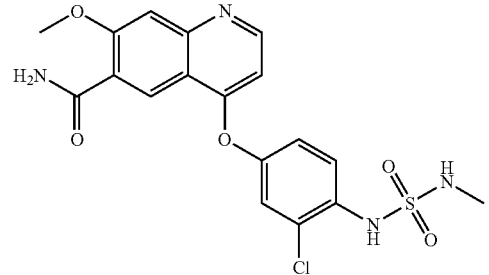

Methylsulfonyl chloride (45 µg, 0.35 µmol) was added dropwise to a solution of compound 1G (30 mg, 87.27 µmol)

and pyridine (490.00 mg, 6.19 mmol) in 2 mL of N-methylpyrrolidone under the protection of nitrogen at minus 10° C., and during this period, the temperature was kept below minus 5° C. After completion of the dropwise addition, the reaction solution was heated to 20° C. and then stirred at this temperature for 18 hours. The mixture was finally purified by preparative HPLC under alkaline conditions to give a compound of Example 163 (5 mg, 13.11%).

LCMS (ESI) m/z: 437.0 (M+1)

$^1$H NMR (400 MHz, METHANOL-$d_4$)=8.97 (s, 1H), 8.68 (d, J=5.5 Hz, 1H), 7.78 (d, J=9.0 Hz, 1H), 7.59-7.52 (m, 1H), 7.46 (d, J=2.8 Hz, 1H), 7.26 (dd, J=2.8, 9.0 Hz, 1H), 6.64 (d, J=5.5 Hz, 1H), 4.15 (s, 3H), 2.71 (s, 3H)

Process V

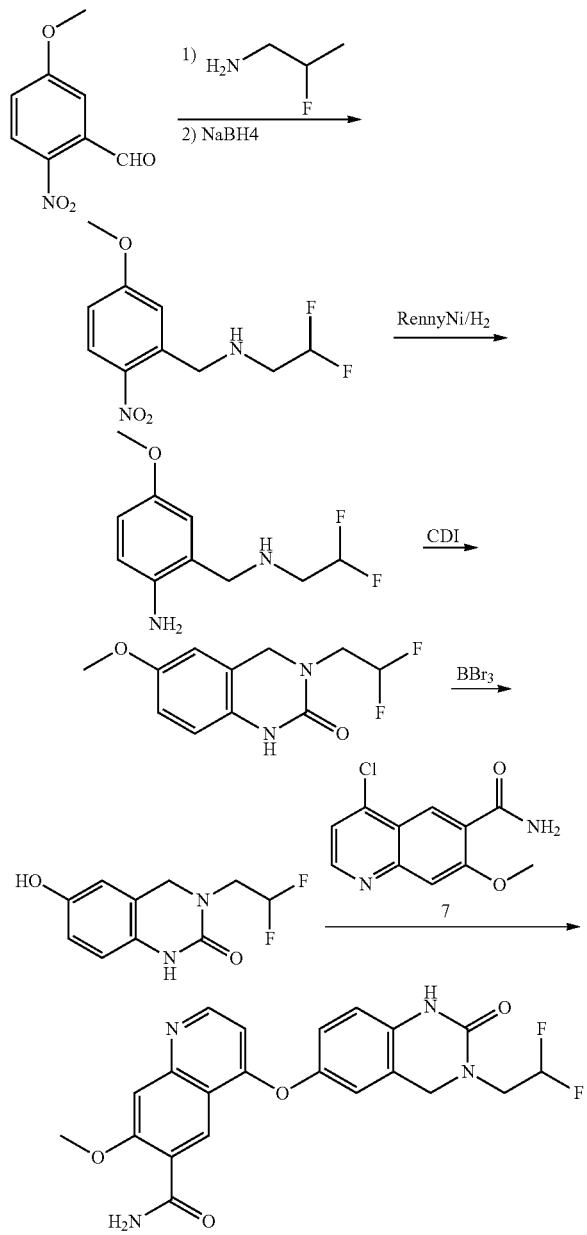

Compound 164A

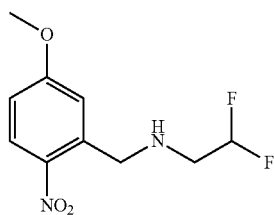

5-methoxy-2-nitro-benzaldehyde (500.00 mg, 2.76 mmol) and 2,2-difluoroethylamine (223.74 mg, 2.76 mmol) were dissolved in dichloromethane (7 mL), the reaction solution was stirred at 20° C. for 2 hours, and then sodium borohydride (114.85 mg, 3.04 mmol) was added and the reaction solution was stirred at 18° C. for 16 hours. The solvent was evaporated under reduced pressure and the resulting residue was isolated by flash silica gel column (the eluent was petroleum ether:ethyl acetate, the content of ethyl ester was 0-15%) to give compound 166A (slightly yellow oil, 150.00 mg, the yield was 22.07%).

$^1$H NMR (400 MHz, CDCl$_3$) 7.50-7.45 (m, 2H), 7.15-7.12 (m, 1H), 5.99-5.71 (m, 1H), 4.04 (s, 2H), 3.87 (s, 3H), 3.02-2.93 (m, 2H)

Compound 164B

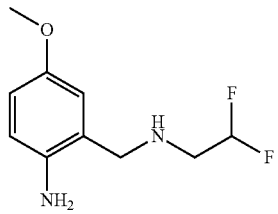

Compound 164A (150.00 mg, 609.24 μmol) was dissolved in methanol (5 mL) and raney nickel (35.76 mg) was added. The reactants were stirred at 20° C. under a 15 psi hydrogen atmosphere for 1 hour, filtered, the filtrate was distilled under reduced pressure to give compound 164B (yellow oil, 120.00 mg, the yield was 91.09%).

$^1$H NMR (400 MHz, CDCl$_3$) 6.92 (dd, J=6.0, 3.2 Hz, 1H), 6.26-6.23 (m, 2H), 6.26-5.68 (m, 1H), 4.57 (s, 2H), 3.82 (s, 2H), 3.76 (s, 3H), 3.0$_{1-2}$.91 (m, 2H).

Compound 164C

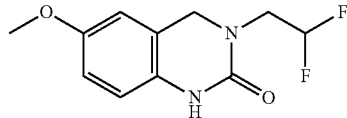

Compound 164B (100.00 mg, 462.47 μmol) and carbonyl diimidazole (112.48 mg, 693.71 μmol) were dissolved in DMF (6 mL). The reaction solution was stirred at 70° C. for 16 hours. Water (10 mL) was added and the solution was extracted with ethyl acetate (10 mL×2). The organic phases were combined, washed with water (10 mL) and saturated NaCl solution (10 mL), dried over anhydrous sodium sulfate, filtered and distilled under reduced pressure to give a crude of compound 164C (yellow oil, 120.00 mg) which was used directly in the next step.

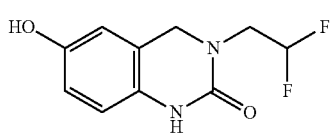
Compound 164D

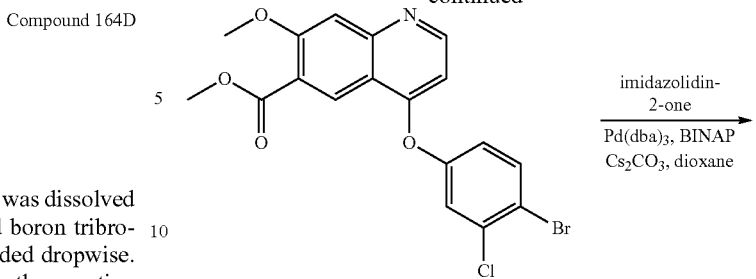
imidazolidin-2-one
Pd(dba)₃, BINAP
Cs₂CO₃, dioxane

Compound 164C (100.00 mg, 412.85 μmop was dissolved in DCM (5 mL), cooled to minus 78° C. and boron tribromide (517.14 mg, 2.06 mmol) was slowly added dropwise. After completion of the dropwise addition, the reaction solution was allowed to react for half an hour at minus 78° C. and then heated to 20° C. and reacted for 5 hours. The reaction solution was added dropwise with water in a dry ice/acetone cooling bath. The organic layer was separated and washed with saturated NaCl solution (10 mL), dried over anhydrous sodium sulfate, filtered and pressurized distilled to give a crude of compound 164D (pale yellow oil, 100.00 mg) which was used directly in the next step.

Example 164

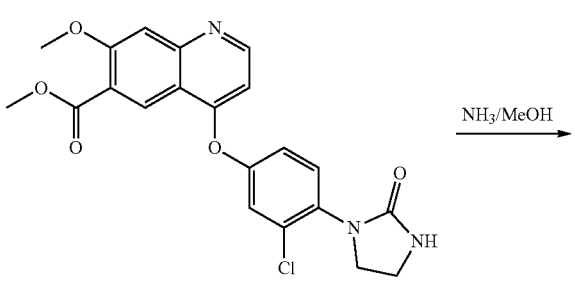
NH₃/MeOH

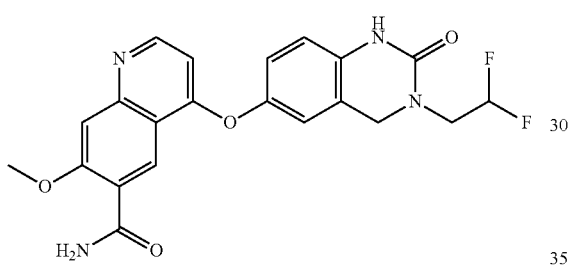

Compound 164D (40.00 mg, 175.28 μmop and the compound of Example 1E (41.48 mg, 175.28 μmop were dissolved in nitrogen-methylpyrrolidone (3 mL) and cesium carbonate (85.66 mg, 262.92 μmop was added. The reactants were reacted in microwave at 100° C. for 1.5 hours and then filtered and directly isolated by preparative chromatography (DIKMA Diamonsil, C18, 200*25*5 μm, trifluoroacetic acid) to give a compound of Example 164 (9.00 mg, the yield was 11.99%).

LCMS (ESI) m/z: 429.0 (M+1)
¹H NMR (400 MHz, CD₃OD) 9.04 (s, 1H), 8.86 (d, J=6.8 Hz, 1H), 7.59 (s, 1H), 7.36 (d, J=6.8 Hz, 1H), 6.98-6.96 (m, 2H), 6.82 (d, J=2.0 Hz, 1H), 6.26-5.98 (m, 1H), 4.72 (s, 2H), 4.21 (s, 3H), 3.86-3.78 (m, 2H).

Process W

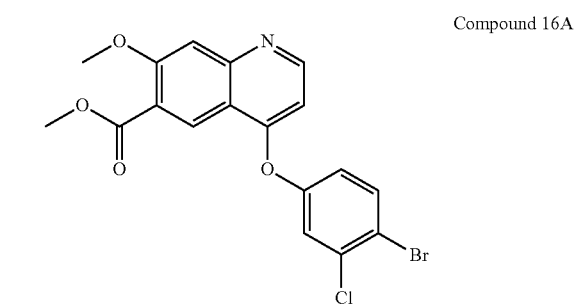 [SMILES: COC(=O)c1cc2c(Oc3ccc(Br)c(Cl)c3)ccnc2cc1OC]
Compound 16A

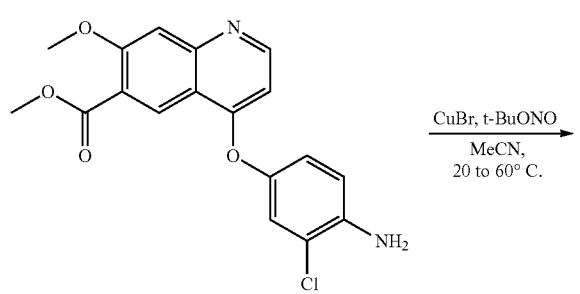
CuBr, t-BuONO
MeCN,
20 to 60° C.

Compound of Example 84D (200.00 mg, 557.44 μmol) was dissolved in acetonitrile (10 mL), cuprous bromide (159.93 mg, 1.11 mmol) and tert-butyl nitrite (114.97 mg, 1.11 mmol) were added. The mixture was stirred at 20° C. for 2 hours and then at 70° C. for 1 hour. The mixture was added with methanol (10 ml) and dichloromethane (20 ml), filtered, the filtrate was concentrated and purified by preparative separation plate (the ratio of petroleum ether/ethyl acetate was 2:1) to give compound 16A (110.00 mg, crude) as a yellow powder.

LCMS (ESI) m/z: 423.7 (M+2)

Compound 16B

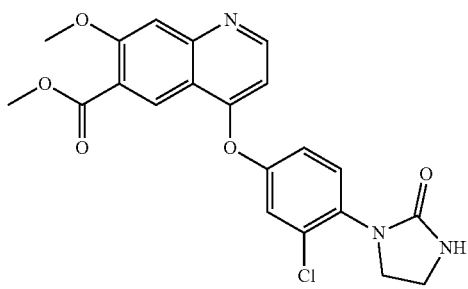

Iimidazolinone (20.37 mg, 236.60 μmol), Pd₂(dba)₃ (21.67 mg, 23.66 μmol), BINAP (44.20 mg, 70.98 μmol) and cesium carbonate (77.09 mg, 236.60 μmol) were added to a solution of compound 16A (50.00 mg, 118.30 μmol) in dioxane (5 ml). The mixture was stirred at 120° C. for 12 hours. The reaction solution was cooled, added with ethyl acetate (20 ml) and water (20 ml), separated, dried and concentrated to give a crude product which was purified by preparative separation plate (the first time: PE/EA=1:1, the second time: DCM/MeOH=10:1) to give compound 16B (40.00 mg) as a yellow powder.

LCMS (ESI) m/z: 428.0 (M+1)

Example 165

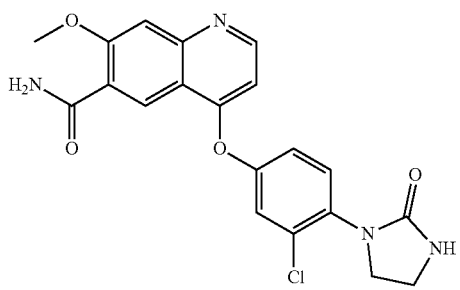 [SMILES: COc1cc2nccc(Oc3ccc(N4CCNC4=O)c(Cl)c3)c2cc1C(N)=O]

Saturated ammonia solution of methanol (5 ml) was added to a mixture of compound 16B (40.00 mg, 93.49 μmol) in 10 ml of methanol. The mixture was stirred at 20° C. for 24 hours and concentrated to give a crude product which was purified by preparative HPLC (HCl system) to give a compound of Example 165 (8 mg, the yield was 19.05%) as a white powder. LCMS (ESI) m/z: 413.2 (M+2)

¹H NMR (400 MHz, DMSO-d₆): 8.96 (d, J=6.02 Hz, 1H), 8.73 (s, 1H), 7.99 (br. s., 1H), 7.92 (br. s., 1H), 7.74 (d, J=2.51 Hz, 1H), 7.71 (s, 1H), 7.65 (d, J=8.53 Hz, 1H), 7.47 (dd, J=2.51, 9.03 Hz, 1H), 6.93 (d, J=6.53 Hz, 2H), 4.09 (s, 3H), 3.8₁₋₃.86 (m, 2H), 3.50 (br. s., 2H).

Example 166

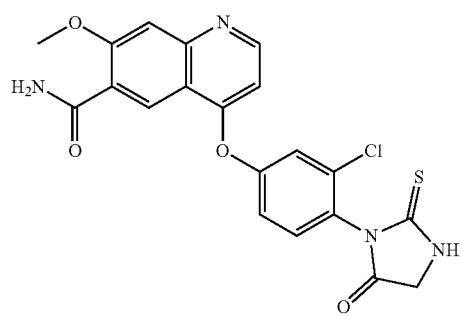 [SMILES: COc1cc2nccc(Oc3ccc(N4C(=O)CNC4=S)c(Cl)c3)c2cc1C(N)=O]

2-aminoacetic acid (23.35 mg, 311.02 μmol) and triethylamine (47.21 mg, 466.53 μmol) were added to the compound of Example 1G (60.00 mg, 155.51 μmol) in DCE (2 ml) and the mixture was reacted at 120° C. for 15 minutes under microwave conditions. The reaction mixture was diluted with 10 ml of methanol and 10 ml of methylene chloride and concentrated to give a crude product which was purified by preparative separation plate (DCM/MeOH=10:1) to give a secondary crude product which was then purified by prep-HPLC (HCl system) to give a pure compound of Example 166 (5.00 mg, the yield was 6.71%) as a white powder.

LCMS (ESI) m/z: 443.1 (M+1)

¹H NMR (400 MHz, DMSO-d₆) 10.56-10.64 (m, 1H), 8.88-8.96 (m, 1H), 8.66-8.73 (m, 1H), 7.90-7.98 (m, 1H), 7.79-7.89 (m, 2H), 7.59-7.67 (m, 2H), 7.48-7.56 (m, 1H), 6.8₁₋₆.88 (m, 1H), 4.34-4.51 (m, 2H), 4.03-4.11 (m, 3H).

Example 167

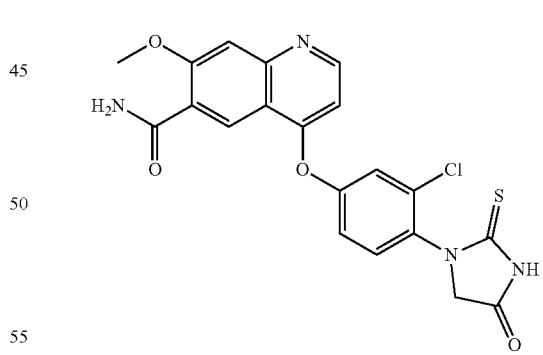

The captioned compound was a white solid prepared by a similar procedure as Example 166, the yield was 6.5%.

LCMS (ESI) m/z: 443.0 (M+1)

¹H NMR (400 MHz, DMSO-d₆) 8.69-8.74 (m, 1H), 8.65-8.69 (m, 1H), 7.85-7.91 (m, 1H), 7.73-7.78 (m, 1H), 7.55-7.59 (m, 1H), 7.5₂₋₇.55 (m, 1H), 7.25-7.33 (m, 1H), 7.14-7.24 (m, 1H), 6.56-6.62 (m, 1H), 3.98-4.09 (m, 5H).

Process X

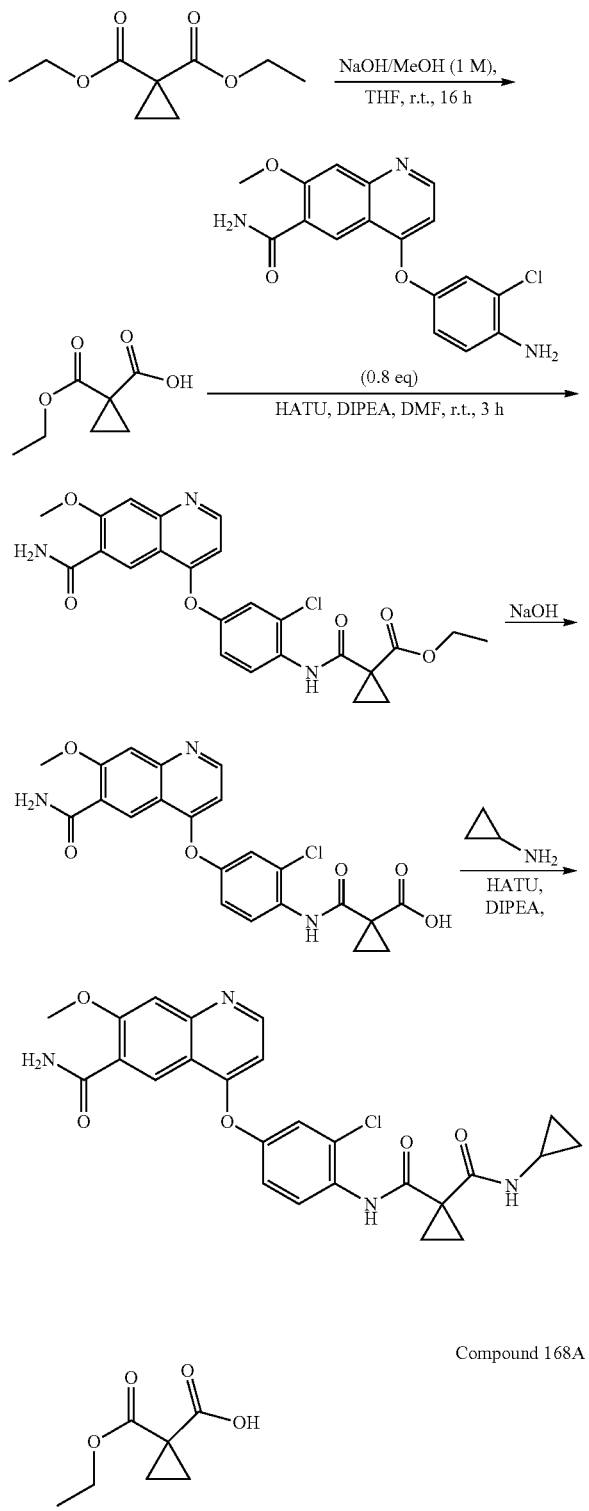

Compound 168A

Ethyl 1,1-cyclopropyl dicarbonate (1.0 g, 5.37 mmol) was added to tetrahydrofuran (3 ml) at 25° C. under the protection of nitrogen, then a mixed solution of sodium hydroxide/methanol (1 mol/L, 5.37 ml) was added thereto, and the mixture was stirred under the protection of nitrogen for 16 hours at 25° C. The solution was concentrated under reduced pressure at 30° C. and then added to water (20 ml). The aqueous phase was washed with ethyl acetate (20 ml*2), the pH was adjusted to 2 with hydrochloric acid (2 mol/L) (20 ml*twice) and extracted with ethyl acetate (20 ml*2). The organic phase was dried over anhydrous sodium sulfate, filtered and concentrated to give compound 168A (creamy white solid, 500 mg, the yield was 64.6%).

$^1$H NMR (400 MHz, CHLOROFORM-d) 3.79 (s, 3H), 1.80-1.88 (m, 2H), 1.72-1.79 (m, 2H)

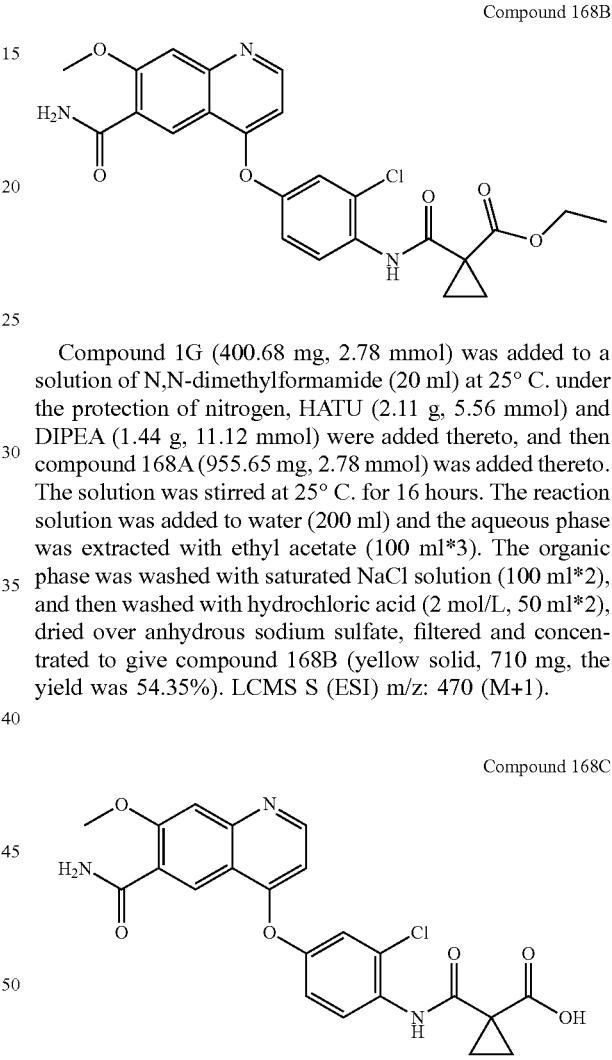

Compound 168B

Compound 1G (400.68 mg, 2.78 mmol) was added to a solution of N,N-dimethylformamide (20 ml) at 25° C. under the protection of nitrogen, HATU (2.11 g, 5.56 mmol) and DIPEA (1.44 g, 11.12 mmol) were added thereto, and then compound 168A (955.65 mg, 2.78 mmol) was added thereto. The solution was stirred at 25° C. for 16 hours. The reaction solution was added to water (200 ml) and the aqueous phase was extracted with ethyl acetate (100 ml*3). The organic phase was washed with saturated NaCl solution (100 ml*2), and then washed with hydrochloric acid (2 mol/L, 50 ml*2), dried over anhydrous sodium sulfate, filtered and concentrated to give compound 168B (yellow solid, 710 mg, the yield was 54.35%). LCMS S (ESI) m/z: 470 (M+1).

Compound 168C

Compound 168B (710 mg, 1.51 mmol) was added to a solution of tetrahydrofuran (5 mL) at 25° C. and then a sodium hydroxide solution (2 mol/L, 3.78 ml) was added and the solution was stirred at 25° C. for 3 hours. The pH of the solution was adjusted to 2. The aqueous phase was filtered and the filter cake was washed with water (20 ml*2), dried and concentrated to give compound 168C (white solid, 650 mg, the yield was 94.43%).

$^1$H NMR (400 MHz, DMSO-$d_6$) 11.70 (s, 1H), 8.96 (d, J=6.02 Hz, 1H), 8.74 (s, 1H), 8.47 (d, J=9.03 Hz, 1H), 7.86-8.06 (m, 2H), 7.77 (br. s., 1H), 7.60 (s, 1H), 7.44 (d, J=8.03 Hz, 1H), 6.95 (d, J=6.02 Hz, 1H), 4.10 (s, 3H), 1.65 (d, J=10.29 Hz, 4H)

Example 168

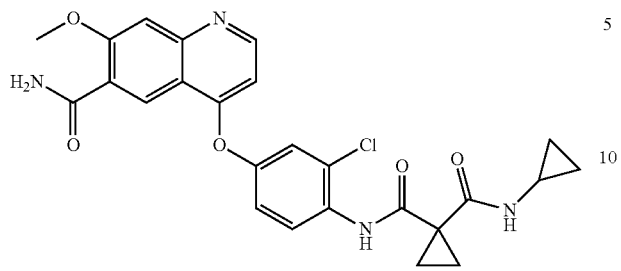

Compound 168C (100 mg, 219.37 μmol) and cyclopropylamine (37.57 mg, 658.11 μmol) were added to a solution of N,N-dimethylformamide (3 ml) at 25° C. under the protection of nitrogen, followed by addition of HATU (166.82 mg, 438.74 μmol), and the mixture was stirred at 25° C. under the protection of nitrogen for 3 hours. The solution was concentrated under reduced pressure at 30° C. and purified by high performance liquid chromatography to give a compound of Example 168 (white solid, 1.2 mg, the yield was 1.03%).

$^1$H NMR (400 MHz, DMSO-$d_6$) 9.05 (s, 1H), 8.91-8.90 (d, J=6.8 Hz, 1H), 8.49-8.46 (d, 1H), 7.65-7.64 (d, J=2.8 Hz, 1H), 7.60 (s, 1H), 7.39-7.36 (dd, J=2.8 Hz, J=9.2, 1H), 7.05-7.03 (s, 1H), 2.73-2.70 (s, 1H), 1.70-1.67 (m, 2H), 1.52-1.49 (m, 2H), 0.79-0.76 (m, 2H), 0.59-0.55 (m, 2H)

Process Y

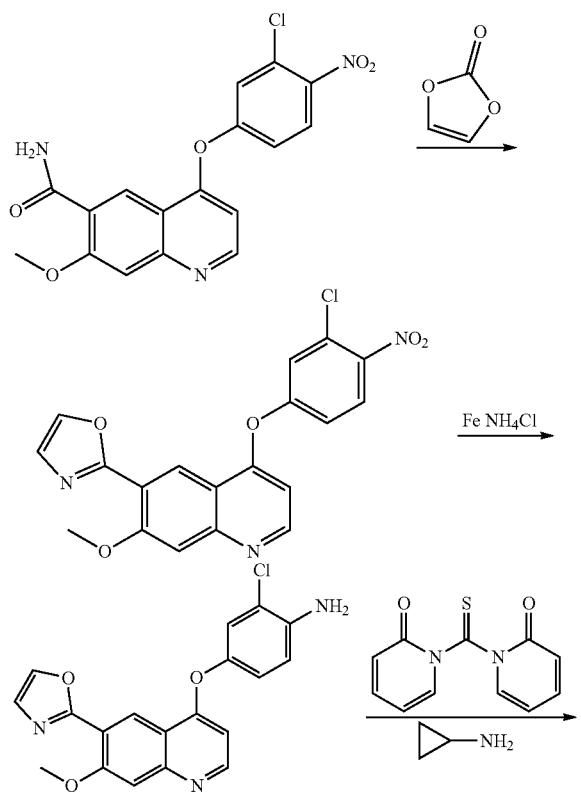

Compound 169A

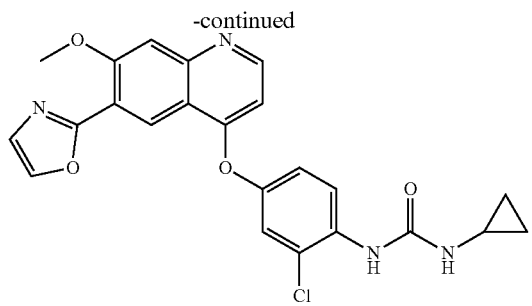

Compound 1F (400 mg, 1.07 mmol) and dimethyl 1,2-vinylene carbonate (150 mg, 1.74 mmol) were stirred in polyphosphoric acid (4.6 g, 1.07 mmol), the mixture was heated to 180-190° C. under the protection of nitrogen and stirred for 30 minutes, then cooled to 60° C., poured into 100 ml of water, basified with saturated sodium bicarbonate and extracted with a mixed solvent of dichloromethane/methanol (6:1) (30 ml*3). The combined organic layers were washed with 10 ml of saturated NaCl solution, dried over anhydrous sodium sulfate, filtered and rotary evaporated. The residue was purified by preparative thin layer chromatography to give a purple compound 169A as solid (20 mg, the yield was 4.7%). LCMS (ESI) m/z: 398.0 (M+1)$^+$ $^1$H NMR (400 MHz, METHANOL-$d_4$)=8.85 (s, 1H), 8.77 (d, J=5.5 Hz, 1H), 8.18 (d, J=9.0 Hz, 1H), 8.12 (s, 1H), 7.69 (d, J=2.5 Hz, 1H), 7.63 (s, 1H), 7.45 (dd, J=2.5, 9.0 Hz, 2H), 7.43 (s, 1H), 6.88 (d, J=5.0 Hz, 2H), 4.14 (s, 3H)

Compound 169B

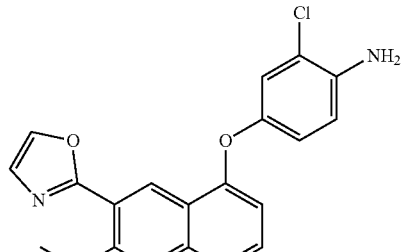

Iron powder (60 mg, 1.07 mmol) and ammonium chloride (26.89 mg, 502.80 μmol) were added to a mixture solution of compound 169A (20 mg, 50.28 μmol) in 8.5 ml of ethanol and 1.5 ml of water, and then heated to 75-80° C. under the protection of nitrogen and stirred for 1 hour, filtered. 100 ml of methylene chloride and 10 ml of water were added to the filtrate, the filtrate was separated to give an organic layer which was dried over anhydrous sodium sulfate and concentrated to give 18.49 mg of crude solid of purple compound 169B which was used directly in the next step.

Example 169

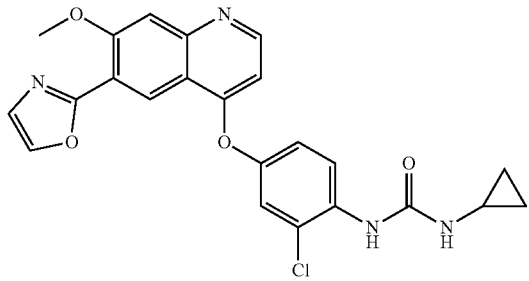 [SMILES: COc1cc2nccc(Oc3ccc(NC(=O)NC4CC4)c(Cl)c3)c2cc1-c1ncco1]

Compound of Example 169 was a yellow solid prepared from compound 169B by a similar procedure as Example 45, the yield was 19.55%.

LCMS (ESI) m/z: 467.0 (M+1)$^+$ $^1$H NMR (400 MHz, METHANOL-d$_4$)=9.15 (s, 1H), 8.95 (d, J=6.8 Hz, 1H), 8.20 (s, 1H), 8.00-7.82 (m, 1H), 7.72-7.64 (m, 2H), 7.50 (s, 1H), 7.43 (d, J=6.8 Hz, 1H), 7.24 (d, J=6.5 Hz, 1H), 4.33-4.17 (m, 4H), 2.88-2.65 (m, 1H), 1.08-0.64 (m, 4H)

Process Z

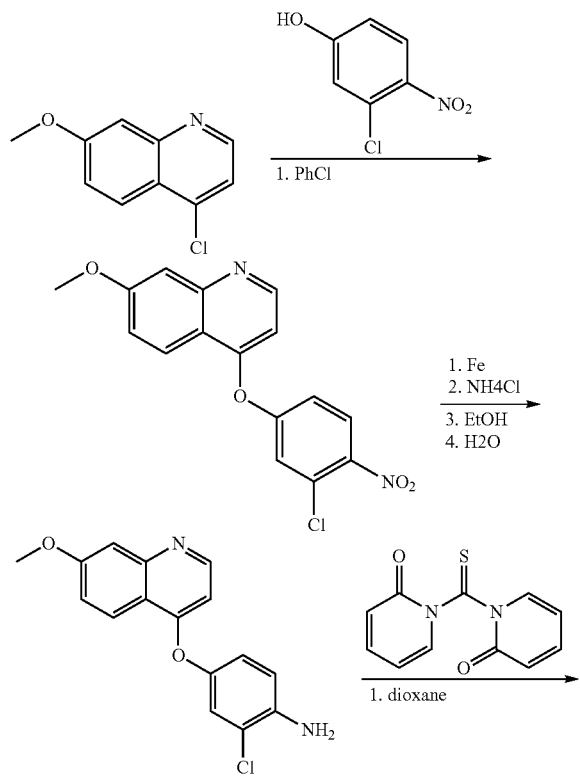

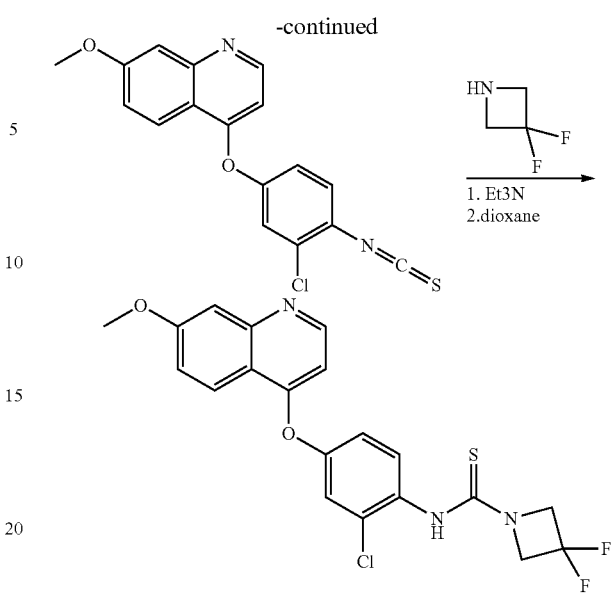

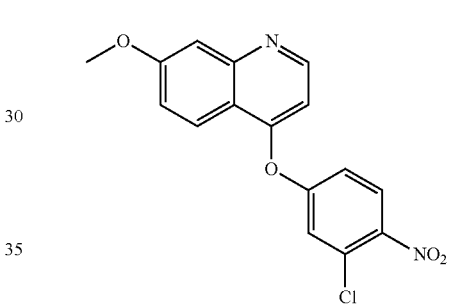

Compound 171A

4-Chloro-7-methoxyquinoline (508 mg, 2.62 mmol) and 3-chloro-4-nitrophenol (682.98 mg, 3.94 mmol) were added to a solution of chlorobenzene (20 ml) at 24° C. under the protection of nitrogen. After stirring at 130° C. under the protection of nitrogen for 18 hours, the mixture was cooled to 25° C. and filtered. The filter cake was washed with toluene (10 ml) and then washed with petroleum ether (10 ml) once. The filter cake was evaporated to dryness at 45° C. to give compound 171A (yellow solid, 570 mg, crude). The product was used directly in the next step without further purification. LCMS (ESI) m/z: 331 (M+1).

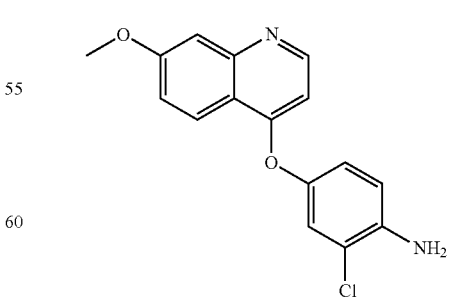

Compound 171B

A mixture of compound 171A (570 mg, 1.72 mmol), ammonium chloride (921.91 mg, 17.24 mmol) and iron powder (962.58 mg, 17.24 mmol) were added to a mixed solution of ethanol and water, the solution was stirred at 100° C. under the protection of nitrogen for 1 hour, cooled to 25° C. and filtered, and the filtrate was evaporated to dryness to give compound 171 B (yellow solid, 300 mg, crude). The product was used directly in the next step without further purification. LCMS (ESI) m/z: 301 (M+1).

Compound 171C

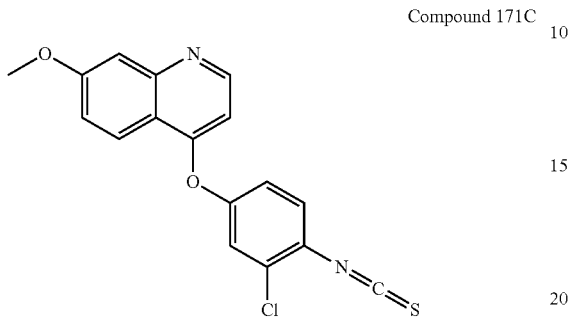

Compound 171B (100 mg, 332.51 μmop was added to dioxane (5 ml), then 1,1'-thiocarbonyldi-2(1H) pyridone (115.84 mg, 498.77 mg) was added thereto and the mixture was stirred at 80-100° C. for 18 hours. The mixture was concentrated till no liquid dropped to give compound 171C (yellow solid, 100 mg, crude). The product was used directly in the next step without further purification. LCMS (ESI) m/z: 343 (M+1)+

Example 171

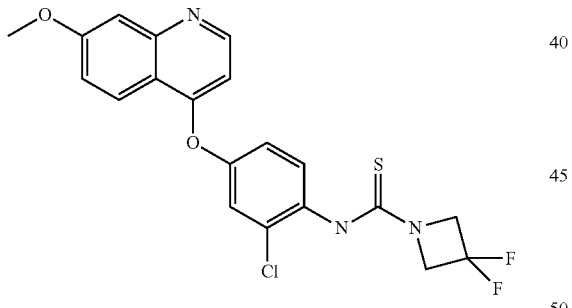

2-Fluorocyclobutylamine (15.07 mg, 161.9 μmol) and triethylamine (22.44 μl) was added to dioxane (5 ml), the mixture was stirred at 25° C. under the protection of nitrogen for 50 minutes, and then compound 171C (37 mg, 107.93 μmol) was added thereto, and the mixture was stirred at 25° C. under the protection of nitrogen for 30 minutes. The mixture was concentrated and the solid was isolated by high performance liquid chromatography (acidic) to give a compound of example 171 (yellow solid, 20 mg, the yield was 41%). LCMS (ESI) m/z: 436.0 (M+1)+

$^1$H NMR (400 MHz, METHANOL-$d_4$)=8.89-8.83 (m, 1H), 8.58 (d, J=9.3 Hz, 1H), 7.74 (d, J=8.8 Hz, 1H), 7.67-7.59 (m, 2H), 7.50 (d, J=2.3 Hz, 1H), 7.40 (dd, J=2.6, 8.7 Hz, 1H), 7.14 (d, J=6.8 Hz, 1H), 4.62 (t, J=11.9 Hz, 4H), 4.12 (s, 3H)

Example 170

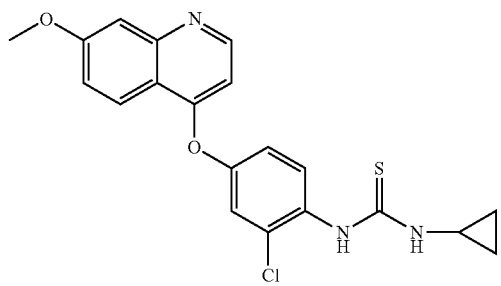 [SMILES: COc1ccc2c(Oc3ccc(NC(=S)NC4CC4)c(Cl)c3)ccnc2c1]

Compound 171C (15.07 mg, 161.9 μmol) and cyclopropylamine (22.44 μl) were added to dioxane (5 ml) and stirred at 26° C. under the protection of nitrogen for 30 minutes. The mixture was concentrated and the solid was isolated by high performance liquid chromatography (acidic) to give a compound of Example 170 (yellow solid, 20 mg, the yield was 33%). LCMS (ESI) m/z: 400 (M+1)+.

Process AA

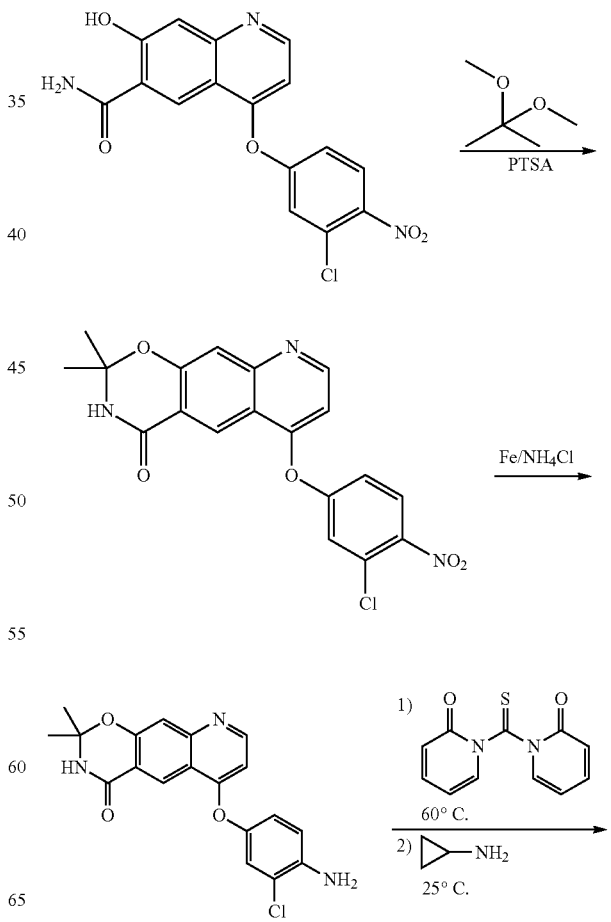

-continued

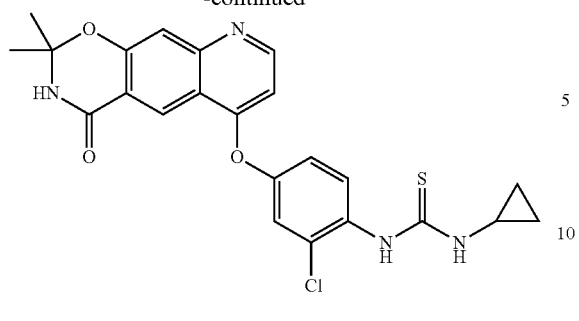

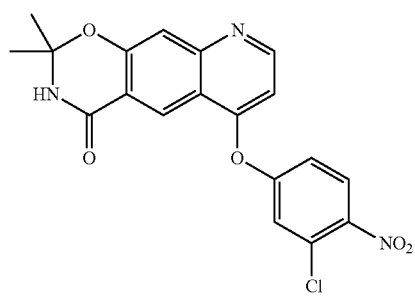

Compound 172A p-Toluenesulfonic acid (47.87 mg, 277.99 μmop was added to a solution of compound 31A (100 mg, 277.99 μmol) and 2,2-dimethoxypropane (5 g, 48.01 mmol) in 20 ml of toluene, and then heated and refluxed for 14 hours. The mixture was cooled and rotary evaporated, 10 ml of saturated sodium bicarbonate was added to the residue, and then the residue was extracted with a 5:1 mixed solution of methylene chloride and methanol (10 ml*3). The organic layers were combined, dried over anhydrous sodium sulfate, filtered and concentrated to give a solid crude of yellow compound 172A (110.1 mg) which was used directly in the next step. LCMS (ESI) m/z: 400 (M+1)$^+$.

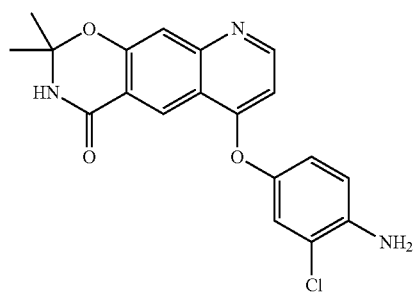

Compound 172B

A crude of compound 172B was yellow solid prepared from the compound of Example 172A by a similar procedure as compound 171B, which was used directly in the next step. LCMS (ESI) m/z: 370.0 (M+1)$^+$.

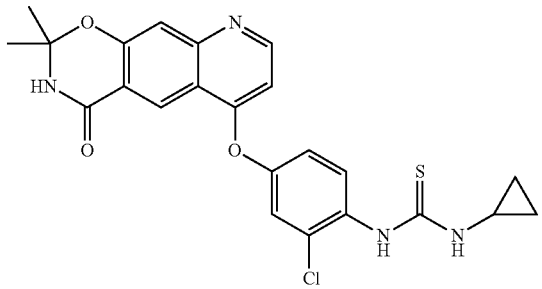

Compound 172C

Compound 172C was yellow solid prepared from the compound of Example 172B by a similar procedure as compound 171, the yield was 15.17%.
LCMS (ESI) m/z: 469.0 (M+1)$^+$.
$^1$H NMR (400 MHz, METHANOL-d$_4$)=9.17 (s, 1H), 8.95 (d, J=6.8 Hz, 1H), 7.94 (br. s., 1H), 7.66 (d, J=2.0 Hz, 1H), 7.61 (s, 1H), 7.45-7.36 (m, 1H), 7.21 (d, J=6.0 Hz, 1H), 2.98-2.68 (m, 1H), 1.87-1.69 (m, 6H), 1.02-0.69 (m, 4H)

Example 173

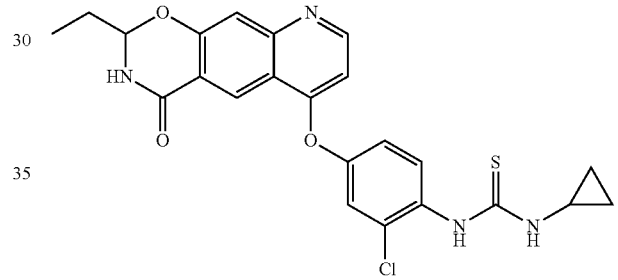

Compound of Example 173 was yellow solid prepared by a similar procedure as Example 172, the yield was 12.18%.
LCMS (ESI) m/z: 490.9 (M+23)
$^1$H NMR (400 MHz, METHANOL-d$_4$)=9.19 (s, 1H), 8.99 (d, J=6.5 Hz, 1H), 7.95 (br. s., 1H), 7.66 (s, 2H), 7.42 (d, J=7.0 Hz, 1H), 7.24 (br. s., 1H), 5.59 (t, J=5.1 Hz, 1H), 2.76 (br. s., 1H), 2.11-1.99 (m, 2H), 1.20 (t, J=7.4 Hz, 3H), 1.00-0.65 (m, 4H)

Example 175

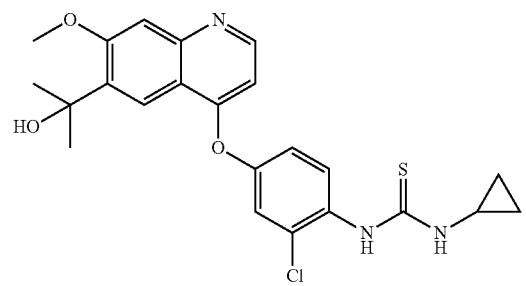 [SMILES: COc1cc2nccc(Oc3ccc(NC(=S)NC4CC4)c(Cl)c3)c2cc1C(C)(C)O]

Compound of Example 46 (130 mg, 55.7 mmol) was added to tetrahydrofuran (10 mL) under the protection of nitrogen, cooled to minus 20° C. under the protection of nitrogen, then methylmagnesium bromide (3M, 1.89 ml) was slowly added. The mixed solution was stirred at 26° C. under the protection of nitrogen for 18 hours, and the mixed solution was slowly introduced into ice saturated ammonium chloride (50 ml) and stirred for 10 minutes. The aqueous phase was extracted with ethyl acetate (50 ml*3) and the organic phase was washed with saturated NaCl solution (50 ml) once, dried over anhydrous sodium sulfate, concentrated and isolated by high performance liquid chromatography to give a compound of Example 175 (yellow solid, 14 mg, the yield was 9.9%). LCMS (ESI) m/z: 495 (M+1).

$^1$H NMR (400 MHz, METHANOL-d$_4$)=8.82 (s, 1H), 8.78 (d, J=6.5 Hz, 1H), 7.90 (br. s., 1H), 7.59 (d, J=2.3 Hz, 1H), 7.50 (s, 1H), 7.35 (dd, J=2.4, 8.4 Hz, 1H), 7.08 (br. s., 1H), 4.15 (s, 2H), 2.75 (s, 1H), 2.68 (s, 1H), 1.71 (s, 6H), 0.94 (br. s., 2H), 0.78 (br. s., 1H)

Process AB

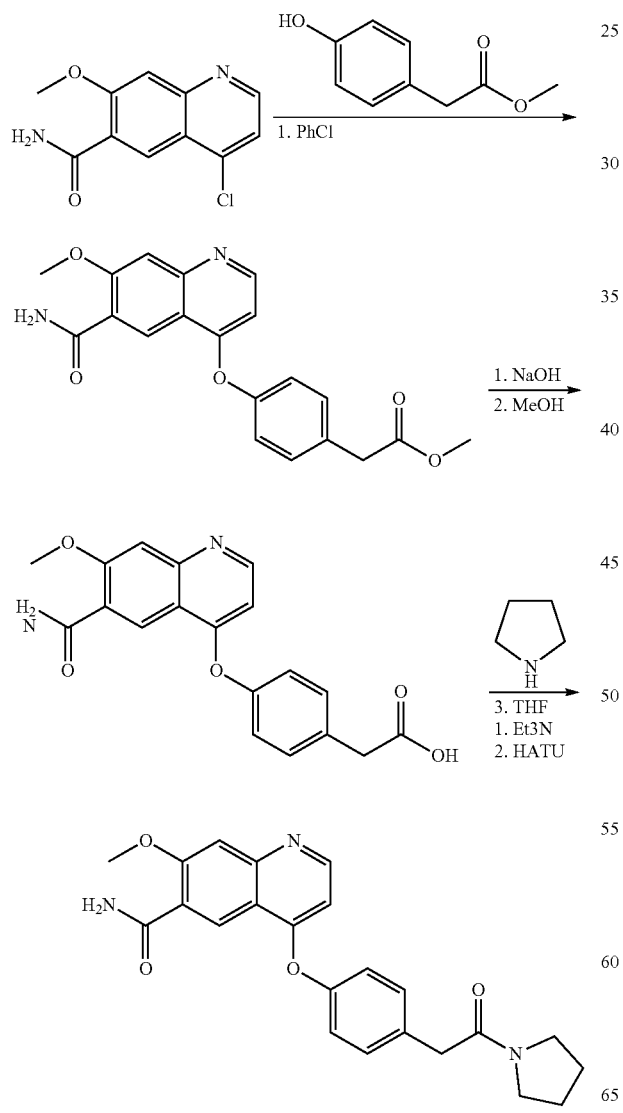

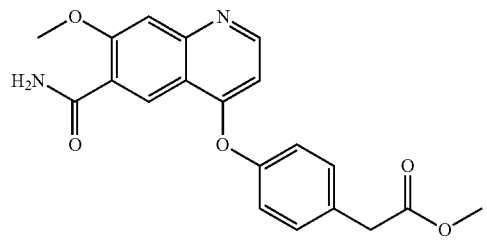

Compound 176A

Compound 1E (500 mg, 2.11 mmol) and methyl p-hydroxyphenylacetate (525 mg, 3.17 mmol) were added to a solution of chlorobenzene (15 ml) under the protection of nitrogen and stirred under the protection of nitrogen at 130° C. for 18 hours. The reaction solution was cooled to 25° C. and isolated by column to give compound 176A (yellow solid, 450 mg). LCMS (ESI) m/z: 367 (M+1).

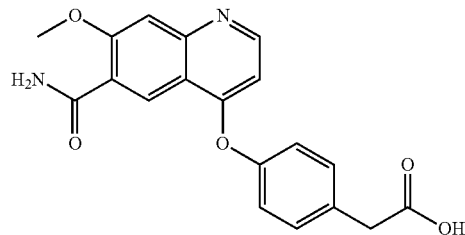

Compound 176B

Compound 176A (220 mg, 600.49 μmop was added to a solution of methanol (15 ml) and then 2 mol/L sodium hydroxide (750.61 μl) was added and the mixture was stirred at 26° C. for 18 hours. The mixture was reacted at 100° C. for 16 hours. The reaction solution was evaporated to no liquid dropped at 40° C., water (50 ml) was added. The aqueous phase was washed with ethyl acetate (50 ml) twice, and the pH of the aqueous phase was adjusted to =6 with 1 mol/L of hydrochloric acid. The aqueous phase was washed with methylene chloride (100 ml) three times and the organic phases were combined and washed once with saturated NaCl solution (50 ml), dried over anhydrous sodium sulfate, filtered and evaporated to give compound 176B (110 mg), which was used directly in the next step without further purification. LCMS (ESI) m/z: 353 (M+1)

Example 176

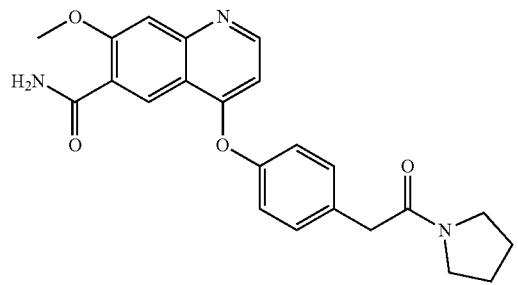 [SMILES: COc1cc2nccc(Oc3ccc(CC(=O)N4CCCC4)cc3)c2cc1C(N)=O]

Compound 176B (50 mg, 141.91 μmop and pyrrole (12.11 mg, 170.29 μmop were added to THF (10 mL) at 25° C.

under the protection of nitrogen and then triethylamine (17.23 mg, 170.29 μmop and HATU (64.75 mg, 170.29 μmop were added and stirred under the protection of nitrogen at 26° C. for 3 hours. The reaction solution was evaporated and isolated by high performance liquid chromatography to give a compound of Example 176 (yellow solid, 14 mg, the yield was 19.6%). LCMS (ESI) m/z: 406 (M+1)

$^1$H NMR (400 MHz, METHANOL-$d_4$)=9.05 (s, 1H), 8.89 (d, J=6.5 Hz, 1H), 7.65 (s, 1H), 7.53 (d, J=8.0 Hz, 2H), 7.36 (d, J=8.3 Hz, 2H), 7.04 (d, J=6.5 Hz, 1H), 4.23 (s, 3H), 3.85 (s, 2H), 3.64 (t, J=6.7 Hz, 2H), 3.49 (t, J=6.8 Hz, 2H), 2.09-2.00 (m, 2H), 1.99-1.89 (m, 2H)

Example 177

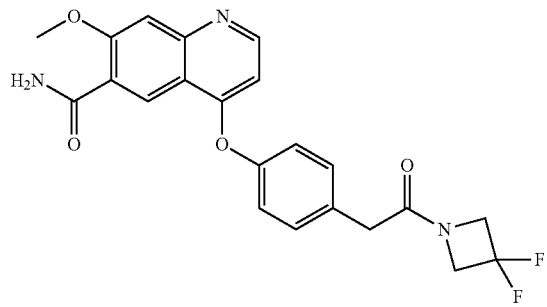 [SMILES: COc1cc2nccc(Oc3ccc(CC(=O)N4CC(F)(F)C4)cc3)c2cc1C(N)=O]

This Example was prepared as described in Example 176. LCMS (ESI) m/z: 428 (M+1)

$^1$H NMR (400 MHz, METHANOL-$d_4$)=9.05 (s, 1H), 8.89 (d, J=6.5 Hz, 1H), 7.65 (s, 1H), 7.55 (d, J=8.3 Hz, 2H), 7.37 (d, J=8.3 Hz, 2H), 7.02 (d, J=6.5 Hz, 1H), 4.73 (t, J=11.9 Hz, 2H), 4.39 (t, J=12.3 Hz, 2H), 4.23 (s, 3H), 3.75 (s, 2H)

Process AC

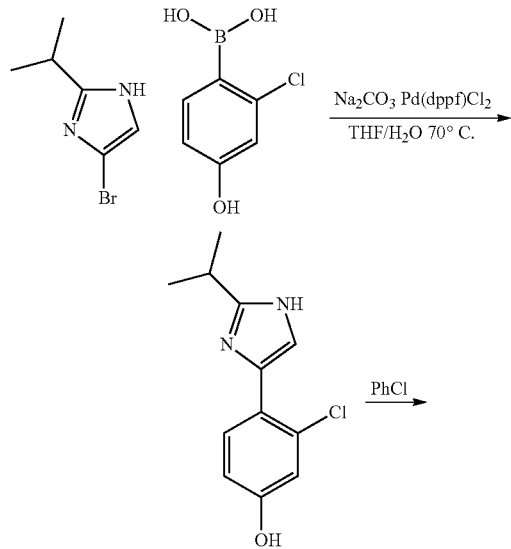

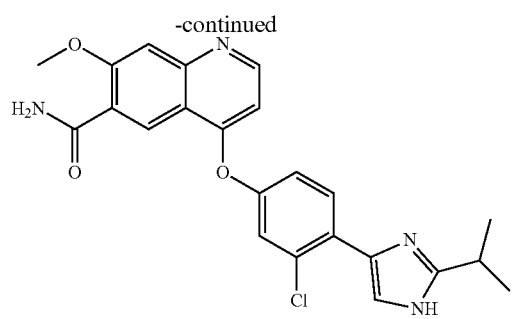

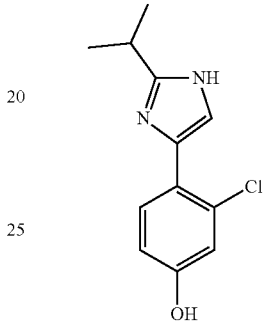

Compound 179A

2-Chloro-4-hydroxy-phenylboronic acid (150 mg, 870.22 μmop, 2-isopropyl-5-bromoimidazole (82.26 mg, 435.11 μmol), 1,1'-bis (diphenylphosphine) ferrocene palladium chloride (31.84 mg, 435.11 μmol) and sodium carbonate (92.23 mg, 870.22 μmol) were stirred in 5 ml of tetrahydrofuran and 0.5 ml of water and then heated to 70° C. under the protection of nitrogen for 16 hours, cooled and diluted with 10 ml of water, and then extracted with ethyl acetate (20 ml*3), the organic layer was combined and dried over anhydrous sodium sulfate, filtered and concentrated to give a 150 mg solid crude of strong yellowish green compound 179A, which was used directly in the next step. LCMS (ESI) m/z: 236.9[M+1]$^+$.

Example 179

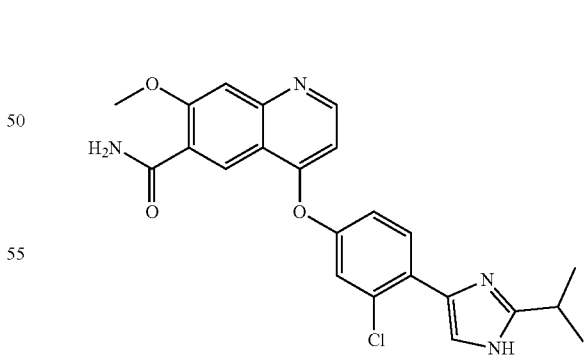

Compound of Example 1E (149.97 mg, 633.71 μmop was added to a solution of compound 179A (150 mg, 633.71 μmop in 2 ml of chlorobenzene and then heated to 130° C. for 16 hours under the protection of nitrogen. After cooling, the mixture was purified by preparative HPLC to give a pale yellow compound of Example 179 as a solid (4 mg, the yield was 1.12%). LCMS (ESI) m/z: 436.9[M+1]$^+$ ¹H NMR (400 MHz, METHANOL-d₄)=9.19-9.07 (m, 1H), 8.28-8.16 (m, 1H), 7.97-7.90 (m, 1H), 7.84-7.74 (m, 2H), 7.66-7.62 (m, 1H), 7.04 (d, J=2.5 Hz, 1H), 6.93 (dd, J=2.5, 8.5 Hz, 1H), 4.19 (s, 3H), 3.07-2.99 (m, 1H), 1.41 (d, J=6.8 Hz, 3H), 1.34-1.26 (m, 3H)

Process AD

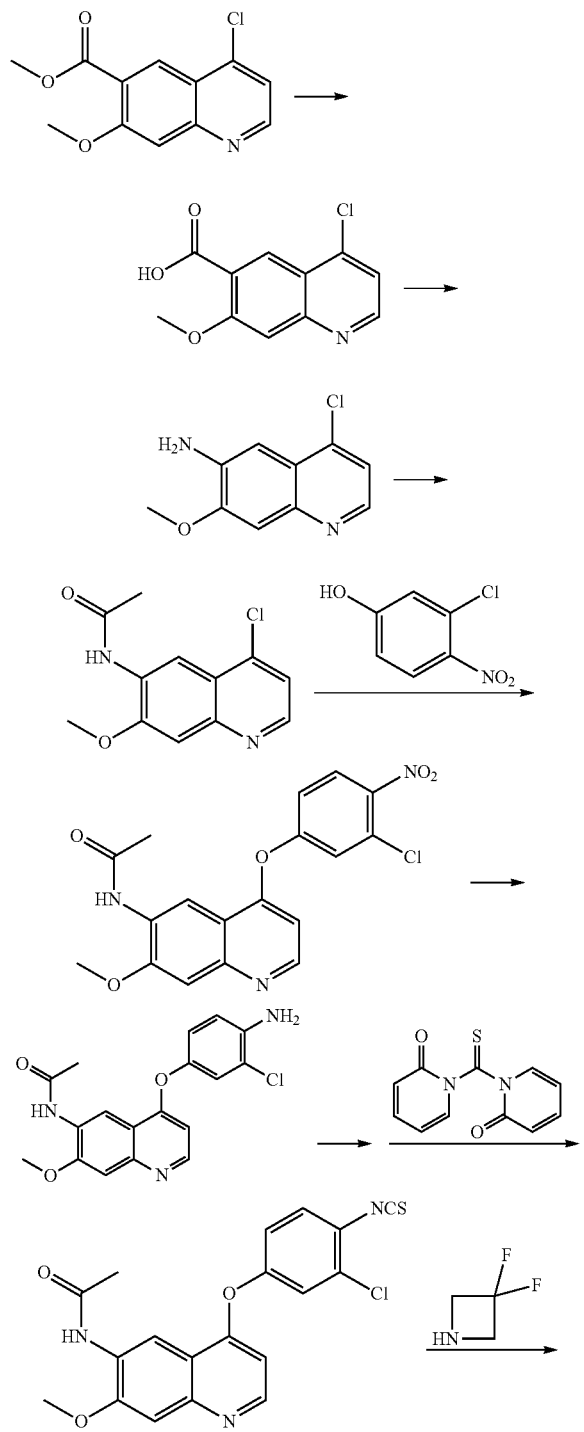

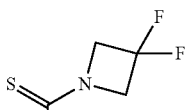

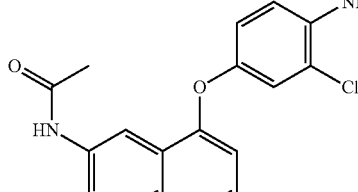

Compound 180A

Lithium hydroxide (3.81 g, 158.95 mmol) was added to a solution of compound 37A (8 g, 31.79 mmol) in tetrahydrofuran/methanol/water=3:2:1 (80 mL). The mixed solution was stirred at 28° C. for 3 hours and the pH was adjusted to 3-4 with dilute hydrochloric acid. The aqueous phase was extracted with isopropanol/dichloromethane=3:1 (200 mL*2). The combined organic layers were washed with NaCl solution (50 mL*2), dried over sodium sulfate, filtered and evaporated to give compound 180A (8 g, crude) which was used directly in the next step without further purification. LCMS (ESI) m/z: 238 (M+1)

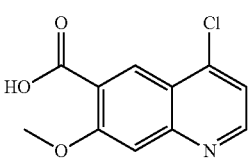

Compound 180B

DPPA (3.47 g, 12.62 mmol) was added to a solution of compound 180A (2.00 g 8.42 mmol) and triethylamine (1.28 g 12.62 mmol) in DMF (10 mL). The mixture was stirred at 28° C. under the protection of nitrogen for 3 hours, and heated to 100° C. and reacted for 1 hour. The aqueous phase was extracted with ethyl acetate (50 mL*3). The combined organic layers were washed with NaCl solution (50 mL*2), dried over sodium sulfate, filtered and evaporated. The residue was purified by column chromatography to give compound 180B (260 mg, the yield was 14.80%). LCMS (ESI) m/z: 209 (M+1)

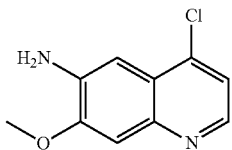

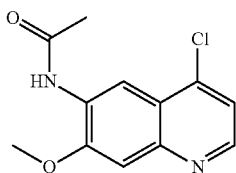

Compound 180C

Acetic anhydride (214.39 mg 2.1 mmol) was added to a solution of compound 180B (220 mg, 1.05 mmol) and triethylamine (320.10 mg, 3.16 mmol) in dichloromethane (3 mL). The mixture was stirred at 40° C. for 16 hours and 15 mL water was added. The mixed solution was extracted with dichloromethane (20 ml×3). The combined organic layers were dried over sodium sulfate, filtered and evaporated to give compound 180C (267 mg) which was used directly in the next step without further purification. LCMS (ESI) m/z: 251 (M+1)

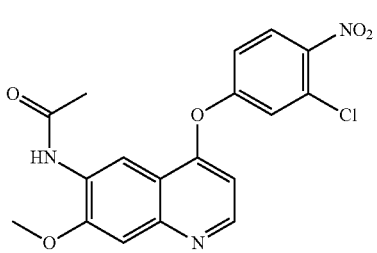

Compound 180D

3-Chloro-4-nitrophenol (277.27 mg 1.60 mmol) was added to a solution of compound 180C (267 mg, 1.07 mmol) in chlorobenzene and stirred at 130° C. under the protection of nitrogen for 16 hours, and then spin-dried at 60° C. The residue was washed with ethyl acetate (10 mL) to give compound 180D (300 mg) which was used directly in the next step without further purification. LCMS (ESI) m/z: 388 (M+1)

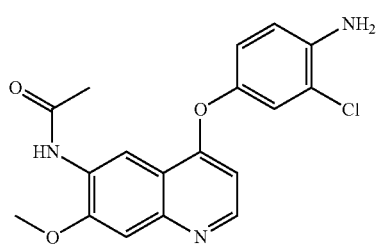

Compound 180E

Reduced iron powder (432.08 mg, 7.74 mmol) and ammonium chloride (413.83 mg, 7.74 mmol) were added to a solution of compound 180D (300 mg, 773.65 mmol) in ethanol/water=8.5:1.5 (30 mL). The mixture was reacted at 100° C. for 1 hours and water (20 mL) was added. The mixed solution was extracted with a solution of ethanol/dichloromethane=3:1 (50 mL*3). The combined organic layers were dried over sodium sulfate, filtered and evaporated to give compound E (267 mg) which was used directly in the next step without further purification. LCMS (ESI) m/z: 358 (M+1)

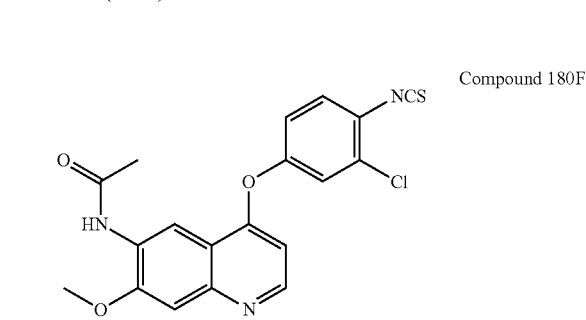

Compound 180F 1,1'-Thiocarbonyldi-2(1H) pyridone (116.85 mg, 503.09 μmop was added to a solution of compound 180E (150 mg, 419 μmol) in dioxane (8 mL) and reacted at 120° C. under the protection of nitrogen for 2 hours after finished the reaction, the compound 180E remained, and 1,1'-Thiocarbonyldi-2(1H) pyridone (116.85 mg, 503.09 μmol) was added and reacted at 120° C. for 12 hours to obtain compound 80 F. The reaction solution was used directly in the next step without further purification. LCMS (ESI) m/z: 400 (M+1)

Example 180

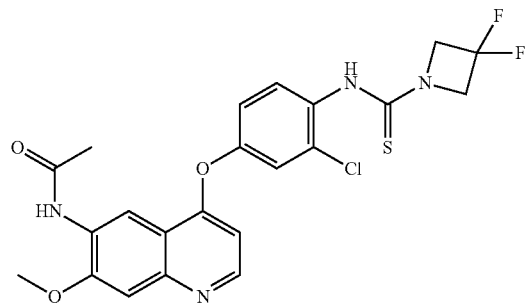 [SMILES: COc1cc2nccc(Oc3ccc(NC(=S)N4CC(F)(F)C4)c(Cl)c3)c2cc1NC(C)=O]

3,3-Difluorocyclobutylamine (161.99 mg, 1.25 mmol) and triethylamine (151.85 mg, 1.50 mmol) were added to a solution of compound 180F (50 mg, 125.05 μmol) in dioxane (3 mL) and stirred at 28° C. for 16 hours. The solution was removed in vacuo and the residue was purified by preparative HPLC to give a compound of Example 180 (11.70 mg, 17.50%). $^1$H NMR (400 MHz, METHANOL-$d_4$)=9.43 (s, 1H), 8.82-8.72 (m, 1H), 7.74 (d, J=8.5 Hz, 1H), 7.66-7.61 (m, 1H), 7.56 (s, 1H), 7.39 (dd, J=2.4, 8.7 Hz, 1H), 7.15 (d, J=6.8 Hz, 1H), 4.62 (t, J=11.9 Hz, 4H), 4.23 (s, 3H), 2.32 (s, 3H) LCMS (ESI) m/z: 493 (M+1)

The following compounds were also prepared by using the similar methods as described in Example 180 mentioned above.

| Examples | Structures | NMR | LCMS (ESI) m/z: (M + 1)+. |
| --- | --- | --- | --- |
| Example 181 | 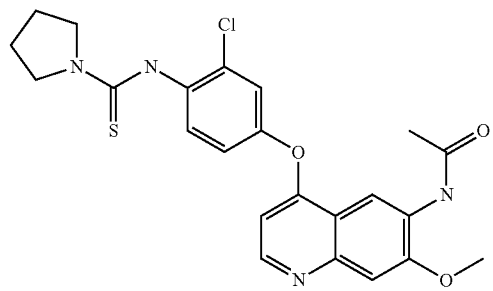 [SMILES: COc1cc2nccc(Oc3ccc(NC(=S)N4CCCC4)c(Cl)c3)c2cc1NC(C)=O] | ¹H NMR (400 MHz, METHANOL-d₄) = 9.45-9.41 (m, 1H), 8.78 (d, J = 6.8 Hz, 1H), 7.69 (d, J = 8.8 Hz, 1H), 7.61 (d, J = 2.5 Hz, 1H), 7.54 (s, 1H), 7.36 (dd, J = 2.5, 8.5 Hz, 1H), 7.23 (d, J = 6.8 Hz, 1H), 4.23 (s, 3H), 3.93-3.64 (m, 4H), 2.32 (s, 3H), 2.21-2.00 (m, 4H) | 471 |
| Example 182 | 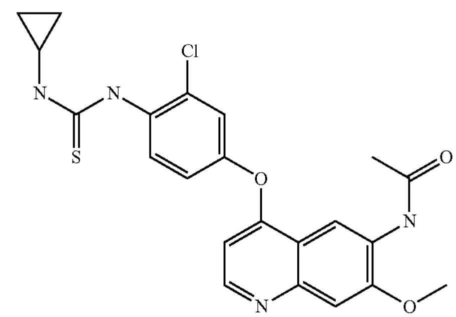 [SMILES: COc1cc2nccc(Oc3ccc(NC(=S)NC4CC4)c(Cl)c3)c2cc1NC(C)=O] | ¹H NMR (400 MHz, METHANOL-d₄) = 9.43 (s, 1H), 8.88-8.70 (m, 1H), 7.91 (br. s., 1H), 7.68-7.50 (m, 2H), 7.38 (d, J = 6.5 Hz. 1H), 7.24-7.06 (m, 1H), 4.31-4.15 (m, 3H), 2.40-2.23 (m, 3H), 1.02-0.62 (m, 4H) | 457 |
Process AE
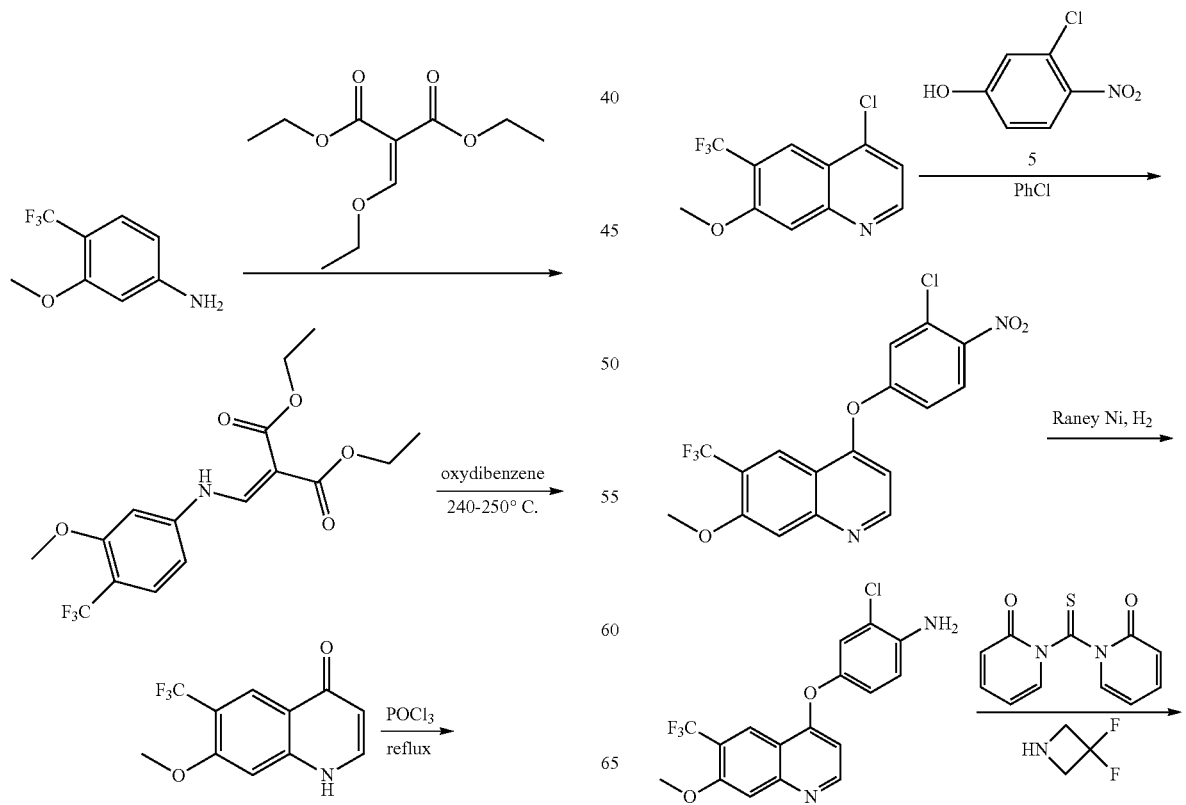

-continued

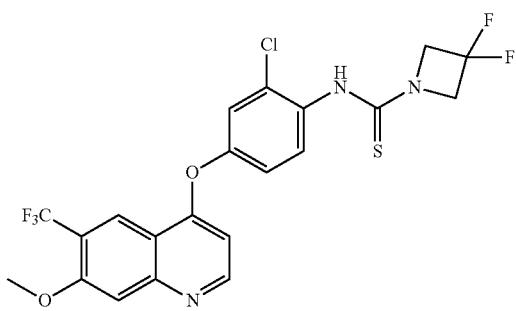 [SMILES: COc1cc2nccc(Oc3ccc(NC(=S)N4CC(F)(F)C4)c(Cl)c3)c2cc1C(F)(F)F]

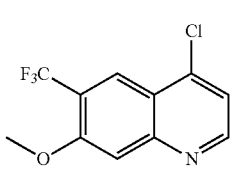

Compound 184C

Compound 184B (1.50 g, 6.17 mmol, 1.00 eq) was dissolved in phosphorus oxychloride (10 mL) and the reaction was refluxed at 106° C. for 5 hours. The completion of the reaction was detected by LCMS. The reaction solution was concentrated, and the phosphorus oxychloride was removed. The crude product was purified by flash column chromatography (eluting with 0-10% methanol/dichloromethane) to obtain compound 184C (250.00 mg, 590.53 µmol, the yield was 9.57%, the purity was 61.8%). LCMS-ESI: m/z 262.0 (M+H)$^+$ Compound 184A

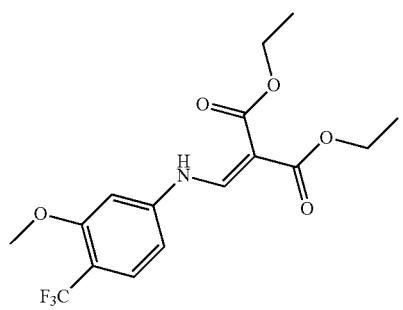

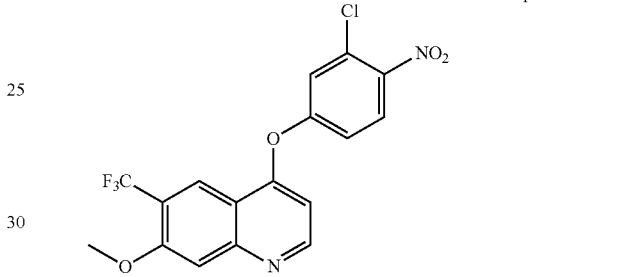

Compound 184D

3-Methoxy-4-trifluoromethylaniline (1.00 g, 5.23 mmol, 1.00 eq) was dissolved in diethyl ethoxymethylidene malonate (3.39 g, 15.69 mmol, 3.00 eq). The reaction was refluxed at 110° C. for 12 hours. The completion of the reaction was detected by LCMS. The reaction solution was concentrated at 60° C. to give compound 184A (1.80 g, yellow solid, crude). The crude product was used directly in the next step without further purification.

LCMS-ESI: m/z 362.1 (M+1)$^+$

Compound 184C (250.00 mg, 955.55 µmol, 1.00 eq) was dissolved in chlorobenzene (5.00 mL) and 3-chloro-4-nitrophenol (199.00 mg, 1.15 mmol, 1.20 eq) was added. The mixture was refluxed at 131° C. for 12 hours under the protection of nitrogen. The completion of the reaction was detected by LCMS. The reaction solution was concentrated and the crude product was purified by flash column chromatography (the eluent was 0-10% methanol/dichloromethane) to give compound 184D (10.00 mg, 17.81 µmol, the yield was 1.86%, the purity was 71%). LCMS-ESI: m/z 399.0 (M+H)$^+$.

Compound 184B

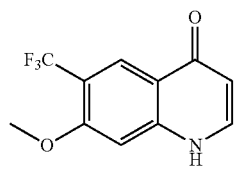

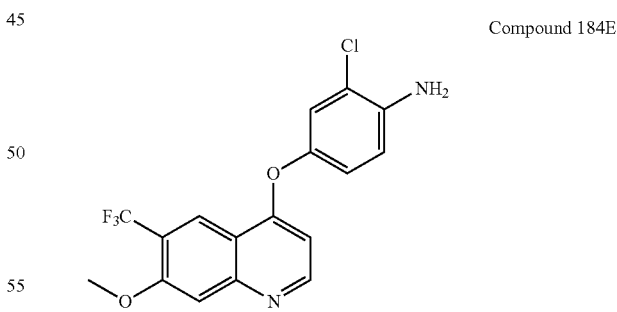

Compound 184E

Compound 184A (1.80 g, 4.98 mmol, 1.00 eq) was dissolved in diphenyl ether (10 mL) and heated to 240-250° C. for 1.5 hours. The completion of the reaction was detected by LCMS and the reaction was cooled to 30° C. and then poured into n-hexane (50 mL) and stirred for 10 minutes, a large amount of solid precipitated, filtered to obtain a crude of compound 184B (1.50 g, black solid), the crude product was used directly in the next step without further purification.

LCMS-ESI: m/z 244.0 (M+H)$^+$

Compound 184D (30.00 mg, 75.24 µmol, 1.00 eq) was dissolved in methanol (3.00 mL), radium Nickel (10%, 0.005 g) was added under the protection of nitrogen and the reaction solution was displaced with hydrogen several times. The reaction was carried out at 25° C. and 15 psi of hydrogen pressure for 0.5 hours. The completion of the reaction was detected by LCMS. The reaction solution was filtered and concentrated to give a crude of compound 184E (25.00 mg, gray solid).

LCMS-ESI: m/z 369.1 (M+H)$^+$.

Example 184

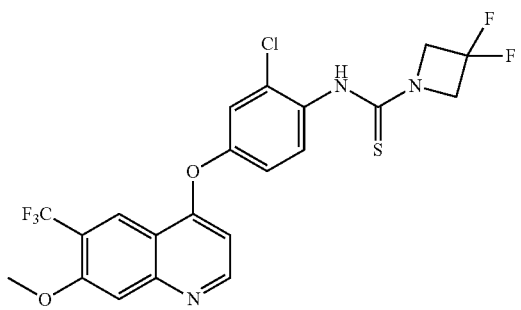 [SMILES: COc1cc2nccc(Oc3ccc(NC(=S)N4CC(F)(F)C4)c(Cl)c3)c2cc1C(F)(F)F]

Compound 184E (25.00 mg, 67.80 μmol, 1.00 eq) was dissolved in dioxane (2.00 mL), 1,1'-thiocarbonyldi-2(1H) pyridone (23.62 mg, 101.70 μmol, 1.50 eq) was added. The reaction was refluxed at 101° C. for 2 hours and the completion of the reaction was detected by LCMS. 20 mg of 1,1'-thiocarbonyldi-2(1H) pyridine was added and was refluxed for 1 hour. LCMS detected that 41% of compound 7 did not react and 10% of sulfur isocyanate formed. The reaction was stopped and the reaction solution was cooled to 25° C. Under the protection of nitrogen, 3,3-difluorocyclobutylamine (6.31 mg, 67.80 μmol, 1.00 eq) and DIEA (8.76 mg, 67.80 μmol, 1.00 eq) were added. The reaction was stirred at 25° C. for 12 hours. The completion of the reaction was detected by LCMS. The reaction solution was concentrated and the crude product was isolated and purified by preparative HPLC (Gemini, 150*25 mm, 10 u HCl) to give compound of Example 184 (1.00 mg, 1.98 μmol, the yield was 2.93%). LCMS-ESI: m/z 504.1 (M+H)$^+$.

$^1$H NMR (400 MHz, METHANOL-d$_4$) 7.42 (d, J=6.5 Hz, 1H), 7.31 (s, 1H), 6.20 (d, J=8.5 Hz, 1H), 6.15-6.04 (m, 2H), 5.94-5.81 (m, 1H), 5.70-5.53 (m, 1H), 3.07 (t, J=12.0 Hz, 4H), 2.66 (s, 3H)

Process AF

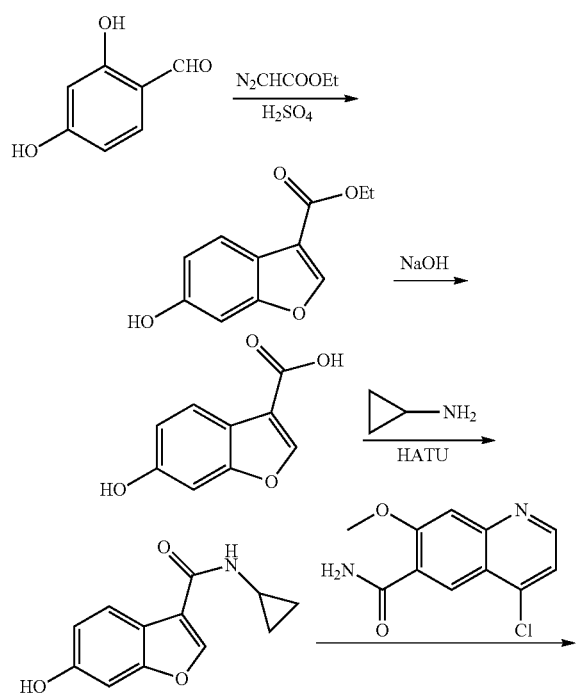

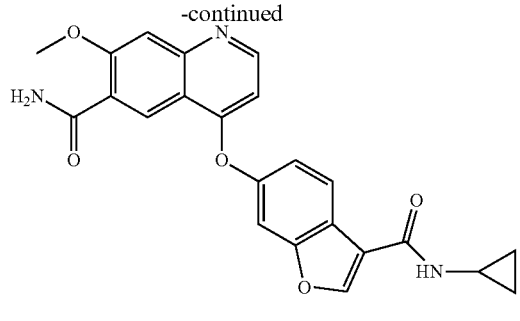

Compound 185A

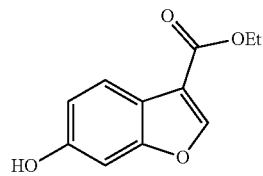

2,4-Dihydroxybenzaldehyde (10 g, 72.4 mmol) was added to dichloromethane (100 ml) at 28° C. under the protection of nitrogen, followed by the addition of boron trifluoride diethyl ether (1.17 g, 7.24 mmol), ethyl diazoacetate (33.04 g, 289.6 mmol) diluted with dichloromethane (50 mL) was slowly added dropwise. The temperature of the mixture was controlled below 36° C. until no gas was released, the solution was stirred at 28° C. for 30 minutes and concentrated to a remaining volume of 20 ml, sulfuric acid (7.1 g, 72.4 mmol) was slowly added dropwise and the mixture was continued to stir for 2 hours at 28° C. The crimson reaction solution was extracted with dichloromethane (100 ml) and the excess sulfuric acid was neutralized with sodium bicarbonate solid, then filtered and isolated by column to obtain compound 185A (yellow solid, 4.3 g, the yield was 23.04%).

Compound 185B

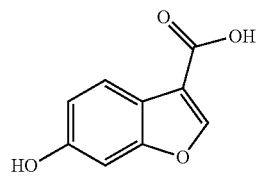

Compound 185A (4.3 g, 20.85 mmol) was added to tetrahydrofuran (20 ml) at 22° C. under the protection of nitrogen, and then sodium hydroxide (4 mol/L, 15.64 ml) was added and stirred at 22° C. for 16 hours under the protection of nitrogen. The reaction solution was diluted with water (100 ml) and washed once with ethyl acetate (30 ml). The aqueous phase was adjusted till the pH was 5 with hydrochloric acid (2 mol/L), extracted with ethyl acetate (60 ml*3). The organic phase was washed with saturated NaCl solution (50 ml) and dried over anhydrous sodium sulfate to give compound 185B (1.5 mg). The product was used directly in the next step without further purification.

Compound 185C

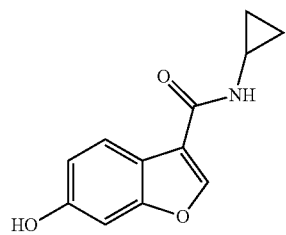

Compound 185B (120 mg, 673.63 μmop and cyclopropylamine hydrochloride (38.46 mg, 673.63 μmop were added to N,N-dimethylformamide (3 ml) at 22° C. under the protection of nitrogen, and then HATU (256.13 mg, 673.63 mmol) and N,N-diisopropylethylamine (435.3 mg, 3.37 mmol) were added and the mixture was stirred at 22° C. under the protection of nitrogen for 1.5 hours. The reaction solution was added to water (20 ml) and extracted with ethyl acetate (50 ml*3). The organic phase was washed with saturated NaCl solution (100 ml) and dried over anhydrous sodium sulfate to give compound 185C (146 mg). LCMS (ESI) m/z: 218 (M+1).

Example 185

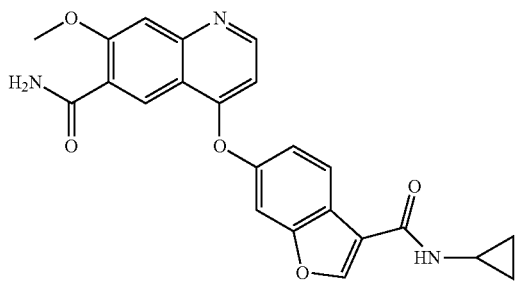 [SMILES: COc1cc2nccc(Oc3ccc4c(C(=O)NC5CC5)coc4c3)c2cc1C(N)=O]

Compound 1E (105.46 mg, 445.63 μmol), the compound of Example 185C (121 mg, 557.04 μmop and sodium tert-butoxide (22.48 mg, 233.96 mmol) were added to dimethylsulfoxide (2 ml) at 22° C. under the protection of nitrogen, and reacted at 100° C. for 16 hours under the protection of nitrogen. The solution was cooled to room temperature and added to water (20 ml), extracted with ethyl acetate (80 ml*3). The organic phase was washed once with saturated NaCl solution (100 ml), concentrated, filtered and purified by liquid chromatography to give a compound of Example 185 (yellow solid, 30 mg, the yield was 13.77%).

LCMS (ESI) m/z: 418 (M+1).

$^1$H NMR (400 MHz, METHANOL-$d_4$)=9.03 (s, 1H), 8.65 (d, J=5.5 Hz, 1H), 8.38 (s, 1H), 8.22 (d, J=8.8 Hz, 1H), 7.59-7.54 (m, 2H), 7.31 (dd, J=2.1, 8.4 Hz, 1H), 6.59 (d, J=5.5 Hz, 1H), 4.16 (s, 3H), 2.89 (m, 1H), 0.89-0.83 (m, 2H), 0.71-0.66 (m, 2H)

The following compounds were also prepared using methods similar to that as described in Example 185.

| Examples | Structures | NMR | LCMS (ESI) m/z: (M + 1) |
| --- | --- | --- | --- |
| Example 201 | 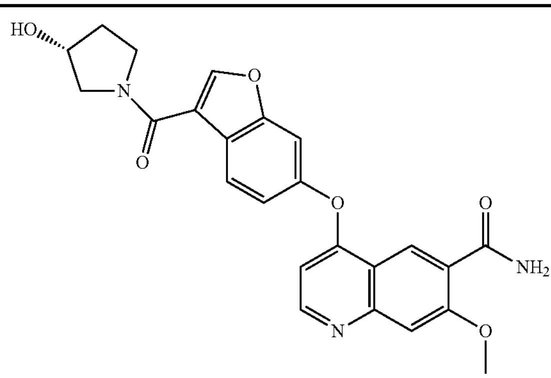 | $^1$H-NMR (CD$_3$OD 400 MHz) δ ppm 9.04 (s, 1H), 8.65 (d, J = 5.2 Hz, 1H), 8.43-8.37 (m, 1H), 8.16-8.12 (m, 1H), 7.59 (d, J = 2.0 Hz, 1H), 7.55 (s, 1H), 7.31 (dd, J = 8.4, 2.0 Hz, 1H), 6.60 (d, J = 5.2 Hz, 1H), 4.53 (m, 1H), 4.16 (s, 3H), 3.76-3.68 (m, 4H), 2.15-2.07 (m, 2H). | 448.1 |
| Example 202 | 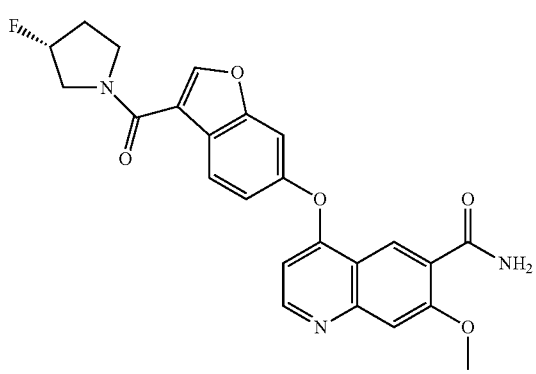 [SMILES: COc1cc2nccc(Oc3ccc4c(C(=O)N5CC[C@@H](F)C5)coc4c3)c2cc1C(N)=O] | 1H-NMR (CD3OD 400 MHz) δ ppm 9.03 (s, 1H), 8.65 (d, J = 5.6 Hz, 1H), 8.51-8.31 (m, 1H), 8.15 (d, J = 8.4 Hz, 1H), 7.66-7.47 (m, 2H), 7.31 (dd, J = 2.0, 8.8 Hz, 1H), 6.60 (d, J = 5.6 Hz, 1H), 5.49-5.29 (m, 1H), 4.16 (s, 3H), 4.09-3.74 (m, 4H), 2.49-2.15 (m, 2H) | 449.9 |

-continued

| Examples | Structures | NMR | LCMS (ESI) m/z: (M + 1) |
|---|---|---|---|
| Example 187 | 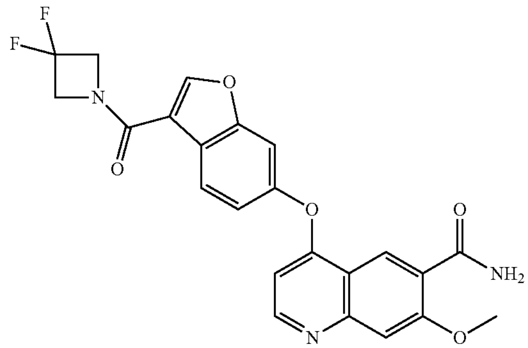 [SMILES: COc1cc2nccc(Oc3ccc4c(C(=O)N5CC(F)(F)C5)coc4c3)c2cc1C(N)=O] | ¹H-NMR (CD₃OD 400 MHz) δ ppm 9.03 (s, 1H), 8.65 (m, 1H), 8.42 (s, 1H), 8.23 (d, J = 8.8 Hz, 1H), 7.61 (m, H), 7.55 (s, 1H), 7.33 (dd, J = 8.8, 2.4 Hz, 1H), 6.59 (d, J = 5.6 Hz, 1H), 4.82-4.76 (m, 4H), 4.15 (s, 3H). | 454.1 |
| Example 200 | 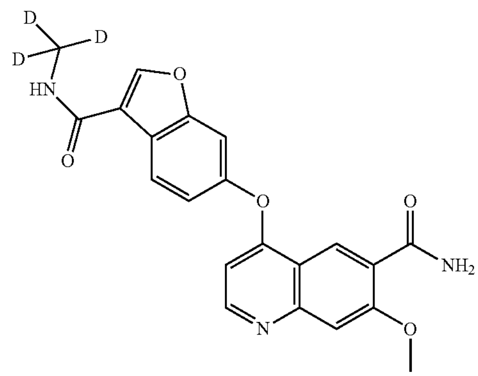 [SMILES: [2H]C([2H])([2H])NC(=O)c1coc2cc(Oc3ccnc4cc(OC)c(C(N)=O)cc34)ccc12] | ¹H-NMR (CD₃OD 400 MHz) δ ppm 9.03 (s, 1H), 8.64 (d, J = 5.6 Hz, 1H), 8.37 (s, 1H), 8.20 (d, J = 8.8 Hz, 1 H), 7.57 (d, J = 2.0 Hz, 1 H), 7.54 (s, 1H), 7.31 (dd, J = 8.4, 2.0 Hz, 1 H), 6.59 (d, J = 5.6 Hz, 1 H), 4.15 (s, 3H). | 395.1 |
| Example 203 | 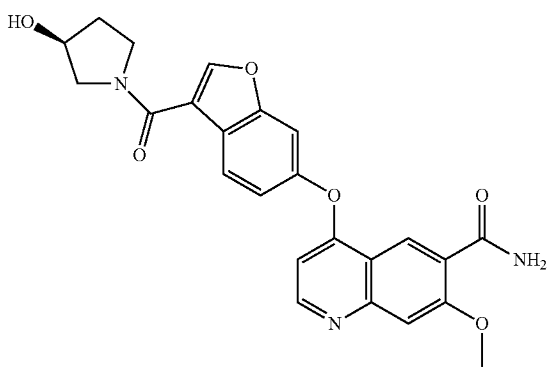 [SMILES: COc1cc2nccc(Oc3ccc4c(C(=O)N5CC[C@H](O)C5)coc4c3)c2cc1C(N)=O] | ¹H NMR (CD₃OD 400 MHz) δ ppm 8.98 (s, 1H), 8.60 (d, J = 5.2 Hz, 1H), 8.38-8.32 (m, 1H), 8.11-8.07 (m, 1H), 7.54 (s, 1H), 7.50 (s, 1H), 7.27-7.24 (m, 1H), 6.55 (d, J = 5.2 Hz, 1H), 4.11 (s, 3H), 3.85-3.64 (m, 5H), 2.12-2.03 (m, 2H). | 448.1 |
| Example 210 | 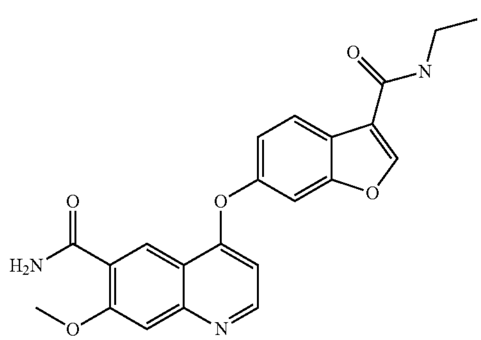 [SMILES: CCNC(=O)c1coc2cc(Oc3ccnc4cc(OC)c(C(N)=O)cc34)ccc12] | ¹H NMR (400 MHz, METHANOL-d₄) = 9.02 (s, 1H), 8.63 (d, J = 5.3 Hz, 1H), 8.40 (s, 1H), 8.20 (d, J = 8.5 Hz, 1H), 7.59-7.50 (m, 2H), 7.30 (dd, J = 2.1, 8.7 Hz, 1H), 6.58 (d, J = 5.5 Hz, 1H), 4.18-4.11 (m, 3H), 3.46 (q, J = 7.3 Hz, 2H), 1.32-1.24 (m, 3H) | 406 |

| Examples | Structures | NMR | LCMS (ESI) m/z: (M + 1) |
|---|---|---|---|
| Example 205 | 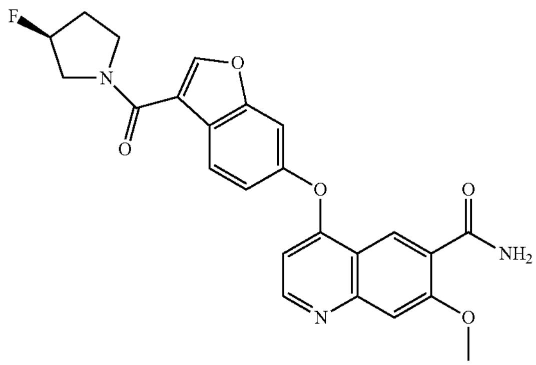 [SMILES: COc1cc2nccc(Oc3ccc4c(C(=O)N5CC[C@H](F)C5)coc4c3)c2cc1C(N)=O] | ¹H NMR (CD₃OD 400 MHz) δ ppm 8.90 (s, 1H), 8.61 (d, J = 5.2 Hz, 1H), 8.42-8.37 (m, 1H), 8.11 (d, J = 8.8 Hz, 1H), 7.56 (s, 1H), 7.51 (s, 1H), 7.28 (d, J = 8.8 Hz, 1H), 6.57 (d, J = 5.2 Hz, 1H), 5.44-5.30 (m, 1H), 4.12 (s, 3H), 4.03-3.75 (m, 4H), 2.36-2.14 (m, 2H). | 450.1 |
| Example 206 | 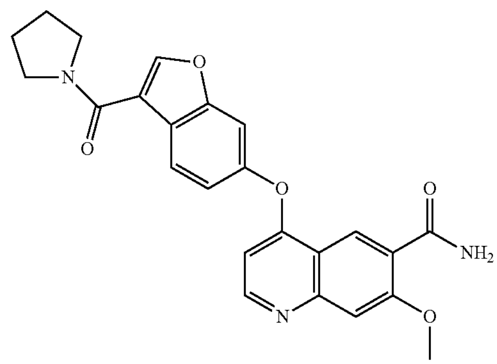 [SMILES: COc1cc2nccc(Oc3ccc4c(C(=O)N5CCCC5)coc4c3)c2cc1C(N)=O] | ¹H-NMR (CD₃OD 400 MHz) δ ppm 9.03 (s, 1H), 8.65 (d, J = 5.6 Hz, 1H), 8.39 (s, 1H), 8.14 (d, J = 8.4 Hz, 1H), 7.62-7.50 (m, 2H), 7.30 (dd, J = 2.0, 8.4 Hz, 1H), 6.60 (d, J = 5.6 Hz, 1H), 4.15 (s, 3H), 3.83-3.64 (m, 4H), 2.05 (m, 4H) | 431.9 |
| Example 186 | 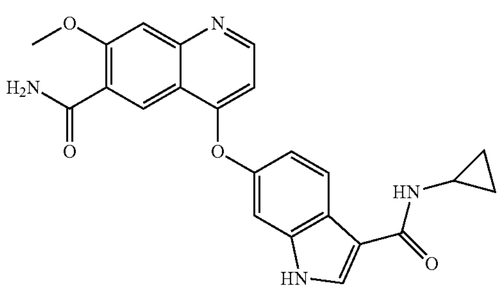 [SMILES: COc1cc2nccc(Oc3ccc4c(C(=O)NC5CC5)c[nH]c4c3)c2cc1C(N)=O] | ¹H-NMR (CD₃OD, 400 MHz) δ ppm 11.54 (m, 0.6 H), 9.11 (s, 1 H), 8.84 (d, J = 7.2 Hz, 1 H), 8.36 (d, J = 8.4 Hz, 1 H), 8.02 (s, 1 H), 7.61 (s, 1 H), 7.48-7.47 (m, 1 H), 7.17-7.14 (m, 1 H), 6.95 (d, J = 6.8 Hz, 1 H), 4.23 (s, 3H), 2.88-2.84 (m, 1H), 0.86-0.81 (m, 2H), 0.69-0.65 (m, 2H). | 417.1 |
| Example 188 | 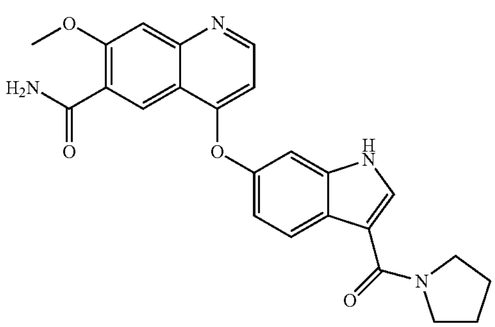 [SMILES: COc1cc2nccc(Oc3ccc4c(C(=O)N5CCCC5)c[nH]c4c3)c2cc1C(N)=O] | ¹H-NMR (CD₃OD 400 MHz) δ ppm 9.01 (s, 1H), 8.55 (d, J = 5.2 Hz, 1H), 8.15 (d, J = 8.8 Hz, 1H), 7.84 (s, 1H), 7.47 (s, 1H), 7.32 (m, 1H), 7.03 (dd, J = 8.8, 2.0 Hz, 1H), 6.49 (d, J = 5.6 Hz, 1H), 4.11 (s, 3H), 3.78-3.66 (m, 4H), 1.99 (m, 4H). | 431.1 |

-continued
| Examples | Structures | NMR | LCMS (ESI) m/z: (M + 1) |
|---|---|---|---|
| Example 189 | 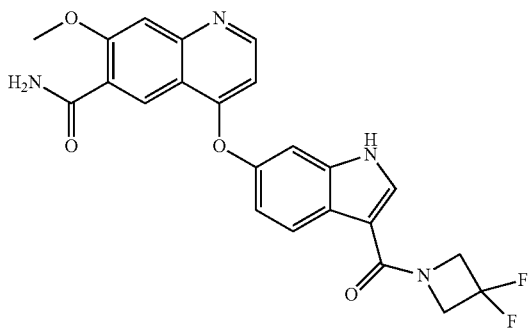 [SMILES: COc1cc2nccc(Oc3ccc4c(C(=O)N5CC(F)(F)C5)c[nH]c4c3)c2cc1C(N)=O] | ¹H-NMR (CD₃OD 400 MHz) δ ppm 9.04 (s, 1H), 8.58 (d, J = 5.2 Hz, 1H), 8.28 (d, J = 8.4 Hz, 1H), 7.86 (s, 1H), 7.51 (s, 1H), 7.37 (m, 1H), 7.10 (dd, J = 8.8, 2.0 Hz, 1H), 6.52 (d, J = 5.6 Hz, 1H), 4.70-4.67 (m, 4H), 4.14 (s, 3H). | 453.1 |
| Example 190 | 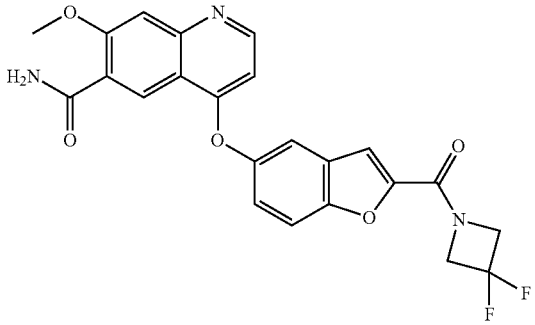 [SMILES: COc1cc2nccc(Oc3ccc4oc(C(=O)N5CC(F)(F)C5)cc4c3)c2cc1C(N)=O] | ¹H-NMR (CD₃OD 400 MHz) δ ppm 9.11 (s, 1H), 8.91-8.89 (d, J = 7.2 Hz, 1H), 7.92-7.85(m, 2H), 7.67 (s, 1H), 7.56-7.53 (m, 2H), 6.99-6.97 (d, J = 6.8, 1H), 5.14 (br, 2H), 4.62 (br, 2H), 4.24(s, 3H). | 454.1 |
| Example 191 | 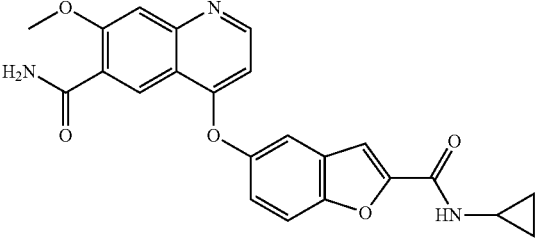 [SMILES: COc1cc2nccc(Oc3ccc4oc(C(=O)NC5CC5)cc4c3)c2cc1C(N)=O] | ¹H-NMR (CD₃OD 400 MHz) δ ppm 9.05 (s, 1H), 8.64-8.63 (d, J = 4.2 Hz, 1H), 7.78-7.68 (m, 1H), 7.67 (s, 1H), 7.55-7.54 (d, J = 1.2, 2H), 7.41-7.38 (m, 1H), 4.16(s, 3H), 2.95-2.91 (m, 1 H), 0.90-0.72 (m, 4H) | 418.1 |
| Example 192 | 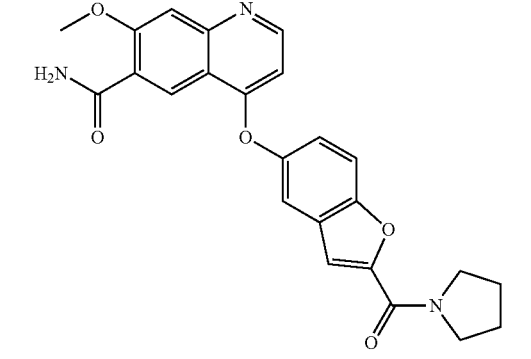 [SMILES: COc1cc2nccc(Oc3ccc4oc(C(=O)N5CCCC5)cc4c3)c2cc1C(N)=O] | ¹H NMR (CDCl₃ 400 MHz) δ ppm 9.34 (s, 1H), 8.64 (s, 1H), 7.83 (s, 1H), 7.62 (d, J = 9.2 Hz, 1H), 7.56 (s, 1H), 7.48 (s, 1H), 7.42 (s, 1H), 7.22 (d, J = 9.2 Hz, 1H), 6.43 (br, 1H), 6.01 (br, 1H), 4.14 (s, 3H), 3.98 (t, J = 6.8, Hz, 2H), 3.74 (t, J = 6.8 Hz, 2H), 2.09-2.04 (m, 2H), 2.01-1.96 (m, 2H). | 432.1 |

| Examples | Structures | NMR | LCMS (ESI) m/z: (M + 1) |
|---|---|---|---|
| Example 194 | 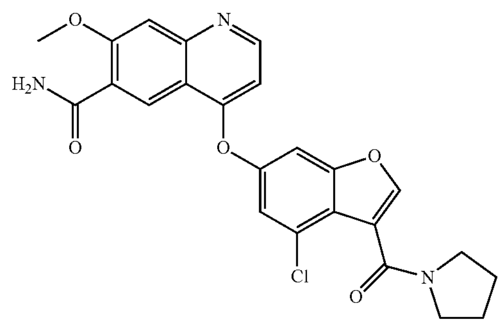 [SMILES: COc1cc2nccc(Oc3cc(Cl)c4c(C(=O)N5CCCC5)coc4c3)c2cc1C(N)=O] | ¹H-NMR (CD₃OD 400 MHz) δ ppm 8.98 (s, 1H), 8.66 (d, J = 6.0 Hz, 1H), 8.62 (s, 1H), 7.54 (s, 1H), 7.05 (s, 1H), 7.02 (s, 1H), 6.65 (d, J = 5.2 Hz, 1H), 4.15 (s, 3H), 3.99 (t, J = 6.6 Hz, 2H), 3.90 (t, J = 6.4 Hz, 2H), 2.13-2.05 (m, 4H). | 466.2 |
| Example 195 | 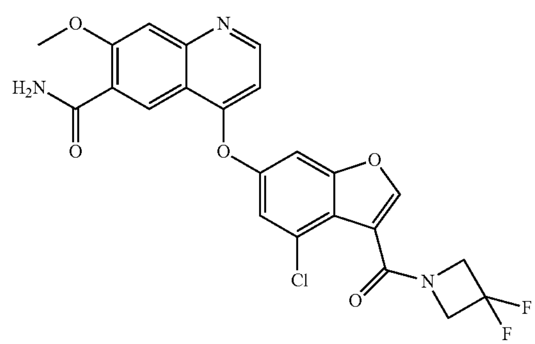 [SMILES: COc1cc2nccc(Oc3cc(Cl)c4c(C(=O)N5CC(F)(F)C5)coc4c3)c2cc1C(N)=O] | ¹H-NMR (CD₃OD 400 MHz) δ ppm 8.97 (s, 1H), 8.67 (d, J = 5.6 Hz, 1H), 8.32 (s, 1H), 7.61 (d, J = 1.6 Hz, 1H), 7.53 (s, 1H), 7.41 (d, J = 2.0 Hz, 1H), 6.66 (d, J = 5.2 Hz, 1H), 4.59 (t, J = 6.0 Hz, 4H), 4.15 (s, 3H). | 488.0 |
| Example 196 | 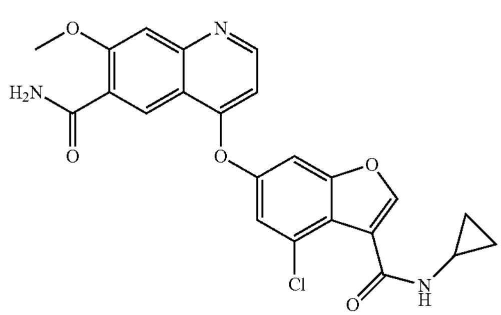 [SMILES: COc1cc2nccc(Oc3cc(Cl)c4c(C(=O)NC5CC5)coc4c3)c2cc1C(N)=O] | ¹H-NMR (CD₃OD 400 MHz) δ ppm 8.98 (s, 1H), 8.68 (d, J = 5.2 Hz, 1H), 8.19 (s, 1H), 7.57 (d, J = 2.0 Hz, 1H), 7.55 (s, 1H), 7.37 (d, J = 2.0 Hz, 1H), 6.65 (d, J = 5.2 Hz, 1H), 4.15 (s, 3H), 0.87-0.83 (m, 2H), 0.71-0.68 (m, 2H). | 452.0 |
| Example 211 | 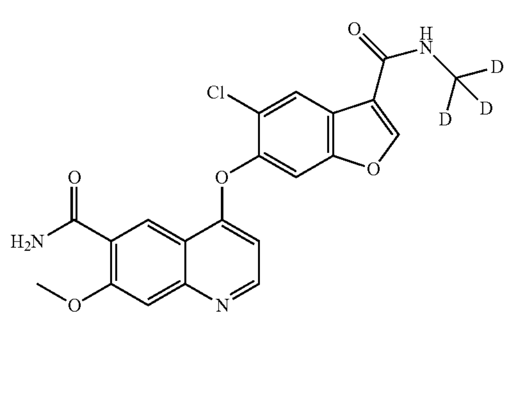 [SMILES: [2H]C([2H])([2H])NC(=O)c1coc2cc(Oc3ccnc4cc(OC)c(C(N)=O)cc34)c(Cl)cc12] | ¹H NMR (400 MHz, METHANOL-d₄) = 9.06 (s, 1H), 8.64 (d, J = 5.3 Hz, 1H), 8.43 (s, 1H), 8.33 (s, 1H), 7.77 (s, 1H), 7.57 (s, 1H), 6.47 (d, J = 5.3 Hz, 1H), 4.16 (s, 3H) | 429 |

| Examples | Structures | NMR | LCMS (ESI) m/z: (M + 1) |
|---|---|---|---|
| Example 197 | 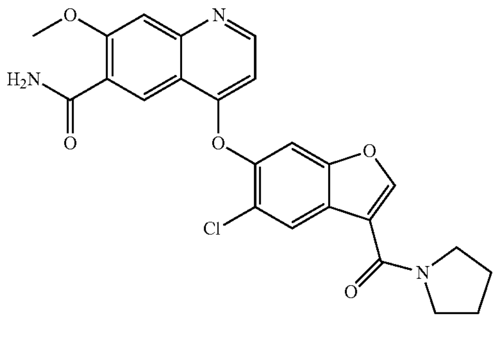 [SMILES: COc1cc2nccc(Oc3cc4occ(C(=O)N5CCCC5)c4cc3Cl)c2cc1C(N)=O] | ¹H NMR (CD₃OD 400 MHz) δ ppm 9.00 (s, 1H), 8.58 (d, J = 5.2 Hz, 1H), 8.42 (s, 1H), 8.23 (s, 1H), 7.72 (s, 1H), 7.51 (s, 1H), 6.41 (d, J = 5.2 Hz, 1H), 4.10 (s, 3H), 3.75 (t, J = 6.4 Hz, 2H), 3.64 (t, J = 6.4 Hz, 2H), 2.04-1.97 (m, 4H). | 466.0 |
| Example 198 | 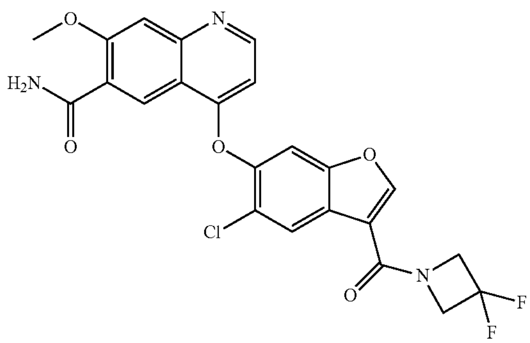 [SMILES: COc1cc2nccc(Oc3cc4occ(C(=O)N5CC(F)(F)C5)c4cc3Cl)c2cc1C(N)=O] | ¹H NMR (CD₃OD 400 MHz) δ ppm 9.09 (s, 1H), 8.89 (d, J = 6.8 Hz, 1H), 8.53 (s, 1H), 8.40 (s, 1H), 7.94 (s, 1H), 7.61 (s, 1H), 6.91 (d, J = 6.8 Hz, 1H), 4.87 (m, 4H), 4.21 (s, 3H). | 488.0 |
| Example 199 | 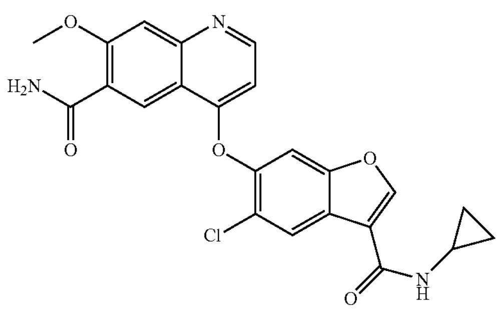 [SMILES: COc1cc2nccc(Oc3cc4occ(C(=O)NC5CC5)c4cc3Cl)c2cc1C(N)=O] | ¹H NMR (CD₃OD 400 MHz) δ ppm 9.04 (s, 1H), 8.62 (d, J = 5.2 Hz, 1H), 8.42 (s, 1H), 8.31 (s, 1H), 7.75 (s, 1H), 7.55 (s, 1H), 6.44 (d, J = 5.2 Hz, 1H), 4.14 (s, 3H), 2.89-2.85 (m, 1H), 0.87-0.82 (m, 2H), 0.68-0.65 (m, 2H). | 542.1 |
| Example 204 | 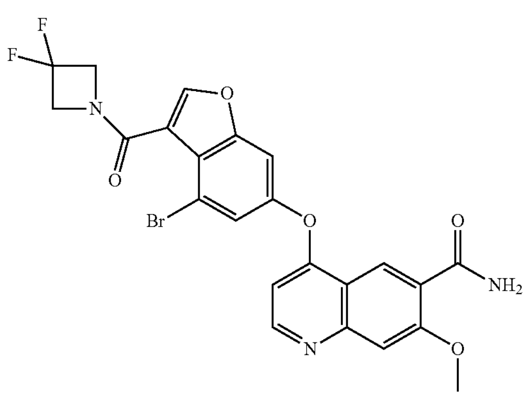 [SMILES: COc1cc2nccc(Oc3cc(Br)c4c(C(=O)N5CC(F)(F)C5)coc4c3)c2cc1C(N)=O] | ¹H NMR (CD₃OD 400 MHz) δ ppm 8.95 (s, 1H), 8.64 (d, J = 5.2 Hz, 1H), 8.26 (s, 1H), 7.63 (s, 1H), 7.54 (s, 1H), 7.52 (s, 1H), 6.63 (d, J = 5.2 Hz, 1H), 4.55-4.51 (m, 4H), 4.11 (s, 3H). | 531.9 |

| Examples | Structures | NMR | LCMS (ESI) m/z: (M + 1) |
|---|---|---|---|
| Example 207 | 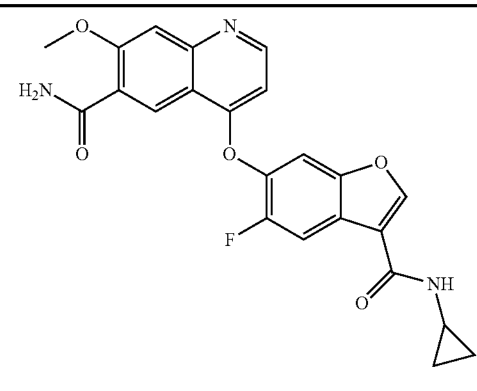 | ¹H NMR (400 MHz, METHANOL-d₄) = 9.04 (s, 1H), 8.66 (d, J = 5.3 Hz, 1H), 8.45 (s, 1H), 8.04 (d, J = 10.3 Hz, 1H), 7.76 (d, J = 6.3 Hz, 1H), 7.57 (s, 1H), 6.59 (d, J = 5.3 Hz, 1H), 4.16 (s, 3H), 2.89 (td, J = 3.5, 7.3 Hz, 1H), 0.89-0.83 (m, 2H), 0.71-0.65 (m, 2H) | 435.9, (M + 1),, 457.9 (M + 23) |
| Example 208 | 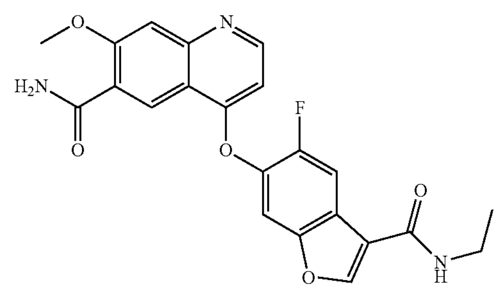 [SMILES: CCNC(=O)c1coc2cc(Oc3ccnc4cc(OC)c(C(N)=O)cc34)c(F)cc12] | ¹H NMR (400 MHz, METHANOL-d₄) = 9.04 (s, 1H), 8.66 (d, J = 5.3 Hz, 1H), 8.50-8.43 (m, 1H), 8.03 (d, J = 10.0 Hz, 1H), 7.77-7.75 (m, 1H), 7.57 (s, 1H), 6.59 (d, J = 5.3 Hz, 1H), 4.16 (s, 3H), 3.46 (q, J = 7.3 Hz, 2H), 1.28 (t, J = 7.4 Hz, 2H) | 445.9 |
| Example 209 | 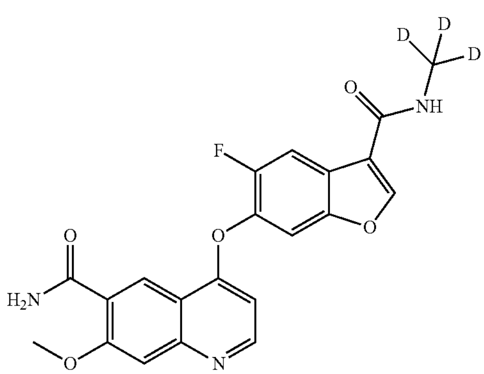 [SMILES: [2H]C([2H])([2H])NC(=O)c1coc2cc(Oc3ccnc4cc(OC)c(C(N)=O)cc34)c(F)cc12] | ¹H NMR (400 MHz, METHANOL-d₄) = 9.04 (s, 1H), 8.66 (d, J = 5.5 Hz, 1H), 8.44 (s, 1H), 8.04 (d, J = 10.3 Hz, 1H), 7.80-7.73 (m, 1H), 7.57 (s, 1H), 6.59 (d, J = 5.5 Hz, 1H), 4.16 (s, 3H) | 413.1 |
Process AG
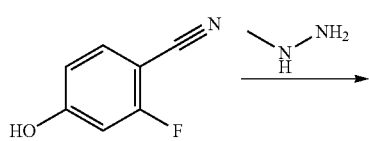
-continued
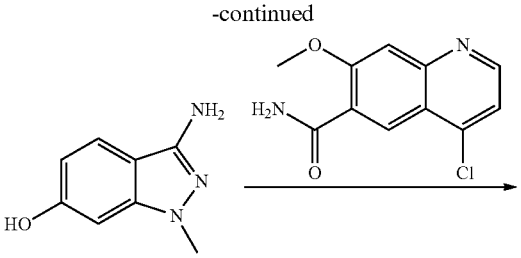

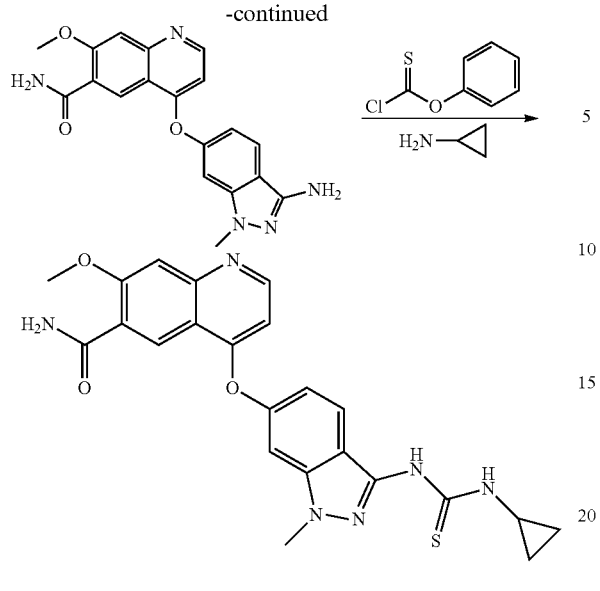
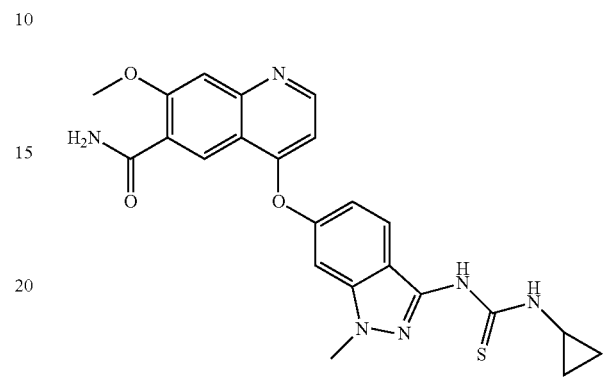

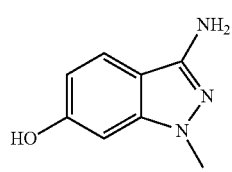

Compound 193A

2-Fluoro-4-hydroxyphenylacetonitrile (3 g, 22 mmol) was dissolved in methylhydrazine (30 g, 260 mmol). The reaction solution was heated to 90° C. for 16 hours, evaporated to dryness under reduced pressure and the residue was isolated by column chromatography (dichloromethane/methanol=10:1, Rf=0.2) to give compound 193A (yellow solid, 1.1 g, 31%).

$^1$H NMR (400 MHz, CHLOROFORM-d) 7.35 (d, J=8.53 Hz, 1H), 6.58-6.62 (m, 1H), 6.56 (s, 1H), 3.74 (s, 3H)

Example 193B

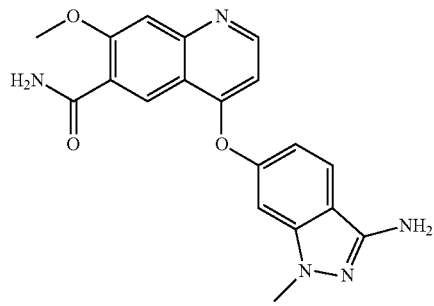 [SMILES: COc1cc2nccc(Oc3ccc4c(N)nn(C)c4c3)c2cc1C(N)=O]

Compound 193A (300 mg, 1.84 mmol), the compound of Example 1E (218 mg, 0.92 mmol) and cesium carbonate (899 mg, 2.76 mmol) were added to dimethylsulfoxide (4 mL). The reaction solution was heated to 100° C. and reacted for 14 hours. The reaction solution was diluted with water and extracted with a mixed solution of dichloromethane/isopropanol (3:1) (3×10 ml). The organic layer was washed with saturated NaCl solution, dried over anhydrous sodium sulfate, filtered, spin-dried and the residue was purified by column chromatography chromium (methylene chloride/methanol=10:1, Rf=0.3) to give compound 193B (yellow brown oily liquid, 190 mg, 34%). LCMS (ESI) m/z: 364.1 (M+1)

Example 193

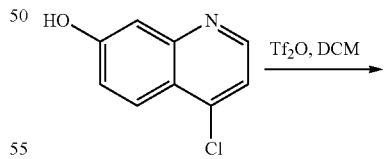

Pyridine (46 mg, 575 μmol) was added to a solution of the compound of Example 193B (317 mg, 523 μmol) and phenyl chlorothionocarbonate (135 mg, 784 μmol) in DMF (2 ml). The reaction solution was stirred at 30° C. for 2 hours, and then cyclopropylamine (60 mg, 1.05 mmol) and N,N'-diisopropylethylamine (135 mg, 1.05 mmol) were added to the reaction solution and continued stirring for 30 minutes. The reaction solution was diluted with water, extracted with a mixed solution of dichloromethane/isopropanol (3:1) (3×5 ml). The organic layer was washed with saturated NaCl solution, dried over anhydrous sodium sulfate, filtered and spin-dried. The residue was purified by preparative HPLC to give a compound of Example 193 (reddish brown solid, 6 mg, 2%).

LCMS (ESI) m/z: 463.1 (M+1)

$^1$H NMR (400 MHz, METHANOL-$d_4$) 9.11 (s, 1H), 8.90 (d, J=7.03 Hz, 1H), 8.19-8.26 (m, 1H), 7.6$_2$-7.65 (m, 1H), 7.16 (d, J=8.78 Hz, 1H), 7.02 (d, J=6.78 Hz, 1H), 4.24-4.25 (m, 1H), 4.00 (s, 1H), 0.73-1.02 (m, 3H)

Process AH

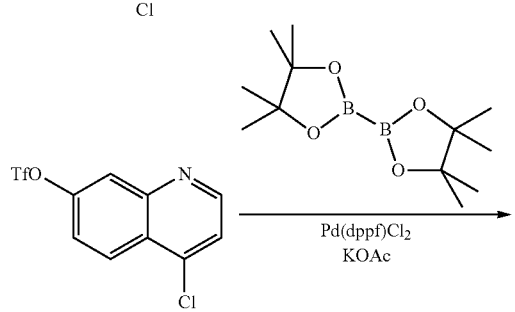

-continued

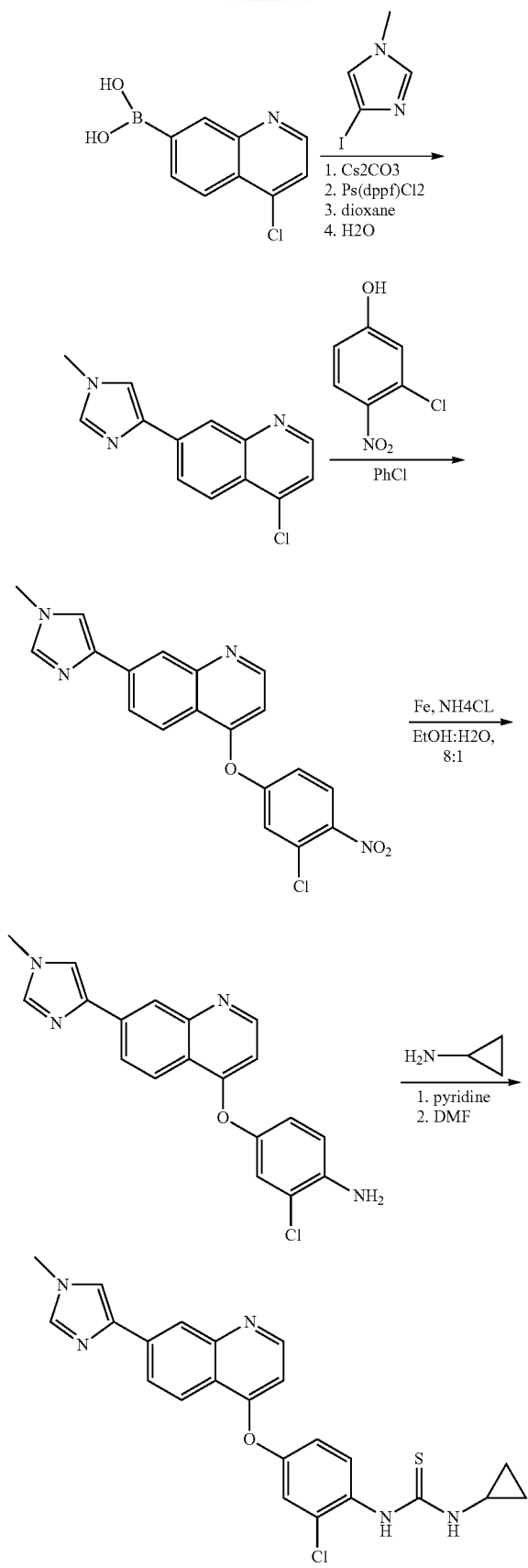

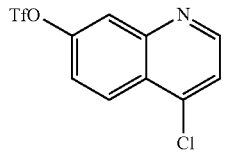

Compound 212A

4-Chloro-7-hydroxyquinoline (500 mg, 2.78 mmol) and pyridine (484.47 mg, 6.12 mmol) were added to dichloromethane (50 mL) at 28° C. under the protection of nitrogen and then trifluoromethanesulfonic anhydride (1.18 g, 4.17 mmol) was slowly added dropwise at 0° C. and the mixture was stirred at 28° C. for 2 hours. The solution was quenched with ammonium chloride saturated solution, extracted with dichloromethane (100 ml*2) and the organic phase was washed with saturated NaCl solution (100 ml), dried and filtered to give compound 212A (300 mg). The product was used directly in the next step without further purification. LCMS (ESI) m/z: 312 (M+1).

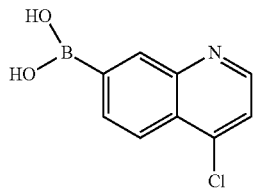

Compound 212B

Compound 212A (200 mg, 641.72 μmol), bis (pinacolato) diboron (195.55 mg, 770.07 μmol), ferrocene dichloropalladium(II) (140.87 mg, 192.52 μmol) and potassium acetate (188.94 mg, 1.93 mmol) were added to 1,4-dioxane (2 mL) at 28° C. under the protection of nitrogen. The solution was heated to 80° C. under the protection of nitrogen and stirred for 16 hours. The solution was cooled to room temperature, diluted with ethyl acetate (50 mL) and filtered, added with water (50 mL) and separated, the aqueous phase was extracted with ethyl acetate (50 mL*2), the organic phase was combined and washed once with saturated NaCl solution (100 mL), dried and evaporated to dryness to give compound 212B (50 mg). The product was used directly in the next step without further purification.
LCMS (ESI) m/z: 208 (M+1).

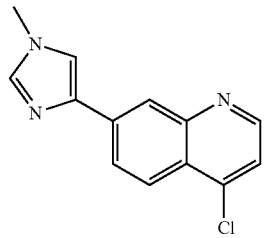

Compound 212C

Compound 212B (120 mg, 578.54 μmol) and 4-iodo-1-methylimidazole (144.4 mg, 694.24 μmol) were added to 1,4-dioxane (1.5 mL) at 28° C. under the protection of nitrogen, and then added with cesium carbonate (565.5 mg, 1.74 mmol) and ferrocene dichloropalladium (84.66 mg, 115.71 μmol), stirred at 100° C. for 16 hours under the protection of nitrogen. The reaction solution was filtered and evaporated to dryness to give compound 212C (120 mg). The product was used directly in the next step without further purification.

LCMS (ESI) m/z: 244 (M+1).

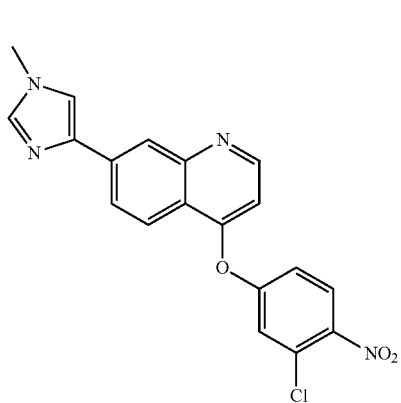

Compound 212D

Compound 212C (222.52 mg, 940.3 μmol) and 3-chloro-4-nitro-phenol (215 mg, 940.3 μmop were added to chlorobenzene (5 mL) at 22° C. under the protection of nitrogen, and reacted at 140° C. for 16 hours under the protection of nitrogen. The solution was cooled to room temperature, evaporated at 60° C. to dryness, and then diluted with water (30 mL), extracted with dichloromethane (50 mL*3), the organic phase was washed once with saturated NaCl solution (100 mL), dried and then evaporated to dryness to give compound 212D (152 mg). LCMS (ESI) m/z: 381 (M+1).

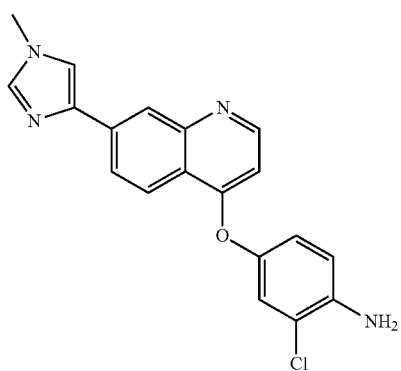

Compound 212E

Compound 212D (222.52 mg, 940.3 μmol) was added to a solution of ethanol (8 mL) and water (1 mL) at 22° C. under the protection of nitrogen, and then added with ammonium chloride (323.09, 6.04 mmol) and iron powder (337.35 mg, 6.04 mmol) to react at 80° C. for 2 hours under the protection of nitrogen. The solution was cooled to room temperature, filtered and evaporated at 45° C. to dryness, and then added with water (100 mL) and dichloromethane (100 mL) for separation. The aqueous phase was extracted with dichloromethane (100 mL*2), the organic phase was washed once with saturated NaCl solution (60 mL), dried and evaporated to dryness to give compound 212E (180 mg).

LCMS (ESI) m/z: 351 (M+1).

Example 212

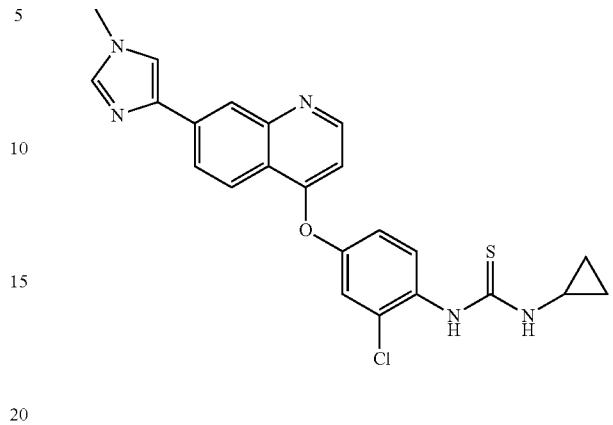

Compound 212E (50 mg, 142.53 μmop and pyridine (56.37 mg, 712.65 mmol) were added to N,N-dimethylformamide (2 mL) at 22° C. under the protection of nitrogen, and then added with ES891-99 (98.42 mg, 570.12 μmol) to react at 24° C. for 2 hours under the protection of nitrogen, and then added with cyclopropylamine (32.55 mg, 570.12 μmol) to react at 24° C. for 0.5 hours under the protection of nitrogen. The reaction solution was isolated by liquid chromatogram to give a compound of Example 212 (yellow solid, 3 mg, the yield was 4.2%).

LCMS S (ESI) m/z: 450 (M+1).

$^1$H NMR (400 MHz, METHANOL-$d_4$)=9.22 (s, 1H), 9.14 (d, J=6.8 Hz, 1H), 8.87 (d, J=8.8 Hz, 1H), 8.49 (s, 1H), 8.23 (d, J=8.8 Hz, 1H), 8.11 (s, 1H), 7.96 (br. s., 1H), 7.69 (s, 1H), 7.44 (d, J=7.3 Hz, 2H), 4.10 (s, 3H), 2.92-2.67 (m, 1H), 0.95 (br. s., 2H), 0.78 (br. s., 2H)

Example 213

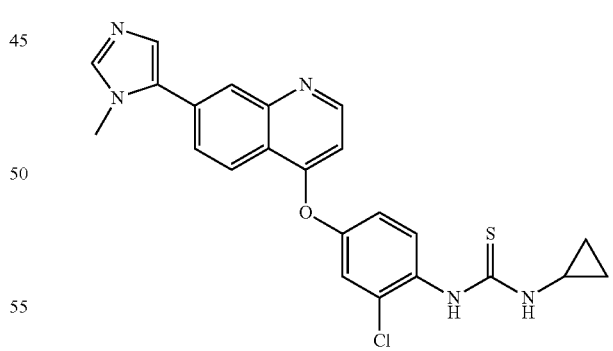

The compound of this Example was prepared by the method as described in Example 212.

LCMS (ESI) m/z: 450 (M+1)

$^1$H NMR (400 MHz, METHANOL-$d_4$)=8.96 (d, J=6.3 Hz, 1H), 8.70 (d, J=9.0 Hz, 1H), 8.65 (s, 1H), 8.46 (s, 1H), 8.26 (d, J=9.0 Hz, 1H), 8.20 (s, 1H), 7.64 (s, 1H), 7.39 (d, J=9.0 Hz, 1H), 7.25 (s, 1H), 4.00 (s, 3H), 0.94 (br. s., 2H), 0.77 (s, 1H)

301

Process A1

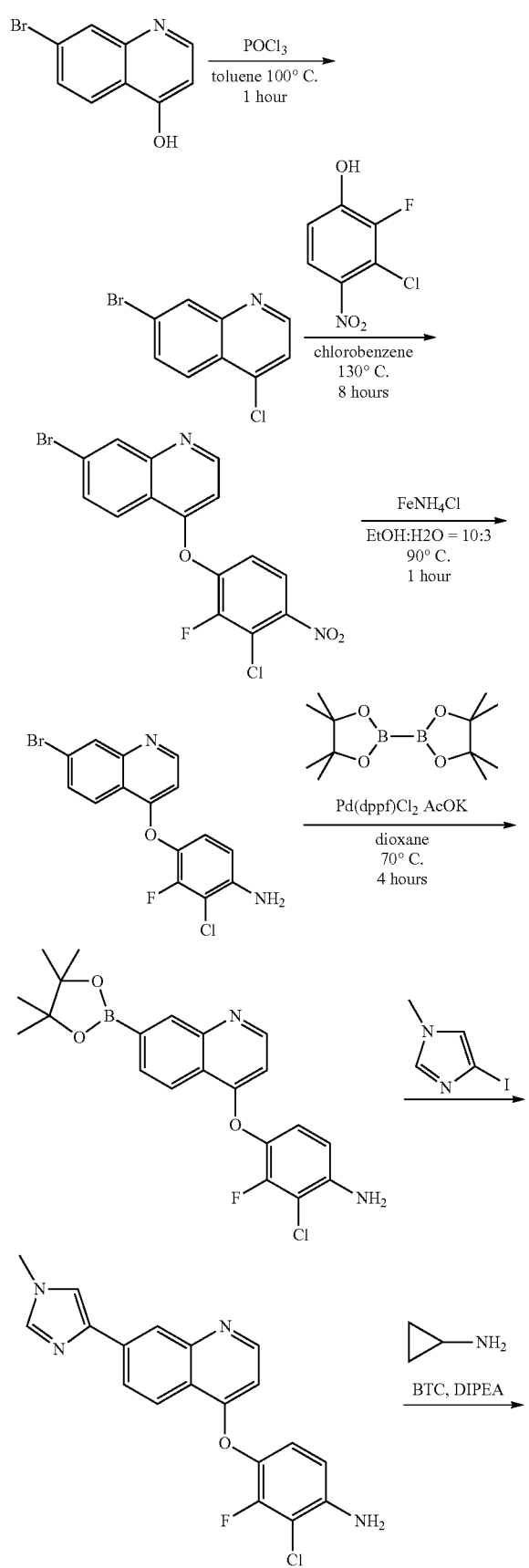

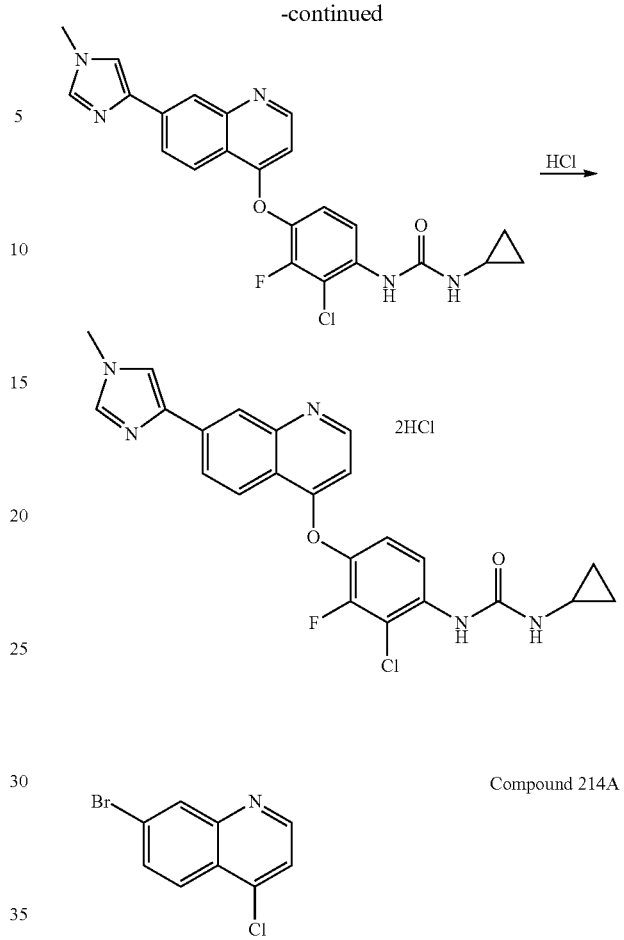

Compound 214A

Phosphorus oxychloride (106.76 g, 696.28 mmol) was added portionwise to 4-chloro-7-bromo-quinoline (60 g, 267.8 mmol) in dioxane (660 mL) at 30° C. After stirring at 100° C. for 40 minutes, the thin layer preparation chromatography showed that 4-chloro-7-bromo-quinoline had reacted completely and the reaction was quenched with water (200 mL) and then extracted with ethyl acetate (200 mL*2), the organic phase was washed with saturated NaCl solution (100 mL*2), dried over solid sodium sulfate and concentrated under reduced pressure to give compound 214A (pale yellow solid, 59 g, the yield was 81.77%).

LCMS (ESI) m/z: 243.8 (M+1).

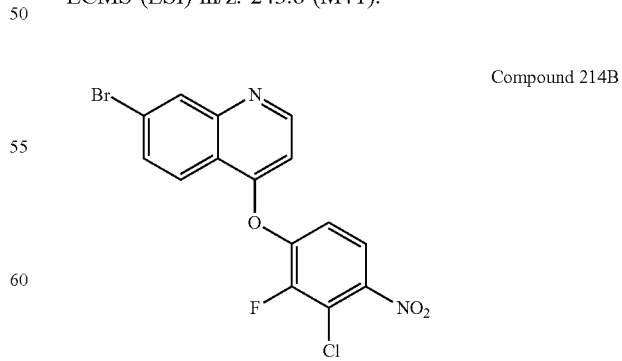

Compound 214B

A mixed solution of compound 214A (25 g, 103.09 mmol) and 2-fluoro-3-chloro-4-nitro-phenol (39.49 g, 206.19 mmol) in chlorobenzene (250 mL) reacted at 130° C. for 12 hours. The thin layer preparation chromatography showed that compound 216A had reacted completely. The reaction solution was cooled to room temperature, a yellow solid was produced then filtered to give compound 214B which was used directly in the next step without further purification.

LCMS (ESI) m/z: 396.8 (M+1)

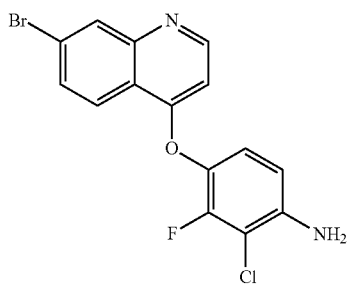

Compound 214C

Ammonium chloride (9.69 g, 181.10 mmol) and reduced iron powder (7.59 g, 135.82 mmol) were added to a mixed solution of compound 214B (18 g, 45.27 mmol) in ethanol (18 mL) and water (2 mL) at 20° C. After stirring at 90° C. for 2 hours, the thin layer preparation chromatography showed that compound 214B had reacted completely. The reaction was filtered through celite and the filtrate was concentrated under reduced pressure to give a residue. Water (10 mL) was added to the residue, and then extracted with dichloromethane (150 mL*2), the organic phase was washed with sodium hydroxide (0.5 mol/L, 50 mL*2), dried over anhydrous sodium sulfate and concentrated by reduced pressure to give compound 214C (brown red solid, 6.20 g, the yield was 29.81%).

LCMS (ESI) m/z: 368.8 (M+1).

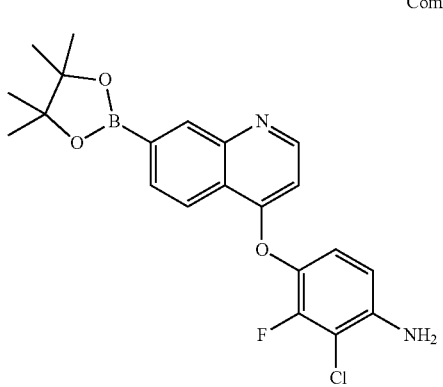

Compound 214D

Potassium acetate (4.81 g, 48.97 mmol) and Pd(dppf)Cl$_2$ (1.19 g, 1.63 mmol) were added to compound 214C (6 g, 16.32 mmol) in dioxane (60 mL) under the protection of nitrogen, the reaction solution was displaced with nitrogen three times. After stirring at 70° C. for 4 hours, the thin layer preparation chromatography showed that compound 214C had reacted completely. The reaction solution was quenched by addition of water (20 mL) and then extracted with ethyl acetate (50 mL*2). The organic phase was washed with saturated NaCl solution (20 mL*2), dried over anhydrous sodium sulfate and concentrated under reduced pressure to give compound 214D (pale yellow solid, 6.50 g, the yield was 81.64%).

LCMS (ESI) m/z: 243.8 (M+1).

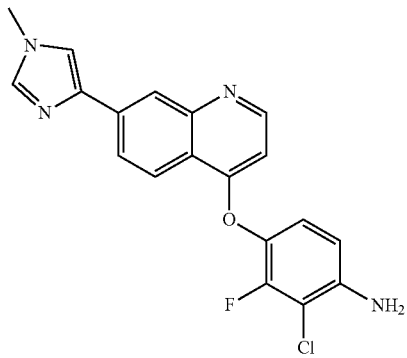

Compound 214E

Under the protection of nitrogen, 4-iodo-1-methylimidazole (651.66 mg 3.13 mmol) and potassium carbonate (1 g, 7.23 mmol) were added to a mixed solution of compound 214D (1 g, 2.41 mmol) in N,N'-dimethylformamide (6 mL) and water (2 mL) under the protection of nitrogen, the reaction solution was displaced with nitrogen three times and reacted in microwaves at 110° C. for 30 minutes. The thin layer preparation chromatography showed that compound 214D had reacted completely. The reaction was quenched by addition of water (10 mL) and then extracted with ethyl acetate (20 mL*3). The organic phase was washed with saturated NaCl solution (10 mL*2), dried over anhydrous sodium sulfate and concentrated under reduced pressure to give the residue which was then purified by column chromatography to give compound 214E (pale yellow solid, 300 mg, the yield was 29.03%). LCMS (ESI) m/z: 369.0 (M+1).

$^1$H NMR (400 MHz, DMSO-d$_6$) ppm 3.75 (s, 3H) 5.83 (s, 2H) 6.47-6.56 (m, 1H) 6.73 (d, J=9.03 Hz, 1H) 7.11-7.25 (m, 1H) 7.75 (s, 1H) 7.91 (s, 1H) 8.08 (d, J=8.03 Hz, 1H) 8.29 (d, J=8.53 Hz, 1H) 8.32-8.38 (m, 1H) 8.60-8.67 (m, 1 Hl

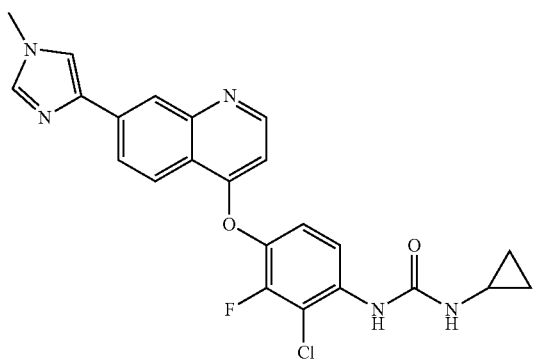

Compound 214F

In ice bath, triphosgene (160.93 mg, 542.31 μmop was added to a solution of compound 214E (200.00 mg, 542.31 μmop and N,N-diisopropylethylamine (350.44 mg, 2.71 μmop in tetrahydrofuran (20.00 mL) which had already stirred for 10 minutes, and then stirred for 3 hours. Cyclopropylamine (619.21 mg, 10.85 mmol) was then added to the reaction solution and then kept stirring for 1 hour. When LC-MS detection showed the reaction had completed, the reaction solution was quenched with water (15.00 mL) and a white solid was present, then filtered to give compound 214F (210.00 mg, 464.73 μmol, the yield was 85.69%). LCMS (ESI) m/z: 452.1 (M+1).

$^1$H NMR (400 MHz, METHANOL-d$_4$) δ ppm 0.58 (br. s., 2H) 0.81 (d, J=5.77 Hz, 2H) 2.66 (m, 1H) 3.85 (s, 3H) 6.63

(d, J=4.77 Hz, 1H) 7.36 (t, J=8.78 Hz, 1H) 7.77 (d, J=3.51 Hz, 2H) 8.09 (d, J=7.78 Hz, 2H) 8.33-8.39 (m, 1H) 8.39-8.45 (m, 1H) 8.58-8.73 (m, 1H)

Example 214

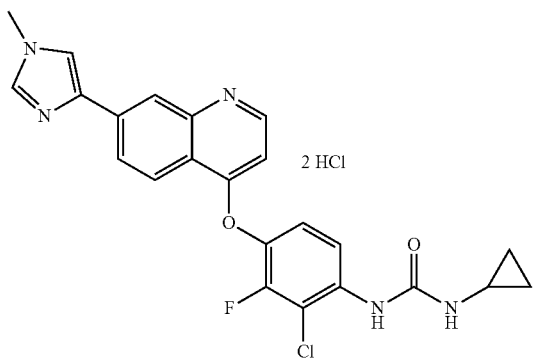 [SMILES: Cn1cnc(-c2ccc3c(Oc4ccc(NC(=O)NC5CC5)c(Cl)c4F)ccnc3c2)c1]

Compound 214F (643 mg, 1.42 mmol) was added to methanol (33 mL) and the reaction solution was then heated to reflux and diluted hydrochloric acid (1 mol/L, 30 drops) was added dropwise to the solution to clarify. The reaction solution was cooled to room temperature and the solution was removed by rotary evaporation to 10 mL and then ethyl acetate (100 mL) was added. A large amount of white solid was precipitated, and then filtered. The solid was washed with ethyl acetate and dried in vacuo to give a compound of Example 214 (white solid, the yield was 74.7%). LCMS (ESI) m/z: 452.1 (M+1).

$^1$H NMR (400 MHz, METHANOL-$d_4$)=9.24 (s, 1H), 9.11 (d, J=6.5 Hz, 1H), 8.85 (d, J=9.0 Hz, 1H), 8.64 (s, 1H), 8.47 (s, 1H), 8.37 (d, J=8.8 Hz, 1H), 8.23 (d, J=9.0 Hz, 1H), 7.51 (t, J=8.8 Hz, 1H), 7.30 (d, J=6.5 Hz, 1H), 4.11 (s, 3H), 2.67 (m, 1H), 0.81 (d, J=5.5 Hz, 2H), 0.59 (br. s., 2H)

The following compounds were also prepared by using the similar methods as described in Example 214:

| Examples | Structures | NMR | LCMS (ESI) m/z: (M + 1) |
|---|---|---|---|
| Example 216 | 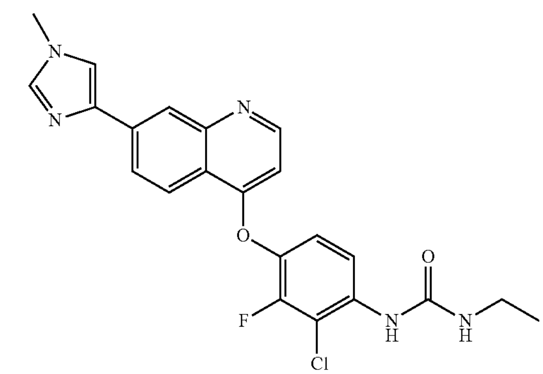 [SMILES: CCNC(=O)Nc1ccc(Oc2ccnc3cc(-c4cn(C)cn4)ccc23)c(F)c1Cl] | $^1$H NMR (400 MHz, METHANOL-$d_4$) d ppm 1.21 (t, J = 7.28 Hz, 3 H) 3.25-3.31 (m, 2 H) 3.86 (s, 3 H) 6.60-6.65 (m, 1 H) 7.31-7.39 (m, 1 H) 7.74-7.79 (m, 2 H) 8.04-8.13 (m, 2 H) 8.34-8.39 (m, 1 H) 8.39-8.44 (m, 1 H) 8.61-8.67 (m, 1 H) | 440.1 |
| Example 218 | 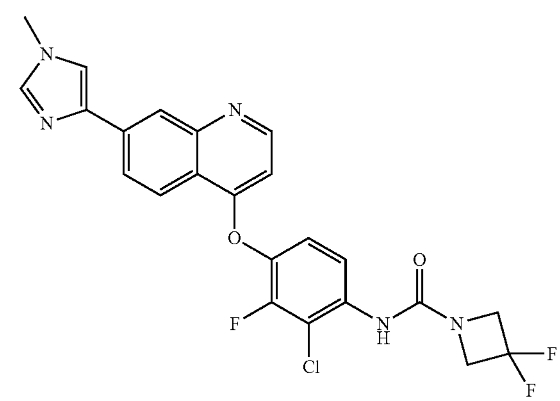 [SMILES: Cn1cnc(-c2ccc3c(Oc4ccc(NC(=O)N5CC(F)(F)C5)c(Cl)c4F)ccnc3c2)c1] | $^1$H NMR (400 MHz, METHANOL-$d_4$) d ppm 3.86 (s, 3 H) 4.44-4.57 (m, 4 H) 6.65-6.71 (m, 1 H) 7.36-7.43 (m, 1 H) 7.60-7.66 (m, 1 H) 7.75-7.81 (m, 1 H) 7.82-7.88 (m, 1 H) 8.06-8.13 (m, 1 H) 8.34-8.39 (m, 1 H) 8.39-8.47 (m, 1 H) 8.62-8.72 (m, 1 H). | 488.2; 510.2 [M + 1; M + 23] |

-continued

| Examples | Structures | NMR | LCMS (ESI) m/z: (M + 1) |
|---|---|---|---|
| Example 219 | 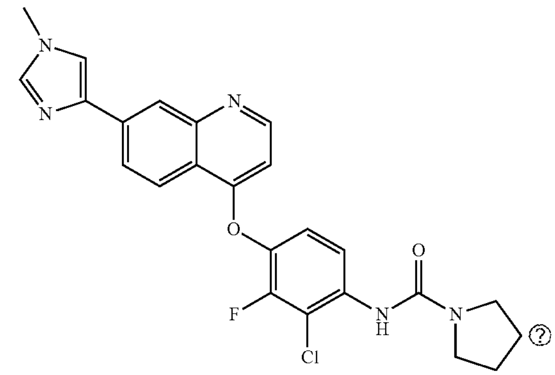 [SMILES: Cn1cnc(-c2ccc3c(Oc4ccc(NC(=O)N5CCCC5)c(Cl)c4F)ccnc3c2)c1] | $^1$H NMR (400 MHz, METHANOL-d$_4$) d ppm 1.97-2.10 (m, 4 H) 3.50-3.60 (m, 4 H) 3.88 (s, 3 H) 6.71-6.77 (m, 1 H) 7.37-7.42 (m, 1 H) 7.67-7.74 (m, 1 H) 7.82-7.86 (m, 1 H) 7.91-7.96 (m, 1 H) 8.09-8.16 (m, 1 H) 8.36-8.41 (m, 1 H) 8.43-8.49 (m, 1 H) 8.67-8.72 (m, 1 H) | 466.2 |
| Example 220 | 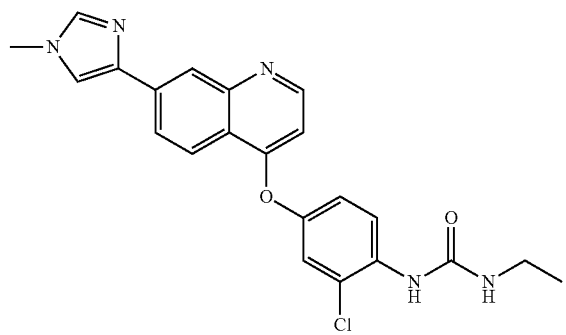 [SMILES: CCNC(=O)Nc1ccc(Oc2ccnc3cc(-c4cn(C)cn4)ccc23)cc1Cl] | 1H NMR (400 MHz, METHANOL-d4) = 8.63 (d, J = 5.3 Hz, 1H), 8.40-8.32 (m, 2H), 8.18 (d, J = 9.0 Hz, 1H), 8.06 (dd, J = 1.4, 8.7 Hz, 1H), 7.76 (d, J = 8.3 Hz, 2H), 7.39 (d, J = 2.8 Hz, 1H), 7.21 (dd, J = 2.8, 8.8 Hz, 1H), 6.65 (d, J = 5.5 Hz, 1H), 3.85 (s, 3H), 3.31-3.24 (m, 2H), 1.21 (t, J = 7.2 Hz, 3H) | 422 |
| Example 221 | 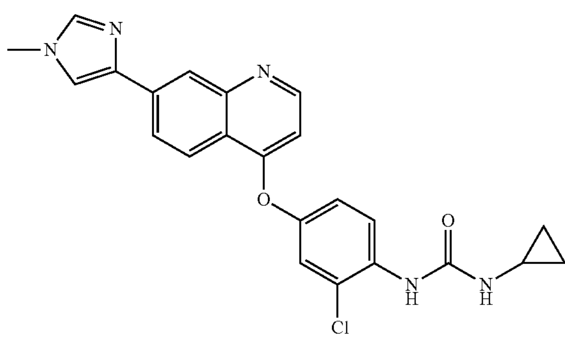 [SMILES: Cn1cnc(-c2ccc3c(Oc4ccc(NC(=O)NC5CC5)c(Cl)c4)ccnc3c2)c1] | $^1$H NMR (400 MHz, METHANOL-d$_4$) 8.63 (d, J = 5.27 Hz, 1H), 8.32-8.43 (m, 2H), 8.21 (d, J = 9.03 Hz, 1H), 8.06 (d, J = 8.78 Hz, 1H), 7.76 (d, J = 8.53 Hz, 2H), 7.40 (d, J = 2.26 Hz, 1H), 7.22 (dd, J = 2.38, 8.91 Hz, 1H), 6.65 (d, J = 5.27 Hz, 1H), 3.85 (s, 3H), 2.65 (tt, J = 3.61, 6.81 Hz, 1H), 0.80 (d, J = 5.77 Hz, 2H), 0.58 (br. s., 2H) | 433.9 |
| Example 226 | 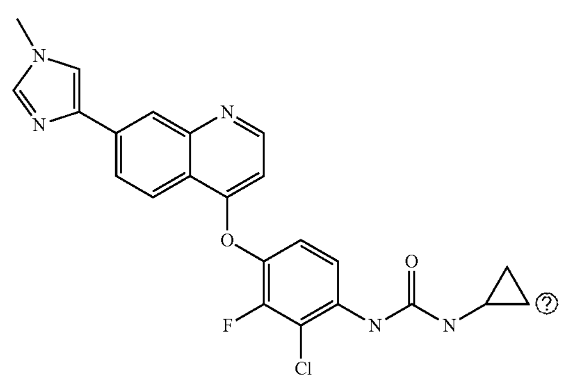 [SMILES: Cn1cnc(-c2ccc3c(Oc4ccc(NC(=O)NC5CC5)c(Cl)c4F)ccnc3c2)c1] | $^1$H NMR (400 MHz, METHANOL-d$_4$) d ppm 0.58 (br. s., 2 H) 0.81 (d, J = 5.77 Hz, 2 H) 1.60 (d, J = 6.53 Hz, 6 H) 2.66 (tt, J = 6.87, 3.54 Hz, 1 H) 4.57 (dt, J = 13.30, 6.65 Hz, 1 H) 6.60-6.67 (m, 1 H) 7.31-7.42 (m, 1 H) 7.87-7.95 (m, 2 H) 8.06-8.16 (m, 2 H) 8.35-8.39 (m, 1 H) 8.39-8.45 (m, 1 H) 8.61-8.67 (m, 1 H) | 514.1 |

-continued
| Examples | Structures | NMR | LCMS (ESI) m/z: (M + 1) |
|---|---|---|---|
| Example 227 | 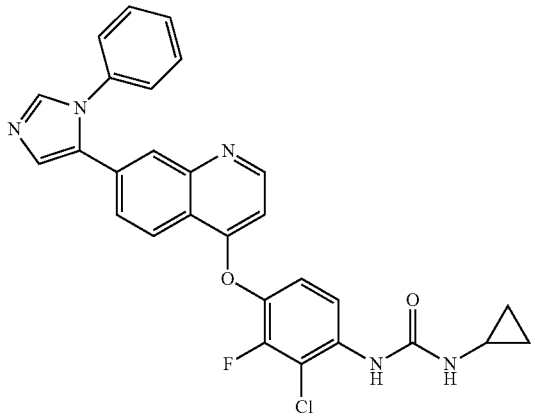 [SMILES: O=C(Nc1ccc(Oc2ccnc3cc(-c4cncn4-c4ccccc4)ccc23)c(F)c1Cl)NC1CC1] | $^1$H NMR (400 MHz, METHANOL-d$_4$) ppm 0.50-0.66 (m, 2 H) 0.74-0.84 (m, 2 H) 2.59-2.71 (m, 1 H) 6.64 (d, J = 5.27 Hz, 1 H) 7.32 (t, J = 8.91 Hz, 1 H) 7.35-7.40 (m, 2 H) 7.47-7.56 (m, 5 H) 7.77-7.84 (m, 1 H) 8.00-8.06 (m, 1 H) 8.06-8.13 (m, 1 H) 8.28-8.34 (m, 1 H) 8.56-8.63 (m, 1 H) | 514.1 |
| Example 228 | 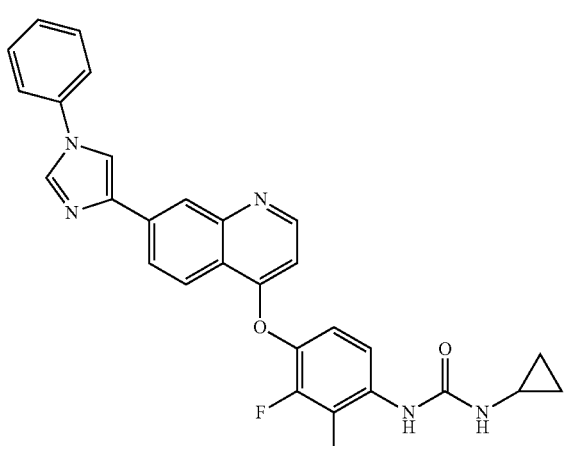 | $^1$H NMR (400 MHz, CHLOROFORM-d) ppm 0.58 (br. s., 2 H) 0.81 (d, J = 5.52 Hz, 2 H) 2.66 (dt, J = 6.78, 3.39 Hz, 1 H) 6.61-6.69 (m, 1 H) 7.33-7.41 (m, 1 H) 7.44-7.52 (m, 1 H) 7.56-7.65 (m, 2 H) 7.68-7.75 (m, 2 H) 8.06-8.14 (m, 1 H) 8.16-8.24 (m, 1 H) 8.27-8.34 (m, 2 H) 8.41-8.48 (m, 1 H) 8.48-8.53 (m, 1 H) 8.61-8.70 (m, 1 H) | 514.1 |
| Example 229 | 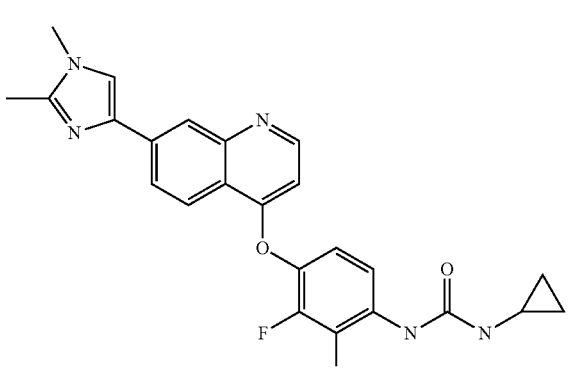 | $^1$H NMR (400 MHz, METHANOL-d$_4$) ppm 0.53-0.62 (m, 2 H) 0.76-0.86 (m, 2 H) 2.48 (s, 3 H) 2.63-2.70 (m, 1 H) 3.74 (s, 3 H) 6.59-6.64 (m, 1 H) 7.32-7.40 (m, 1 H) 7.62-7.67 (m, 1 H) 8.02-8.12 (m, 2 H) 8.29-8.35 (m, 1 H) 8.35-8.43 (m, 1 H) 8.60-8.66 (m, 1 H) | 466.1 |
Process AJ
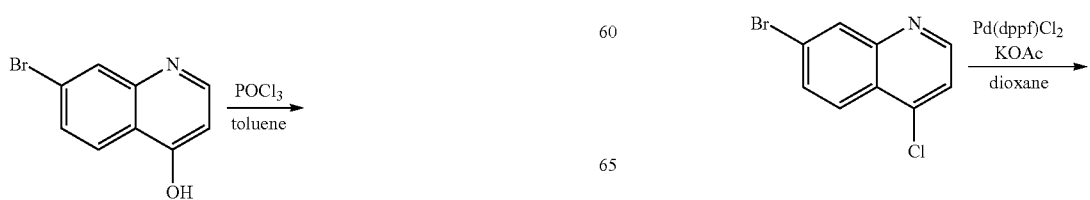

-continued

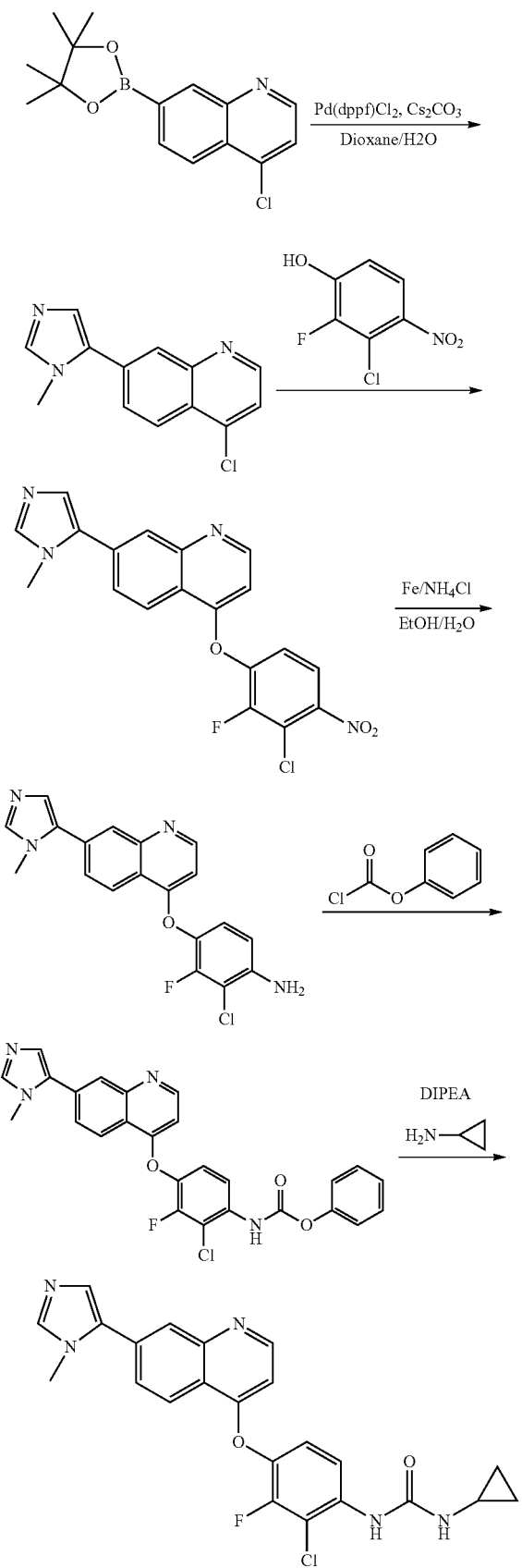

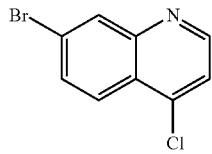

Compound 215A

Phosphorus oxychloride (35.6 g, 232 mmol) was added dropwise to a solution of 7-bromo-4-hydroxyquinoline (20 g, 89.3 mmol) in toluene (220 mL) at 30° C. over 10 minutes. The reaction solution was heated to 100° C. and reacted for 40 minutes. The excess of phosphorus oxychloride was distilled off by rotary evaporation and the residue was added to dichloromethane (200 mL), washed with water, dried over anhydrous sodium sulfate, filtered and evaporated to dryness. The residue was isolated by column chromatography (dichloromethane, Rf=0.5) to give compound 215A (creamy white solid, 12 g, 55%).

LCMS (ESI) m/z: 243.8 (M+1)

$^1$H NMR (400 MHz, CHLOROFORM-d) 7.53 (d, J=4.77 Hz, 1H) 7.76 (dd, J=9.03, 1.76 Hz, 1H) 8.13 (d, J=9.03 Hz, 1H) 8.34 (d, J=1.76 Hz, 1H) 8.80 (d, J=4.77 Hz, 1H)

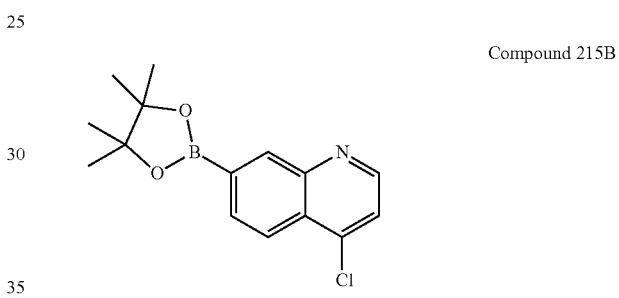

Compound 215B

Compound 215A (12 g, 49.5 mmol), 1,1-bis (triphenylphosphine) ferrocene dichloropalladium (3.62 g, 4.95 mmol), bis (pinacolato) diboron (18.85 g, 74.2 mmol) and potassium acetate (14.6 g, 148.4 mmol) were added to a solution of 1,4-dioxane (120 mL). The reaction solution was filled with nitrogen to degas for 3 minutes and then heated to 70° C. for 3 hours under the protection of nitrogen. The reaction was quenched by addition of 50 mL of water, and the reaction solution was extracted with ethyl acetate (2×200 mL). The organic phase was combined, washed with saturated NaCl solution, dried over anhydrous sodium sulfate, filtered and evaporated to dryness. The residue was isolated by column chromatography (petroleum ether/ethyl acetate=10:1 to 5:1, Rf=0.5) to give compound 215B (white solid, 11 g, 69%).

LCMS (ESI) m/z: 290.1 (M+1)

$^1$H NMR (400 MHz, CHLOROFORM-d) 8.89-8.77 (m, 1H), 8.67-8.57 (m, 1H), 8.29-8.15 (m, 1H), 8.07-7.94 (m, 1H), 7.59-7.47 (m, 1H), 1.42 (s, 10H)

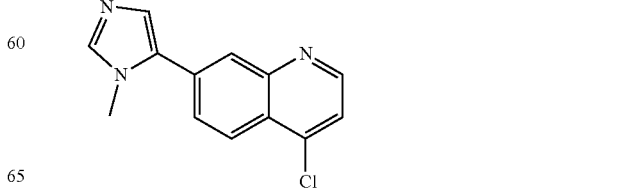

Compound 215C

Compound 215B (710 mg, 2.45 mmol), 5-iodo-1-methyl-imidazole (561 mg, 2.7 mmol), 1,1-bis (triphenylphosphine) ferrocene dichloropalladium (359 mg, 490 μmol) and cesium carbonate (2.4 g, 7.36 mmol) were added to a mixed solution of 1,4-dioxane (6 mL) and water (6 mL). The reaction solution was heated to 100° C. and reacted for 16 hours under the protection of nitrogen. The reaction solution was diluted with water (5 mL) and extracted with ethyl acetate (3×5 mL). The organic layers were combined, washed with saturated NaCl solution, dried over anhydrous sodium sulfate, filtered and evaporated to dryness. The residue was isolated by column chromatography (dichloromethane/methanol=20:1, Rf=0.4) to give compound 215C (yellow solid, 350 mg, 59%).

LCMS (ESI) m/z: 243.9 (M+1)

$^1$H NMR (400 MHz, CHLOROFORM-d)=8.84 (d, J=4.5 Hz, 1H), 8.32 (d, J=8.8 Hz, 1H), 8.17 (s, 1H), 7.80-7.73 (m, 1H), 7.66 (br. s., 1H), 7.54 (d, J=4.8 Hz, 1H), 7.41 (br. s., 1H), 3.86 (s, 3H)

Compound 215D

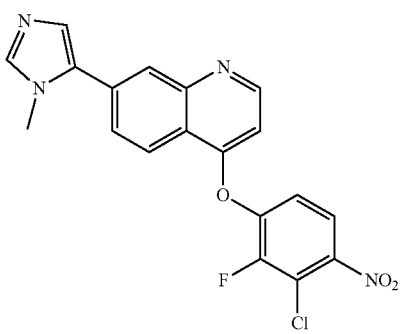

Compound 215C (350 mg, 1.44 mmol) and Compound 95B (414 mg, 2.16 mmol) were added to chlorobenzene (8 mL). The reaction was heated to 140° C. and reacted for 14 hours, and then evaporated to dryness. The residue was isolated by column chromatography (dichloromethane/methanol=20:1, Rf=0.4) to give compound 215D (yellow oily matter, 150 mg, 26%).

LCMS (ESI) m/z: 399.1 (M+1)

Compound 215E

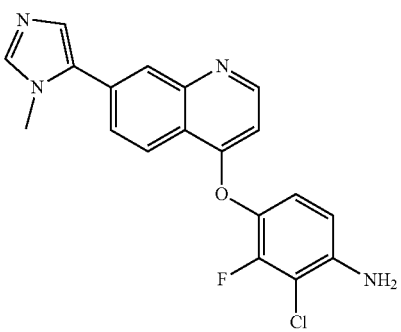

Iron powder (63 mg, 1.13 mmol) and ammonium chloride (81 mg, 1.5 mmol) were added to a mixed solution of compound 215D (150 mg, 376 μmol) in ethanol (2 mL) and water (0.2 mL). The reaction solution was heated to 80° C. and reacted for 15 minutes, filtered and rotary evaporated to dryness to give compound 215E (brown jelly matter, 50 mg, 36%) and the crude product was used directly in the next step.

LCMS (ESI) m/z: 369.0 (M+1)

Compound 215F

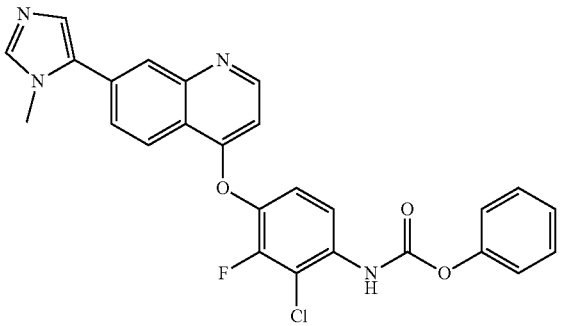

Compound 215E (50 mg 136 μmop, phenylchloroformate (21 mg, 136 μmol) and pyridine (11 mg, 136 μmol) were added to anhydrous DMF (1 mL). The reaction solution was reacted at 25° C. for 2 hours. After the completion of the reaction, the reaction solution was used directly in the next step. LCMS (ESI) m/z: 489.1 (M+1)

Example 215

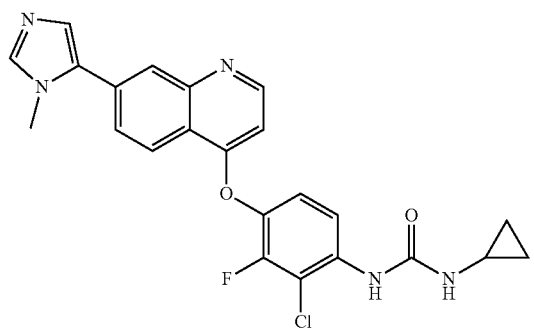 [SMILES: Cn1cncc1-c1ccc2c(Oc3ccc(NC(=O)NC4CC4)c(Cl)c3F)ccnc2c1]

Cyclopropylamine (7 mg, 123 μmol) and N,N-diisopropylethylamine (16 mg, 123 μmol) were added to a solution of compound 215F (the crude product was used directly in this step) in DMF. The reaction solution was reacted at 25° C. for 1 hour. The reaction solution was quenched by addition of water (3 mL) and extracted with ethyl acetate (3×5 mL). The organic layer was washed with saturated NaCl solution, dried over anhydrous sodium sulfate, filtered and spin-dried. The residue was isolated by preparative HPLC to give a compound of Example 215 (yellow solid, 11 mg, 18%).

LCMS (ESI) m/z: 452.0 (M+1)

$^1$H NMR (400 MHz, METHANOL-d$_4$) 8.72 (d, J=5.3 Hz, 1H), 8.52 (d, J=8.8 Hz, 1H), 8.15 (s, 1H), 8.11 (d, J=9.3 Hz, 1H), 7.90-7.83 (m, 2H), 7.40-7.36 (m, 1H), 7.34 (br. s., 1H), 6.73 (d, J=5.0 Hz, 1H), 3.91 (s, 3H), 2.67 (td, J=3.5, 6.8 Hz, 1H), 0.84-0.49 (m, 4H)

The following compounds were prepared by using the similar methods as described in Example 215:

| Examples | Structures | NMR | LCMS (ESI) m/z: (M + 1) |
|---|---|---|---|
| Example 230 | 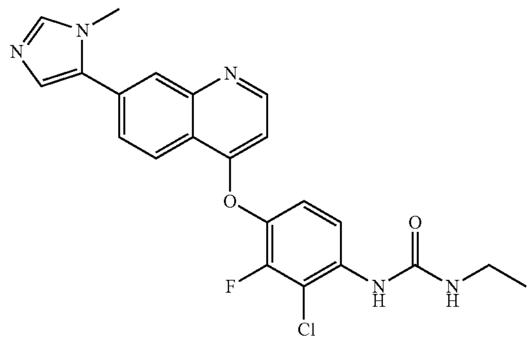 [SMILES: CCNC(=O)Nc1ccc(Oc2ccnc3cc(-c4cncn4C)ccc23)c(F)c1Cl] | ¹H NMR (400 MHz, METHANOL-d₄) ppm 1.21 (t, J = 7.28 Hz, 3 H) 3.24-3.31 (m, 2 H) 3.91 (s, 3 H) 6.72 (d, J = 5.52 Hz, 1 H) 7.31-7.40 (m, 2 H) 7.83-7.91 (m, 2 H) 8.05-8.12 (m, 1 H) 8.15 (s, 1 H) 8.52 (d, J = 8.53 Hz, 1 H) 8.72 (d, J = 5.52 Hz, 1 H) | 440.1 |
| Example 231 | 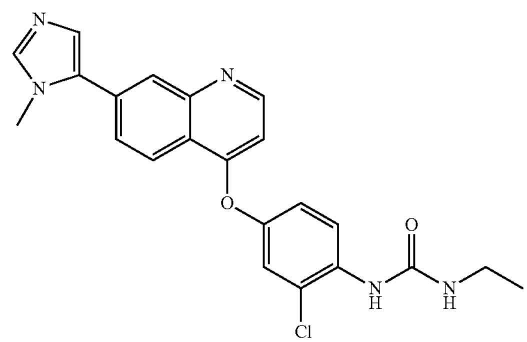 [SMILES: CCNC(=O)Nc1ccc(Oc2ccnc3cc(-c4cncn4C)ccc23)cc1Cl] | ¹H NMR (400 MHz, METHANOL-d₄) ppm 1.17-1.24 (m, 3 H) 3.25-3.31 (m, 2 H) 3.90 (s, 3 H) 6.75 (d, J = 5.27 Hz, 1 H) 7.23 (dd, J = 9.03, 2.76 Hz, 1 H) 7.33 (s, 1 H) 7.41 (d, J = 2.76 Hz, 1 H) 7.80-7.88 (m, 2 H) 8.13 (d, J = 1.00 Hz, 1 H) 8.21 (d, J = 9.03 Hz, 1 H) 8.49 (d, J = 8.78 Hz, 1 H) 8.71 (d, J = 5.27 Hz, 1 H) | 421.9 |
| Example 232 | 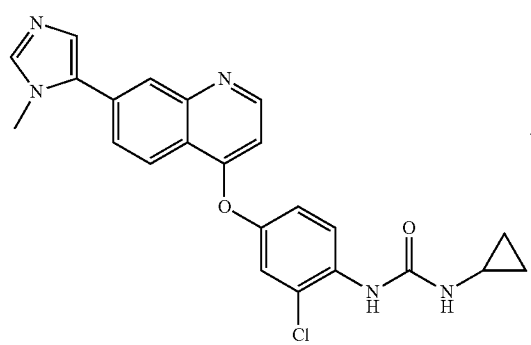 | ¹H NMR (400 MHz, METHANOL-d₄) ppm 0.79-0.93 (m, 5 H) 2.66 (tt, J = 6.90, 3.64 Hz, 1 H) 3.90 (s, 3 H) 6.75 (d, J = 5.27 Hz, 1 H) 7.24 (dd, J = 9.03, 2.76 Hz, 1 H) 7.32 (s, 1 H) 7.43 (d, J = 2.76 Hz, 1 H) 7.80-7.88 (m, 2 H) 8.14 (s, 1 H) 8.23 (d, J = 9.03 Hz, 1 H) 8.50 (d, J = 8.53 Hz, 1 H) 8.71 (d, J = 45.27 Hz, 1 H) | 433.9 |
Process AK
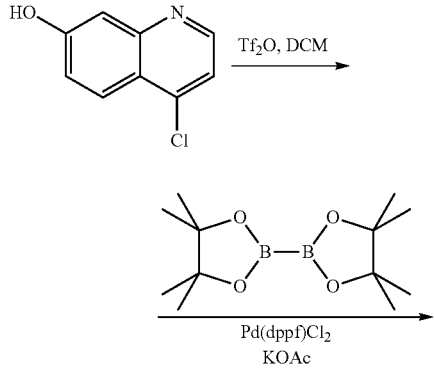
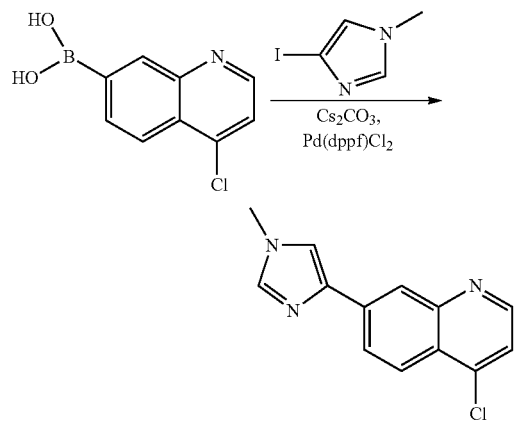

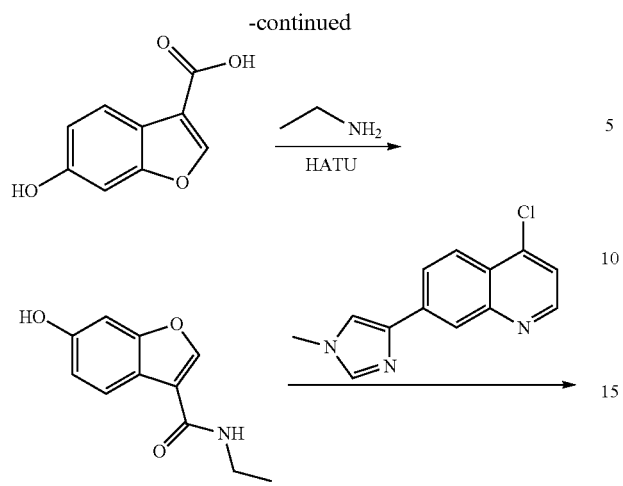

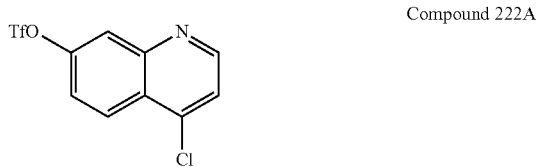 [SMILES: O=S(=O)(Oc1ccc2c(Cl)ccnc2c1)C(F)(F)F]

Compound 222A 4-chloro-7-hydroxyquinoline (500 mg, 2.78 mmol) and pyridine (484.47 mg, 6.12 mmol) were added to dichloromethane (50 mL) at 28° C. under the protection of nitrogen, and trifluoromethanesulfonic anhydride (1.18 g, 4.17 mmol) was slowly added dropwise at 0° C. and stirred at 28° C. for 2 hours. The solution was quenched with saturated ammonium chloride solution (100 mL*2) and extracted with dichloromethane (100 mL*2). The organic phase was washed with saturated NaCl solution (100 mL), filtered and dried to give compound 222A (300 mg), and the product was used directly in the next step without further purification.

LCMS (ESI) m/z: 312 (M+1).

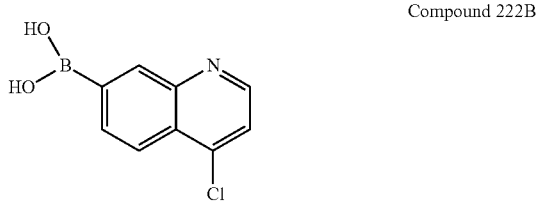 [SMILES: OB(O)c1ccc2c(Cl)ccnc2c1]

Compound 222B

Compound 222A (200 mg, 641.72 μmol), bis(pinacolato)diboron (195.55 mg, 770.07 μmol), ferrocene dichloropalladium (140.87 mg, 192.52 μmol) and potassium acetate (188.94 mg, 1.93 mmol) were added to 1,4-dioxane (2 mL) at 28° C. under the protection of nitrogen. The solution was heated to 80° C. under the protection of nitrogen and stirred for 16 hours. The solution was cooled to room temperature, diluted with ethyl acetate (50 mL) and filtered, and then added with water (50 mL) for separation. The aqueous phase was extracted with ethyl acetate (50 mL*2), the organic phase was combined, washed once with saturated NaCl solution (100 mL) and evaporated to dryness to give compound 222B (50 mg). The product was used directly in the next step without further purification.

LCMS (ESI) m/z: 208 (M+1).

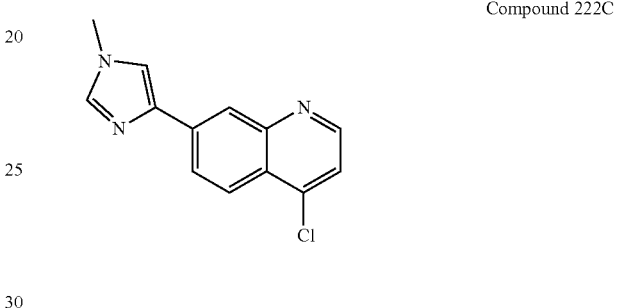

Compound 222C

Compound 222B (120 mg, 578.54 μmol) and 4-iodo-1-methyl-imidazole (144.4 mg, 694.24 μmol) were added to 1,4-dioxane (1.5 mL) at 28° C. under the protection of nitrogen, and then added with cesium carbonate (565.5 mg, 1.74 mmol) and ferrocene dichloropalladium (84.66 mg, 115.71 μmol) and stirred at 100° C. for 16 hours under the protection of nitrogen. The reaction solution was filtered and evaporated to dryness to give compound 222C (120 mg). The product was used directly in the next step without further purification.

LCMS (ESI) m/z: 244 (M+1).

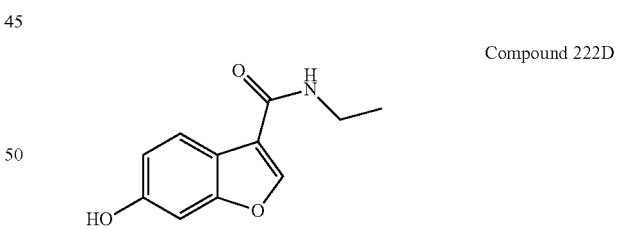

Compound 222D

Compound 185B (100 mg, 561.36 μmol) and ethylamine hydrochloride (45.77 mg, 561.36 μmol) were added to N,N-dimethylformamide (2 mL) at 22° C. under the protection of nitrogen, and then added with HATU (213.45 mg, 561.36 mmol) and N,N-diisopropylethylamine (362.75 mg, 2.81 mmol), and stirred at 22° C. for 2 hours under the protection of nitrogen. The reaction solution was added to water (100 mL) and extracted with ethyl acetate (50 mL*3), the organic phase was washed with saturated NaCl solution (115 mL) and dried over anhydrous sodium sulfate to give compound 222D (200 mg).

LCMS (ESI) m/z: 206 (M+1).

Example 222

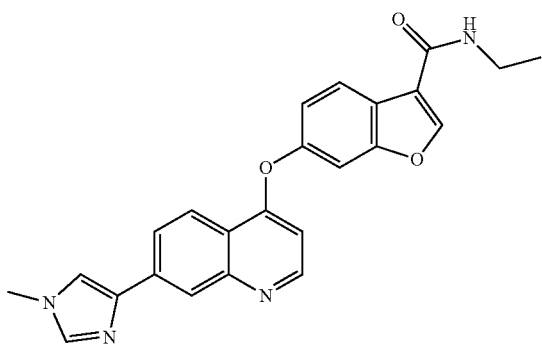 [SMILES: CCNC(=O)c1coc2cc(Oc3ccnc4cc(-c5cn(C)cn5)ccc34)ccc12]

Compound 222C (163.88 mg, 672.48 μmol), compound 222D (138 mg, 672.48 μmop) and cesium carbonate (438.21 mg, 1.88 mmol) were added to N,N-dimethylformamide (2 ml) at 22° C. under the protection of nitrogen, and reacted in the microwave at 120° C. for 1 hour. The solution was filtered and purified by liquid chromatogram to give a compound of Example 222 (yellow solid, 46 mg, the yield was 15.92%).

LCMS (ESI) m/z: 413 (M+1).

$^1$H NMR (400 MHz, METHANOL-$d_4$)=8.61-8.54 (m, 1H), 8.40-8.30 (m, 3H), 8.16 (d, J=8.3 Hz, 1H), 8.01 (d, J=8.5 Hz, 1H), 7.78-7.65 (m, 2H), 7.47 (d, J=1.5 Hz, 1H), 7.23 (dd, J=1.6, 8.4 Hz, 1H), 6.56 (d, J=5.3 Hz, 1H), 3.82 (s, 3H), 3.45 (q, J=7.1 Hz, 2H), 1.30-1.28 (m, 1H), 1.27 (t, J=7.2 Hz, 3H)

The following compounds were also prepared by using the similar methods as described in Example 222 mentioned above:

| Examples | Structures | NMR | LCMS (ESI) m/z: (M + 1)<sup>+</sup> |
|---|---|---|---|
| Example 223 | 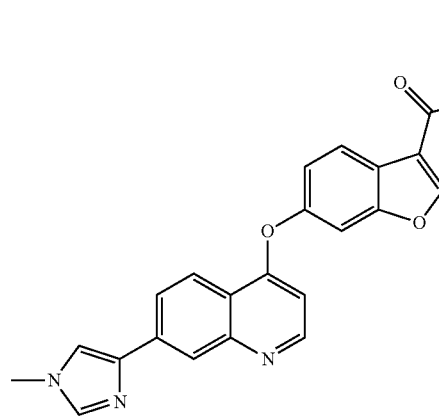 | $^1$H NMR (400 MHz, METHANOL-$d_4$) = 8.61 (d, J = 5.5 Hz, 1H), 8.43 (d, J = 8.8 Hz, 1H), 8.39-8.34 (m, 2H), 8.22 (d, J = 8.5 Hz, 1H), 8.08 (dd, J = 1.8, 8.8 Hz, 1H), 7.80-7.72 (m, 3H), 7.64 (dd, J = 3.3, 5.8 Hz, 1H), 7.55 (d, J = 2.0 Hz, 1H), 7.30 (dd, J = 2.0, 8.5 Hz, 1H), 6.62 (d, J = 5.5 Hz, 1H), 3.85 (s, 4H), 2.92-2.86 (m, 1H), 0.85-0.83 (m, 2H), 0.69 (dd, J = 2.1, 3.9 Hz, 2H) | 425 |
| Example 224 | 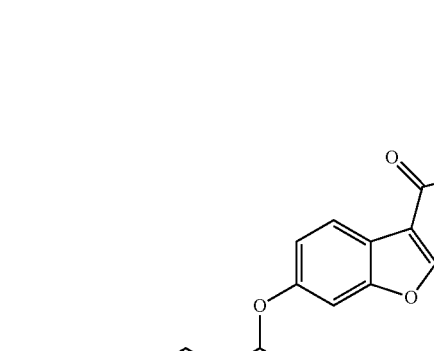 | $^1$H NMR (400 MHz, METHANOL-$d_4$) = 8.59 (d, J = 5.3 Hz, 1H), 8.47-8.31 (m, 3H), 8.18 (d, J = 8.5 Hz, 1H), 8.04 (d, J = 8.8 Hz, 1H), 7.74 (d, J = 15.3 Hz, 2H), 7.51 (s, 1H), 7.27 (d, J = 8.5 Hz, 1H), 6.59 (d, J = 5.3 Hz, 1H), 3.83 (s, 3H) | 402 |

| Examples | Structures | NMR | LCMS (ESI) m/z: (M + 1)+ |
|---|---|---|---|
| Example 225 | 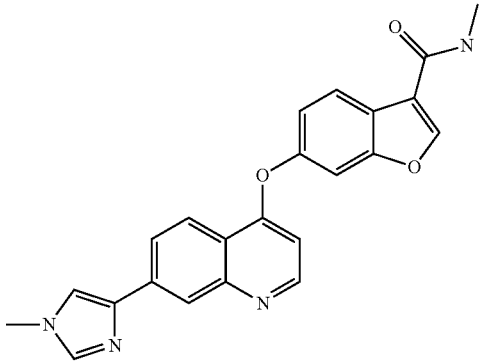 | ¹H NMR (400 MHz, METHANOL-d₄) = 8.58 (d, J = 5.3 Hz, 1H), 8.40-8.32 (m, 3H), 8.18 (d, J = 8.5 Hz, 1H), 8.04 (dd, J = 1.6, 8.7 Hz, 1H), 7.77-7.70 (m, 2H), 7.51 (d, J = 2.0 Hz, 1H), 7.26 (dd, J = 2.3, 8.5 Hz, 1H), 6.58 (d, J = 5.3 Hz, 1H), 3.83 (s, 3H), 2.97 (s, 3H) | 399 |

Experimental Example 1: In Vitro Enzyme Activity Assay of the Compounds of the Present Invention Experimental Objectives The enzyme activity was measured by Z'-LYTE™ Detection Kinase Assay. The $IC_{50}$ value of the compounds was used as an index to evaluate the inhibitory effect of the compounds on VEGFR2, FGFR1 and PDGFRB.

Experimental Materials

Recombinant human VEGFR2 and FGFR1 proteases were purchased from Life technology, PDGFRB Protease was purchased from Millipore.

Z-LYTE™ Kit Tyr1 and Tyr4 were purchased from Life technology. Multi-microplate reader, Envision (PerkinElmer) read board was used.

Experimental Methods

The test compounds were diluted 3 times with a concentration gradient, the final concentration was from 10 µM to 0.17 nM with a total of 11 concentrations, and each concentration had two parallel holes; the content of DMSO in the assay was 1%.

VEGFR2 Enzymatic Reaction:

3 nM VEGFR2 protein kinase, 2 µM Tyr1 peptide, 100 µM ATP, 50 mM HEPES (pH 7.5), 10 mM $MgCl_2$, 1 mM EGTA, 0.01% BRIJ-35. The detector plate was Black Proxiplate 384-Plus plate (PerkinElmer), the reaction was performed at room temperature for 60 minutes, and the reaction system was 10 µl.

FGFR1 Enzymatic Reaction:

1 nM FGFR1 protein kinase, 2 µM Tyr4 peptide, 25 µM ATP, 50 mM HEPES (pH 7.5), 10 mM $MgCl_2$, 1 mM EGTA, 0.01% BRIJ-35, 2 mM $MnCl_2$, 1 mM DTT. The detector plate was Black Proxiplate 384-Plus plate (PerkinElmer), the reaction was performed at room temperature for 60 minutes, and the reaction system was 10 µl.

PDGFRB Enzymatic Reaction:

40 nM PDGFRB protein kinase, 2 µM Tyr4 peptide, 100 µM ATP, 50 mM HEPES (pH 7.5), 10 mM $MgCl_2$, 1 mM EGTA, 0.01% BRIJ-35, 2 mM $MnCl_2$, 1 mM DTT. The detector plate was Black Proxiplate 384-Plus plate (PerkinElmer), the reaction was performed at room temperature for 60 minutes, and the reaction system was 10 µl.

Reaction Detection:

The reaction was stopped by adding 5 µl of DV reagent B (1:128) to the kinase reaction solution and incubated at 23° C. for 60 minutes. The Envision instrument was used to read the plate.

Data Analysis

The data was converted to phosphorylation rate and inhibition rate and the 4 parameter curve fitting (Model 205 in XLFIT5, iDBS) was used to get $IC_{50}$ data of the compounds.

The experimental results were shown in Table 1:

TABLE 1

The test results of $IC_{50}$ detected by Z'-LYTE ™

| Test samples (Compounds) | VEGFR2 | FGFR1 | PDGFRB |
|---|---|---|---|
| Example 1 | AAA | A | AA |
| Example 2 | AA | A | AA |
| Example 3 | A | A | A |
| Example 4 | AA | A | A |
| Example 5 | AA | A | AA |
| Example 6 | AAA | A | AA |
| Example 7 | AA | A | A |
| Example 8 | A | A | A |
| Example 9 | A | A | AAA |
| Example 10 | AA | A | AA |
| Example 11 | A | A | AA |
| Example 12 | AAA | AA | AA |
| Example 14 | A | A | AA |
| Example 15 | A | A | AA |
| Example 16 | AAA | A | AA |
| Example 17 | A | A | AA |
| Example 18 | A | A | A |
| Example 19 | A | A | AAA |
| Example 20 | AA | A | AAA |
| Example 21 | AAA | A | AA |
| Example 22 | AA | A | AA |
| Example 23 | A | A | AA |
| Example 27 | AA | A | AA |
| Example 28 | AAA | AA | AAA |
| Example 29 | AA | A | AA |
| Example 30 | A | A | A |
| Example 32 | AAA | A | A |
| Example 33 | A | A | AA |
| Example 35 | AAA | AA | AA |
| Example 36 | A | A | A |
| Example 41 | AAA | A | A |
| Example 42 | A | A | A |
| Example 43 | A | A | AAA |

TABLE 1-continued

The test results of IC$_{50}$ detected by Z'-LYTE ™

| Test samples (Compounds) | VEGFR2 | FGFR1 | PDGFRB |
|---|---|---|---|
| Example 43 | A | A | AAA |
| Example 51 | A | A | AA |
| Example 52 | AAA | A | AA |
| Example 55 | AA | AA | A |
| Example 56 | AAA | AA | AAA |
| Example 57 | AAA | A | AA |
| Example 59 | AAA | A | AA |
| Example 60 | A | A | A |
| Example 61 | A | A | AA |
| Example 63 | AA | A | AAA |
| Example 64 | AA | A | AAA |
| Example 65 | AA | A | AAA |
| Example 66 | AA | A | A |
| Example 67 | AA | A | A |
| Example 68 | AA | AA | AA |
| Example 69 | AA | A | AA |
| Example 70 | AAA | A | AAA |
| Example 71 | AA | A | AA |
| Example 73 | AA | A | A |
| Example 74 | AA | A | A |
| Example 75 | A | A | A |
| Example 85 | A | A | A |
| Example 86 | A | A | A |
| Example 87 | AA | A | A |
| Example 92 | AA | A | AA |
| Example 93 | A | A | A |
| Example 94 | A | A | A |
| Example 72 | AA | A | AA |
| Example 24 | A | A | A |
| Example 26 | AA | A | A |
| Example 34 | A | A | AA |
| Example 25 | A | A | A |
| Example 126 | AAA | N/A | N/A |
| Example 127 | AAA | N/A | N/A |
| Example 31 | A | A | A |
| Example 58 | AAA | A | AA |
| Example 174 | AAA | A | AAA |
| Example 37 | AAA | A | AA |
| Example 178 | A | A | A |
| Example 38 | AA | A | A |
| Example 39 | AA | A | AA |
| Example 40 | AA | A | AA |
| Example 47 | A | A | A |
| Example 48 | A | A | AA |
| Example 49 | A | A | AA |
| Example 50 | AAA | A | AA |
| Example 53 | A | A | AA |
| Example 54 | AA | A | A |
| Example 62 | AA | A | AA |
| Example 183 | A | A | A |
| Example 45 | A | A | A |
| Example 76 | A | A | A |
| Example 80 | AA | A | A |
| Example 81 | A | A | AA |
| Example 82 | A | A | AA |
| Example 83 | AA | A | AA |
| Example 90 | A | AA | A |
| Example 91 | AA | A | A |
| Example 84 | A | A | A |
| Example 88 | A | A | A |
| Example 89 | A | A | A |
| Example 95 | AAA | AA | AA |
| Example 98 | AAA | AAA | AA |
| Example 78 | AAA | AA | AAA |
| Example 103 | AAA | AA | A |
| Example 105 | A | A | A |
| Example 106 | AAA | AA | AA |
| Example 108 | AA | AA | A |
| Example 111 | AA | AA | A |
| Example 112 | AAA | AAA | AAA |
| Example 123 | AAA | AAA | AA |
| Example 124 | AAA | AAA | AAA |
| Example 77 | AAA | A | AA |
| Example 101 | A | A | AA |
| Example 113 | A | A | A |
| Example 107 | AAA | A | AA |
| Example 115 | A | A | A |
| Example 117 | AA | A | AA |
| Example 118 | AA | A | AA |
| Example 119 | AA | A | AAA |
| Example 120 | AA | A | AA |
| Example 121 | AA | A | A |
| Example 122 | AA | A | AAA |
| Example 125 | A | N/A | N/A |
| Example 128 | A | N/A | N/A |
| Example 129 | A | N/A | N/A |
| Example 130 | A | N/A | N/A |
| Example 136 | A | A | A |
| Example 137 | A | A | A |
| Example 138 | A | A | A |
| Example 139 | A | A | A |
| Example 140 | A | A | A |
| Example 141 | A | A | A |
| Example 142 | A | A | A |
| Example 143 | A | A | A |
| Example 144 | A | A | A |
| Example 145 | A | A | AAA |
| Example 146 | A | A | A |
| Example 147 | A | A | A |
| Example 148 | A | A | AAA |
| Example 149 | A | A | A |
| Example 150 | A | A | AAA |
| Example 151 | A | A | AAA |
| Example 152 | A | A | A |
| Example 153 | A | A | A |
| Example 154 | A | A | A |
| Example 155 | A | A | AAA |
| Example 160 | A | A | A |
| Example 131 | A | N/A | N/A |
| Example 132 | A | N/A | N/A |
| Example 133 | A | N/A | N/A |
| Example 134 | A | N/A | N/A |
| Example 135 | A | N/A | N/A |
| Example 161 | A | A | A |
| Example 156 | A | A | A |
| Example 157 | A | A | A |
| Example 158 | A | A | A |
| Example 159 | A | N/A | N/A |
| Example 162 | A | A | A |
| Example 164 | A | A | A |
| Example 165 | A | A | A |
| Example 166 | AAA | A | AA |
| Example 167 | AAA | A | AAA |
| Example 168 | A | A | A |
| Example 169 | AA | A | AA |
| Example 171 | A | A | A |
| Example 170 | AAA | A | A |
| Example 172 | A | A | A |
| Example 173 | A | A | A |
| Example 175 | A | A | A |
| Example 176 | A | A | A |
| Example 177 | A | A | AA |
| Example 179 | A | N/A | N/A |
| Example 180 | A | A | A |
| Example 181 | A | A | A |
| Example 182 | AA | A | A |
| Example 184 | A | A | A |
| Example 185 | AAA | AA | A |
| Example 201 | A | A | A |
| Example 202 | A | A | A |
| Example 187 | A | A | A |
| Example 200 | AAA | AA | AAA |
| Example 203 | A | A | AA |
| Example 210 | AAA | A | AAA |
| Example 205 | A | A | A |
| Example 206 | A | A | A |
| Example 186 | AAA | A | A |
| Example 188 | A | A | A |
| Example 189 | A | A | A |
| Example 190 | A | A | A |

TABLE 1-continued

The test results of IC$_{50}$ detected by Z'-LYTE ™

| Test samples (Compounds) | VEGFR2 | FGFR1 | PDGFRB |
|---|---|---|---|
| Example 191 | A | A | A |
| Example 192 | A | N/A | N/A |
| Example 194 | A | A | A |
| Example 195 | A | A | A |
| Example 196 | A | A | A |
| Example 211 | AA | A | AAA |
| Example 197 | A | A | A |
| Example 198 | A | A | A |
| Example 199 | AA | A | AAA |
| Example 204 | A | A | A |
| Example 207 | AAA | A | AAA |
| Example 208 | AA | A | AAA |
| Example 209 | AA | AA | AAA |
| Example 193 | A | A | AA |
| Example 212 | AAA | A | AAA |
| Example 213 | AAA | AA | AA |
| Example 214 | AAA | AAA | AA |
| Example 216 | AAA | AAA | AA |
| Example 218 | AAA | AA | AAA |
| Example 219 | AAA | AAA | AA |
| Example 220 | AAA | AAA | AA |
| Example 221 | AAA | AAA | AA |
| Example 226 | AAA | AAA | AA |
| Example 227 | AA | A | A |
| Example 228 | A | A | A |
| Example 229 | AAA | AAA | AAA |
| Example 215 | AAA | AA | AA |
| Example 222 | AAA | AAA | AA |
| Example 223 | AAA | AAA | AA |
| Example 224 | AAA | AAA | AAA |
| Example 225 | AAA | AAA | AA |

Remark:
VEGFR2: 200 nM ≤ A < 1 uM, 50 nM ≤ AA < 200 nM, AAA < 50 nM, N/A indicates unmeasured.
FGFR1: 200 nM ≤ A < 1 uM, 50 nM ≤ AA < 200 nM, AAA < 50 nM, N/A indicates unmeasured.
PDGFRB: 200 nM ≤ A < 1 uM, 50 nM ≤ AA < 200 nM, AAA < 50 nM, N/A indicates unmeasured.
Conclusions:
The compounds of the present invention had excellent inhibitory activity against VEGFR2, FGFR1 and PDGFRB in vitro, wherein,
1. By comparing Example 122 and Example 123, Example 113 and Example 108, Example 115 and Example 111, Example 117 and Example 103, Example 118 and Example 106, Example 119 and Example 95, Example 120 and Example 98, it was found that the structure of thiourea could greatly enhance its inhibitory activity against VEGFR2 and FGFR1 kinase than the structure of urea.
2. By comparing Example 1 and Example 78, Example 28 and Example 112, Example 32 and Example 98, Example 56 and Example 124, Example 74 and Example 106, Example 87 and Example 123, it was found that the addition of fluoride to the ortho position of chlorine on the benzene ring can greatly enhance the inhibitory activity of its FGFR1 kinase;
3. By comparing Example 77 and Example 78, it was found that fluoride and chloride in the same side can significantly increase the inhibitory activity against FGFR1 kinase than they were in opposite side.

Experimental Example 2: In Vitro Cytologic Inhibitory Activity Assay of the Compounds of the Present Invention Experimental Objectives The intracellular ATP changes were measured by CellTiter-Glo® Luminescent Cell Viability Assay. The IC$_{50}$ value of the compounds was used as an index to evaluate the inhibitory effect of the compounds on HUVEC in vitro.

Experimental Materials

HUVEC cell line (ATCC), EGM-2 BulletKit (Lonza), hVEGF-165 (Cell Signaling), trypsin (Invitrogen), DPBS (Hyclone), 384 cell plate (Greiner), 384 compound plate (Greiner), CO$_2$ incubator (Thermo), centrifuge (Eppendorf), Vi-cell cell counter (Beckman Coulter), Bravo Automatic Liquid Workstation (Agilent), Envision (Perkin Elmer)

Experimental Methods

A: Cell recovery and growth.

B: Cell plating: HUVEC cells were resuspended with starved medium (only containing 2% FBS and 0.1% GA-1000) and diluted to a concentration of 20,000/mL. The diluted cells were added to a 384 plate (Greiner), 50 µl per well. The cell plates were placed in a 37° C., 5% CO$_2$ incubator overnight.

C: Drug addition: the test compounds were diluted 4 times to obtain a total of 10 doses at a final concentration of 10 uM to 0.038 nM, two parallel wells. The middle plate was added with 47.6 uL of starved medium per well. 2.4 µl of compounds was transferred from a gradient dilution compound plate to a middle plate and mixed well. 5 µl of liquid was transferred from the middle plate to a cell plate. Incubate for 1 hour at 37° C. in a 5% CO$_2$ incubator, 5 µl of starved medium containing hVEGF-165 (the final concentration was 20 ng/ml) and Heparin (the final concentration was 1 ng/m) were added and incubated at 37° C. in a 5% CO$_2$ incubator for 72 hours.

D: After 72 hours, 30 µl of assay reagents was added and incubated at room temperature for 10-30 minutes, Envision was used to read the plate.

Data Processing

The reading was converted into suppression rate (%) (Max−Sample)/(Max−Min)*100%. Parameter curve fitting (Model 205 in XLFIT5, iDBS) was used to measure to obtain IC$_{50}$ data.

The experimental results were shown in Table 2:

TABLE 2

The test results of IC$_{50}$ detected by CellTiter-Glo ® T

| Test samples (Compounds) | HUVEC |
|---|---|
| Example 1 | AA |
| Example 2 | AA |
| Example 6 | AA |
| Example 12 | AA |
| Example 16 | AA |
| Example 21 | AA |
| Example 28 | AA |
| Example 50 | A |
| Example 55 | A |
| Example 56 | AA |
| Example 58 | A |
| Example 59 | A |
| Example 70 | AA |
| Example 78 | AA |
| Example 95 | A |
| Example 98 | A |
| Example 103 | A |
| Example 107 | AA |
| Example 112 | AA |
| Example 123 | A |
| Example 124 | AA |
| Example 127 | AA |
| Example 130 | A |
| Example 131 | A |
| Example 174 | AA |
| Example 185 | AA |
| Example 190 | A |
| Example 191 | A |
| Example 200 | AA |
| Example 207 | A |
| Example 209 | A |
| Example 210 | AA |
| Example 212 | A |
| Example 214 | AA |
| Example 215 | AA |
| Example 216 | AA |
| Example 218 | A |
| Example 219 | AA |
| Example 220 | AA |
| Example 221 | AA |
| Example 222 | AA |
| Example 223 | AA |

TABLE 2-continued

The test results of IC$_{50}$ detected by CellTiter-Glo® T

| Test samples (Compounds) | HUVEC |
|---|---|
| Example 224 | AA |
| Example 225 | AA |

Remark:
AA < 100 nM, 100 nM ≤ A < 1 uM.
Conclusions:
the compounds of the present invention had excellent inhibitory activity against HUVEC.

Experimental Example 3: Tumor Growth Inhibition (TGI) Analysis

The evolution and growth trends of the tumor was evaluated by the relationship between tumor volume and time. The long axis (L) and short axis (W) of the subcutaneous tumor were measured twice a week by the caliper and the volume of the tumor (TV) was calculated by the formula ((L×W$^2$)/2). TGI was calculated by the difference between the median tumor volume of the mice in the solvent group and the median tumor volume of the mice in the drug group expressed as a percentage of the tumor volume in the solvent control group Calculated by the following formula:

% TGI=((intermediate tumor volume (control)−intermediate tumor volume (administration group))/ intermediate tumor volume (control group))× 100%

The original statistical analysis was performed by repeated variance analysis, and then a multiple comparisons were performed using the Scheffe psot hoc test method. Individual solvent (0.5% methylcellulose+0.2% Tween aqueous solution) was a negative control.

The experimental results were shown in Table 3.

TABLE 3

Test results of antitumor activity in mice

| | Calu 6 Transplant model | TGI % (last administration) |
|---|---|---|
| Example 1 | 50 mg/kg, QD | 57 |
| Example 200 | 100 mg/kg, QD | 59 |
| Example 216 | 10 mg/kg, QD | 83 |

The compounds of the present invention had excellent inhibitory activity on three kinases which are VEGFR2, FGFR1 and PDGFRB and had HUVEC cell inhibitory activity in vitro, and can act as a small molecule peptidase kinase inhibitor, which had the inhibiting effect on cell proliferation and angiogenesis, had excellent anti-tumor activity and had an excellent effect on the treatment of neoplastic diseases of various mammals (including humans).

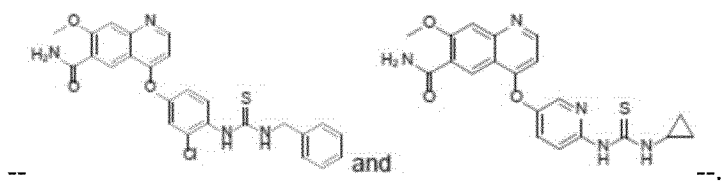

The invention claimed is:

1. A compound or an enantiomer, a diastereomer, a geometric isomer, a solvate or a pharmaceutically acceptable salt thereof represented by formula (II);
wherein, the structural formula of the formula (II) is as follows:

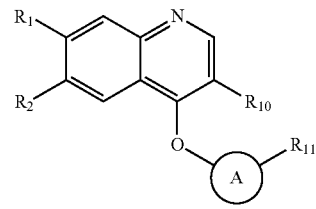

(II)

$R_1$ is $C_{1-6}$ alkoxy, $C_{1-6}$ heteroalkyl-O— or imidazolyl, each optionally substituted by a member selected from the group consisting of H, $C_{1-6}$ alkyl and aryl;

$R_2$ is selected from H, OH, NH$_2$, halogen, CN, —C(=O)N($R_{2d1}$)($R_{2d2}$), —NH($R_{2d1}$)C(=O)$R_{2d2}$, —C(=O)OR$_{2d3}$ and $C_{1-7}$ alkyl; wherein the $C_{1-7}$ alkyl is optionally substituted by a member selected from the group consisting of halogen and OH, wherein, $R_{2d1}$, $R_{2d2}$ and $R_{2d3}$ are each independently selected from H, OH, NH$_2$, CN, $C_{1-7}$ alkyl, $C_{1-7}$ heteroalkyl, 3-6 membered cycloalkyl and 3-6 membered heterocycloalkyl, or $R_{2d1}$ and $R_{2d2}$ together form a 4-7 membered ring, wherein the $C_{1-7}$ alkyl, $C_{1-7}$ heteroalkyl, 3-6 membered cycloalkyl and 3-6 membered heterocycloalkyl are each optionally substituted by a member selected from the group consisting of halogen, OH, Me and Et;

$R_{10}$ is selected from H, OH, NH$_2$, CN and halogen;

A is phenyl, which is optionally substituted by a member selected from the group consisting of H, F, Cl, Br, I, OH, CN, NH$_2$,

Me and Et, $R_{11}$ is

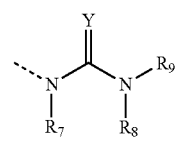

wherein, Y is S;

$R_7$, $R_8$ and $R_9$ are each independently selected from H; and $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

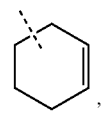

each optionally substituted by a member selected from the group consisting of halogen, CF$_3$, CN, D, OH,

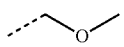

and $C_{1-3}$ alkyl; or the structural unit

is selected from

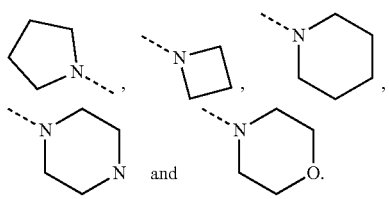

each optionally substituted by a member selected from the group consisting of halogen, $CF_3$, CN, D, OH,

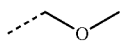

and $C_{1-3}$ alkyl; or the structural unit

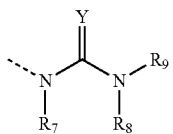

is selected from

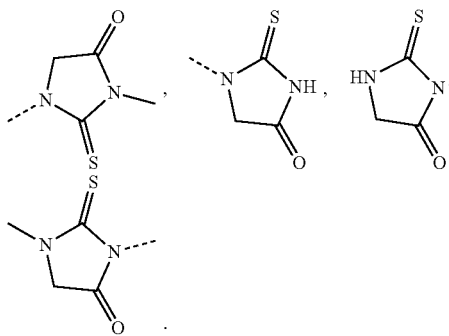

2. A compound or an enantiomer, a diastereomer, a geometric isomer, a solvate or a pharmaceutically acceptable salt thereof according to claim 1, wherein $R_7$, $R_8$ and $R_9$ are each independently selected from H; and $C_{1-4}$ alkyl, $C_{1-2}$ alkyl-S—$C_{1-3}$ alkyl-, $C_{1-2}$ alkyl-N—$C_{1-3}$ alkyl-, $C_{1-2}$ alkyl-O—$C_{1-3}$ alkyl-, 3-6 membered cycloalkyl, 3-6 membered cycloalkyl-$C_{1-2}$ alkyl, pyrrolidone, 5-6 membered lactone, pyrrolidinyl, piperidinyl, tetrahydropyranyl, morpholinyl, thiazolyl, pyrazolyl, phenyl, pyridyl, morpholinyl-$C_{1-2}$ alkyl-, phenyl-$C_{1-2}$ alkyl-, pyridyl-$C_{1-2}$ alkyl-, $C_{0-2}$ alkyl-alkynyl-$C_{1-2}$ alkyl- and

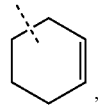

each optionally substituted by a member selected from the group consisting of halogen, $CF_3$, CN, D, OH,

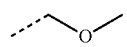

and $C_{1-30}$ alkyl.

3. A compound or an enantiomer, a diastereomer, a geometric isomer, a solvate or a pharmaceutically acceptable salt thereof according to claim 2, wherein $R_7$, $R_8$ and $R_9$ are each independently selected from H; and Me,

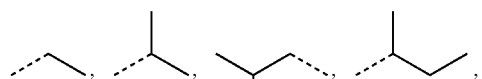

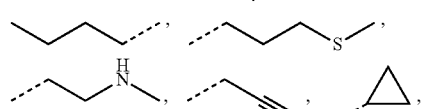

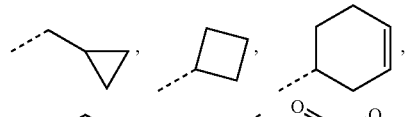

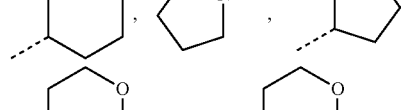

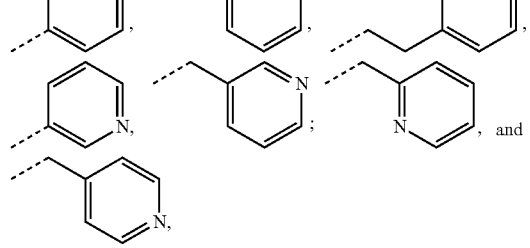

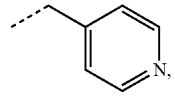

each optionally substituted by a member selected from the group consisting of halogen, $CF_3$, CN, D, OH,

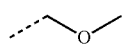

and $C_{1-3}$ alkyl; or
the structural unit

is selected from

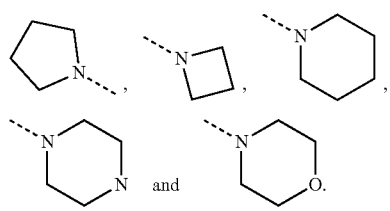

each optionally substituted by a member selected from the group consisting of halogen, $CF_3$, CN, D, OH,

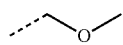

and $C_{1-3}$ alkyl.

4. A compound or an enantiomer, a diastereomer, a geometric isomer, a solvate or a pharmaceutically acceptable salt thereof according to claim 3, wherein $R_7$, $R_8$ and $R_9$ are each independently selected from H, Me,

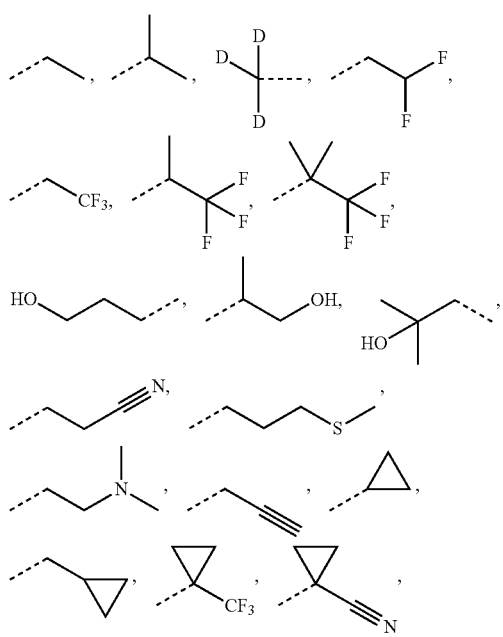

-continued

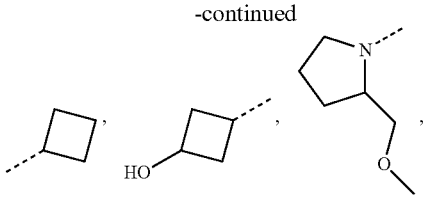

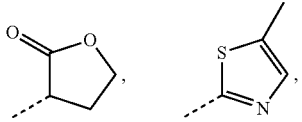

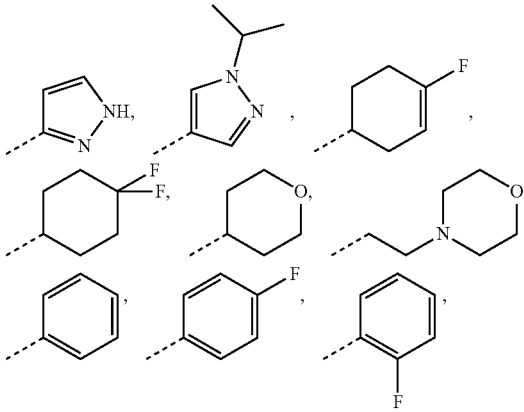

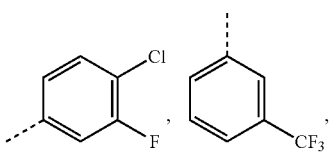

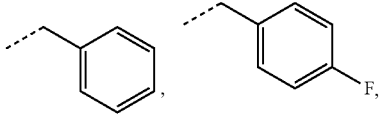

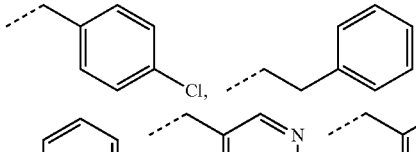

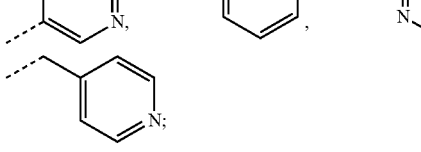

or the structural unit

is selected from

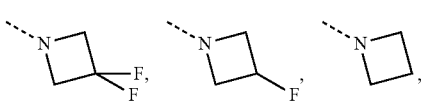

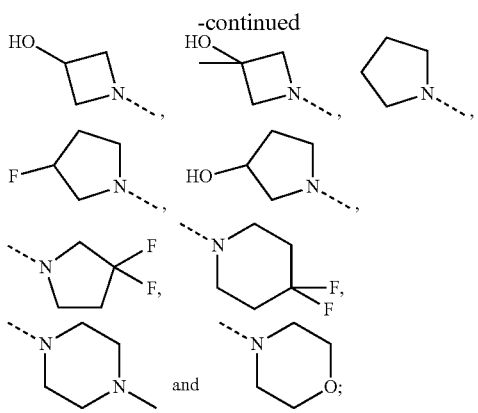

or the structural unit

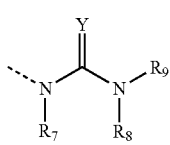

is selected from

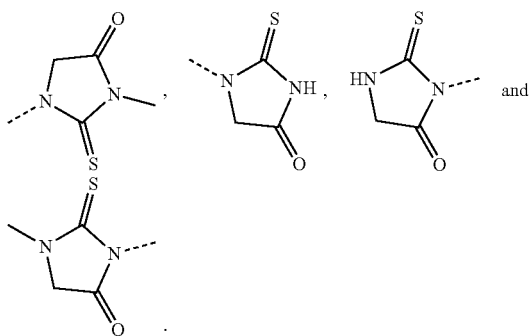

5. A compound or an enantiomer, a diastereomer, a geometric isomer, a solvate or a pharmaceutically acceptable salt thereof according to claim 1, wherein $R_1$ is selected from $C_{1-6}$ alkoxy, $O(CH_2)_n R_{1d1}$ and

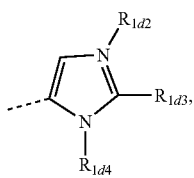

wherein n is an integer of 1 to 6, $R_{1d1}$ is $C_{1-6}$ alkoxy or $NR_{1d5}R_{1d6}$, wherein, $R_{1d5}$ and $R_{1d6}$ are each independently H or $C_{1-6}$ alkyl, $R_{1d2}$, $R_{1d3}$ and $R_{1d4}$ are each independently H, $C_{1-6}$ alkyl or aryl;

$R_2$ is selected from H, CN, halo $C_{1-3}$ alkyl, hydroxy $C_{1-3}$ alkyl, —C(=O)N($R_{2d1}$)($R_{2d2}$), —NH($R_{2d1}$)C(=O) $R_{2d2}$ and —C(=O)O$R_{2d3}$.

6. A compound or an enantiomer, a diastereomer, a geometric isomer, a solvate or a pharmaceutically acceptable salt thereof according to claim 1, wherein A is

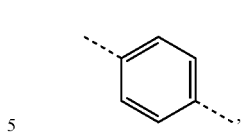

which is optionally substituted by a member selected from the group consisting of H, F, Cl, Br, I, OH, CN, $NH_2$,

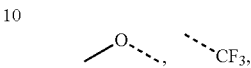

Me and Et.

7. A compound or an enantiomer, a diastereomer, a geometric isomer, a solvate or a pharmaceutically acceptable salt thereof according to claim 1, wherein $R_{11}$ is

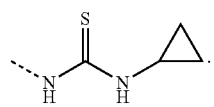

8. A compound or an enantiomer, a diastereomer, a geometric isomer, a solvate or a pharmaceutically acceptable salt thereof according to claim 1, wherein $R_1$ is

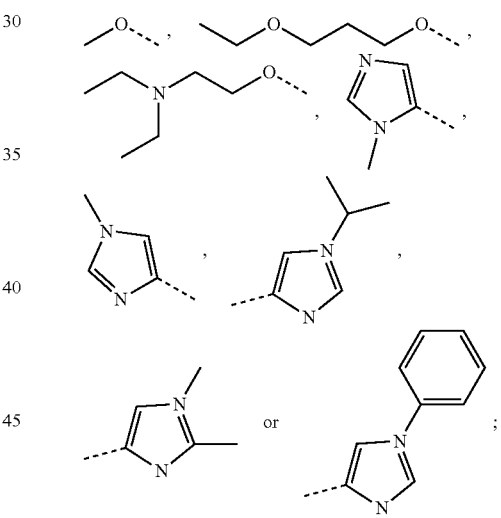

$R_2$ is selected from H, CN, $CF_3$,

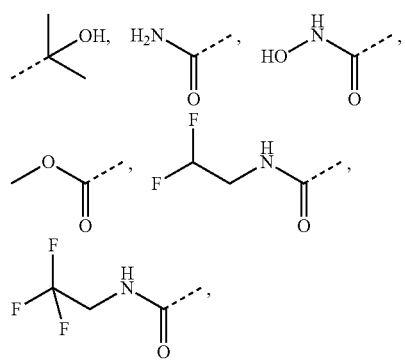

-continued

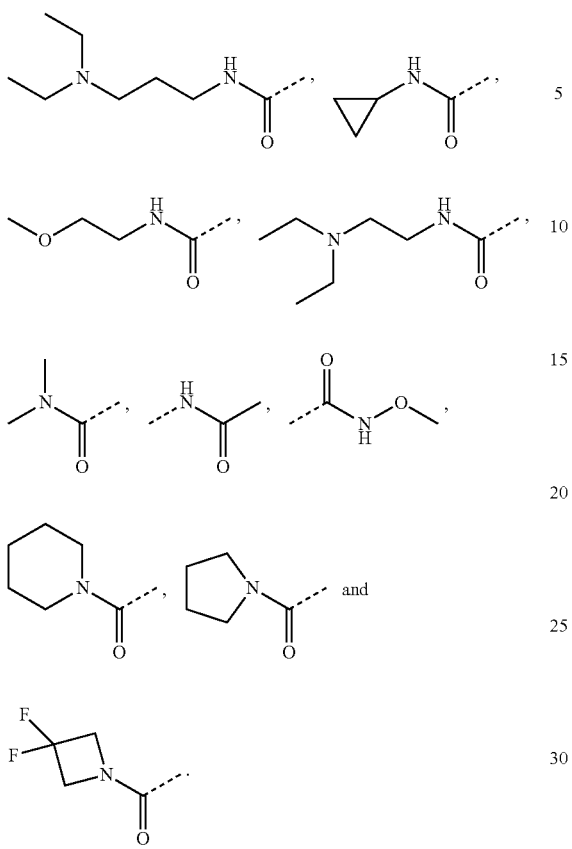

9. A compound or an enantiomer, a diastereomer, a geometric isomer, a solvate or a pharmaceutically acceptable salt thereof according to claim 1, wherein $R_{2d1}$, $R_{2d2}$ and $R_{2d3}$ are each independently selected from H, OH, methyl,

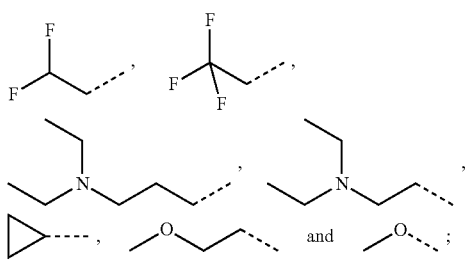

or the structural unit —$N(R_{2d1}R_{2d2}$—) is selected from the group consisting of

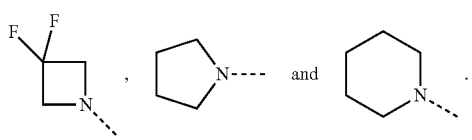

10. A compound or an enantiomer, a diastereomer, a geometric isomer, a solvate or a pharmaceutically acceptable salt thereof according to claim 1, wherein the structure is shown as formula (III)

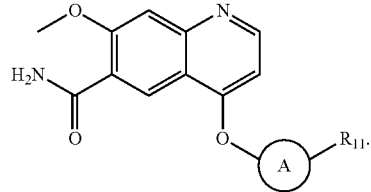

(III)

11. A compound or an enantiomer, a diastereomer, a geometric isomer, a solvate or a pharmaceutically acceptable salt thereof according to claim 1, wherein the structure is shown as formula (V)

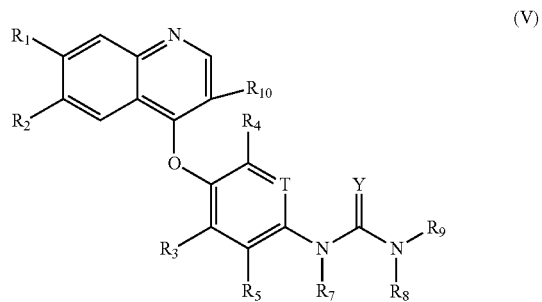

(V)

wherein, in the formula (V), Y is S;

T is $C(R_6)$;

$R_3$, $R_4$, $R_5$, $R_6$ are each independently selected from H, OH, $NH_2$, CN, halogen, Me and Et;

$R_7$, $R_8$, $R_9$ are each independently selected from H; and $C_{1-7}$ alkyl, $C_{1-7}$ heteroalkyl, 3-6 membered cycloalkyl, 3-6 membered heterocycloalkyl, 5-6 membered aryl, 5-6 membered heteroaryl, 3-6 membered cycloalkyl-$C_{1-3}$ alkyl-, 3-6 membered heterocycloalkyl-$C_{1-3}$ alkyl-, 3-6 membered heterocycloalkyl-$C_{1-3}$ alkyl-, 5-6 membered aryl-$C_{1-3}$ alkyl-, $C_{2-7}$ alkynyl and

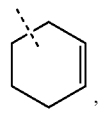

each optionally substituted by a member selected from the group consisting of halogen, $CF_3$, CN, D, OH,

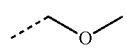

and $C_{1-3}$ alkyl.

12. A compound or an enantiomer, a diastereomer, a geometric isomer, a solvate or a pharmaceutically acceptable salt thereof according to claim 11, wherein $R_3$, $R_4$, $R_5$, $R_6$ are each independently selected from H, F, Cl, Br, I, OH, CN, $NH_2$.

13. A compound or an enantiomer, a diastereomer, a geometric isomer, a solvate or a pharmaceutically acceptable salt thereof according to claim 11, wherein $R_7$, $R_8$ and $R_9$ are each independently selected from H; and Me,

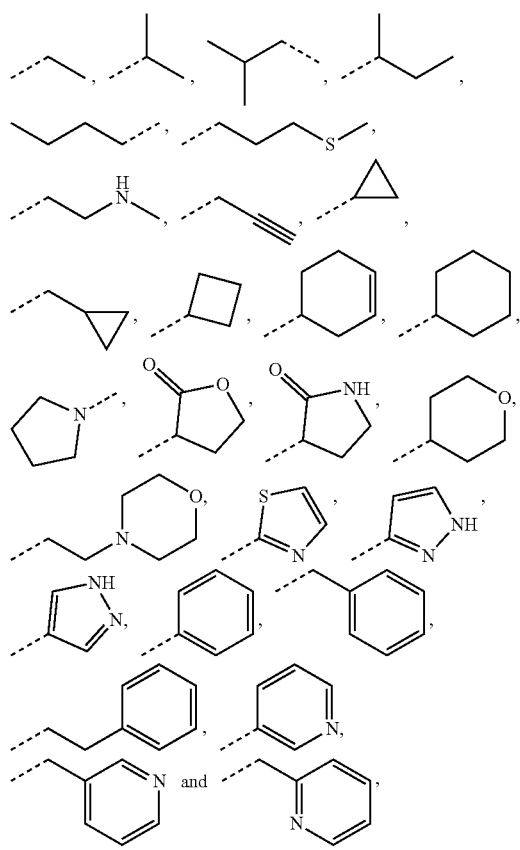

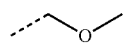

each optionally substituted by a member selected from the group consisting of halogen, CF$_3$, CN, D, OH

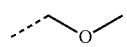

and C$_{1-3}$ alkyl.

14. A compound or an enantiomer, a diastereomer, a geometric isomer, a solvate or a pharmaceutically acceptable salt thereof according to claim 1, wherein the structure is shown as formula (IX)

(IX)

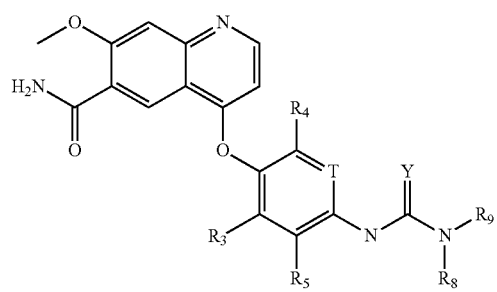

wherein, Y is S;
T is C(R$_6$);
R$_3$, R$_4$, R$_5$, R$_6$ are each independently selected from H, OH, NH$_2$, CN, halogen, and Me and Et;
R$_8$, R$_9$ are each independently selected from H; and C$_{1-7}$ alkyl, C$_{1-7}$ heteroalkyl, 3-6 membered cycloalkyl, 3-6 membered heterocycloalkyl, 5-6 membered aryl, 5-6 membered heteroaryl, 3-6 membered cycloalkyl-C$_{1-3}$ alkyl-, 3-6 membered heterocycloalkyl-C$_{1-3}$ alkyl-, 5-6 membered aryl-C$_{1-3}$ alkyl-, C$_{2-7}$ alkynyl,

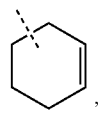

each optionally substituted by a member selected from the group consisting of halogen, CF$_3$, CN, D, OH,

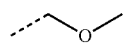

and C$_{1-3}$ alkyl.

15. A compound or an enantiomer, a diastereomer, a geometric isomer, a solvate or a pharmaceutically acceptable salt thereof according to claim 14, wherein R$_3$, R$_4$, R$_5$, R$_6$ are each independently selected from H, F, Cl, Br, I, OH, CN, NH$_2$.

16. A compound or an enantiomer, a diastereomer, a geometric isomer, a solvate or a pharmaceutically acceptable salt thereof according to claim 14, wherein R$_8$ and R$_9$ are each independently selected from H, Me,

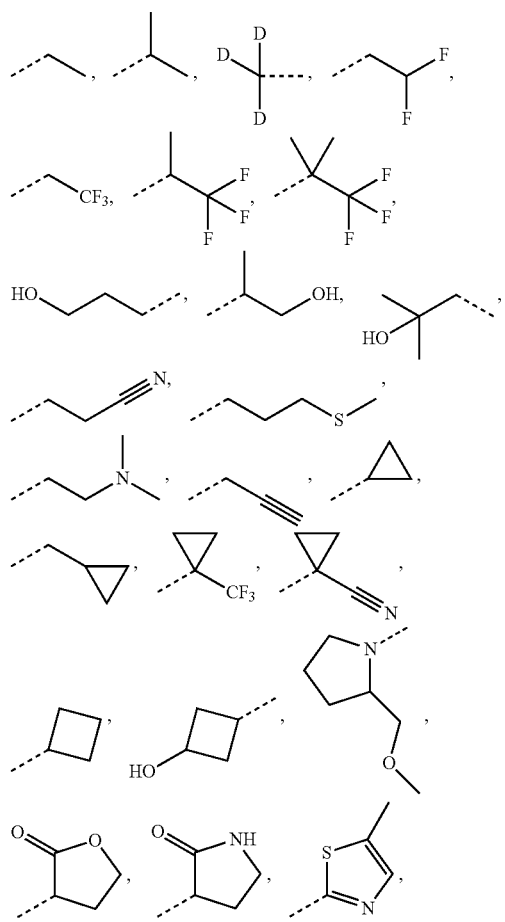

-continued
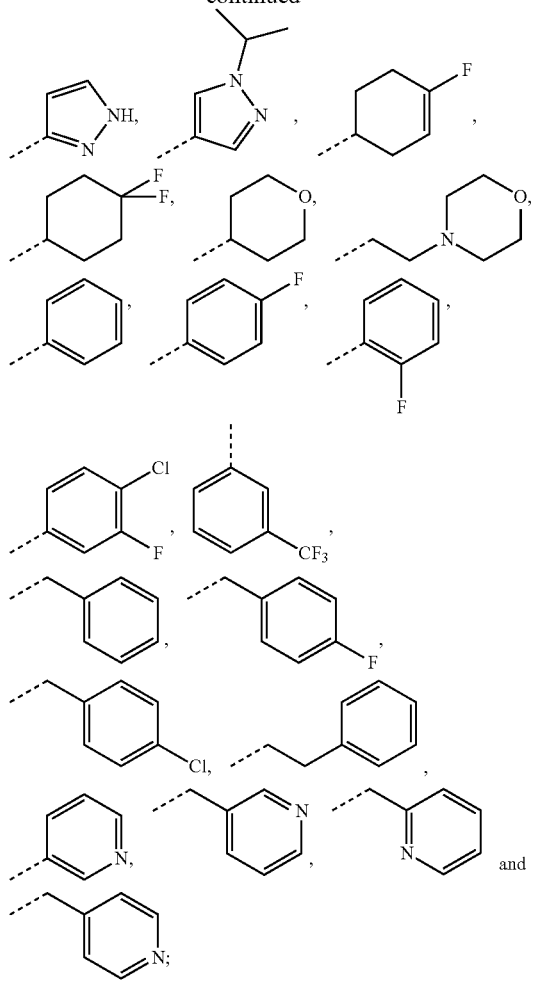
or the structural unit
is selected from
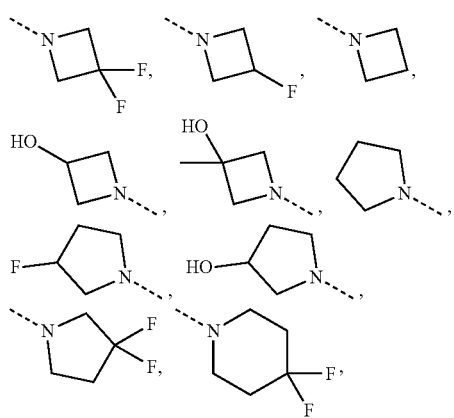
-continued
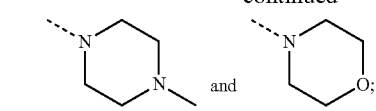
or the structural unit
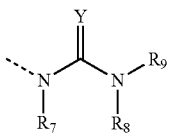
is selected from
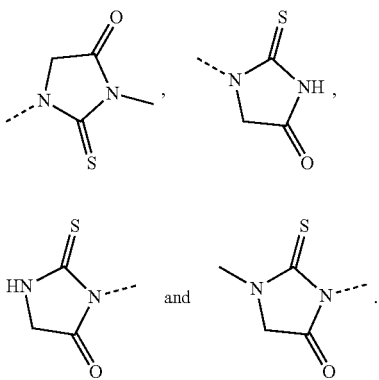
17. A compound or an enantiomer, a diastereomer, a geometric isomer, a solvate or a pharmaceutically acceptable salt thereof, wherein the structure of the compound is selected from:
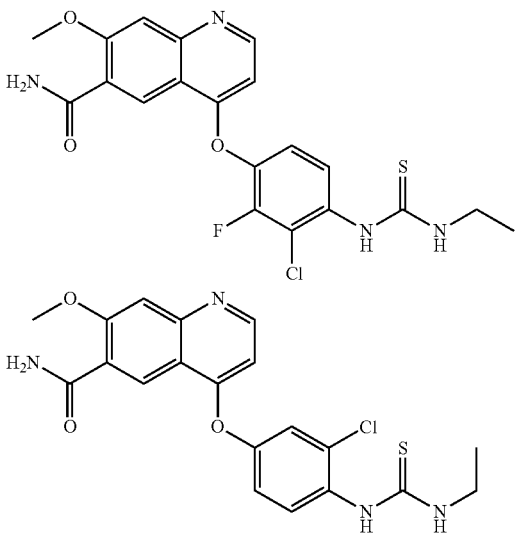

341
-continued
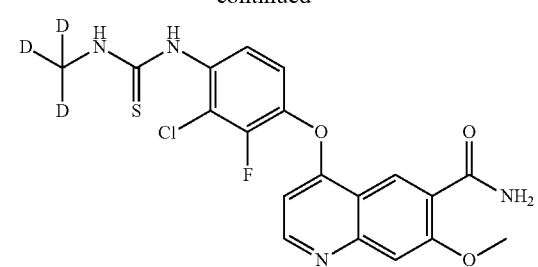
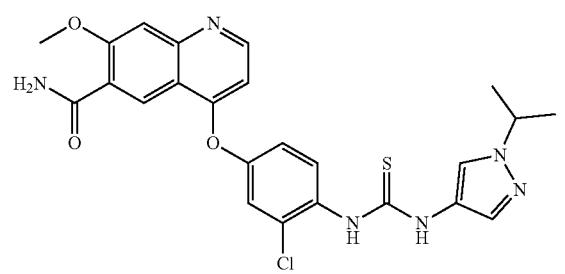
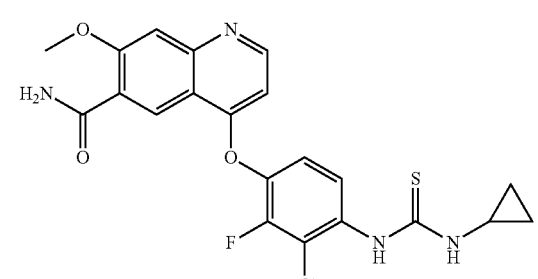
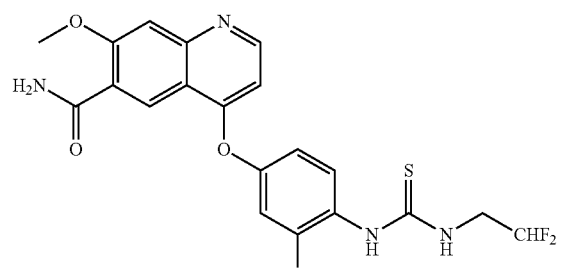
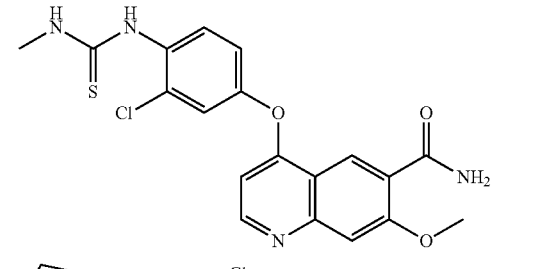
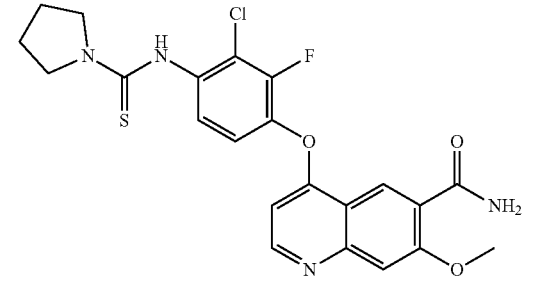
342
-continued
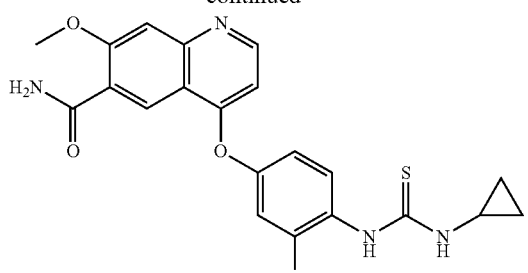
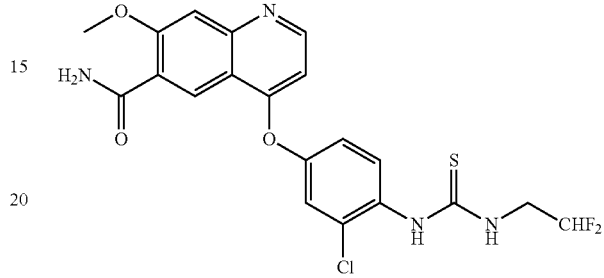
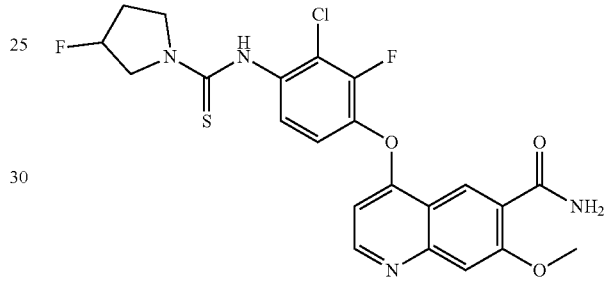
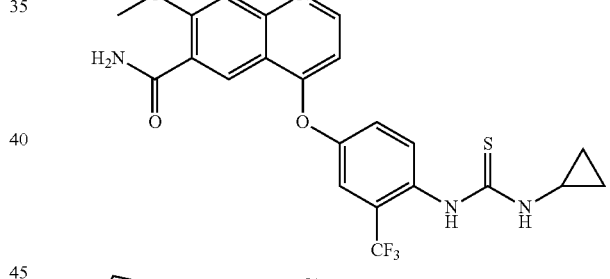
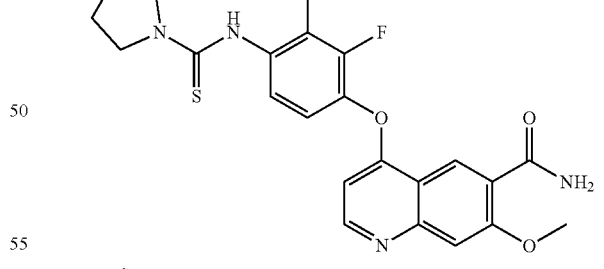
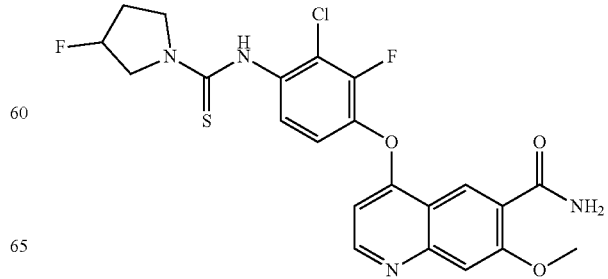

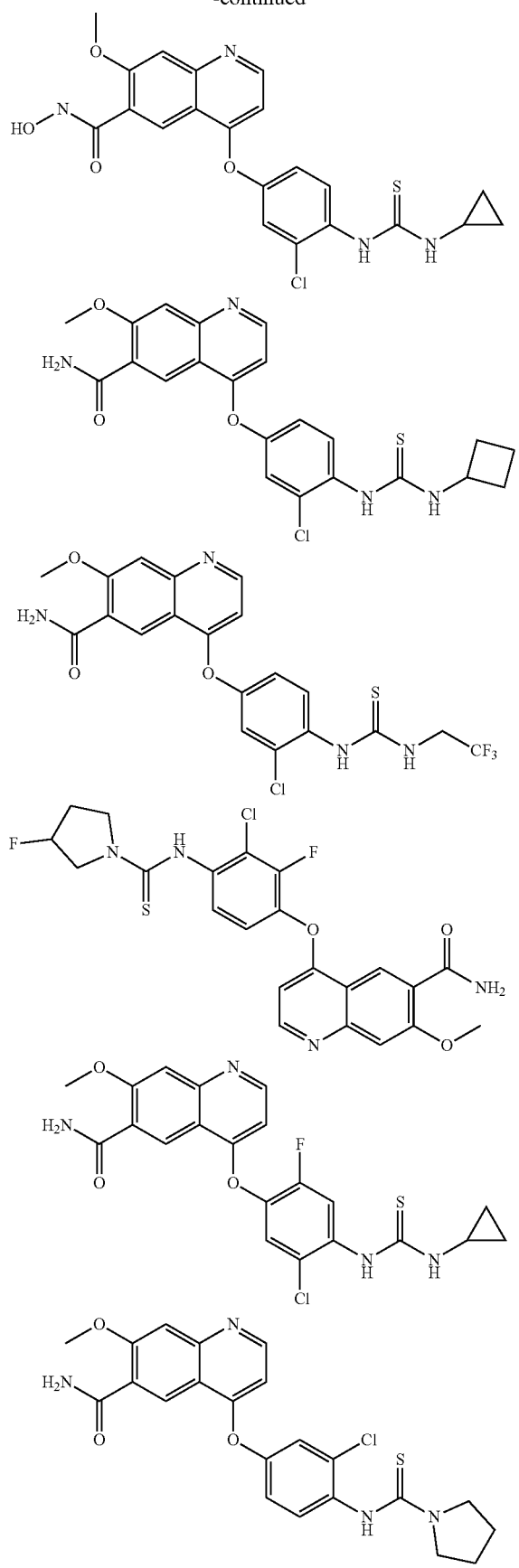
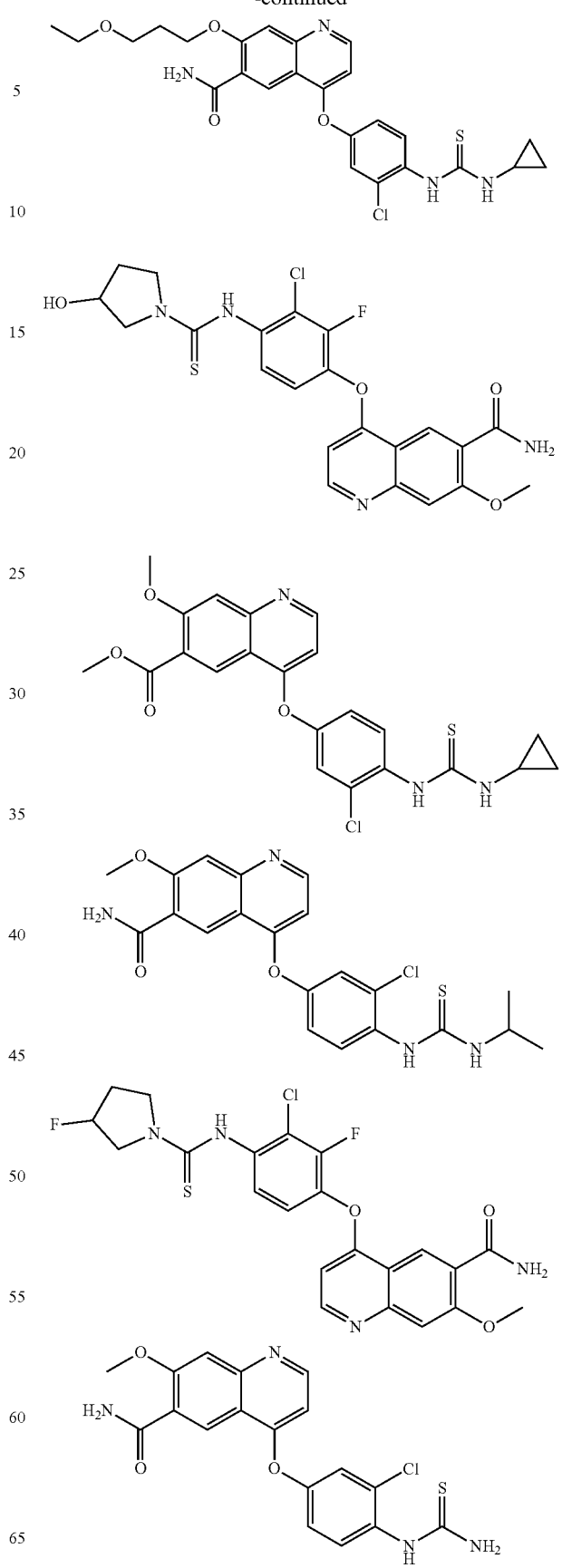

345
-continued
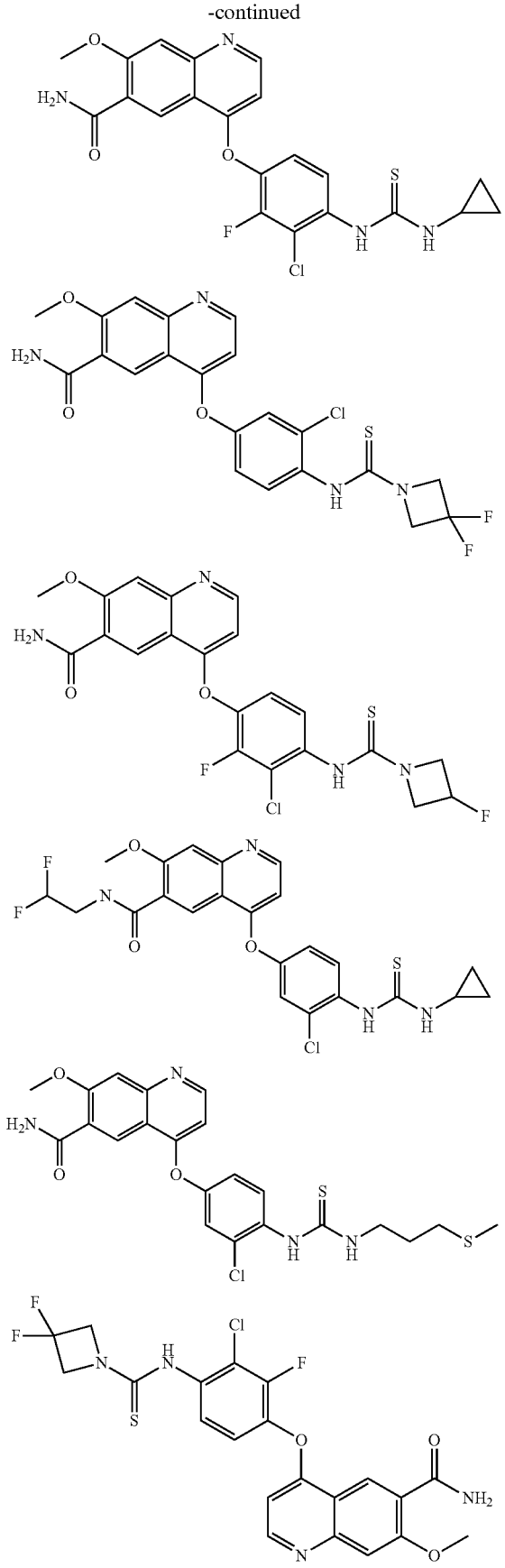
346
-continued
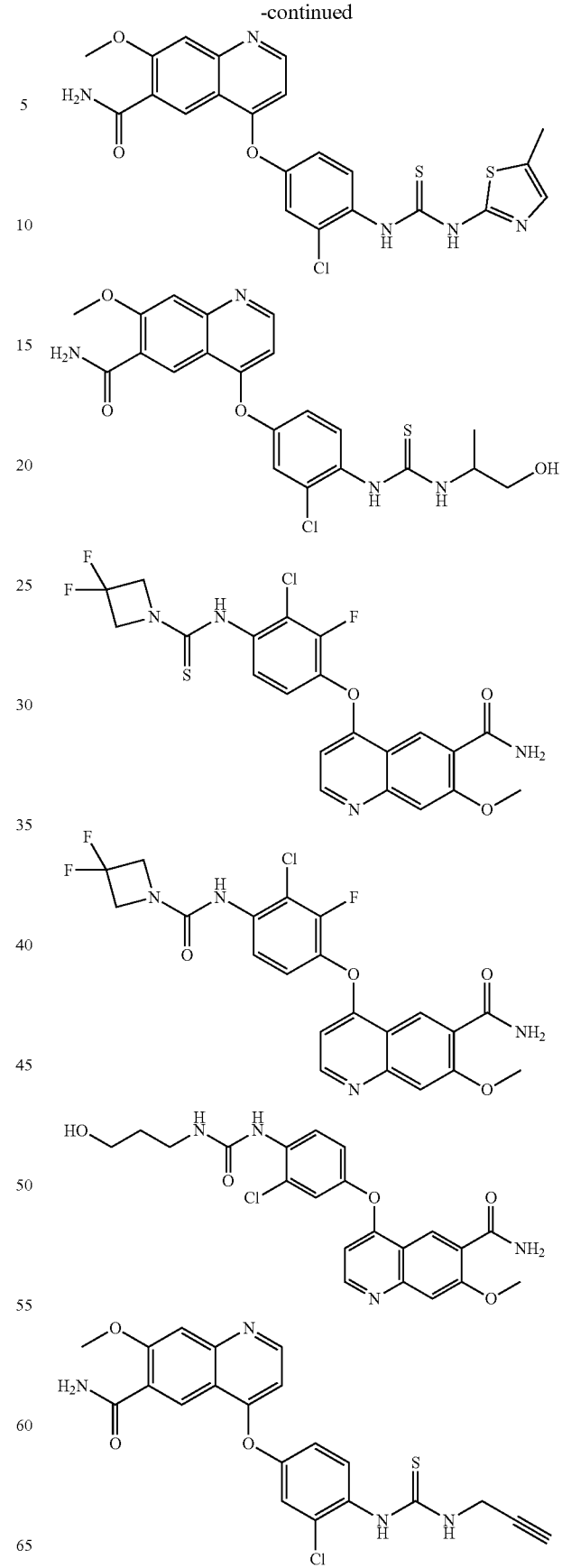

347
-continued
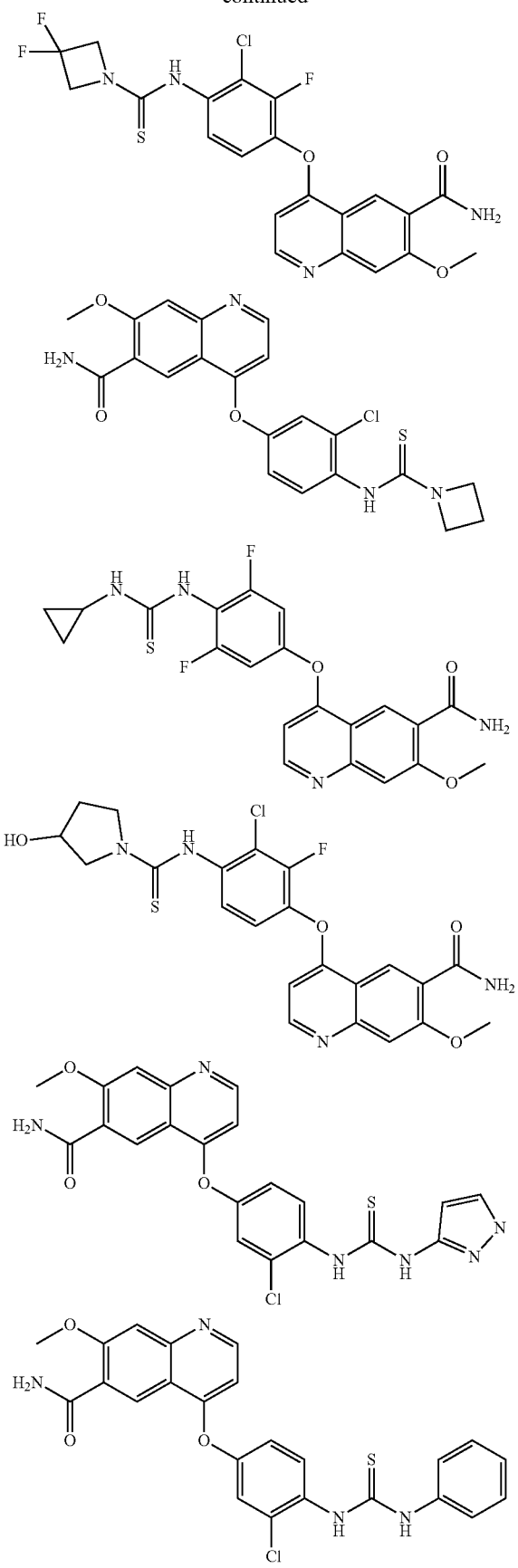
348
-continued
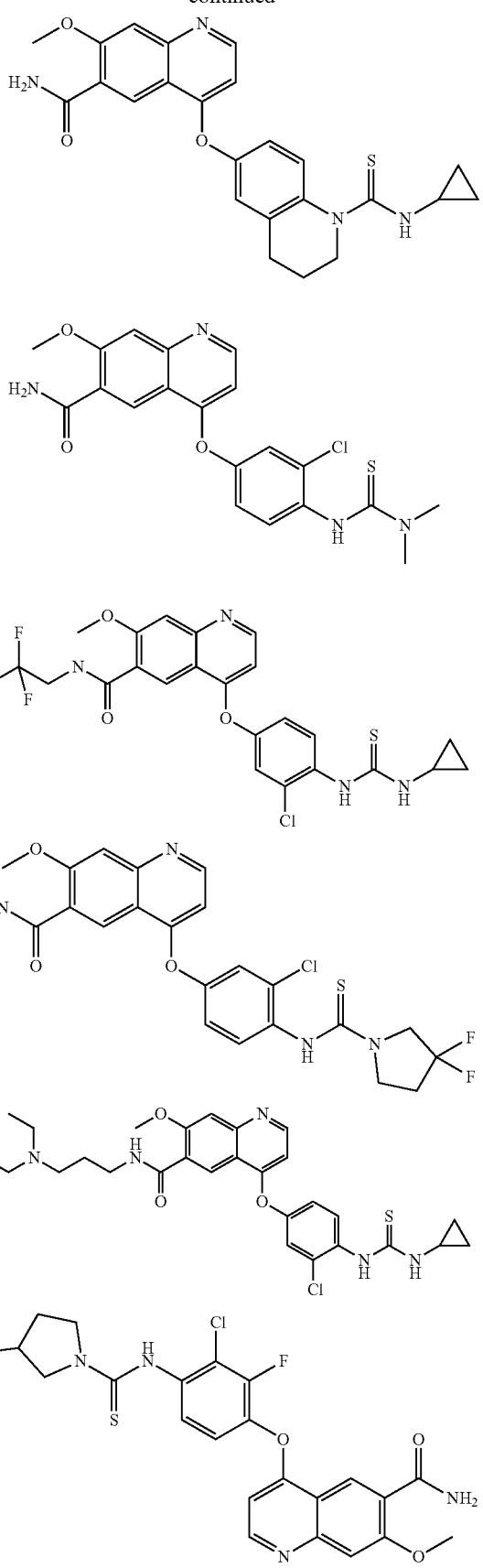

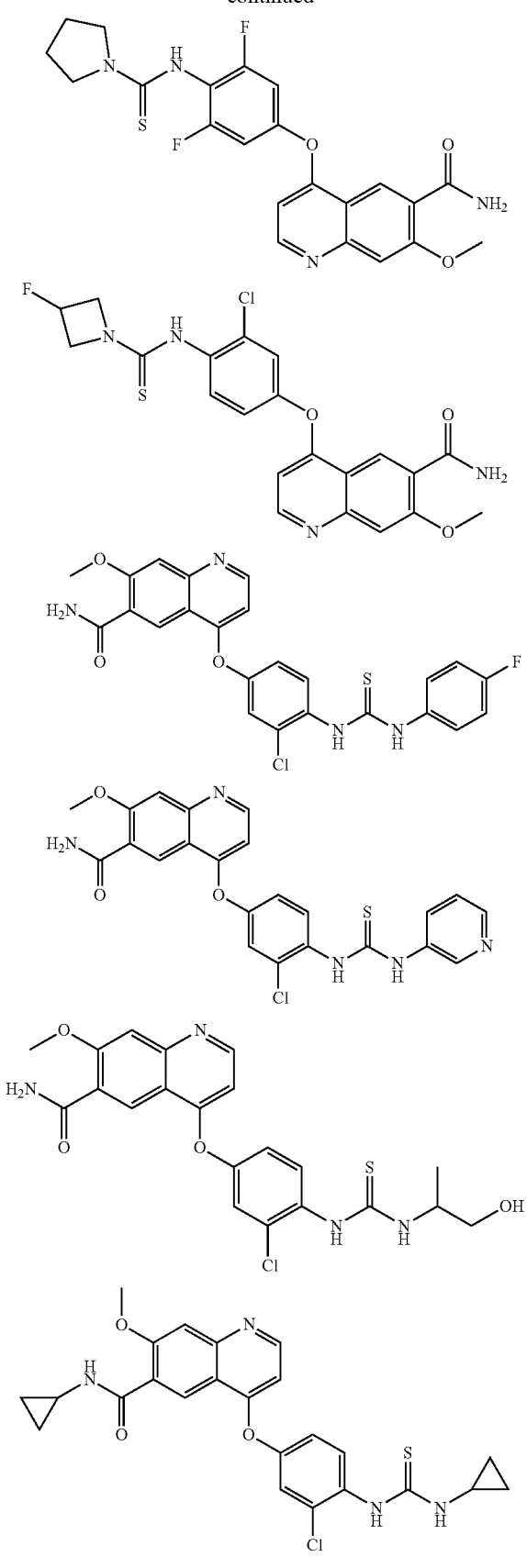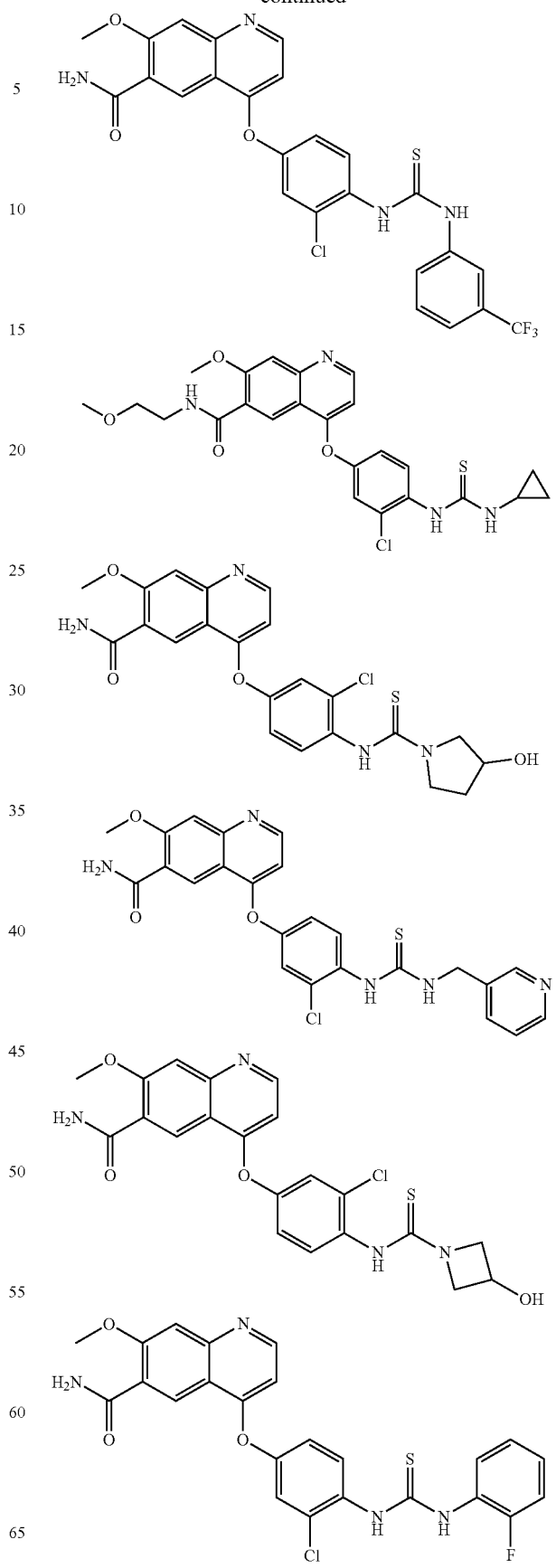

351
-continued
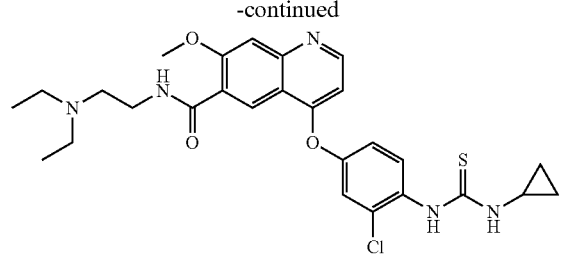
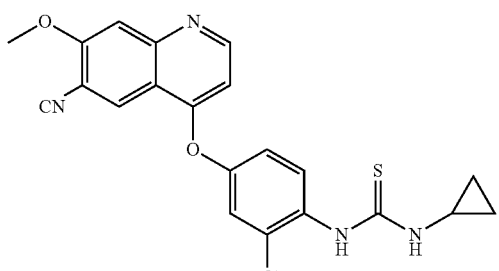
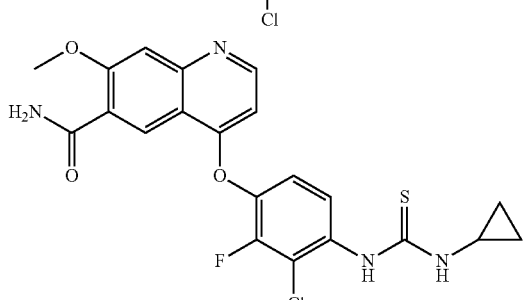
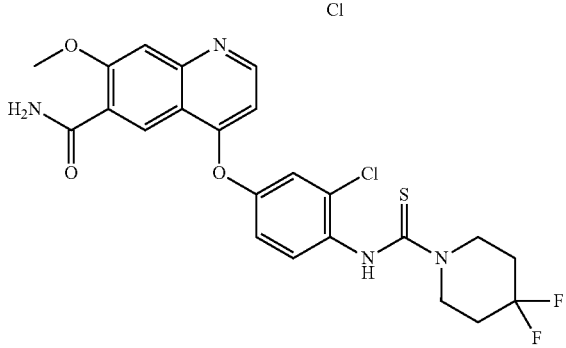
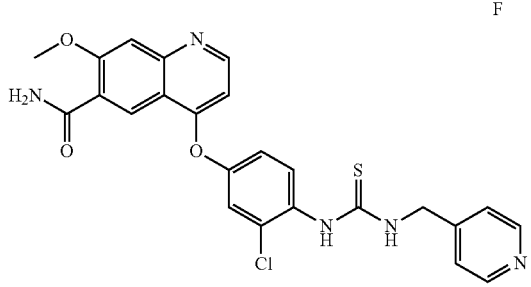
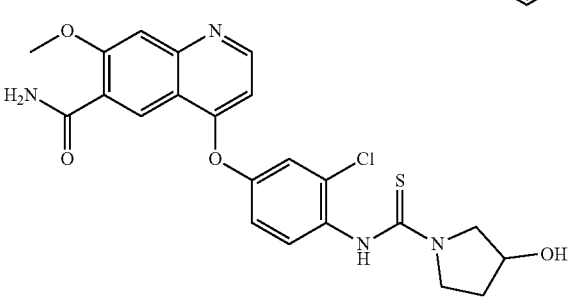
352
-continued
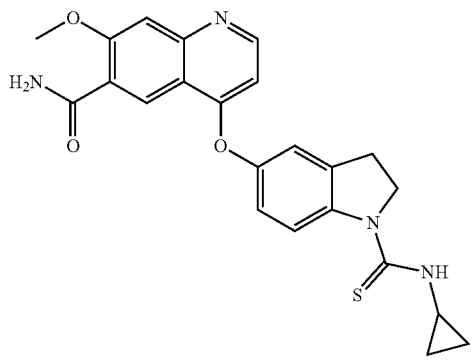
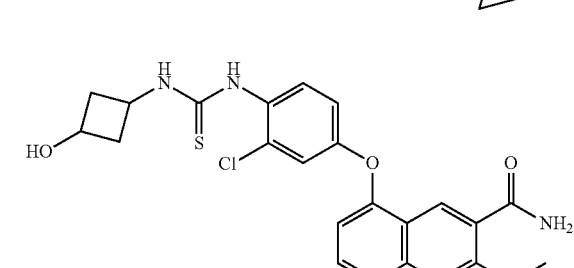
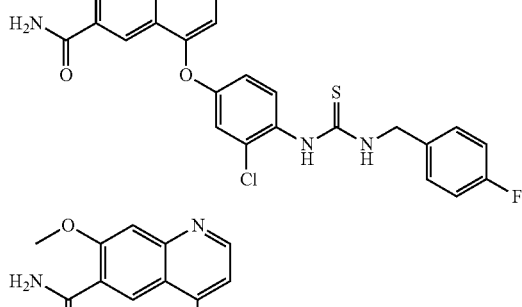
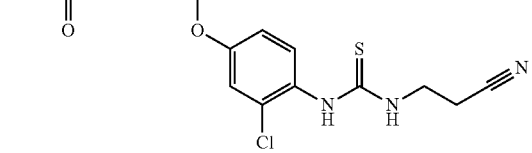
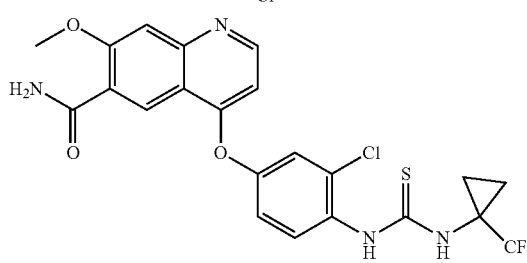
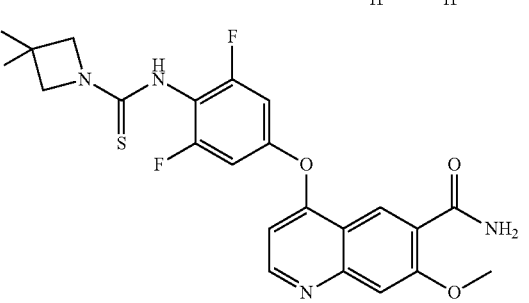

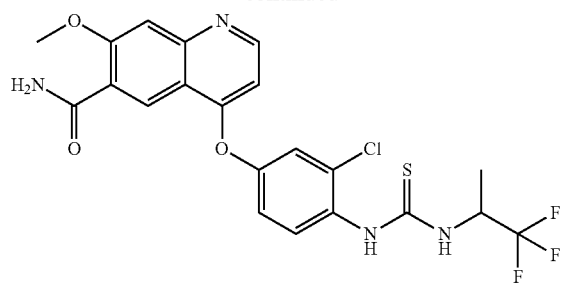
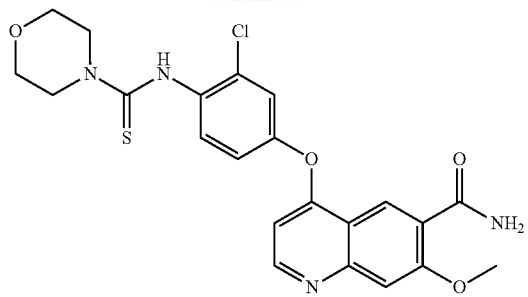
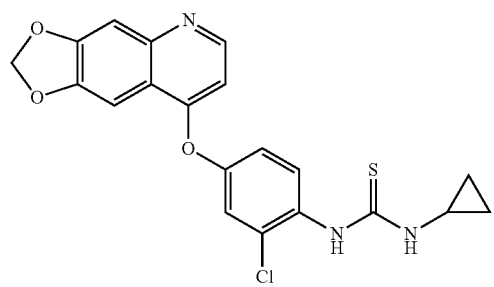
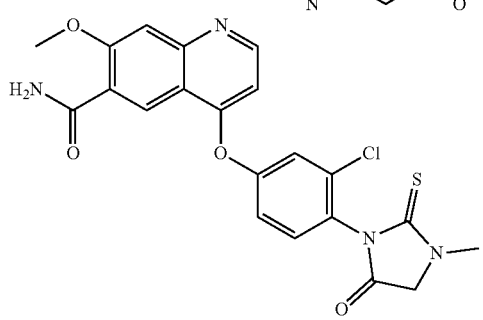
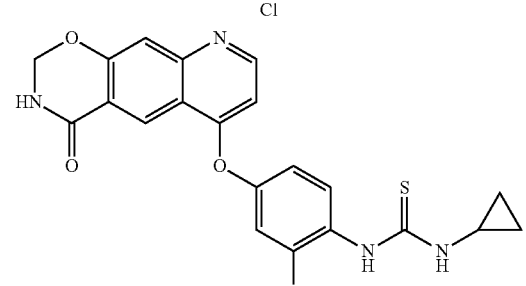
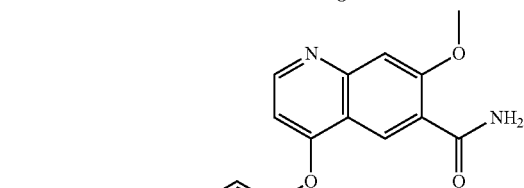
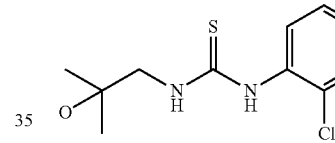
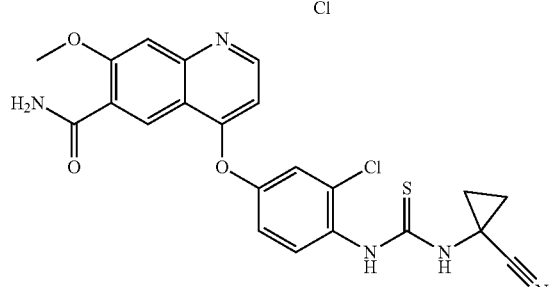
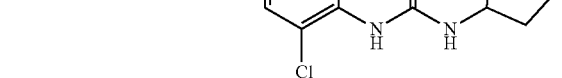
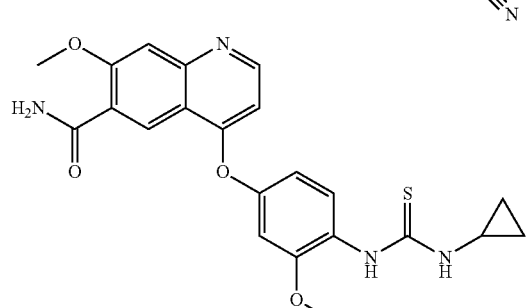
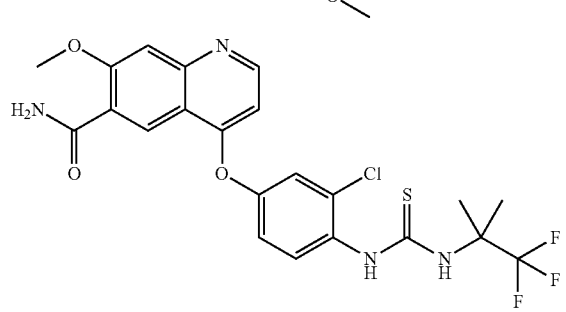
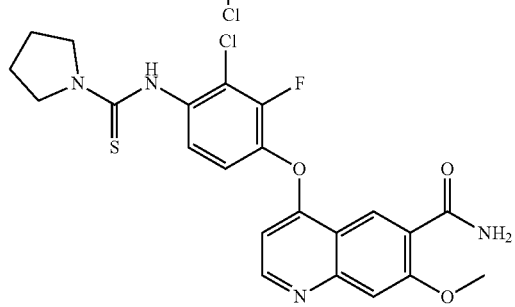

355
-continued
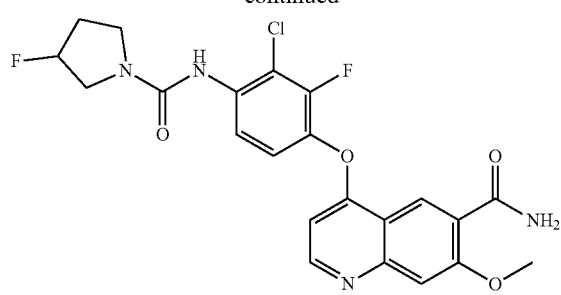
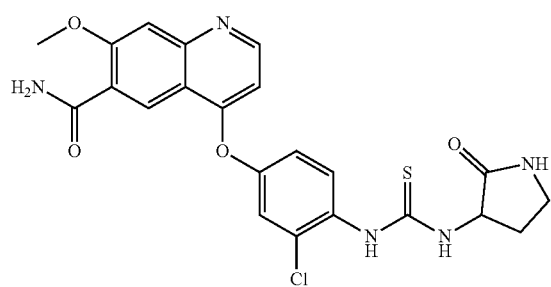
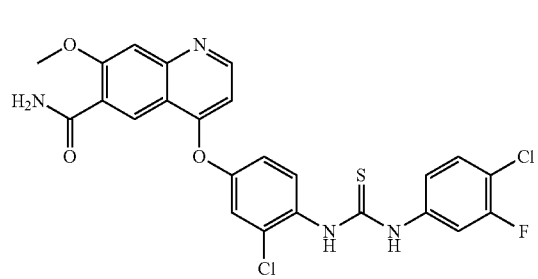
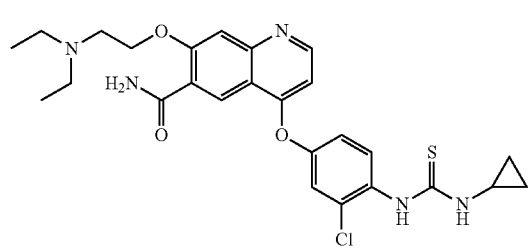
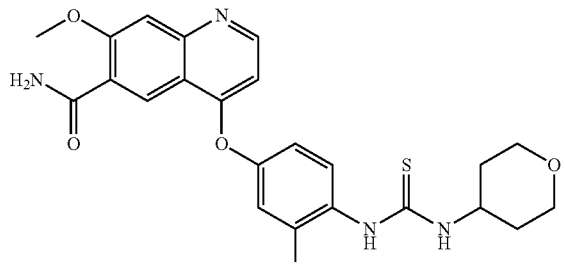
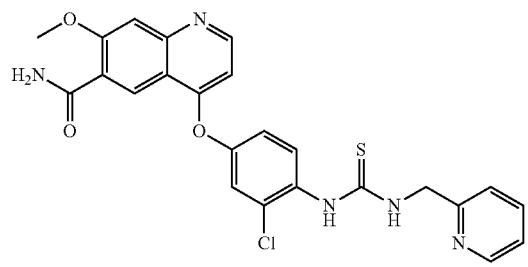
356
-continued
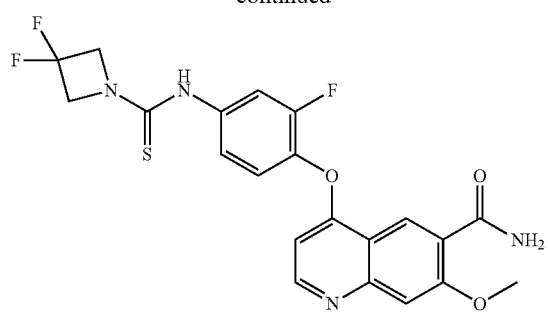
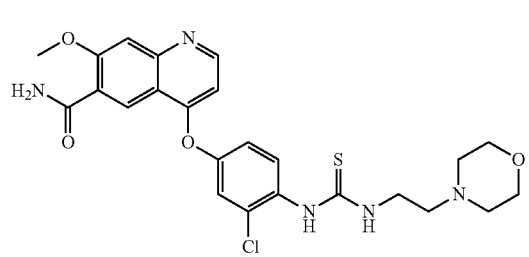
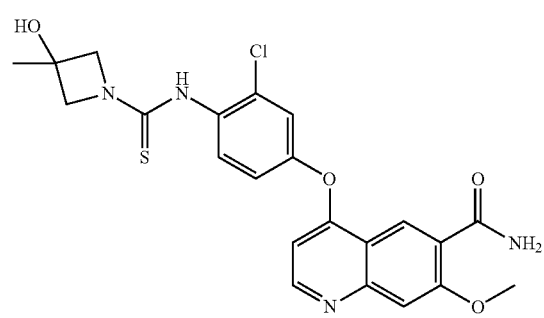
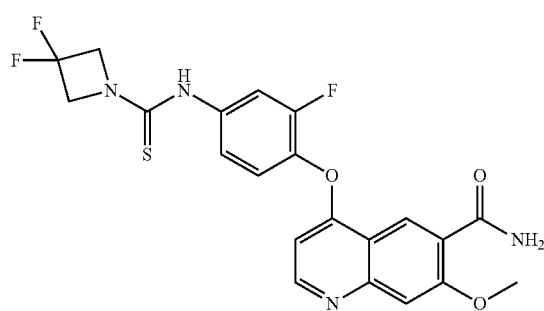
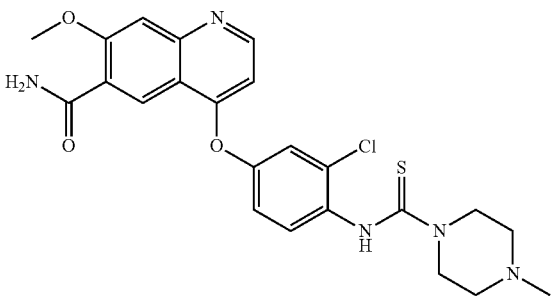

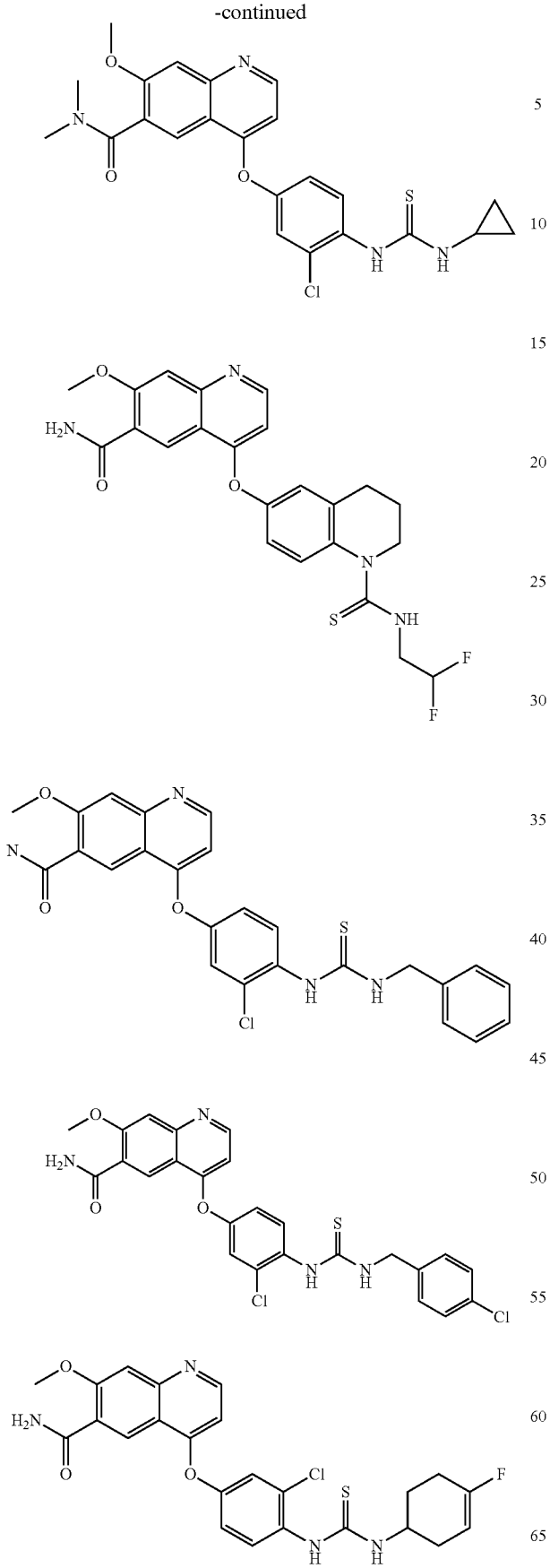
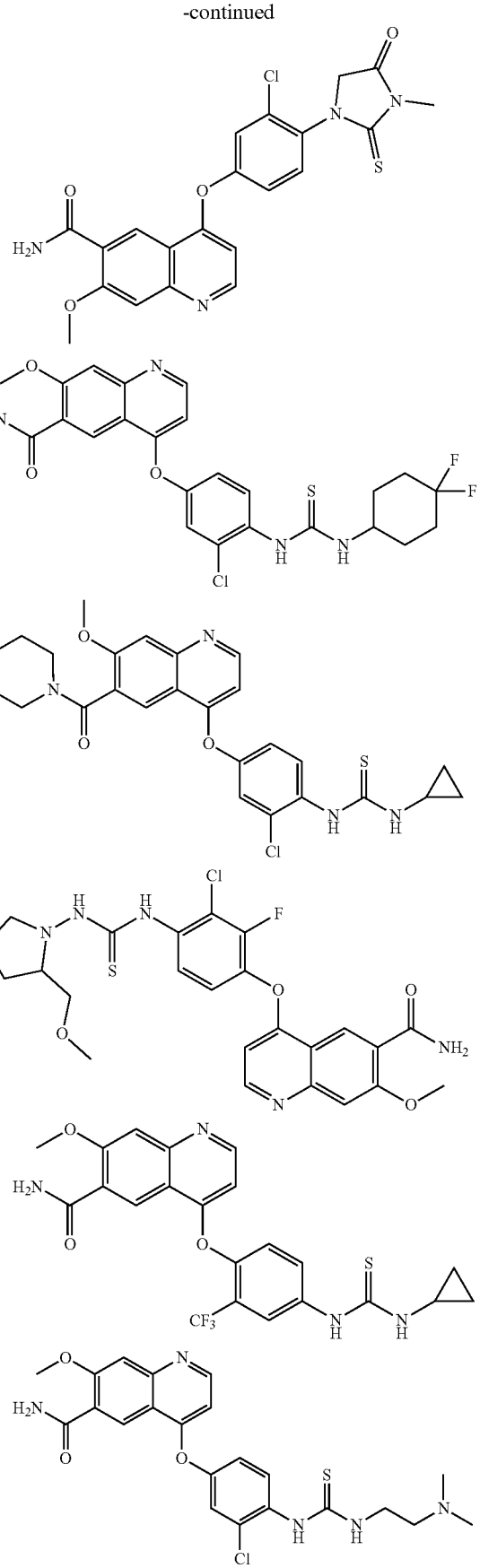

359
-continued
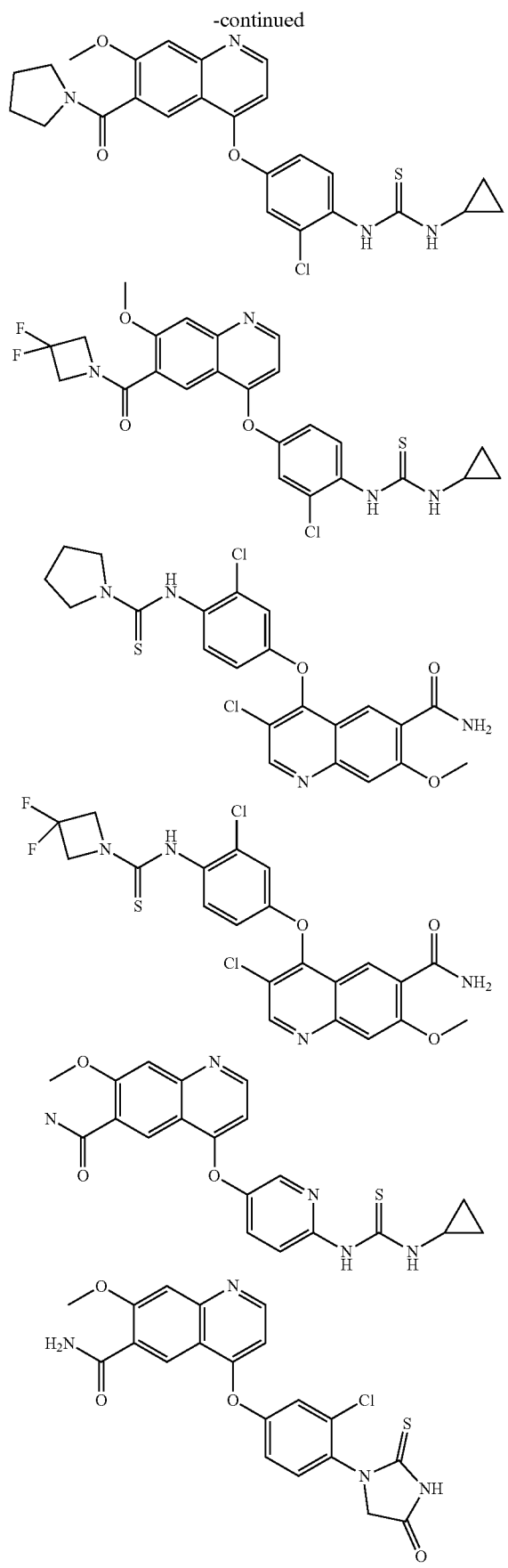
360
-continued
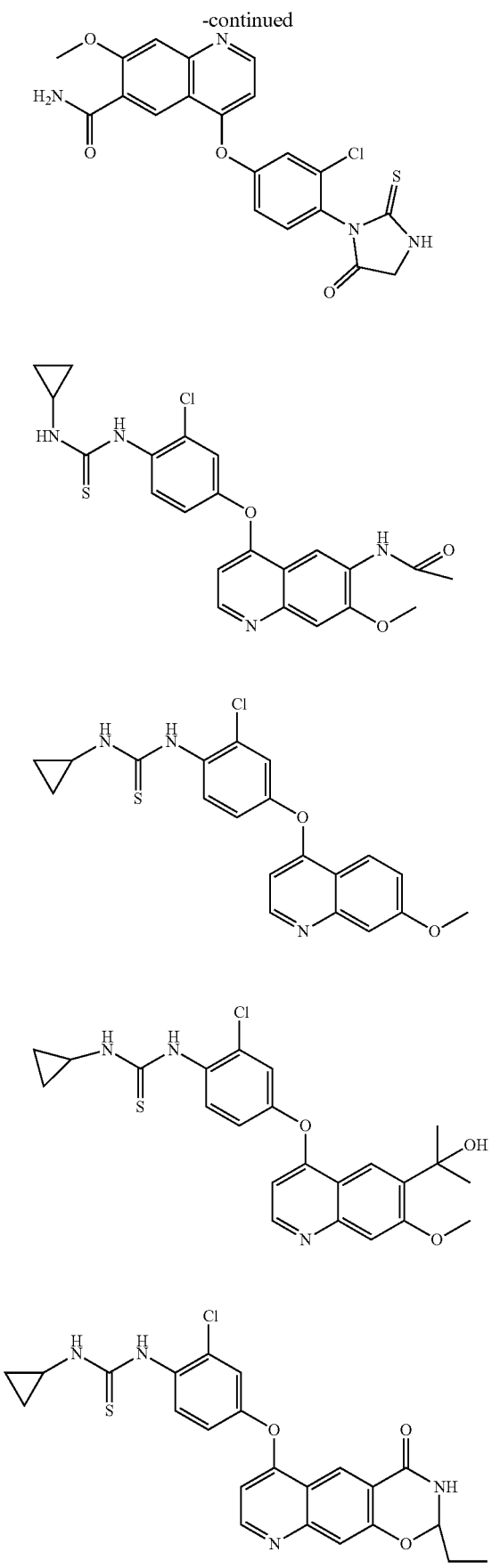

361
-continued
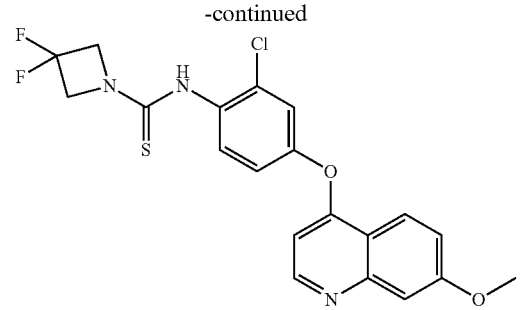
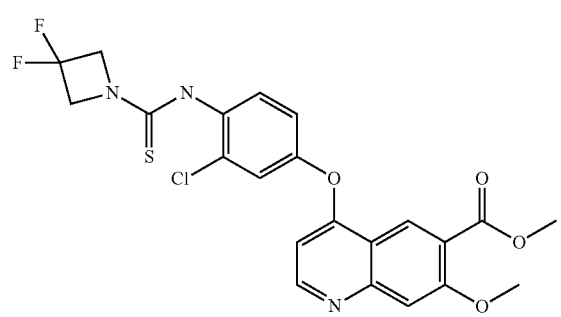
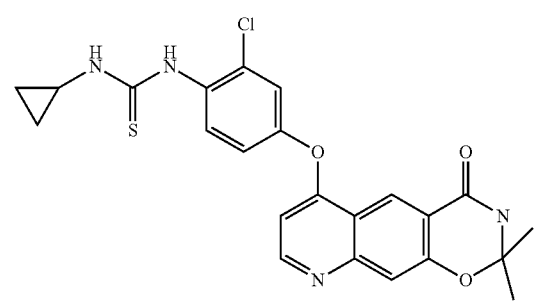
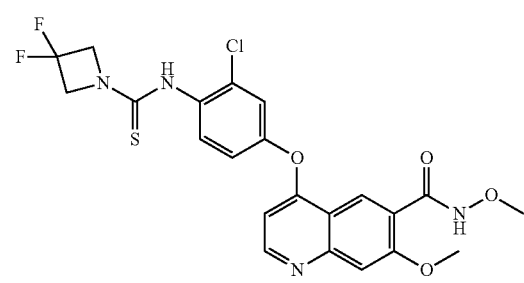
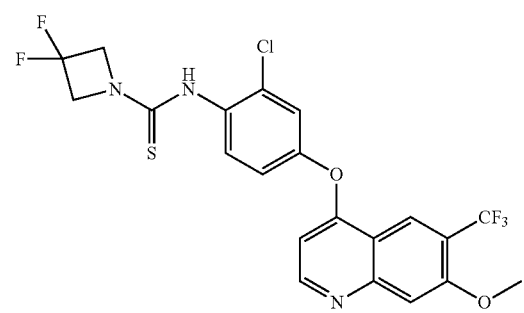
362
-continued
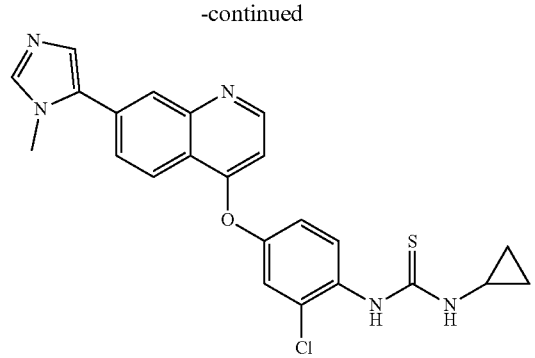
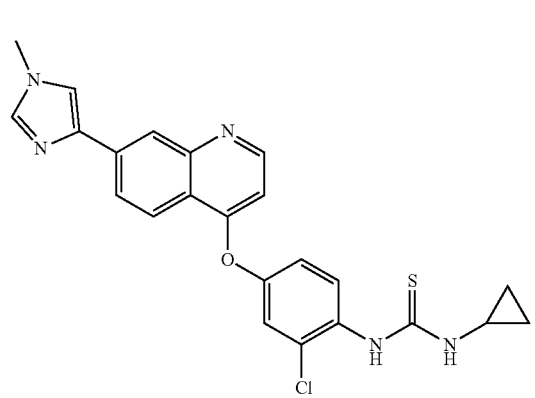
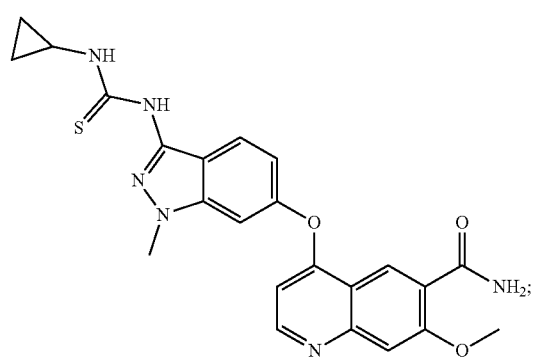
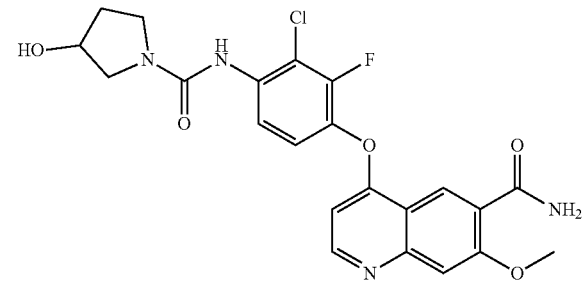
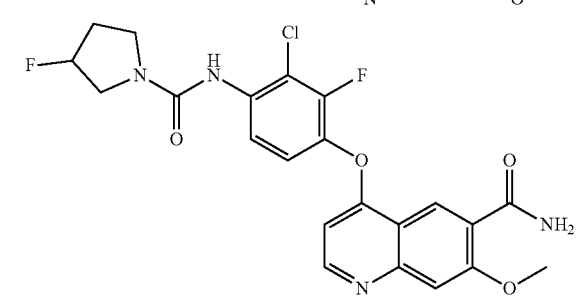

363
-continued
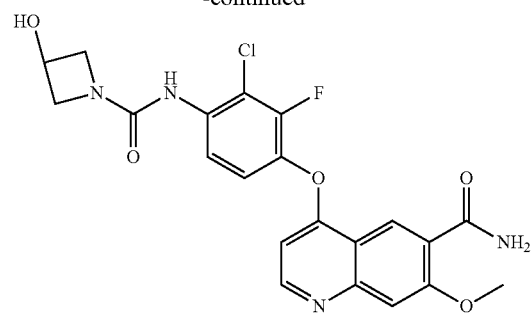
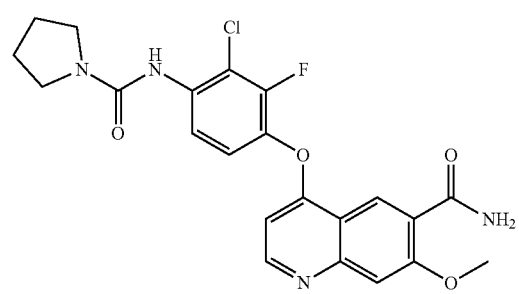
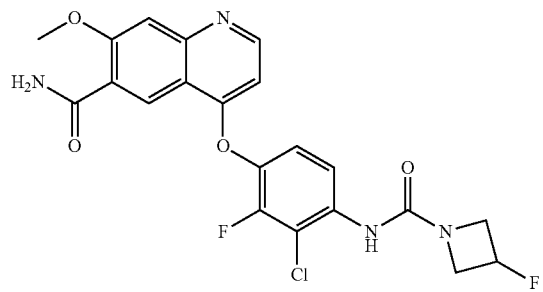
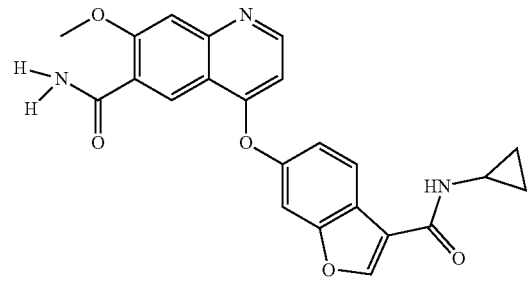
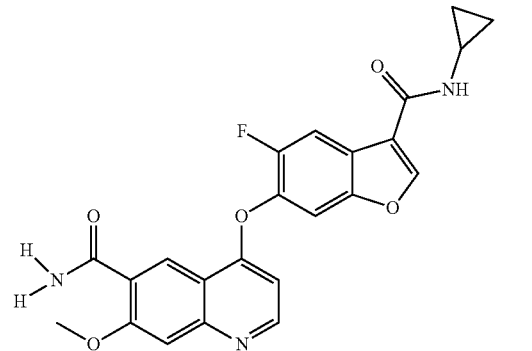
364
-continued
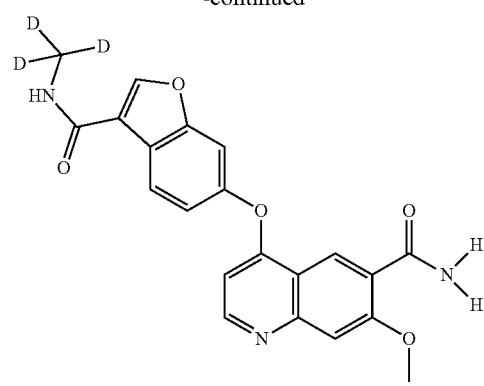
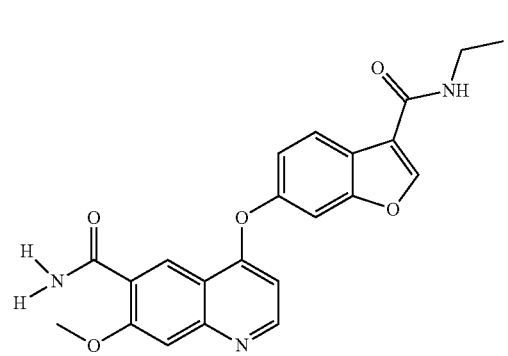
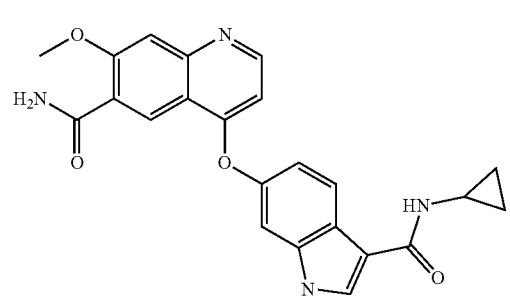
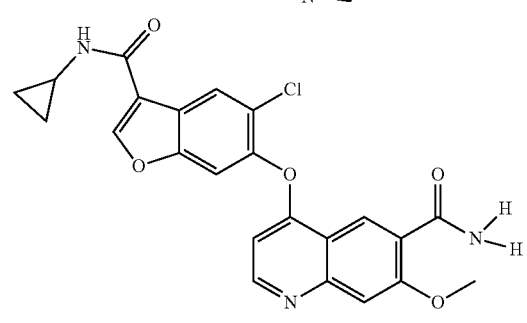
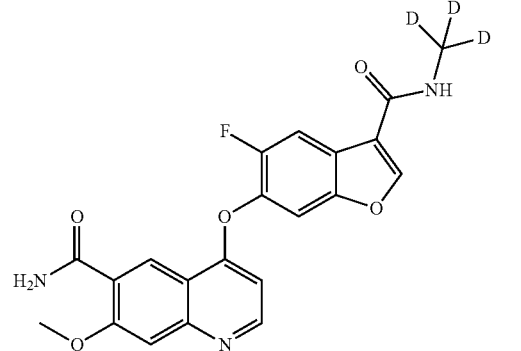

365
-continued
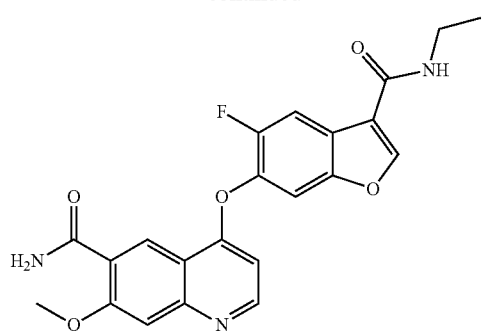
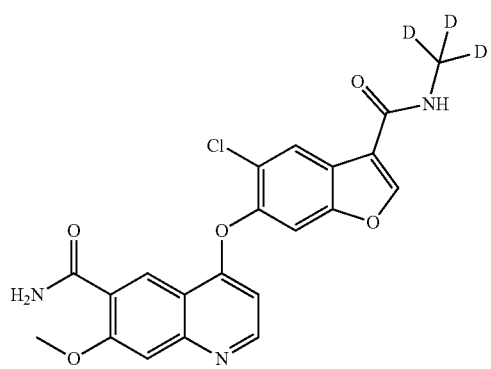
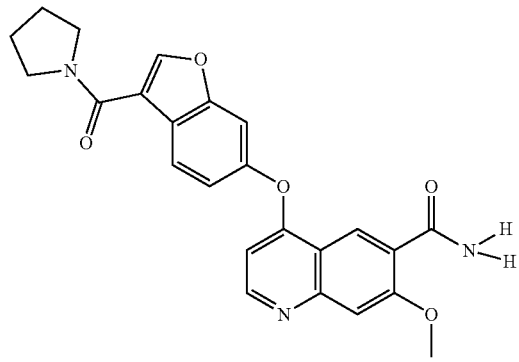
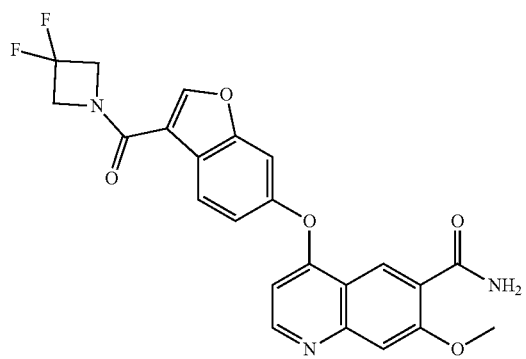
366
-continued
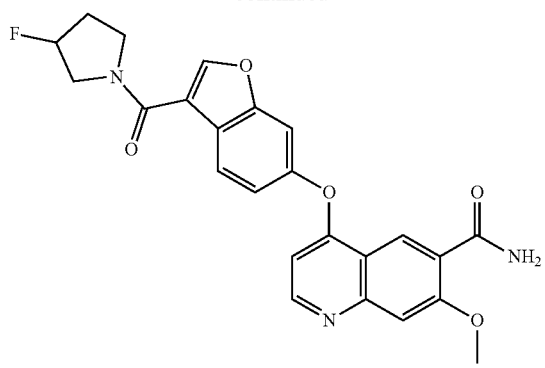
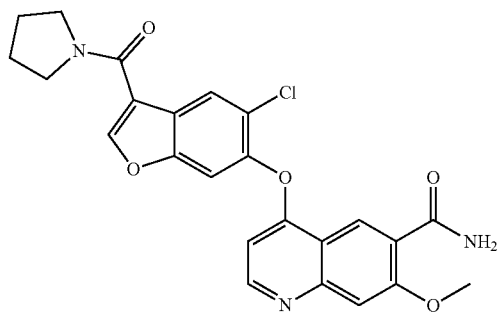

367
-continued
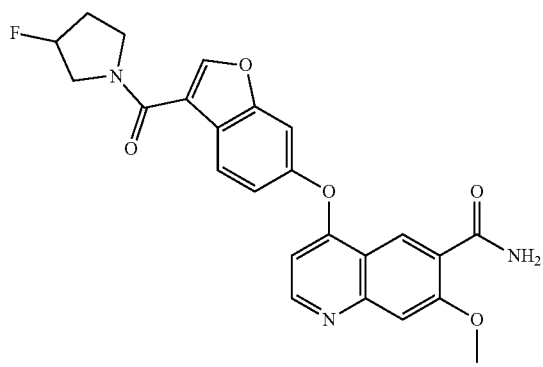
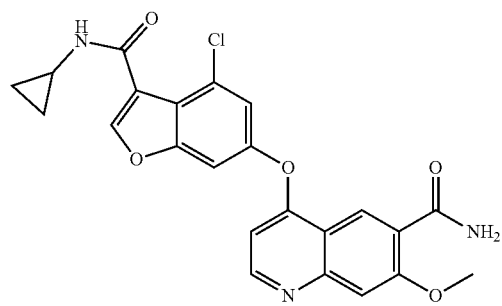
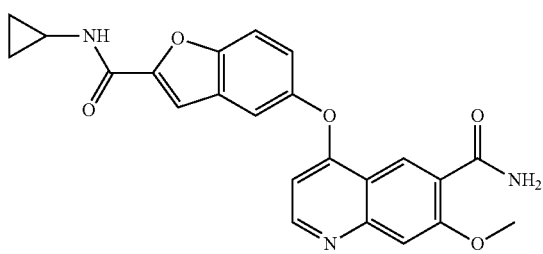
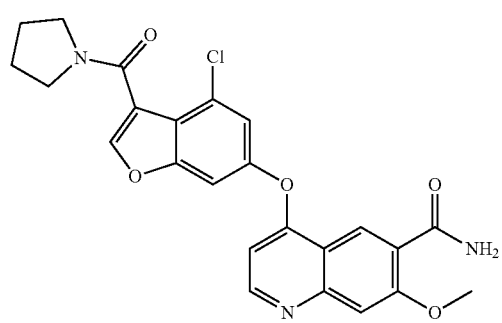
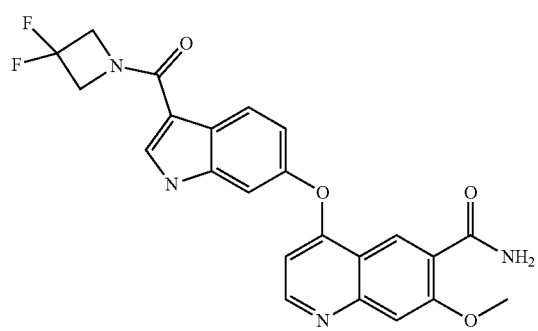
368
-continued
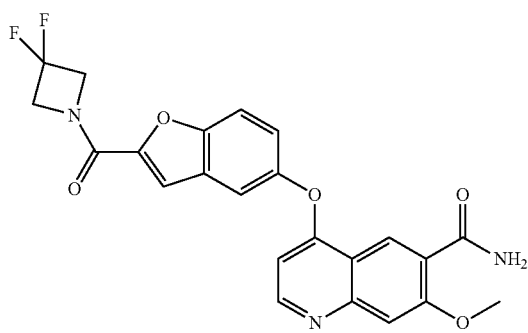
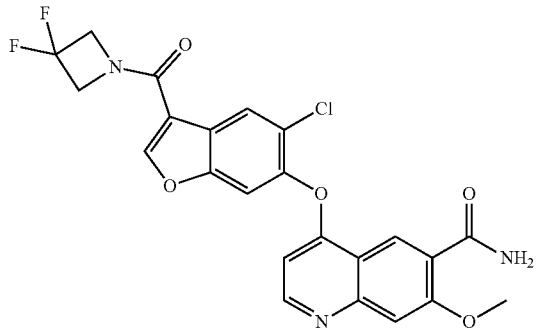
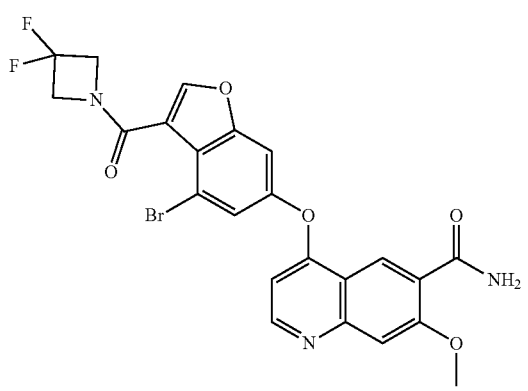
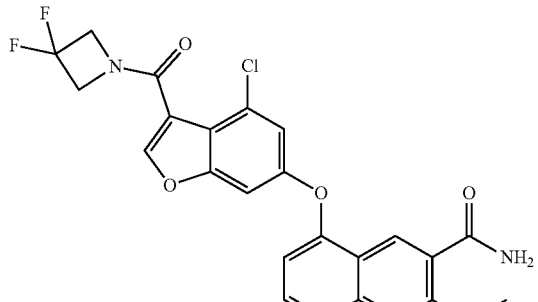
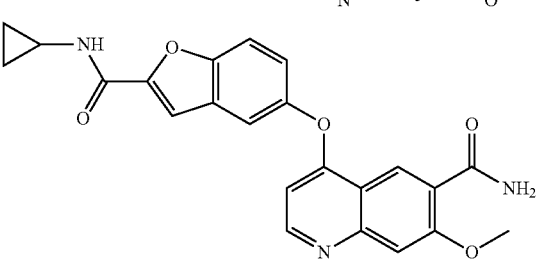

369
-continued
370
-continued
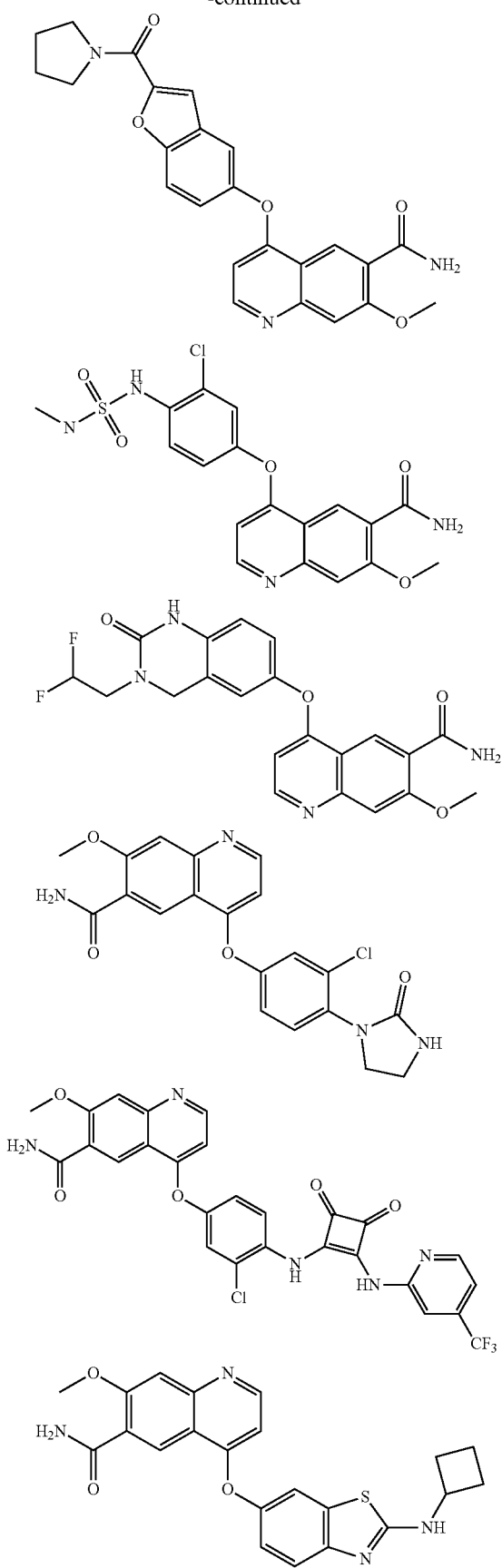
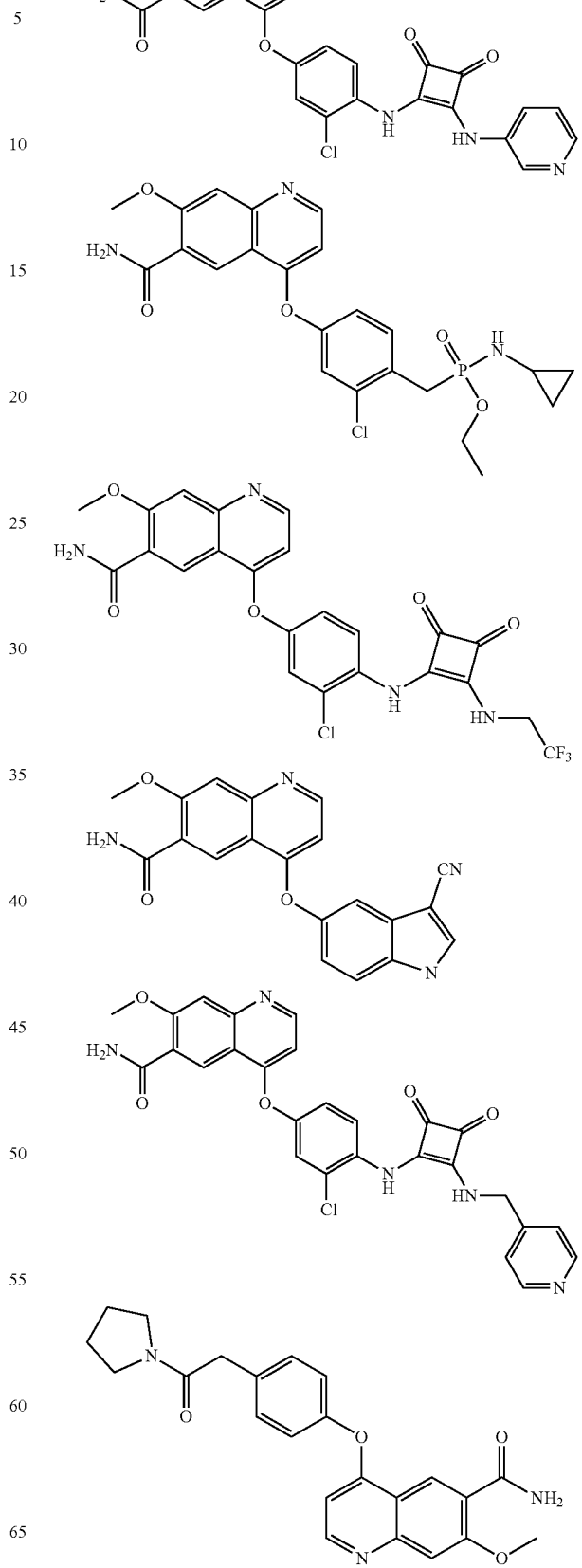

371
-continued
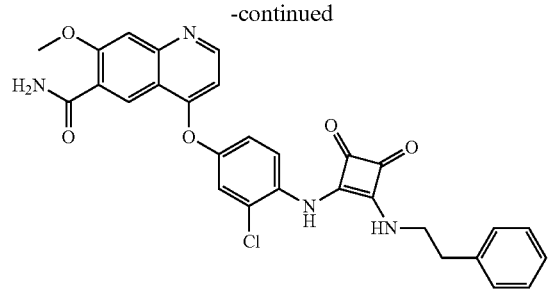
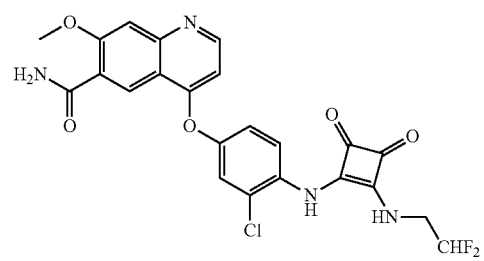
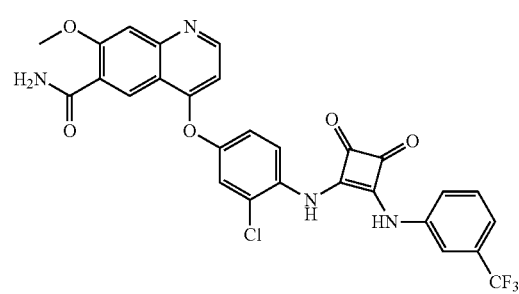
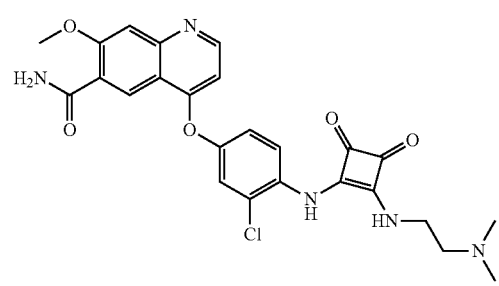
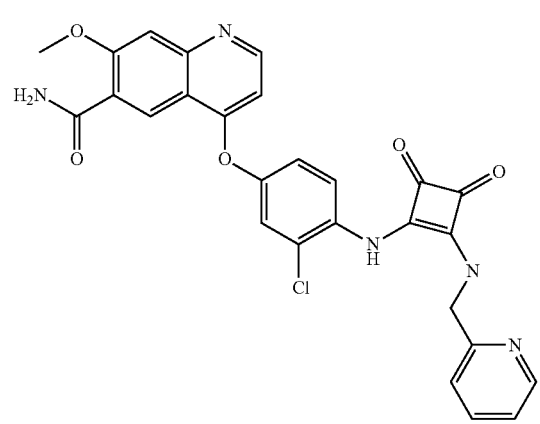
372
-continued
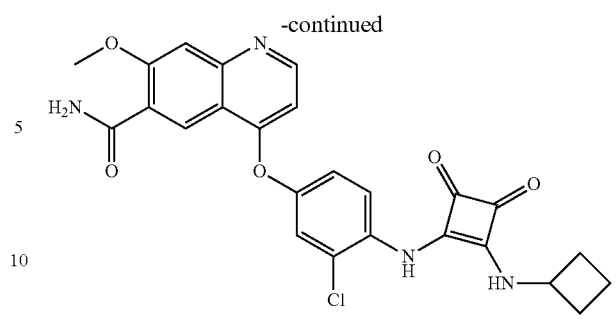
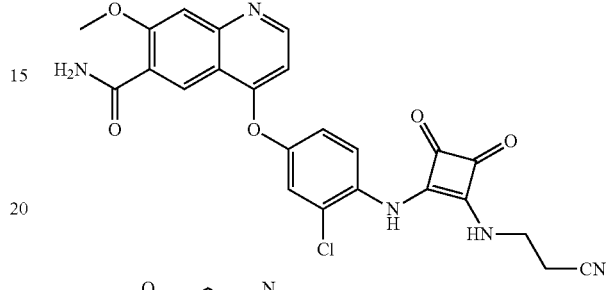
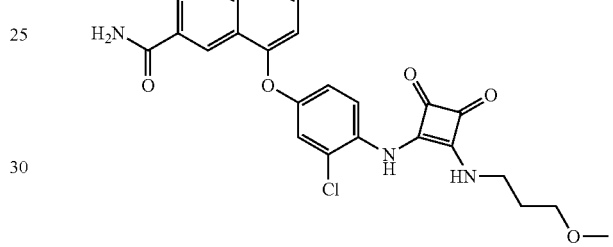
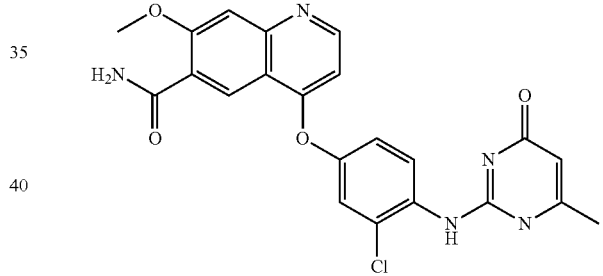
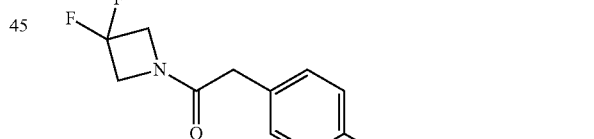
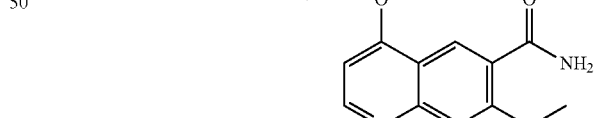
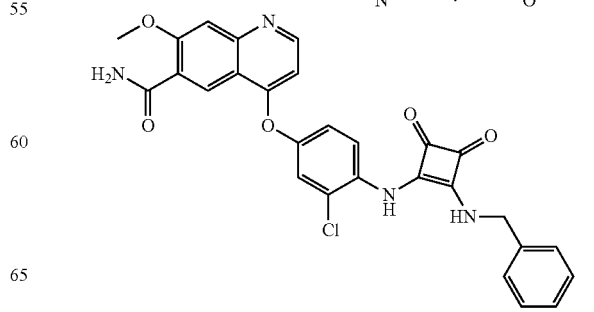

373
-continued
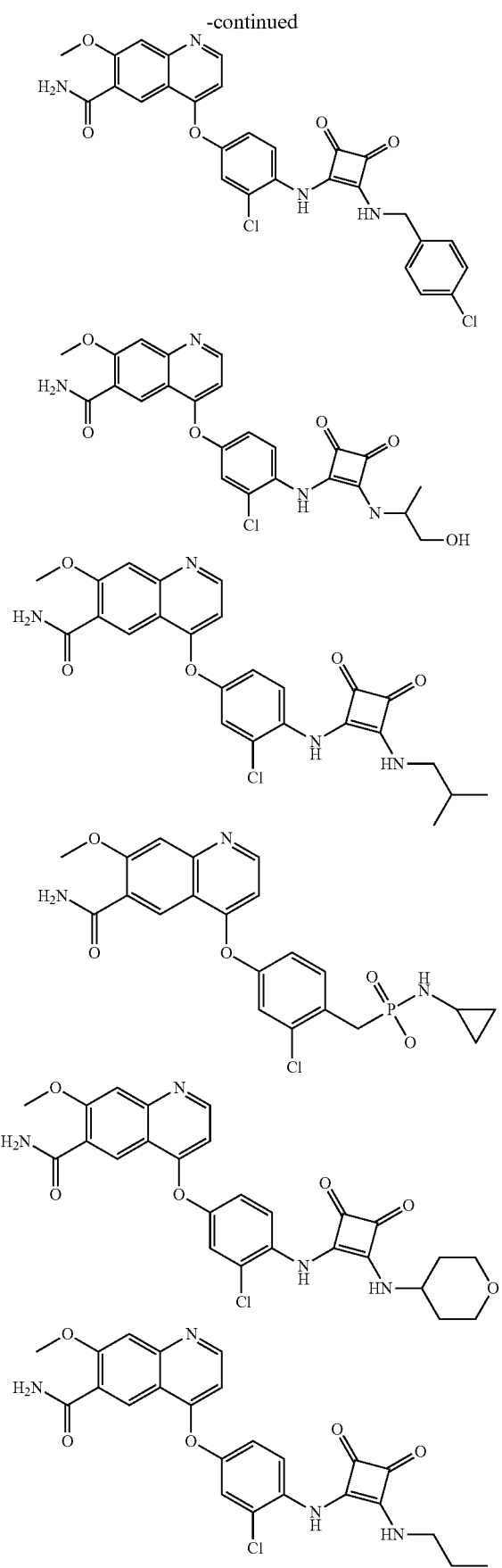
374
-continued
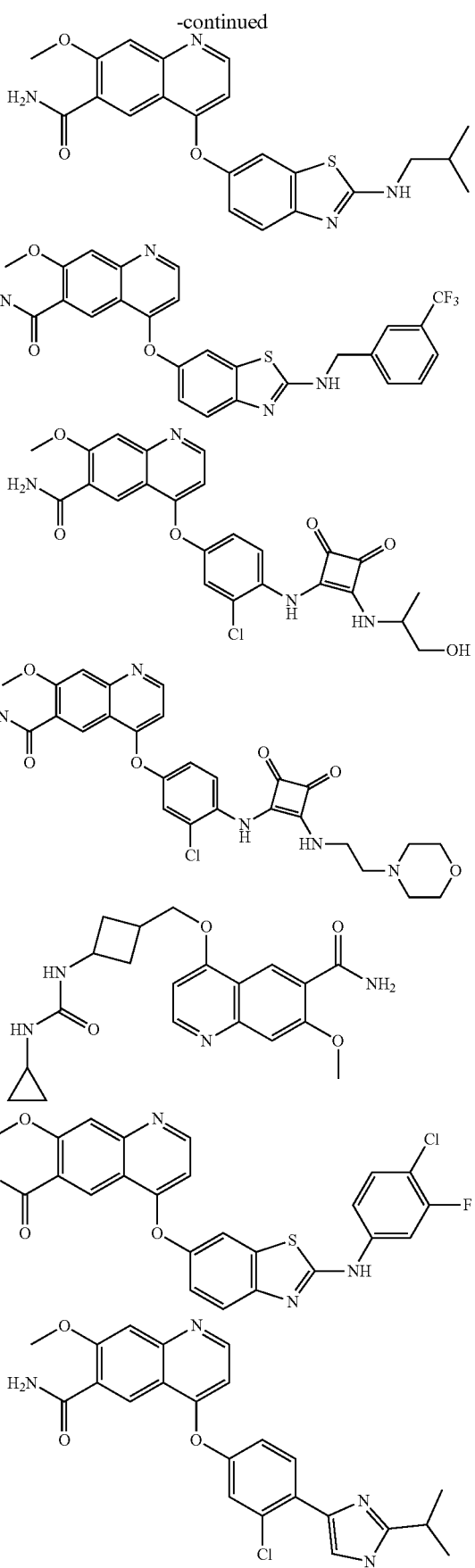

375
-continued
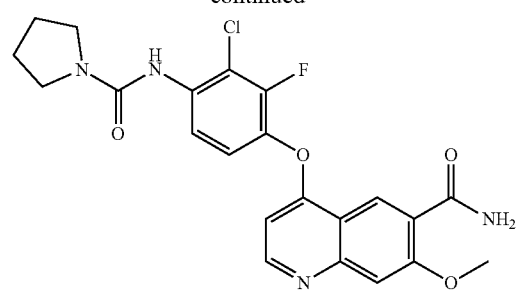
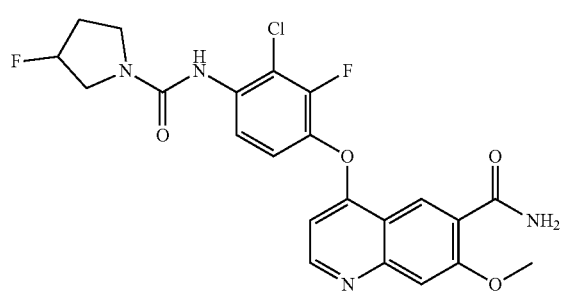
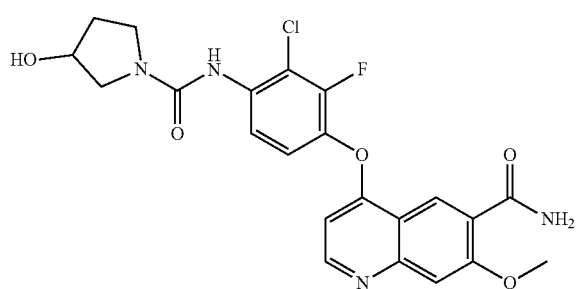
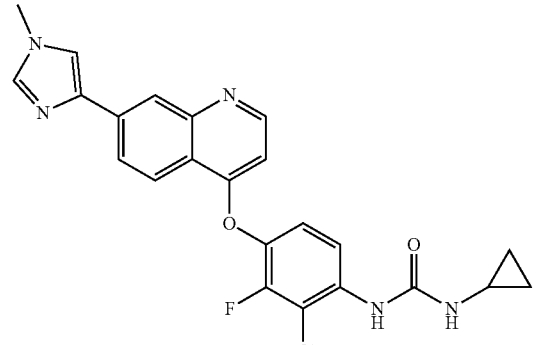
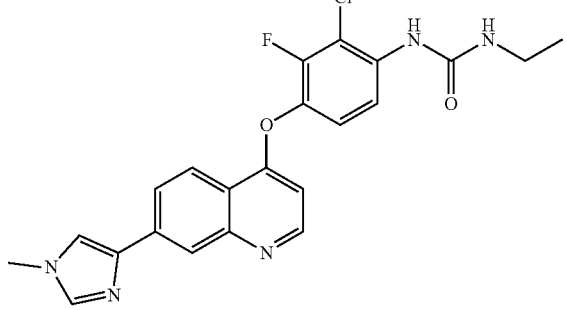
376
-continued
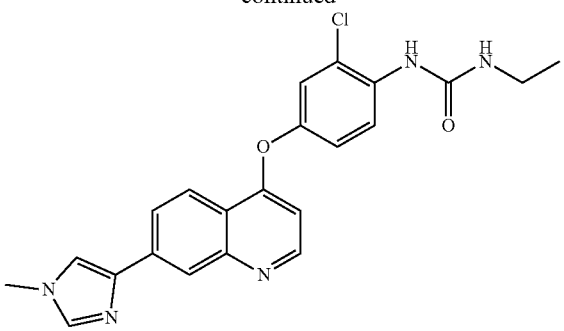
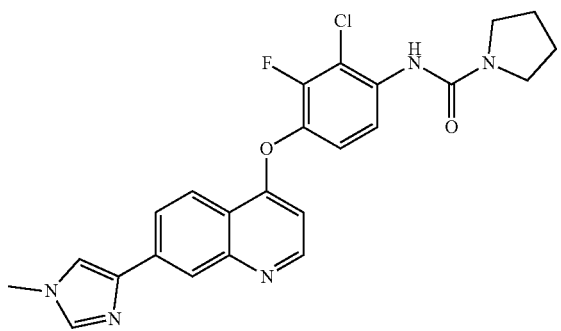
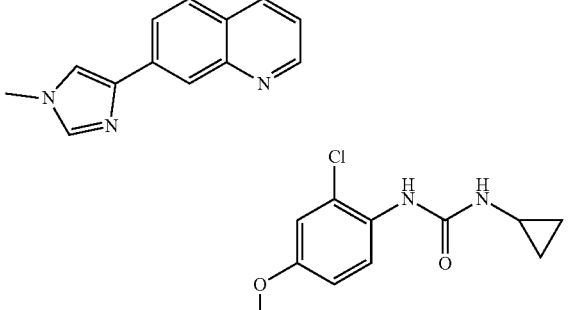
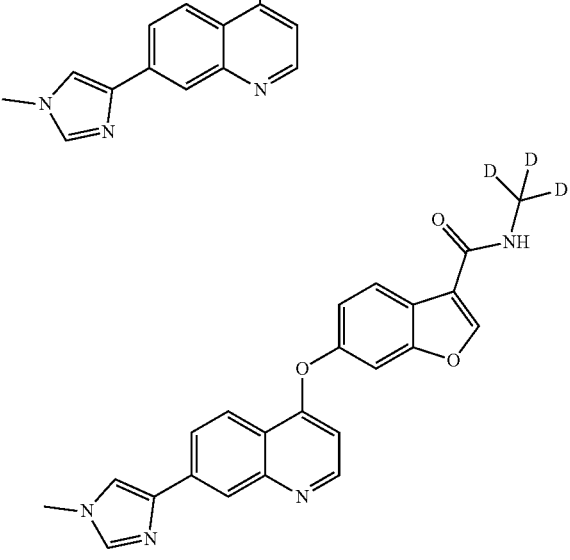

377
-continued
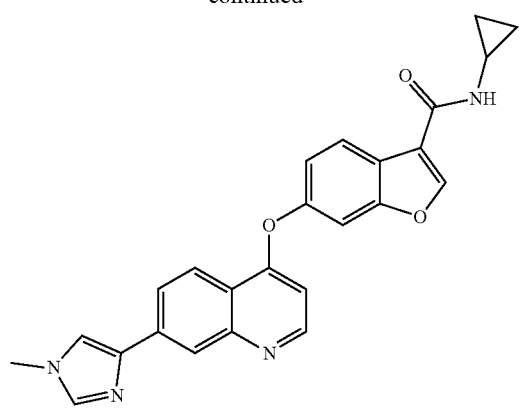
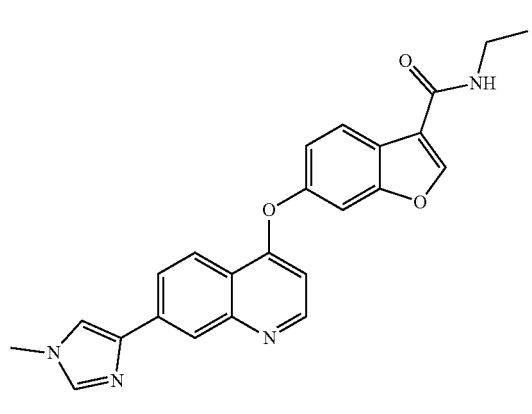
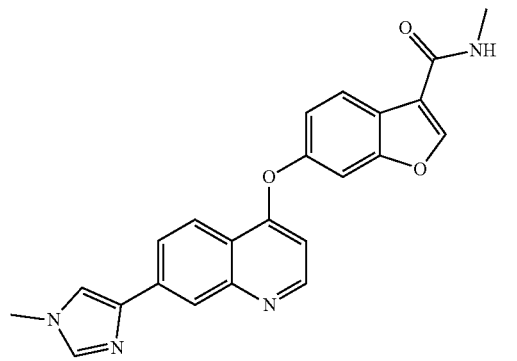
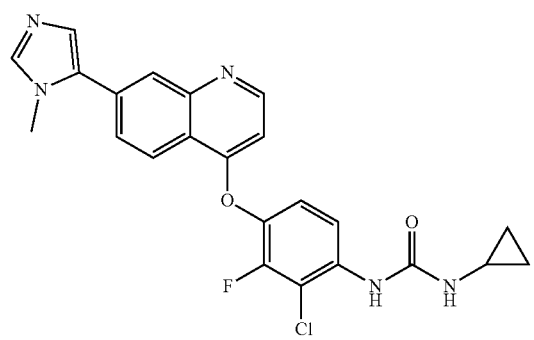 [SMILES: Cn1cncc1-c1ccc2c(Oc3ccc(NC(=O)NC4CC4)c(Cl)c3F)ccnc2c1]
378
-continued
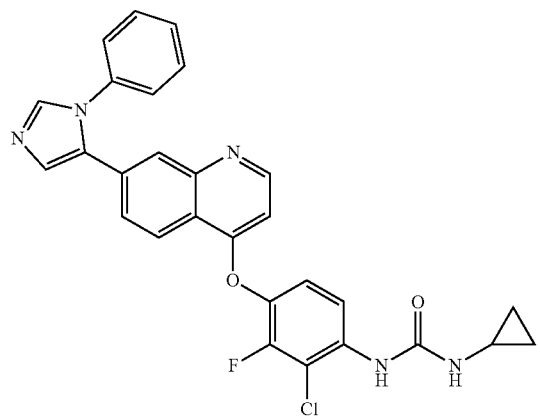
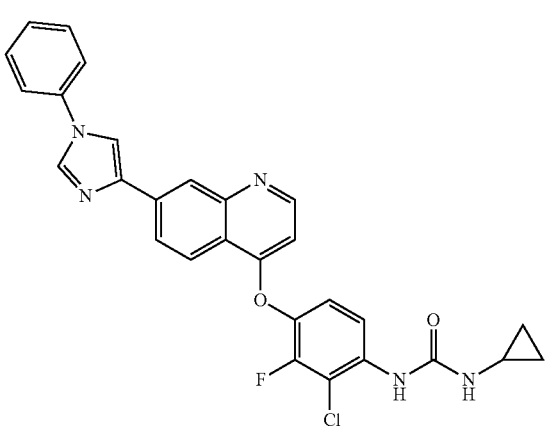
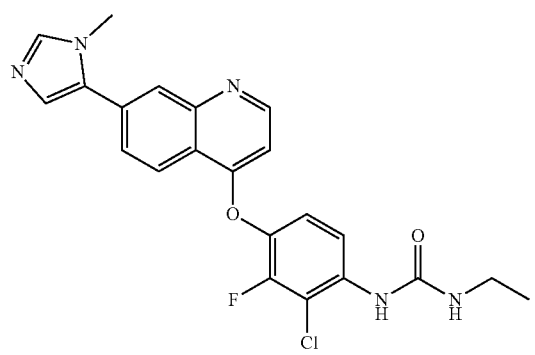
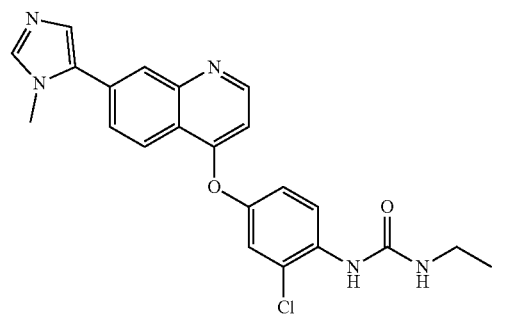 [SMILES: CCNC(=O)Nc1ccc(Oc2ccnc3cc(-c4cncn4C)ccc23)cc1Cl]

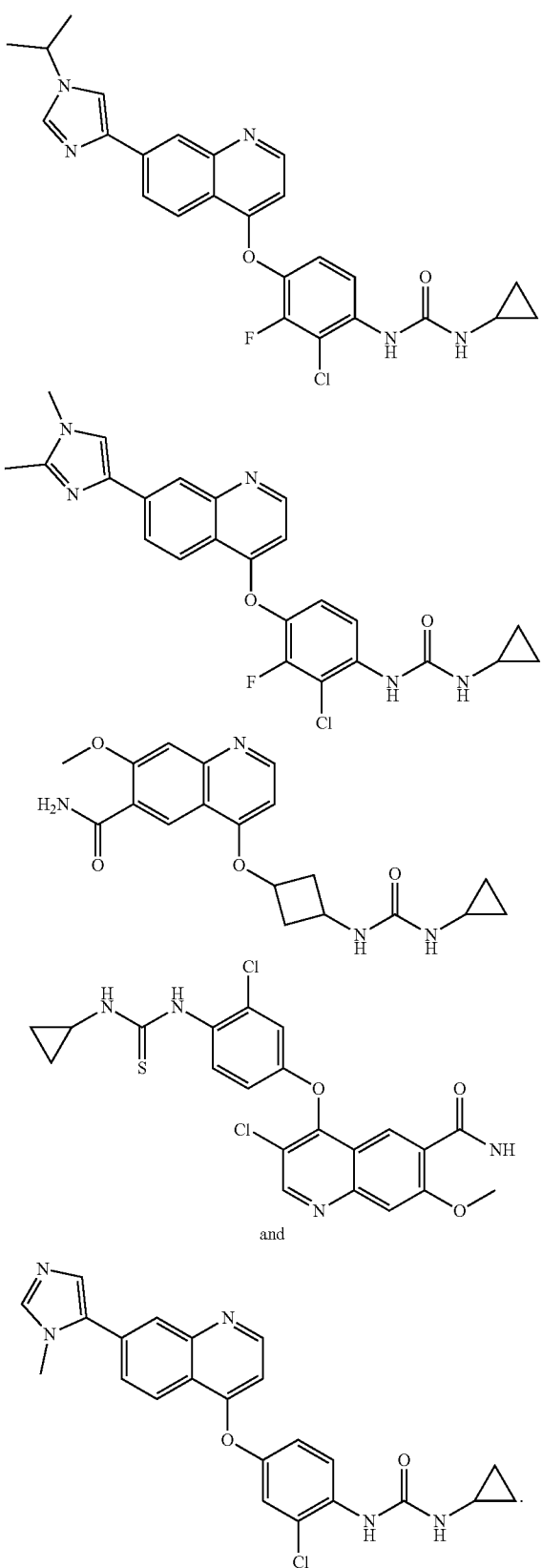

and

18. A pharmaceutical composition comprising the compound or enantiomer, diastereoisomer, geometric isomer, solvate or pharmaceutically acceptable salt thereof according to claim 1 and at least one pharmaceutically acceptable carrier, the pharmaceutical composition is tablet, suppository, dispersible tablet, enteric tablet, chewable tablet, orally disintegrating tablet, capsule, sugar coated tablet, granule, dry powder, oral solution, small volume injection, or freeze-dried powder injection, the pharmaceutically acceptable carrier includes one or more substances selected from diluents, solubilizers, disintegrants, suspending agents, lubricants, binders, fillers, flavoring agents, sweetening agents, antioxidants, surfactants, preservatives, encapsulants and pigments.

19. A method for treating tumors comprising administering to a patient in need thereof a therapeutically effective amount of the compound or enantiomer, diastereoisomer, geometric isomer, solvate or pharmaceutically acceptable salt thereof according to claim 1, wherein the tumors comprises solid tumors and blood-borne tumors; the solid tumors comprises rhabdomyosarcoma, retinoblastoma, ewing sarcoma, neuroblastoma and osteosarcoma; the blood-borne tumors comprises, but are not limited to leukemia, lymphoma, multiple myeloma, and various acute or chronic myeloid neoplasms.

20. A compound or an enantiomer, a diastereomer, a geometric isomer, a solvate or a pharmaceutically acceptable salt thereof according to claim 1, wherein A is selected from

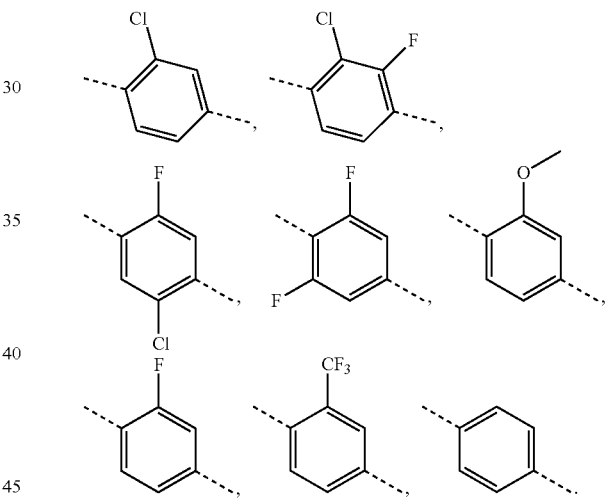

21. A compound or an enantiomer, a diastereomer, a geometric isomer, a solvate or a pharmaceutically acceptable salt thereof according to claim 11, wherein $R_7$, $R_8$ and $R_9$ are each independently selected from H, Me,

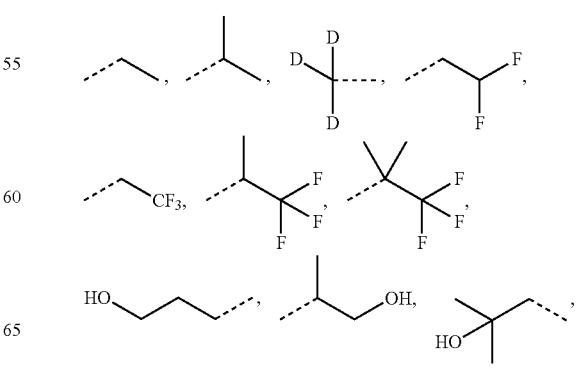

381
-continued
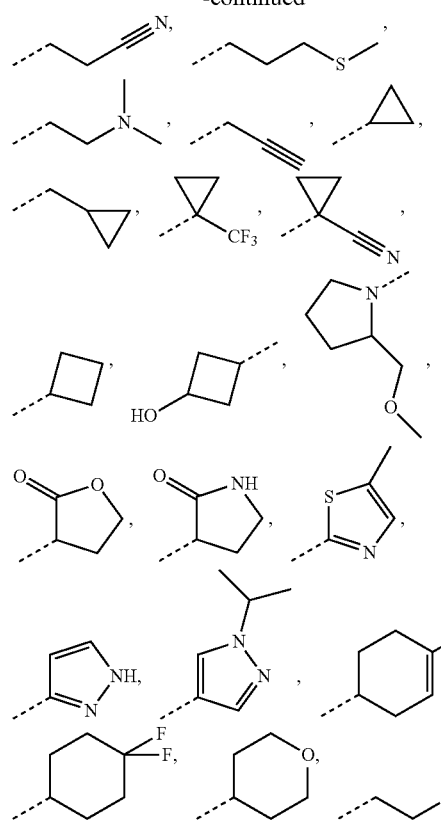
382
-continued
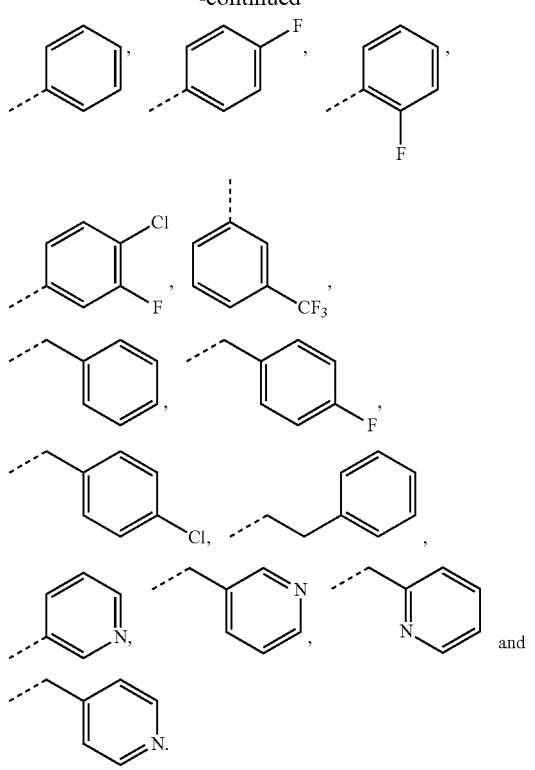
* * * * *

UNITED STATES PATENT AND TRADEMARK OFFICE
CERTIFICATE OF CORRECTION

PATENT NO. : 10,654,808 B2
APPLICATION NO. : 15/562825
DATED : May 19, 2020
INVENTOR(S) : Chaofeng Long et al.

It is certified that error appears in the above-identified patent and that said Letters Patent is hereby corrected as shown below:

In the Claims

Column 330, the formula beginning at Line 21, reading -$C_{1-30}$- should be read as --$C_{1-3}$--.

Column 336, the formula beginning at Line 41, after "3-6 membered heterocycloalkyl-$C_{1-3}$ alkyl-," delete "3-6 membered heterocycloalkyl-$C_{1-3}$ alkyl-,".

Column 337, the formula beginning at Line 50-60, reading - 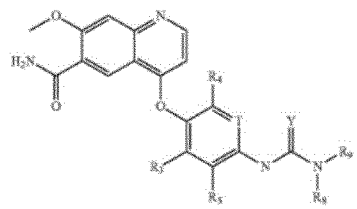 - should be read as -- 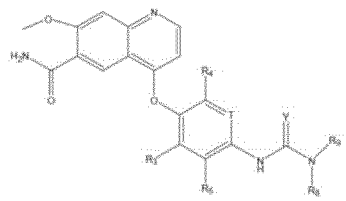 --.

Column 340, the formula beginning at Line 8-38, below " 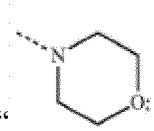 " delete "or the structural unit 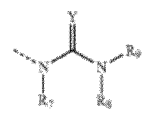 is selected from Signed and Sealed this
Nineteenth Day of July, 2022

Katherine Kelly Vidal
*Director of the United States Patent and Trademark Office*

CERTIFICATE OF CORRECTION (continued)
U.S. Pat. No. 10,654,808 B2

Page 2 of 5

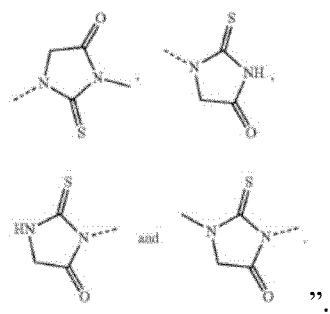

Column 346, the formula beginning at Line 48-55, reading -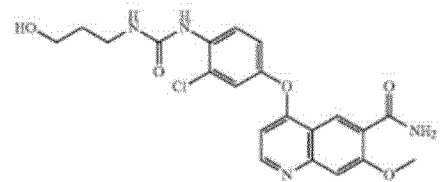- should be read as --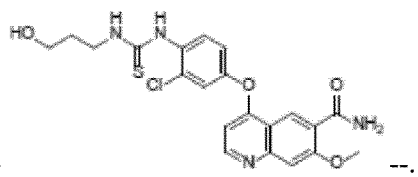--.

Column 357, the formula beginning at Line 33-45, below "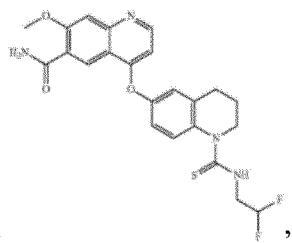" delete

"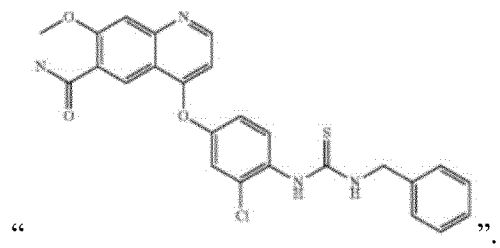".

Column 359, the formula beginning at Line 45-55, below "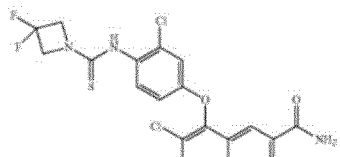" delete

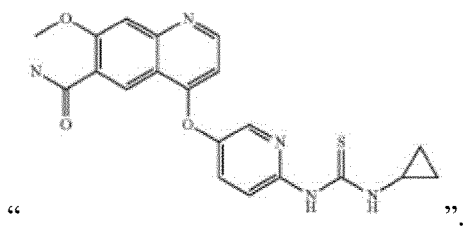
" ".
Column 361, the formula beginning at Line 45-55, below " 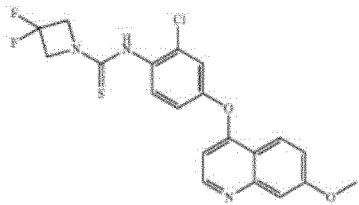 " delete
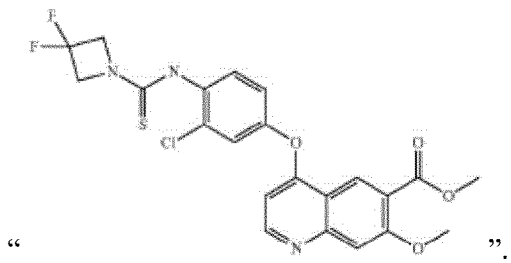
" ".
Column 373, the formula beginning at Line 15-23, delete " 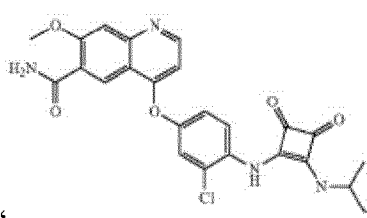 " and
insert -- 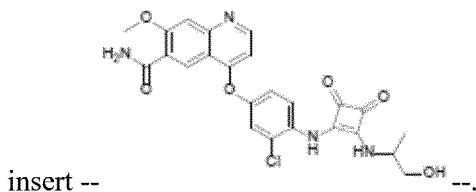 --.
Column 379, the formula beginning at Line 1, before " 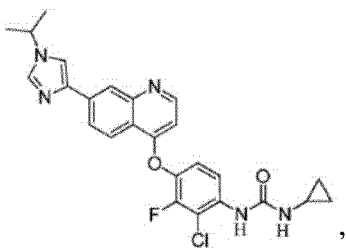 " insert

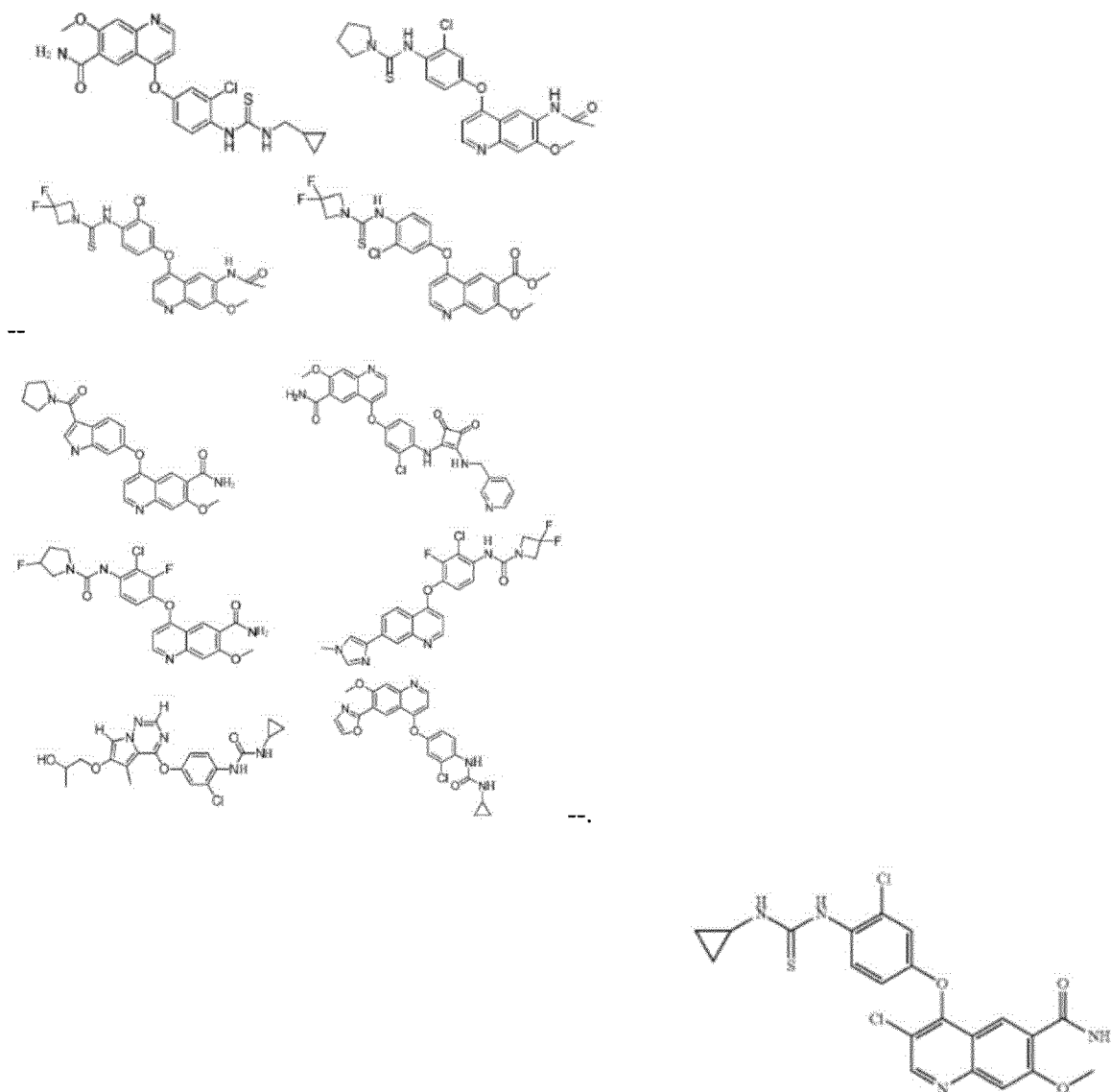
Column 379, the formula beginning at Line 40-50, reading -- 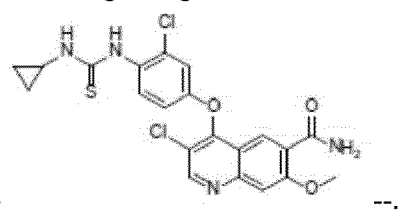 should be read as -- 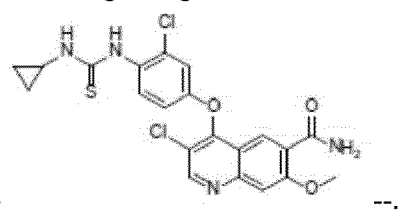 --.
Column 379, the formula beginning at Line 50-64, after " 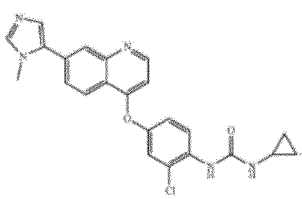 " insert

CERTIFICATE OF CORRECTION (continued)
U.S. Pat. No. 10,654,808 B2